(12) United States Patent
Vendely et al.

(10) Patent No.: US 11,253,253 B2
(45) Date of Patent: Feb. 22, 2022

(54) METHOD OF APPLYING A BUTTRESS TO A SURGICAL STAPLER AND EFFECTOR

(71) Applicant: Ethicon LLC, Guaynabo, PR (US)

(72) Inventors: Michael J. Vendely, Lebanon, OH (US); Trevor J. Barton, Cincinnati, OH (US); Jason L. Harris, Lebanon, OH (US); Charles J. Scheib, Loveland, OH (US); Emily A. Schellin, Cincinnati, OH (US); Prudence A. Turner, Independence, KY (US); Steven G. Hall, Cincinnati, OH (US); Victoria Dalessandro, Scotch Plains, NJ (US); Jackie Donners, Pennington, NJ (US); Mark Timmer, Jersey City, NJ (US); Rao S. Bezwada, Whitehouse Station, NJ (US); Aidan Craigwood, Cambridge (GB); Caroline Hagerman, Cambridge (GB); Ashley Easter, Cambridge (GB); Kathrin Holtzmann, Cambridge (GB); Frederick E. Shelton, IV, Hillsboro, OH (US); Mark S. Zeiner, Mason, OH (US)

(73) Assignee: Cilag GmbH International, Zug (CH)

( * ) Notice: Subject to any disclaimer, the term of this patent is extended or adjusted under 35 U.S.C. 154(b) by 182 days.

(21) Appl. No.: 16/377,348

(22) Filed: Apr. 8, 2019

(65) Prior Publication Data
US 2019/0298338 A1    Oct. 3, 2019

Related U.S. Application Data

(63) Continuation of application No. 16/191,722, filed on Nov. 15, 2018, now Pat. No. 11,051,806, which is a
(Continued)

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/07207* (2013.01); *A61B 17/07292* (2013.01);
(Continued)

(58) Field of Classification Search
CPC . A61B 17/068; A61B 17/072; A61B 17/0644; A61B 17/664; A61B 17/07292; A61B 17/07207; A61B 2017/00004
See application file for complete search history.

(56) References Cited

U.S. PATENT DOCUMENTS

| | | | |
|---|---|---|---|
| 4,805,823 | A | 2/1989 | Rothfuss |
| 5,415,334 | A | 5/1995 | Williamson et al. |

(Continued)

FOREIGN PATENT DOCUMENTS

| | | |
|---|---|---|
| CN | 101366647 A | 2/2009 |
| CN | 201806743 U | 4/2011 |

(Continued)

OTHER PUBLICATIONS

Extended European Search Report and Written Opinion dated Jan. 20, 2017 for Application No. EP 16185368.4, 10 pgs.
(Continued)

*Primary Examiner* — Vi X Nguyen
(74) *Attorney, Agent, or Firm* — Frost Brown Todd LLC

(57) ABSTRACT

A buttress is applied to an end effector of a surgical stapler. The buttress is loaded on a platform of a buttress applier cartridge. The end effector is closed upon the platform. An adhesive layer of the buttress secures the buttress to the end effector. The buttress is thus adhered to the end effector when the end effector is opened. The end effector is then
(Continued)

actuated on tissue of a patient, thereby stapling the buttress to the tissue.

16 Claims, 130 Drawing Sheets

Related U.S. Application Data continuation of application No. 14/926,764, filed on Oct. 29, 2015, now Pat. No. 10,166,023.

(60) Provisional application No. 62/209,041, filed on Aug. 24, 2015.

(51) Int. Cl.
*A61B 50/30* (2016.01)
*A61B 90/90* (2016.01)
*A61B 50/31* (2016.01)
*A61B 42/00* (2016.01)
*A61B 17/00* (2006.01)
*A61B 90/00* (2016.01)
*A61B 50/00* (2016.01)

(52) U.S. Cl.
CPC .............. *A61B 42/00* (2016.02); *A61B 50/30* (2016.02); *A61B 50/31* (2016.02); *A61B 90/90* (2016.02); *A61B 2017/00115* (2013.01); *A61B 2017/00221* (2013.01); *A61B 2017/00526* (2013.01); *A61B 2017/00734* (2013.01); *A61B 2017/00893* (2013.01); *A61B 2017/00946* (2013.01); *A61B 2017/00951* (2013.01); *A61B 2017/0688* (2013.01); *A61B 2017/07271* (2013.01); *A61B 2050/005* (2016.02); *A61B 2050/0059* (2016.02); *A61B 2050/0065* (2016.02); *A61B 2050/314* (2016.02); *A61B 2090/037* (2016.02); *A61B 2090/081* (2016.02); *A61B 2090/0807* (2016.02)

(56) References Cited

U.S. PATENT DOCUMENTS

| | | | |
|---|---|---|---|
| 5,441,191 A | 8/1995 | Linden | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,752,965 A | 5/1998 | Francis et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 5,915,616 A * | 6/1999 | Viola | A61B 17/072 227/179.1 |
| 6,231,565 B1 | 5/2001 | Tovey et al. | |
| 6,273,897 B1 | 8/2001 | Dalessandro et al. | |
| 6,364,888 B1 | 4/2002 | Niemeyer et al. | |
| 6,783,524 B2 | 8/2004 | Anderson et al. | |
| 6,939,358 B2 | 9/2005 | Palacios et al. | |
| 6,978,921 B2 | 12/2005 | Shelton, IV et al. | |
| 6,988,649 B2 | 1/2006 | Shelton, IV et al. | |
| 7,000,818 B2 | 2/2006 | Shelton, IV et al. | |
| 7,083,075 B2 * | 8/2006 | Swayze | A61B 17/07207 227/176.1 |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,524,320 B2 | 4/2009 | Tierney | |
| 7,691,098 B2 | 4/2010 | Wallace | |
| 7,721,930 B2 | 5/2010 | McKenna et al. | |
| 7,806,891 B2 | 10/2010 | Nowlin et al. | |
| 8,141,762 B2 | 3/2012 | Bedi et al. | |
| 8,210,032 B2 | 7/2012 | Sanford et al. | |
| 8,210,411 B2 | 7/2012 | Yates et al. | |
| 8,371,491 B2 | 2/2013 | Huitema et al. | |
| 8,408,439 B2 | 4/2013 | Huang et al. | |
| 8,453,904 B2 | 6/2013 | Eskaros et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,801,735 B2 | 8/2014 | Shelton, IV et al. | |
| 8,814,025 B2 | 8/2014 | Miller et al. | |
| 8,820,605 B2 | 9/2014 | Shelton, IV | |
| 8,844,789 B2 | 9/2014 | Shelton, IV et al. | |
| 8,899,464 B2 | 12/2014 | Hueil et al. | |
| 8,998,060 B2 | 4/2015 | Bruewer et al. | |
| 9,060,770 B2 | 6/2015 | Shelton, IV et al. | |
| 9,101,359 B2 | 8/2015 | Smith et al. | |
| 9,186,142 B2 | 11/2015 | Fanelli et al. | |
| 9,198,644 B2 | 12/2015 | Balek et al. | |
| 9,198,662 B2 | 12/2015 | Barton et al. | |
| 9,211,120 B2 | 12/2015 | Scheib et al. | |
| 9,220,501 B2 | 12/2015 | Baxter, III et al. | |
| 9,282,962 B2 | 3/2016 | Schmid et al. | |
| 9,300,773 B2 | 3/2016 | Mittleman et al. | |
| 9,301,759 B2 | 4/2016 | Spivey et al. | |
| 9,307,965 B2 | 4/2016 | Ming et al. | |
| 9,364,233 B2 | 6/2016 | Alexander, III et al. | |
| 9,386,988 B2 | 7/2016 | Baxter, III et al. | |
| 9,393,018 B2 | 7/2016 | Wang et al. | |
| 9,398,911 B2 | 7/2016 | Auld | |
| 9,445,808 B2 | 9/2016 | Woodard et al. | |
| 9,492,170 B2 | 11/2016 | Bear et al. | |
| 9,517,065 B2 | 12/2016 | Simms et al. | |
| 9,597,082 B2 | 3/2017 | Stokes et al. | |
| 9,622,746 B2 | 4/2017 | Simms et al. | |
| 9,629,626 B2 | 4/2017 | Soltz et al. | |
| 9,717,497 B2 | 8/2017 | Zerkle et al. | |
| 9,770,245 B2 | 9/2017 | Swayze et al. | |
| 9,795,379 B2 | 10/2017 | Leimbach et al. | |
| 9,808,248 B2 | 11/2017 | Hoffman | |
| 9,839,420 B2 | 12/2017 | Shelton, IV et al. | |
| 9,839,421 B2 | 12/2017 | Zerkle et al. | |
| 9,848,871 B2 | 12/2017 | Harris et al. | |
| 9,867,615 B2 | 1/2018 | Fanelli et al. | |
| 9,913,642 B2 | 3/2018 | Leimbach et al. | |
| 9,936,954 B2 | 4/2018 | Shelton, IV et al. | |
| 9,999,408 B2 | 6/2018 | Boudreaux et al. | |
| 10,052,105 B2 | 8/2018 | Tannhauser et al. | |
| 10,085,745 B2 | 10/2018 | Dalessandro et al. | |
| 10,092,292 B2 | 10/2018 | Boudreaux et al. | |
| 10,123,798 B2 | 11/2018 | Baxter, III et al. | |
| 10,166,023 B2 | 1/2019 | Vendely et al. | |
| 10,172,611 B2 | 1/2019 | Shelton, IV et al. | |
| 10,194,912 B2 | 2/2019 | Scheib et al. | |
| 10,201,348 B2 | 2/2019 | Scheib et al. | |
| 10,213,198 B2 | 2/2019 | Aronhalt et al. | |
| 10,238,388 B2 | 3/2019 | Shelton, IV et al. | |
| 10,251,649 B2 | 4/2019 | Schellin et al. | |
| 10,292,701 B2 | 5/2019 | Scheib et al. | |
| 10,314,580 B2 | 6/2019 | Scheib et al. | |
| 10,314,588 B2 | 6/2019 | Turner et al. | |
| 10,327,764 B2 | 6/2019 | Harris et al. | |
| 10,335,147 B2 | 7/2019 | Rector et al. | |
| 10,342,532 B2 | 7/2019 | Zeiner et al. | |
| 10,342,542 B2 | 7/2019 | Barton et al. | |
| 10,349,939 B2 | 7/2019 | Shelton, IV et al. | |
| 10,349,940 B2 | 7/2019 | Zeiner et al. | |
| 10,357,248 B2 | 7/2019 | Shellin et al. | |
| 10,639,039 B2 | 5/2020 | Vendely et al. | |
| 11,039,832 B2 | 6/2021 | Vendely et al. | |

(56) References Cited

U.S. PATENT DOCUMENTS

| | | | |
|---|---|---|---|
| 11,045,188 | B2 | 6/2021 | Vendely et al. |
| 11,051,806 | B2 | 7/2021 | Vendely et al. |
| 11,058,419 | B2 | 7/2021 | Vendely et al. |
| 2005/0070929 | A1 | 3/2005 | Dalessandro et al. |
| 2006/0173470 | A1 | 8/2006 | Oray et al. |
| 2008/0169328 | A1 | 7/2008 | Shelton, IV |
| 2009/0205986 | A1 | 8/2009 | Baker et al. |
| 2009/0206126 | A1 | 8/2009 | Huitema et al. |
| 2009/0206131 | A1 | 8/2009 | Weisenburgh, II et al. |
| 2009/0206142 | A1 | 8/2009 | Huitema et al. |
| 2010/0012704 | A1 | 1/2010 | Racenet et al. |
| 2010/0234861 | A1 | 9/2010 | Oray et al. |
| 2011/0290856 | A1 | 12/2011 | Shelton, IV et al. |
| 2012/0289979 | A1 | 11/2012 | Eskaros et al. |
| 2012/0292367 | A1 | 11/2012 | Morgan et al. |
| 2013/0068816 | A1 | 3/2013 | Vasudevan et al. |
| 2013/0075447 | A1 | 3/2013 | Weisenburgh, II et al. |
| 2013/0206813 | A1 | 8/2013 | Nalagatla |
| 2014/0021242 | A1 | 1/2014 | Hodgkinson et al. |
| 2015/0076212 | A1 | 3/2015 | Shelton, IV et al. |
| 2015/0090765 | A1 | 4/2015 | Hess et al. |
| 2016/0089146 | A1 | 3/2016 | Harris et al. |
| 2017/0049444 | A1 | 2/2017 | Schellin et al. |
| 2017/0055980 | A1 | 3/2017 | Vendely et al. |
| 2017/0055986 | A1 | 3/2017 | Harris et al. |
| 2017/0056017 | A1 | 3/2017 | Vendely et al. |
| 2017/0086837 | A1 | 3/2017 | Vendely et al. |
| 2017/0086842 | A1 | 3/2017 | Shelton, IV et al. |
| 2017/0119385 | A1 | 5/2017 | Shelton, IV et al. |
| 2017/0119386 | A1 | 5/2017 | Scheib et al. |
| 2017/0119390 | A1 | 5/2017 | Schellin et al. |
| 2017/0119392 | A1 | 5/2017 | Shelton, IV et al. |
| 2019/0150918 | A1 | 5/2019 | Vendely et al. |
| 2019/0167262 | A1 | 6/2019 | Vendely et al. |
| 2019/0167263 | A1 | 6/2019 | Vendely et al. |
| 2021/0169471 | A1 | 6/2021 | Vendely et al. |

FOREIGN PATENT DOCUMENTS

| | | |
|---|---|---|
| CN | 102307531 A | 1/2012 |
| CN | 203195731 U | 9/2013 |
| CN | 103957818 A | 7/2014 |
| CN | 103961149 A | 8/2014 |
| CN | 104224286 A | 12/2014 |
| CN | 104321023 A | 1/2015 |
| CN | 104 379 068 A | 2/2015 |
| CN | 104411255 A | 3/2015 |
| CN | 104837416 A | 8/2015 |
| EP | 2 090 248 A2 | 8/2009 |
| EP | 2 764 833 A2 | 8/2014 |
| EP | 3 072 457 A2 | 9/2016 |
| EP | 3072460 A2 | 9/2016 |
| JP | 2001-502575 A | 2/2001 |
| JP | 2012-130729 | 7/2012 |
| JP | 2015-514471 A | 5/2015 |
| WO | WO 2005/079675 A2 | 9/2005 |
| WO | WO 2013/043707 A2 | 3/2013 |
| WO | WO 2013/119365 A1 | 8/2013 |

OTHER PUBLICATIONS

European Exam Report dated Jan. 3, 2018 for Application No. EP 16185368.4, 4 pgs.
European Exam Report dated Oct. 16, 2018 for Application No. EP 16185368.4, 4 pgs.
Extended European Search Report and Written Opinion dated Jan. 24, 2017 for Application No. EP 16185370.0, 11 pgs.
European Exam Report dated Jan. 15, 2018 for Application No. EP 16185370.0, 4 pgs.
European Communication, Decision to Grant a European Patent, dated Jul. 4, 2019 for Application No. EP 16185370.0, 2 pgs.
European Search Report and Written Opinion dated Jan. 24, 2017 for Application No. EP 16185387.4, 10 pgs.
European Communication, Decision to Grant a European Patent, dated Aug. 30, 2018 for Application No. EP 16185387.4, 2 pgs.
European Search Report and Written Opinion dated Jan. 30, 2017 for Application No. EP 16185376.7, 14 pgs.
European Communication, Decision to Grant a European Patent, dated Jan. 10, 2019 for Application No. EP 16185376.7, 2 pgs.
European Search Report, Partial, dated Jan. 25, 2017 for Application No. 16185375.9, 7 pgs.
Extended European Search Report and Written Opinion dated Jun. 8, 2017 for Application No. EP 16185375.9, 16 pgs.
European Communication, Decision to Grant a European Patent, dated Dec. 6, 2018 for Application No. EP 16185375.9, 2 pgs.
Extended European Search Report and Written Opinion dated Oct. 18, 2017 for Application No. EP 18182626.4, 8 pgs.
International Search Report and Written Opinion dated Dec. 23, 2016 for Application No. PCT/US2016/048352, 16 pgs.
International Search Report and Written Opinion dated Feb. 17, 2017 for Application No. PCT/US2016/048356, 17 pgs.
International Search Report and Written Opinion dated Jan. 2, 2017 for Application No. PCT/US2016/048359, 12 pgs.
International Search Report and Written Opinion dated Dec. 21, 2016 for Application No. PCT/US2016/048362, 11 pgs.
International Search Report and Written Opinion dated Dec. 6, 2016 for Application No. PCT/US2016/048364, 12 pgs.
U.S. Appl. No. 62/209,041, filed Aug. 24, 2015.
U.S. Appl. No. 14/926,322, Vendely et al., filed Oct. 29, 2015.
U.S. Appl. No. 16/191,722, Vendely et al., filed Nov. 15, 2018.
U.S. Appl. No. 16/211,436, Vendely et al., filed Dec. 6, 2018.
U.S. Appl. No. 16/211,438, Vendely et al., filed Dec. 6, 2018.
U.S. Appl. No. 17/130,898; Vendely et al., filed Dec. 22, 2020.
European Search Report and Written Opinion dated Feb. 5, 2021 for Application No. EP 20208018.0, 9 pgs.
Indian Examination Report dated Feb. 12, 2021 for Application No. Ni 201817005619, 5 pgs.
U.S. Appl. No. 14/926,296.
U.S. Appl. No. 14/926,322.
U.S. Appl. No. 16/191,722.
U.S. Appl. No. 16/211,436.
U.S. Appl. No. 16/211,438.
Brazilian Search Report and Written Opinion dated Jun. 15, 2020 for Application No. BR 112018003524-6, 4 pgs.
Brazilian Search Report and Written Opinion dated Jun. 15, 2020 for Application No. BR 112018003490-8, 4 pgs.
Brazilian Search Report and Written Opinion dated Jun. 15, 2020 for Application No. BR 12018003480-0, 4 pgs.
Brazilian Search Report and Written Opinion dated Jun. 15, 2020 for Application No. BR 112018003512-2, 4 pgs.
Brazilian Search Report and Written Opinion dated May 5, 2020 for Application No. BR 112018003463-0, 4 pgs.
Chinese Office Action and Search Report dated Mar. 30, 2020 for Application No. CN 2016800620957, 9 pgs.
Chinese Office Action and Search Report dated Mar. 20, 2020 for Application No. CN 2016800620887, 16 pgs.
Chinese Office Action and Search Report dated Mar. 24, 2020 for Application No. CN 201680061225.5, 16 pgs.
Chinese Office Action and Search Report dated Mar. 20, 2020 for Application No. CN 201680062109.5, 10 pgs.
Chinese Office Action and Search Report dated Mar. 20, 2020 for Application No. CN 201680061209.6, 12 pgs.
Japanese Office Action, Notification of Reasons for Refusal, dated Oct. 6, 2020 for Application No. JP 2018-510411, 4 pgs.
Japanese Office Action, Notification of Reasons for Refusal, dated May 12, 2020 for Application No. JP 2018-510440, 5 pgs.
Japanese Office Action, Notification of Reasons for Refusal, dated Jun. 30, 2020 for Application No. JP 2018-510443, 3 pgs.
Japanese Office Action, Notification of Reasons for Refusal, dated Jul. 14, 2020 for Application No. JP 2018-510445, 6 pgs.
Japanese Office Action, Notification of Reasons for Refusal, dated Jun. 30, 2020 for Application No. JP 2018-510448, 3 pgs.
Indian Office Action dated May 29, 2021, for Application No. 201817005618, 5 pages.
Indian Office Action dated Jul. 29, 2021, for Application No. 201817005931, 5 pages.

(56) References Cited

OTHER PUBLICATIONS

Indian Office Action dated May 18, 2021, for Application No. 201817005932, 7 pages.
Indian Office Action dated Jun. 29, 2021, for Application No. 201817006147, 5 pages.

* cited by examiner

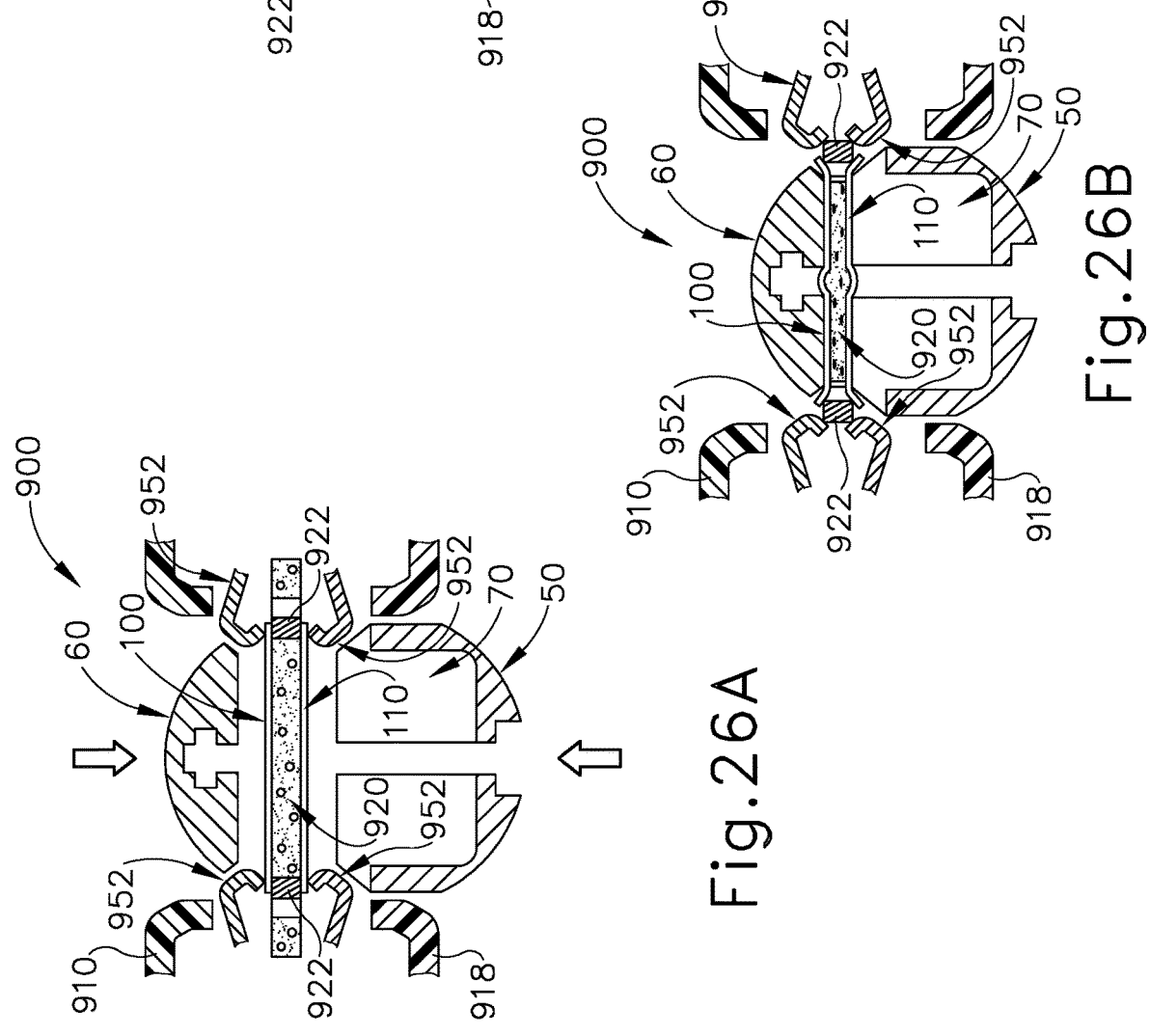

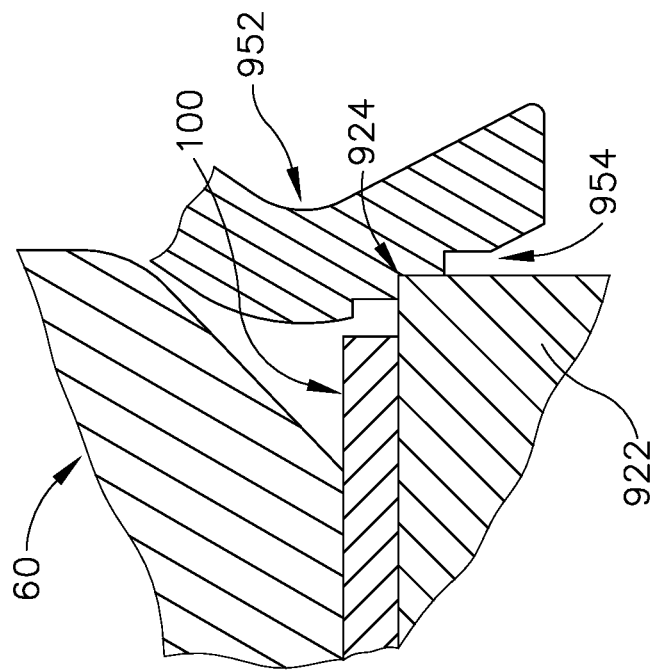
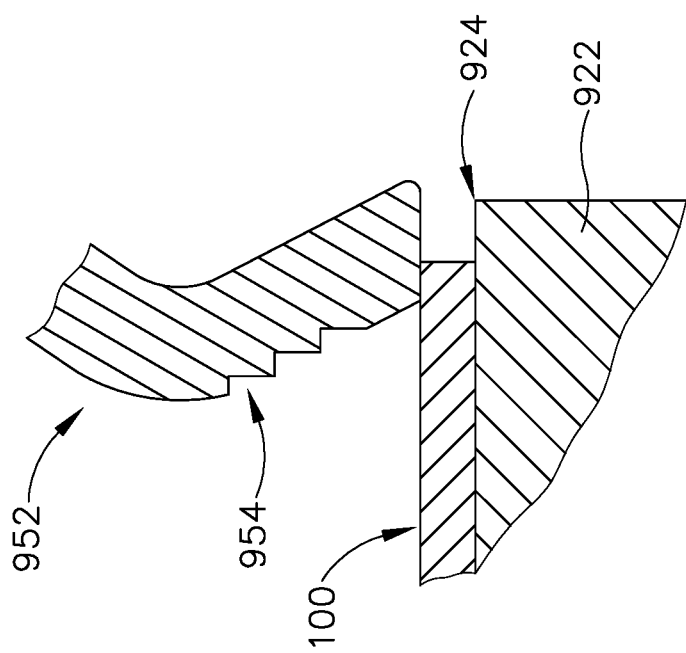
Fig.27B
Fig.27A

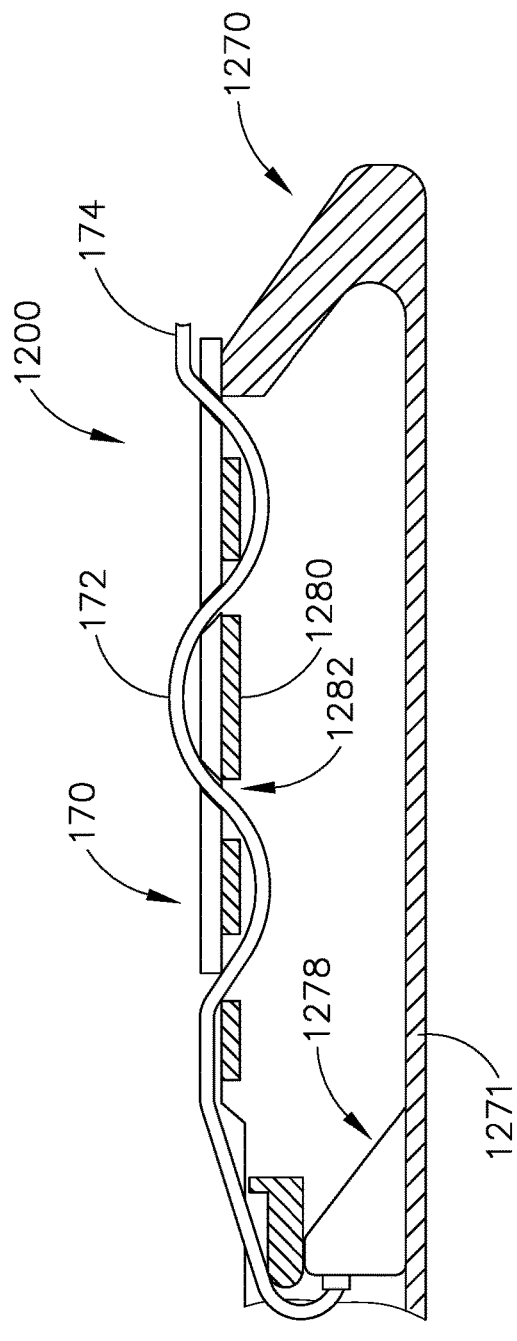
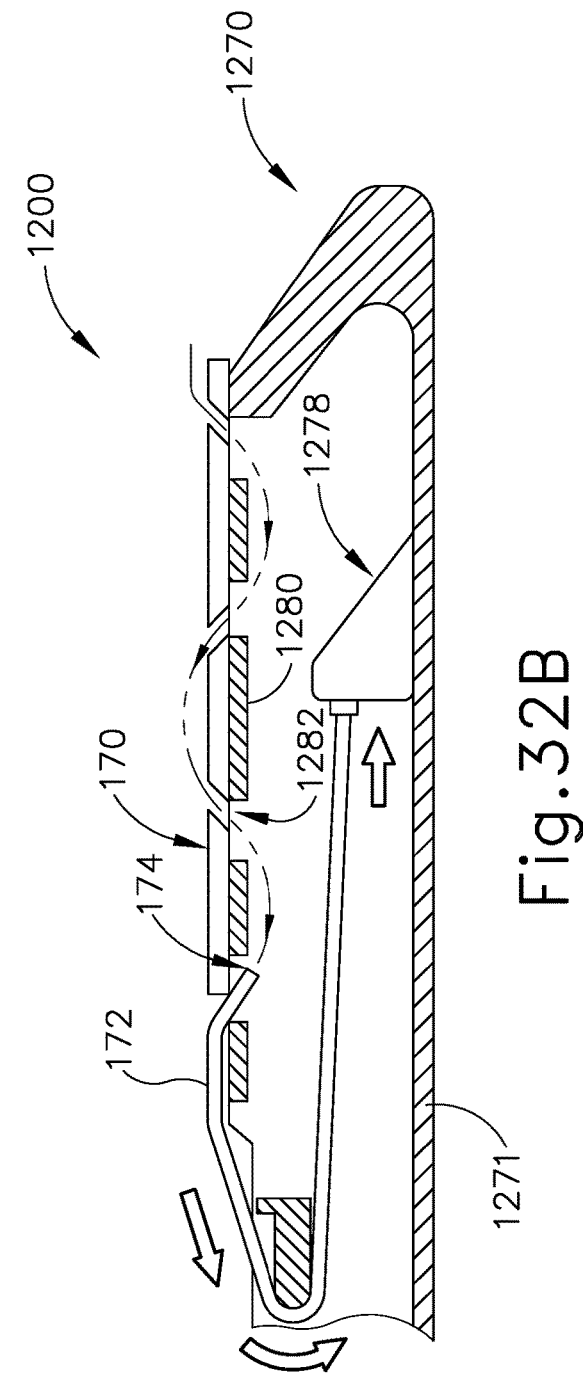
Fig. 32A
Fig. 32B

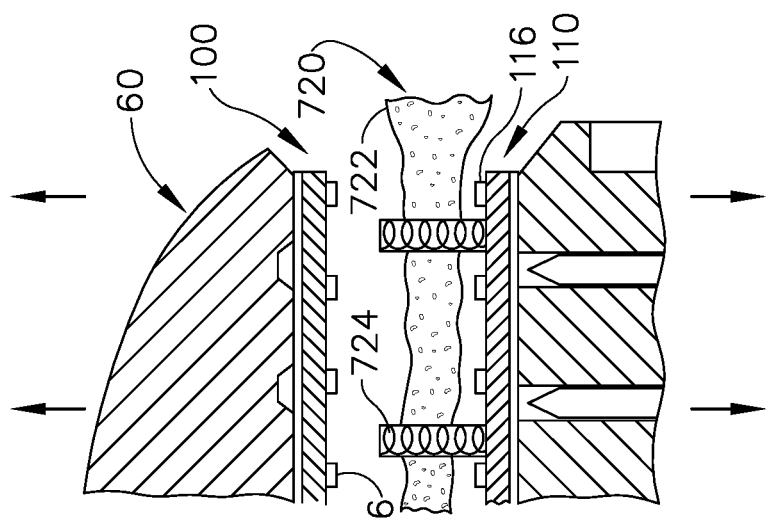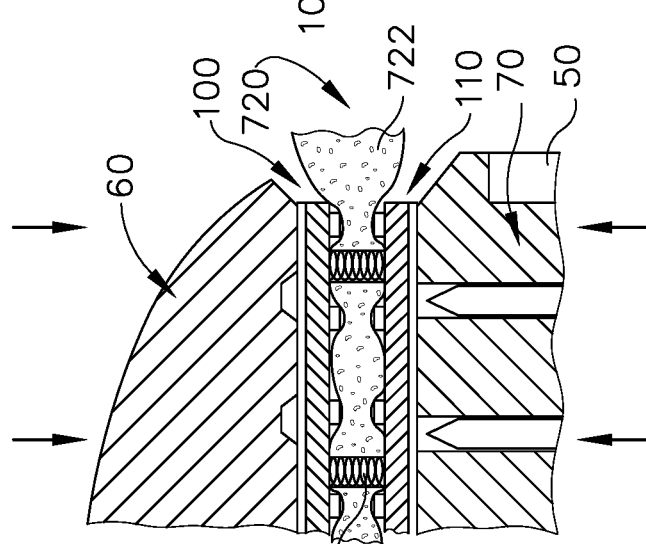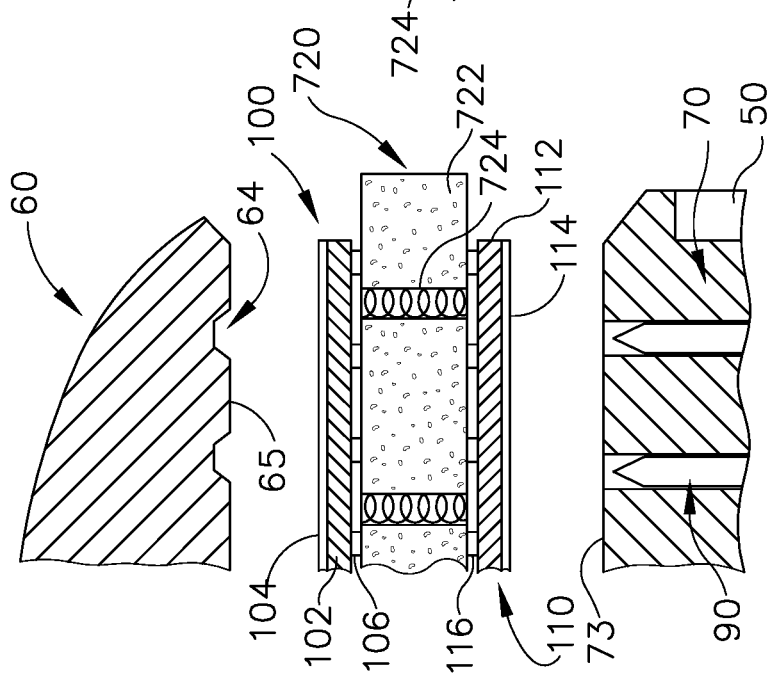

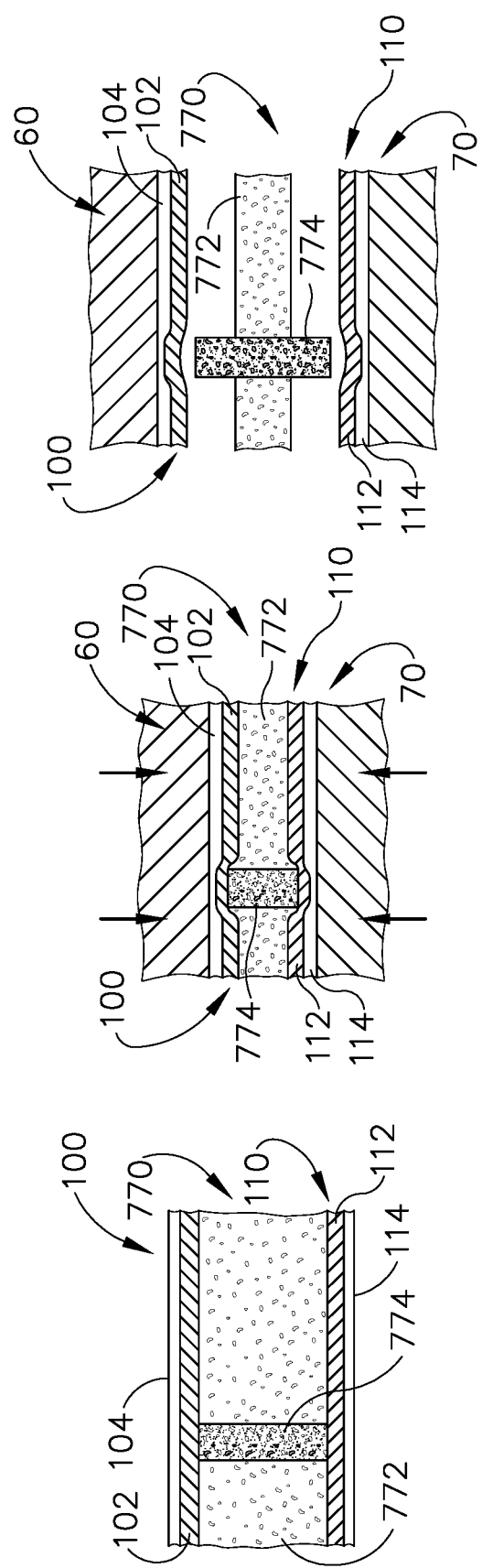

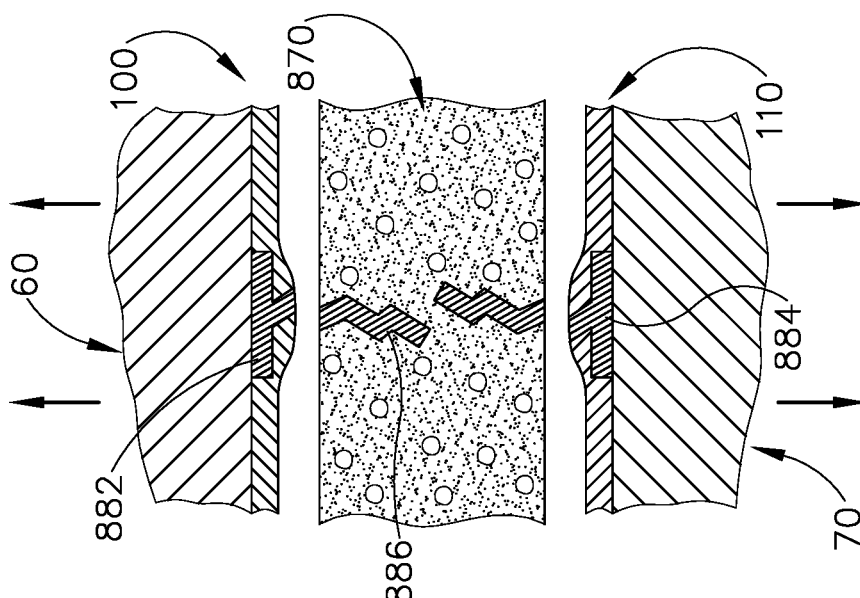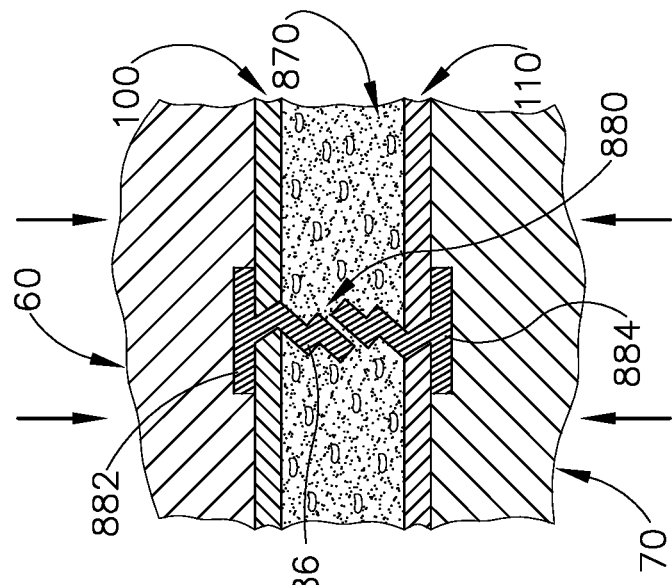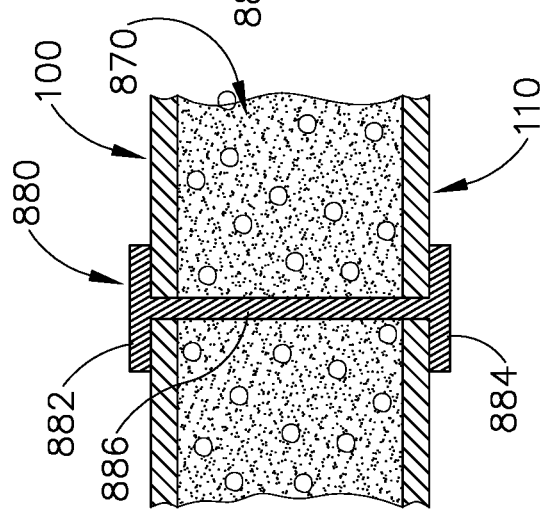

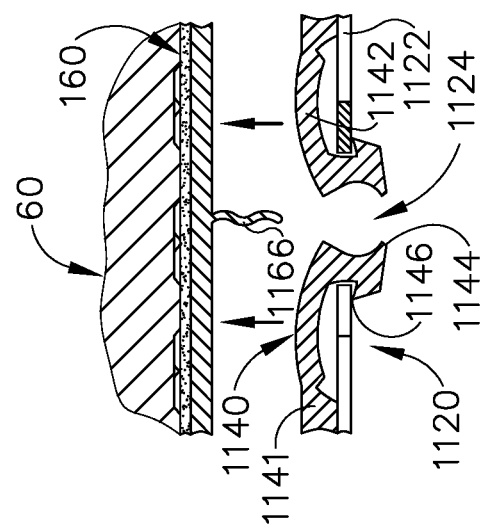
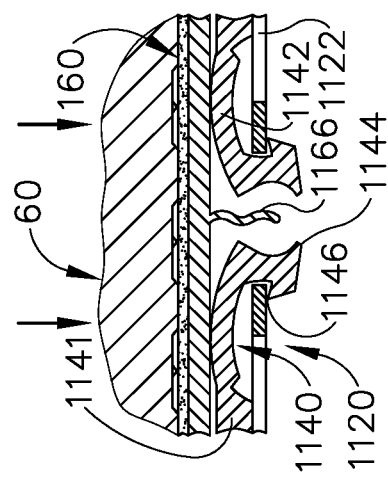
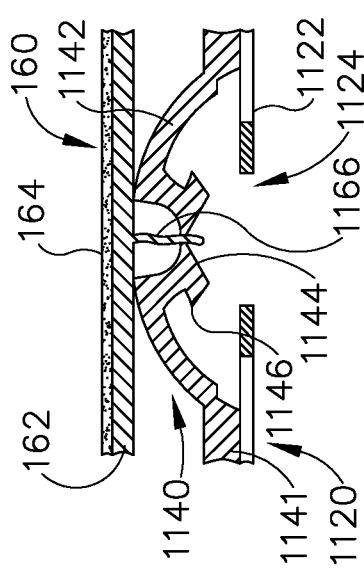
Fig.58C
Fig.58B
Fig.58A

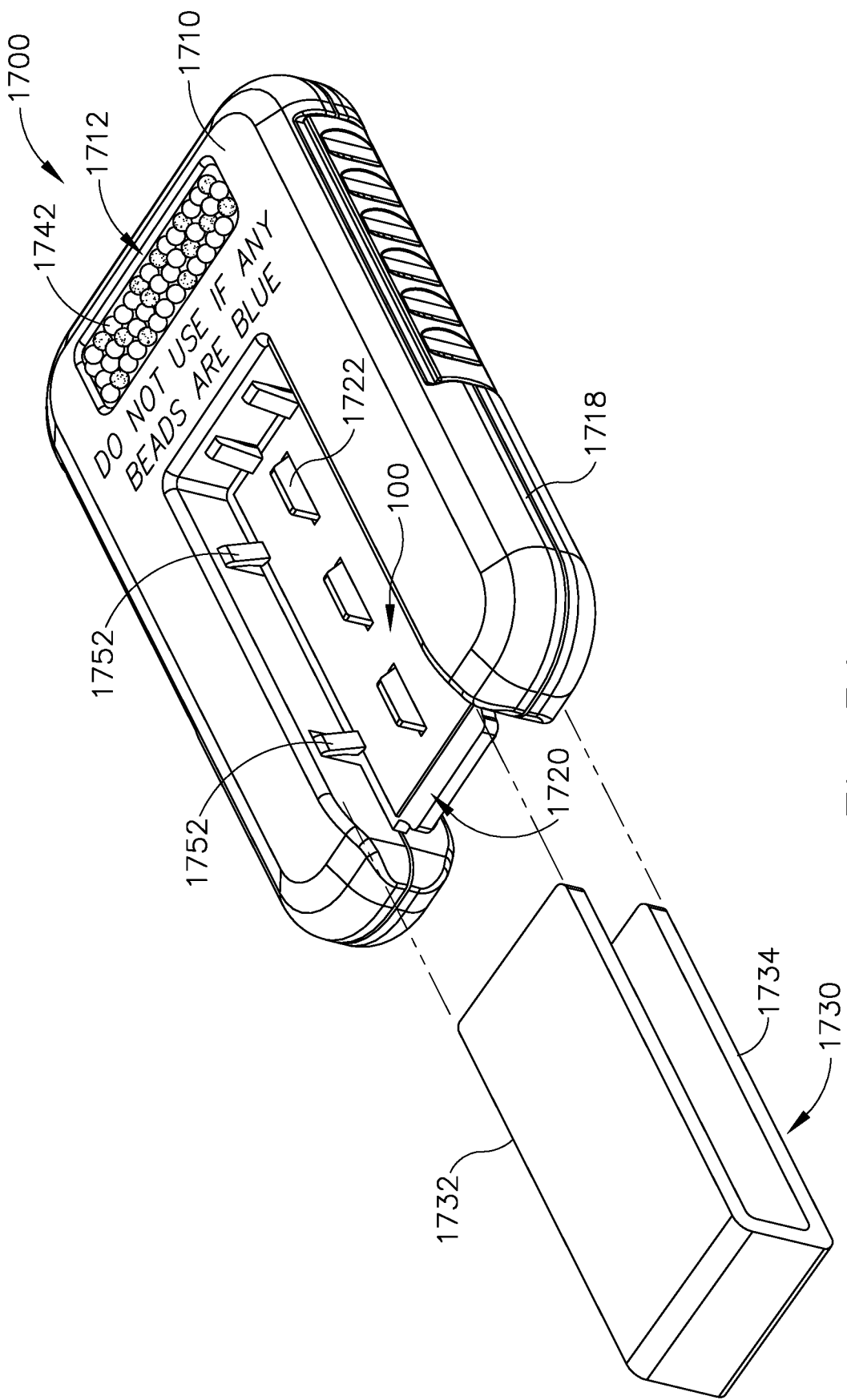

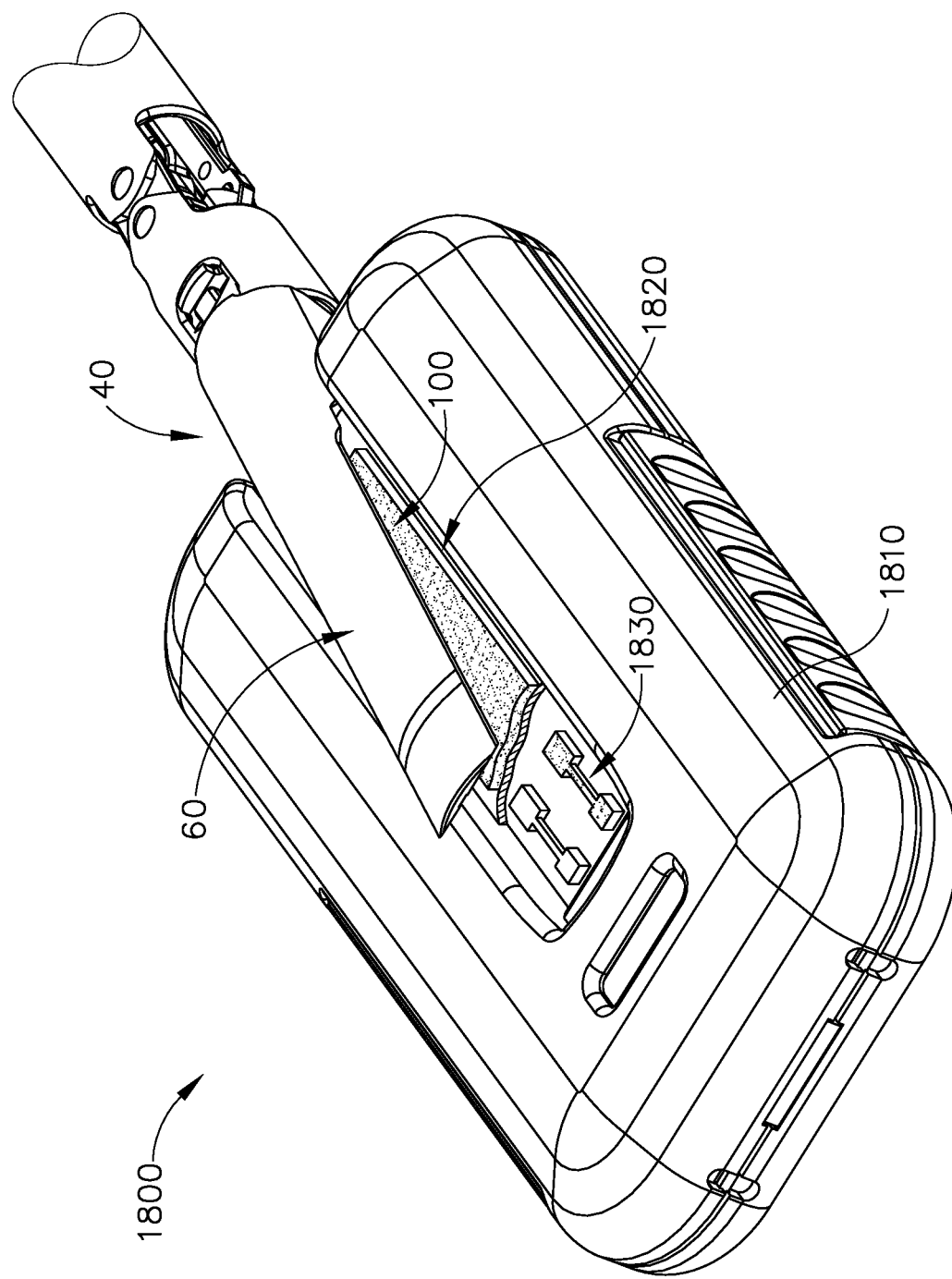

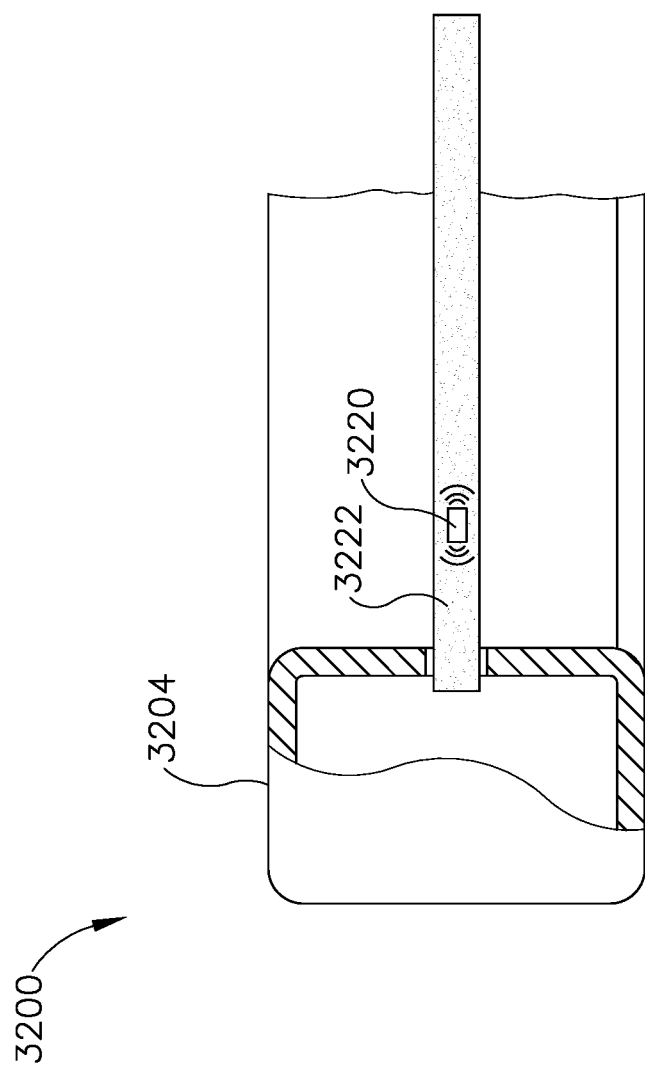

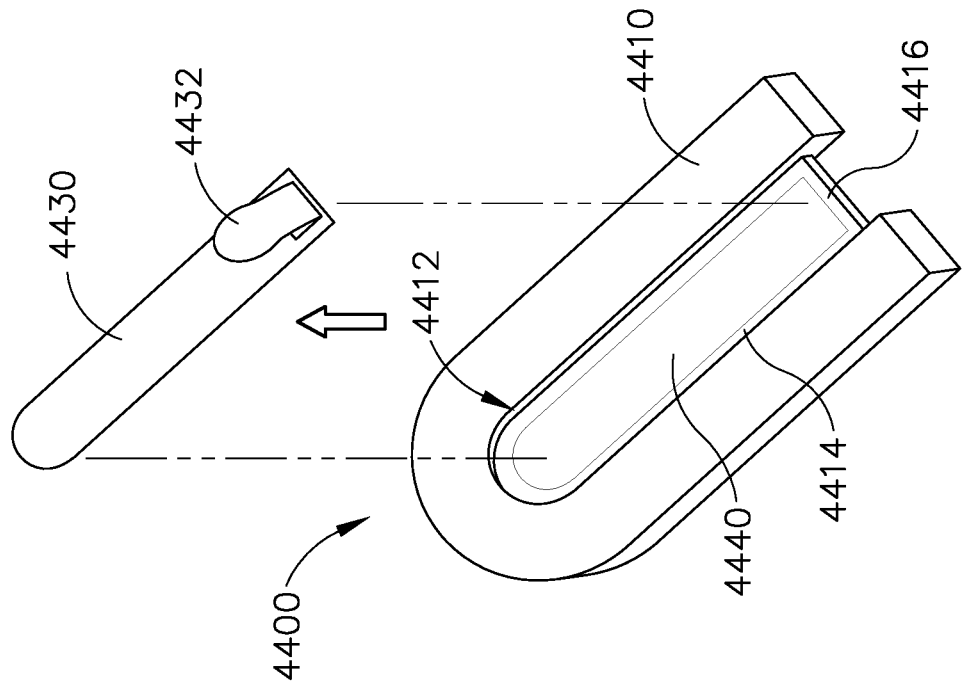
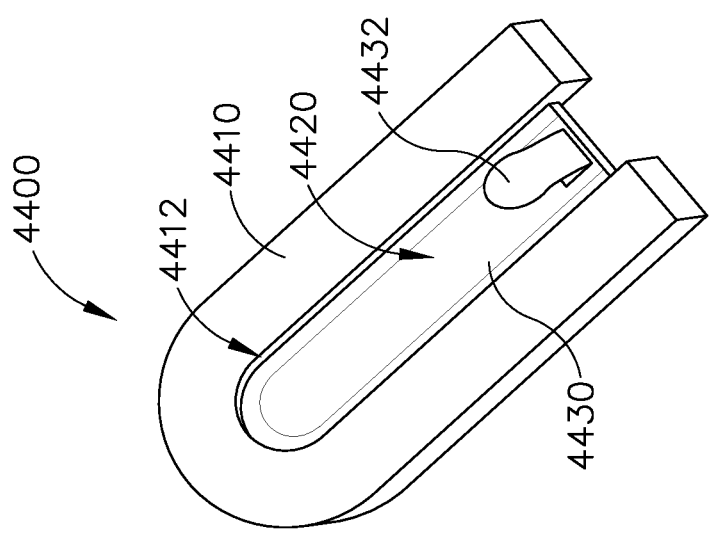
Fig.86B
Fig.86A

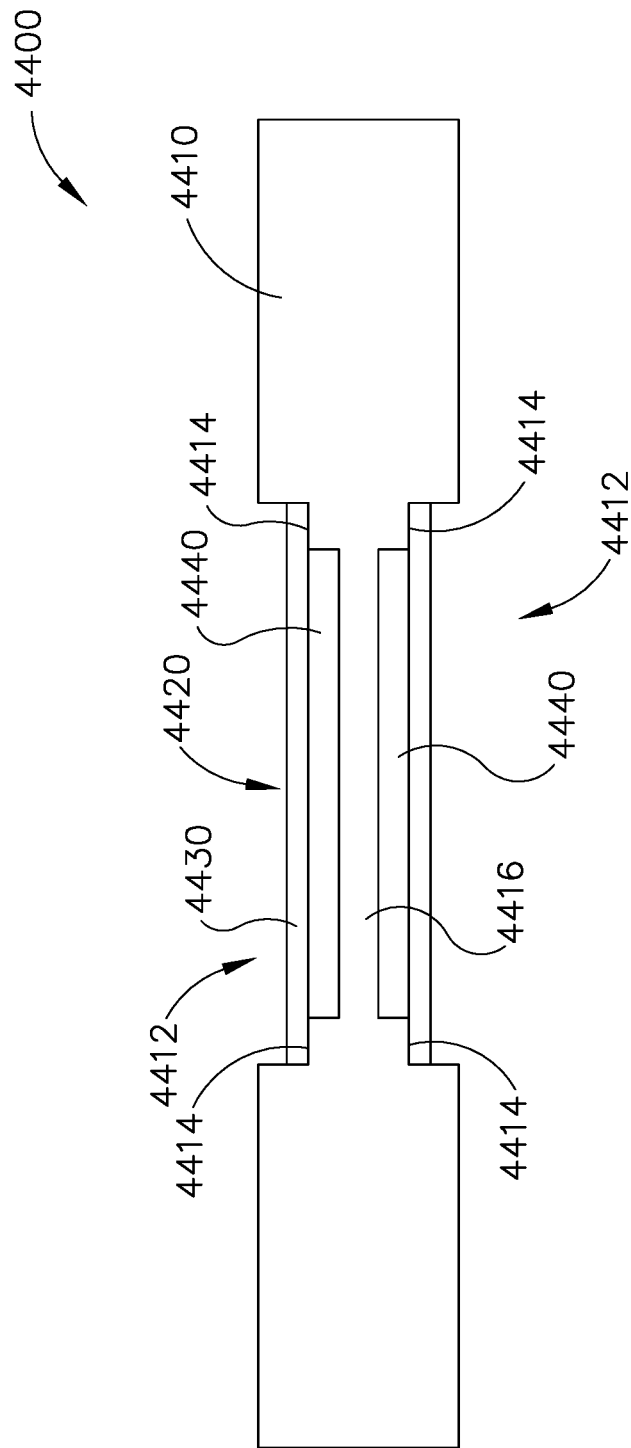

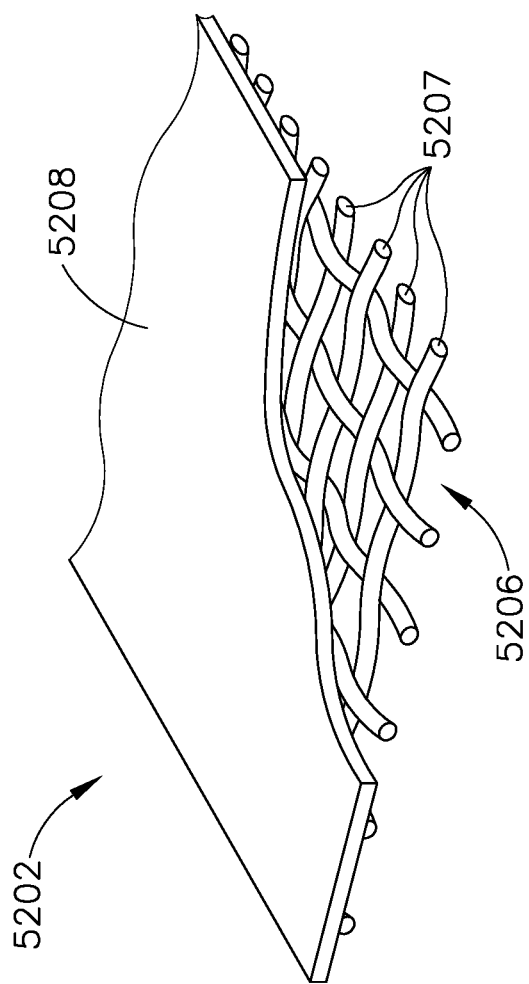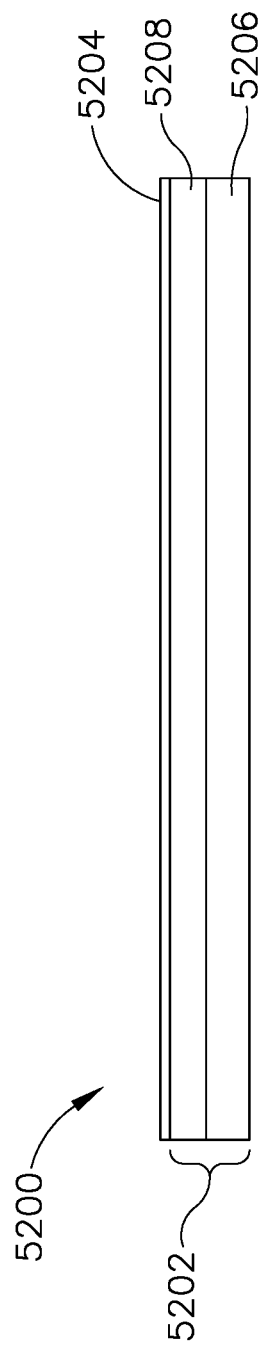
Fig.90
Fig.91

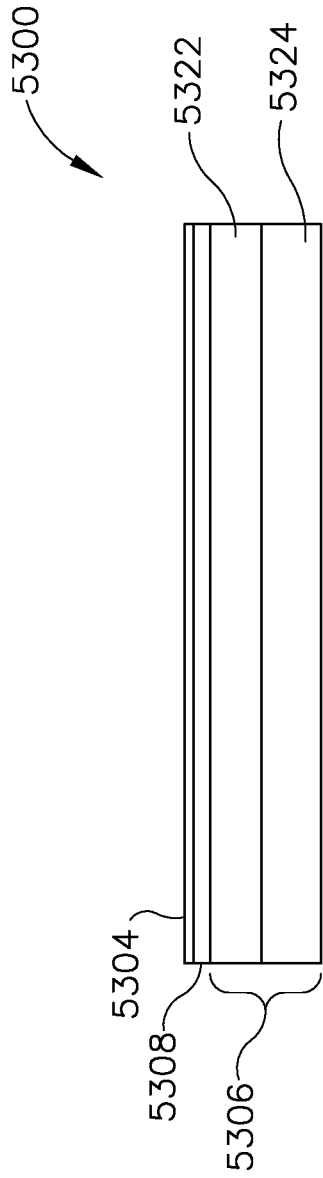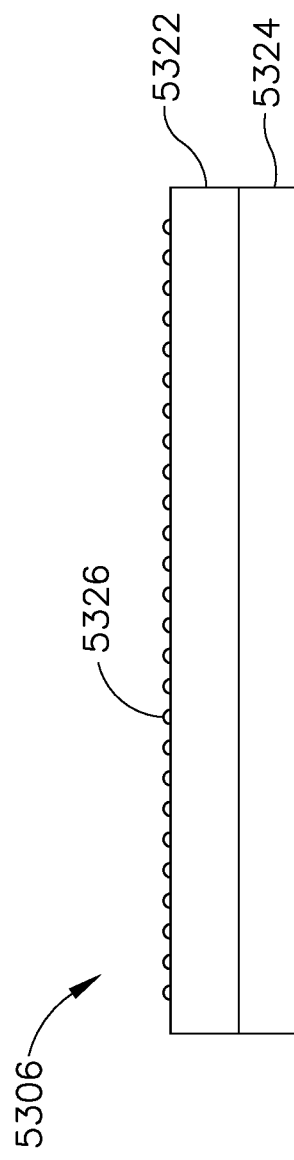

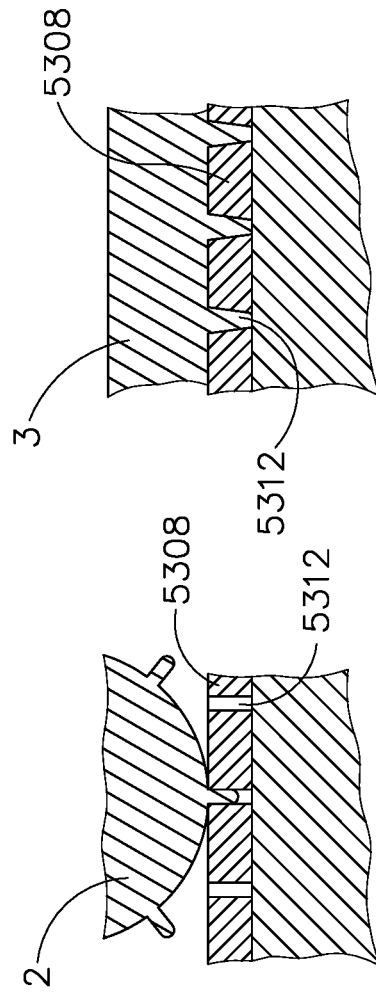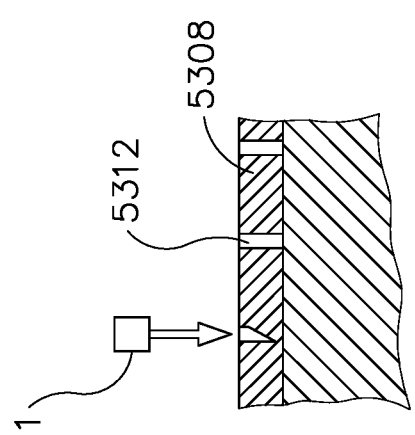
Fig.101 Fig.100 Fig.99

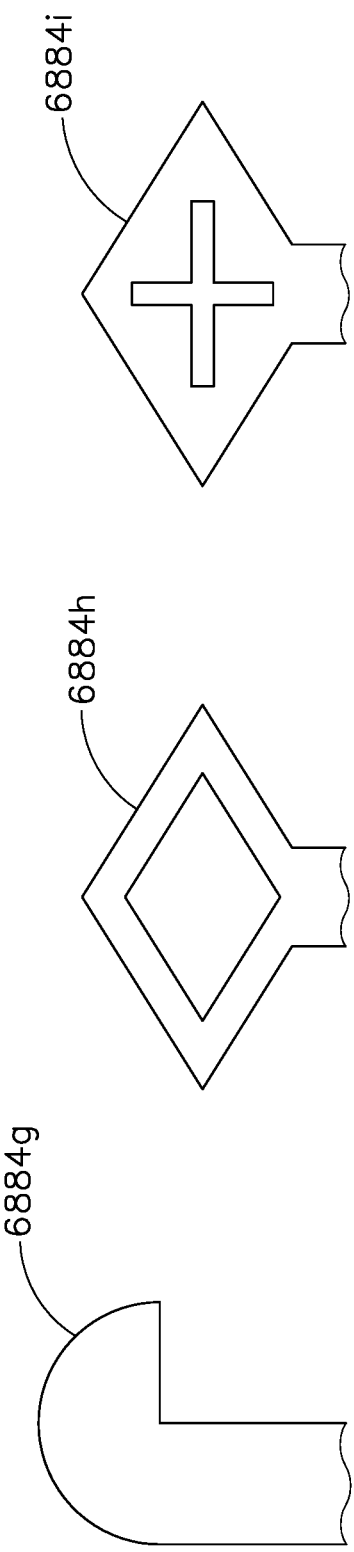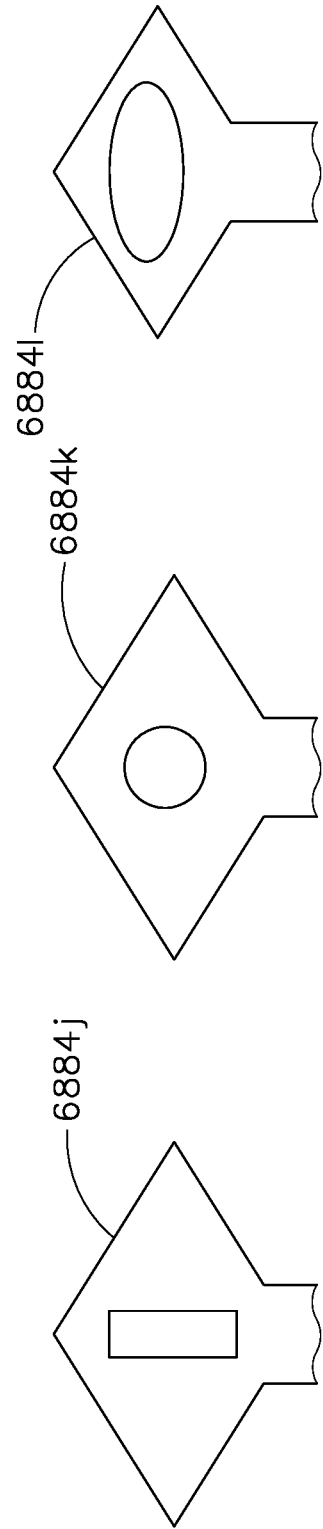

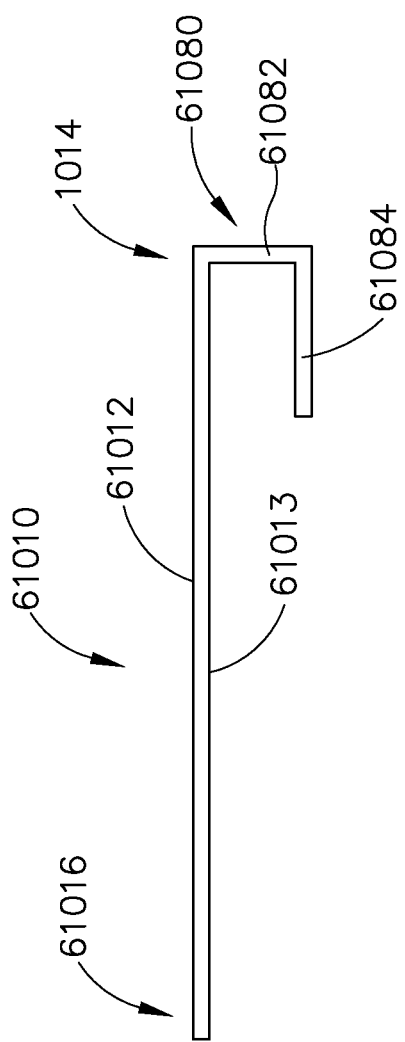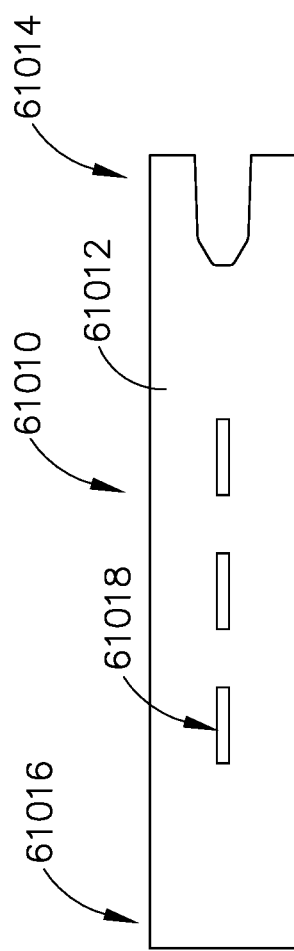

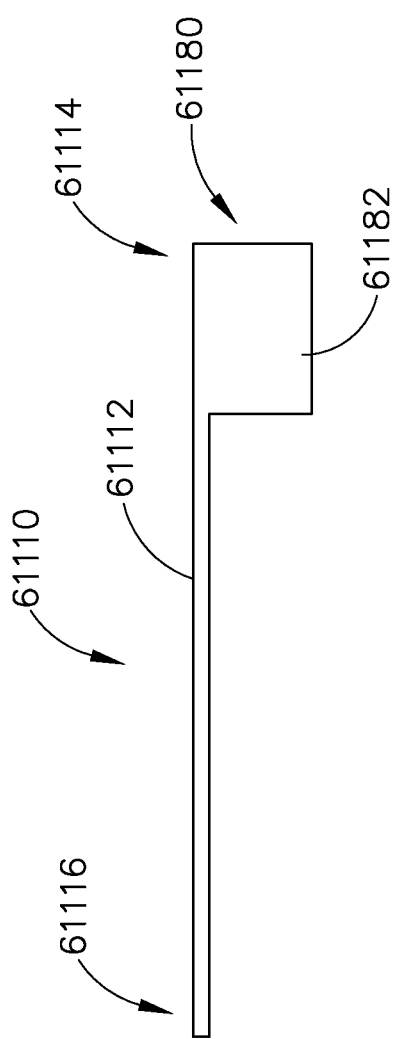
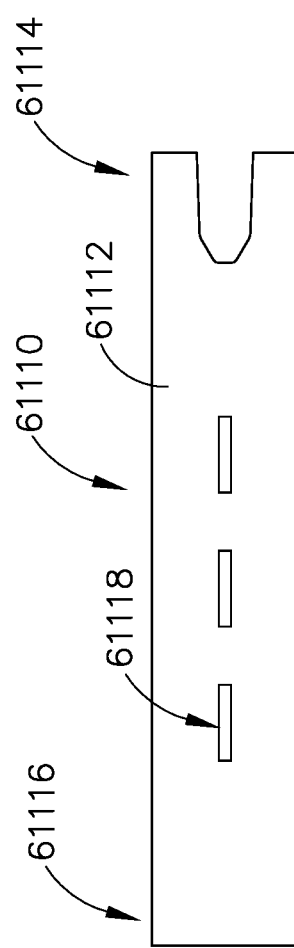

METHOD OF APPLYING A BUTTRESS TO A SURGICAL STAPLER AND EFFECTOR

PRIORITY

This application is a continuation of U.S. patent application Ser. No. 16/191,722, filed Nov. 15, 2018, issued as U.S. Pat. No. 11,051,806 on Jul. 6, 2021, which is a continuation of U.S. patent application Ser. No. 14/926,764, filed Oct. 29, 2015 and issued as U.S. Pat. No. 10,166,023 on Jan. 1, 2019, which claims priority to U.S. Patent App. No. 62/209,041, entitled "Method and Apparatus for Applying a Buttress to End Effector of a Surgical Stapler," filed Aug. 24, 2015, the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014, now U.S. Pat. No. 9,186,142, issued Nov. 17, 2015; U.S. Patent Pub. No. 2014/0239041, entitled "Lockout Feature for Movable Cutting Member of Surgical Instrument," published Aug. 28, 2014, now U.S. Pat. No. 9,717,497, issued Aug. 1, 2017; U.S. Patent Pub. No. 2014/0239042, entitled "Integrated Tissue Positioning and Jaw Alignment Features for Surgical Stapler," published Aug. 28, 2014, now U.S. Pat. No. 9,517,065, issued Dec. 13, 2017; U.S. Patent Pub. No. 2014/0239036, entitled "Jaw Closure Feature for End Effector of Surgical Instrument," published Aug. 28, 2014, now U.S. Pat. No. 9,839,421, issued Dec. 12, 2017; U.S. Patent Pub. No. 2014/0239040, entitled "Surgical Instrument with Articulation Lock having a Detenting Binary Spring," published Aug. 28, 2014, now U.S. Pat. No. 9,867,615, issued Jan. 16, 2018; U.S. Patent Pub. No. 2014/0239043, entitled "Distal Tip Features for End Effector of Surgical Instrument," published Aug. 28, 2014 now U.S. Pat. No. 9,622,746, issued Apr. 18, 2017; U.S. Patent Pub. No. 2014/0239037, entitled "Staple Forming Features for Surgical Stapling Instrument," published Aug. 28, 2014, now U.S. Pat. No. 10,092,292, issued Oct. 9, 2018; U.S. Patent Pub. No. 2014/0239038, entitled "Surgical Instrument with Multi-Diameter Shaft," published Aug. 28, 2014, now U.S. Pat. No. 9,795,379, issued Oct. 24, 2017; and U.S. Patent Pub. No. 2014/0239044, entitled "Installation Features for Surgical Instrument End Effector Cartridge," published Aug. 28, 2014, now U.S. Pat. No. 9,808,248, issued Nov. 7, 2017.

The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014, now U.S. Pat. No. 9,597,082, issued Mar. 21, 2017; U.S. Pub. No. 2014/0246473, entitled "Rotary Powered Surgical Instruments with Multiple Degrees of Freedom," published Sep. 4, 2014, now U.S. Pat. No. 9,398,911, issued Jul. 26, 2016; U.S. Pub. No. 2013/0206813, entitled "Linear Stapler," published Aug. 15, 2013, abandoned May 5, 2016; U.S. Pub. No. 2008/0169328, entitled "Buttress Material for Use with a Surgical Stapler," published Jul. 17, 2008, abandoned Oct. 5, 2011; U.S. patent application Ser. No. 14/300,804, entitled "Woven and Fibrous Materials for Reinforcing a Staple Line," filed Jun. 10, 2014, now U.S. Pat. No. 9,848,871, issued Dec. 26, 2017; U.S. patent application Ser. No. 14/300,811, entitled "Devices and Methods for Sealing Staples in Tissue", now U.S. Pat. No. 9,936,954, issued Apr. 10, 2018; and U.S. patent application Ser. No. 14/498,070, entitled "Radically Expandable Staple Line" filed Sep. 26, 2014, now U.S. Pub. No. 2016/0089146, published Mar. 31, 2016, issued as U.S. Pat. No. 10,426,476 on Oct. 1, 2019. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 26A depicts a partial, cross-sectional end view of another exemplary buttress applier cartridge positioned in the end effector of FIG. 2, with the end effector in a partially open configuration, and with ratcheting retention arms of the buttress applier cartridge in a buttress engaging configuration;

FIG. 26B depicts a partial, cross-sectional end view of the buttress applier cartridge of FIG. 26A positioned in the end effector of FIG. 2, with the end effector in a closed configuration, thereby driving the ratcheting retention arms to a buttress disengaging configuration;

FIG. 26C depicts a partial, cross-sectional end view of the buttress applier cartridge of FIG. 26A positioned in the end effector of FIG. 2, with the end effector in an open configuration, with the buttress assembly adhered to the end effector, and with the retention arms remaining in the buttress disengaging configuration;

FIG. 27A depicts a partial, cross-sectional detail view of a ratcheting retention arm of the buttress applier cartridge of FIG. 26A in the buttress engaging configuration;

FIG. 27B depicts a partial, cross-sectional detail view of a ratcheting retention arm of the buttress applier cartridge of FIG. 26A in the buttress disengaging configuration;

FIG. 32A depicts a cross-sectional side view of the staple cartridge of FIG. 30, with a wedge sled in a proximal position;

FIG. 32B depicts a cross-sectional side view of the staple cartridge of FIG. 30, with the wedge sled in a distal position;

FIG. 48A depicts a partial, cross-sectional end view of a buttress assembly disposed on a platform of the buttress applier cartridge of FIG. 47, with the buttress assembly and platform positioned in the end effector of FIG. 2, and with the end effector in an open configuration;

FIG. 48B depicts a partial, cross-sectional end view of the buttress assembly and platform of FIG. 48A, with the end effector in a closed configuration;

FIG. 48C depicts a partial, cross-sectional end view of the buttress assembly and anvil of FIG. 48A, with the end effector in an open configuration, and with an upper portion of the buttress assembly adhered to the anvil and a lower portion of the buttress assembly adhered to the deck of the staple cartridge;

FIG. 49A depicts a partial, cross-sectional end view of a buttress assembly disposed on an exemplary variation of the platform of FIG. 48A;

FIG. 49B depicts a partial, cross-sectional end view of the buttress assembly and platform of FIG. 49A, with the buttress assembly and platform positioned in the end effector of FIG. 2, and with the end effector in a closed configuration;

FIG. 49C depicts a partial, cross-sectional end view of the buttress assembly and anvil of FIG. 49A, with the end effector in an open configuration, and with an upper portion of the buttress assembly adhered to the anvil and a lower portion of the buttress assembly adhered to the deck of the staple cartridge;

FIG. 56A depicts a partial, cross-sectional end view of a platform and buttress assembly of another exemplary alternative buttress applier cartridge, with a retention post assembly in an intact state;

FIG. 56B depicts a partial, cross-sectional end view of the platform and buttress assembly of FIG. 56A, with the end effector of FIG. 2 compressing the platform and buttress assembly, thereby transitioning the retention post assembly to a fractured state;

FIG. 56C depicts a partial, cross-sectional end view of the platform and buttress assembly of FIG. 56A, with the end effector in an open configuration, with the buttress assembly adhered to the end effector, and with a portion of the retention post assembly remaining in a fractured state in the platform;

FIG. 58A depicts a partial, cross-sectional detail view of a retention feature of the buttress applier cartridge of FIG. 57, with the retention feature securing a buttress assembly to the buttress applier cartridge;

FIG. 58B depicts a partial, cross-sectional detail view of the anvil of the end effector of FIG. 2 compressing the buttress assembly against the retention feature, thereby deflecting the retention feature;

FIG. 58C depicts a partial, cross-sectional detail view of the anvil of the end effector of FIG. 2 with the buttress assembly adhered thereto, spaced away from the retention feature, with the retention feature remaining in the deflected state;

FIG. 59 depicts a perspective view of another exemplary alternative buttress applier cartridge;

FIG. 65 depicts a perspective view of another exemplary alternative buttress applier cartridge, with a portion of the buttress applier cartridge cut away to reveal internal components, and with a platform positioned in the end effector of FIG. 2 while the end effector is in an open configuration;

FIG. 79C depicts a cross-sectional side view of the buttress applier cartridge of FIG. 73, with the upper and lower buttress assemblies having been removed by the end effector of FIG. 75;

FIG. 84 depicts a perspective view of an exemplary alternative buttress assembly with an integral protective film;

FIG. 85 depicts a cross-sectional end view of the buttress assembly of FIG. 84;

FIG. 86A depicts a perspective view of an exemplary adhesive applier cartridge, with a protective film secured to the cartridge;

FIG. 86B depicts a perspective view of the cartridge of FIG. 86A, with the protective film removed;

FIG. 87 depicts a cross-sectional end view of the cartridge of FIG. 86A;

FIG. 88 depicts a perspective view of the upper buttress and the lower buttress of FIG. 4 applied to the end effector of FIG. 2;

FIG. 89 depicts a perspective view of the upper buttress and the lower buttress of FIG. 4 applied to the end effector of FIG. 2 with a gap on the upper buttress and the lower buttress for the longitudinally extending channels of the end effector;

FIG. 90 depicts a partial perspective view of an exemplary multilayer buttress body, with a portion of a layer broken away to reveal another layer;

FIG. 91 depicts a side view of the multilayer buttress body of FIG. 90 combined with an adhesive layer to form a multilayer buttress assembly configured for use with the end effector of FIG. 2;

FIG. 92 depicts a side elevational view of another exemplary multilayer buttress assembly configured for use with the end effector of FIG. 2;

FIG. 93 depicts a side elevational view of the multilayer buttress assembly of FIG. 92 without an adhesive layer and without a film layer;

FIG. 94A depicts a top plan view of the mesh layer of the multilayer buttress of FIG. 92 in a relaxed position;

Figure 1:
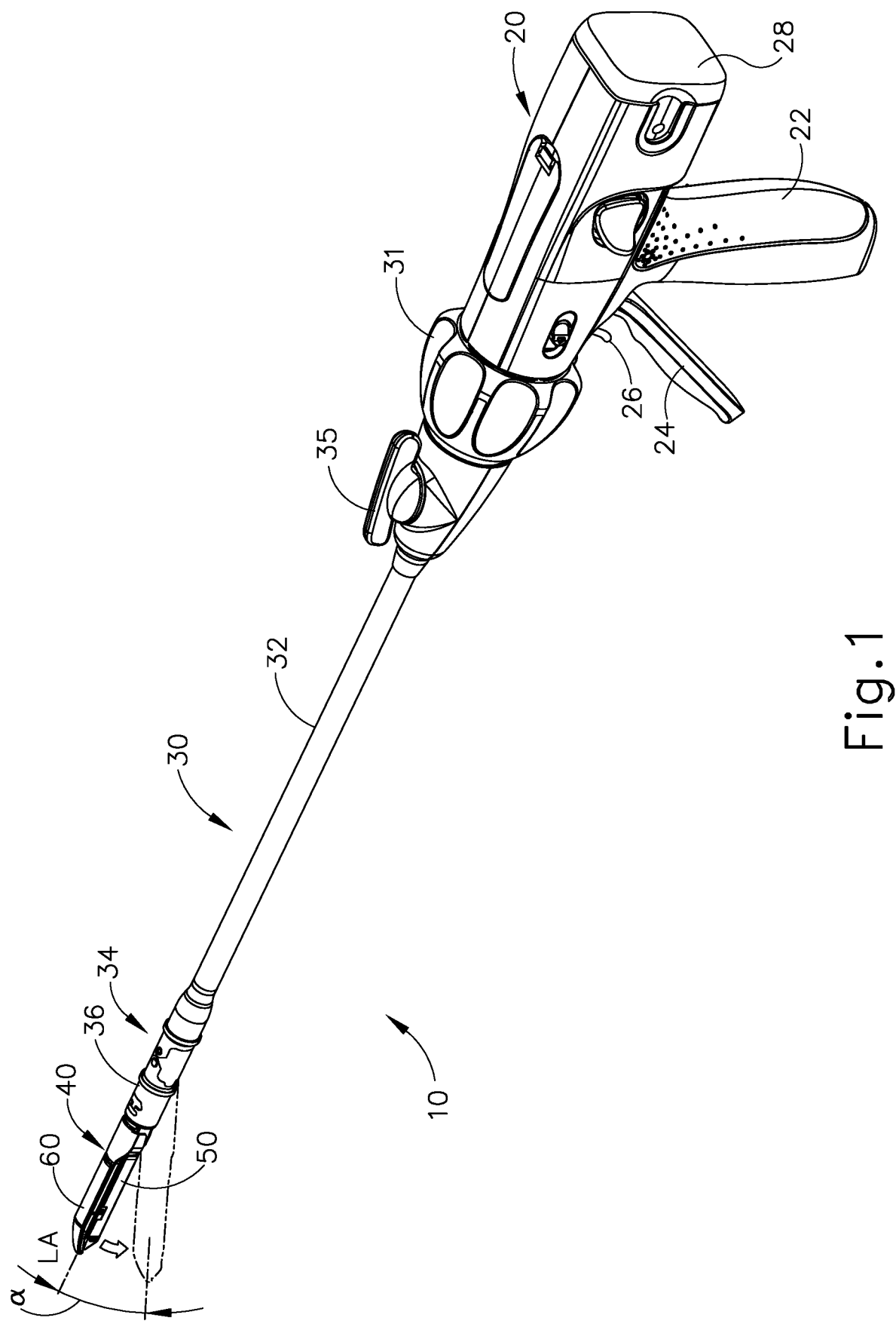
FIG. 1 depicts a perspective view of an exemplary articulating surgical stapling instrument.
Figure 2:
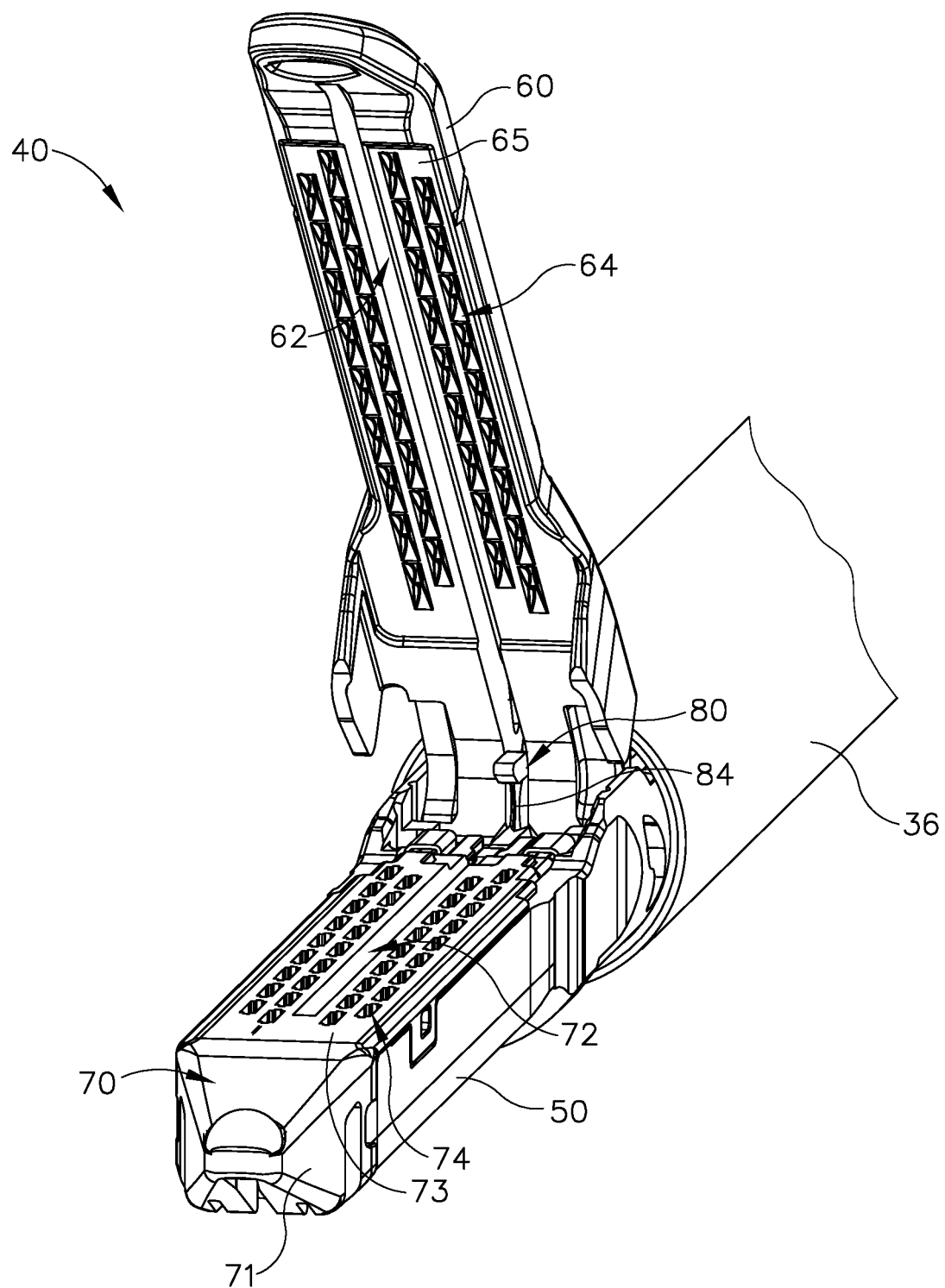
FIG. 2 depicts a perspective view of an end effector of the instrument of FIG. 1, with the end effector in an open configuration.
Figure 4:
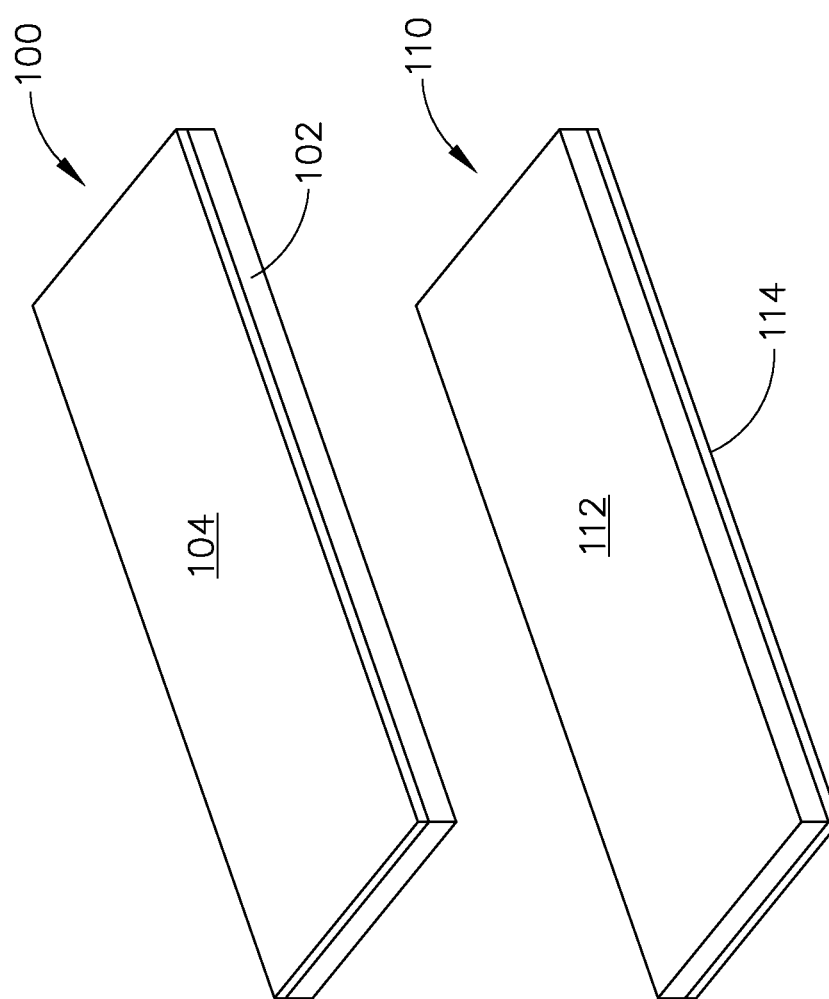
FIG. 4 depicts a perspective view of an exemplary upper buttress and an exemplary lower buttress, each of which may be applied to the end effector of FIG. 2.
Figure 94B:
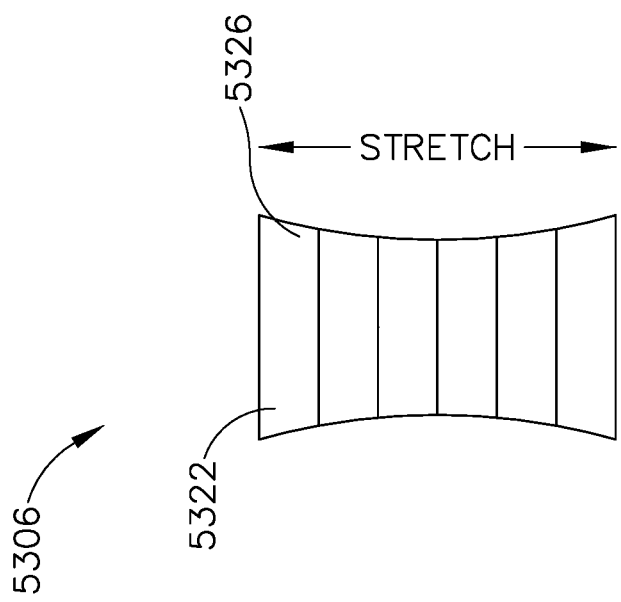
Figure 95B:
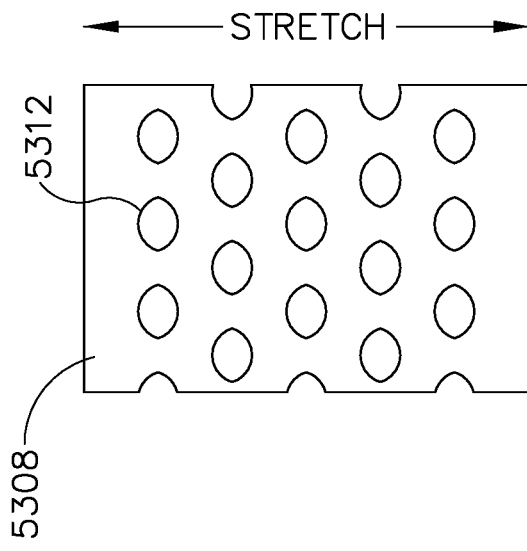
Figure 95A:
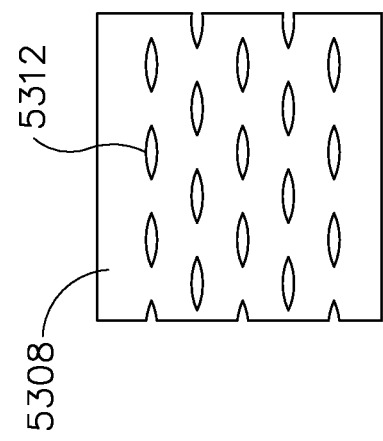
Figure 98:
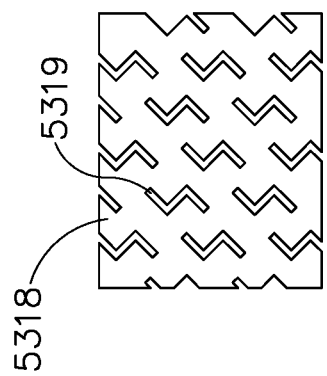
Figure 97:
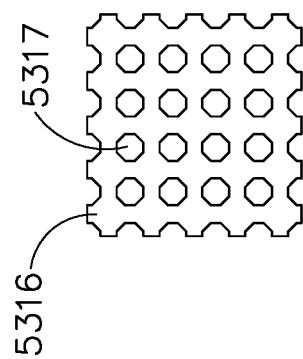
Figure 96:
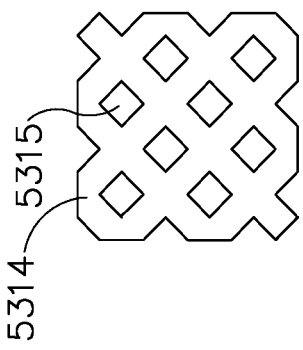
Figure 102:
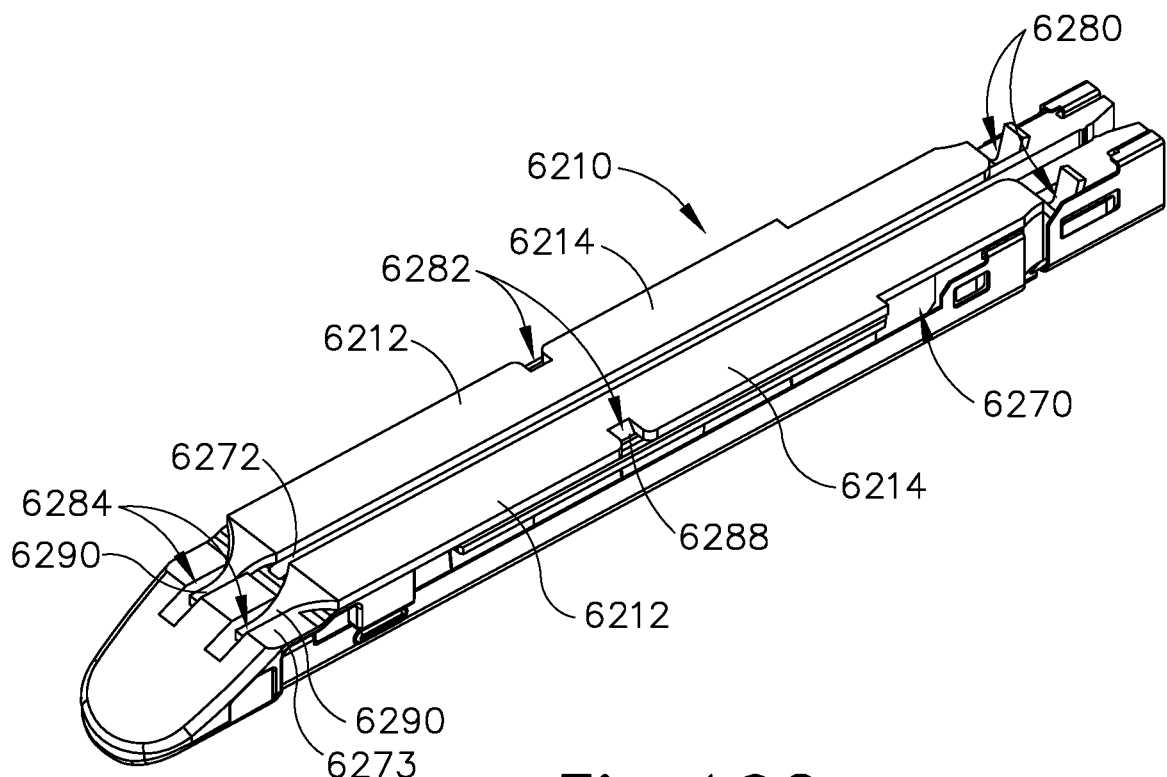
Figure 103:
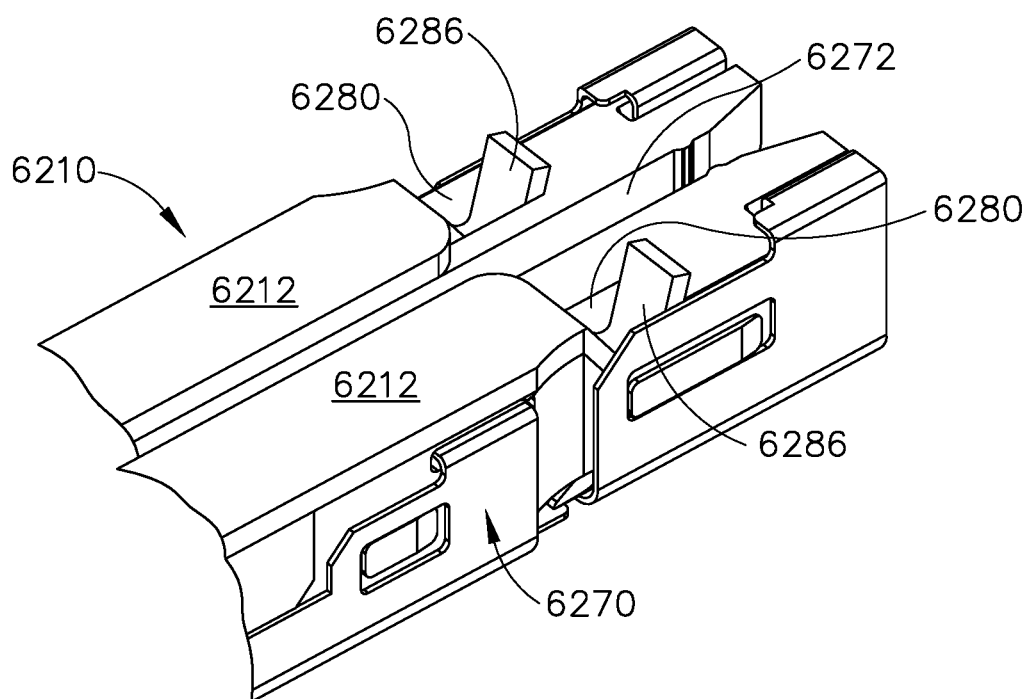
Figure 104A:
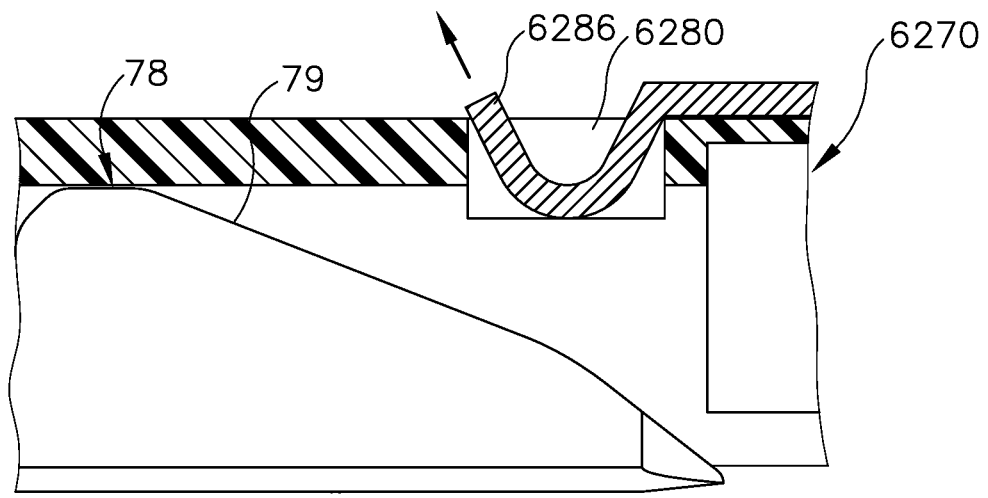
Figure 104B:
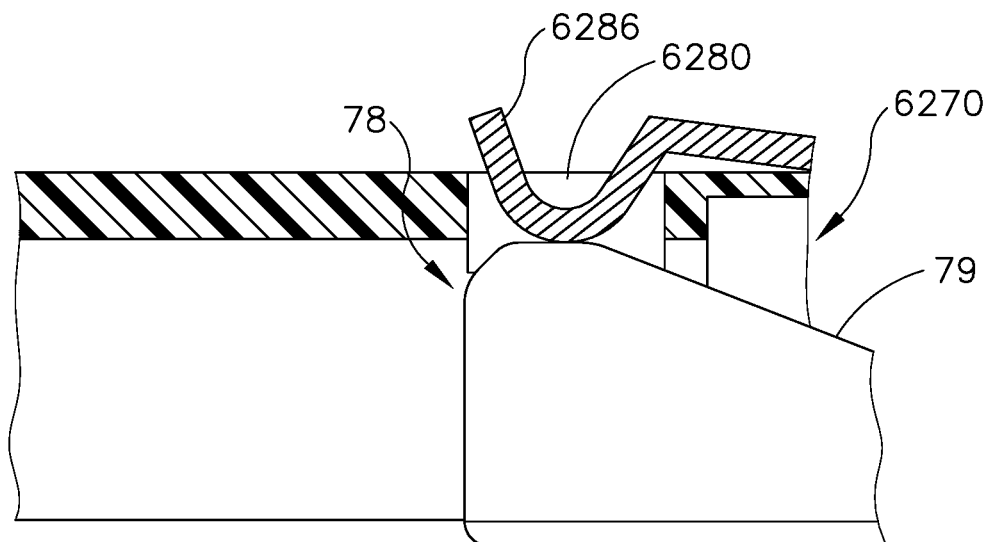
Figure 105:
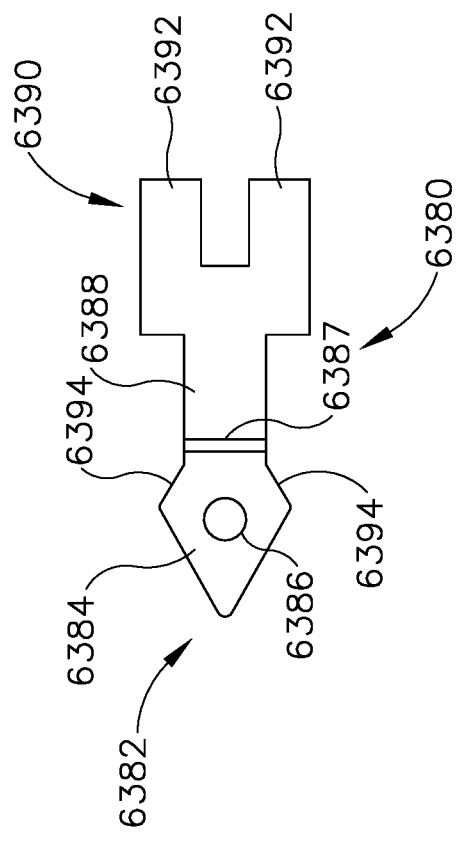
Figure 106:
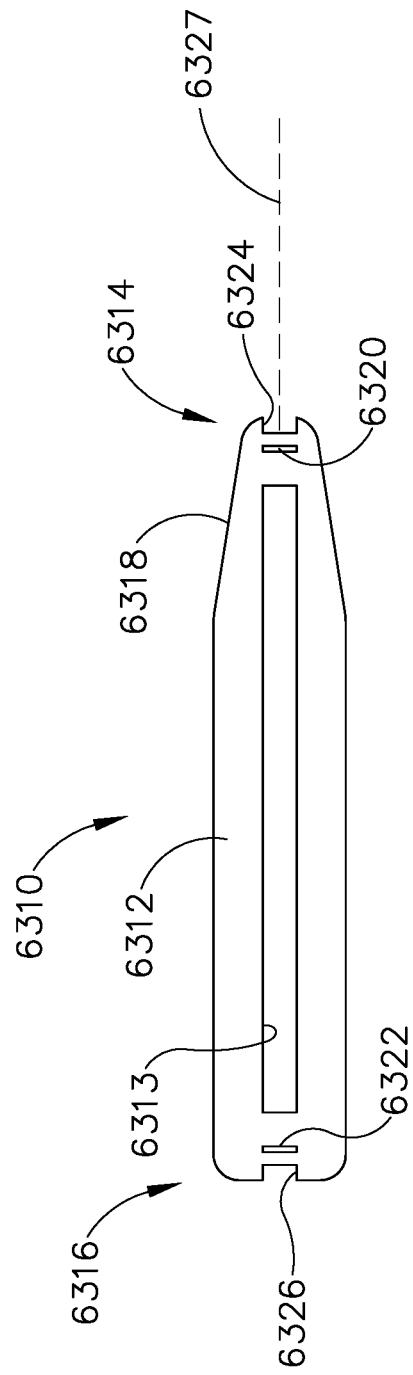
Figure 107:
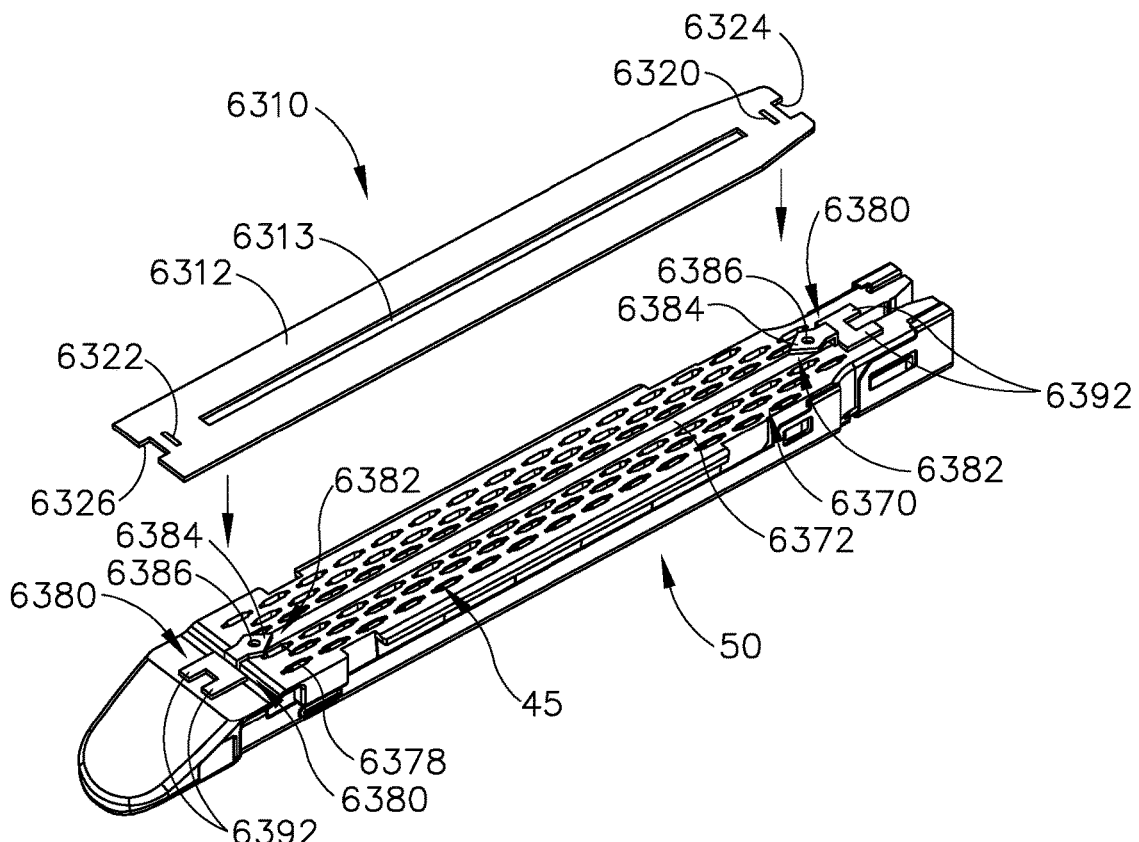
Figure 108:
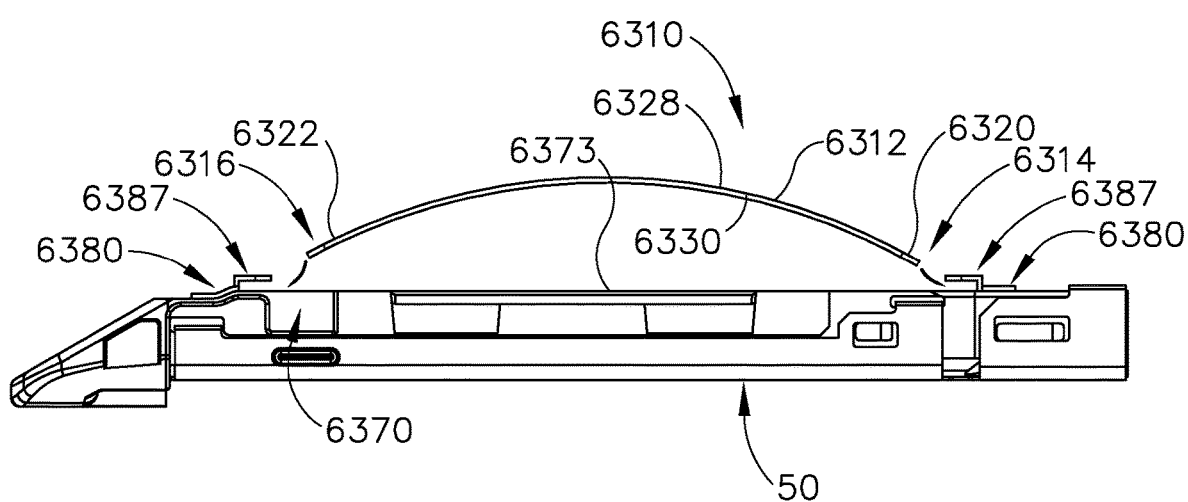
Figure 109:
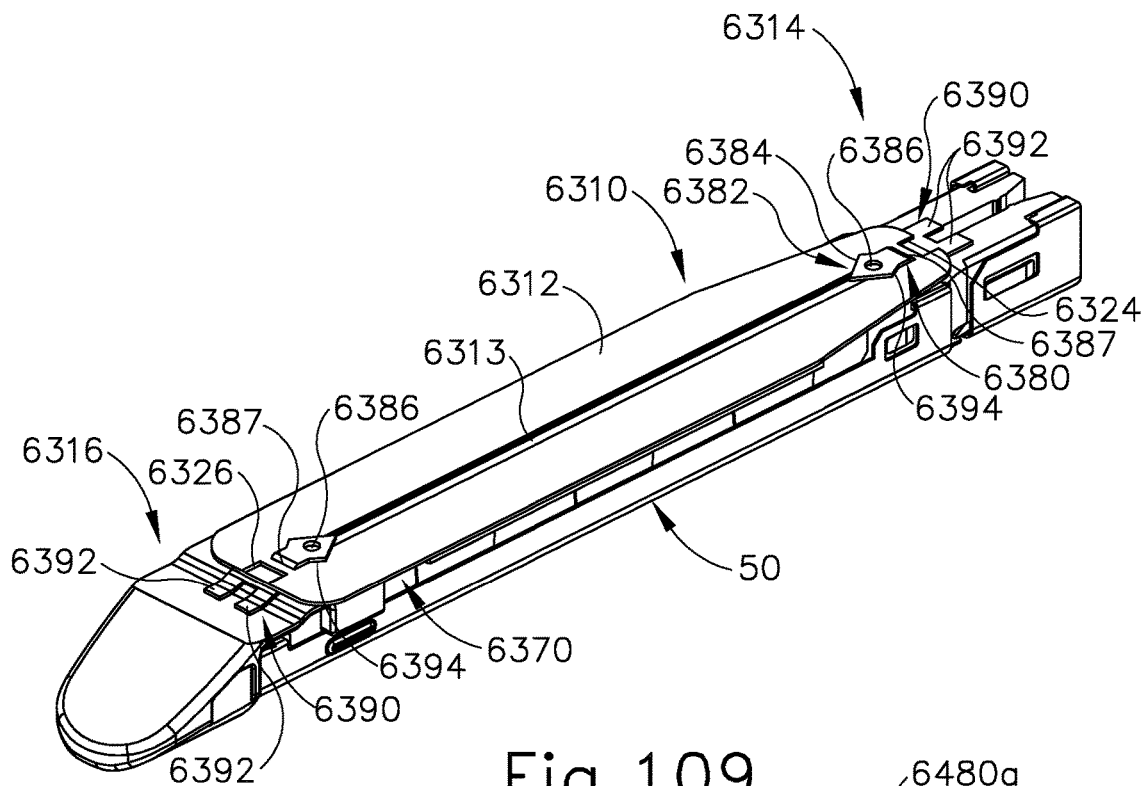
Figure 110:
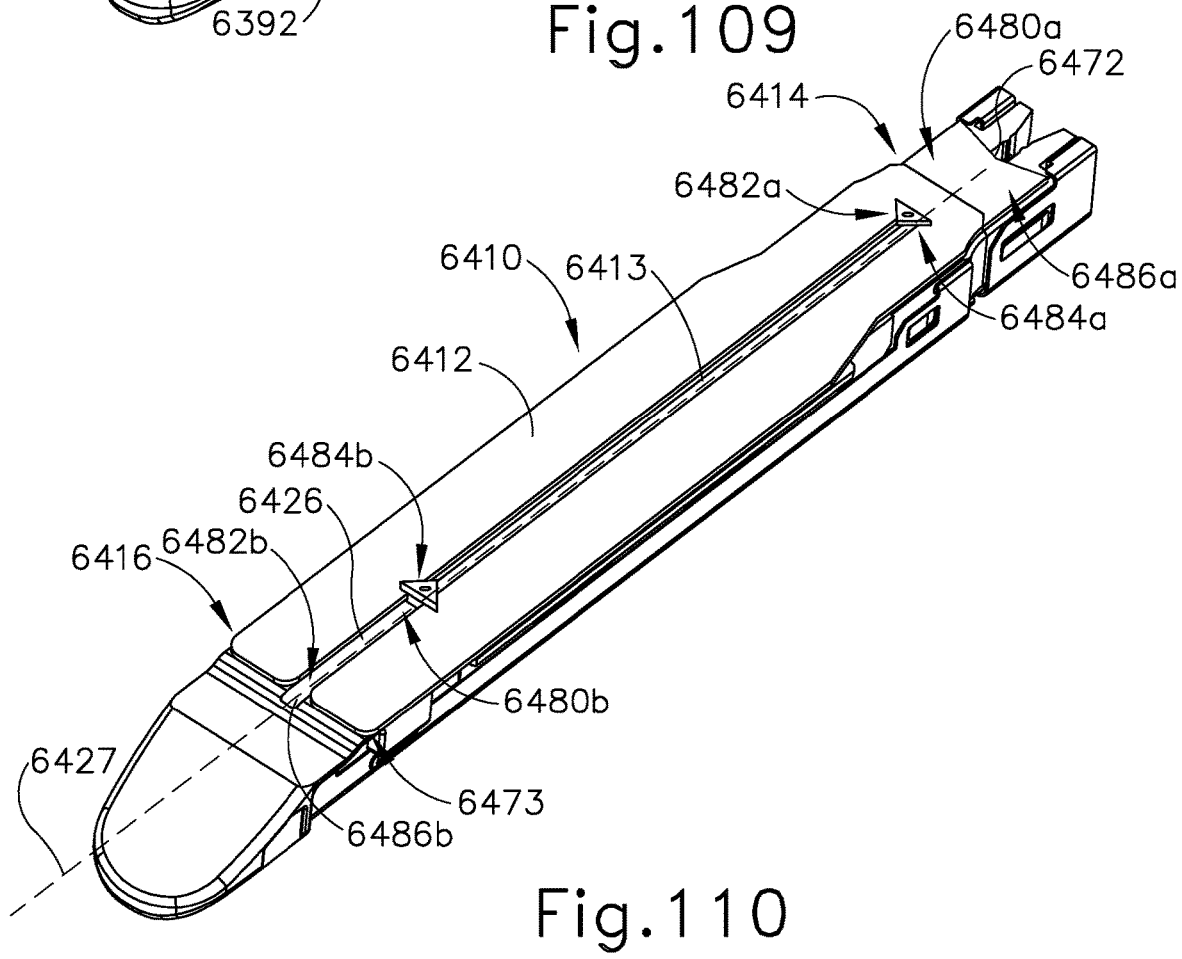
Figure 111:
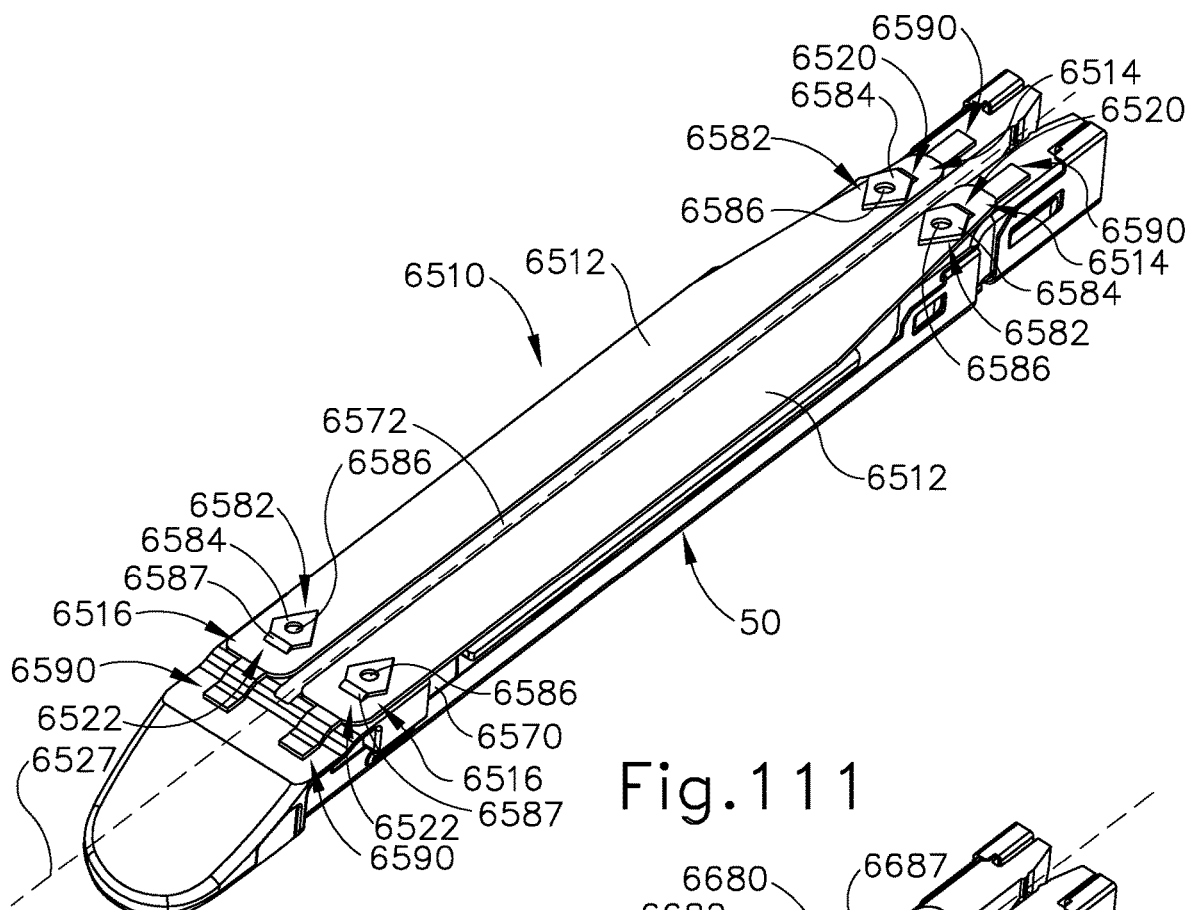
Figure 112:
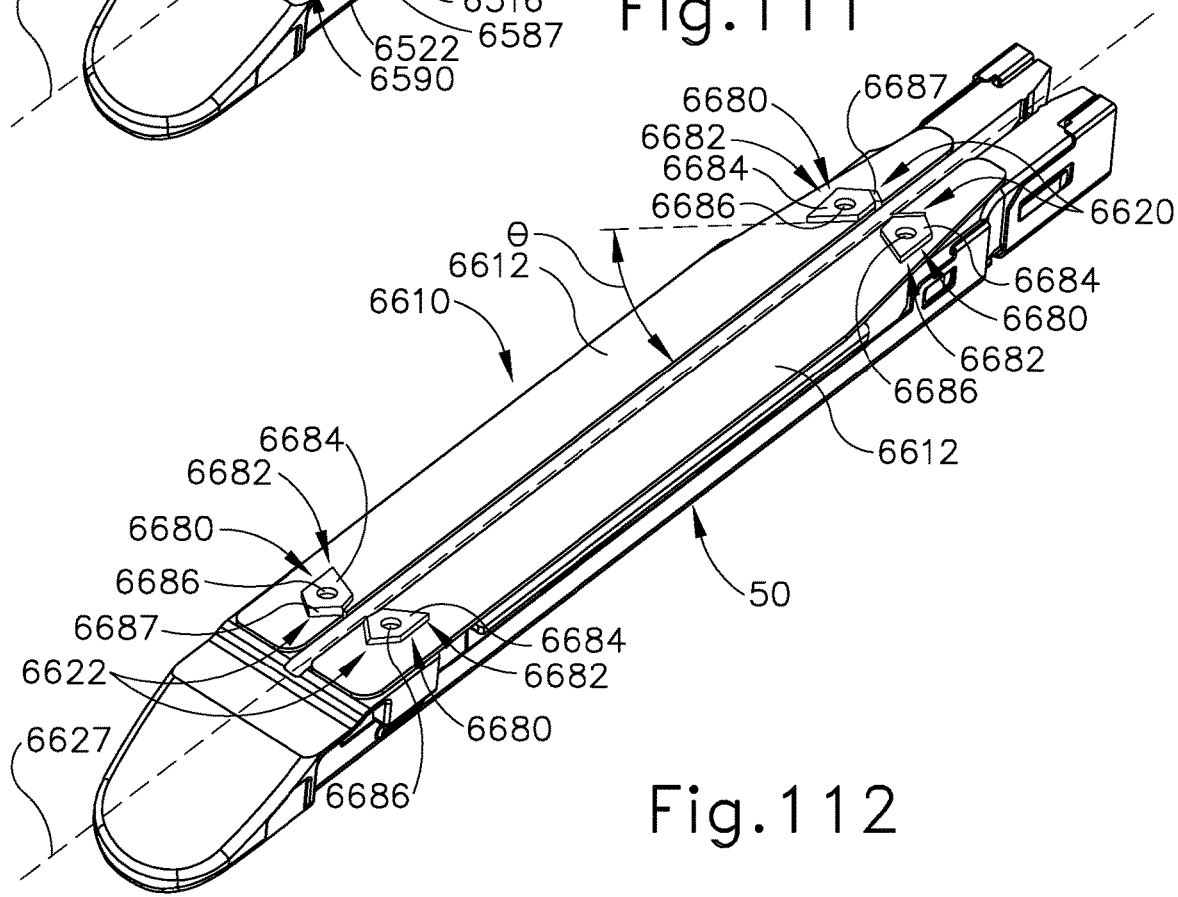
Figure 113:
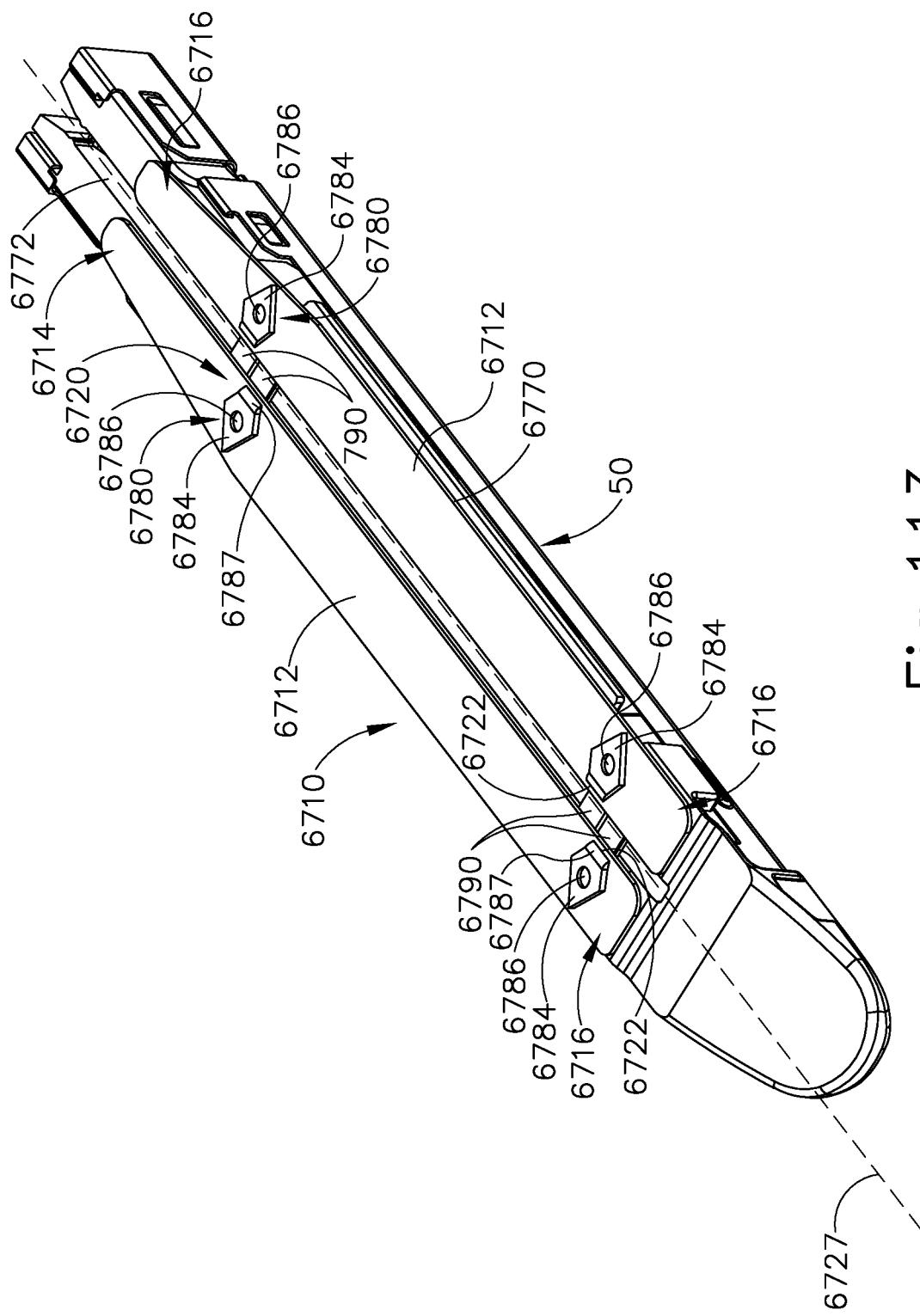
Figure 116:
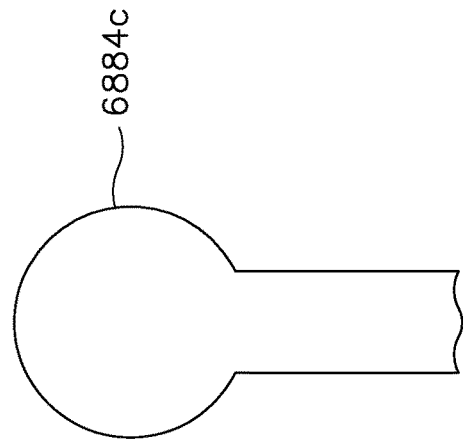
Figure 119:
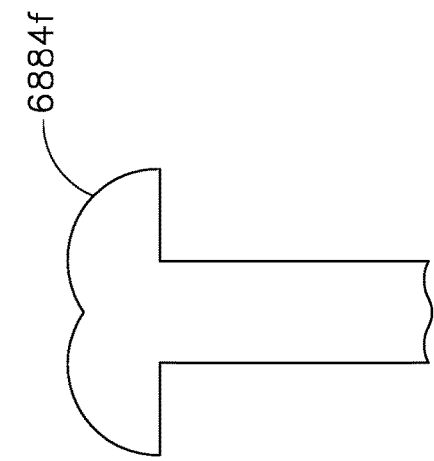
Figure 115:
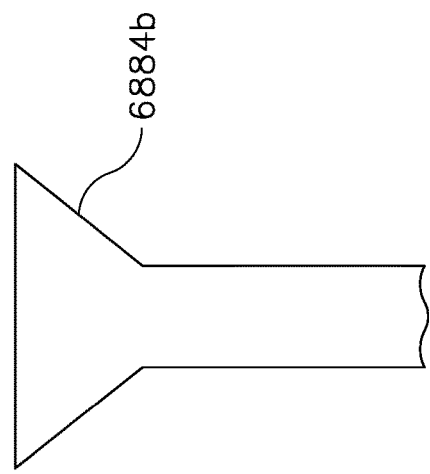
Figure 118:
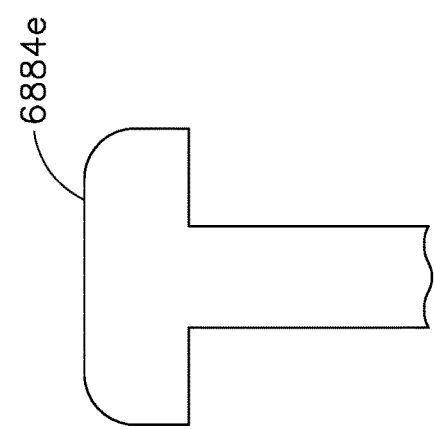
Figure 114:
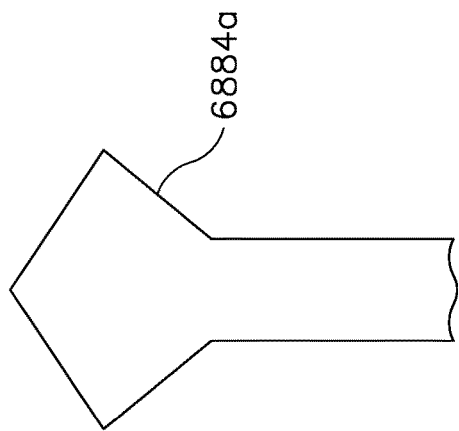
Figure 117:
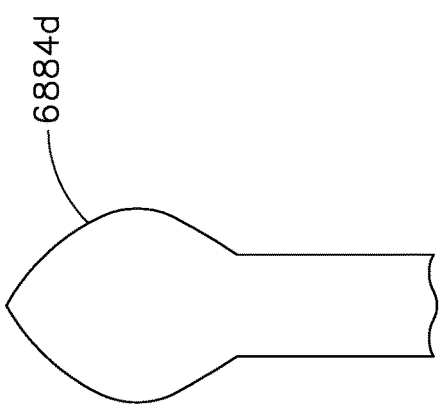
Figure 126:
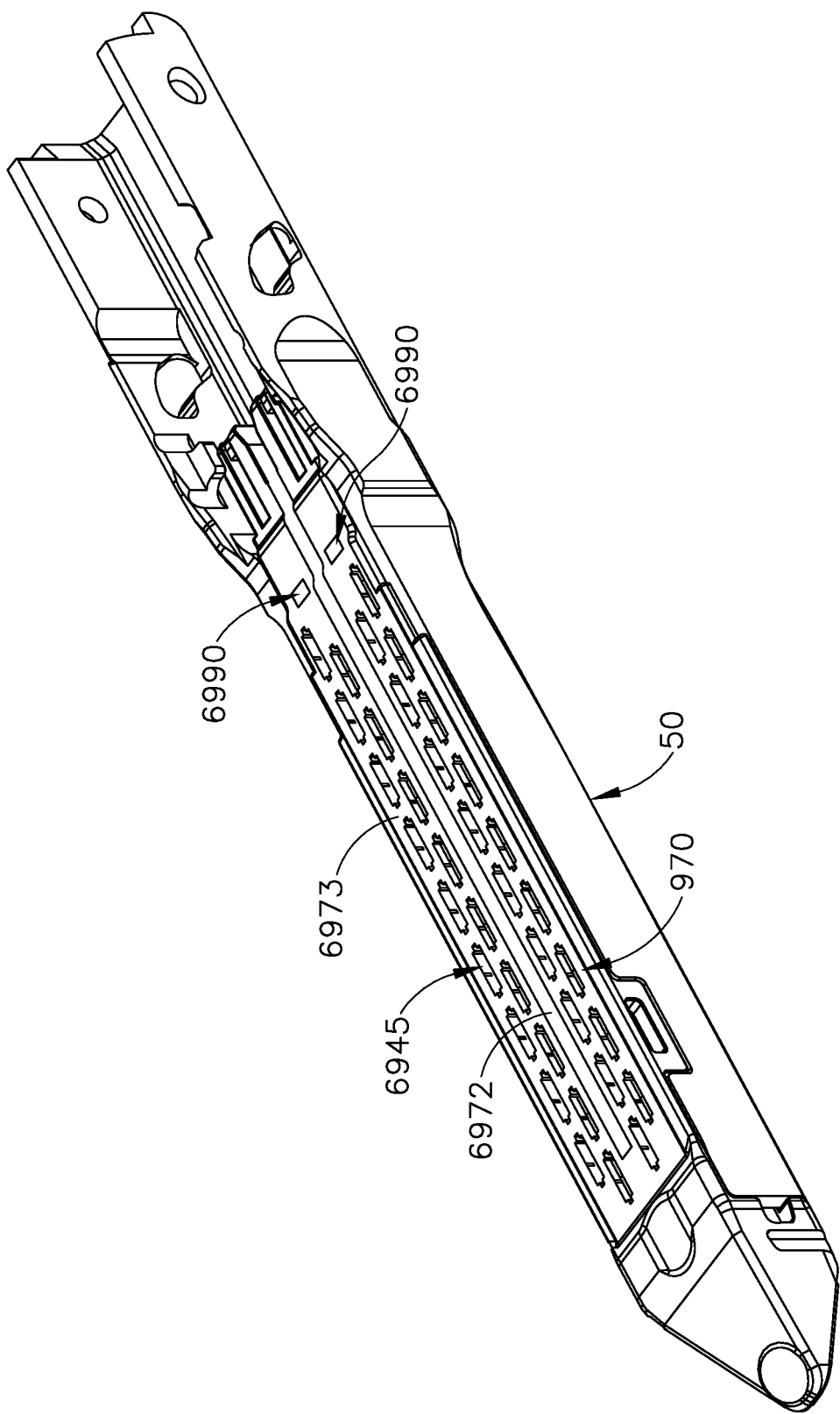
Figure 127:
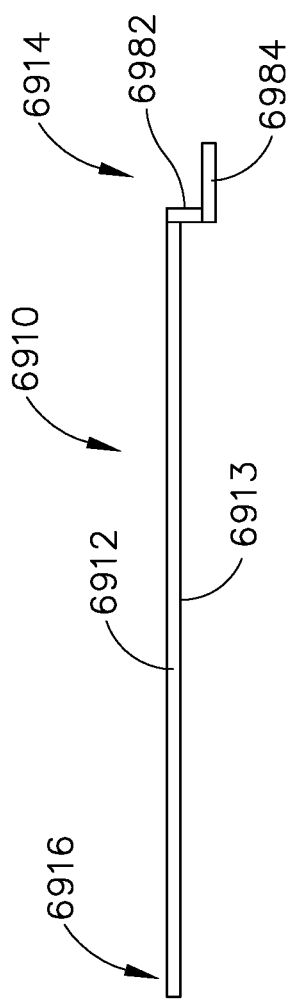
Figure 128:
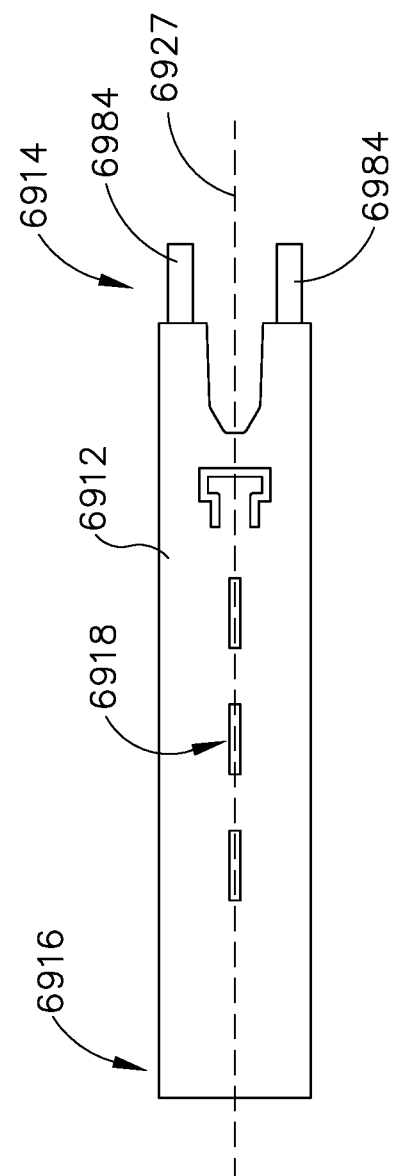
Figure 129:
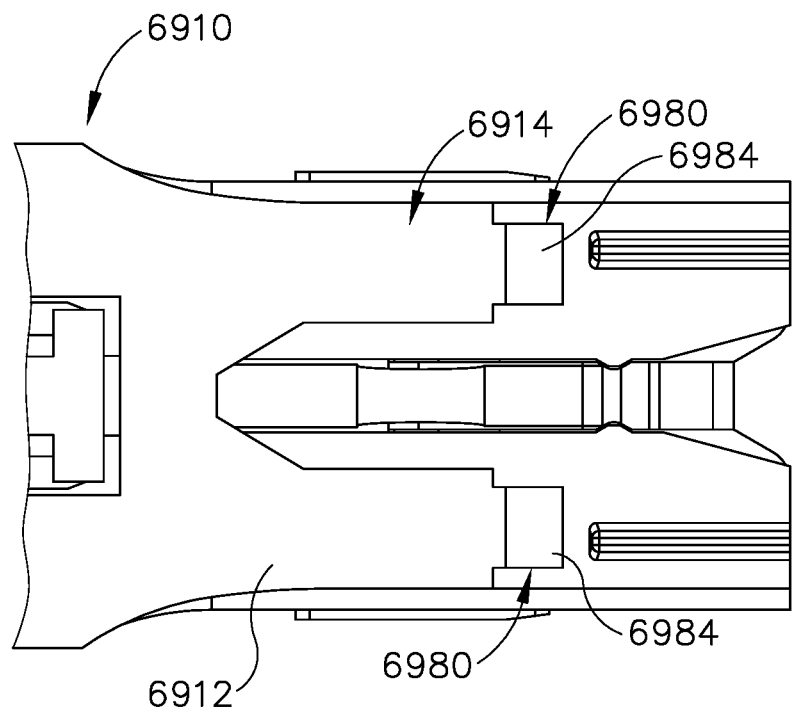
Figure 130:
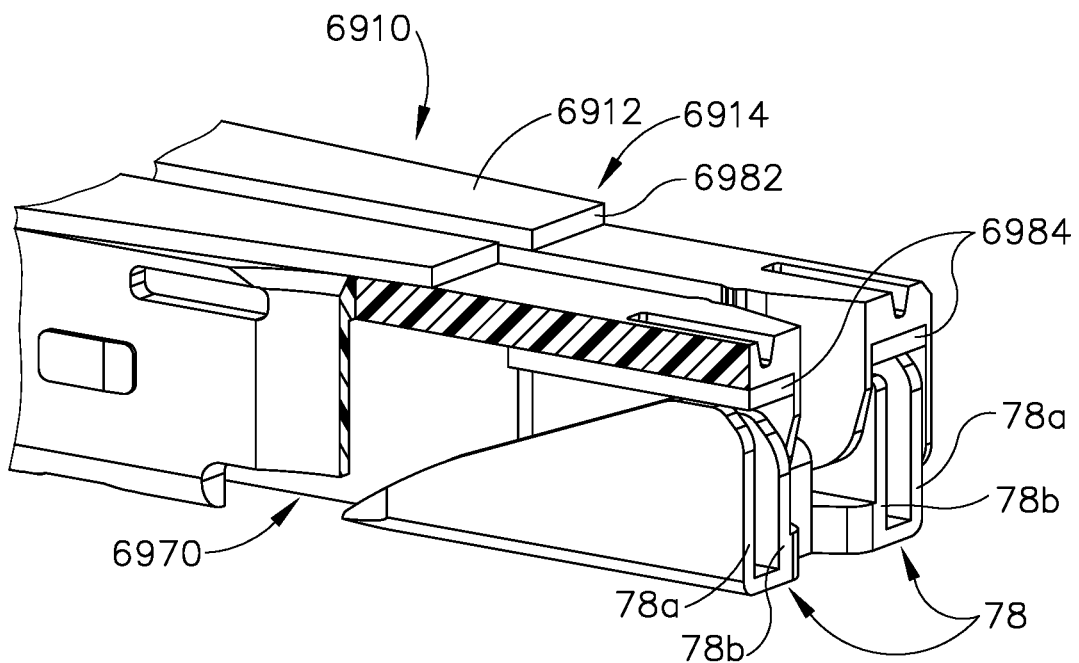
Figure 131:
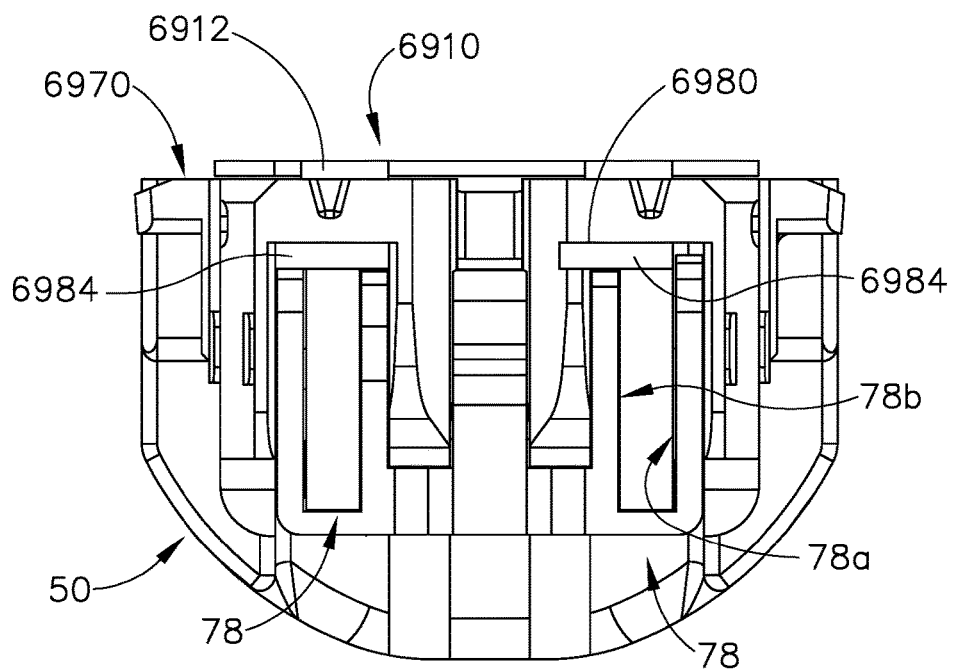
Figure 132:
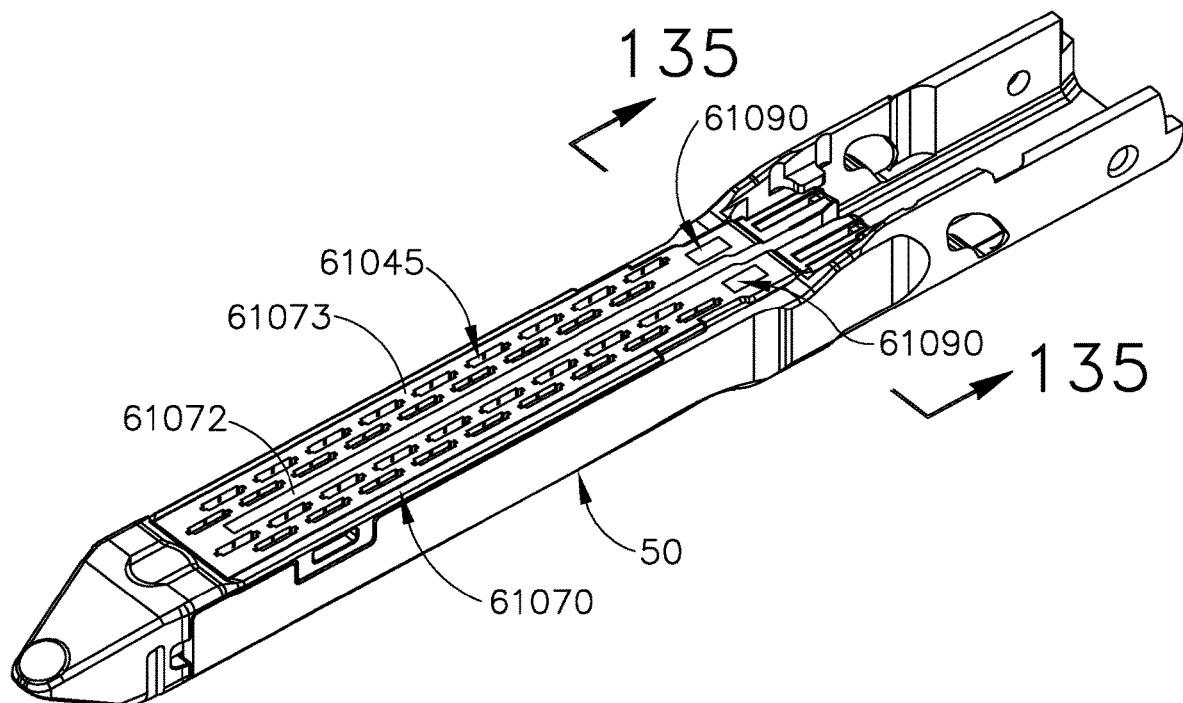
Figure 135:
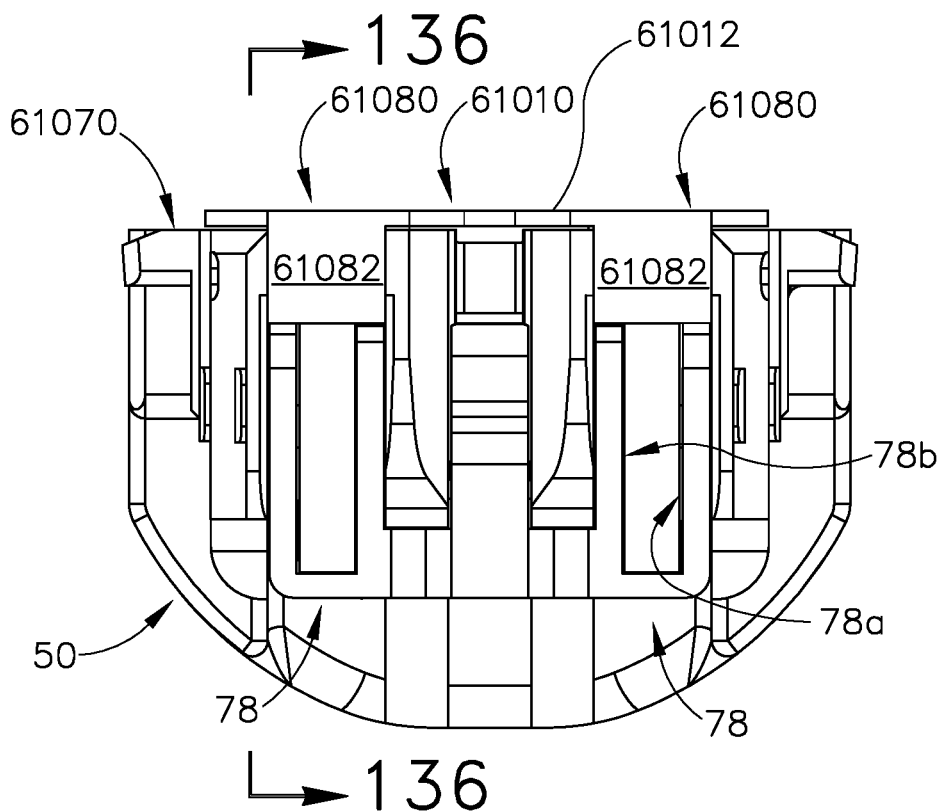
Figure 136:
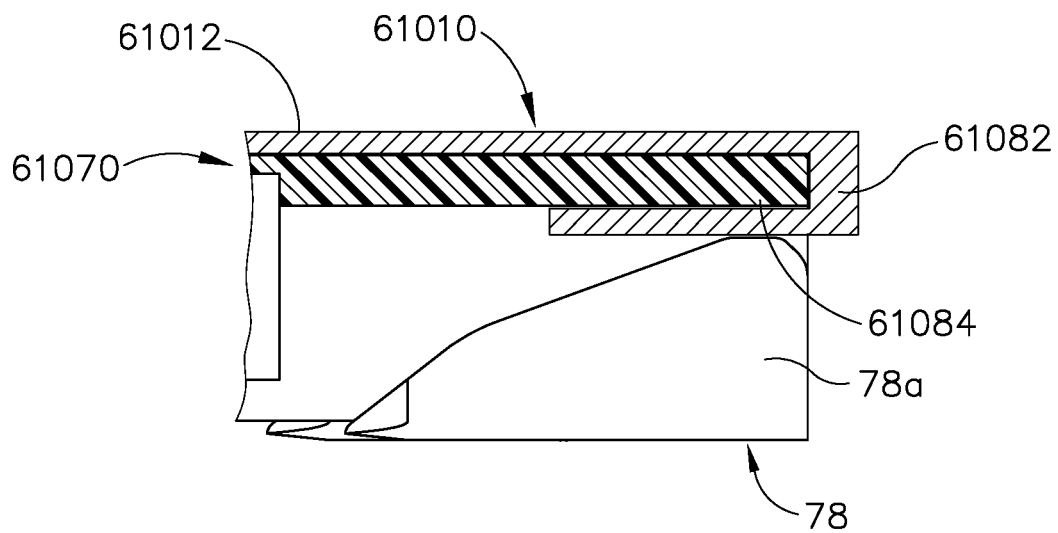
Figure 137:
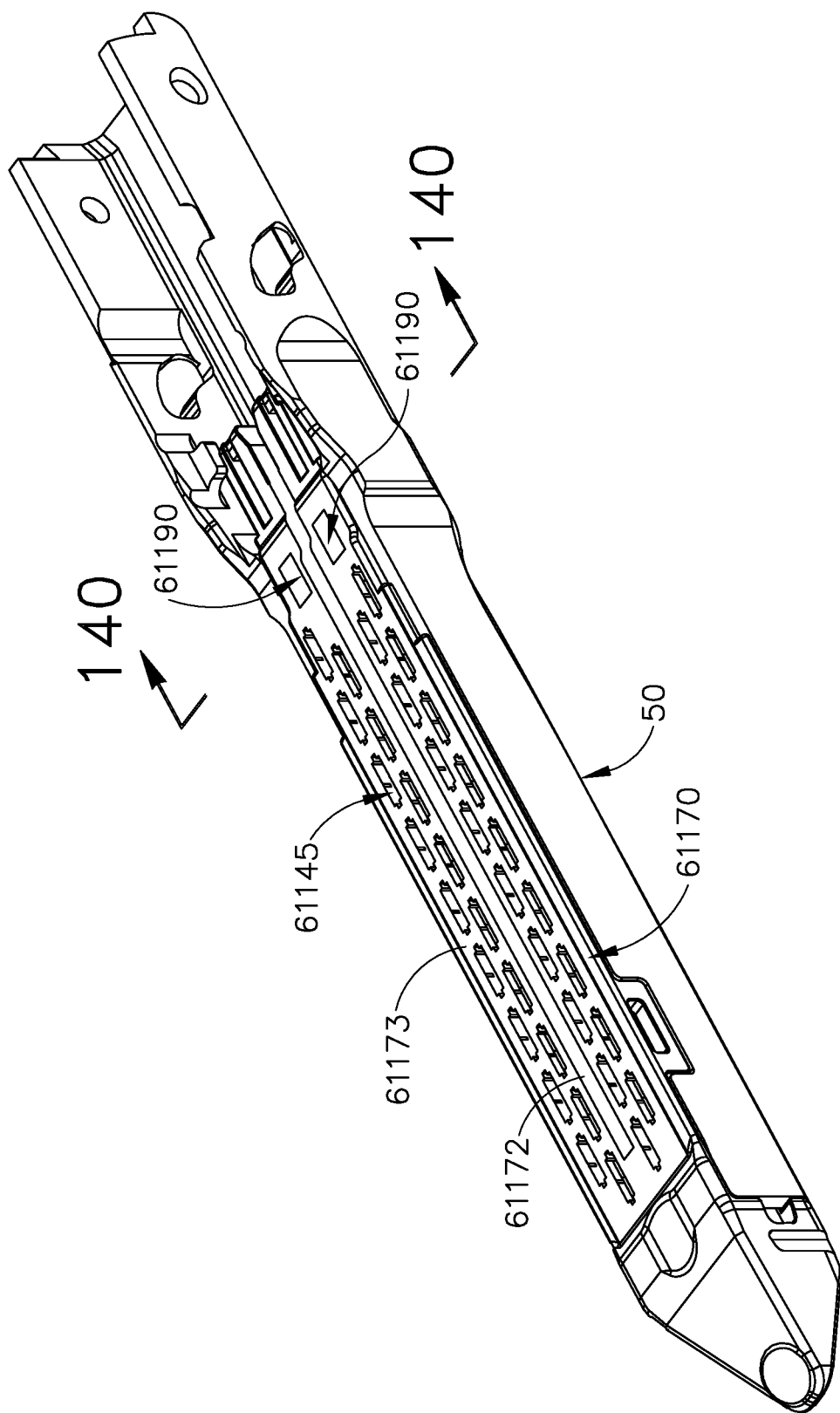
Figure 140:
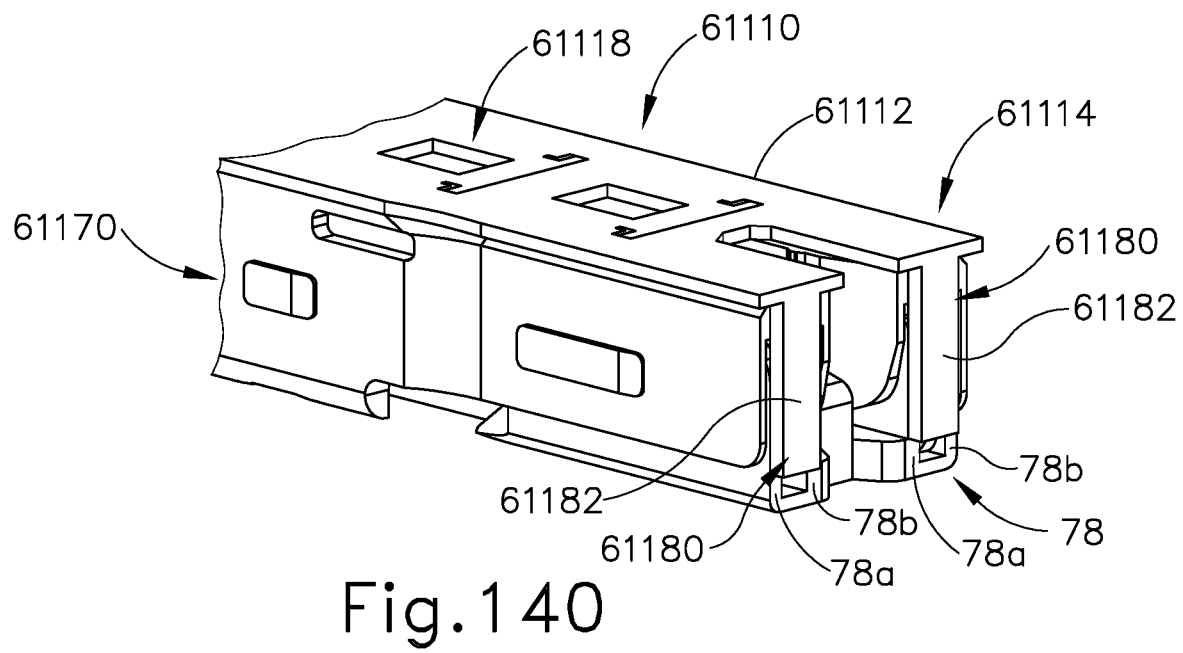
Figure 141:
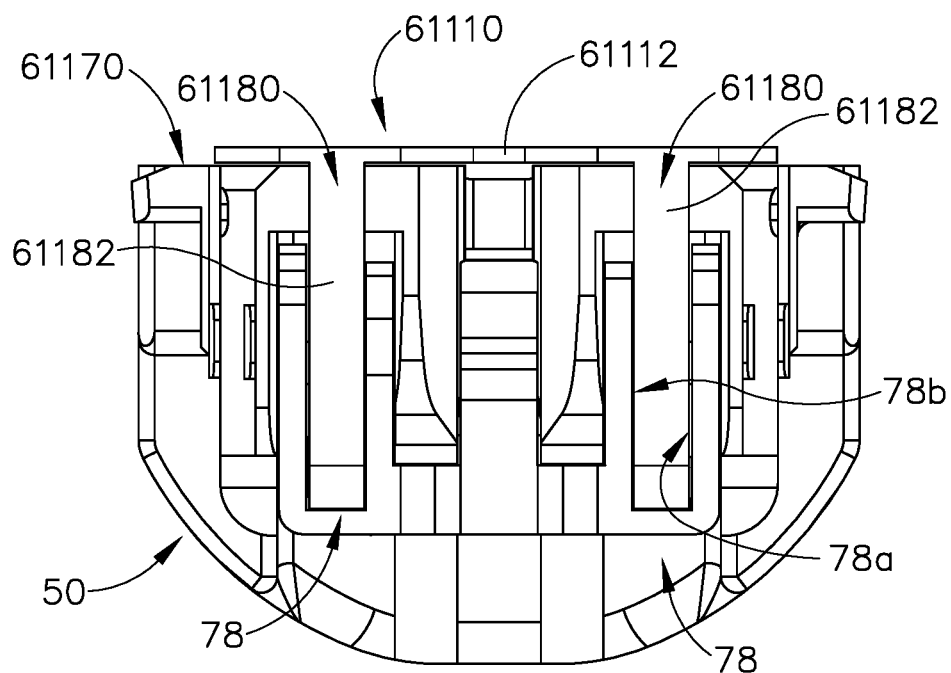
Figure 142:
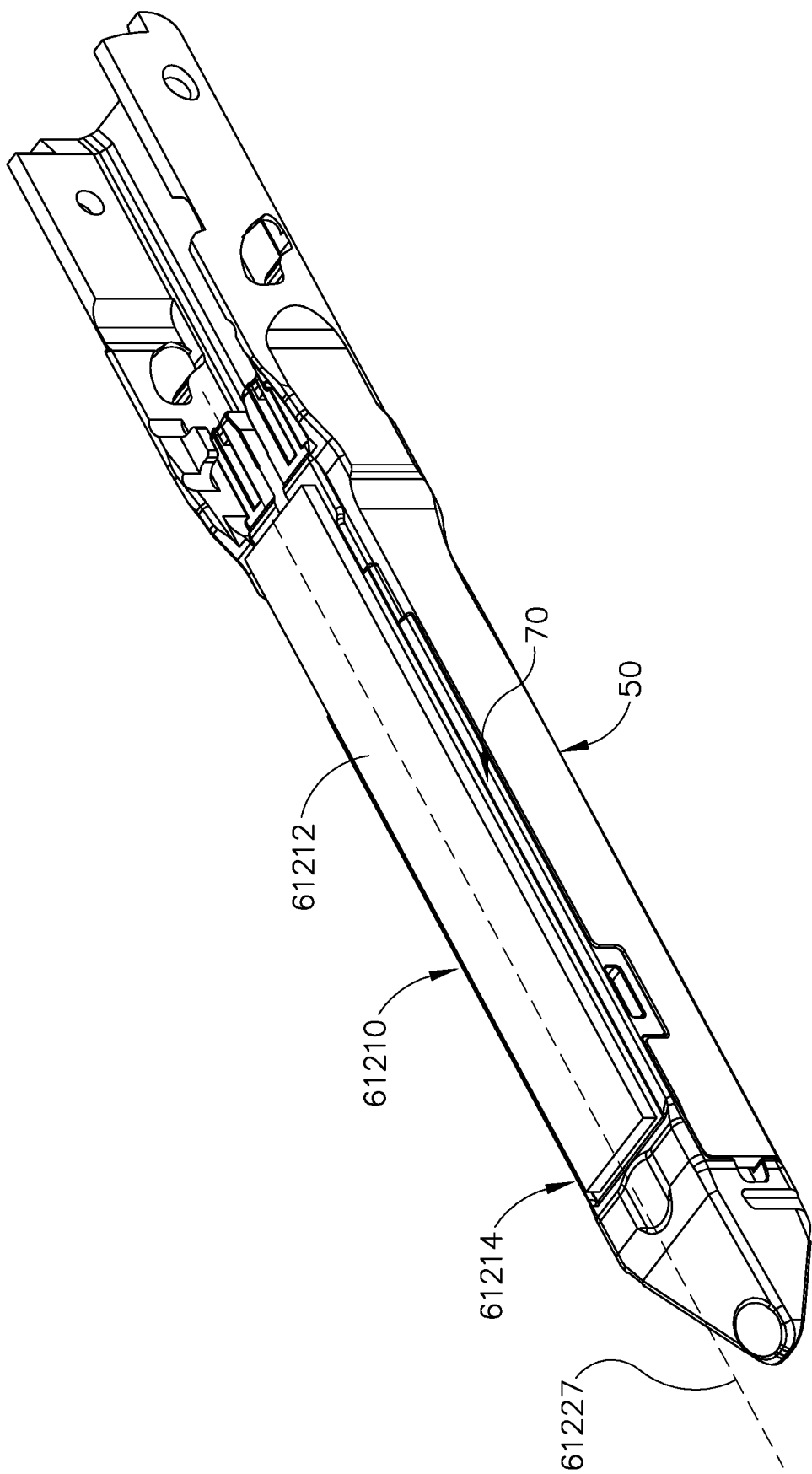
Figure 143:
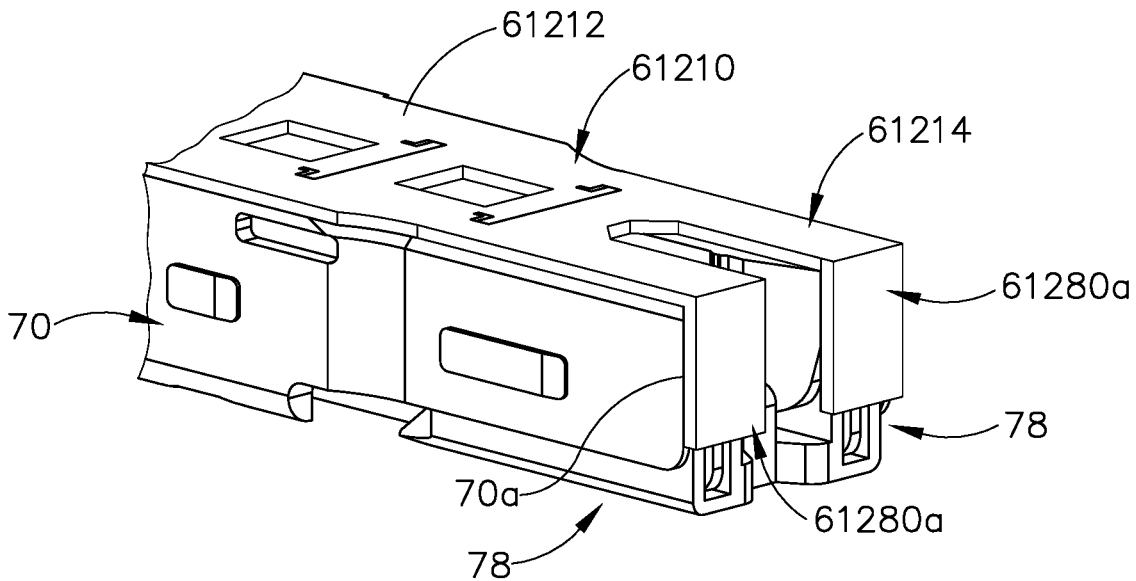
Figure 144:
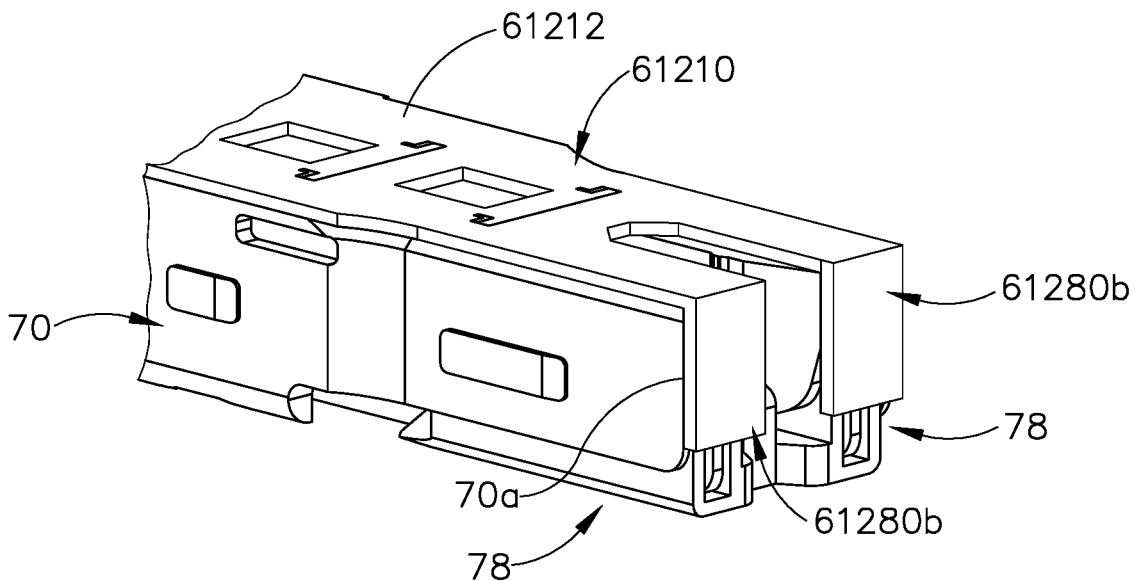
Figure 145:
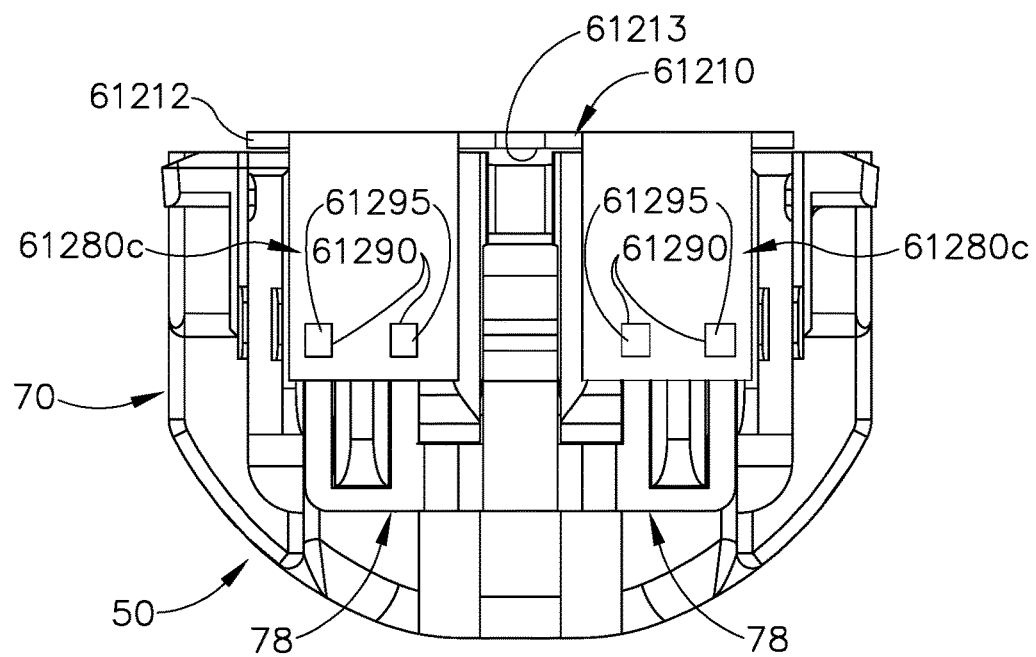
Figure 146:
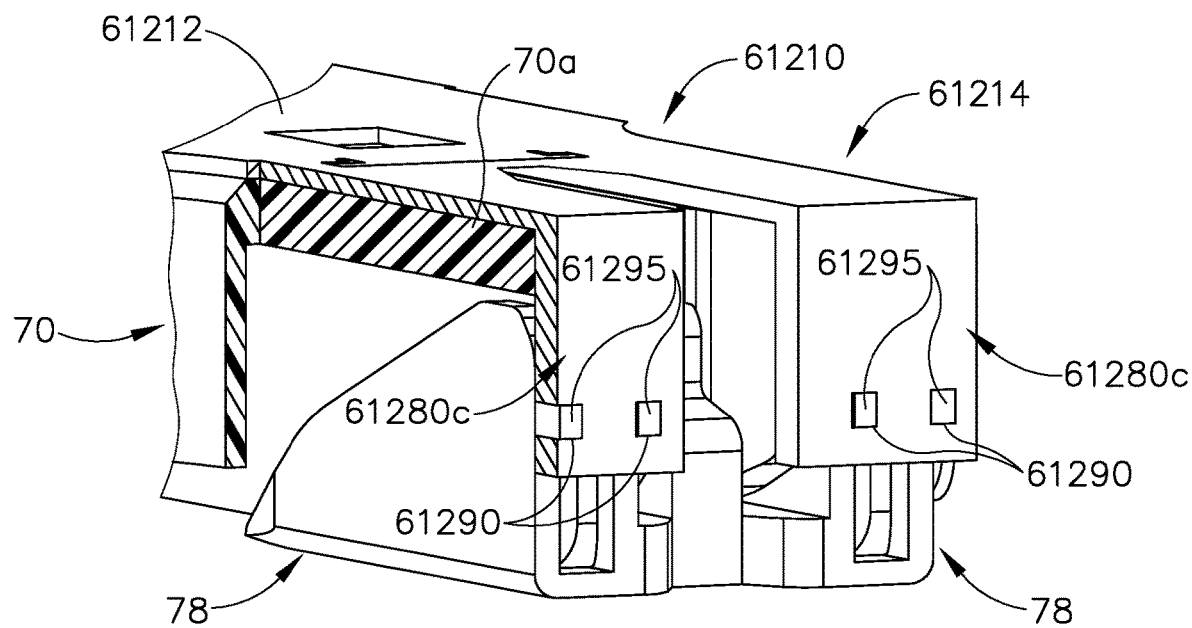
Figure 147:
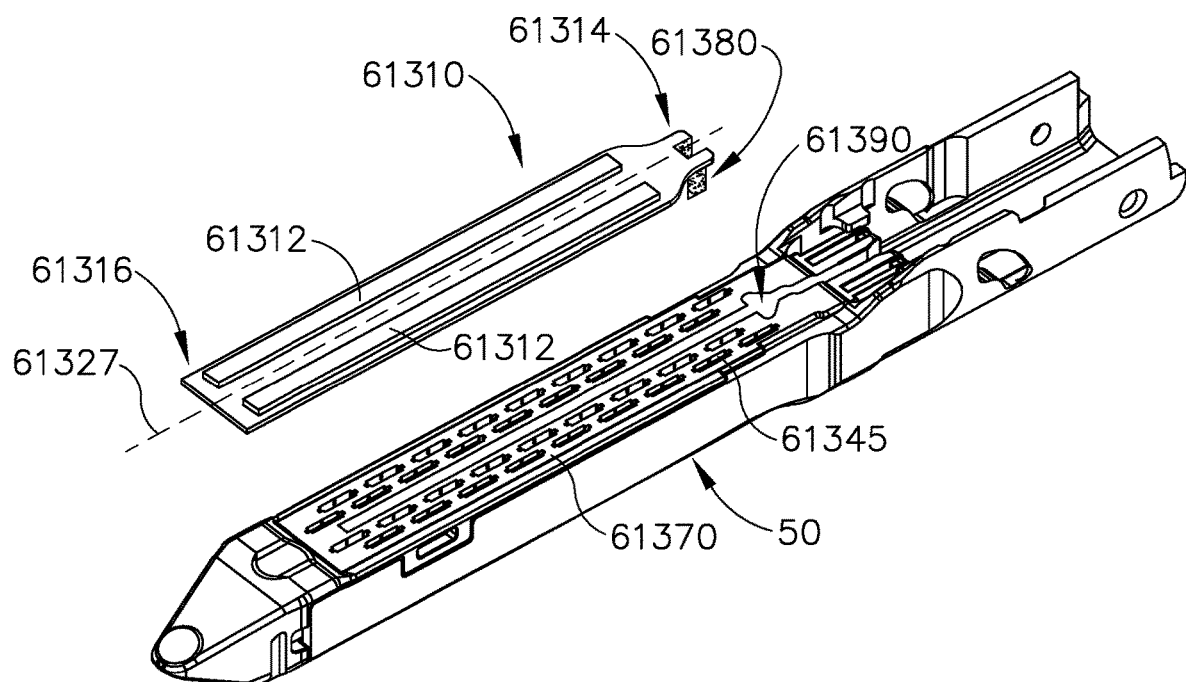
Figure 148:
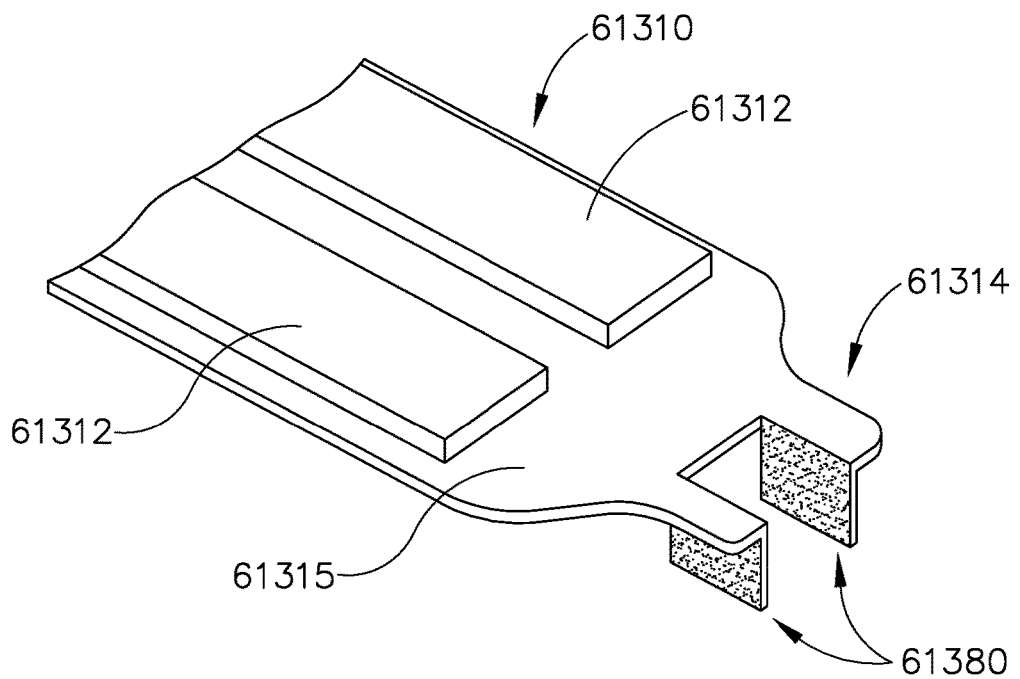
Figure 149A:
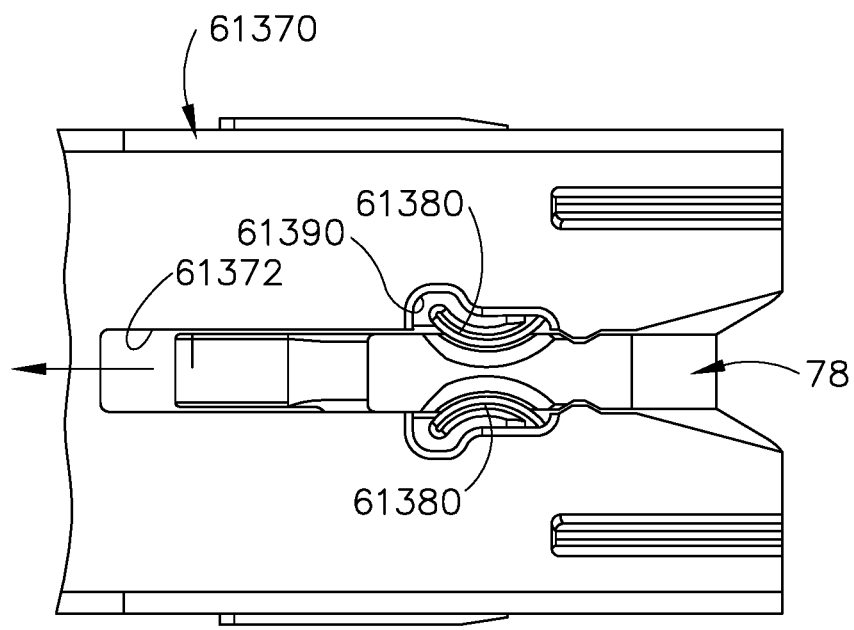
Figure 149B:
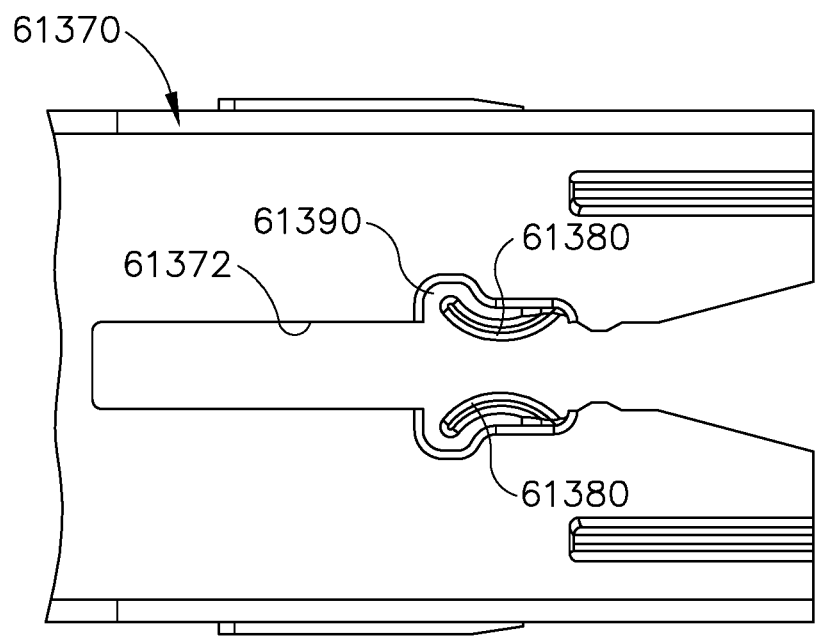
Figure 150:
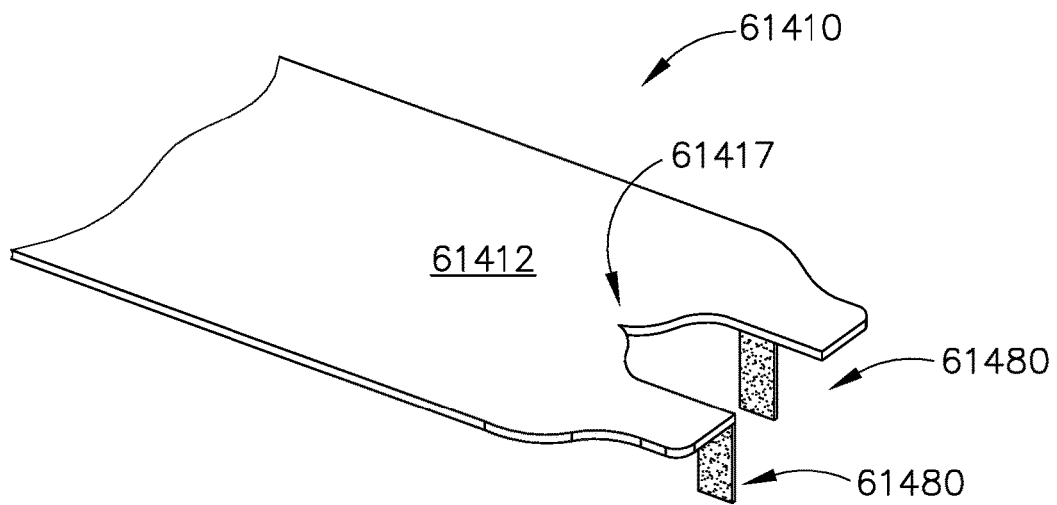
Figure 151:
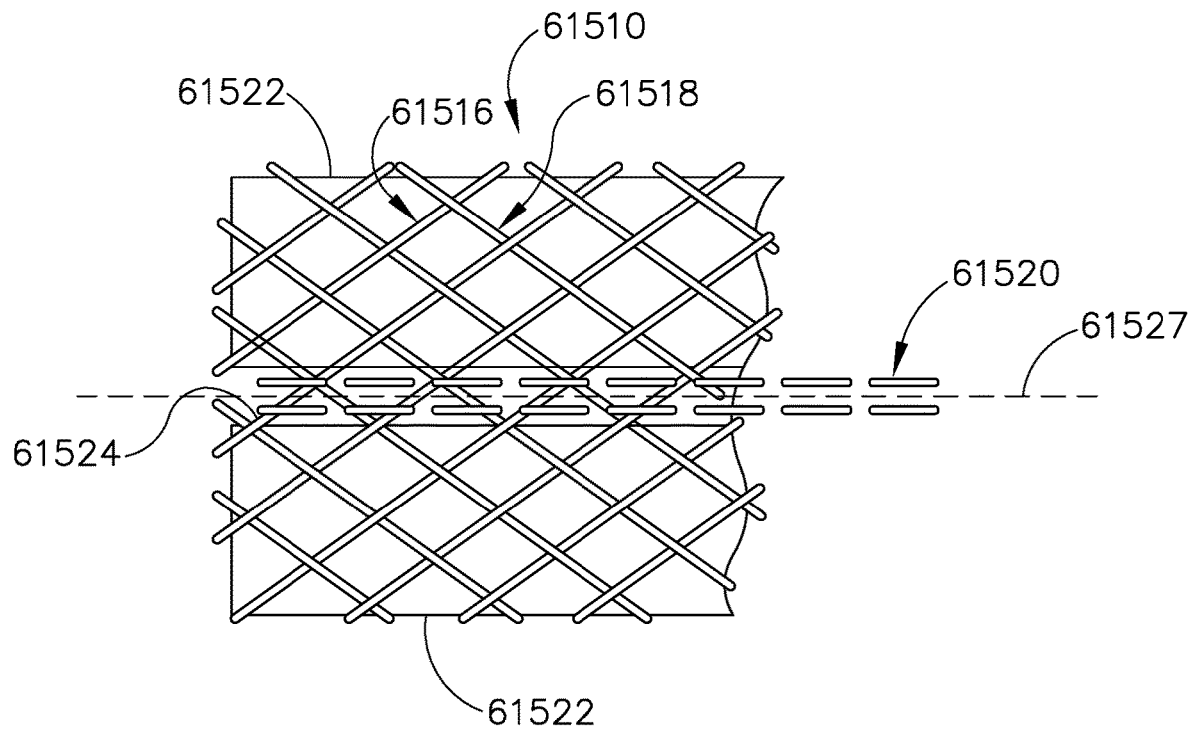
Figure 152:
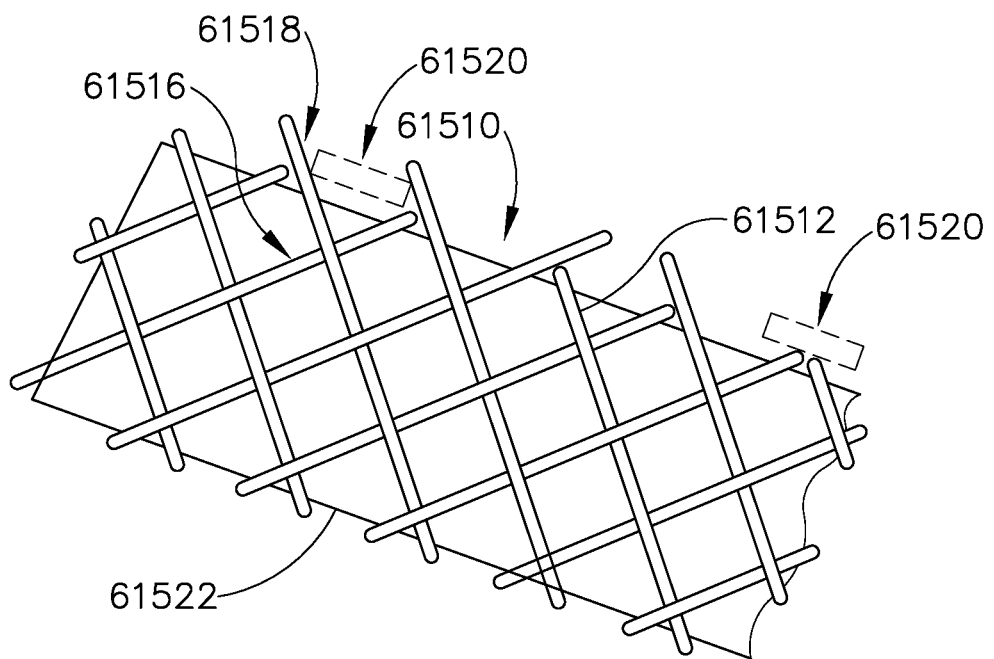
Figure 153:
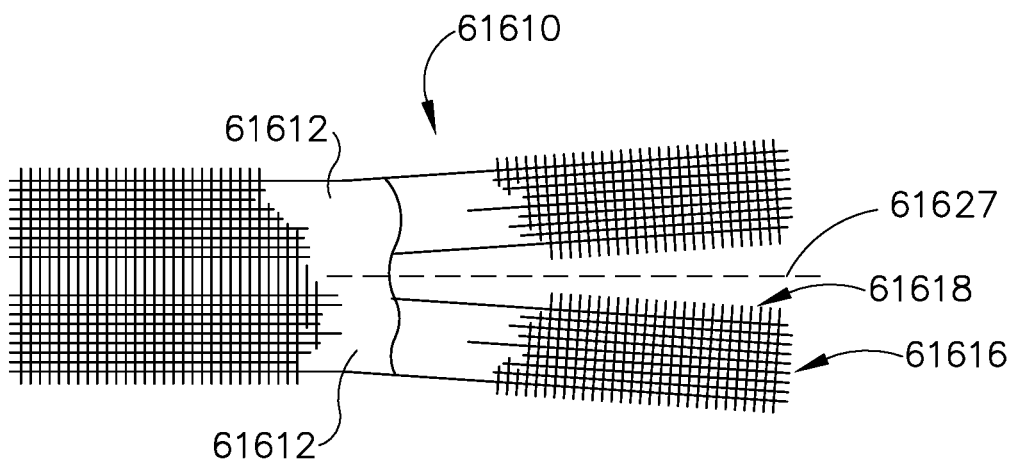
Figure 154:
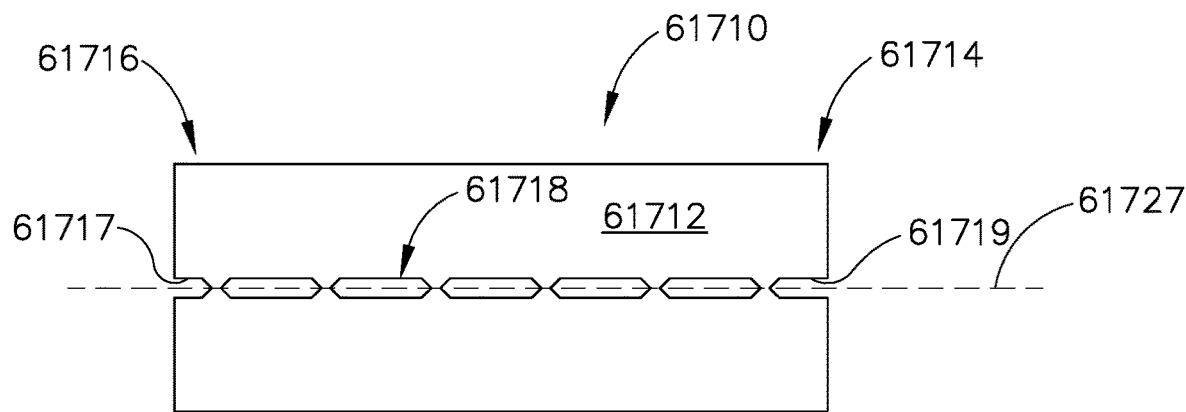
Figure 155:
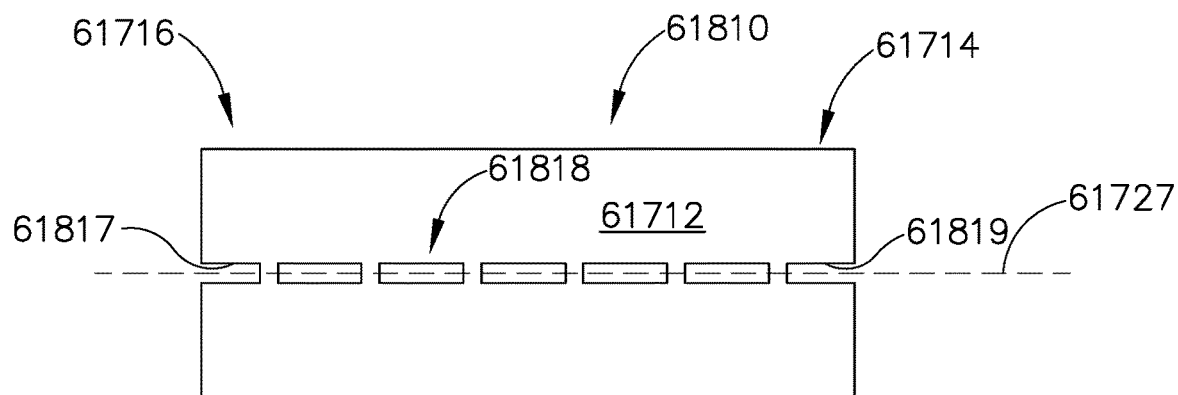
Figure 156:
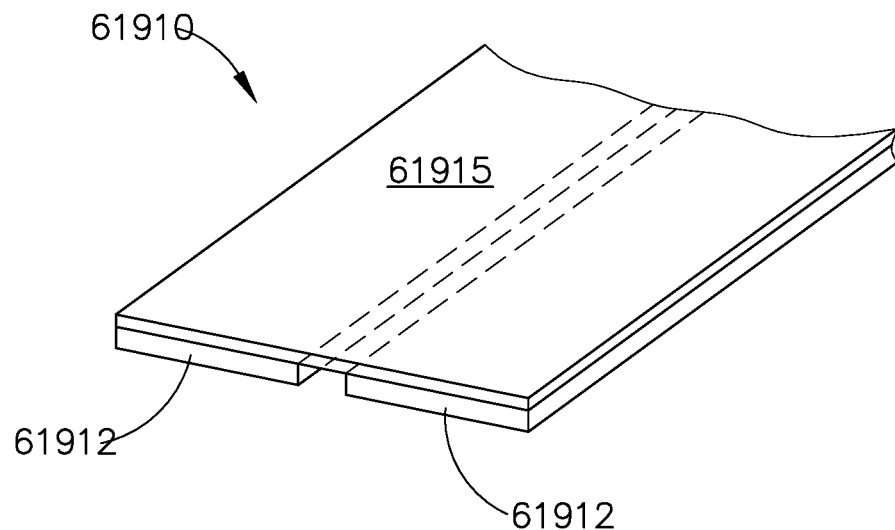
Figure 157:
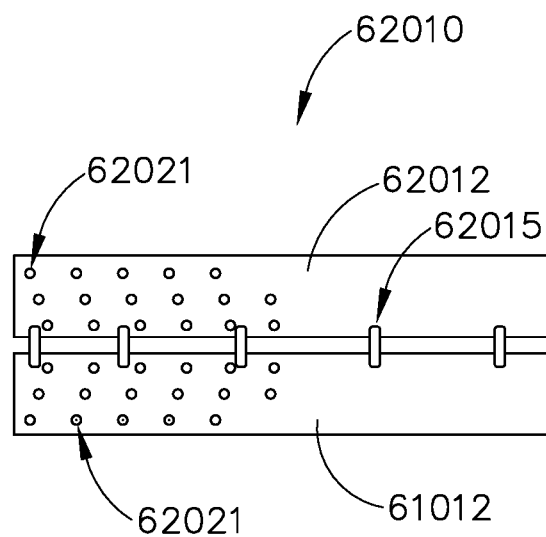
Figure 158:
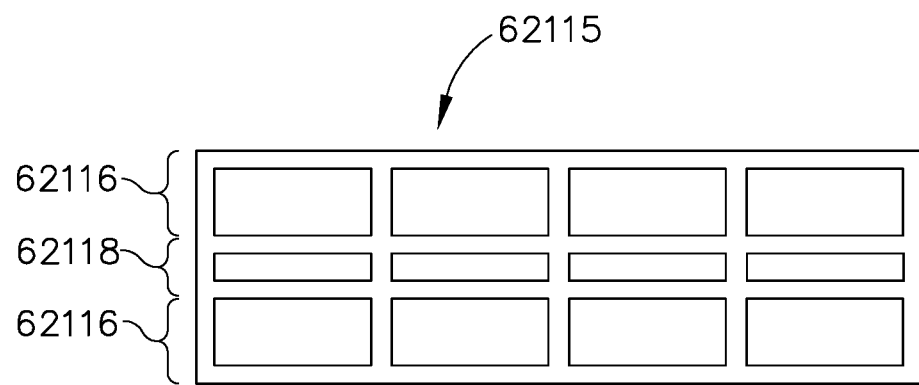
Figure 159A:
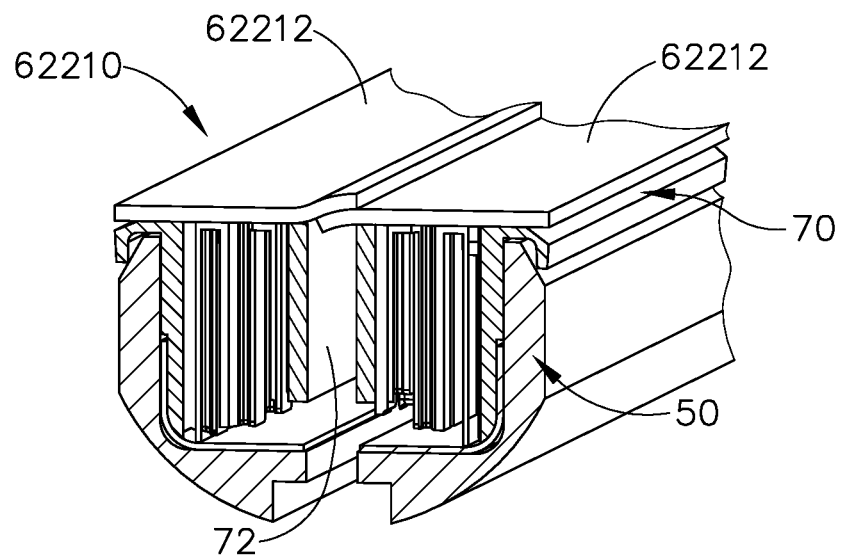
Figure 159B:
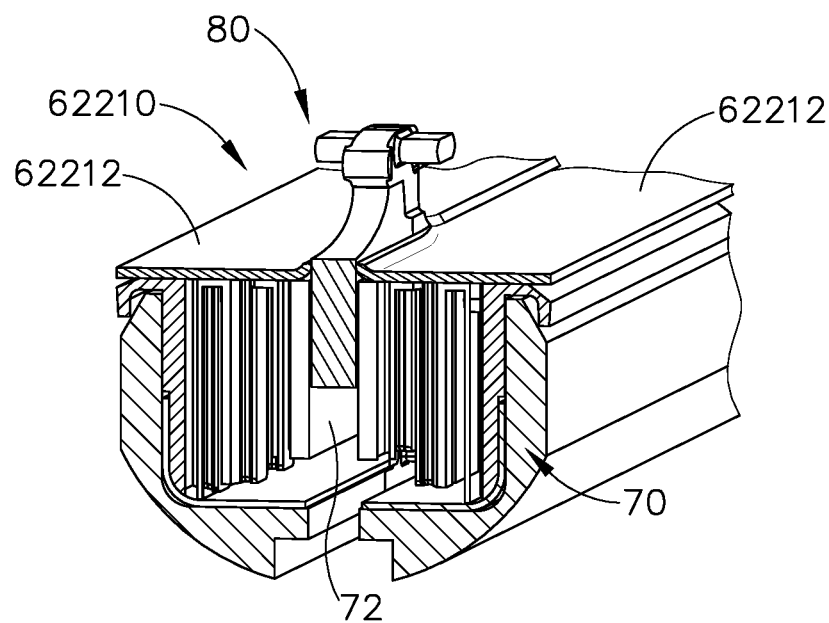
Figure 160:
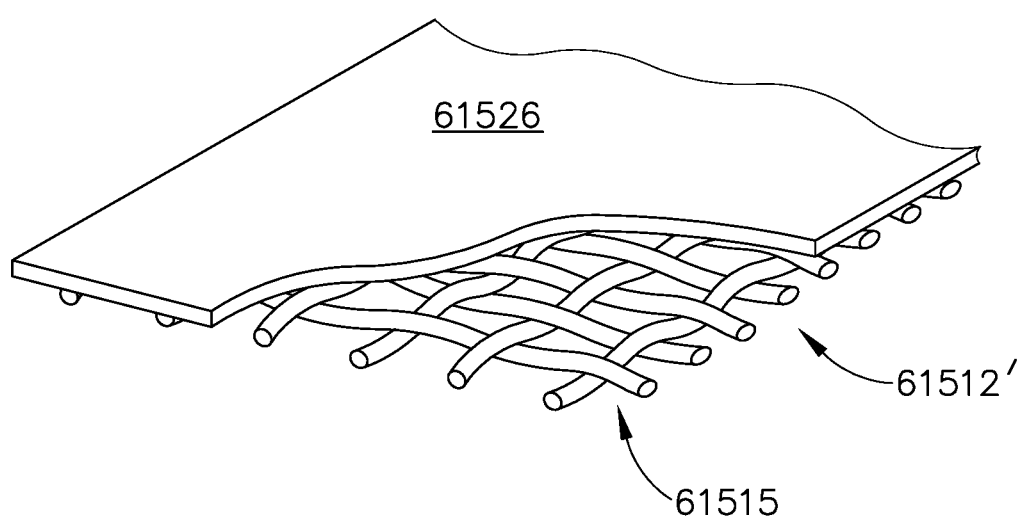
Figure 161:
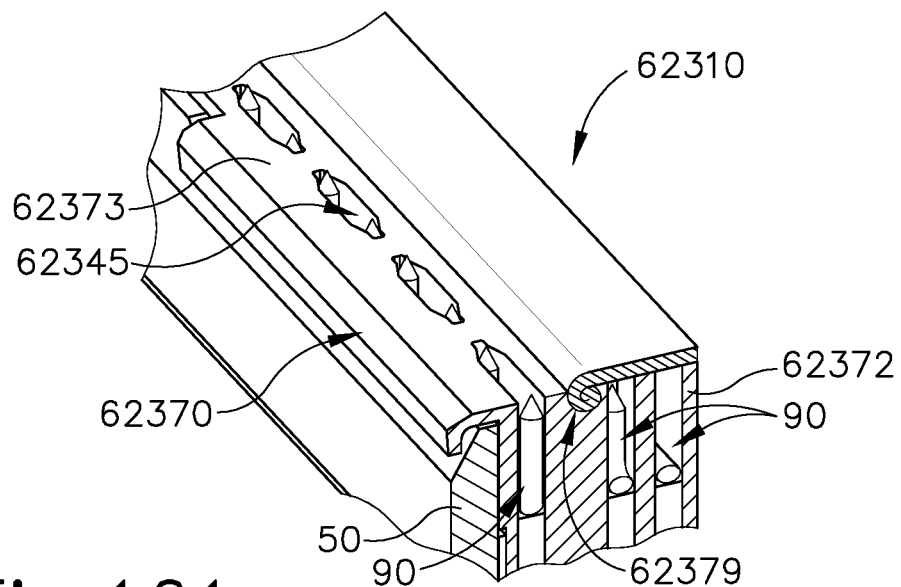
Figure 162A:
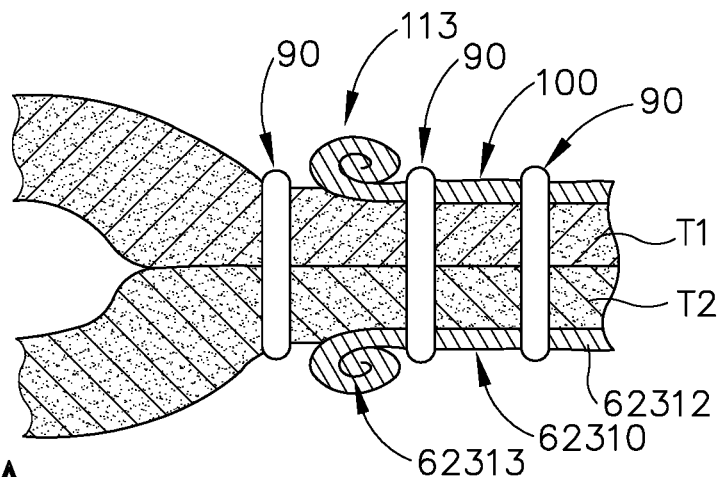
Figure 162B:
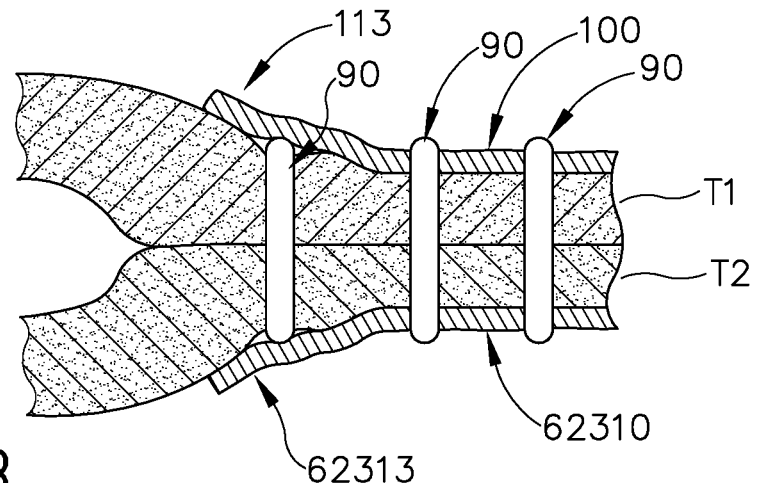
Figure 163:
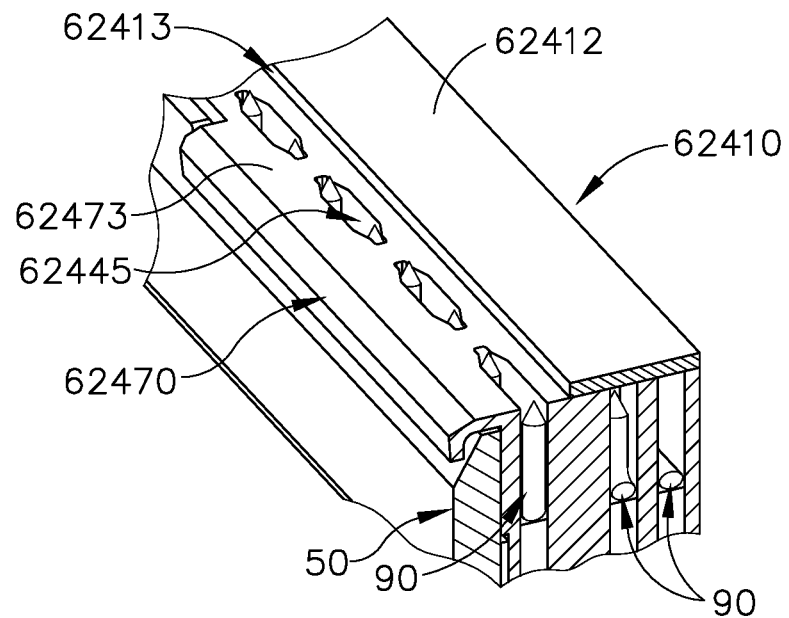
Figure 164:
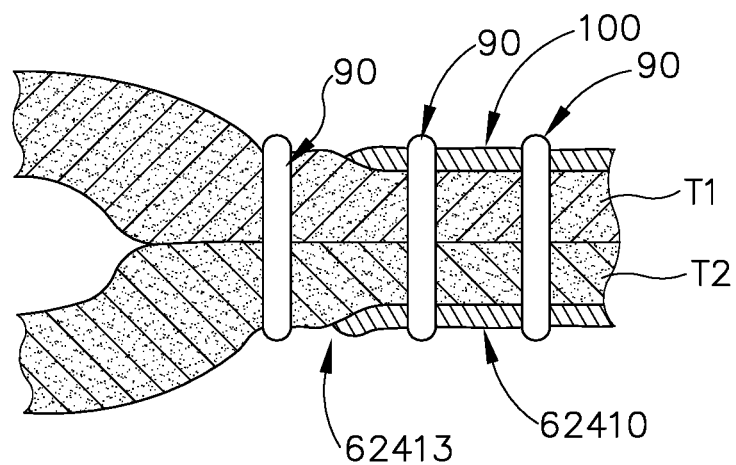
Figure 165:
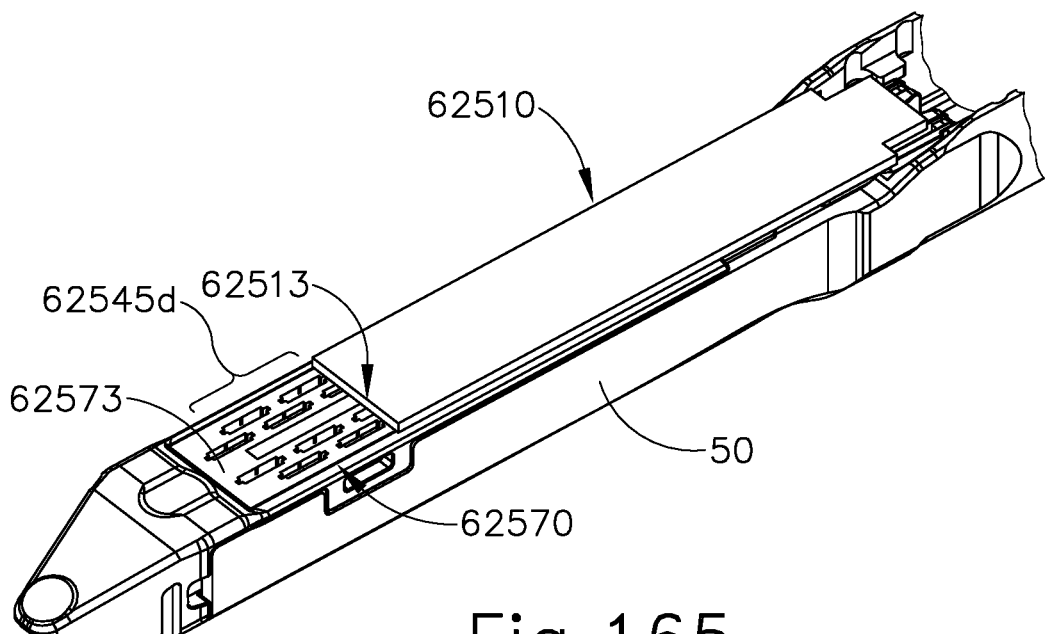
Figure 166:
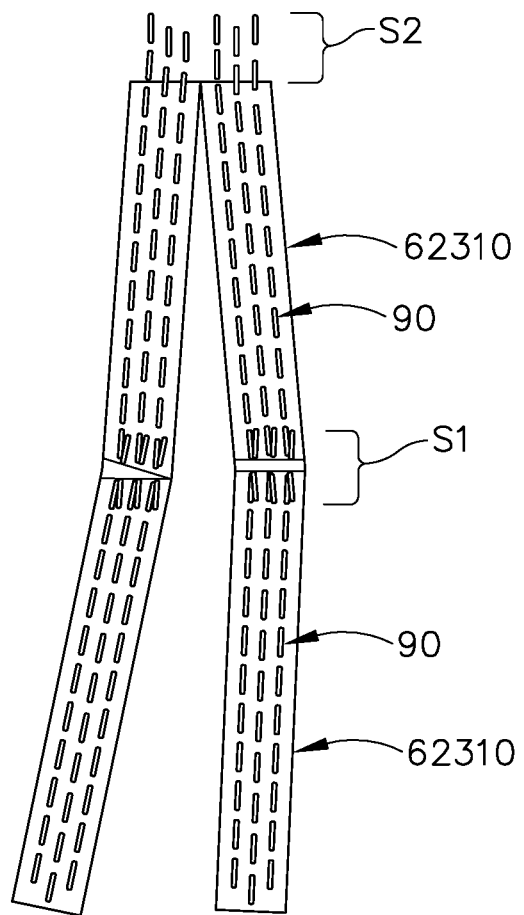
Figure 167:
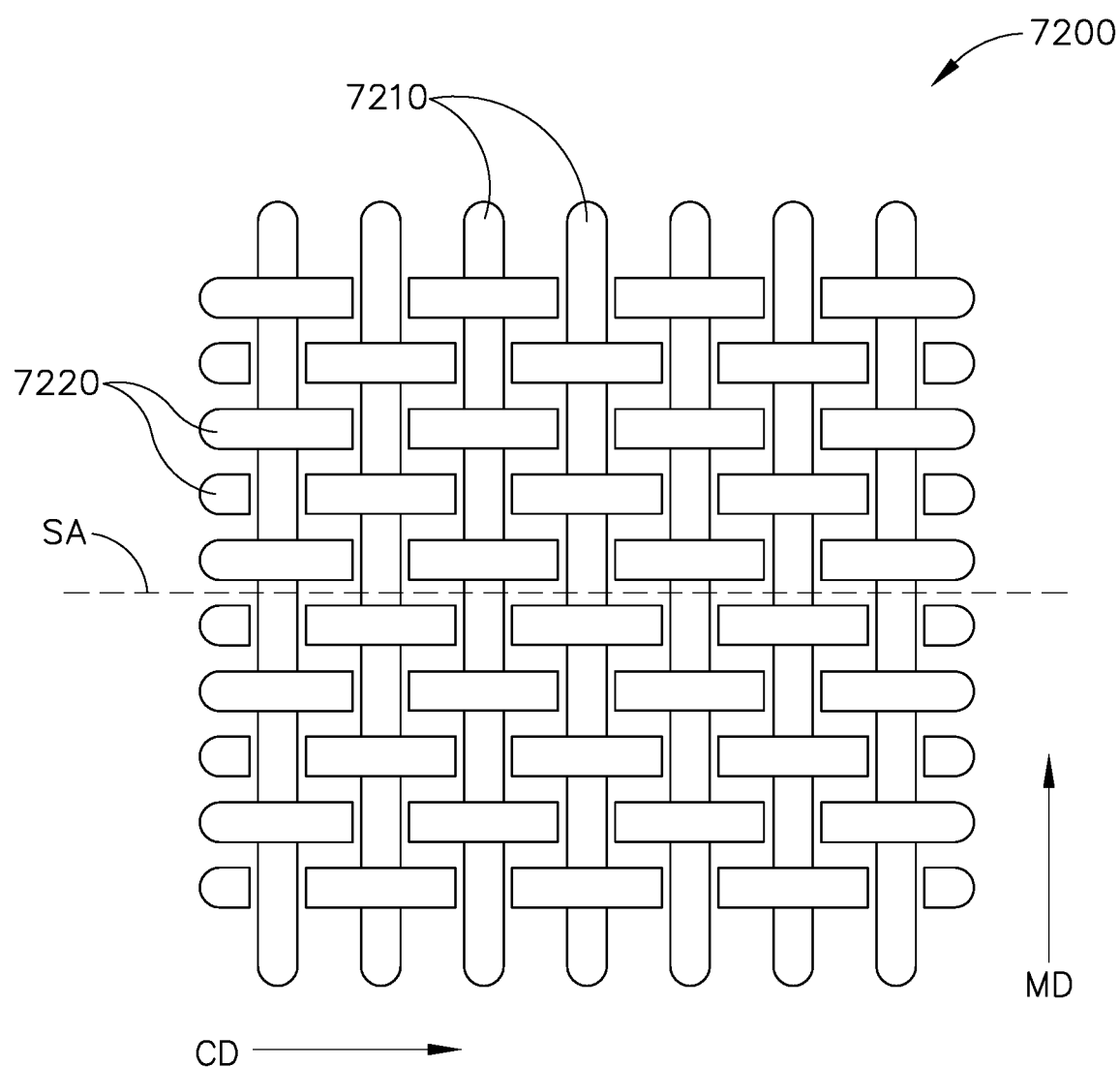
Figure 168:
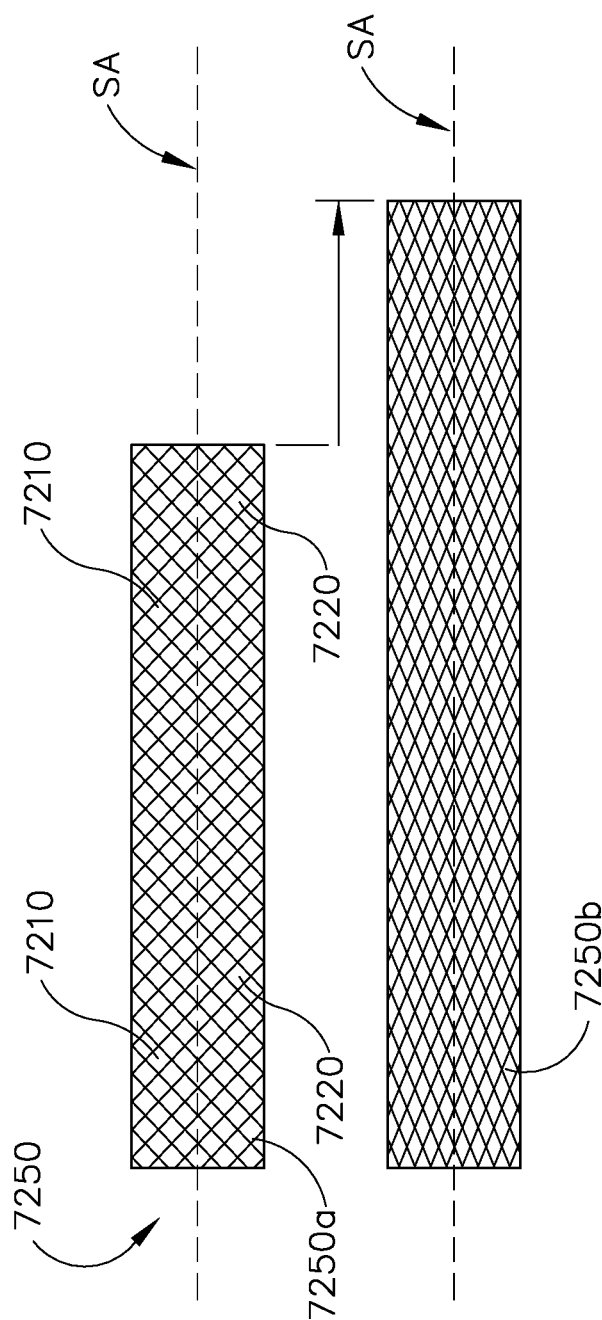
Figure 169:
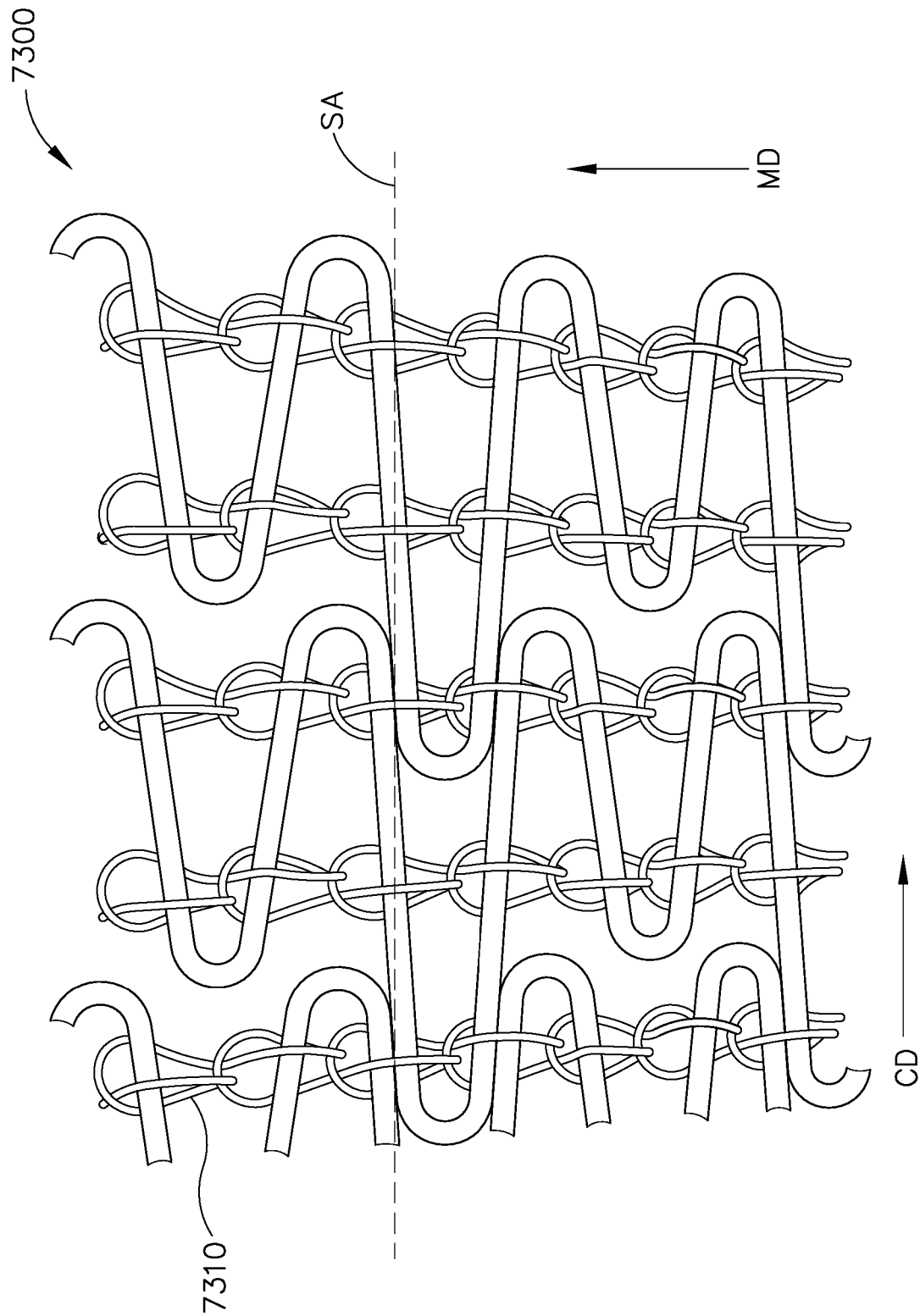
Figure 170:
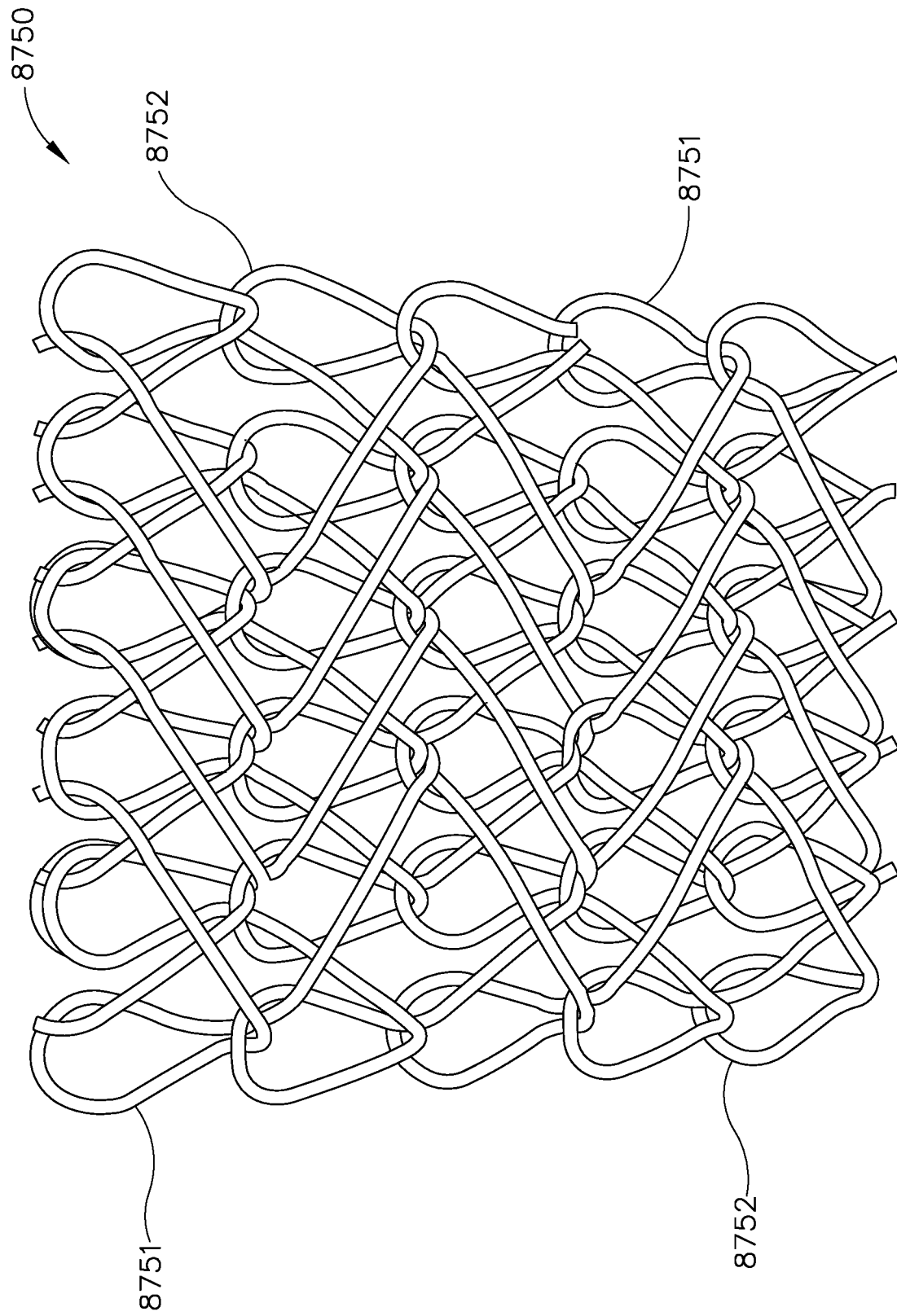
Figure 171:
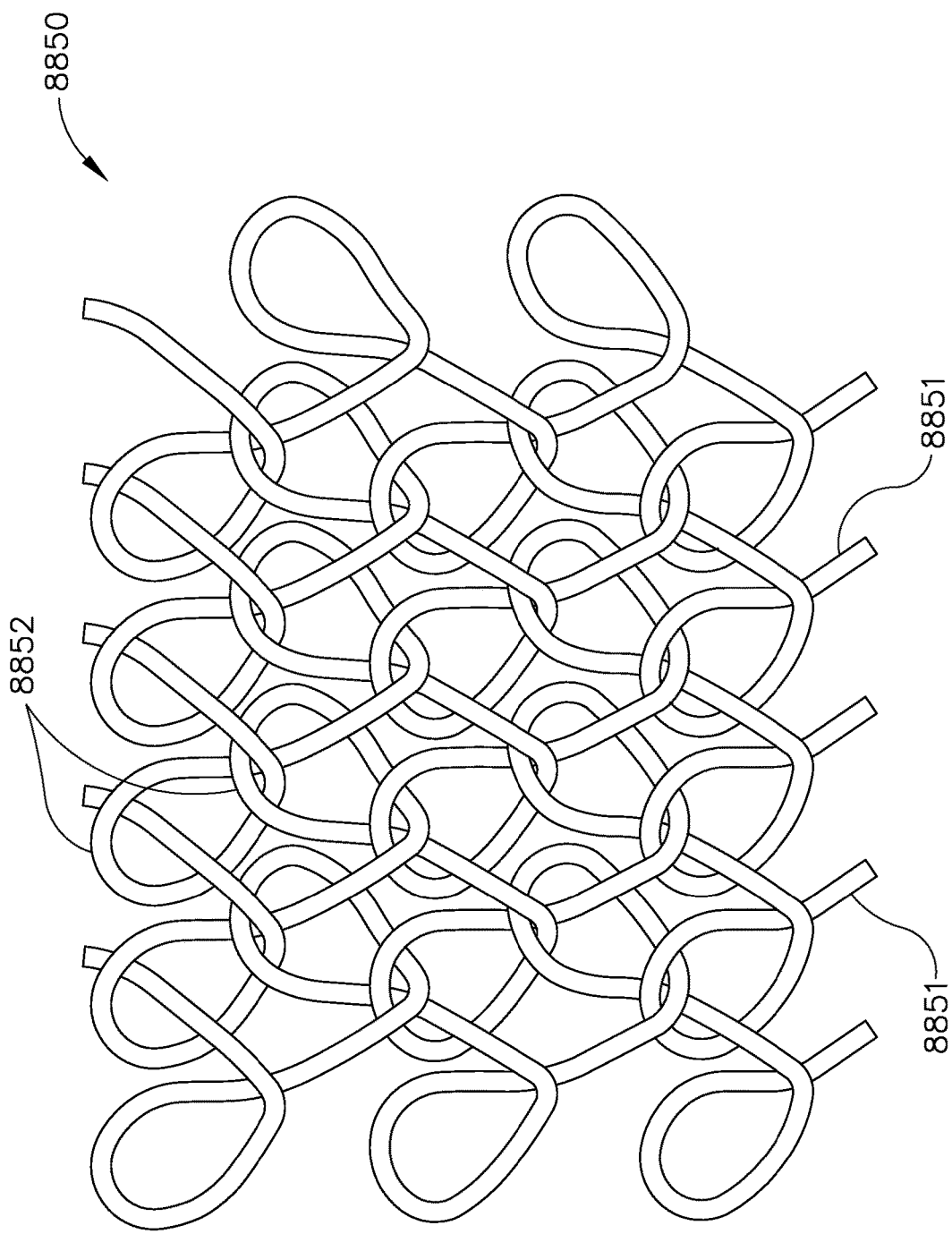
Figure 172:
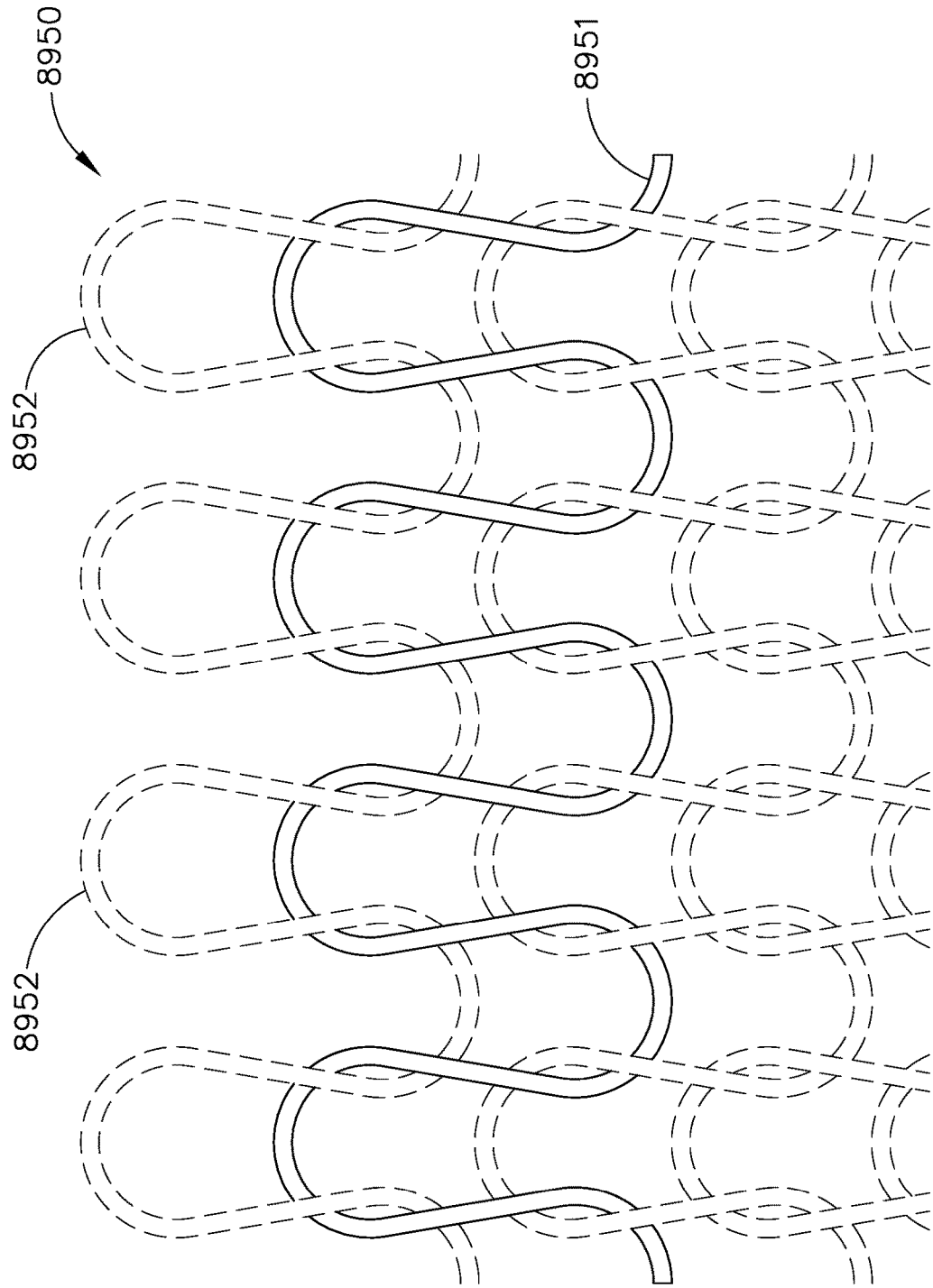
Figure 173:
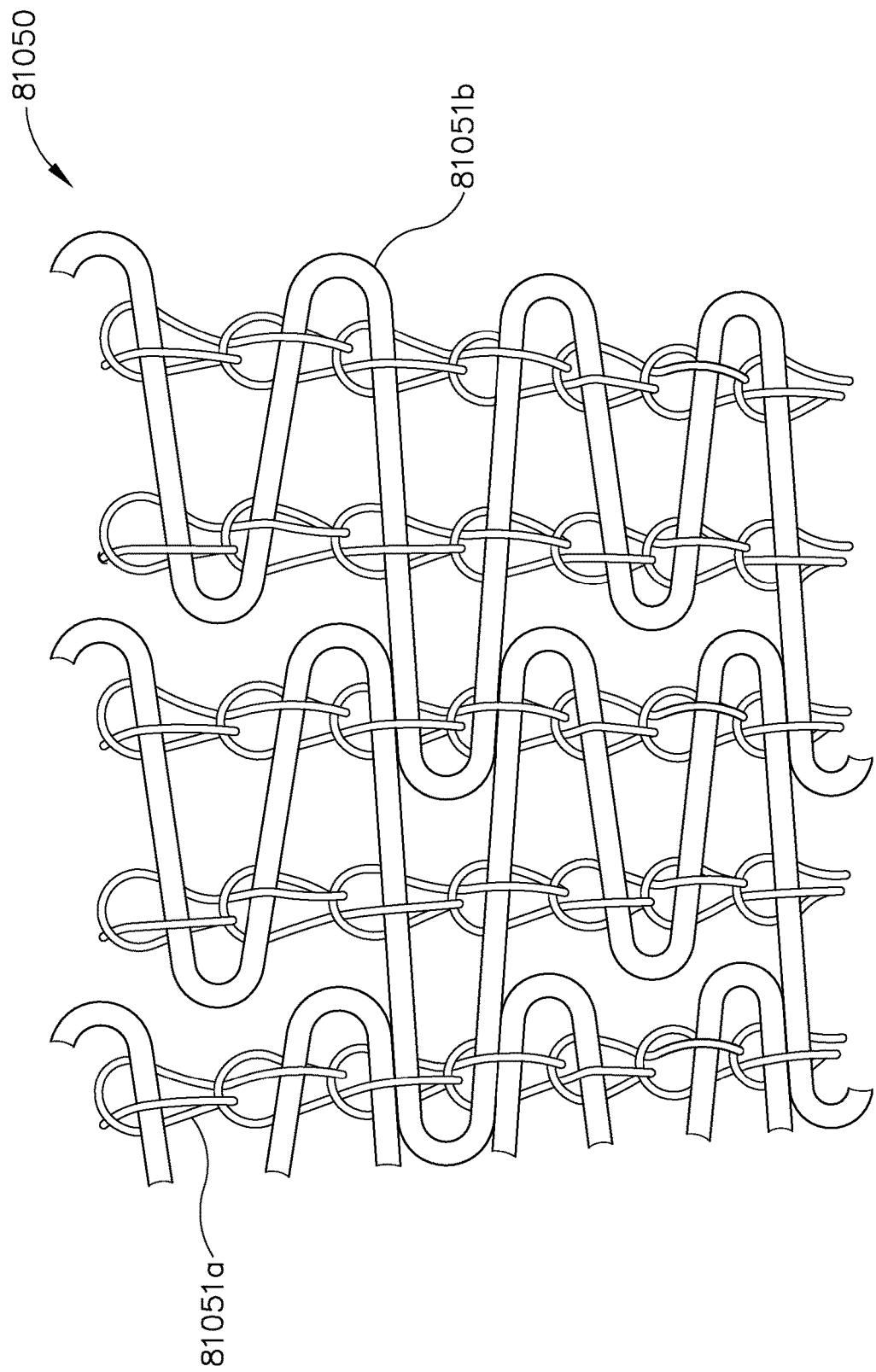
Figure 174:
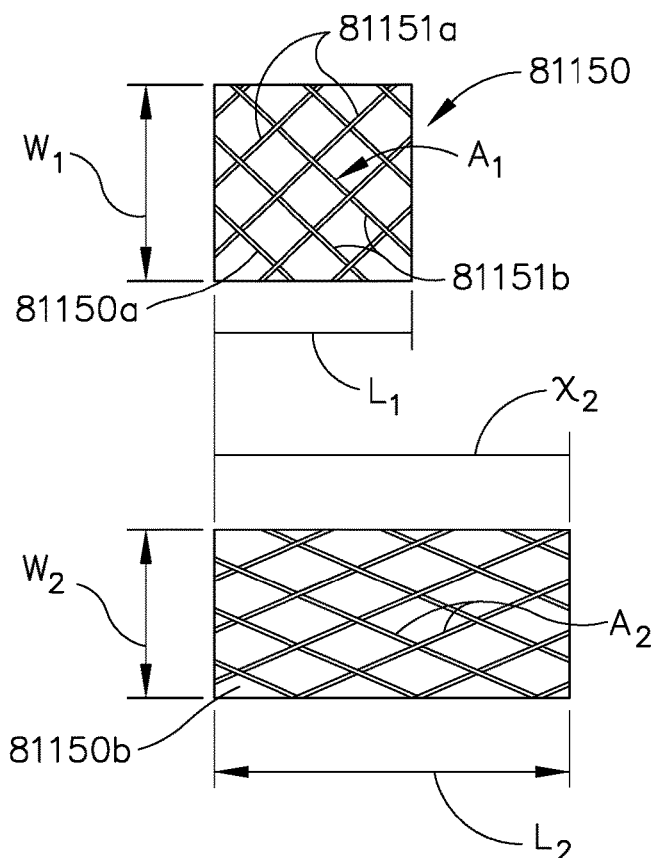
Figure 175:
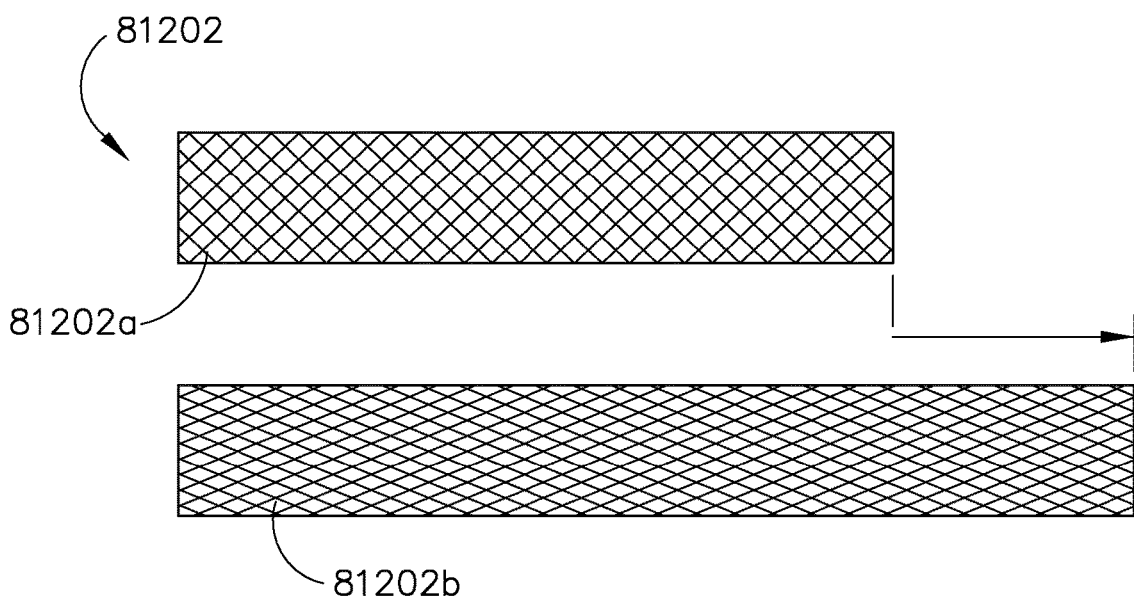
Figure 176:
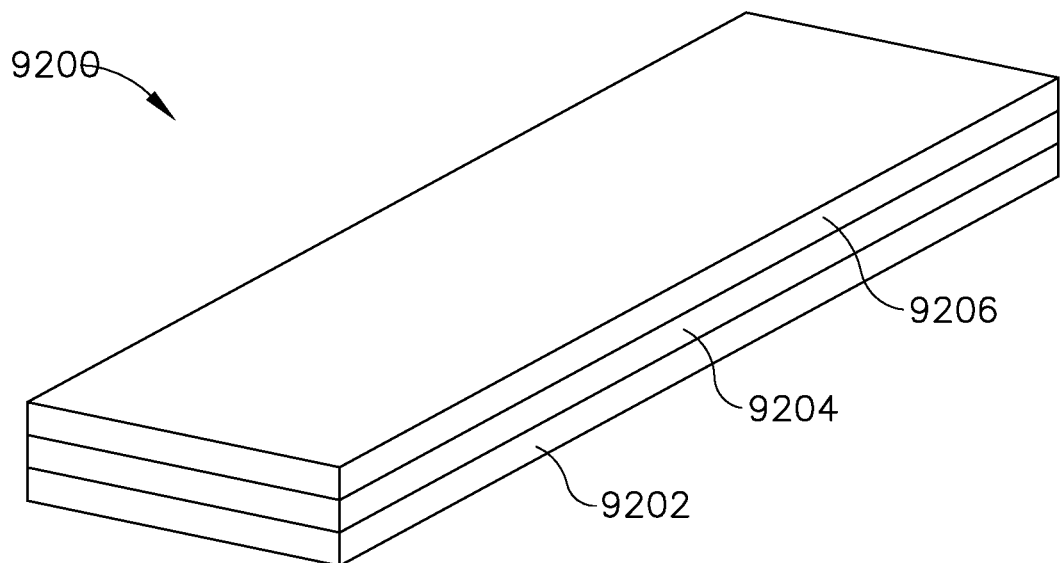
Figure 177:
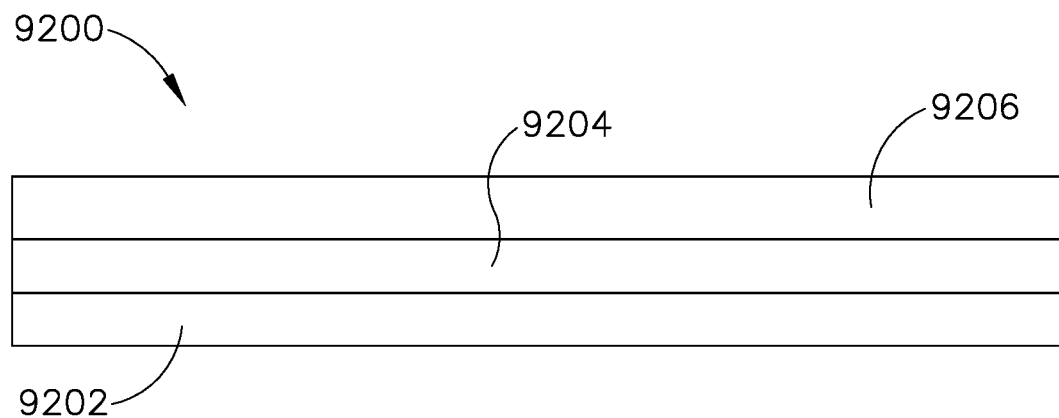
Figure 178:
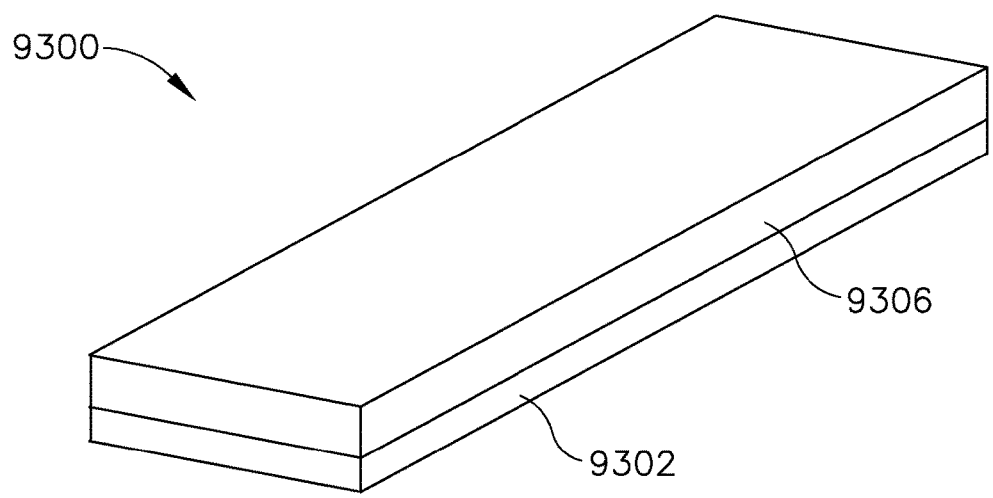
Figure 179:
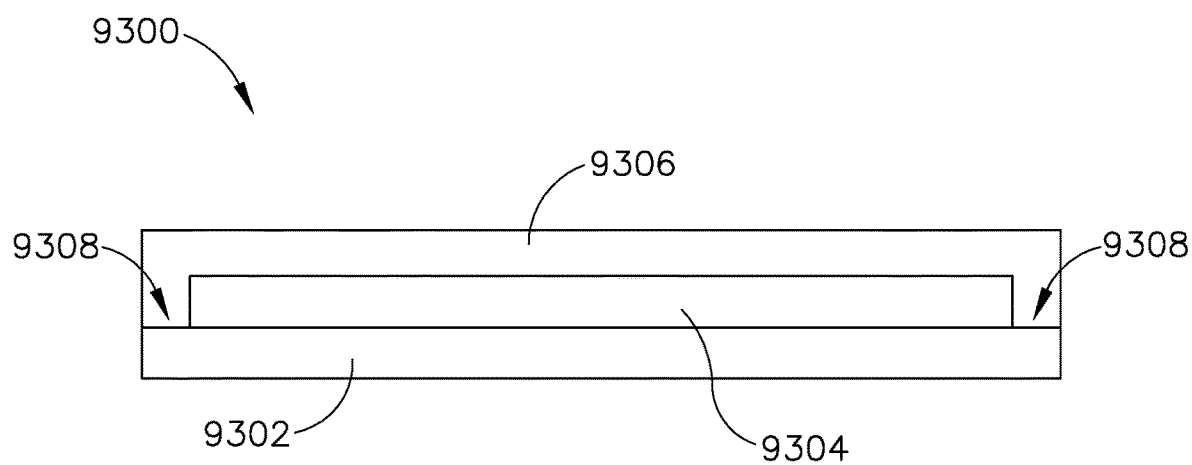
Figure 180:
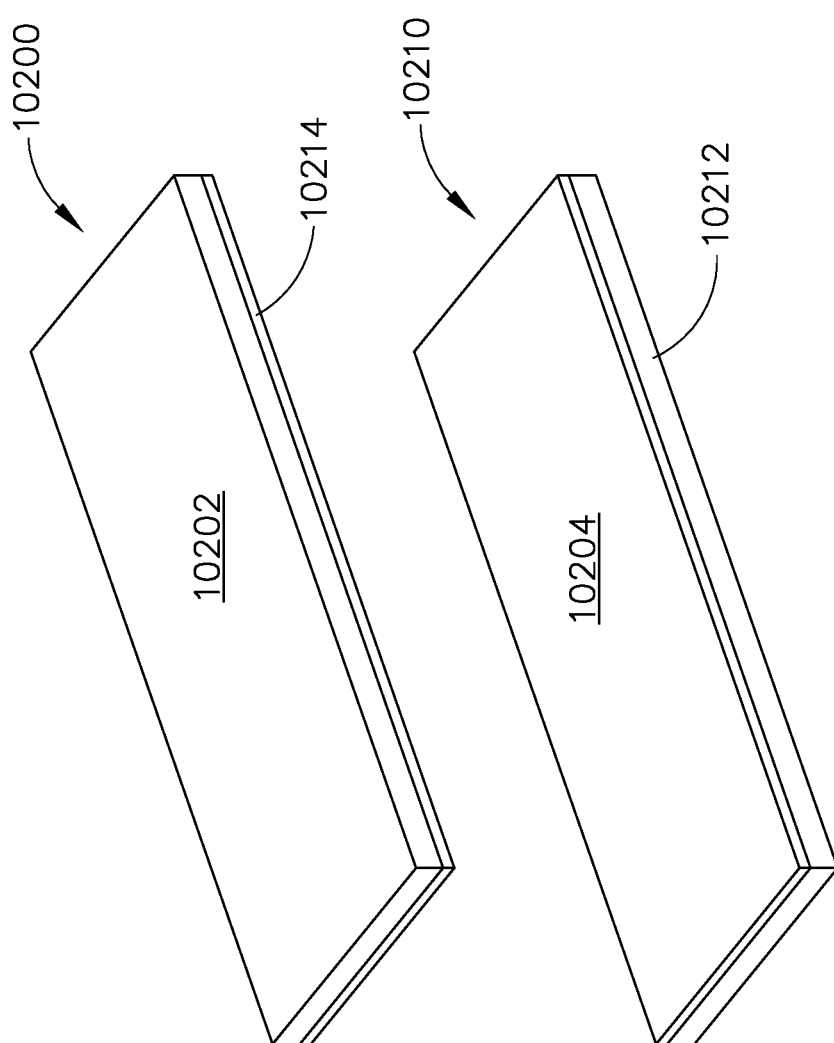
Figure 181:
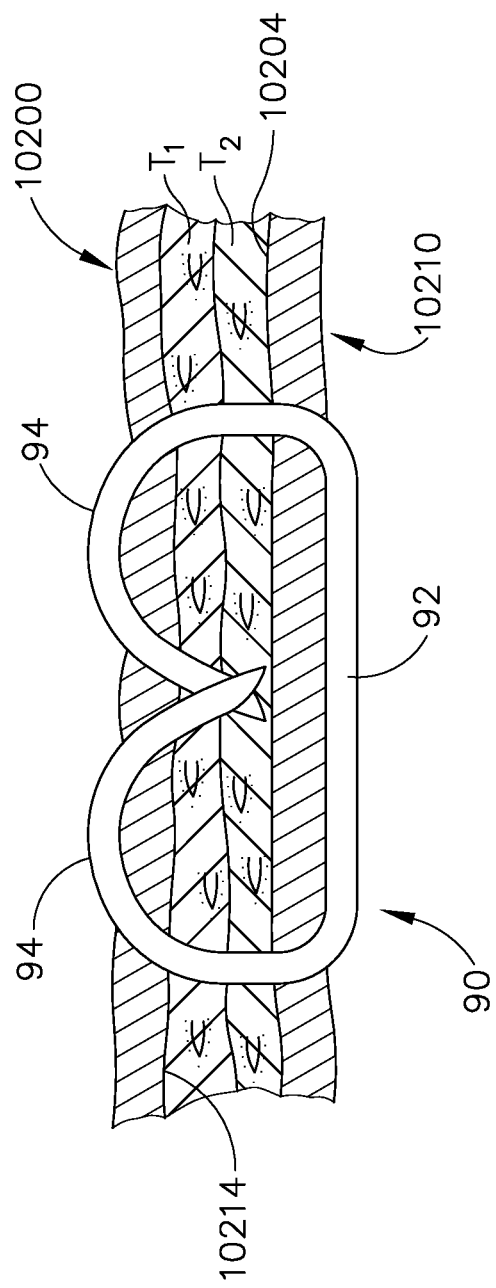
Figure 182:
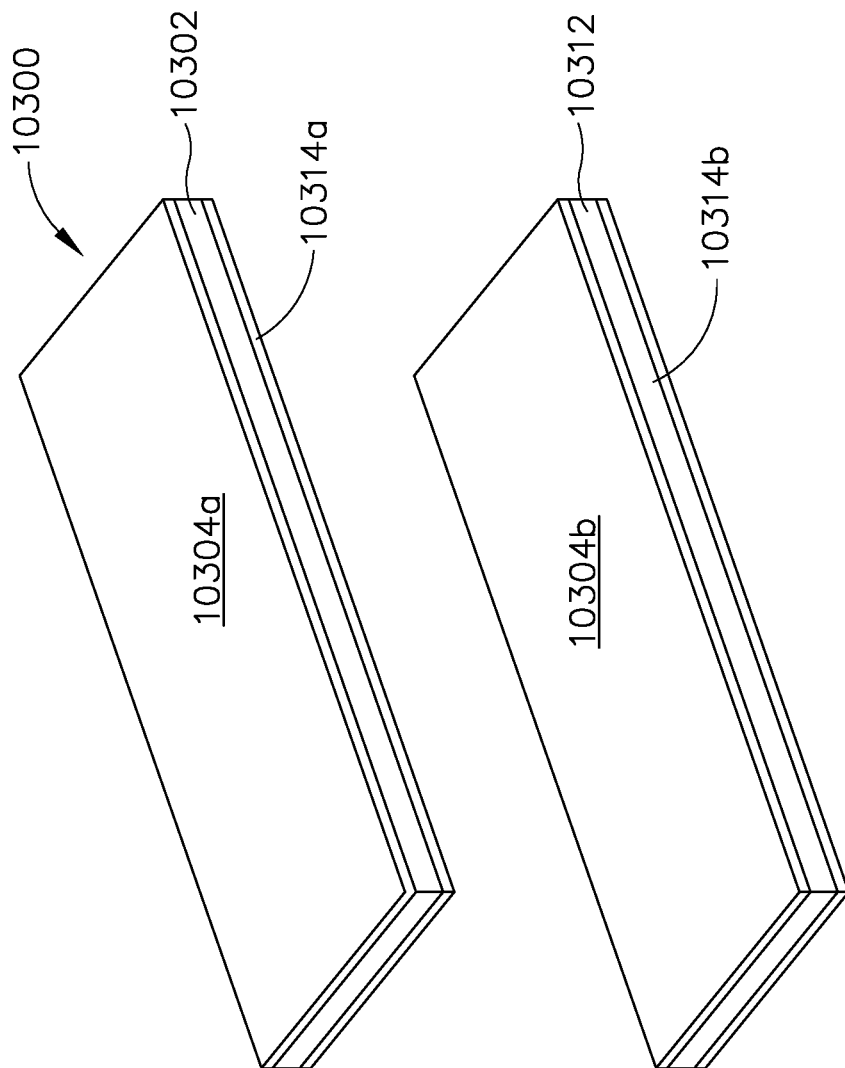
Figure 183:
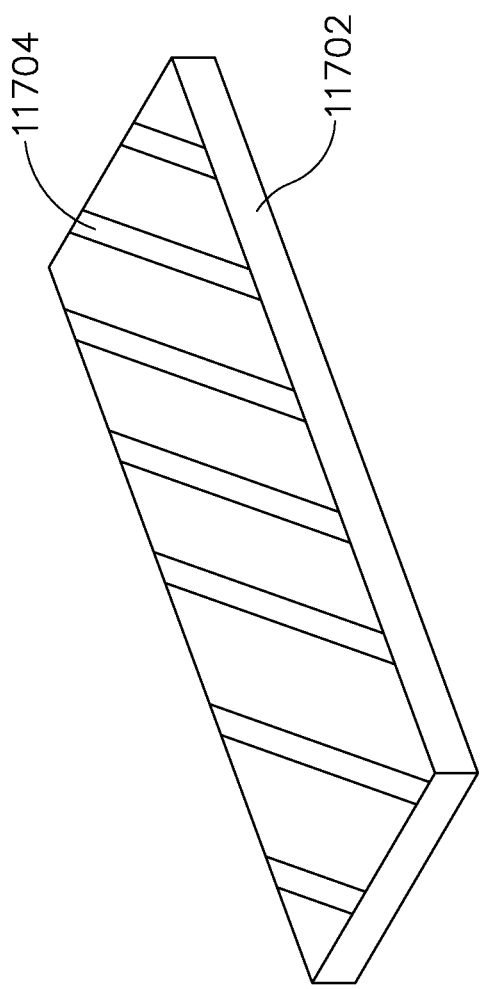
Figure 184:
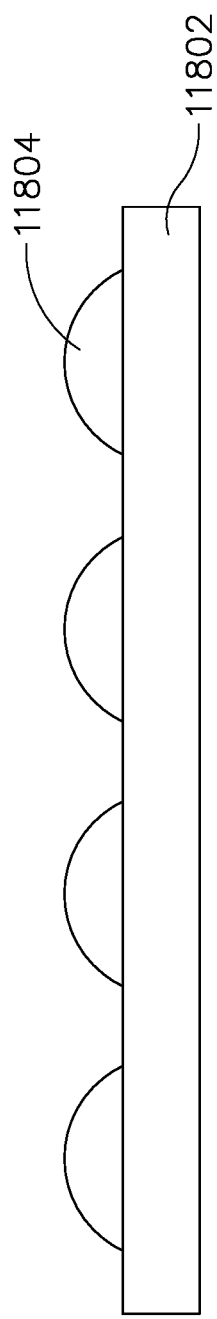
Figure 185:
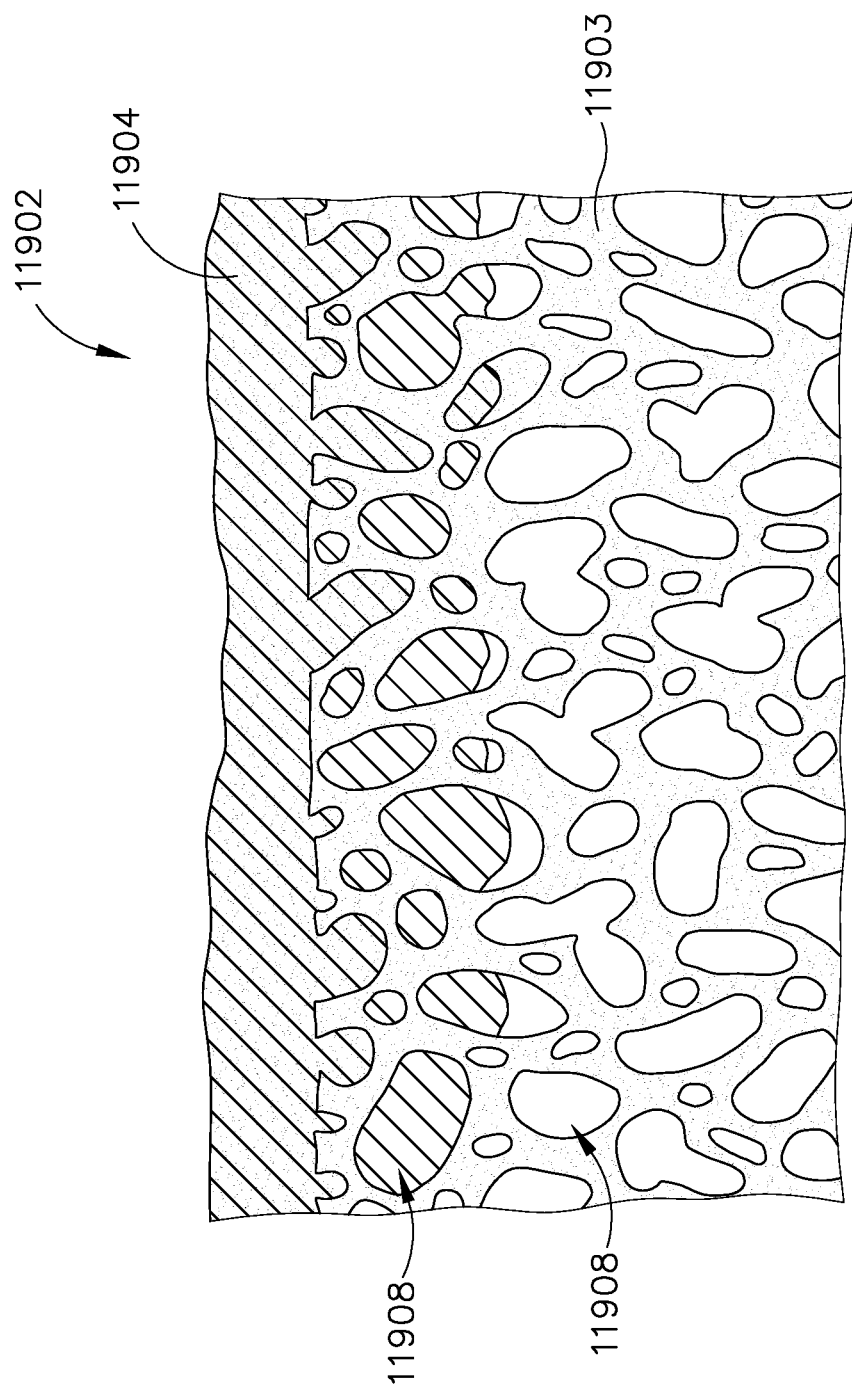

FIG. 94B depicts a top plan view of the mesh layer of the multilayer buttress of FIG. 92 in a stretched position;

FIG. 95A depicts a top plan view of the film layer of the multilayer buttress of FIG. 92 in a relaxed position;

FIG. 95B depicts a top plan view of the film layer of the multilayer buttress of FIG. 92 in a stretched position;

FIG. 96 depicts a top plan view of an alternative example of a film layer that may be incorporated in the multilayer buttress of FIG. 92;

FIG. 97 depicts a top plan view of another alternative example of a film layer that may be incorporated in the multilayer buttress of FIG. 92;

FIG. 98 depicts a top plan view of another alternative example of a film layer that may be incorporated in the multilayer buttress of FIG. 92;

FIG. 99 depicts a partial cross-sectional view of an exemplary method of using a laser to form holes in the film layer of the multilayer buttress of FIG. 92;

FIG. 100 depicts a partial cross-sectional view of an exemplary method of using a roller to form holes in the film layer of the multilayer buttress of FIG. 92;

FIG. 101 depicts a partial cross-sectional view of an exemplary method of using a press to form holes in the film layer of the multilayer buttress of FIG. 92;

FIG. 102 depicts a perspective view of another exemplary alternative staple cartridge incorporated into the lower jaw of end effector of instrument of FIG. 1, including an exemplary alternative buttress assembly;

FIG. 103 depicts a detailed perspective view of the staple cartridge and buttress assembly of FIG. 102, showing retention features for releasably coupling the buttress assembly to the staple cartridge;

FIG. 104A depicts a partial cross-sectional side view of the staple cartridge and buttress assembly of FIG. 102, showing the retention features coupling the buttress assembly to the staple cartridge;

FIG. 104B depicts a partial cross-sectional side view of the staple cartridge and buttress assembly of FIG. 102, showing the retention features having been decoupled to release the buttress assembly from the staple cartridge;

FIG. 105 depicts a top plan view of a connector portion suitable for coupling a buttress assembly to a staple cartridge;

FIG. 106 depicts a top plan view of an exemplary alternative buttress assembly;

FIG. 107 depicts a perspective view of an exemplary alternative staple cartridge incorporated into the lower jaw of end effector of instrument of FIG. 1, showing the connector portion of FIG. 105 and the buttress assembly of FIG. 106;

FIG. 108 depicts a side elevational view of the staple cartridge of FIG. 107, showing the buttress assembly of FIG. 106 being directed into engagement with the connector portions of FIG. 105;

FIG. 109 depicts a perspective view of another exemplary alternative staple cartridge incorporated into the lower jaw of end effector of instrument of FIG. 1, including another exemplary alternative buttress assembly and connector portion;

FIG. 110 depicts a perspective view of another exemplary alternative staple cartridge incorporated into the lower jaw of end effector of instrument of FIG. 1, including another exemplary alternative buttress assembly and connector portion;

FIG. 111 depicts a perspective view of another exemplary alternative staple cartridge incorporated into the lower jaw of end effector of instrument of FIG. 1, including another exemplary alternative buttress assembly and connector portion;

FIG. 112 depicts a perspective view of another exemplary alternative staple cartridge incorporated into the lower jaw of end effector of instrument of FIG. 1, including another exemplary alternative buttress assembly and connector portion;

FIG. 113 depicts a perspective view of another exemplary alternative staple cartridge incorporated into the lower jaw of end effector of instrument of FIG. 1, including another exemplary alternative buttress assembly and connector portion;

FIG. 114 depicts a top plan view of an exemplary alternative head portion suitable for incorporation into any of the connector portions shown in FIGS. 105 and 107-113;

FIG. 115 depicts a top plan view of an exemplary alternative head portion suitable for incorporation into any of the connector portions shown in FIGS. 105 and 107-113;

FIG. 116 depicts a top plan view of another exemplary alternative head portion suitable for incorporation into any of the connector portions shown in FIGS. 105 and 107-113;

FIG. 117 depicts a top plan view of another exemplary alternative head portion suitable for incorporation into any of the connector portions shown in FIGS. 105 and 107-113;

FIG. 118 depicts a top plan view of another exemplary alternative head portion suitable for incorporation into any of the connector portions shown in FIGS. 105 and 107-113;

FIG. 119 depicts a top plan view of another exemplary alternative head portion suitable for incorporation into any of the connector portions shown in FIGS. 105 and 107-113;

FIG. 120 depicts a top plan view of another exemplary alternative head portion suitable for incorporation into any of the connector portions shown in FIGS. 105 and 107-113;

FIG. 121 depicts a top plan view of another exemplary alternative head portion suitable for incorporation into any of the connector portions shown in FIGS. 105 and 107-113;

FIG. 122 depicts a top plan view of another exemplary alternative head portion suitable for incorporation into any of the connector portions shown in FIGS. 105 and 107-113;

FIG. 123 depicts a top plan view of another exemplary alternative head portion suitable for incorporation into any of the connector portions shown in FIGS. 105 and 107-113;

FIG. 124 depicts a top plan view of another exemplary alternative head portion suitable for incorporation into any of the connector portions shown in FIGS. 105 and 107-113;

FIG. 125 depicts a top plan view of another exemplary alternative head portion suitable for incorporation into any of the connector portions shown in FIGS. 105 and 107-113;

FIG. 126 depicts a perspective view of another exemplary alternative staple cartridge incorporated into the lower jaw of end effector of instrument of FIG. 1, FIG. 127 depicts a side elevational view of another exemplary alternative buttress assembly;

FIG. 128 depicts a top plan view of the buttress assembly of FIG. 127;

FIG. 129 depicts a detailed top plan view showing an attachment feature of the buttress assembly of FIG. 127 having been engaged with the staple cartridge of FIG. 126;

FIG. 130 depicts a cross-sectional perspective view of an attachment feature of the buttress assembly of FIG. 127 having been engaged with the staple cartridge of FIG. 126;

FIG. 131 depicts a cross-sectional end view showing the attachment feature of the buttress assembly of FIG. 127 having been engaged with the staple cartridge of FIG. 126;

FIG. 132 depicts a perspective view of another exemplary alternative staple cartridge incorporated into the lower jaw of end effector of instrument of FIG. 1;

FIG. 133 depicts a side elevational view of another exemplary alternative buttress assembly;

FIG. 134 depicts a top plan view of the buttress assembly of FIG. 133;

FIG. 135 depicts a cross-sectional view, taken along line 135-135 of FIG. 132, showing an attachment feature of the buttress assembly of FIG. 133 having been engaged with the staple cartridge of FIG. 132;

FIG. 136 depicts a cross-sectional view, taken along line 136-136 of FIG. 135, showing the attachment feature of the buttress assembly of FIG. 133 having been engaged with the staple cartridge of FIG. 132;

FIG. 137 depicts a perspective view of another exemplary alternative staple cartridge incorporated into the lower jaw of end effector of instrument of FIG. 1;

FIG. 138 depicts a side elevational view of another exemplary alternative buttress assembly;

FIG. 139 depicts a top plan view of the buttress assembly of FIG. 138;

FIG. 140 depicts a cross-sectional perspective view, taken along line 140-140 of FIG. 137, showing an attachment feature of the buttress assembly of FIG. 138 having been engaged with the staple cartridge of FIG. 137;

FIG. 141 depicts a cross-sectional end view showing the attachment feature of the buttress assembly of FIG. 138 having been engaged with the staple cartridge of FIG. 137;

FIG. 142 depicts a perspective view of another exemplary alternative staple cartridge incorporated into the lower jaw of end effector of instrument of FIG. 1, including another exemplary alternative buttress assembly;

FIG. 143 depicts a perspective view of the proximal end of the staple cartridge of FIG. 142, showing an exemplary attachment feature of the buttress assembly of FIG. 142;

FIG. 144 depicts a perspective view of the proximal end of the staple cartridge of FIG. 142, showing an exemplary attachment feature that may be used with the buttress assembly of FIG. 142;

FIG. 145 depicts an end view of the proximal end of the staple cartridge of FIG. 142, showing an exemplary attachment feature that may be used with the buttress assembly of FIG. 142;

FIG. 146 depicts a cross-sectional perspective view of the proximal end of the staple cartridge of FIG. 142 with the attachment feature of FIG. 145;

FIG. 147 depicts a perspective view of another exemplary alternative staple cartridge incorporated into the lower jaw of end effector of instrument of FIG. 1, including another exemplary alternative buttress assembly;

FIG. 148 depicts a partial perspective view of the proximal end of the buttress assembly of FIG. 147;

FIG. 149A depicts a bottom plan view of retention features of the buttress assembly of FIG. 147 engaged with a sled of the cartridge of FIG. 147;

FIG. 149B depicts a bottom plan view of retention features of the buttress assembly of FIG. 147, showing the sled having moved distally and out of engagement with the retention features;

FIG. 150 depicts a partial perspective view of the proximal end of another exemplary alternative buttress assembly that may be applied to the end effector of FIG. 2;

FIG. 151 depicts a partial top plan view of another exemplary alternative buttress assembly that may be applied to the end effector of FIG. 2;

FIG. 152 depicts a perspective view of the buttress assembly of FIG. 151 after having been severed after actuation of the end effector FIG. 2;

FIG. 153 depicts a top plan view of another exemplary alternative buttress assembly that may be applied to the end effector of FIG. 2, showing part of the buttress assembly having been severed after actuation of the end effector;

FIG. 154 depicts a top plan view of another exemplary alternative buttress assembly that may be applied to the end effector of FIG. 2;

FIG. 155 depicts a top plan view of another exemplary alternative buttress assembly that may be applied to the end effector of FIG. 2;

FIG. 156 depicts a partial perspective view of another exemplary alternative buttress assembly that may be applied to the end effector of FIG. 2;

FIG. 157 depicts a top plan view of another exemplary alternative buttress assembly that may be applied to the end effector of FIG. 2;

FIG. 158 depicts a top plan view of a connecting member that may be applied to the end effector of FIG. 2 to connect two portions of a buttress assembly;

FIG. 159A depicts a perspective view of another exemplary alternative staple cartridge incorporated into the lower jaw of the end effector of FIG. 2, including another exemplary alternative buttress assembly;

FIG. 159B depicts a perspective view of the staple cartridge of FIG. 159A, showing the buttress assembly having been displaced from a channel of the cartridge by a knife member;

FIG. 160 depicts a perspective view of another exemplary alternative buttress assembly that may be applied to the end effector of FIG. 2;

FIG. 161 depicts a cross-sectional end view of a portion of the end effector of FIG. 2 with an exemplary alternative buttress assembly applied to the end effector;

FIG. 162A depicts a cross-sectional end view of a portion of the buttress assembly of FIG. 161 applied to tissue with staples, with an end portion of the buttress assembly shown in a rolled configuration;

FIG. 162B depicts a cross-sectional end view of a portion of the buttress assembly of FIG. 161 applied to tissue with staples, with the end portion of the buttress assembly shown in a unrolled configuration;

FIG. 163 depicts a cross-sectional end view of a portion of the end effector of FIG. 2 with an exemplary alternative buttress assembly applied to the end effector;

FIG. 164 depicts a cross-sectional end view of a portion of the buttress assembly of FIG. 163 applied to tissue with staples;

FIG. 165 depicts a perspective view of another exemplary alternative staple cartridge incorporated into the lower jaw of end effector of instrument of FIG. 1, including another exemplary alternative buttress assembly;

FIG. 166 depicts a top plan view of tissue severed and stapled multiple times in succession using the cartridge and buttress assembly of FIG. 165;

FIG. 167 depicts an enlarged schematic view of an exemplary planar fabric comprising woven fibers, suitable for incorporation into the buttresses of FIG. 4;

FIG. 168 depicts two top plan views showing a buttress body in a stretched state and the buttress body in a relaxed state;

FIG. 169 depicts an enlarged schematic view of an exemplary planar fabric comprising knitted fibers, suitable for incorporation into the buttresses of FIG. 4;

FIG. 170 depicts an enlarged schematic view of an exemplary planar fabric comprising fibers knitted in a tricot pattern, suitable for incorporation into the buttresses of FIG. 4;

FIG. 171 depicts an enlarged schematic view of an exemplary planar fabric comprising fibers knitted in a weft insertion pattern, suitable for incorporation into the buttresses of FIG. 4;

FIG. 172 depicts an enlarged schematic view of an exemplary planar fabric comprising fibers knitted in a weft pattern, suitable for incorporation into the buttresses of FIG. 4;

FIG. 173 depicts an enlarged schematic view of an exemplary planar fabric comprising knitted fibers, suitable for incorporation into the buttresses of FIG. 4;

FIG. 174 depicts two top plan views showing a woven planar fabric in a stretched state and the woven planar fabric in a relaxed state;

FIG. 175 depicts two top plan views showing a buttress body in a stretched state and the buttress body in a relaxed state;

FIG. 176 depicts a perspective view of an exemplary alternative buttress;

FIG. 177 depicts a cross-sectional end view of the buttress of FIG. 176;

FIG. 178 depicts a perspective view of another exemplary alternative buttress;

FIG. 179 depicts a cross-sectional end view of the buttress of FIG. 177;

FIG. 180 depicts a perspective view of another exemplary upper buttress and an another exemplary lower buttress, each of which may be applied to the end effector of FIG. 2;

FIG. 181 depicts a cross-sectional view of a staple and the upper and lower buttresses of FIG. 180 having been secured to the tissue by the end effector of FIG. 2;

FIG. 182 depicts a perspective view of another exemplary upper buttress and another exemplary lower buttress, each of which may be applied to the end effector of FIG. 2;

FIG. 183 depicts a perspective view of an exemplary alternative buttress assembly;

FIG. 184 depicts a cross-sectional side view of another exemplary alternative buttress assembly; and FIG. 185 depicts a cross-sectional side view of another exemplary alternative buttress assembly.

The drawings are not intended to be limiting in any way, and it is contemplated that various embodiments of the invention may be carried out in a variety of other ways, including those not necessarily depicted in the drawings.

The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (α). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, now U.S. Pat. No. 9,186,142, issued Nov. 17, 2015, the disclosure of which is incorporated by reference herein; and/or U.S. patent application Ser. No. 14/314,125, entitled "Articulation Drive Features for Surgical Stapler," filed Jun. 25, 2014, now U.S. Pub. No. 2015/0374360, published Dec. 31, 2105, issued as U.S. Pat. No. 10,292,701 on May 21, 2019, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, now U.S. Pat. No. 9,795,379, issued Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 3:
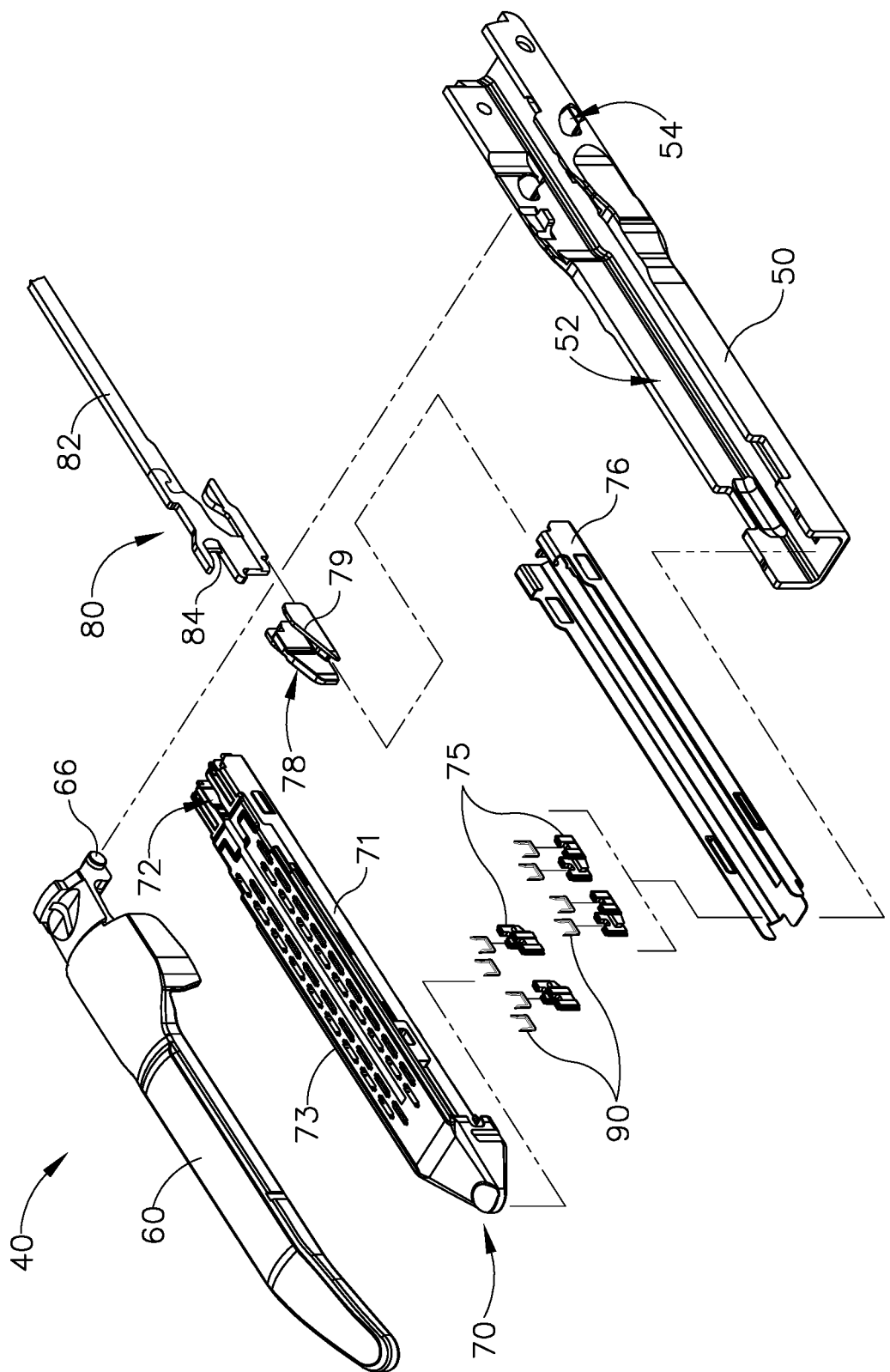
FIG. 3 depicts an exploded perspective view of the end effector of FIG. 2.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, now U.S. Pat. No. 9,808, 248, issued Nov. 7, 2017, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position, staple drivers (75) are in downward positions and staples (90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U. U.S. Pub. No. 2014/0239042, entitled "Integrated Tissue Positioning and Jaw Alignment Features for Surgical Stapler," published Aug. 28, 2014, now U.S. Pat. No. 9,517, 065, issued Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, now U.S. Pat. No. 9,808,248, issued Nov. 7, 2017, the disclosure of which is incorporated by reference herein. Other suitable forms that staple cartridge (70) may take will be apparent to those of ordinary skill in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, now U.S. Pat. No. 9,517,065, issued Dec. 13, 2016; at least some of the teachings of U.S. Pub. No. 2014/0239036, entitled "Jaw Closure Feature for End Effector of Surgical Instrument," published Aug. 28, 2014, now U.S. Pat. No. 9,839, 421, issued Dec. 12, 2107; and/or at least some of the teachings of U.S. Pub. No. 2014/0239037, entitled "Staple Forming Features for Surgical Stapling Instrument," published Aug. 28, 2014, now U.S. Pat. No. 10,092,292, issued Oct. 9, 2018, the disclosure of which is incorporated by reference herein. Other suitable forms that anvil (60) may take will be apparent to those of ordinary skill in the art in view of the teachings herein.

In the present example, a knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,848,871 on Dec. 26, 2017, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, now U.S. Pub No. 2015/0374373, published Dec. 31, 2015, issued as U.S. Pat. No. 10,355,147 on Jul. 2, 2019, the disclosure of which is incorporated by reference herein.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also in the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein.; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. patent application Ser. No. 14/226,142, entitled "Surgical Instrument Comprising a Sensor System," filed Mar. 26, 2014, now U.S. Pat. No. 9,913,642, issued Mar. 13, 2018, the disclosure of which is incorporated by reference herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Buttress Assembly for Surgical Stapler

In some instances, it may be desirable to equip end effector (40) with a buttress material to reinforce the mechanical fastening of tissue provided by staples (90). Such a buttress may prevent the applied staples (90) from pulling through the tissue and may otherwise reduce a risk of tissue tearing at or near the site of applied staples (90). In addition to or as an alternative to providing structural support and integrity to a line of staples (90), a buttress may provide various other kinds of effects such as spacing or gap-filling, administration of therapeutic agents, and/or other effects. In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various examples of forms that a buttress may take will be described in greater detail below. Various ways in which a buttress may be secured to a staple cartridge (70) or an anvil (60) will also be described in greater detail below.

A. Exemplary Composition of Buttress Assembly for Surgical Stapler

FIG. 4 shows an exemplary pair of buttress assemblies (100, 110) with a basic composition. Buttress assembly (100) of this example comprises a buttress body (102) and an upper adhesive layer (104). Similarly, buttress assembly (110) comprises a buttress body (112) and a lower adhesive layer (114). In the present example, each buttress body (102, 112) comprises a strong yet flexible material configured to structurally support a line of staples (90). By way of example only, each buttress body (102, 112) may comprise a mesh of polyglactin 910 material by Ethicon, Inc. of Somerville, N.J. Alternatively, any other suitable materials or combinations of materials may be used in addition to or as an alternative to polyglactin 910 material to form each buttress body (102, 112). Each buttress body (102, 112) may take any other suitable form and may be constructed of any other suitable material(s). By way of further example only, each buttress body (102, 112) may comprise one or more of the following: NEOVEIL absorbable PGA felt by Gunze Limited, of Kyoto, Japan; SEAMGUARD polyglycolic acid:trimethylene carbonate (PGA:TMC) reinforcement material by W.L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIODESIGN biologic graft material by Cook Medical, Bloomington, Ind.; and/or SURGICEL NU-KNIT hemostat material by Ethicon, Inc. of Somerville, N.J. Still other suitable materials that may be used to form each buttress body (102, 112) will be apparent to those of ordinary skill in the art in view of the teachings herein.

In addition or in the alternative, each buttress body (102, 112) may comprise a material including, for example, a hemostatic agent such as fibrin to assist in coagulating blood and reduce bleeding at the severed and/or stapled surgical site along tissue (90). As another merely illustrative example, each buttress body (102, 112) may comprise other adjuncts or hemostatic agents such as thrombin may be used such that each buttress body (102, 112) may assist to coagulate blood and reduce the amount of bleeding at the surgical site. Other adjuncts or reagents that may be incorporated into each buttress body (102, 112) may further include but are not limited to medical fluid or matrix components. Merely illustrative examples of materials that may be used to form each buttress body (102, 112), as well as materials that may be otherwise incorporated into each buttress body (102, 112), are disclosed in U.S. patent application Ser. No. 14/667,842, entitled "Method of Applying a Buttress to a Surgical Stapler," filed Mar. 25, 2015, now U.S. Pub. No. 2016/0278774, published Sep. 26, 2016, issued as U.S. Pat. No. 10,349,939 on Jul. 16, 2019, the disclosure of which is incorporated by reference herein. Alternatively, any other suitable materials may be used.

By way of further example only, each buttress body (102, 112) may be constructed in accordance with at least some of the teachings of U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018, the disclosure of which is incorporated by reference herein; U.S. Patent Pub. No. 2013/0068816, entitled "Surgical Instrument and Buttress Material," published Mar. 21, 2013, abandoned Jun. 28, 2016, the disclosure of which is incorporated by reference herein; U.S. Patent Pub. No. 2013/0062391, entitled "Surgical Instrument with Fluid Fillable Buttress," published March 14, now U.S. Pat. No. 9,999,408, issued Jun. 19, 2018, the disclosure of which is incorporated by reference herein; U.S. Patent Pub. No. 2013/0068820, entitled "Fibrin Pad Matrix with Suspended Heat Activated Beads of Adhesive," published Mar. 21, 2013, now U.S. Pat. No. 8,814,025, issued Aug. 26, 2014, the disclosure of which is incorporated by reference herein; U.S. Patent Pub. No. 2013/0082086, entitled "Attachment of Surgical Staple Buttress to Cartridge," published Apr. 4, 2013, now U.S. Pat. No. 8,899,464, issued Dec. 2, 2104, the disclosure of which is incorporated by reference herein; U.S. Patent Pub. No. 2013/0037596, entitled "Device for Applying Adjunct in Endoscopic Procedure," published Feb. 14, 2013, now U.S. Pat. No. 9,492,170, issued Nov. 15, 2016, the disclosure of which is incorporated by reference herein; U.S. Patent Pub. No. 2013/0062393, entitled "Resistive Heated Surgical Staple Cartridge with Phase Change Sealant," published Mar. 14, 2013, now U.S. Pat. No. 8,998,060, issued Apr. 7, 2015, the disclosure of which is incorporated by reference herein; U.S. Patent Pub. No. 2013/0075446, entitled "Surgical Staple Assembly with Hemostatic Feature," published Mar. 28, 2013, now U.S. Pat. No. 9,393,018, issued Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, now U.S. Pat. No. 9,101,359, issued Aug. 11, 2015, the disclosure of which is incorporated by reference herein; U.S. Patent Pub. No. 2013/0075445, entitled "Anvil Cartridge for Surgical Fastening Device," published Mar. 28, 2013, now U.S. Pat. No. 9,198,644, issued Dec. 1, 2015, the disclosure of which is incorporated by reference herein; U.S. Patent Pub. No. 2013/0075447, entitled "Adjunct Therapy for Applying Hemostatic Agent," published Mar. 28, 2013, abandoned Oct. 7, 2016, the disclosure of which is incorporated by reference herein; U.S. Patent Pub. No. 2013/0256367, entitled "Tissue Thickness Compensator Comprising a Plurality of Medicaments," published Oct. 3, 2013, now U.S. Pat. No. 9,211,120, issued Dec. 15, 2015, the disclosure of which is incorporated by reference herein; U.S. patent application Ser. No. 14/300,954, entitled "Adjunct Materials and Methods of Using Same in Surgical Methods for Tissue Sealing," filed Jun. 10, 2014, now U.S. Patent. Pub. No. 2015/0351758, published Dec. 10, 2015, issued as U.S. Pat. No. 10,172,611 on Jan. 8, 2019, the disclosure of which is incorporated by reference herein; U.S. patent application Ser. No. 14/827,856, entitled "Implantable Layers for a Surgical Instrument," filed Aug. 17, 2015, now U.S. Patent Pub. No. 2017/0049444, published Feb. 23, 2017, issued as U.S. Pat. No. 10,835,249 on Nov. 17, 2020, the disclosure of which is incorporated by reference herein; U.S. patent application Ser. No. 14/840,613, entitled "Drug Eluting Adjuncts and Methods of Using Drug Eluting Adjuncts," filed Aug. 31, 2015 now U.S. Patent Pub. No. 2017/0055986, published Mar. 2, 2017, issued as U.S. Pat. No. 10,569,071 on Feb. 25, 2020, the disclosure of which is incorporated by reference herein; U.S. patent application Ser. No. 14/871,071, entitled "Compressible Adjunct with Crossing Spacer Fibers," filed Sep. 30, 2015 now U.S. Patent Pub. No. 2017/0086837, published Mar. 30, 2017, issued as U.S. Pat. No. 10,433,846 on Oct. 8, 2019, the disclosure of which is incorporated by reference herein; and/or U.S. patent application Ser. No. 14/871,131, entitled "Method for Applying an Implantable Layer to a Fastener Cartridge," filed Sep. 30, 2015, now U.S. Patent Pub. No. 2017/0086842, published Mar. 30, 2017, the disclosure of which is incorporated by reference herein.

In the present example, adhesive layer (104) is provided on buttress body (102) in order to adhere buttress body (102) to underside (65) of anvil (60). Similarly, adhesive layer (114) is provided on buttress body (112) in order to adhere buttress body (112) to deck (73) of staple cartridge (70). Adherence of the buttress body (102) to underside (65) of anvil (60) or to deck (73) of staple cartridge (70) can occur through a variety of mechanisms including but not limited to a pressure sensitive adhesive. In some versions, each adhesive layer (104, 114) comprise a pressure sensitive adhesive material. Examples of various suitable materials that may be used to form adhesive layers (104, 114) are disclosed in U.S. patent application Ser. No. 14/667,842, entitled "Method of Applying a Buttress to a Surgical Stapler," filed Mar. 25, 2015, now U.S. Patent Pub. No. 2016/0278774, published Sep. 16, 2016, issued as U.S. Pat. No. 10,349,939 on Jul. 16, 2019, the disclosure of which is incorporated by reference herein. Alternatively, any other suitable materials may be used. It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (104, 114) will be apparent to those of ordinary skill in the art in view of the teachings herein.

B. Exemplary Materials and Techniques for Providing Adhesion of Buttress to Surgical Stapler As noted above, a buttress assembly (100, 110) may include a layer (104, 114) of adhesive material (or other form of adhesive material) that adheres buttress body (102, 112) to either underside (65) of anvil (60) or deck (73) of staple cartridge (70). Such an adhesive material may provide proper positioning of buttress body (102, 112) before and during actuation of end effector (40); then allow buttress body (102, 112) to separate from end effector (40) after end effector (40) has been actuated, without causing damage to buttress body (102, 112) that is substantial enough to compromise the proper subsequent functioning of buttress body (102, 112).

Figure 5A:
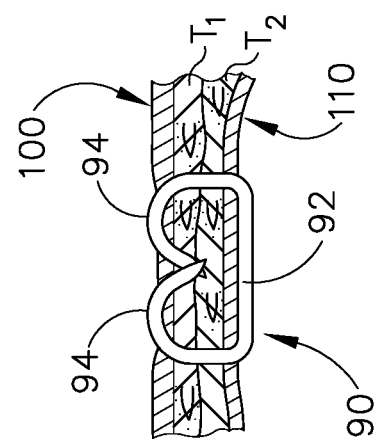
FIG. 5A depicts a cross-sectional end view of a portion of the end effector of FIG. 2 with a buttress assembly formed by the buttresses of FIG. 4 applied to the end effector, with tissue positioned between the buttresses in the end effector, and with the anvil in an open position.
Figure 5B:
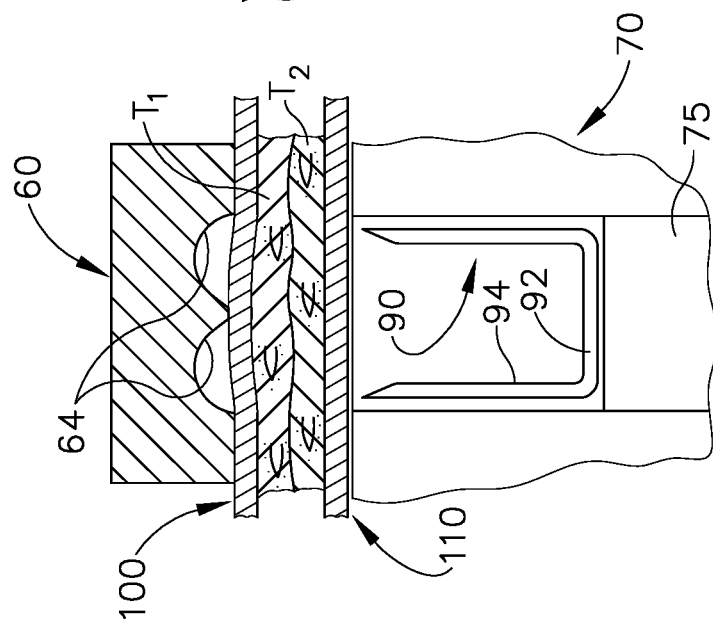
FIG. 5B depicts a cross-sectional end view of the combined end effector and buttress assembly of FIG. 5A, with tissue positioned between the buttresses in the end effector, and with the anvil in a closed position.
Figure 5C:
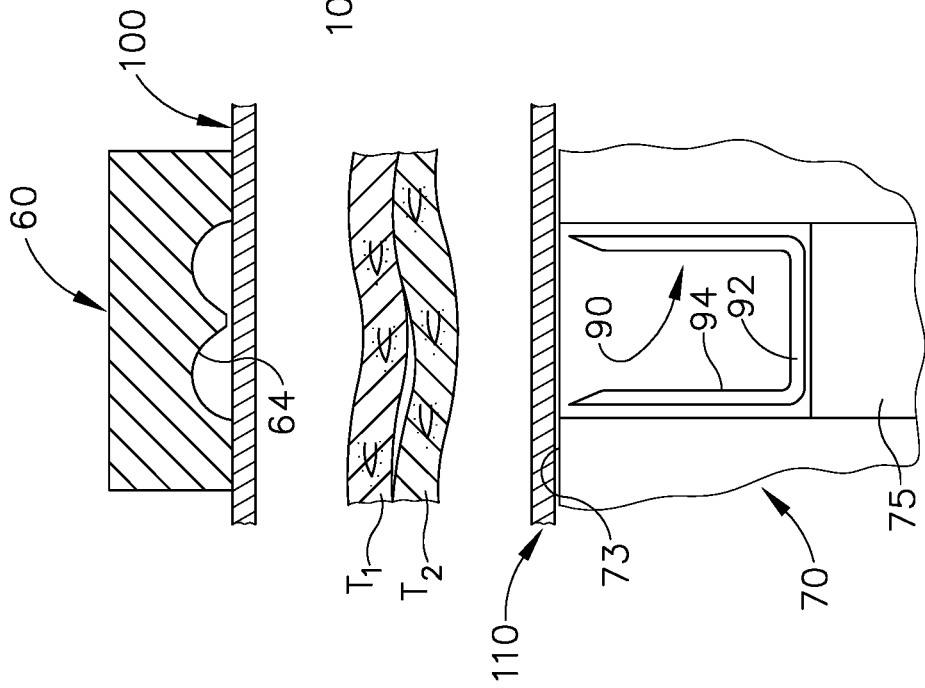
FIG. 5C depicts a cross-sectional view of a staple and the buttress assembly of FIG. 5A having been secured to the tissue by the end effector of FIG. 2.

FIGS. 5A-5C show a sequence where an end effector (40) that has been loaded with buttress assemblies (100, 110) is actuated to drive staples (90) through two apposed layers of tissue ($T_1$, $T_2$), with buttress assemblies (100, 110) being secured to the same layers of tissue ($T_1$, $T_2$) by staples (90). In particular, FIG. 5A shows layers of tissue ($T_1$, $T_2$) positioned between anvil (60) and staple cartridge (70), with anvil (60) in the open position. Buttress assembly (100) is adhered to the underside (65) of anvil (60) via adhesive layer (104); while buttress assembly (110) is adhered to deck (73) of staple cartridge (70) via adhesive layer (114). Layers of tissue ($T_1$, $T_2$) are thus interposed between buttress assemblies (100, 110). Next, trigger (24) is pivoted toward pistol grip (22) to drive closure tube (32) and closure ring (36) distally. This drives anvil (60) to the closed position as shown in FIG. 5B. At this stage, layers of tissue ($T_1$, $T_2$) are compressed between anvil (60) and staple cartridge (70), with buttress assemblies (100, 110) engaging opposite surfaces of tissue layers ($T_1$, $T_2$). End effector (40) is then actuated as described above, driving staple (90) through buttress assemblies (100, 110) and tissue (90). As shown in FIG. 5C, crown (92) of driven staple (90) captures and retains buttress assembly (110) against layer of tissue ($T_2$). Deformed legs (94) of staple (90) capture and retain buttress assembly (100) against layer of tissue ($T_1$).

Figure 6:
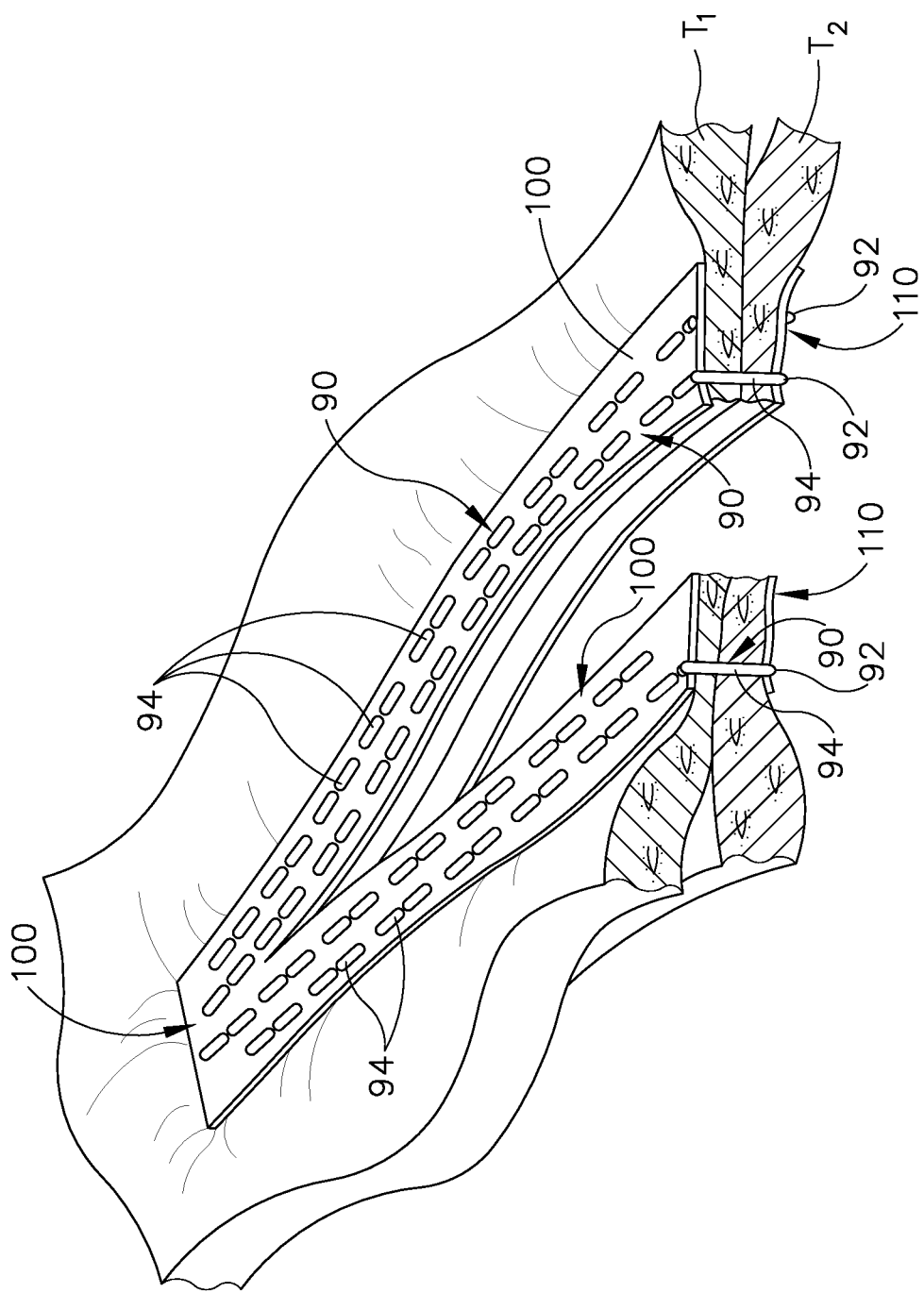
FIG. 6 depicts a perspective view of staples and the buttress assembly of FIG. 5A having been secured to the tissue by the end effector of FIG. 2.

It should be understood that a series of staples (90) will similarly capture and retain buttress assemblies (100, 110) against layers of tissue ($T_1$, $T_2$), thereby securing buttress assemblies (100, 110) to tissue ($T_1$, $T_2$) as shown in FIG. 6. As end effector (40) is pulled away from tissue (90) after deploying staples (90) and buttress assemblies (100, 110), buttress assemblies (100, 110) disengage end effector), such that buttress assemblies (100, 110) remain secured to tissue ($T_1$, $T_2$) with staples (90). Buttress tissue ($T_1$, $T_2$) thus provide structural reinforcement to the lines of staples (90). As can also be seen in FIG. 6, knife member (80) also cuts through a centerline of buttress tissue assemblies (100, 110), separating each buttress assemblies (100, 110) into a corresponding pair of sections, such that each section remains secured to a respective severed region of tissue ($T_1$, $T_2$).

In the foregoing example, buttress assembly (100) is sized to span across the full width of underside (65), such that buttress assembly (100) spans across channel (62). Thus, knife member (80) cuts through buttress assembly (100) during actuation of end effector (40) as described above. In some other examples, such as those described below, buttress assembly (100) is provided in two separate, laterally spaced apart portions, with one portion being disposed on underside (65) on one side of channel (62) and another portion being disposed on underside (65) on the other side of channel (62). In such versions, buttress assembly (100) does not span across channel (62), such that knife member (80) does not cut through buttress assembly (100) during actuation of end effector (40).

Likewise, buttress assembly (110) may be sized to span across the full width of deck (73), such that buttress assembly (110) spans across channel (72), and such that knife member (80) cuts through buttress assembly (110) during actuation of end effector (40) as described above. Alternatively, buttress assembly (110) may be provided in two separate, laterally spaced apart portions, with one portion being disposed on deck (73) on one side of channel (72) and another portion being disposed on deck (73) on the other side of channel (72), such that buttress assembly (110) does not span across channel (72), and such that knife member (80) does not cut through buttress assembly (110) during actuation of end effector (40).

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, now U.S. Patent Pub No. 2016/0278774, published Sep. 26, 2016, issued as U.S. Pat. No. 10,349,939 on Jul. 16, 2019, the disclosure of which is incorporated by reference herein.

III. Exemplary Buttress Applier Cartridges

As noted above, buttress assembly (100) may be applied to the underside (65) of anvil (60), and buttress (110) may be applied to deck (73) of staple cartridge (70), before tissue ($T_1$, $T_2$) is positioned in end effector (40), and before end effector (40) is actuated. Because end effector (40) may be actuated many times during use of instrument (10) in a single surgical procedure, it may be desirable to enable an operator to repeatedly and easily load buttress assemblies (100) on underside (65) of anvil (60) during that single surgical procedure. In other words, because end effector (40) may be actuated many times during use of instrument (10) in a single surgical procedure, it may be insufficient to simply provide anvil (60) pre-loaded with a buttress assembly (100) without facilitating the re-loading of anvil (60) with additional buttress assemblies (100) after end effector (40) has been actuated.

Similarly, those of ordinary skill in the art will recognize that staple cartridge (70) will need to be replaced each time end effector (40) is actuated. When end effector (40) is actuated several times during use of instrument (10) in a single surgical procedure, several staple cartridges (70) may thus be used during that surgical procedure. It may seem that each of these staple cartridges (70) may be provided with buttress assembly (110) pre-loaded on deck (73). However, there are some reasons why it may be undesirable to provide a staple cartridge (70) with buttress assembly (110) pre-loaded on deck (73). In other words, it may be desirable to provide loading of buttress assembly (110) on deck (73) immediately prior to usage of staple cartridge in the surgical procedure, rather than loading buttress assembly (110) on deck (73) a substantial time prior to the surgical procedure. For instance, buttress assembly (110) may not be compatible with the same sterilization techniques as staple cartridge (70), such that it may present processing difficulties to package staple cartridge (70) with buttress assembly (110) pre-loaded on deck (73). In addition, the material forming buttress assembly (110) may have certain environmental sensitivities that staple cartridge (70) does not have, such that it may be beneficial to enable buttress assembly (110) and staple cartridge (70) to be stored separately before use. Moreover, buttress assembly (110) may not be warranted or otherwise desired in some surgical procedures, such that it may be desirable to enable a physician to easily choose whether staple cartridge (70) should be loaded with buttress assembly (110) before that staple cartridge (70) is used in the surgical procedure.

In view of the foregoing, it may be desirable to enable an operator to repeatedly and easily load buttress assemblies (100, 110) on end effector (40) on an ad hoc basis during a given surgical procedure. It may also be desirable to provide a device that provides support and protection to buttress assemblies (100, 110) before buttress assemblies (100, 110) are loaded on end effector (40), in addition to that same device also enabling buttress assemblies (100, 110) to be easily loaded on end effector. The examples described below relate to various cartridge assemblies that provide such support, protection, and loading of buttress assemblies (100, 110). It should be understood that the following examples are merely illustrative. Numerous variations will be apparent to those of ordinary skill in the art in view of the teachings herein.

A. Exemplary Buttress Applier Cartridge with Active Retainer Arms

Figure 7:
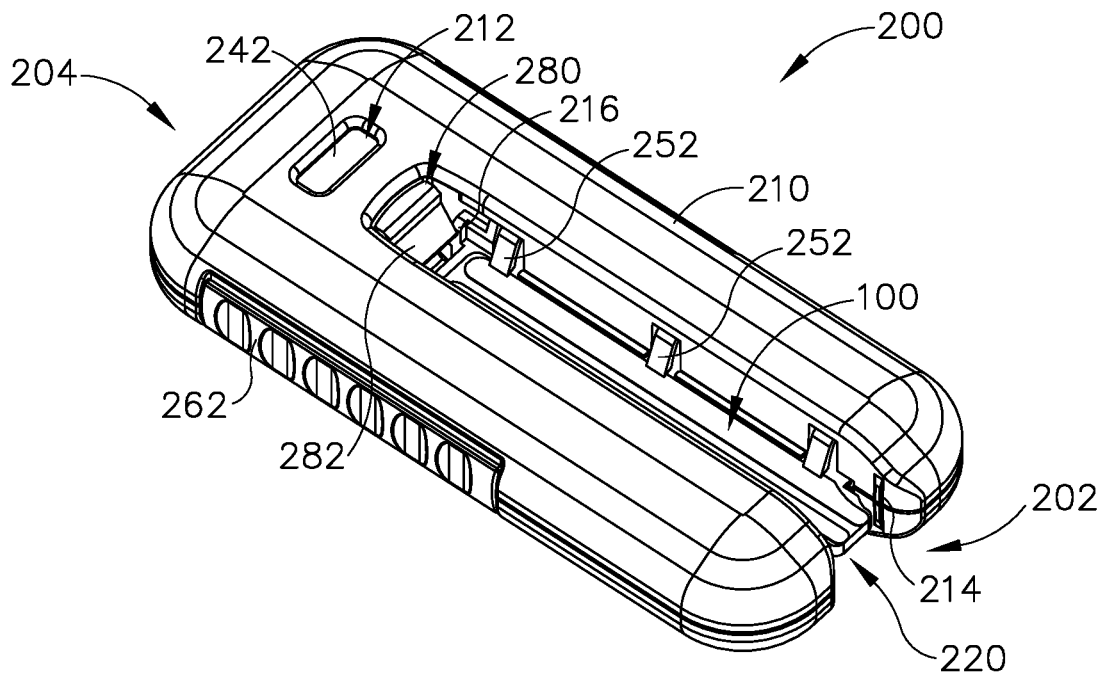
FIG. 7 depicts a perspective view of an exemplary buttress applier cartridge that may be used to carry and apply the buttress assembly of FIG. 5A.
Figure 8:
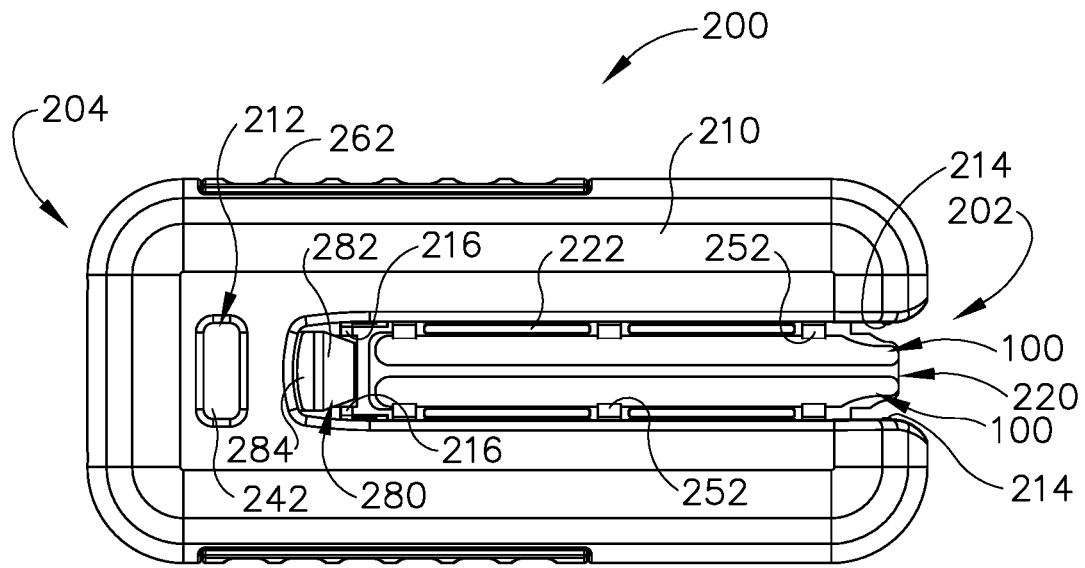
FIG. 8 depicts a top plan view of the buttress applier cartridge of FIG. 7.
Figure 9:
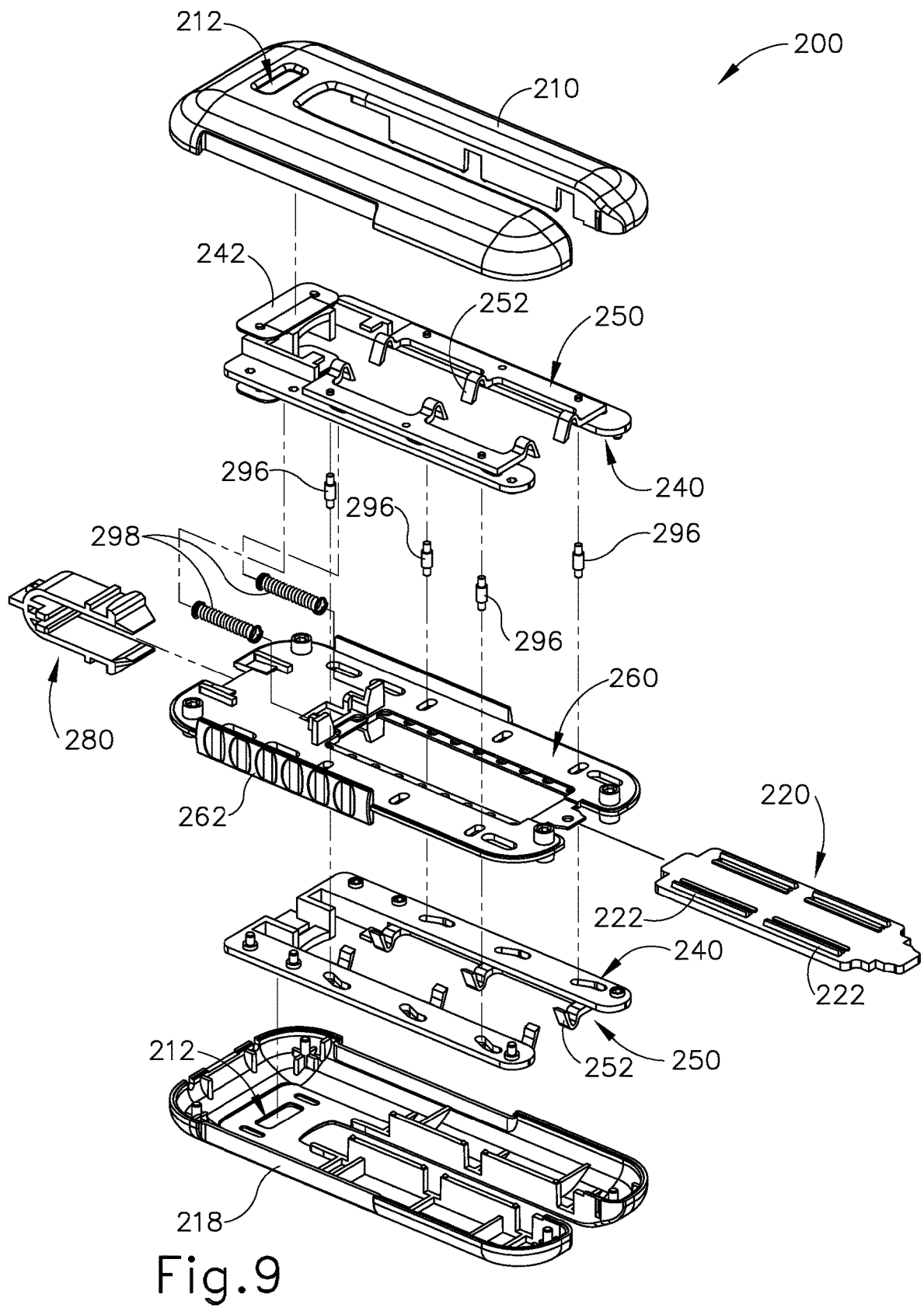
FIG. 9 depicts an exploded perspective view of the buttress applier cartridge of FIG. 7.

FIGS. 7-17B show an exemplary buttress applier cartridge (200) that may be used to support and protect buttress assemblies (100, 110). Cartridge (200) may also be used to easily load buttress assemblies (100, 110) on end effector (40). As best seen in FIGS. 7-8, cartridge (200) of this example comprises an open end (202) and a closed end (204). Open end (202) is configured to receive end effector (40) as will be described in greater detail below. Cartridge (200) further includes a first housing (210) and a second housing (218), which each generally define a "U" shape to present open end (202). As best seen in FIG. 9, various components are interposed between housings (210, 218). In particular, these components include a platform (220), a pair of actuator sleds (240), a pair of retainers (250), a chassis (260), and a sled retainer (280). Each of these components will be described in greater detail below.

Platform (220) of the present example is configured to support a pair of buttress assemblies (100) on one side of platform (220) and another pair of buttress assemblies (110) on the other side of platform (220). Platform (220) is exposed in recesses that are formed between the prongs of the "U" configuration of housings (210, 218). The location of platform (220) and buttress assemblies (100, 110) in such recesses may prevent inadvertent contact between buttress assemblies (100, 110) and other devices in the operating room. In other words, housings (210, 218) may provide some degree of physical shielding of buttress assemblies (100, 110).

In the present example, each buttress assembly (100, 110) is provided in a respective pair of portions that are separated to avoid spanning across channels (62, 72) of anvil (60) and staple cartridge (70), respectively, though it should be understood that platform (220) may just as easily support wide versions of buttress assemblies (100, 110) that unitarily span across channels (62, 72) of anvil (60) and staple cartridge (70), respectively. The outer edges of platform (220) are captured between housings (210, 218) and include retention features (222) in the form of ridges that further engage housings (210, 218) to prevent platform (220) from sliding relative to housings (210, 218). In some versions, platform (220) is formed of a material that provides a high coefficient of friction, thereby reducing any tendency that buttress assemblies (100, 110) might otherwise have to slide along corresponding surfaces of platform (220). For instance, platform (220) may comprise an elastomeric material and/or a foam material. In some instances, platform (220) is formed of a compressible foam material that is configured to maintain a compressed configuration after being compressed by end effector (40). By way of example only, platform (220) may comprise Santoprene, closed-cell polyurethane foam, any other compressible material, and/or a material that may be made compressible via geometry (e.g., a rubber material with deformable standing features). Various suitable materials and structural configurations that may be used to form platform (220) will be apparent to those of ordinary skill in the art in view of the teachings herein.

Figure 11:
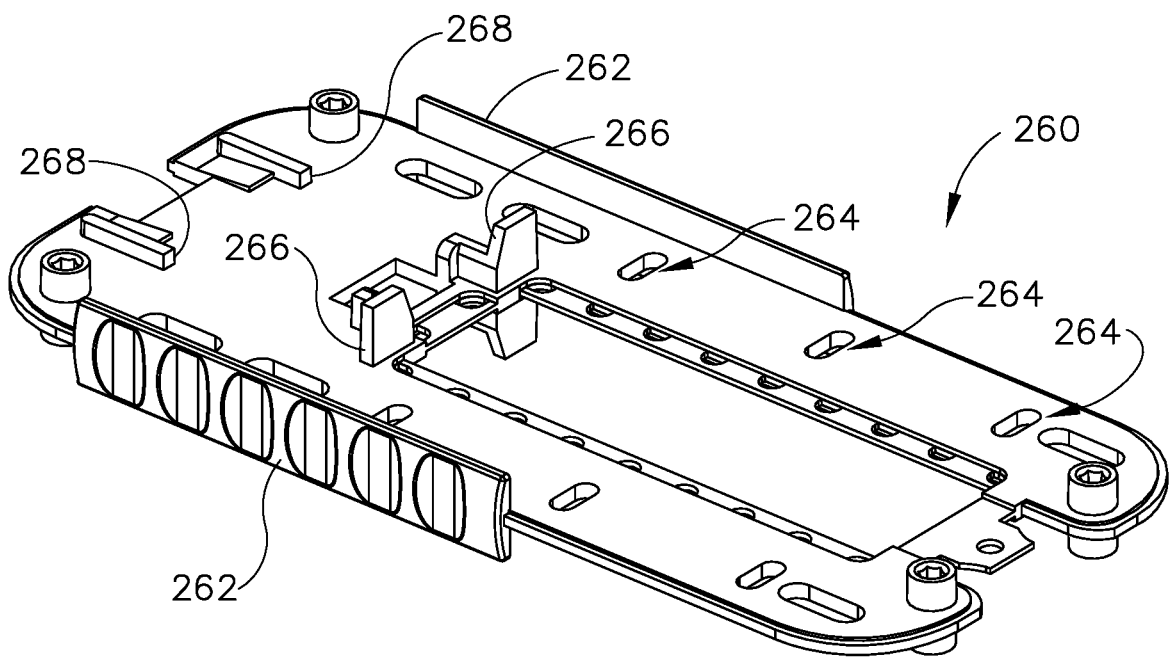
FIG. 11 depicts a perspective view of a chassis of the buttress applier cartridge of FIG. 7.
Figure 15A:
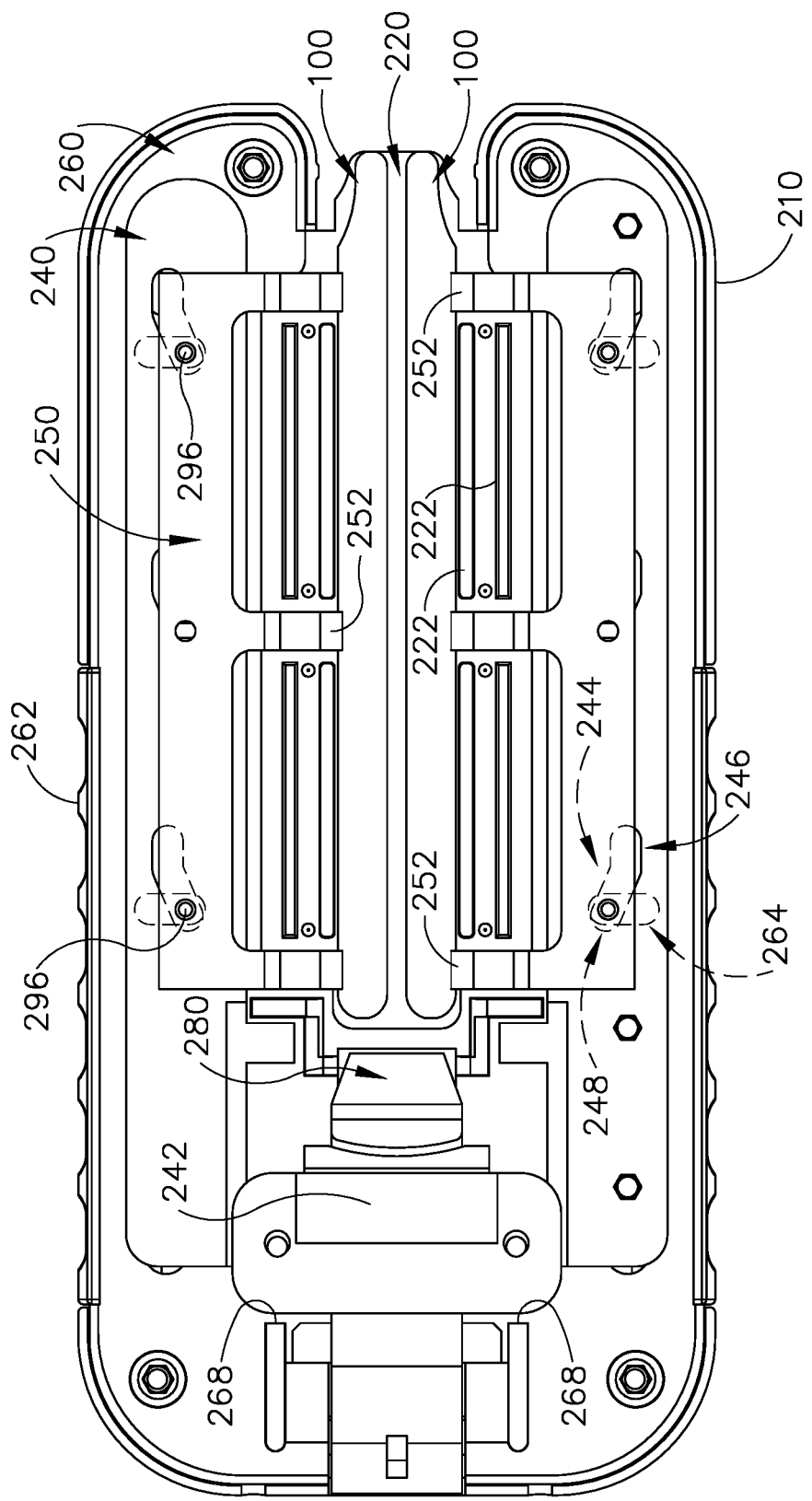
FIG. 15A depicts a top plan view of the buttress applier cartridge of FIG. 7, with a housing member removed, with a buttress assembly loaded on a platform of the buttress applier cartridge, and with retainers positioned to secure the buttress assembly to the platform.
Figure 15B:
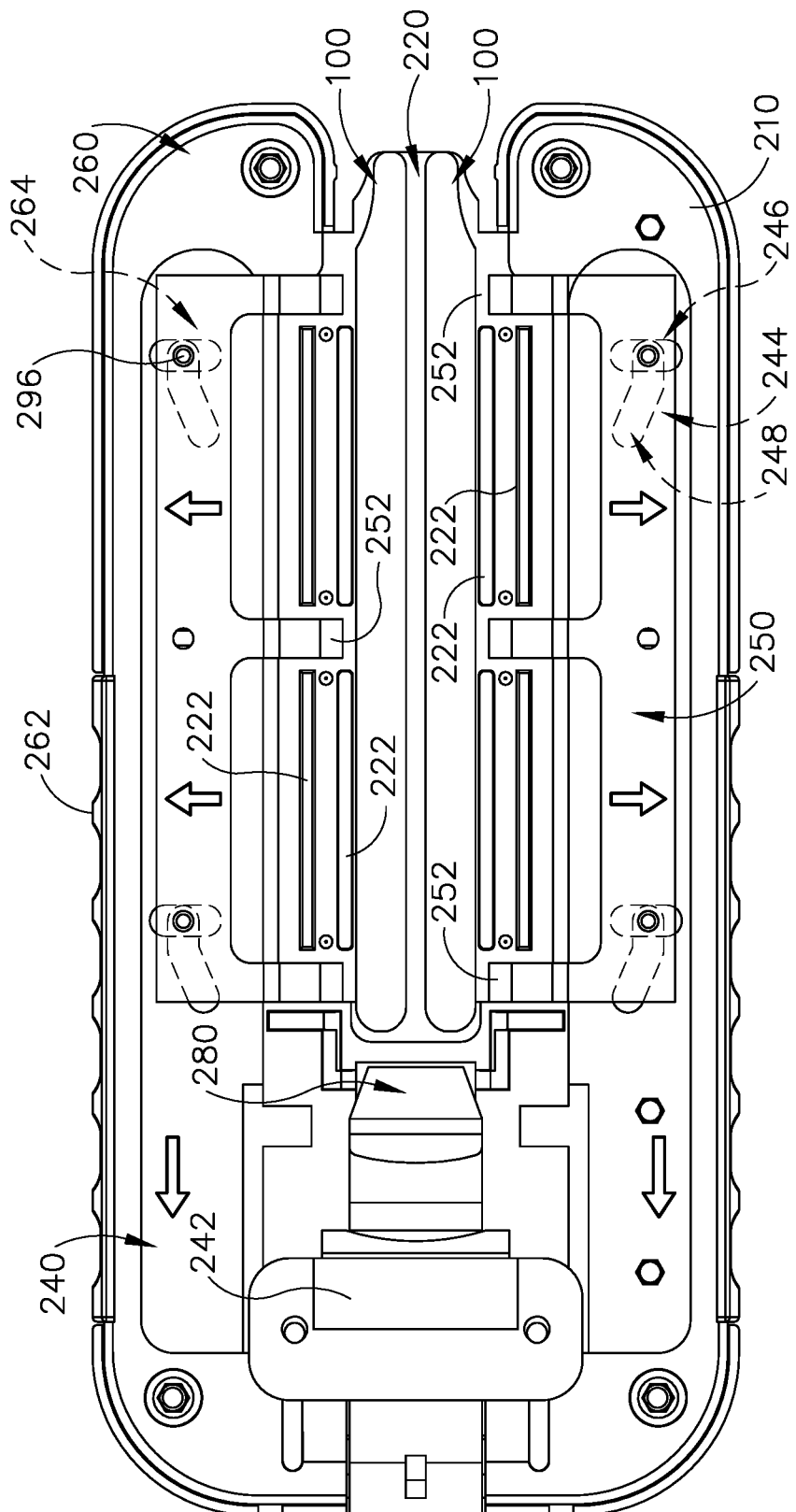
FIG. 15B depicts a top plan view of the buttress applier cartridge of FIG. 7, with a housing member removed, with a buttress assembly loaded on a platform of the buttress applier cartridge, and with retainers positioned to release the buttress assembly to the platform.

Chassis (260) is configured to cooperate with housings (210, 218) to provide a mechanical ground for moving components of cartridge (200) and provide structural support for components of cartridge (200). As shown in FIGS. 7-8, chassis (260) includes integral gripping features (262) that are exposed on opposite sides of housings (210, 218). Gripping features (262) have a surface geometry that is configured to promote an operator's grip of cartridge (200) during use of cartridge (200). Various suitable configurations that may be used for gripping features (262) will be apparent to those of ordinary skill in the art in view of the teachings herein. Similarly, various surface treatments (e.g., elastomeric material, etc.) that may be applied to gripping features (262) will be apparent to those of ordinary skill in the art in view of the teachings herein. As best seen in FIG. 11, chassis (260) further includes a set of laterally oriented slots (264), a first pair of bosses (266), and a second pair of bosses (268). Slots (264) are configured to slidably receive pins (296) as shown in FIGS. 9 and 15A-15B. In particular, pins (296) may translate laterally within slots (264) (i.e. toward and away from the central longitudinal axis extending along the center of platform (220)). In the present example, there are six slots (264) and only four pins (296), such that two of the slots (264) are not used. In other versions, there are six pins (296) such that all six slots (264) are used. In still other versions, there are only four slots (264), corresponding with the four pins (296) of the present example.

Figure 12:
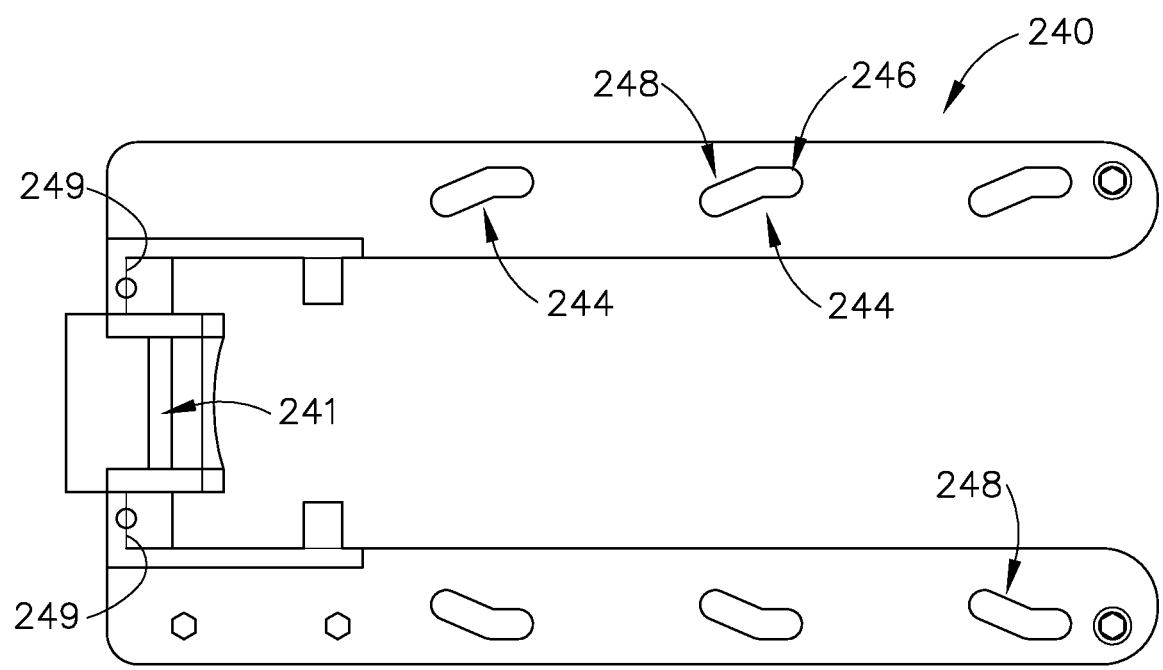
FIG. 12 depicts a top plan view of an actuator sled of the buttress applier cartridge of FIG. 7.

Actuator sleds (240) are slidably positioned on opposite faces of chassis (260). As shown in FIG. 12, each actuator sled includes a locking recess (241), a set of slots (244), and a pair of boss features (249). As shown in FIG. 9, a set of coil springs (298) are positioned between bosses (266) of chassis (260) and boss features (249) of actuator sled (240). Coil springs (298) resiliently bias actuator sleds (240) proximally relative to chassis (260). As will be described in greater detail below, locking recess (241) is configured to selectively engage a locking ridge (286) of sled retainer (280) to selectively lock the longitudinal position of actuator sleds (240) relative to chassis (260), thereby resisting the resilient bias of coil springs (298). As shown in FIGS. 9 and 15A-15B, an indicator plate (242) is secured to the proximal end of each actuator sled (240), such that indicator plates (242) will translate unitarily with actuator sleds (240). Indicator plates (242) are positioned to correspond with windows (212) that are formed in housings (210, 218), such that indicator plates (242) are visible through windows (212) when actuator sleds (240) are in a distal position and when actuator sleds (240) are in a proximal position. As will be described in greater detail below, indicator plates (242) may include different colored regions or other markings that provide visual indication through windows (212), visually indicating whether actuator sleds (240) are in the distal position or the proximal position.

As shown in FIGS. 9 and 15A-15B, slots (244) are positioned to also receive pins (296). Each slot (244) includes a longitudinally extending portion (246) and an obliquely extending portion (248). Pins (296) are configured to travel along the longitudinally extending portion (246) of each corresponding slot (244) and along the obliquely extending portion (248) of each corresponding slot (244). In the present example, there are six slots (244) and only four pins (296), such that two of the slots (244) are not used. In other versions, there are six pins (296) such that all six slots (244) are used. In still other versions, there are only four slots (244), corresponding with the four pins (296) of the present example.

Figure 13:
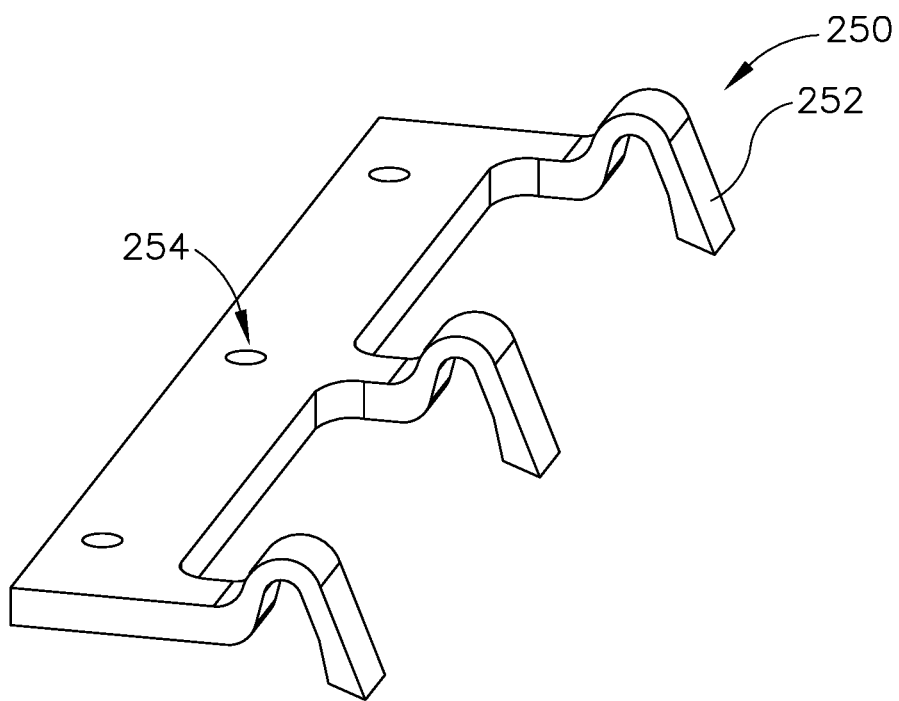
FIG. 13 depicts a perspective view of a retainer of the buttress applier cartridge of FIG. 7.

Retainers (250) are slidably disposed on respective actuator sleds (240), such that each actuator sled (240) is slidably interposed between chassis (260) and a corresponding retainer (250). As shown in FIG. 13, each retainer (250) includes a set of arms (252) and a set of openings (254). Openings (254) are positioned to receive pins (296). Pins (296) are secured within openings (254) such that pins (296) do not move within corresponding openings (254). Retainers (250) thus travel unitarily with pins (296) in this example, as will be described in greater detail below. In the present example, there are six openings (254) and only four pins (296), such that two of the openings (254) are not used. In other versions, there are six pins (296) such that all six openings (254) are used. In still other versions, there are only four openings (254), corresponding with the four pins (296) of the present example.

Arms (252) of the present example are configured to selectively secure buttress assemblies (100, 110) to platform (220). In particular, FIGS. 7-8, 14A, and 15A show retainers (250) positioned such that buttress assemblies (100, 110) are interposed between the free ends of arms (252) and platform (220). As described in greater detail below, retainers (250) are movable laterally outwardly such that arms (252) disengage buttress assemblies (100, 110), thereby enabling buttress assemblies (100, 110) to be removed from platform (220). In the present example, arms (252) are resilient and are thus configured to resiliently bear against buttress assemblies (100, 110), thereby pinching buttress assemblies (100, 110) against platform (220). Other suitable ways in which arms (252) may engage buttress assemblies (100, 110) will be apparent to those of ordinary skill in the art in view of the teachings herein.

Figure 10:
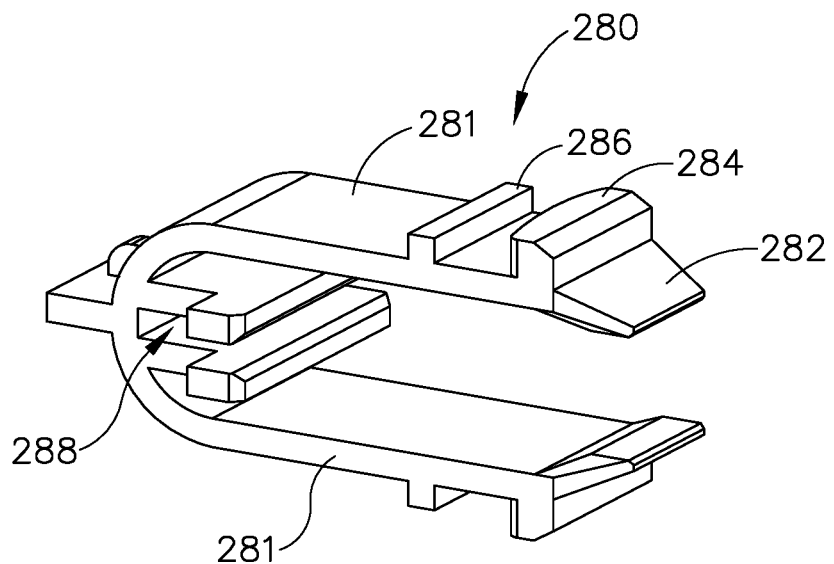
FIG. 10 depicts a perspective view of a sled retainer of the buttress applier cartridge of FIG. 7.
Figure 14A:
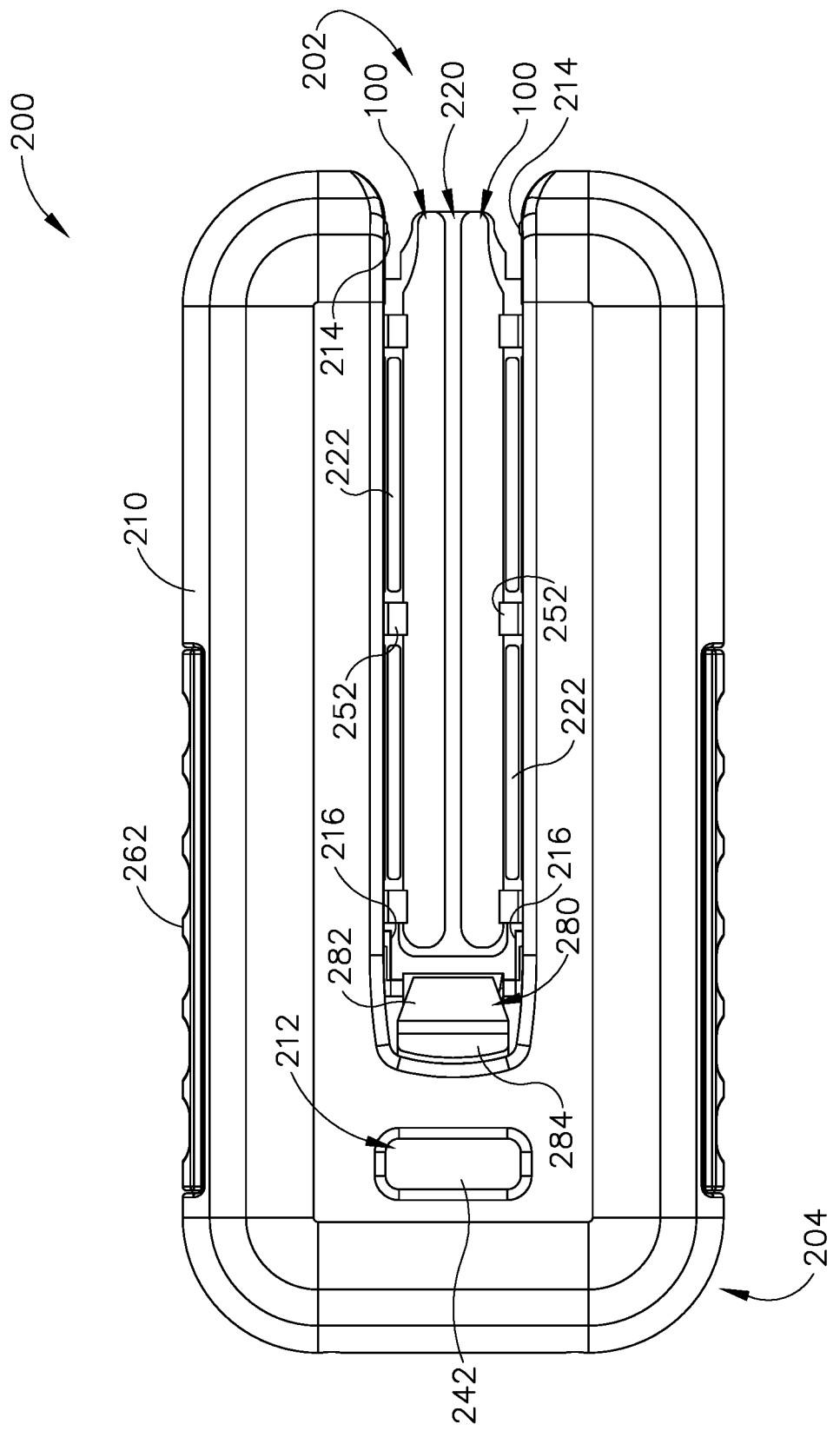
FIG. 14A depicts a top plan view of the buttress applier cartridge of FIG. 7, with a buttress assembly loaded on a platform of the buttress applier cartridge, and with retainers positioned to secure the buttress assembly to the platform.
Figure 14B:
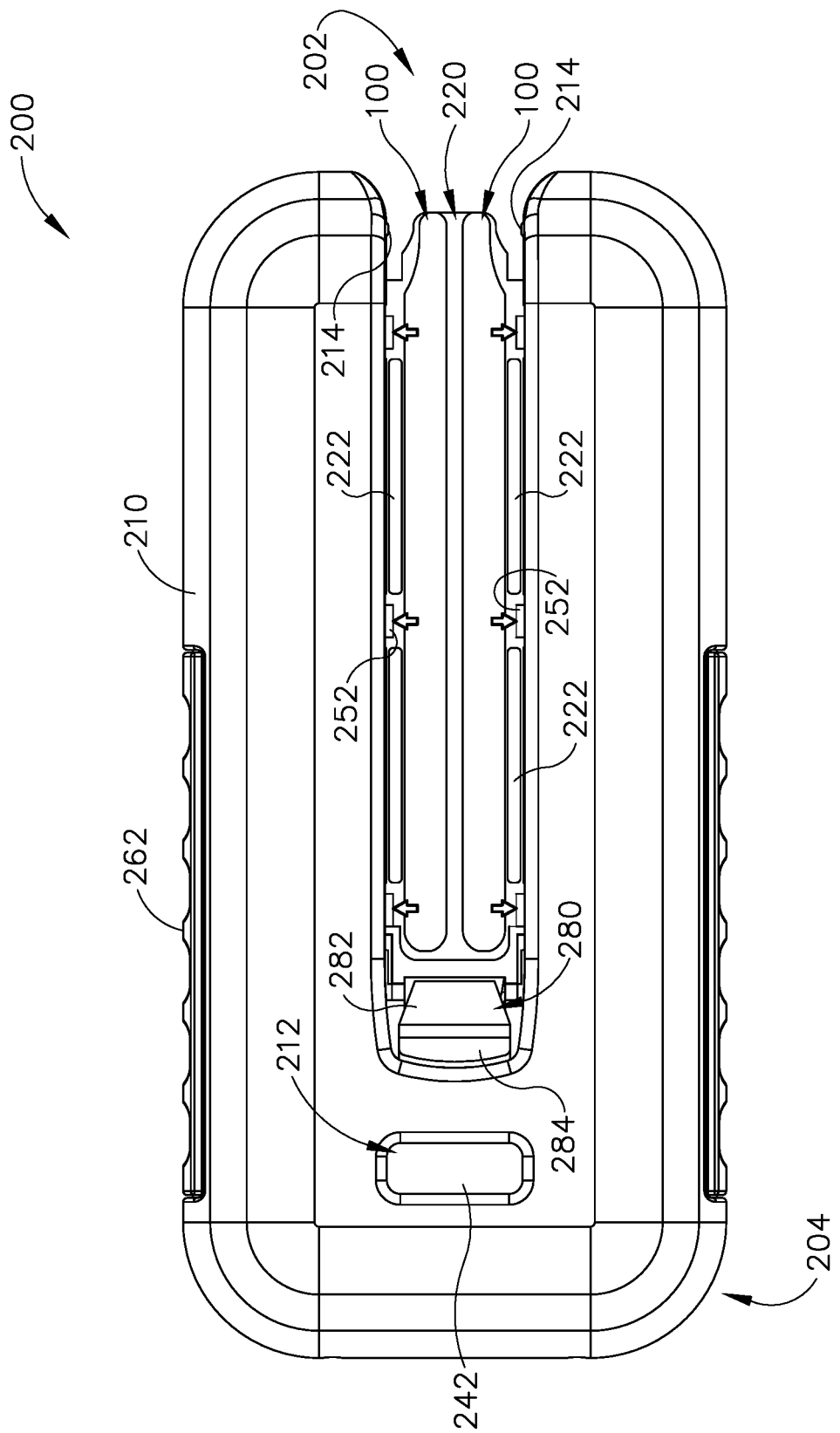
FIG. 14B depicts a top plan view of the buttress applier cartridge of FIG. 7, with a buttress assembly loaded on a platform of the buttress applier cartridge, and with retainers positioned to release the buttress assembly to the platform.

As shown in FIG. 10, sled retainer (280) includes a pair of arms (281) that together generally define a "U" shape. The free end of each arm (281) includes a tapered cam surface (282) and a housing engagement feature (284). As best seen in FIGS. 8 and 14A-14B, housing engagement features (284) are positioned to engage corresponding surfaces of housings (210, 218). Each arm (281) further includes a respective locking ridge (286) spaced proximally from the corresponding housing engagement feature (284). Sled retainer (280) further defines a channel (288) in the region where arms (281) meet each other. As shown in FIG. 9, channel (288) is configured to receive the proximal end of chassis (260).

Figure 16A:
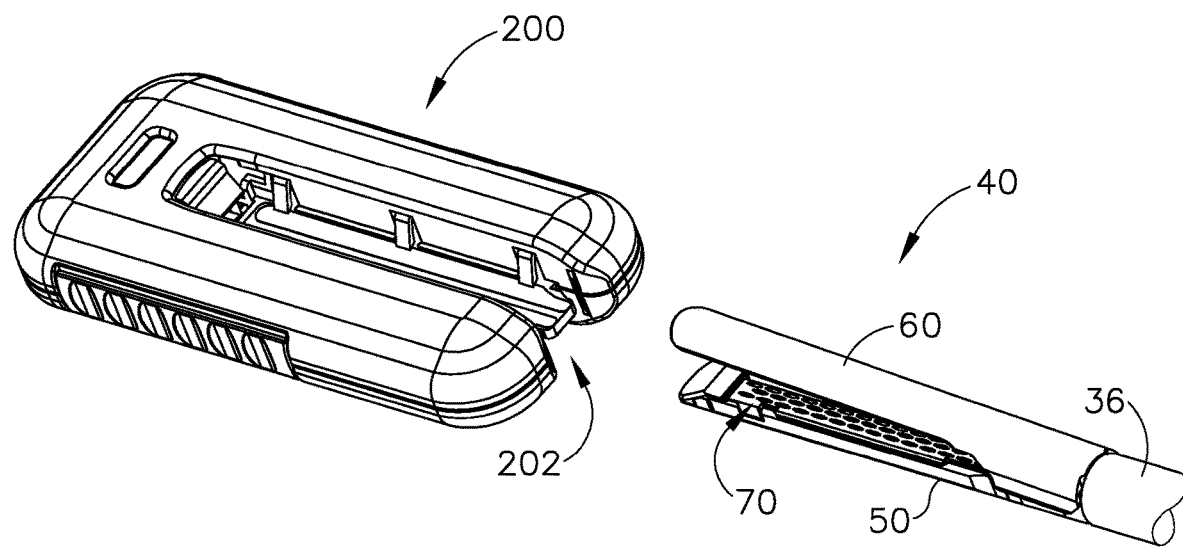
FIG. 16A depicts a perspective view of the end effector of FIG. 2 and the buttress applier cartridge of FIG. 7, with the end effector approaching the buttress applier cartridge.
Figure 16B:
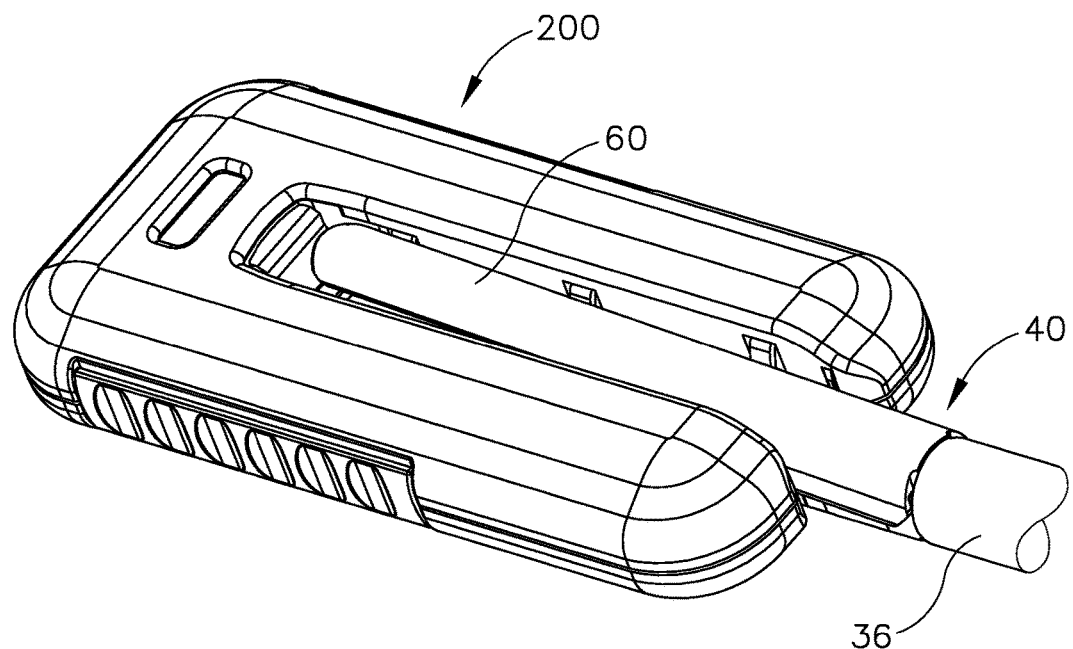
FIG. 16B depicts a perspective view of the end effector of FIG. 2 and the buttress applier cartridge of FIG. 7, with the buttress applier cartridge positioned in the end effector.
Figure 17A:
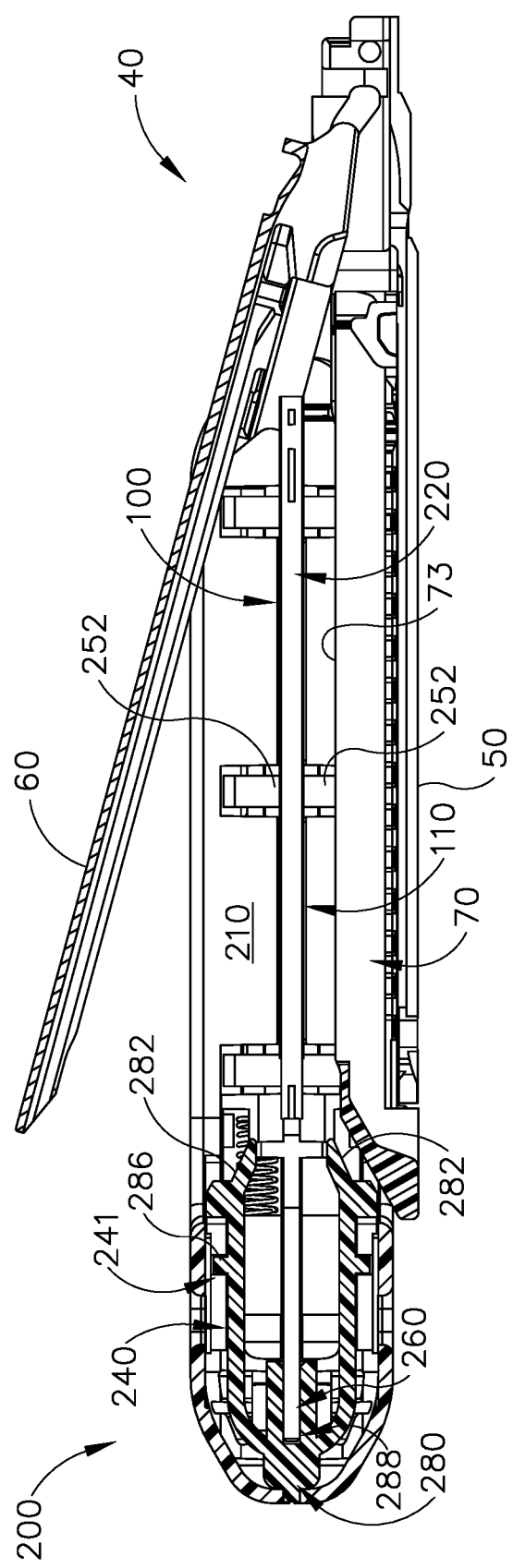
FIG. 17A depicts a cross-sectional side view of the end effector of FIG. 2 and the buttress applier cartridge of FIG. 7, with the buttress applier cartridge positioned in the end effector, and with the end effector in an open configuration.
Figure 17B:
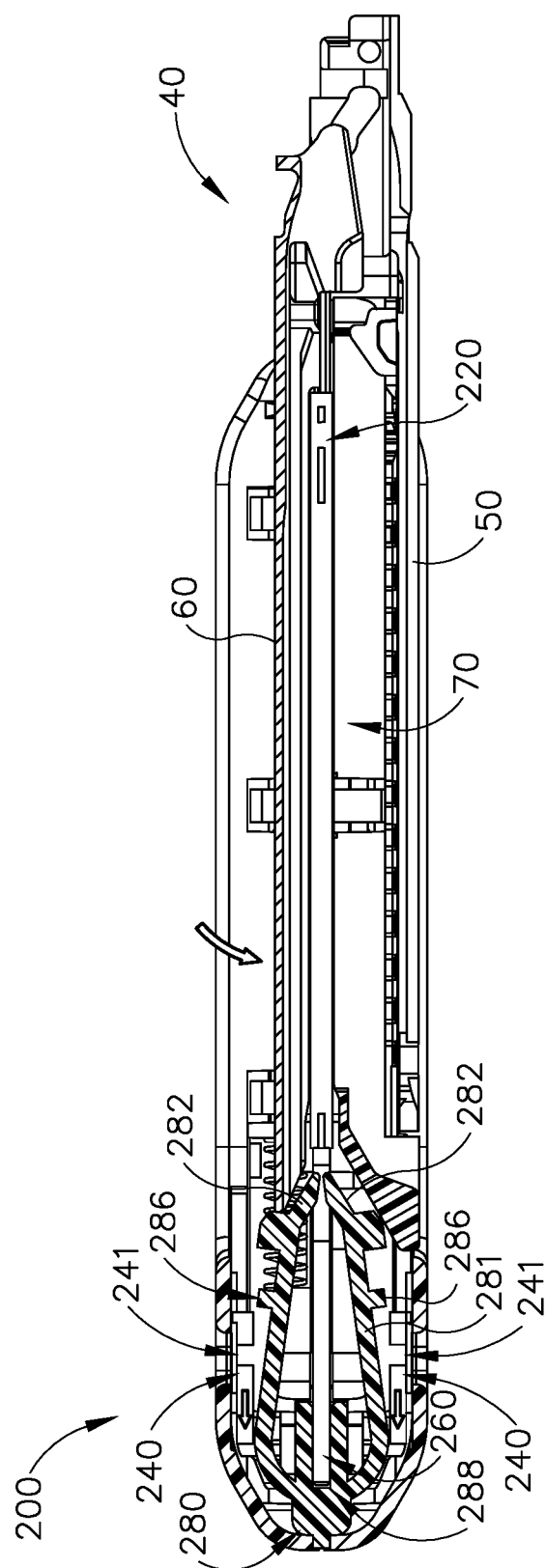
FIG. 17B depicts a cross-sectional side view of the end effector of FIG. 2 and the buttress applier cartridge of FIG. 7, with the buttress applier cartridge positioned in the end effector, and with the end effector in a closed configuration.

FIGS. 14A-17B show cartridge (200) in different stages of operation. In particular, FIGS. 14A, 15A, and 17A show cartridge (200) in a configuration where retainer arms (252) are positioned to hold buttress assemblies (100, 110) against platform (220); while FIGS. 14B, 15B, and 17B show cartridge (200) in a configuration where retainer arms (252) are positioned to release buttress assemblies (100, 110) from platform (220). While FIGS. 14A-17B only show buttress assembly (100) on platform (220), it should be understood that buttress assembly (110) would be retained on and released from platform (220) in an identical fashion.

To use cartridge (200) to load end effector (40), the operator would first position cartridge (200) and end effector (40) such that end effector is aligned with open end (202) of cartridge (200) as shown in FIG. 16A. The operator would then advance end effector (40) distally (and/or retract cartridge (200) proximally) to position platform (220) and buttress assemblies (100, 110) between anvil (60) and staple cartridge (70) as shown in FIG. 16B. This will ultimately result in the arrangement shown in FIG. 17A. While end effector (40) is not shown in FIG. 14A or 15A, it should be understood that cartridge (200) is in the same state in FIG. 17A as the state shown in FIGS. 14A and 15A. In this state, actuator sleds (240) are in a first longitudinal position (i.e., closer to open end (202)). Coil springs (298) are resiliently urging actuator sleds (240) toward a second longitudinal position (i.e., closer to closed end (204)). However, as best seen in FIG. 17A, locking ridges (286) of sled retainer (280) are disposed in locking recesses (241) of actuator sleds (240), thereby holding actuator sleds (240) in the first longitudinal position. With actuator sleds (240) in the first longitudinal position, retainers (250) are located at inward positions to retain buttress assemblies (100, 110) against platform (220). As shown in FIG. 15A, at this stage, pins (296) are positioned at the inner ends of slots (264) of chassis (260); and in the ends of obliquely extending portions (248) of slots (244).

In order to load buttress assemblies (100, 110) on end effector (40), the operator may simply close end effector (40) by pivoting anvil (60) toward staple cartridge (70), as described above, to reach the state shown in FIG. 17B. As shown, closure of end effector (40) results in the distal ends of anvil (60) and staple cartridge (70) bearing against cam surfaces (282) of sled retainer (280). This causes arms (281) of sled retainer to deform toward each other, such that locking ridges (286) disengage locking recesses (241) of actuator sleds (240). With locking ridges (286) disengaged from locking recesses (241) of actuator sleds (240), coil springs (298) drive actuator sleds (240) proximally to the second longitudinal position. Actuator sleds (240) engage bosses (268) of chassis (260) when actuator sleds (240) reach the proximal position, such that bosses (268) provide a hard stop. It should be understood that this sudden engagement between actuator sleds (240) and bosses (268) may produce a click or snap sound, providing audible feedback to the operator indicating actuation of cartridge (200).

In the present example, cartridge (200) is configured such that both arms (281) must be deformed toward each other at the same time in order for actuator sleds (240) to be unlocked and thereby permitted to translate proximally to the second longitudinal position. If only one arm (281) is deformed toward the other arm (281), the locking ridge (286) of the non-deformed arm (281) will remain disposed in the corresponding locking recess (241) of actuator sled (240), thereby continuing to hold actuator sled (240) in the first longitudinal position. By requiring both arms (281) to be deformed toward each other at the same time in order for actuator sleds (240) to be unlocked, the configuration of sled retainer (280) will reduce the risk of cartridge (200) being actuated prematurely or inadvertently.

As best seen in the transition from the view shown in FIG. 15A (actuator sleds (240) in the first longitudinal position) to the view shown in FIG. 15B (actuator sleds (240) in the second longitudinal position), slots (244) act as cams against pins (296) and thereby drive retainers (250) outwardly as actuator sleds (240) travel proximally. In particular, pins (296) traverse obliquely extending portions (248) of slots (244) and then longitudinally extending portions (246) of slots (244). Obliquely extending portions (248) of slots (244) drive pins (296) outwardly during this range of travel. Since retainers (250) travel unitarily with pins (296), retainers (250) travel outwardly as well. Laterally oriented slots (264) of chassis (260) accommodate the outward lateral movement of pins (296) but prevent pins (296) from moving longitudinally during the transition from the state shown in FIG. 15A to the state shown in FIG. 15B.

Upon reaching the state shown in FIG. 15B, retainers (250) are disengaged from buttress assemblies (100, 110). This state is also shown in FIG. 14B. It should be understood that end effector (40) is still in the closed configuration at this stage, as also shown in FIG. 17B. Thus, with end effector (40) clamping on both buttress assemblies (100, 110), adhesive layers (104, 114) are adhered to underside (65) of anvil (60) and deck (73) of staple cartridge (70). End effector (40) may then be re-opened (i.e., pivoting anvil (60) away from staple cartridge (70)) and pulled away from cartridge (200). With retainers (250) disengaged from buttress assemblies (100, 110), end effector (40) may freely pull buttress assemblies (100, 110) away from platform (220) as end effector (40) is pulled away from cartridge (200). With buttress assemblies (100, 110) loaded on end effector (40), end effector (40) may then be used as described above with reference to FIGS. 5A-6.

Referring back to FIGS. 7-8, housings (210, 218) of the present example include proximal guide features (214) and distal guide features (216). Guide features (214, 216) are configured to assist in providing proper alignment of end effector (40) with cartridge (200). In particular, guide features (214, 216) are configured to engage the lateral sides of lower jaw (50) and anvil (60) to ensure that the central longitudinal axis of end effector (40) is coplanar with the central longitudinal axis of platform (220). Such alignment will prevent buttress assemblies (100, 110) from being applied to underside (65) or deck (73) in a skewed orientation. In some versions, guide features (214, 216) engage the lateral sides of lower jaw (50) and anvil (60) as soon as end effector (40) is positioned as shown in FIG. 16B (i.e., before anvil (60) is pivoted to the closed position). In some other versions, guide features (214, 216) do not engage the lateral sides of lower jaw (50) and anvil (60) until anvil (60) is pivoted closer to the closed position. In the present example, guide features (214, 216) are unitarily formed features of housings (210, 218). In some other versions, guide features (214, 216) are movable relative to housings (210, 218) and are resiliently biased to provide self-centering guidance to the lateral sides of lower jaw (50) and anvil (60). Various suitable forms that guide features (214, 216) may take will be apparent to those of ordinary skill in the art in view of the teachings herein.

As noted above, indicator plates (242) may include different colored regions or other markings (e.g., text, pictograms, etc.) that provide visual indication through windows (212), visually indicating whether actuator sleds (240) are in the first longitudinal position (FIG. 15A) or the second longitudinal position (FIG. 15B). The operator may thus view indicator plate (242) through window (212) to determine whether cartridge (200) has successfully released buttress assemblies (100, 110). An operator may also view indicator plate (242) through window (212) to determine whether cartridge (200) has been previously used. Various suitable markings that may be provided on indicator plates (242) to provide visual feedback indicating the state of cartridge (200) will be apparent to those of ordinary skill in the art in view of the teachings herein.

B. Exemplary Buttress Applier Cartridge with Passive Retainer Arms

Figure 18:
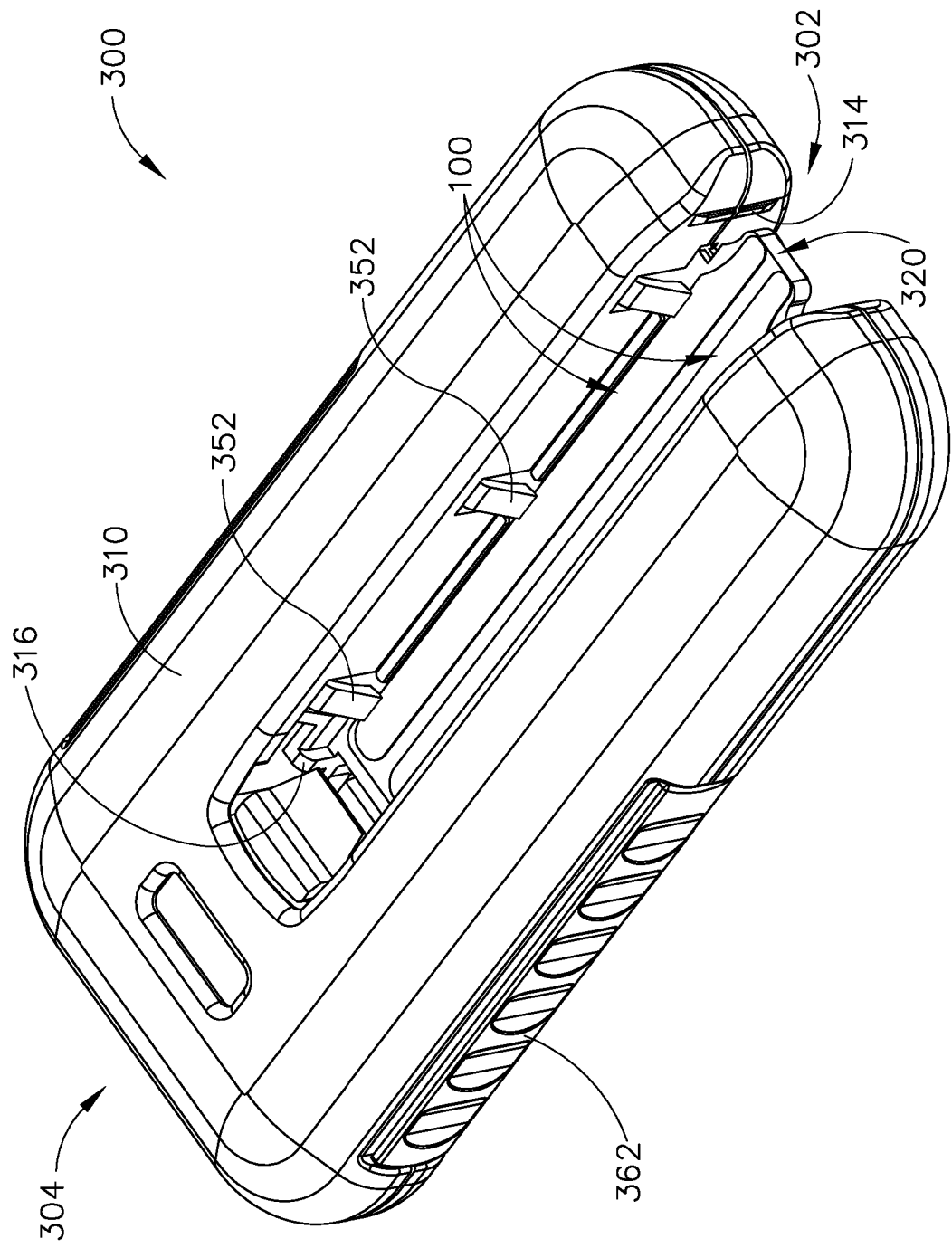
FIG. 18 depicts a perspective view of another exemplary buttress applier cartridge that may be used to carry and apply the buttress assembly of FIG. 5A.
Figure 19:
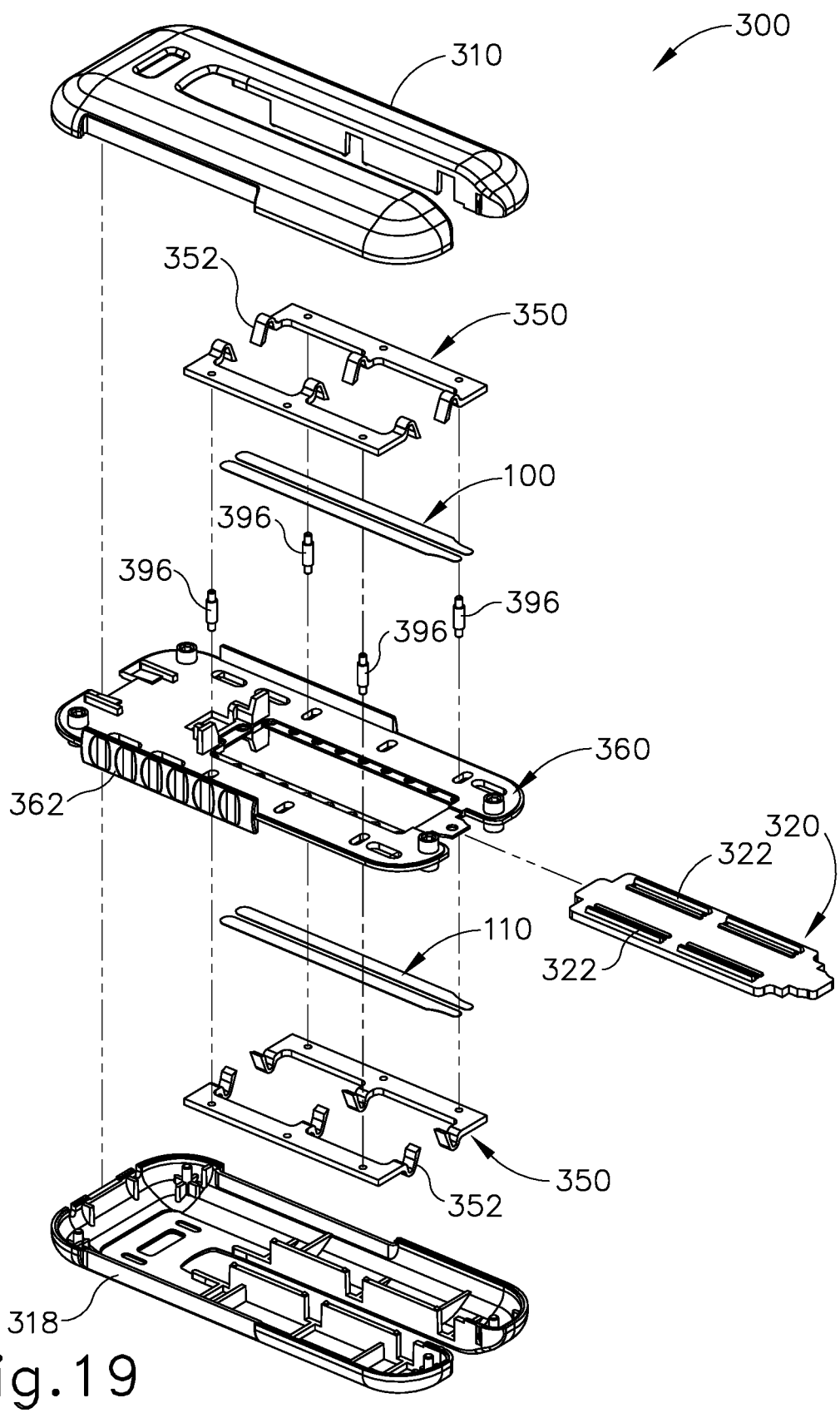
FIG. 19 depicts an exploded perspective view of the buttress applier cartridge of FIG. 18.

FIGS. 18-19 show another exemplary buttress applier cartridge (300) that may be used to support and protect buttress assemblies (100, 110). Cartridge (300) may also be used to easily load buttress assemblies (100, 110) on end effector (40). As best seen in FIG. 18, cartridge (300) of this example comprises an open end (302) and a closed end (304). Open end (302) is configured to receive end effector (40) as described above. Cartridge (300) further includes a first housing (310) and a second housing (318), which each generally define a "U" shape to present open end (302). As best seen in FIG. 19, various components are interposed between housings (310, 318). In particular, these components include a platform (320), a pair of retainers (350), and a chassis (360). Each of these components will be described in greater detail below.

Housings (310, 318) are configured substantially identically to housings (210, 218) described above. For instance, housings (310, 318) include guide features (314, 316) just like guide features (214, 216) described above. However, housings (310, 318) lack windows (212). Platform (320) of this example is identical to platform (220) described above, including the presence of retention features (322) in the form of ridges that further engage housings (310, 318) to prevent platform (320) from sliding relative to housings (310, 318). Chassis (360) is also identical to chassis (260), including the presence of integral gripping features (362) like gripping features (262) described above. Chassis (360) also includes laterally oriented slots just like slots (264) of chassis (260).

Retainers (350) are substantially similar to retainers (250). Retainers (350) are coupled together via pins (396), which are slidably disposed in the laterally oriented slots of chassis (360). Pins (396) provide coordinated lateral movement of retainers (350). In particular, the retainers (350) that are coupled together via pins (396) will move laterally in unison with each other. Retainers (350) include resilient retention arms (352). Arms (352) are similar to arms (252) in that arms (352) will effectively pinch buttress assemblies (100, 110) against platform (320) with a resilient bias.

When cartridge (300) is positioned relative to end effector (40) in an arrangement similar to that shown in FIG. 16B, and then end effector (40) is closed about platform (320) to reach an arrangement similar to that shown in FIG. 17B, anvil (60) and staple cartridge (70) will bear against corresponding surfaces of arms (352) and thereby cause arms (352) to slide laterally outwardly. Arms (352) will thus disengage buttress assemblies (100, 110) and thereby release buttress assemblies (100, 110) from platform (320). Underside (65) of anvil (60) will press against adhesive layer (104) of buttress assembly (100) and thereby adhere buttress assembly (100) to anvil (60). Similarly, deck (73) of staple cartridge (70) will press against adhesive layer (114) of buttress assembly (110) and thereby adhere buttress assembly (110) to staple cartridge (70). With buttress assemblies (100, 110) released from platform (320) and adhered to end effector (40), end effector (40) may be transitioned back to the open configuration and pulled away from cartridge (300). End effector (40) may then be used in a surgical procedure with buttress assemblies (100, 110) loaded thereon.

It should be understood that retainers (350) may remain located at laterally outward positions after releasing buttress assemblies (100, 110) from platform (320). For instance, the free ends of arms (352) may be bearing into corresponding surfaces of platform (320) providing friction that substantially maintains the positioning of retainers (350) relative to platform (320). An operator may visually observe the laterally outward positioning of retainers (350) and may thereby conclude that cartridge (300) has released buttress assemblies (100, 110). Alternatively, cartridge (300) may include various other kinds of features to provide visual feedback (and/or other feedback) indicating the state of cartridge (300).

In some alternative versions, arms (352) deform outwardly (instead of sliding outwardly) in order to release buttress assemblies (100, 110) in response to closure of end effector (40) about platform (320). In still other versions, arms (352) do not deform or translate outwardly in response to closure of end effector (40) about platform (320). Instead, the adhesion resulting from engagement between underside (65) of anvil (60) with adhesive surface (104) of buttress assembly (100), and the adhesion resulting from engagement between deck (73) of staple cartridge (73) with adhesive surface (114) of buttress assembly (110), will provide a secure engagement between buttress assemblies (100, 110) and end effector (40). This adhesive engagement may be secure enough to enable end effector (40) to pull buttress assemblies (100, 110) away from the free ends of arms (352) without damaging buttress assemblies (100, 110) or otherwise compromising the positioning of buttress assemblies (100, 110) on end effector (40), while arms (352) maintain the configuration and positioning shown in FIG. 18.

C. Exemplary Buttress Applier Cartridge with Passive Retaining Housing Features

Figure 20:
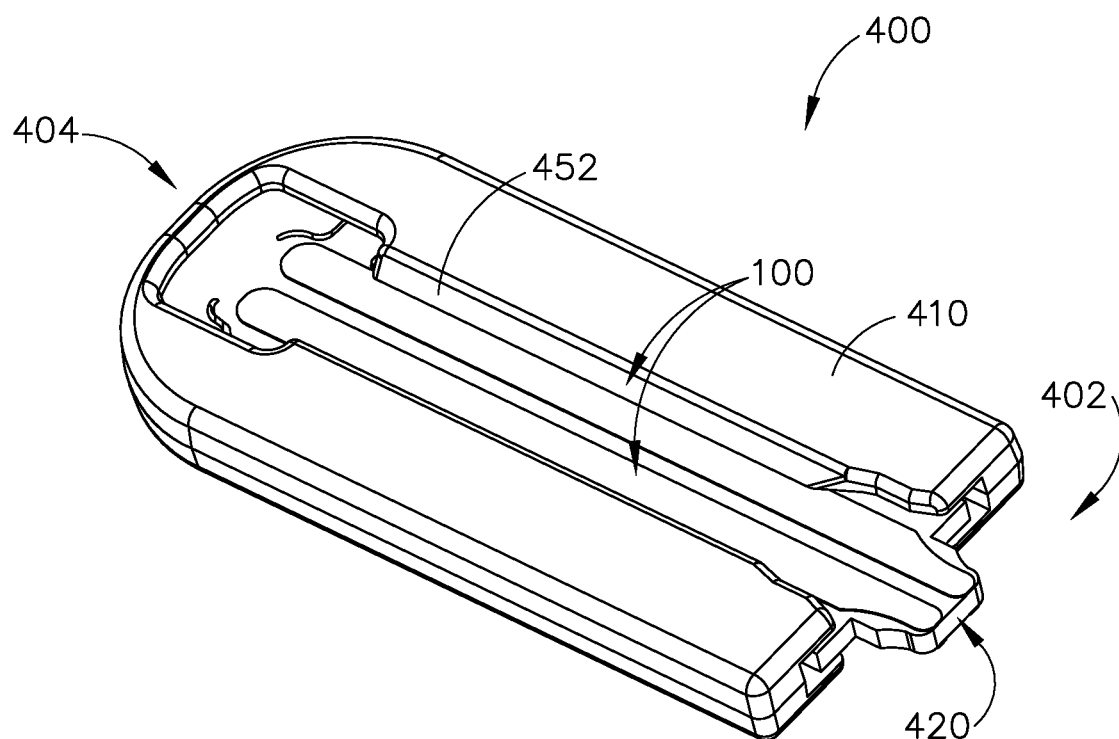
FIG. 20 depicts a perspective view of another exemplary buttress applier cartridge that may be used to carry and apply the buttress assembly of FIG. 5A.
Figure 21:
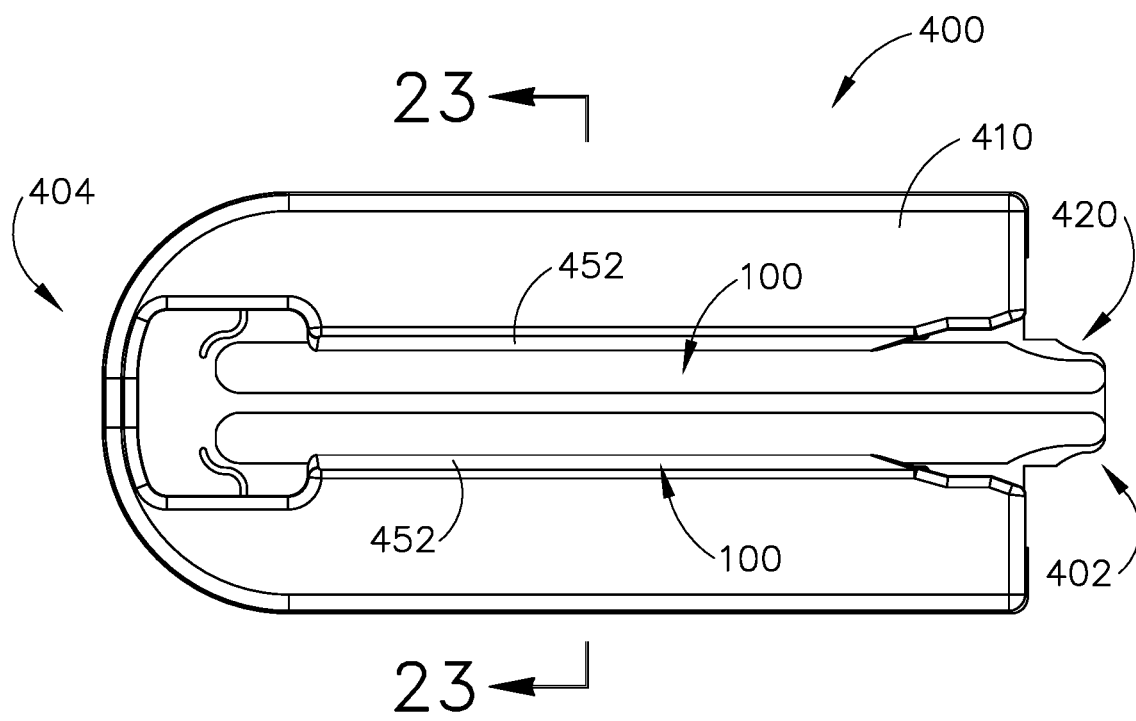
FIG. 21 depicts a top plan view of the buttress applier cartridge of FIG. 20.
Figure 22:
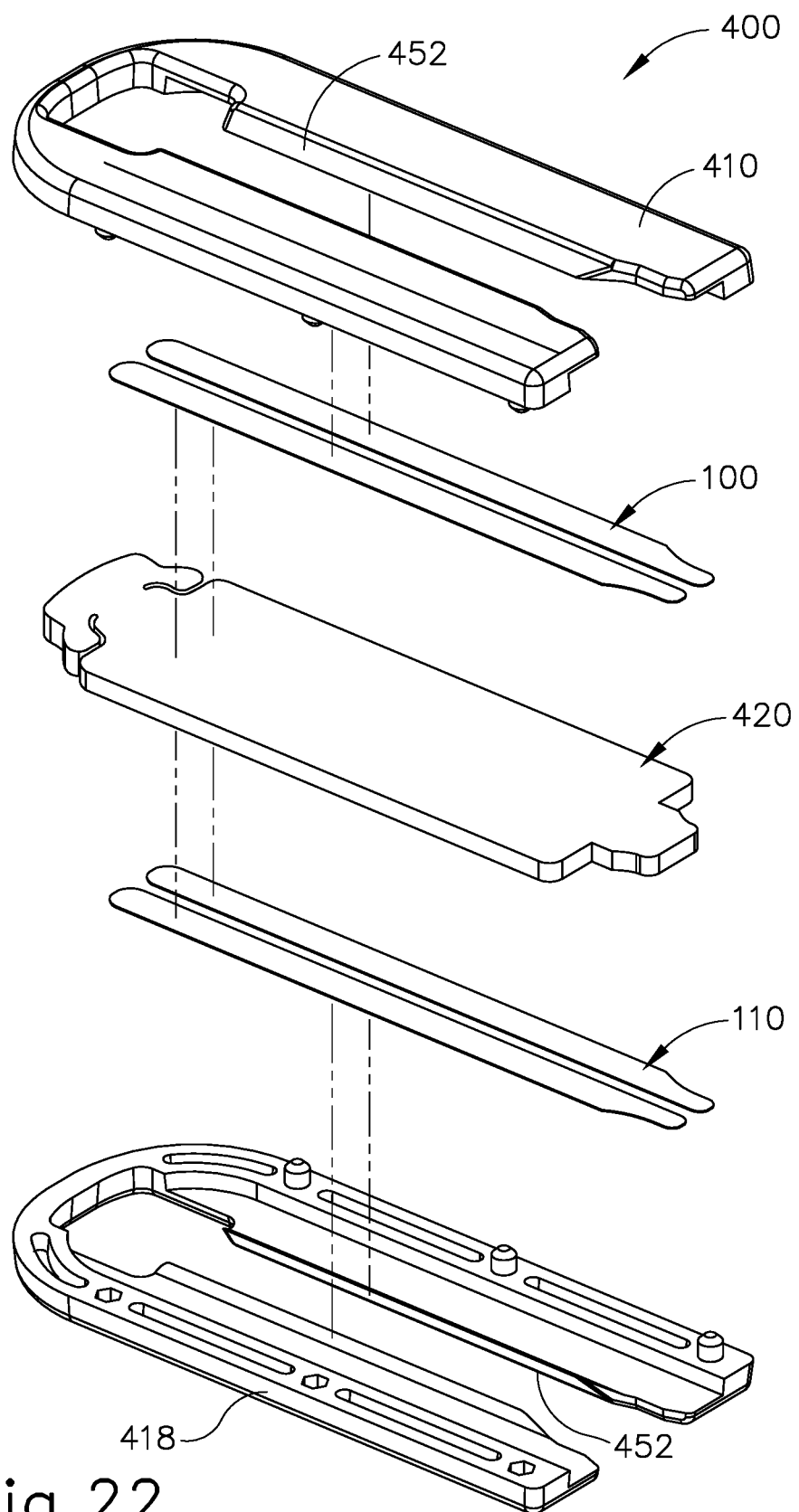
FIG. 22 depicts an exploded perspective view of the buttress applier cartridge of FIG. 20.

FIGS. 20-23 show another exemplary buttress applier cartridge (400) that may be used to support and protect buttress assemblies (100, 110). Cartridge (400) may also be used to easily load buttress assemblies (100, 110) on end effector (40). As best seen in FIG. 20-21, cartridge (400) of this example comprises an open end (402) and a closed end (404). Open end (402) is configured to receive end effector (40) as described above. Cartridge (400) further includes a first housing (410) and a second housing (418), which each generally define a "U" shape to present open end (402). As best seen in FIG. 22, a platform (420) is interposed between housings (410, 418).

Figure 23:
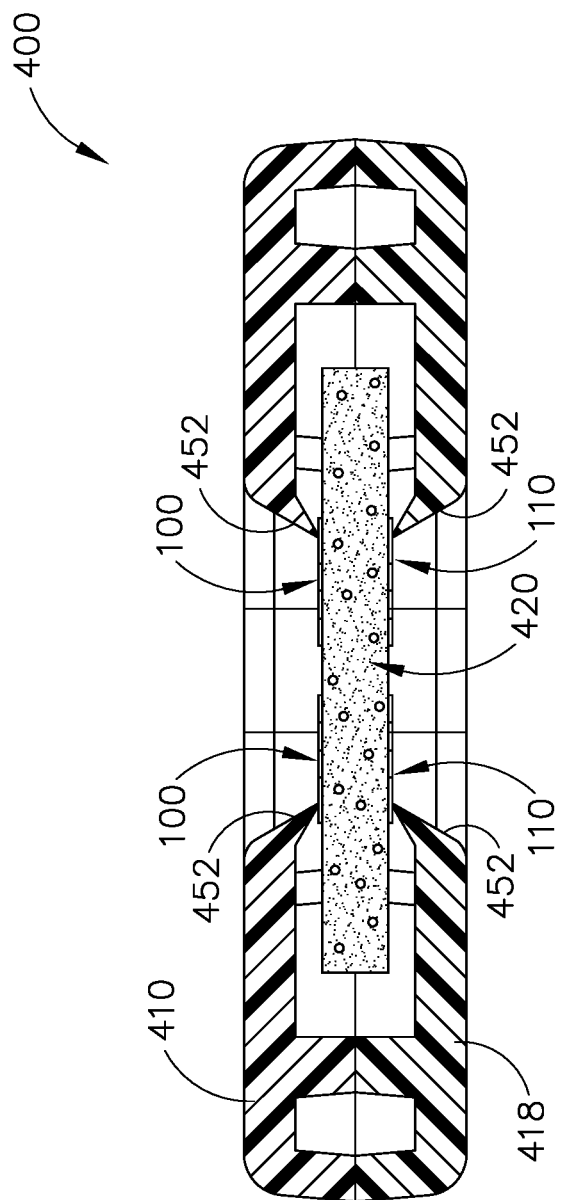
FIG. 23 depicts a cross-sectional view of the applier cartridge of FIG. 20, taken along line 23-23 of FIG. 21.

Each housing (410, 418) of the present example comprises an integral retention fin (452). Fins (452) extend longitudinally along substantial portions of the lengths of corresponding buttress assemblies (100, 110). As best seen in FIG. 23, retention fins (452) of housing (410) secure buttress assembly (100) to platform (420); while retention fins (452) of housing (418) secure buttress assembly (110) to platform (420). At least a portion of each housing (410, 418) may comprise a resilient material such that retention fins (452) resiliently bear against corresponding buttress assemblies (100, 110). In addition or in the alternative, platform (420) may comprise a resilient material that is biased to expand outwardly, such that platform (420) bears buttress assemblies (100, 110) against corresponding retention fins (452). Various suitable materials that may be used to form housings (410, 418) and platform (420) will be apparent to those of ordinary skill in the art in view of the teachings herein.

When cartridge (400) is positioned relative to end effector (40) in an arrangement similar to that shown in FIG. 16B, and then end effector (40) is closed about platform (420) to reach an arrangement similar to that shown in FIG. 17B, anvil (60) and staple cartridge (70) will bear against corresponding surfaces of retention fins (452) and thereby cause retention fins (452) to deform laterally outwardly. Retention fins (452) will thus disengage buttress assemblies (100, 110) and thereby release buttress assemblies (100, 110) from platform (420). Underside (65) of anvil (60) will press against adhesive layer (104) of buttress assembly (100) and thereby adhere buttress assembly (100) to anvil (60). Similarly, deck (73) of staple cartridge (70) will press against adhesive layer (114) of buttress assembly (110) and thereby adhere buttress assembly (110) to staple cartridge (70). With buttress assemblies (100, 110) released from platform (420) and adhered to end effector (40), end effector (40) may be transitioned back to the open configuration and pulled away from cartridge (400). End effector (40) may then be used in a surgical procedure with buttress assemblies (100, 110) loaded thereon.

In some other versions, retention fins (452) do not deform or translate outwardly in response to closure of end effector (40) about platform (320). Instead, the adhesion resulting from engagement between underside (65) of anvil (60) with adhesive surface (104) of buttress assembly (100), and the adhesion resulting from engagement between deck (73) of staple cartridge (73) with adhesive surface (114) of buttress assembly (110), will provide a secure engagement between buttress assemblies (100, 110) and end effector (40). This adhesive engagement may be secure enough to enable end effector (40) to pull buttress assemblies (100, 110) away from retention fins (452) without damaging buttress assemblies (100, 110) or otherwise compromising the positioning of buttress assemblies (100, 110) on end effector (40), while retention fins (452) maintain the configuration and positioning shown in FIGS. 20-21 and 23.

IV. Exemplary Alternative Platforms for Buttress Applier Cartridges

In the examples above, platforms (220, 320, 420) are provided as generally flat, stationary members that simply provide support to buttress assemblies (100, 110) until buttress assemblies (100, 110) are adhered to end effector (40). It may be desirable to provide additional functionality to platform (220, 320, 420). For instance, it may be desirable to enable platform (220, 320, 420) to slide relative to housings (210, 218, 310, 318, 410, 418). For instance, when the operator clamps down on buttress assemblies (100, 110) and platform (220, 320, 420) with end effector (40), the operator may wish to pull platform (220, 320, 420) toward the operator, through open end (202, 302, 402), with end effector (40) still clamped down on buttress assemblies (100, 110) and platform (220, 320, 420). This may further promote removal of buttress assemblies (100, 110) from platform (220, 320, 420) and/or enable the operator to more readily confirm visually that buttress assemblies (100, 110) have been removed from platform (220, 320, 420). Several merely illustrative variations of platform (220, 320, 420) will be described in greater detail below. Further variations will be apparent to those of ordinary skill in the art in view of the teachings herein.

Figure 24:
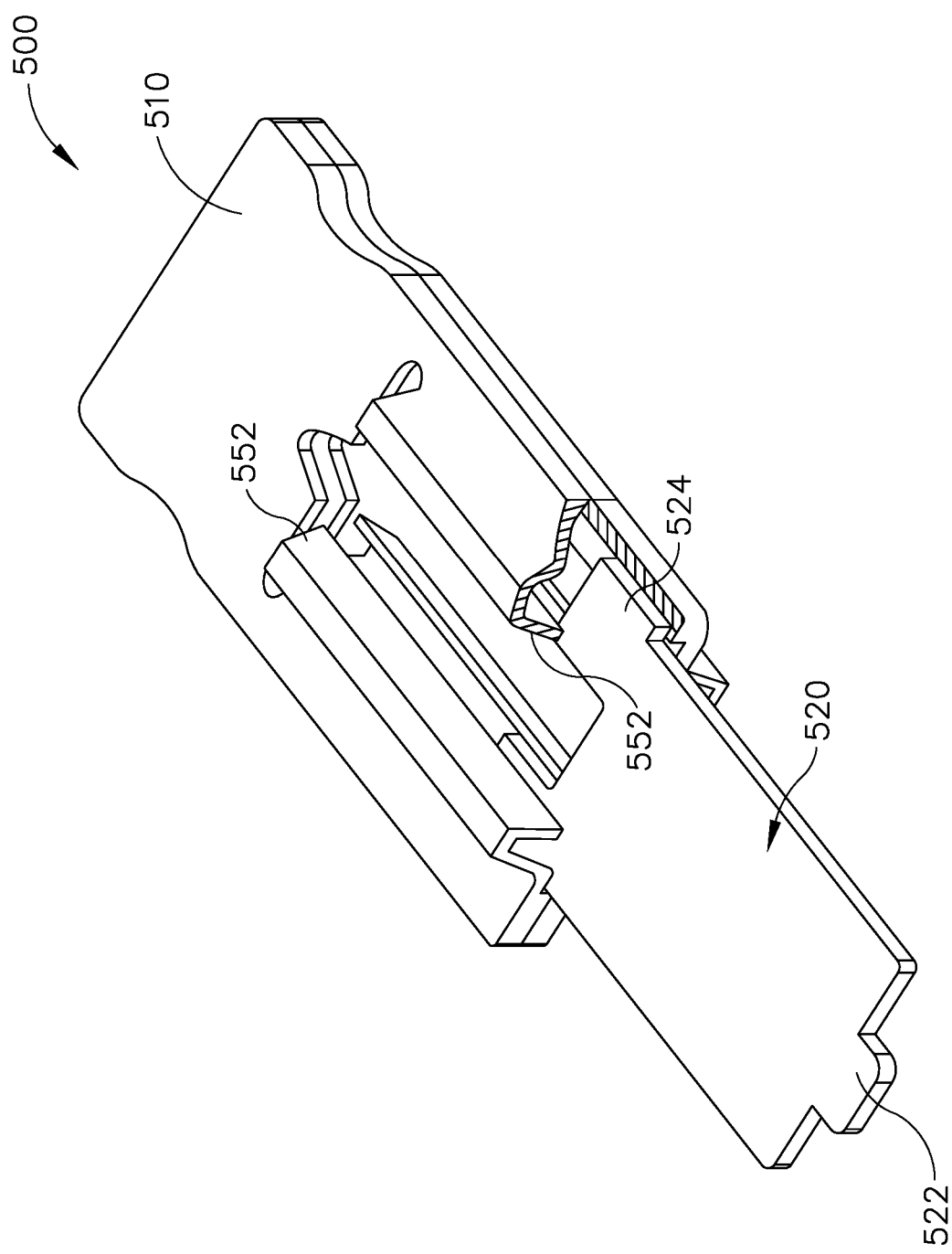
FIG. 24 depicts a perspective view of another exemplary buttress applier cartridge that may be used to carry and apply the buttress assembly of FIG. 5A, with a sliding platform in an extended position.

FIG. 24 shows an exemplary alternative buttress applier cartridge (500) that may be used to support and protect buttress assemblies (100, 110). Cartridge (500) may also be used to easily load buttress assemblies (100, 110) on end effector (40). Cartridge (500) of this example includes a housing (510) and a platform (520). Housing (510) of the present example comprises a pair of longitudinally extending retention fins (552) that are configured to releasably secure buttress assemblies (100, 110) to platform (520) just like retention fins (452) described above. It should be understood that fins (552) are provided by way of example only; and that cartridge (500) may instead include any other suitable kinds of buttress assembly (100, 110) retention features, including but not limited to those described elsewhere herein.

Platform (520) of the present example includes a longitudinally projecting tongue (522) and a pair of outwardly extending tabs (524). Tongue (522) is located at one end of platform (520) while tabs (524) are located at the other end of platform (520). While buttress assemblies (100, 110) are not shown in FIG. 24, it should be understood that platform (520) may receive and hold buttress assemblies (100, 110) just like platforms (220, 320, 420) described above.

In the present example, platform (520) is configured to slide longitudinally relative to housing (510). In particular, when an operator clamps down on buttress assemblies (100, 110) and platform (520) with end effector (40), the operator may pull platform (520) toward the operator, with end effector (40) still clamped down on buttress assemblies (100, 110) and platform (520) until platform (520) is translated to the position shown in FIG. 24. At this stage, tabs (524) engage the end of housing (510) and thereby prevent platform (520) from translating further. The operator may then release platform (520) by transitioning end effector (40) back to the open position, carrying away buttress assemblies (100, 110) on end effector (40).

In the present example, fins (552) cooperate to slightly compress platform (520), providing friction that prevents platform (520) from inadvertently translating to the advanced position shown in FIG. 24. However, the compression exerted by fins (552) on platform (520) still enables platform (520) to be pulled to the advanced position shown in FIG. 24, as described above, without tearing platform (520). It should also be understood that the friction provided by fins (552) against platform (520) may substantially hold platform (520) in the advanced position shown in FIG. 24.

Figure 25A:
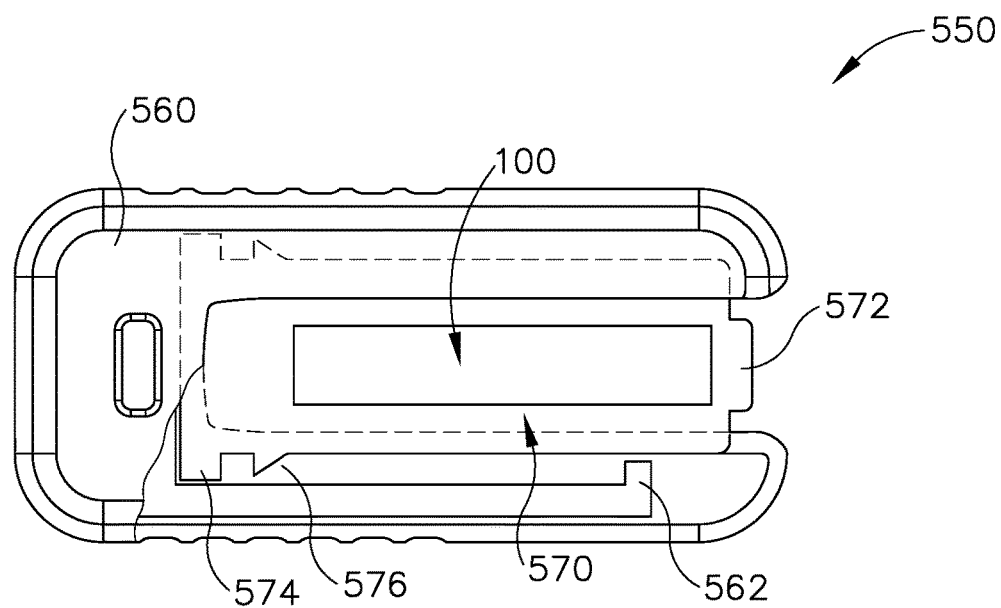
FIG. 25A depicts a top plan view of another exemplary buttress applier cartridge that may be used to carry and apply the buttress assembly of FIG. 5A, with a portion of the housing broken away to reveal internal features, and with a sliding platform in a retracted position.
Figure 25B:
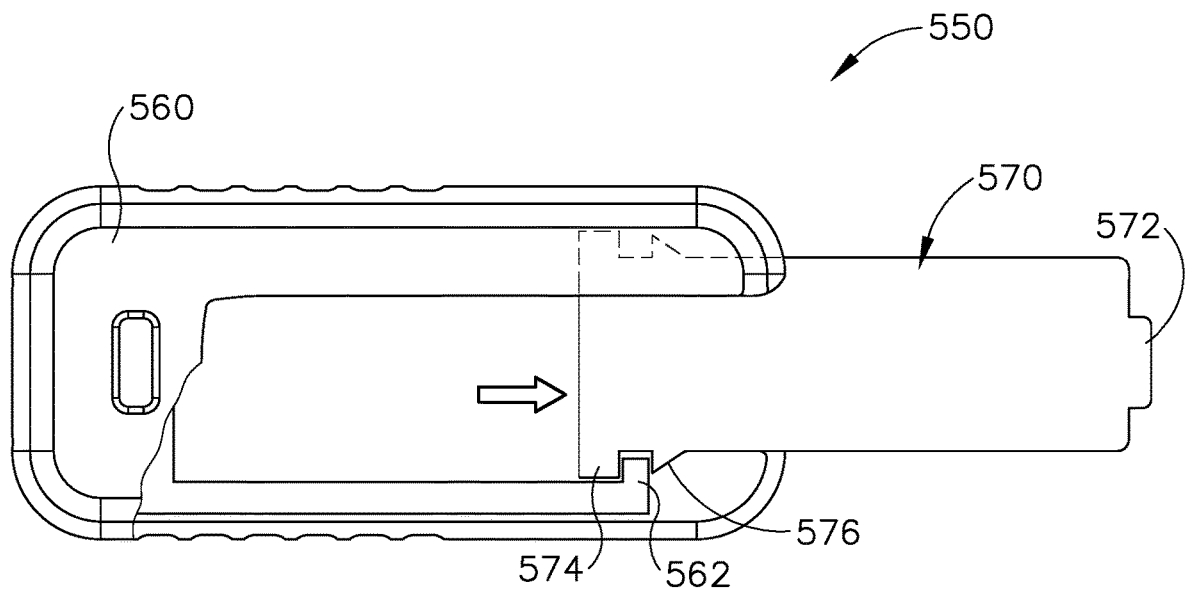
FIG. 25B depicts a top plan view of the buttress applier cartridge of FIG. 25A, with a portion of the housing broken away to reveal internal features, and with the sliding platform in an extended position.

It may be desirable to rely on more than just friction to hold a sliding platform in an advanced position. FIGS. 25A-25B show another exemplary alternative buttress applier cartridge (550) that may be used to support and protect buttress assemblies (100, 110) on a platform (570) that may be secured in an advanced position. Cartridge (550) may also be used to easily load buttress assemblies (100, 110) on end effector (40). Cartridge (550) of this example includes a housing (560) and platform (570). While not shown, cartridge (550) may include retention fins and/or any other suitable kinds of buttress assembly (100, 110) retention features, including but not limited to those described elsewhere herein.

Platform (570) of the present example includes a longitudinally projecting tongue (572), a pair of outwardly extending tabs (574), and a pair of outwardly extending locking pawls (576). Tongue (572) is located at one end of platform (570) while tabs (574) are located at the other end of platform (570). While buttress assemblies (100, 110) are not shown in FIGS. 25A-25B, it should be understood that platform (570) may receive and hold buttress assemblies (100, 110) just like platforms (220, 320, 420) described above.

In the present example, platform (570) is configured to slide longitudinally relative to housing (510). In particular, when an operator clamps down on buttress assemblies (100, 110) and platform (570) with end effector (40), the operator may pull platform (570) toward the operator, with end effector (40) still clamped down on buttress assemblies (100, 110) and platform (570) until platform (570) is translated from the position shown in FIG. 25A to the position shown in FIG. 25B. At this stage, tabs (574) engage inwardly extending bosses (562) of housing (560), which thereby prevent platform (570) from translating further. In addition, pawls (576) engage bosses (562) to prevent platform (570) from translating back to the retracted position. It should be understood that pawls (576) may deform inwardly as platform (570) translates from the position shown in FIG. 25A to the position shown in FIG. 25B. Once platform (570) has reached the position shown in FIG. 25B, the operator may then release platform (570) by transitioning end effector (40) back to the open position, carrying away buttress assemblies (100, 110) on end effector (40).

It should be understood that either of the slidable platforms (520, 570) described above may be readily incorporated into any of the cartridges (200, 300, 400) described above.

V Exemplary Alternative Buttress Retention Features for Buttress Applier Cartridges As described above, a cartridge (200, 300, 400) may secure buttress assemblies (100, 110) to platform (220, 320, 420) using arms (252, 352) or fins (452). However, it will be understood that arms (252, 352) and fins (452) are merely illustrative examples of structures that may be used to secure buttress assemblies (100, 110) to platform (220, 320, 420). Several additional structures that may be used to secure buttress assemblies (100, 110) to platform (220, 320, 420) will be described in greater detail below, while still further examples will be apparent to those of ordinary skill in the art in view of the teachings herein. It should be understood that the following teachings may be readily incorporated into any of the various buttress applier cartridges described herein.

A. Exemplary Buttress Applier Cartridge with Ratcheting Retaining Arms

FIGS. 26A-26C show another exemplary buttress applier cartridge (900) that may be used to support and protect buttress assemblies (100, 110). Cartridge (900) may also be used to easily load buttress assemblies (100, 110) on end effector (40). Cartridge (900) of this example includes housings (910, 918) and a platform (920). Platform (920) of this example is substantially identical to platforms (220, 320, 420) described above, except that platform (920) of this example includes rigid lateral edges (922) extending along the length of each longitudinally extending side of platform (920). Cartridge (900) of this example further includes ratcheting retainer arms (952). Arms (952) of this example are substantially similar to arms (352) of cartridge (300). However, unlike arms (352), arms (952) include ratcheting teeth (954) as best seen in FIGS. 27A-27B. Ratcheting teeth (954) are configured to engage rigid lateral edges (922) of platform (920) to hold arms (952) in a releasing position as described below.

FIGS. 26A and 27A show cartridge (900) in a state prior to engagement with end effector (40). At this stage, the free ends of arms (952) engage the lateral edges of buttress assemblies (100, 110) and thereby secure buttress assemblies (100, 110) to platform (920). In particular, the lateral edges of buttress assemblies (100, 110) are captured between the free ends of arms (952) and rigid lateral edges (922) of platform (920). In the present example, arms (952) are resiliently biased to bear against buttress assemblies (100, 110) to maintain this engagement and thereby secure buttress assemblies (100, 110) to platform (920).

FIGS. 26B and 27B show cartridge (900) as end effector (40) is clamping down on buttress assemblies (100, 110) and platform (920). As shown, the lateral edges of anvil (60) and staple cartridge (70) engage arms (952), thereby urging the upper set of arms (952) toward the lower set of arms (952). The resulting movement of arms (952) causes arms (952) to move outwardly away from buttress assemblies (100, 110), thereby disengaging buttress assemblies (100, 110). In addition, as best seen in FIG. 27B, this movement of arms (952) causes teeth (954) of arms (952) to ratchet along rigid lateral edges (922) of platform (920). As best seen in FIG. 26B, the intermediate region of platform (920) compresses while edges (922) of platform (920) do not compress during closure of end effector. This difference in compressibility across the width of platform (920) enables edges (922) to further urge the lateral edges of buttress assemblies (100, 110) into adhesive engagement with the chamfered lateral edges of anvil (60) and staple cartridge (70).

FIG. 26C shows cartridge (900) released from end effector (40). As shown, buttress assemblies (100, 110) are adhered to anvil (60) and staple cartridge (70), such that end effector (40) is ready for use in a surgical procedure as described above. In addition, arms (952) remain secured in a releasing position due to the engagement between teeth (954) of arms (952) with rigid lateral edges (922) of platform (920).

B. Exemplary Buttress Applier Cartridge with Multi-Buttress Layers

In some instances, it may be desirable to enable a single buttress applier cartridge to be used to apply several layers of buttress assemblies (100, 110) to an end effector (40) during a single surgical procedure. In other words, it may be desirable to enable an operator to use a cartridge to apply a first set of buttress assemblies (100, 110) to an end effector (40), use the end effector (40) to apply staples (90) and that first set of buttress assemblies (100, 110) to tissue, then use the same cartridge to apply a second set of buttress assemblies (100, 110) to the same end effector (40) (after staple cartridge (70) has been replaced), then use the same end effector (40) to apply staples (90) and that second set of buttress assemblies (100, 110) to tissue, and so on.

Figure 28:
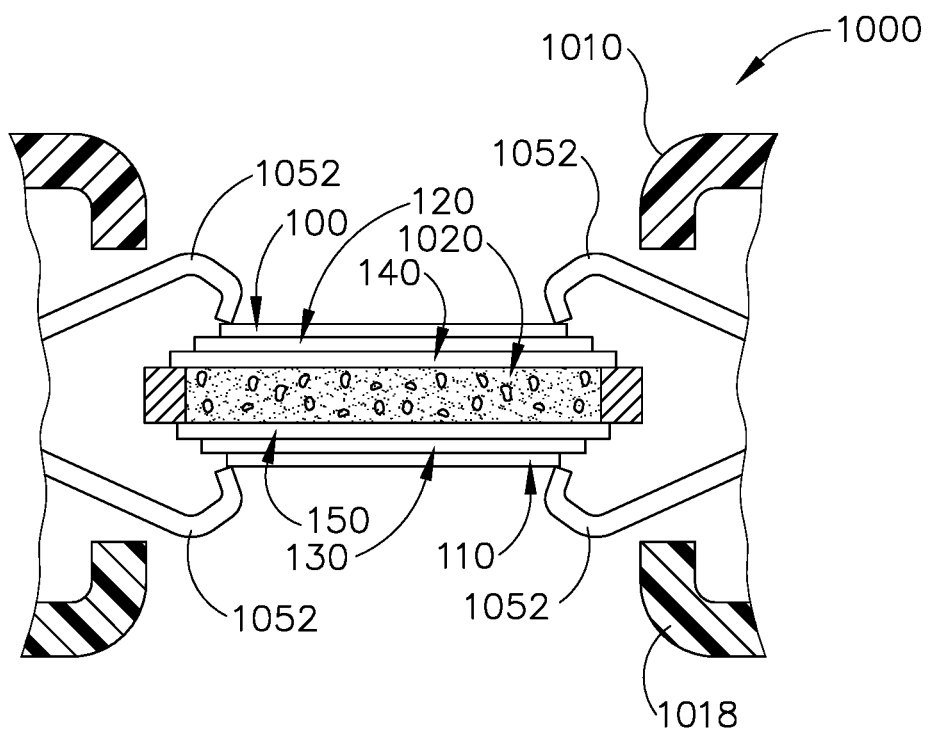
FIG. 28 depicts a partial, cross-sectional end view of another exemplary buttress applier cartridge, with a platform carrying a plurality of buttress assemblies, and with retainer arms in first positions.
Figure 29:
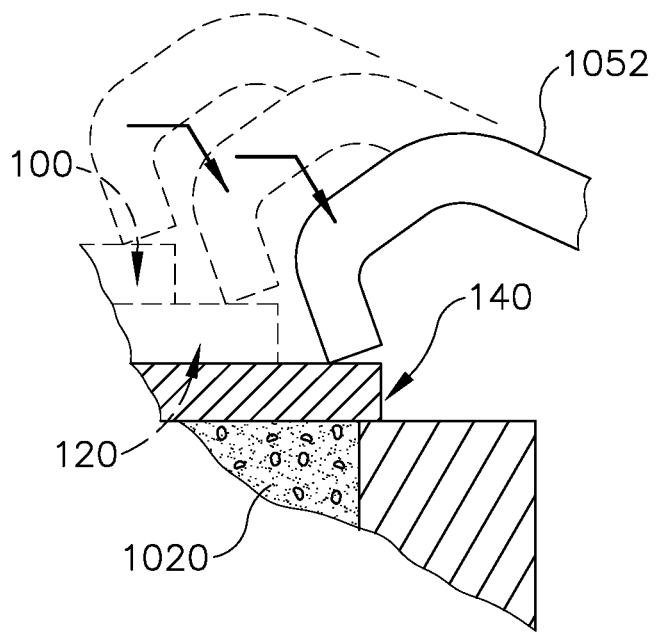
FIG. 29 depicts a partial, cross-sectional detail view of a retainer arm of the buttress applier cartridge transitioning from the first position to second and third positions.

FIGS. 28-29 show one merely illustrative way in which a single buttress applier cartridge to be used to apply several layers of buttress assemblies (100, 110) to an end effector (40) during a single surgical procedure. In particular, FIG. 28 shows an exemplary buttress applier cartridge (1000) that may be used to support and protect buttress assemblies (100, 110, 120, 130, 140, 150). Cartridge (1000) may also be used to easily load buttress assemblies (100, 110, 120, 130, 140, 150) on end effector (40). Cartridge (1000) of this example includes housings (1010, 1018), a platform (1020), and retainer arms (1052). Platform (1020) of this example is substantially identical to platforms (220, 320, 420) described above. Arms (1052) of this example are substantially similar to arms (352) of cartridge (300).

Cartridge (1000) of the present example differs from other buttress applier cartridges described herein in that cartridge (1000) includes several layers of buttress assemblies (100, 110, 120, 130, 140, 150) on each side of platform (1020). In particular, cartridge (1000) include three layers of buttress assemblies (100, 120, 140) on the upper surface of platform (1020); and three layers of buttress assemblies (110, 130, 150) on the lower surface of platform (1020). Buttress assemblies (100, 120, 140) are thus configured and positioned to engage underside (65) of anvil (50); while buttress assemblies (110, 130, 150) are configured and positioned to engage deck (73) of staple cartridge (70). In the present example, buttress assemblies (100, 120, 140) have a progressively increasing lateral width, such that the uppermost buttress assembly (100) has the narrowest width, the intermediate buttress assembly (120) has an intermediate width, and the lowermost buttress assembly (140) has the widest width. Similarly, buttress assemblies (110, 130, 150) have a progressively increasing lateral width, such that the lowermost buttress assembly (110) has the narrowest width, the intermediate buttress assembly (130) has an intermediate width, and the uppermost buttress assembly (150) has the widest width.

Arms (1052) are resiliently biased to bear against buttress assemblies (100, 110, 120, 130, 140, 150) to thereby secure buttress assemblies (100, 110, 120, 130, 140, 150) to platform (1020). When end effector (40) is clamped down on buttress assemblies (100, 110, 120, 130, 140, 150) and platform (1020) a first time, the lateral edges of anvil (60) and staple cartridge (70) engage arms (1052), thereby urging the upper set of arms (1052) toward the lower set of arms (1052). This causes arms (1052) to disengage buttress assemblies (100, 110) and directly engage buttress assemblies (120, 130); while buttress assemblies (100, 110) are adhered to anvil (60) and staple cartridge (70), respectively. When end effector (40) is subsequently opened, buttress assemblies (100, 110) remain adhered to anvil (60) and staple cartridge (70) and are thus pulled away from cartridge (1000), while buttress assemblies (120, 130, 140, 150) remain secured to platform (1020).

When end effector (40) is then clamped down on buttress assemblies (120, 130, 140, 150) and platform (1020) a second time (e.g., after end effector (40) has been actuated on tissue and reloaded with a new staple cartridge (70)), the lateral edges of anvil (60) and staple cartridge (70) engage arms (1052) again, thereby urging the upper set of arms (1052) toward the lower set of arms (1052) again. This causes arms (1052) to disengage buttress assemblies (120, 130) and directly engage buttress assemblies (140, 150); while buttress assemblies (120, 130) are adhered to anvil (60) and staple cartridge (70), respectively. When end effector (40) is subsequently opened, buttress assemblies (120, 130) remain adhered to anvil (60) and staple cartridge (70) and are thus pulled away from cartridge (1000), while buttress assemblies (140, 150) remain secured to platform (1020).

When end effector (40) is then clamped down on buttress assemblies (140, 150) and platform (1020) a third time (e.g., after end effector (40) has been actuated on tissue and reloaded with a new staple cartridge (70)), the lateral edges of anvil (60) and staple cartridge (70) engage arms (1052) again, thereby urging the upper set of arms (1052) toward the lower set of arms (1052) again. This causes arms (1052) to disengage buttress assemblies (140, 150) and directly engage platform (1020); while buttress assemblies (140, 150) are adhered to anvil (60) and staple cartridge (70), respectively. When end effector (40) is subsequently opened, buttress assemblies (140, 150) remain adhered to anvil (60) and staple cartridge (70) and are thus pulled away from cartridge (1000).

It should be understood from the foregoing that the varying widths of buttress assemblies (100, 110, 120, 130, 140, 150) enable arms (1052) to engage corresponding sets of buttress assemblies (100, 110, 120, 130, 140, 150) in a succession each time end effector (40) is closed upon buttress assemblies (100, 110, 120, 130, 140, 150) and platform (1020). This succession is best seen in FIG. 29. It should also be understood that any other suitable number of layers of buttress assemblies (100, 110, 120, 130, 140, 150) may be used.

VI. Exemplary Alternative Staple Cartridge with Integral Buttress

In the examples described above, a buttress assembly (110) is applied to a staple cartridge (70) by using a buttress applying cartridge right before end effector (40) will be actuated in a surgical procedure. In some instances, it may be desirable to provide a staple cartridge (70) that includes a buttress assembly (110) that is pre-loaded on deck (730). Such a pre-loaded buttress assembly (110) may be provided regardless of whether or not a buttress applying cartridge will be used to apply a buttress assembly (100) to underside (65) of anvil (60) right before end effector (40) will be actuated in a surgical procedure.

Figure 30:
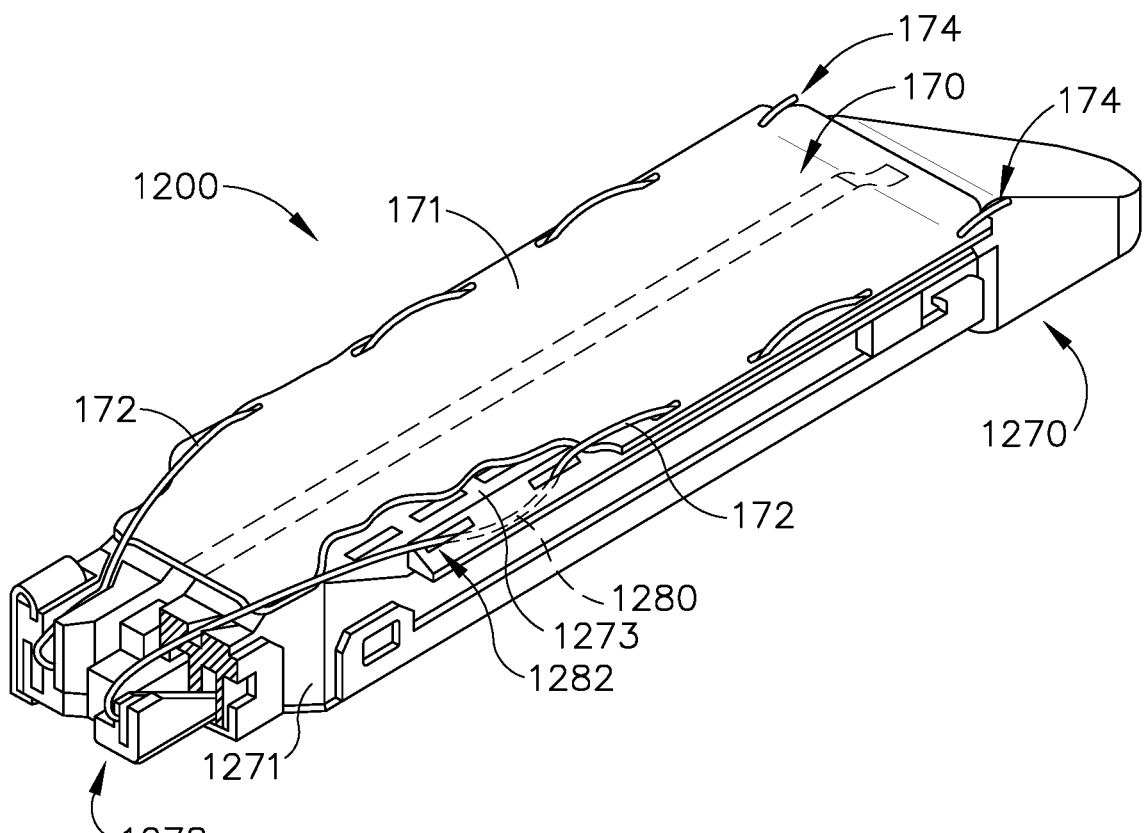
FIG. 30 depicts a perspective view of an exemplary alternative staple cartridge that may be loaded into the end effector of FIG. 2, with a buttress loaded thereon by a thread.

FIG. 30 shows an exemplary cartridge assembly (1200) that includes a modified staple cartridge (1270) pre-loaded with a buttress assembly (170). Staple cartridge (1270) of this example is substantially identical to staple cartridge (70) described above except that staple cartridge (1270) includes a pair of laterally extending engagement wings (1280) extending along the lateral sides of deck (1273). Wings (1280) define suture slots (1282) that are configured to receive corresponding strands of suture (172) as will be described below. Buttress assembly (170) includes a body (171) that is substantially identical to body (112) of buttress assembly (110) described above. In the present example, buttress assembly (170) lacks an adhesive layer like adhesive layer (114). In some other versions, buttress assembly (170) includes an adhesive layer to assist in securing buttress assembly (170) to deck (1273) of staple cartridge (1270).

In the present example, suture (172) is used to releasably secure buttress assembly (170) to staple cartridge (1270). Cartridge assembly (1200) includes two strands of suture (172), each strand being located at a respective lateral side of cartridge assembly (1200). As shown in FIG. 30 and FIG. 32A, each strand of suture (172) is woven through body (171) and suture slots (1282) of a corresponding wing (1280). The free end (174) of each suture (172) is positioned at the distal end of body (171) while the other end of each suture (172) is secured to wedge sled (1278) of staple cartridge (1270). Wedge sled (1278) of this example is configured and operable just like wedge sled (78) of staple cartridge (70).

Cartridge assembly (1200) may be loaded in lower jaw (50) just like staple cartridge (70), with buttress assembly (170) already secured to staple cartridge (1270). When staple cartridge (1270) is actuated to drive staples (90) through tissue as described above with respect to staple cartridge (70), wedge sled (1278) and suture (172) will cooperate to release buttress assembly (170) from staple cartridge (1270). In particular, as shown in FIG. 32B, wedge sled (1278) will pull suture (172) distally when wedge sled (1278) is driven distally as end effector (40) is actuated. Suture (172) will thus be pulled through body (171) and suture slots (1282) of wing (1280). In the present example, suture (172) has a length such that free end (174) of suture (172) will be pulled free of buttress assembly (170) when wedge sled (1278) reaches a distal-most position in response to full actuation of end effector (40). In some versions, suture (172) has a length such that free end (174) of suture (172) will be pulled into the interior of staple cartridge (1270) when wedge sled (1278) reaches a distal-most position in response to full actuation of end effector (40).

Figure 31:
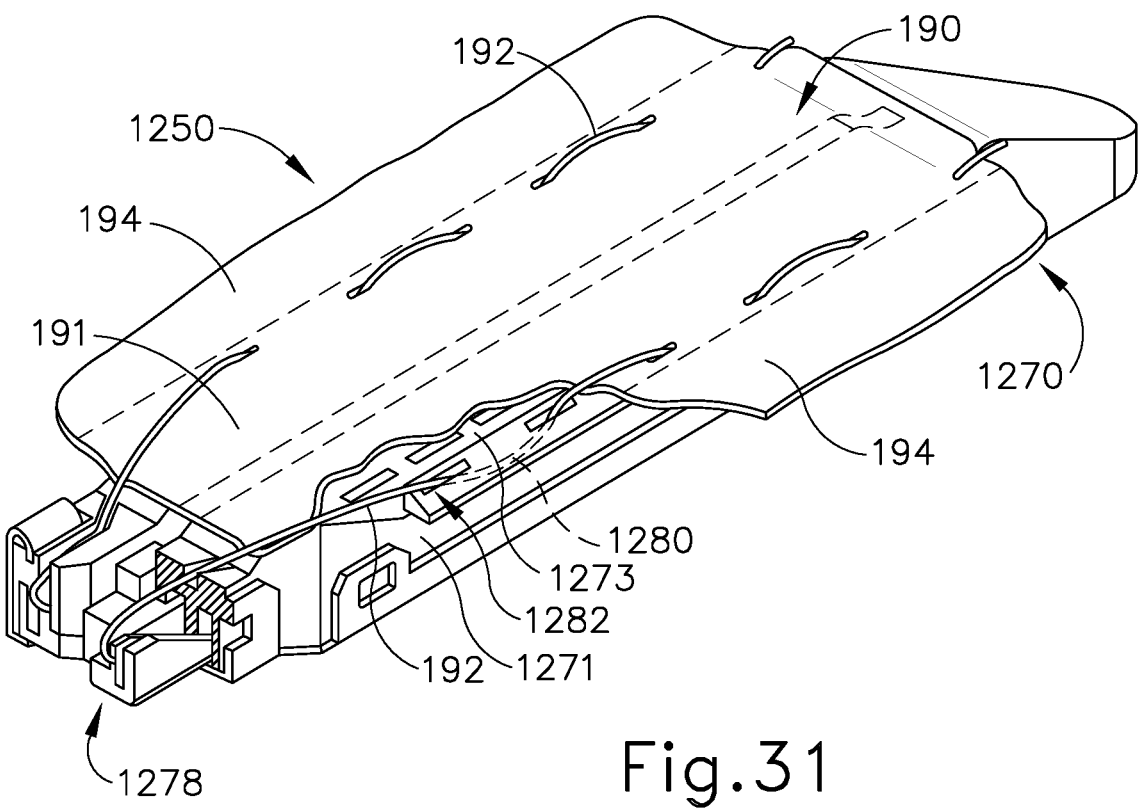
FIG. 31 depicts a perspective view of another exemplary alternative staple cartridge that may be loaded into the end effector of FIG. 2, with another buttress loaded thereon by a thread.

FIG. 31 shows another exemplary cartridge assembly (1250) that is a merely illustrative variation of cartridge assembly (1200) described above. Cartridge assembly (1200) of this example comprises the same staple cartridge (1270) pre-loaded with a different buttress assembly (190). Buttress assembly (190) includes a body (191) that is substantially identical to body (112) of buttress assembly (110) described above. Suture (192) is used to secure body (191) to staple cartridge (1270) in the same manner in which suture (172) is used to secure body (171) to staple cartridge (1270). In the present example, buttress assembly (190) lacks an adhesive layer like adhesive layer (114). In some other versions, buttress assembly (190) includes an adhesive layer to assist in securing buttress assembly (190) to deck (1273) of staple cartridge (1270). The difference between buttress assembly (190) and buttress assembly (170) is that buttress assembly (190) includes outwardly extending wing portions (194). Otherwise, buttress assembly (190) is secured to and released from staple cartridge (1270) just like buttress assembly (170) as shown in FIGS. 32A-32B. It should be understood that wing portions (194) may assist with tissue ingrowth and/or other buttress anchoring properties. In addition or in the alternative, wing portions (194) may provide a smooth transition from the relatively thick, uncompressed region of tissue to the relatively thin, compressed tissue where formed staples (90) are in the tissue. In some versions, wing portions (194) are formed with a weave density that is different from (i.e., greater than or lesser than) the weave density of the remainder of buttress assembly (190).

Figure 33:
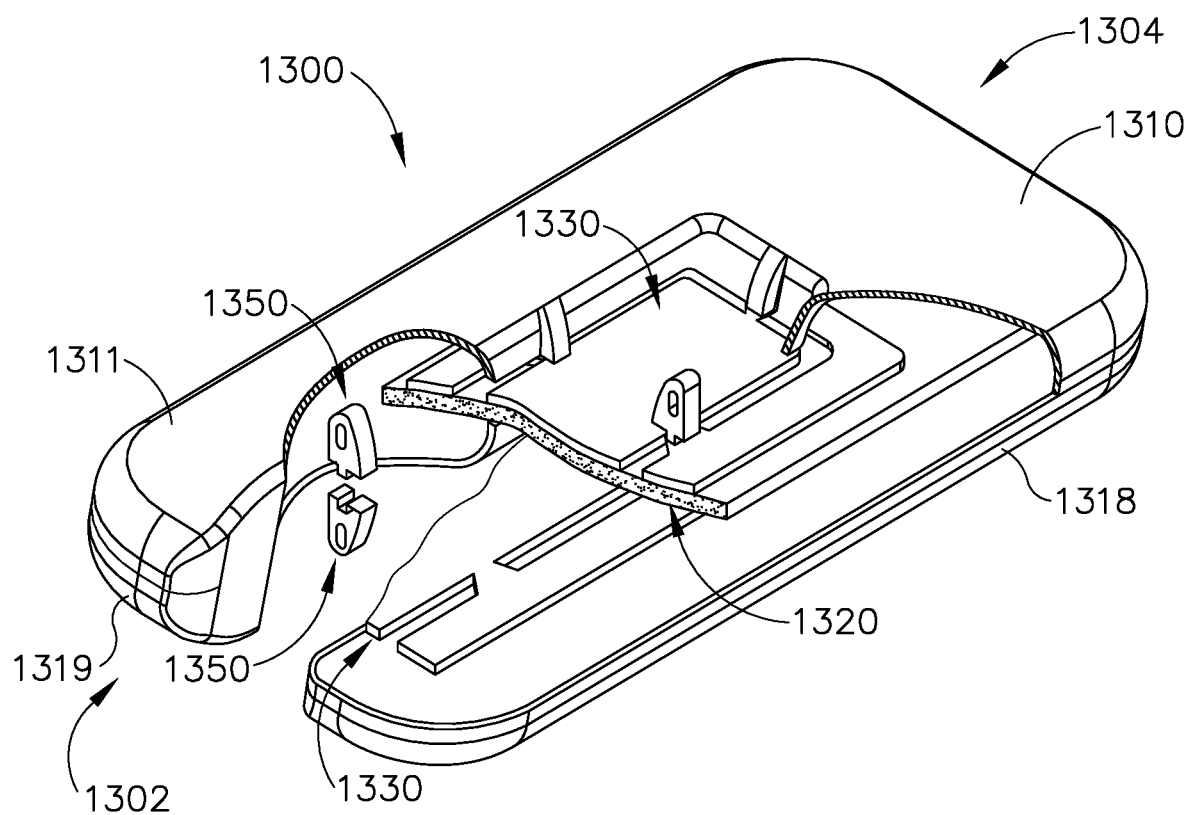
FIG. 33 depicts a perspective view of another exemplary alternative buttress applier cartridge, with a portion of the cartridge cut away to reveal internal components.

VII. Exemplary Cutting Buttress Releasing Features for Buttress Applier Cartridge In the foregoing examples that include buttress applier cartridges, the entire body (102, 112) of each buttress assembly (100, 110) is fully released from the buttress applier cartridge after an end effector (40) has been closed and opened to apply buttress assemblies (100, 110) to end effector (40). In some instances, it may be desirable to have the buttress applier cartridge retain a first portion of the body of the buttress assembly, even after a second portion of the buttress assembly has been applied to an end effector (40). To that end, FIG. 33 shows an exemplary alternative buttress applier cartridge (1300) that may be used to support and protect upper and lower buttress assemblies (1330). Cartridge (1300) may also be used to easily load upper and lower buttress assemblies (1330) on end effector (40). Cartridge (1300) of this example includes an open end (1302) and a closed end (1304) defined by upper and lower housings (1310, 1318). Cartridge (1300) further includes and a platform (1320) supporting a pair of buttress assemblies (1330). Buttress assemblies (1330) are releasably secured to cartridge (1300) by a set of retainers (1350).

Figure 34:
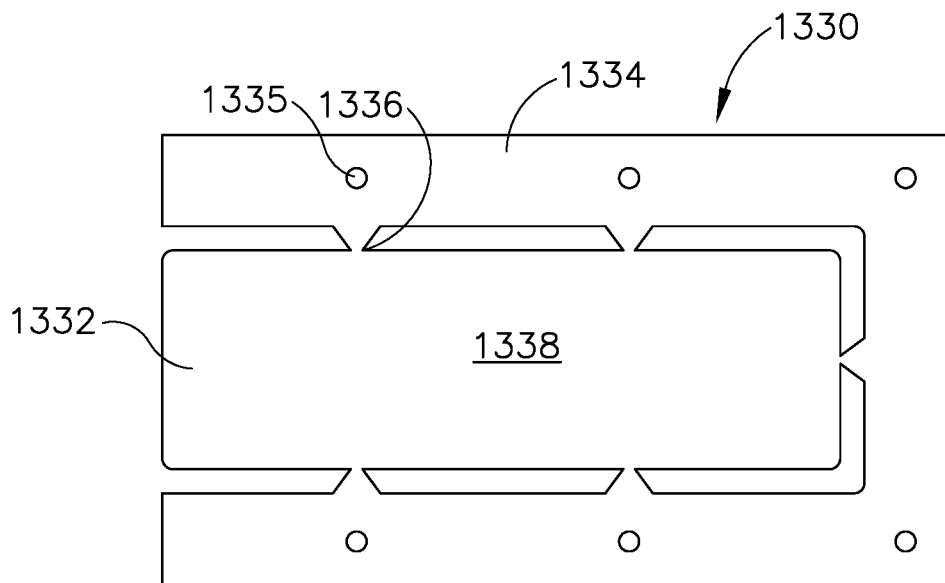
FIG. 34 depicts a top plan view of a buttress assembly of the buttress applier cartridge of FIG. 33.

FIG. 34 shows buttress assembly (1330) in greater detail. Buttress assembly (1130) includes an inner body portion (1332) and an outer body portion (1334) that are joined together by a set of bridge portions (1336) in the form of webs. An adhesive layer (1338) is positioned on inner body portion (1332) but not outer body portion (1334). The material composition of body portions (1332, 1334) and adhesive layer (1338) may be the same for that described above with respect to body portion (102, 112) and adhesive layer (104, 114), respectively. Inner body portion (1332) is rectangular and is sized and configured to correspond with the gap defined laterally between the prongs (1311) of housing (1310), which is the same as the gap defined laterally between the prongs (1319) of housing (1318). It should be understood that the size and configuration of this gap also corresponds to the clamping footprint of end effector (40). Outer body portion (1334) has a "U" shape and is sized and configured to fit within the hollow interior defined between housings (1310, 1318). Outer body portion (1334) includes a set of openings that are sized and positioned to receive corresponding posts of housings (1310, 1318), to thereby secure the positioning of outer body portion (1334) between housings (1310, 1318).

Bridge portions (1336) of buttress assembly (1330) are sized and positioned to correspond with retainers (1350). As best seen in FIGS. 50A-50B, each retainer (1350) comprises a buttress engagement foot (1352), an integral blade (1354), a cam surface (1356), and ratchet teeth (1358). Foot (1352) is rounded in this example and is configured to press bridge portion (1336) against platform (1320), thereby assisting in holding the position of buttress assembly (1330) on platform (1320). Blade (1354) projects downwardly and is configured to sever bridge portion (1336) as will be described in greater detail below. Cam surface (1356) is configured to engage anvil (60) during closure of end effector (40) as will also be described in greater detail below. While the present example is provided in the context of engagement with anvil (60), it should be understood that cam surfaces (1356) of retainers (1350) on the underside of platform (1320) would similarly engage staple cartridge (70) during closure of end effector (40). Ratchet teeth (1358) are positioned and configured to engage a fixed pawl (1312). Fixed pawl (1312) is unitary with (or is otherwise fixedly secured to) housing (1310, 1318).

Figure 35A:
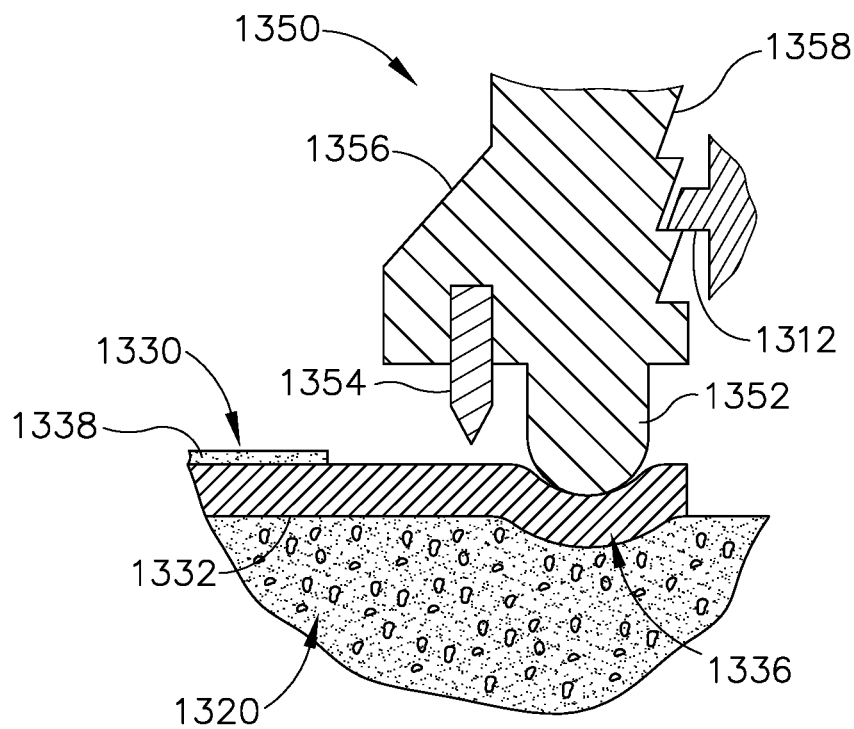
FIG. 35A depicts a cross-sectional detail view of a buttress retention member of the buttress applier cartridge of FIG. 33, with the buttress retention member in a first position.
Figure 35B:
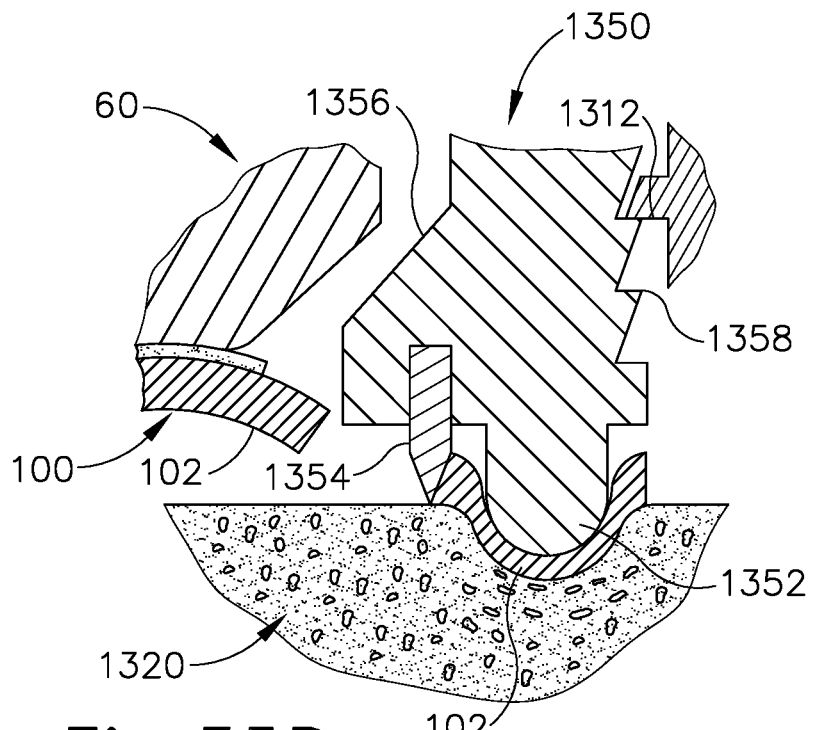
FIG. 35B depicts a cross-sectional detail view of a buttress retention member of the buttress applier cartridge of FIG. 33, with the buttress retention member driven to a second position by the anvil of the end effector of FIG. 2.
Figure 36A:
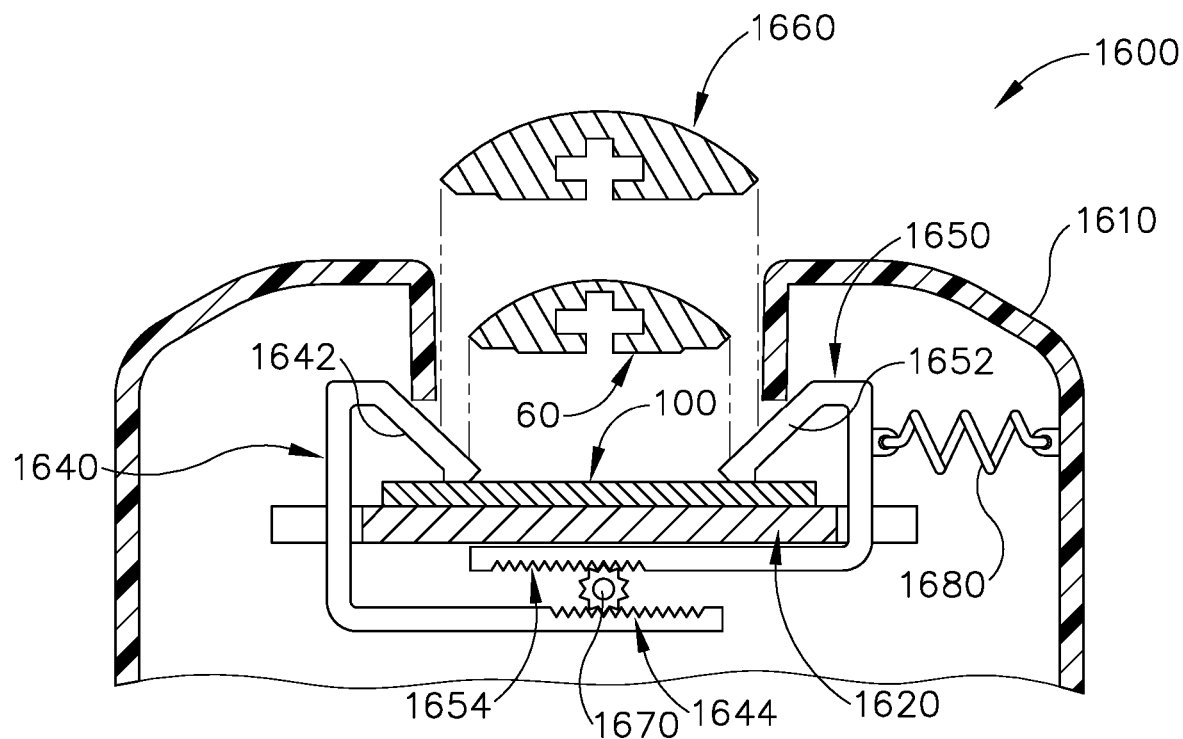
FIG. 36A depicts a partial cross-sectional end view of another exemplary alternative buttress applier cartridge, with the anvil of the end effector of FIG. 2 positioned over a platform of the buttress applier cartridge.
Figure 36B:
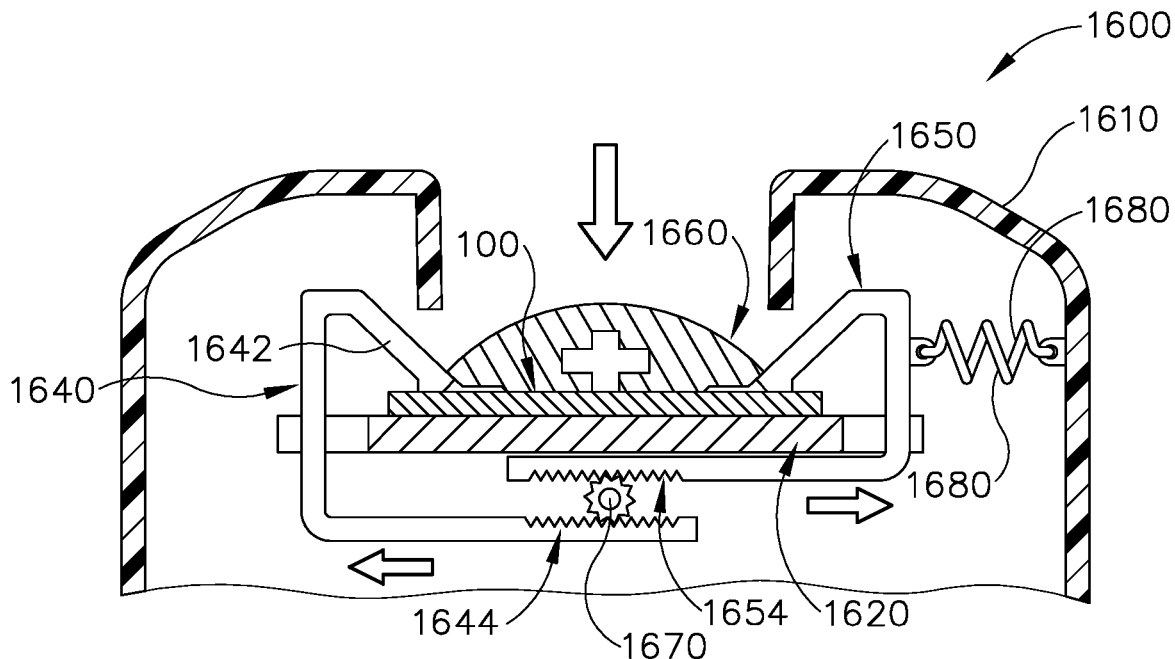
FIG. 36B depicts a partial cross-sectional end view of the buttress applier cartridge of FIG. 36A, with the anvil engaging guide features and a buttress on the platform.

In the state shown in FIG. 35A, teeth (1358) cooperate with pawl (1312) to maintain a vertical position of retainer (1350) where foot (1352) is pressing bridge portion (1336) against platform (1320). Blade (1354) is spaced away from bridge portion (1336). As end effector (40) is closed about buttress assemblies (1330) and platform (1320), the lateral edge of anvil (60) engages cam surface (1356) and thereby drives retainer (1350) downwardly to the position shown in FIG. 35B. Platform (1320) is formed of a compliant material in this example, such that platform (1320) accommodates the additional pressing of foot (1352) into platform (1320). As retainer (1350) is driven downwardly, blade (1354) severs bridge portion (1336), thereby decoupling inner body portion (1332) from outer body portion (1334). Inner body portion (1332) is thus free to be pulled away from platform (1320). Adhesive layer (1338) adheres inner body portion (1332) to underside (65) of anvil (60), such that anvil (60) will freely pull inner body portion (1332) away from cartridge (1300) as end effector (40) is subsequently opened. Teeth (1358) again cooperate with pawl (1312) to maintain the lowered vertical position of retainer (1350). It should be understood that teeth (1358) will ratchet along pawl (1312) during the transition from the state shown in FIG. 35A to the state shown in FIG. 35B.

VIII. Exemplary End Effector Alignment Features for Buttress Applier Cartridge

In some instances, it may be desirable to configure buttress assembly (100) such that the lateral width of buttress assembly (100) closely matches the lateral width of underside (65) of anvil (60). Likewise, it may be desirable to configure buttress assembly (110) such that the lateral width of buttress assembly (110) closely matches the lateral width of deck (73) of anvil (70). Matching these widths may present little to no margin of error with respect to alignment of end effector (40) with buttress assemblies (100, 110). It may therefore be desirable to provide features that ensure or otherwise promote proper alignment of end effector (40) with buttress assemblies (100, 110). Such alignment may include proper lateral positioning of end effector along a lateral plane (i.e., a plane that is parallel to the planes defined by buttress assemblies (100, 110)). Such alignment may also include proper "yaw" positioning about an axis that is perpendicular to the same lateral plane (i.e., a plane that is parallel to the planes defined by buttress assemblies (100, 110)). Several examples of features that may be used to ensure or otherwise promote proper alignment of end effector (40) with buttress assemblies (100, 110) are described in greater detail below, while other examples will be apparent to those of ordinary skill in the art in view of the teachings herein.

In addition to or as an alternative to providing visual cues to promote proper alignment between end effector (40) and a buttress applier cartridge, it may be desirable to incorporate structural features in a buttress applier cartridge to ensure proper alignment. A few merely illustrative examples of structural guide features are described in greater detail below, while other examples will be apparent to those of ordinary skill in the art in view of the teachings herein.

Those of ordinary skill in the art will further recognize that surgical stapling and severing instruments (10) may come in a variety of sizes, including different sizes with end effectors (40) having different lateral widths. It may therefore be desirable to enable a buttress applier cartridge to be used with end effectors (40) having different lateral widths. Moreover, it may be desirable for such a buttress applier cartridge to also provide proper lateral alignment between buttress assemblies (100, 110) and end effectors (40) having different lateral widths. To that end, FIGS. 54A-54B show an exemplary buttress applier cartridge (1600) that is configured to accommodate a relatively narrow anvil (60) and a relatively wide anvil (1660). While FIGS. 54A-54B only show an upper portion of cartridge (1600) associated with anvils (60, 1660), it should be understood that cartridge (1600) may have a similarly configured lower portion that is associated with staple cartridges (70) and lower jaws (50) of different widths.

Cartridge (1600) of the present example comprises a housing (1610), a platform (1620), a first retention feature (1640), a second retention feature (1650), a pinion (1670), and a resilient member (1680). Platform (1620) supports buttress assembly (100) just like various other platforms described herein. Retention feature (1640) comprises a retention arm (1642) and an integral rack (1644). Retention feature (1650) also comprises a retention arm (1652) and an integral rack (1654). While just two retention features (1640, 1650) are shown in FIGS. 54A-54B, it should be understood that several additional retention features (1640, 1650) may be positioned along the length of cartridge (1600). Racks (1644, 1654) are engaged with pinion (1670), which is rotatably supported in housing (1610). Racks (1644, 1654) are engaged with pinion (1670) at regions of pinion (1670) that are angularly offset by 180 degrees. Thus, racks (1644, 1654) will translate simultaneously in opposing directions as pinion (1670) rotates. Resilient member (1680) is positioned between retention feature (1650) and housing (1610). In the present example, resilient member (1680) is in the form of a coil spring that urges retention features (1640, 1650) toward each other.

Arms (1642, 1652) are configured to bear against buttress assembly (100) to thereby secure buttress assembly (100) against platform (1620). Arms (1642, 1652) are also angled to cooperate with outer lateral edges of anvil (60, 1660) as anvil (60, 1660) is clamped down toward buttress assembly (100) and platform (1620). In particular, as anvil (60, 1660) is clamped down toward buttress assembly (100) and platform (1620), the outer edges outer lateral edges of anvil (60, 1660) will engage angled surfaces of arms (1642, 1652), which will drive arms (1642, 1652) outwardly. Because arms (1642, 1652) are coupled together via racks (1644, 1654) and pinion (1670), arms (1642, 1652) will translate outwardly simultaneously, at the same rate, for the same distance. While this occurs, the angled surfaces of arms (1642, 1652) will guide anvil (60, 1660) downwardly along a path that is centered along a vertical plane passing longitudinally through the central longitudinal axis of buttress assembly (100) and platform (1620). In other words, retention features (1640, 1650) and pinion (1670) will cooperate to not only accommodate anvils (60, 1660) having different widths; but also to ensure that anvil (60, 1660) remains properly centered along the vertical plane passing through the lateral center of buttress assembly (100) and platform (1620). Retention features (1640, 1650) and pinion (1670) thus ensure that buttress assembly (100) has proper lateral alignment on anvil (60, 1660) regardless of whether a narrow anvil (60) or wide anvil (1660) is used.

IX. Exemplary Multi-Stage Buttress Applier Cartridge

Figure 37:
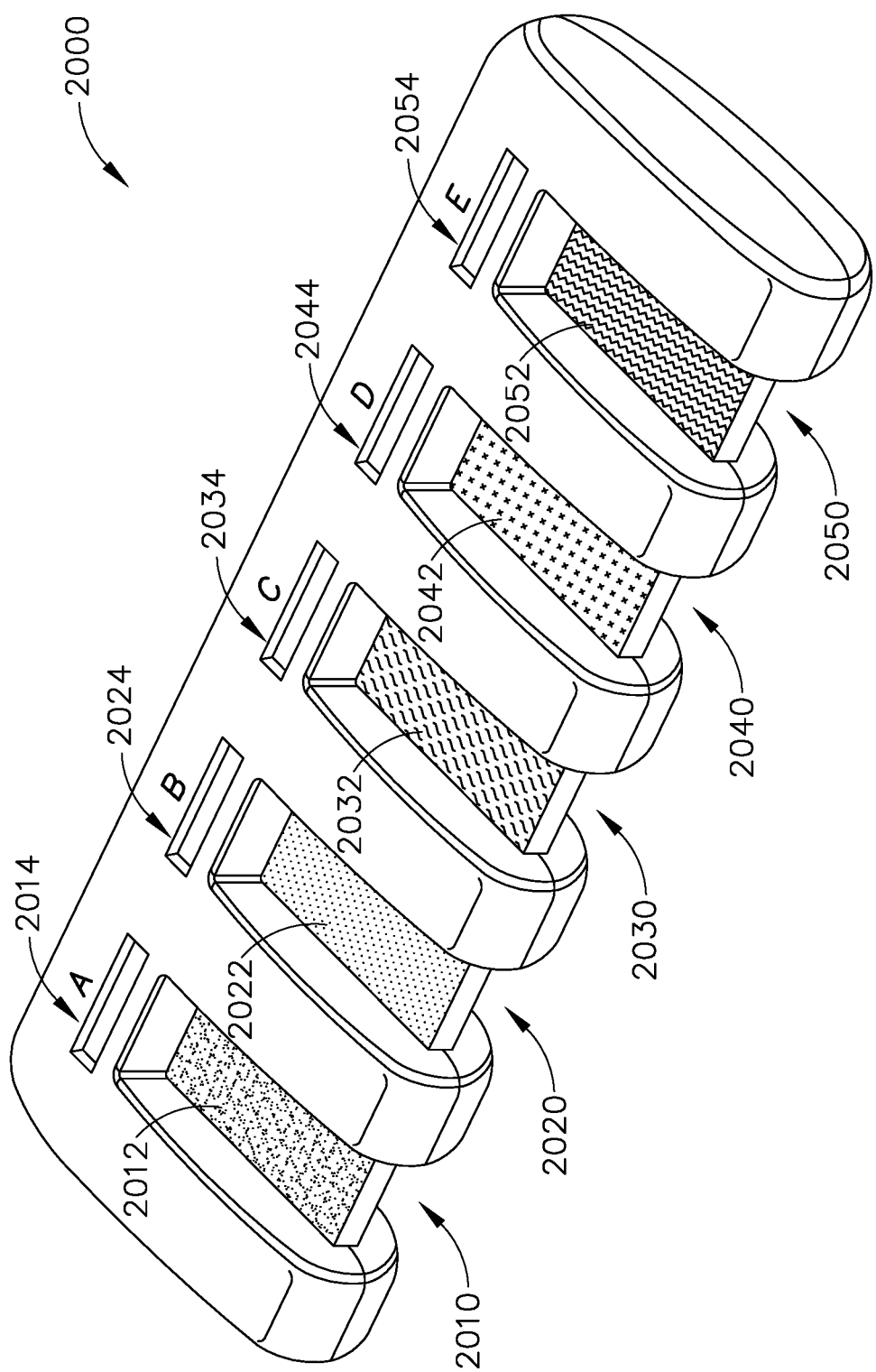
FIG. 37 depicts a perspective view of another exemplary alternative buttress applier cartridge.

In some instances, it may be desirable to provide an operator with a buttress applier cartridge that provides the operator with more options than just simply applying buttress assemblies (100, 110) in a single stroke of end effector (40). For instance, FIG. 37 shows a buttress applier cartridge (2000) that provides a plurality of stations (2010, 2020, 2030, 2040, 2050) for an operator to choose from. Each station (2010, 2020, 2030, 2040, 2050) is sized and configured to receive end effector (40). Each station (2010, 2020, 2030, 2040, 2050) includes a respective panel (2012, 2022, 2032, 2042, 2052) that the operator may clamp on with end effector (40). In the present example, panel (2012) includes a low strength adhesive disposed thereon. Panel (2022) includes a high strength adhesive disposed thereon. Panel (2032) includes a buttress body (e.g., like buttress body (102) disposed thereon. In some versions, panel (2032) includes a plurality of buttress bodies (e.g., similar to the arrangement described above with reference to FIGS. 28-29). It should therefore be understood that cartridge (2000) may be used repeatedly to apply a series of buttress assemblies (100, 110) to a single end effector (40) during a single surgical procedure. Panel (2042) includes a hydrophilic drying material disposed thereon. Panel (2052) includes an abrasive material disposed thereon. Of course, these are just merely illustrative examples, and it should be understood that panels (2012, 2022, 2032, 2042, 2052) may have any other suitable features and/or materials disposed thereon. In the present example, each station (2010, 2020, 2030, 2040, 2050) includes an identifier (2014, 2024, 2034, 2044, 2054) associated with each panel (2012, 2022, 2032, 2042, 2052). Each identifier (2014, 2024, 2034, 2044, 2054) indicates the features or materials that re disposed on the corresponding panel (2012, 2022, 2032, 2042, 2052).

In an exemplary use of cartridge (2000), an operator may first clamp end effector (40) on panel (2012) to pick up adhesive; then clamp on panel (2032) to pick up bodies (102, 112), thereby forming buttress assemblies (100, 110) on end effector (40). The operator may then insert end effector (40) into a patient and then actuate end effector (40) to apply staples (90) and buttress bodies (102, 112) to tissue. The operator may then remove end effector (40) from the patient, remove the spent cartridge (70) from lower jaw (50), and swish end effector (40) in saline to at least partially clean end effector (40). The operator may then use panel (2052) to scrub end effector (2052) to remove any excess adhesive material from underside (65) of anvil (60), swish end effector (40) again in saline, then dry end effector (40) on panel (2042). The operator may then load a new staple cartridge (70) in lower jaw (50) and repeat the above process by clamping again on panel (2012) to pick up adhesive, etc. Of course, cartridge (2000) may be used in any other suitable fashion. It should be understood that an operator may clamp end effector (40) on any number of panels (2012, 2022, 2032, 2042, 2052) and in any suitable sequence.

It should also be understood that some variations of cartridge (2000) may include a panel having a lubricant. The lubricant may be applied to end effector (40) after buttress assemblies (100, 110) are applied do end effector (40). The lubricant may facilitate placement of buttress assemblies (100, 110) on tissue without buttress assemblies (100, 110) becoming misaligned on end effector (40) due to sliding contact with tissue. Other suitable variations will be apparent to those of ordinary skill in the art in view of the teachings herein.

X. Exemplary Alternative Buttress Assembly Configurations

As noted above, the configurations of buttress assemblies (100, 110) shown in FIG. 4 are merely illustrative examples. Moreover, as shown in FIG. 19 and other drawings of the present application, each buttress assembly (100, 110) may be provided in two laterally spaced apart portions, with the two portions of each buttress assembly (100, 110) being separated by a gap that complements the width of channels (62, 72) in anvil (60) and staple cartridge (70). In versions where a buttress assembly (100, 110) is provided in two portions that are laterally separated by a gap, it may be desirable to provide one or more features that generally maintain the lateral spacing of those portions. Such features may also ensure (or at least promote) that the portions remain generally parallel with each other in addition to ensuring (or at least promoting) that the portions are separated by a consistent gap. FIGS. 38-41 show merely illustrative examples of structures that may be used to provide such functionality in buttress assemblies (100, 110). It should be understood that the modifications described below may be readily incorporated into any of the versions of buttress assemblies (100, 110) described above; and that the modified buttress assemblies described below may be readily used with any of the various buttress applier cartridges described above.

Figure 38:
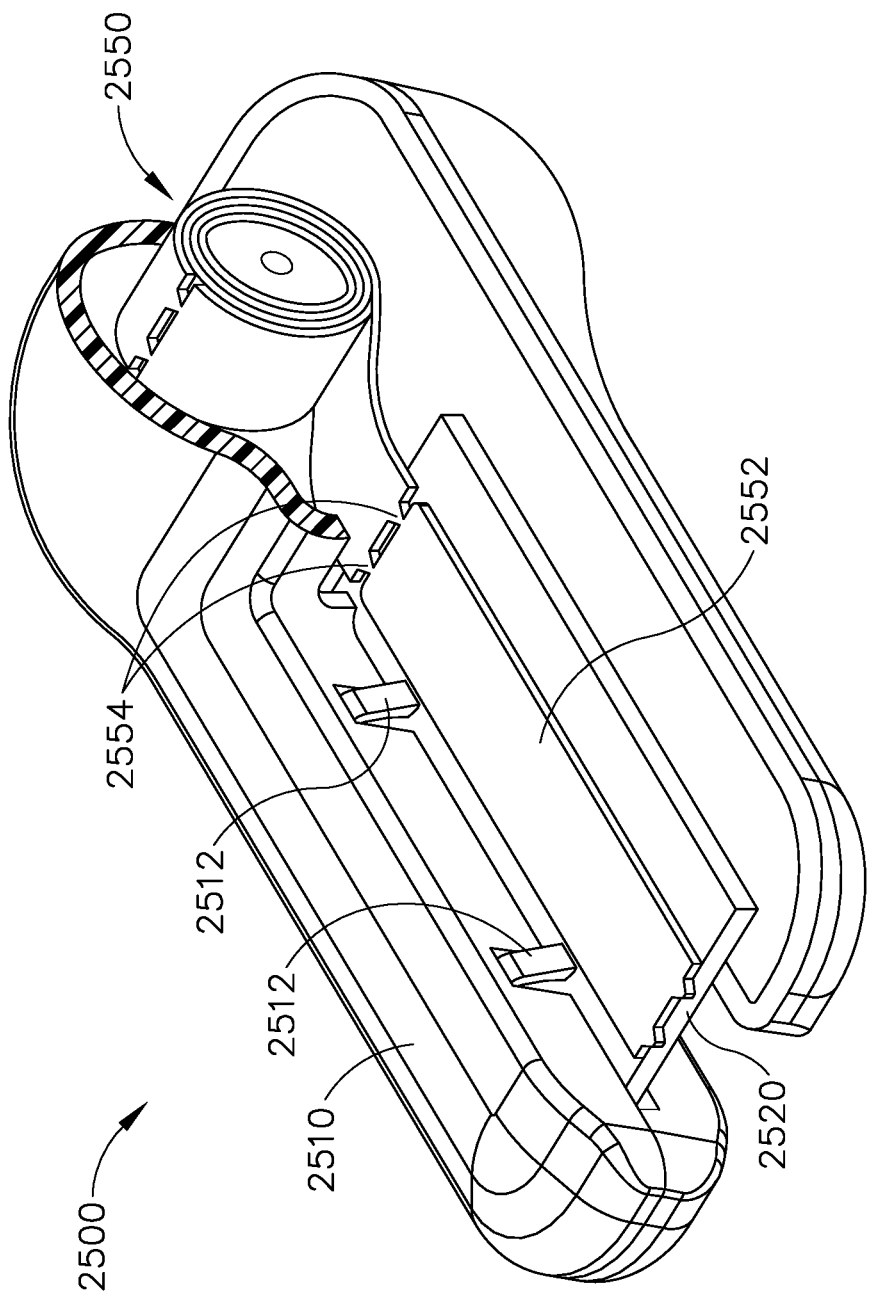
FIG. 38 depicts a perspective view of another exemplary alternative buttress applier cartridge and package with another exemplary alternative buttress assembly.
Figure 39:
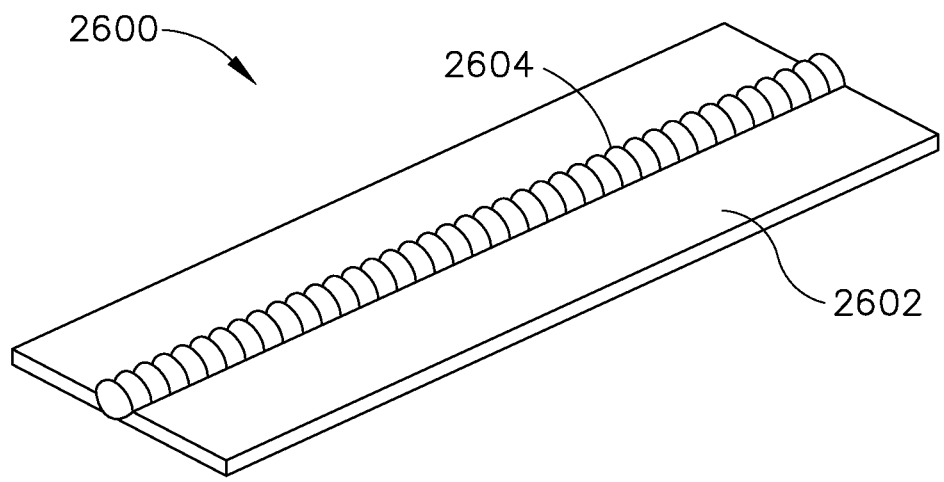
FIG. 39 depicts a perspective view of an exemplary alternative buttress assembly.

FIG. 38 shows a buttress applier cartridge (2500) containing yet another exemplary alternative buttress assembly (2550). Cartridge (2500) of this example comprises a housing (2510), retention features (2512), and a platform (2520) similar to other housings, retention features, and platforms described herein. Buttress assembly (2500) of this example is substantially identical to buttress assembly (100, 110) except that buttress assembly (2500) is in the form of a roll that is contained within housing (2510). The roll comprises a plurality of segments (2552) that are separated by weak portions (2554). Each segment (2552) has a length complementing the length of underside (65) and/or the length of deck (73). Weak portions (2554) are configured to enable an operator to easily tear one segment (2552) from the next segment (2552). Thus, the operator may use the same cartridge (2500) to apply several different segments (2552) to an end effector (40) during a single surgical procedure. It should be understood that buttress assembly (2550) may also be incorporated into cartridge (2000) described above with reference to FIG. 37 (e.g., with buttress assembly (2550) being applied via panel (2032)). Other suitable variations will be apparent to those of ordinary skill in the art in view of the teachings herein.

FIGS. 38-41 show an exemplary alternative buttress assembly (2600) that comprises a buttress body (2602) and an attachment feature (2604). Buttress body (2602) may be constructed and operable just like any other buttress body described herein and/or like any buttress body described in any references cited herein. Attachment feature (2604) comprises a hollow tubular structure that is secured to one side of buttress body (2602). In particular, attachment feature (2604) extends along the full length of buttress body (2602) and is laterally centered on buttress body (2602). While attachment feature (2604) extends continuously along the full length of buttress body (2602) in this example, it should be understood that attachment feature (2604) may instead be broken into segments that are longitudinally spaced apart from each other. In the present example, attachment feature (2604) comprises an extruded absorbable polymer (e.g., PGA, etc.) that is thermally bonded to buttress body (2602). Alternatively, any other suitable material(s) may be used to form attachment feature (2604); and any other suitable techniques may be used to secure attachment feature (2604) to buttress body (2602).

Figures 40A, 40B:
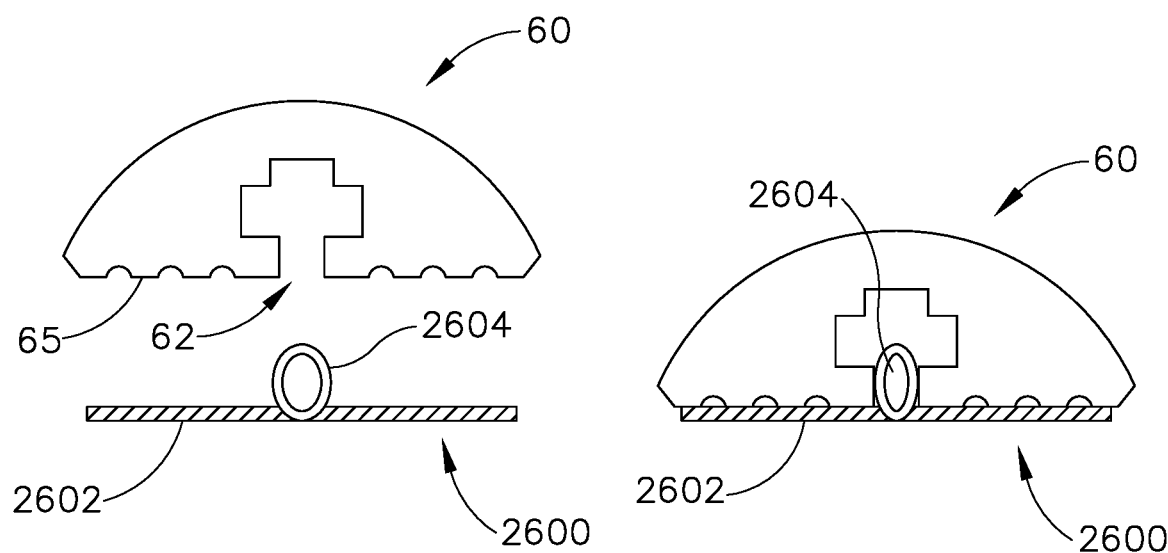
FIG. 40A depicts an end view of the anvil of the end effector of FIG. 2 positioned positioned over the buttress assembly of FIG. 39.
FIG. 40B depicts an end view of the buttress assembly of FIG. 39 secured to the anvil of the end effector of FIG. 2.

Attachment feature (2604) is resiliently biased to have a circular cross-sectional configuration as best seen in FIG. 40A. However, attachment feature (2604) is configured and dimension such that attachment feature (2604) may be compressed inwardly to deformably fit within channel (62) of anvil (60) as shown in FIG. 40B. When attachment feature (2604) is located within channel (62), the hoop stresses imposed by the resilient bias of attachment feature (2604) will provide friction against the inner sidewalls of anvil (60) that define channel (62), thereby securing attachment feature (2604) within channel (62). The secure positioning of attachment feature (2604) within channel (62) will further secure buttress body (2602) against underside (65) of anvil (60). It should therefore be understood that attachment feature (2604) may be used in lieu of providing an adhesive layer on buttress body (2602) to secure buttress body (2602) against underside (65) of anvil (60). Alternatively, attachment feature (2604) may be used to supplement an adhesive layer on buttress body (2602) to secure buttress body (2602) against underside (65) of anvil (60). It should also be understood that attachment feature (2604) may be fitted within channel (62) by anvil (60) closing down on buttress assembly (2600), such that buttress assembly (2600) may be readily used with the various buttress applier cartridges described herein.

Figure 41:
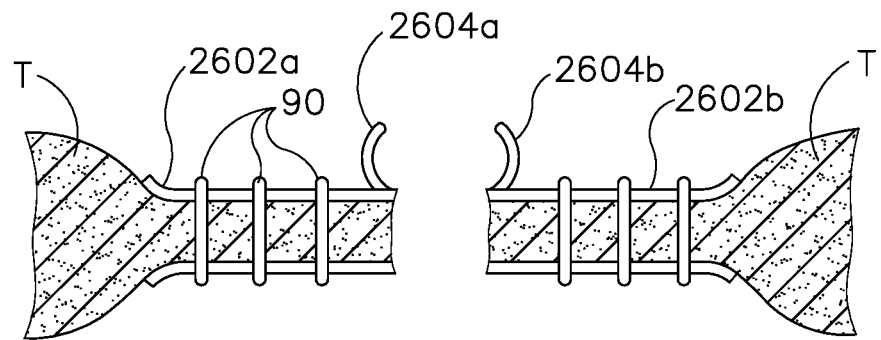
FIG. 41 depicts a cross-sectional view of the buttress assembly of FIG. 39 secured to tissue and severed.

When an end effector (40) that is loaded with buttress assembly (2600) is actuated, knife member (80) may bisect attachment feature (2604) along a longitudinal cut path while knife member (80) simultaneously bisects buttress body (2602) along the same path. This may result in a configuration as shown in FIG. 41. In particular, FIG. 41 shows buttress body (2602) bisected into two pieces (2602a, 2602b) that are secured to corresponding regions of tissue (T) via staples (90); with attachment feature (2604) also having been bisected into two corresponding pieces (2604a, 2604b). While buttress assembly (2600) is shown and described in the foregoing example as being used with anvil (60), it should be understood that buttress assembly (2600) may also be readily used with staple cartridge (70). In particular, attachment feature (2604) may be positioned on the underside of a buttress body (2602); and may fit within channel (72) of staple cartridge (70).

XI. Exemplary Alternative Features for Securing Buttress Assembly to Anvil

Figure 42:
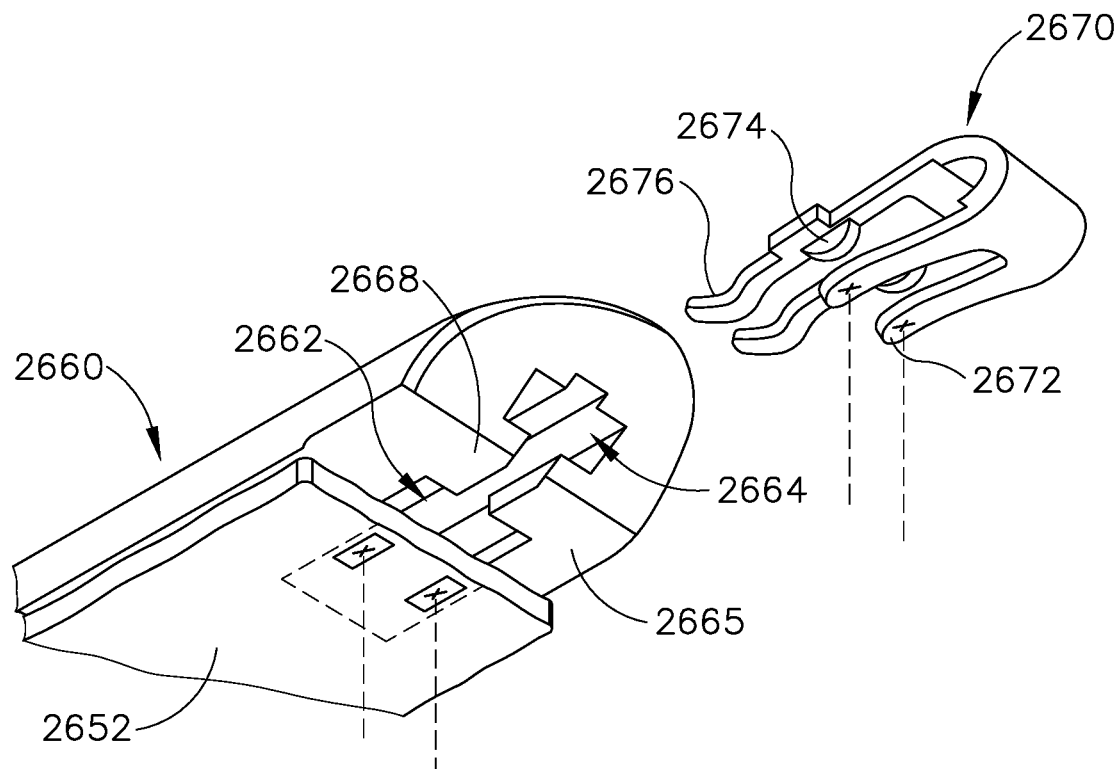
FIG. 42 depicts a perspective view of a distal end of an exemplary alternative anvil with a buttress retention clip separated from the anvil.
Figure 43A:
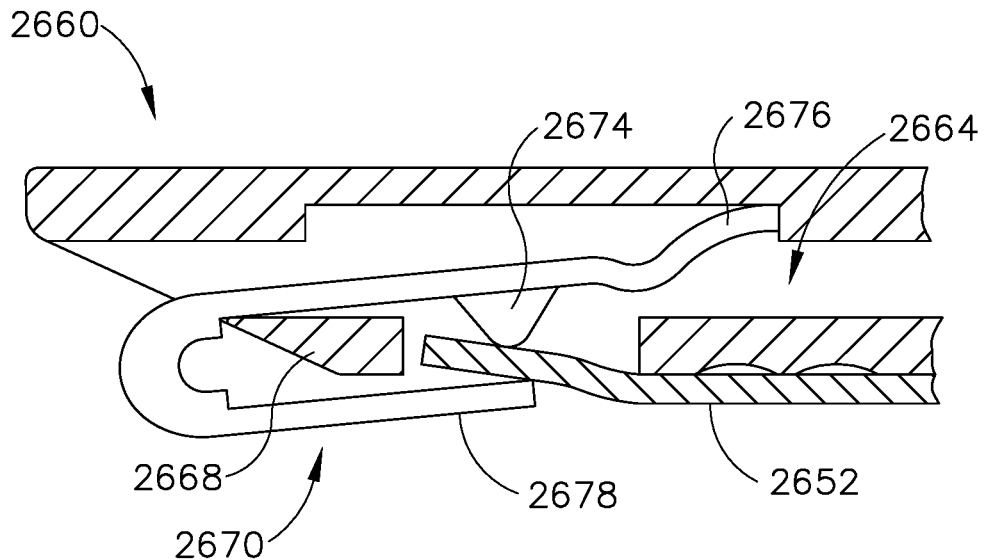
FIG. 43A depicts a cross-sectional side view of the distal end of the anvil and buttress retention clip of FIG. 42, with the clip retaining a buttress against the anvil.
Figure 43B:
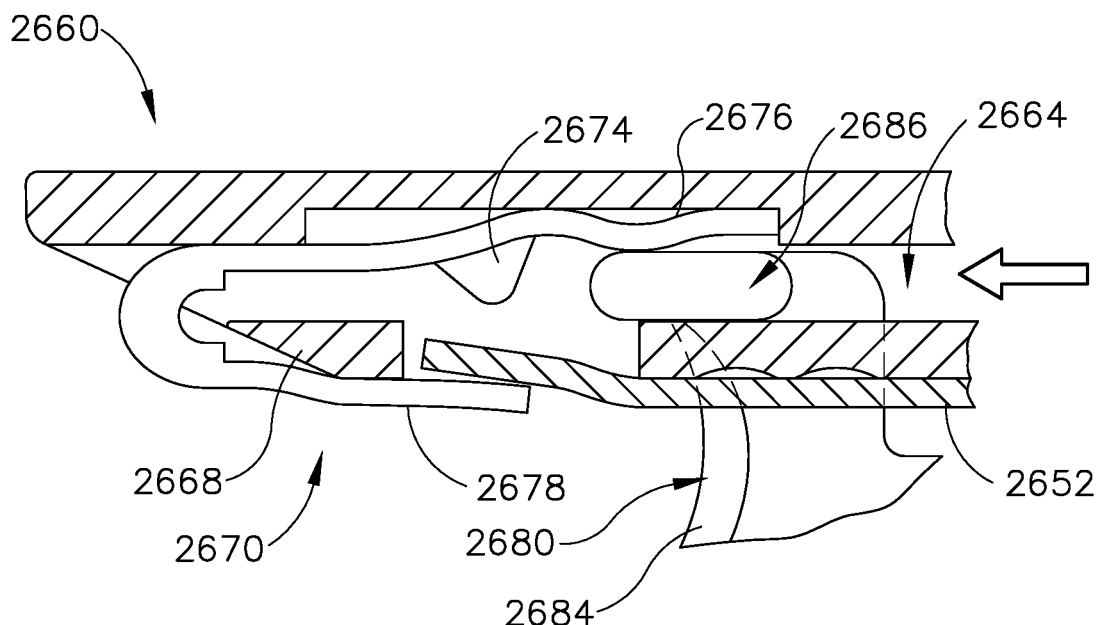
FIG. 43B depicts a cross-sectional side view of the distal end of the anvil and buttress retention clip of FIG. 42, with the clip releasing the buttress from the anvil.

As indicated above with respect to attachment feature (2604), it may be desirable to use something other than an adhesive (or in addition to an adhesive) in order to removably secure a buttress body to an end effector (40). To that end, FIGS. 42-43B show an exemplary alternative combination of a buttress body (2652), anvil (2660), and retention clip (2670). Buttress body (2652) may be constructed and operable just like any other buttress body described herein and/or like any buttress body described in any references cited herein. Anvil (2660) of this example is substantially identical to anvil (2660) described above; except that anvil (2660) of this example includes a transverse slot (2664) that is in communication with longitudinally extending channel (2662). Moreover, the distal end of anvil (2660) includes inwardly directed projections (2688) adjacent to channel (2662) and slot (2664).

Clip (2670) of the present example generally defines a "U" shape and includes a set of buttress engagement prongs (2672), a set of humps (2674), and a set of flange prongs (2676). As best seen in FIGS. 43A-43B, clip (2670) is configured to wrap around projections (2688), with flange prongs (2676) being positioned in slot (2664) and with buttress engagement prongs (2678) extending underneath projections (2688). Clip (2670) is resiliently biased to assume the configuration shown in FIG. 43A. In this configuration, prongs (2678) pinch the distal end of buttress body (2652) against underside (2665) of anvil (2660). Since clip (2670) is secured to anvil (2660), the pinching of buttress body (2652) between prongs (2678) and humps (2674) will assist in securing buttress body (2652) against underside (2665) of anvil (2660). In some versions, clip (2670) serves as a substitute for an adhesive to secure buttress body (2652) against underside (2665) of anvil (2660). In some other versions, clip (2670) serves as a supplement to an adhesive to secure buttress body (2652) against underside (2665) of anvil (2660).

Clip (2670) of the present example is configured to interact with a modified version of knife member (80) to selectively release buttress body (2652) from underside (2665) of anvil (2660) when end effector (40) is actuated. In particular, FIG. 43B shows a modified knife member (2680) interacting with clip member (2670). Knife member (2680) is substantially identical to knife member (80) and includes a cutting edge (2684); but knife member (2680) further includes a pair of upper flanges (2686) in this example. Flanges (2686) extend transversely outwardly from the upper region of knife member (2680) and are slidably disposed in slot (2664) of anvil (2660). As knife member (2680) is translated to the distal position shown in FIG. 43B, flanges (2686) engage prongs (2676) and thereby drive a first portion of clip (2670) upwardly. Projections (2668) bear downwardly on a second portion of clip (2670) as flanges (2686) drive the first portion of clip (2670) upwardly. This provides separation between prongs (2678) and humps (2674), such that clip (2670) releases buttress body (2652) as shown in FIG. 43B. It should therefore be understood that knife member (2680) will deform clip (2670) and thereby cause clip (2670) to release buttress body (2652) when knife member (2680) reaches a distal position during actuation of end effector (40).

While retention clip (2670) is shown and described in the foregoing example as being used with a modified anvil (2660), it should be understood that retention clip (2670) (or a modification thereof) may also be readily used with a modification of staple cartridge (70). In particular, retention clip (2670) may be located at the distal end of staple cartridge (70) and may deform in response to engagement by a lower flange of knife member (2680), thereby releasing a lower buttress body from the deck (73) of the modified staple cartridge (70).

XII. Surgical Stapler Buttress Applicator with Multi-Zone Platform for Pressure Focused Release In the example above, platform (220) is provided as a generally flat, stationary members that simply provide support to buttress assemblies (100, 110) until buttress assemblies (100, 110) are adhered to end effector (40). It may be desirable to provide additional functionality to platform (220). For instance it may be desirable to incorporate features into platform (220) that further promote adhesion of buttress assemblies (100, 110) to end effector (40). This may be done by providing variation of pressure among certain areas of end effector (40) when end effector (40) clamps down on buttress assemblies (100, 110) and platform (220). In particular, pressure may be localized or otherwise applied differently based on the location on platform (220) by providing surface features that concentrate compressive forces in certain regions of the entire clamping footprint of end effector (40). The concentration of compressive forces in these regions may provide greater adhesion in those regions than might otherwise be achieved through versions where platform (220) is simply flat. The following examples include several ways in which platform (220) may provide different amounts of pressure based on the location on the platform. It should be understood that any of the platforms described below may be readily incorporated into cartridge (200) as described above.

Figure 44:
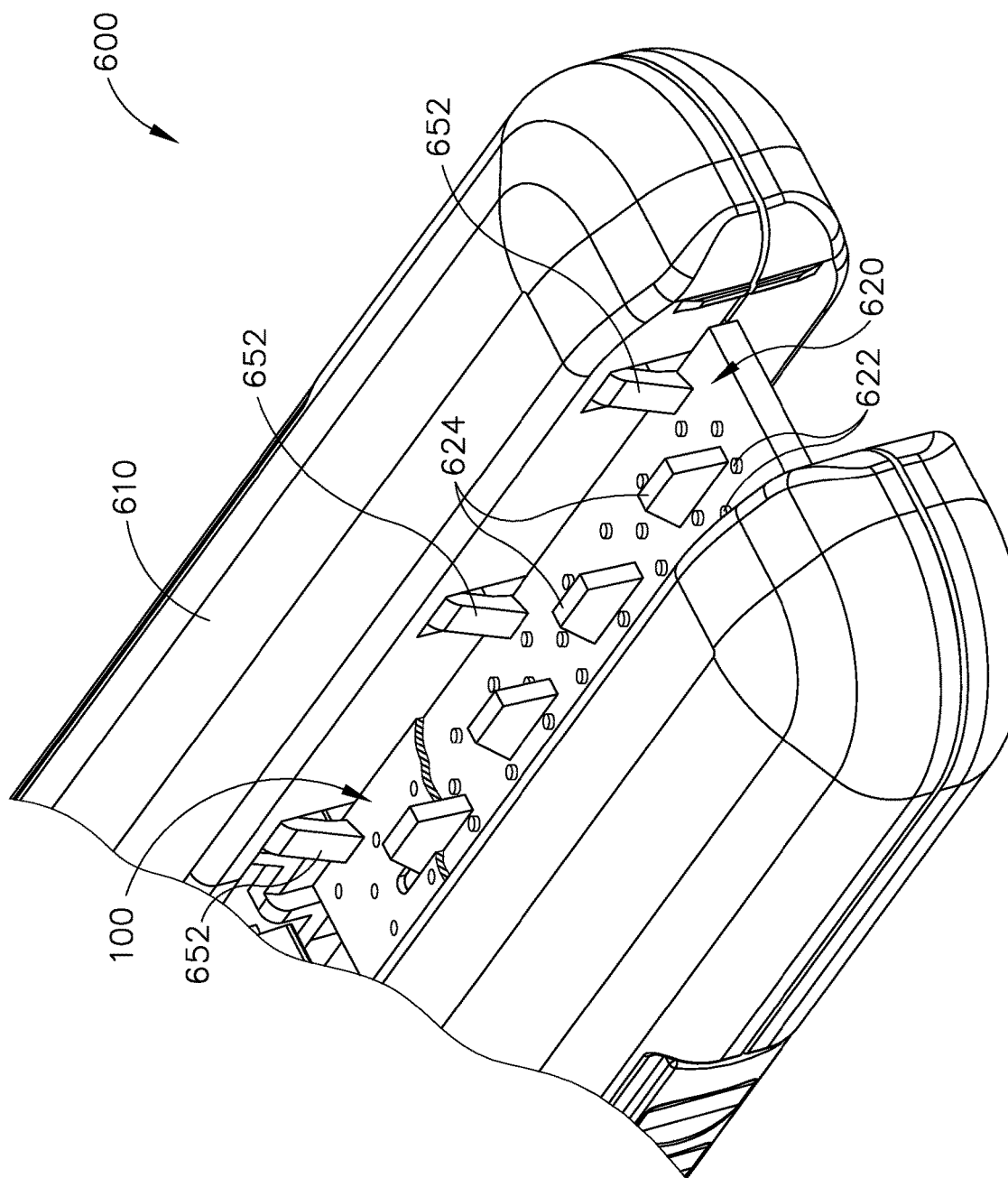
FIG. 44 depicts a partial perspective view of an open end of another exemplary buttress applier cartridge that may be used to carry and apply the buttress assembly of FIG. 5A.

A. Exemplary Buttress Applier Cartridge with Platform Having Localized Pressure Applying Surface Features FIG. 44 shows an exemplary alternative buttress applier cartridge (600) that may be used to support and protect buttress assemblies (100, 110). Cartridge (600) may also be used to easily load buttress assemblies (100, 110) on end effector (40). Cartridge (600) of this example includes a housing (610), a platform (620), and a plurality of retention members (652) that are configured to releasably secure buttress assemblies (100, 110) to platform (520) just like arms (252) or arms (352) described above. It should be understood that retention members (652) are provided by way of example only; and that cartridge (600) may instead include any other suitable kinds of buttress assembly (100, 110) retention features, including but not limited to those described elsewhere herein.

Platform (620) of the present example includes a plurality of protrusions (622) and a plurality of fins (624). In some versions, protrusions (622) and/or fins (624) are rigid. Protrusions (622) are in the form of an array of short, flat-topped pegs in the present example, though it should be understood that protrusions (622) may take a variety of alternative forms. Fins (624) are sized and arranged to fit in channel (62) of anvil (60). It should be understood that fins (624) may cooperate with the sidewalls defining channel (62) to ensure that anvil (60) is properly aligned with buttress assembly (100) as anvil (60) is closed down toward buttress assembly (100) and platform (620). It should also be understood that the underside of platform (620) (i.e., the side carrying buttress assembly (110), associated with staple cartridge (70)), may also include protrusions (622) and fins (624). Fins (624) on the underside of platform (620) may be sized and arranged to fit in channel (72) of staple cartridge (70). Moreover, as will be described in greater detail below, fins (624) on the underside of platform (620) may be configured to prevent cartridge (600) from being used with a staple cartridge (70) that has already been fired.

Figure 45A:
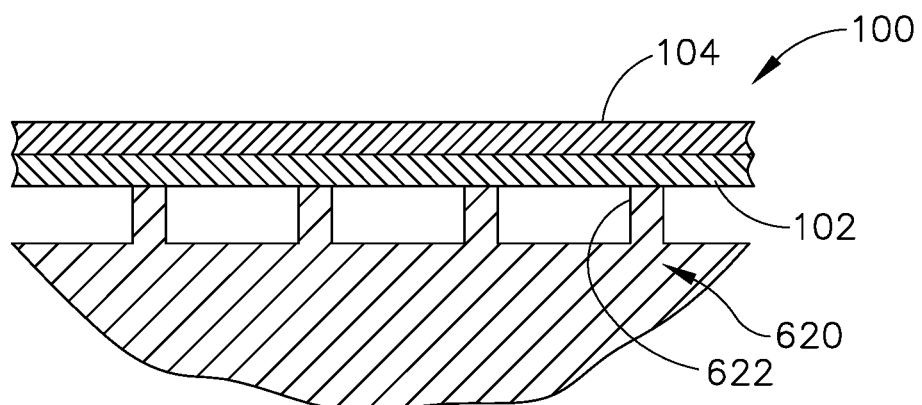
FIG. 45A depicts a partial, cross-sectional end view of a buttress assembly disposed on a platform of the buttress applier cartridge of FIG. 44.
Figure 45B:
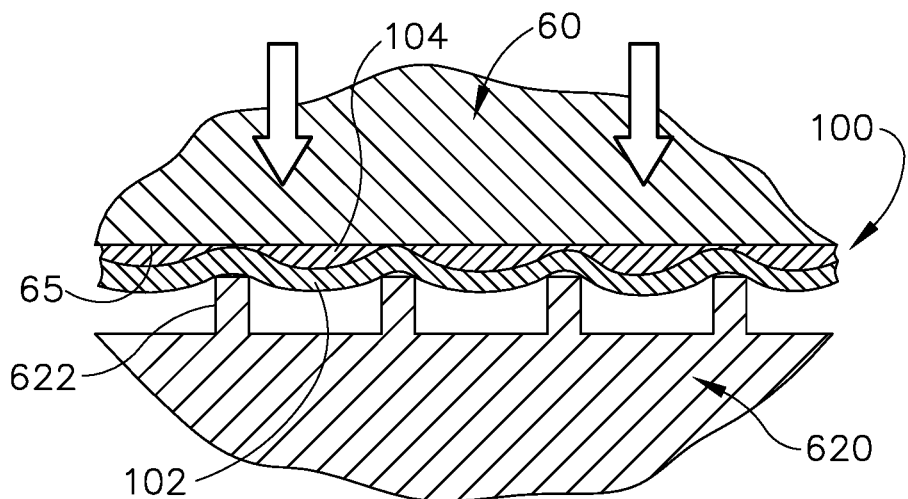
FIG. 45B depicts partial, cross-sectional end view of the buttress assembly and platform of FIG. 45A, with an anvil of the end effector of FIG. 2 pressing the buttress assembly against pressure applying features of the platform.
Figure 45C:
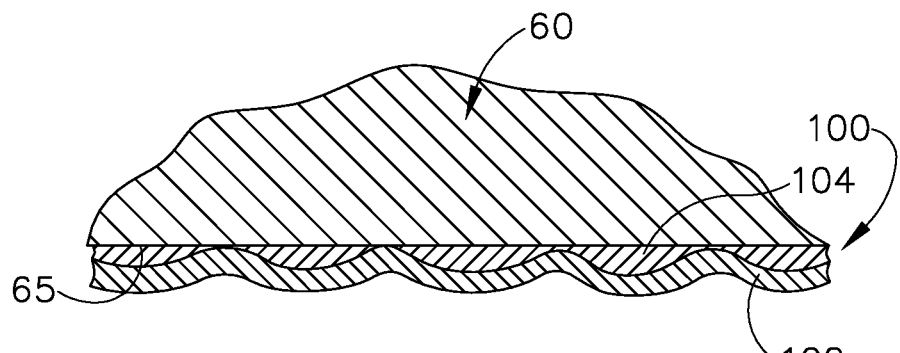
FIG. 45C depicts a partial, cross-sectional end view of the buttress assembly and anvil of FIG. 45B, with the buttress assembly adhered to the anvil.

As shown in FIG. 45A, protrusions (622) directly engage body (102) of buttress assembly (100), and thereby support buttress assembly (100) at a plurality of discrete locations along body (102). FIG. 45B shows anvil (60) clamping down on buttress assembly (100) and platform (620). As shown, protrusions (622) provide localized pressure on adhesive layer (104) against the underside (65) of anvil (60). This localization provides greater pressure at the regions associated with protrusions (622) than would otherwise be applied on adhesive layer (104) against the underside (65) of anvil (60) if platform (620) lacked protrusions (622). When anvil (60) is pulled away from platform (620) (e.g., when end effector (40) is returned to the open position), buttress assembly (100) is adhered to underside (65), with adhesion maximized at the locations associated with protrusions (622) as shown in FIG. 45C.

Figure 46A:
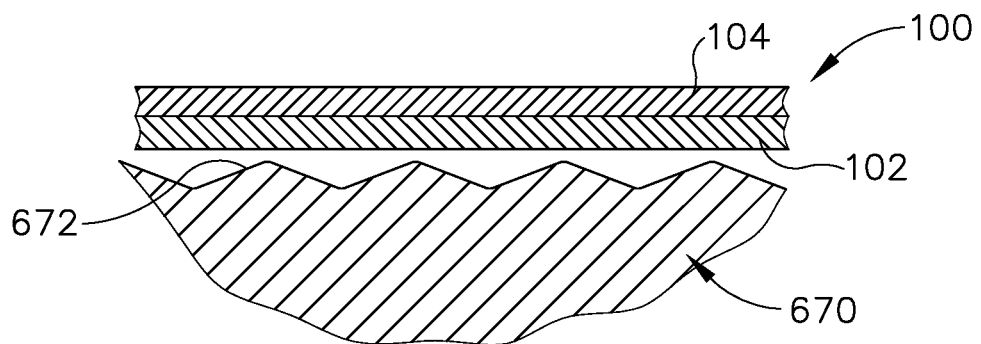
FIG. 46A depicts a partial, cross-sectional end view of a buttress assembly disposed on an exemplary variation of the platform of FIG. 45A.
Figure 46B:
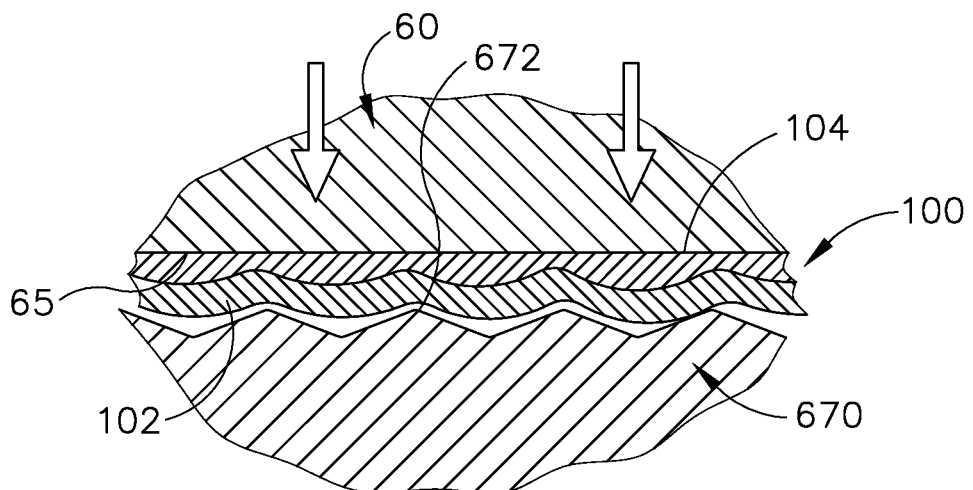
FIG. 46B depicts a partial, cross-sectional end view of the buttress assembly and platform of FIG. 46A, with an anvil of the end effector of FIG. 2 pressing the buttress assembly against pressure applying features of the platform.
Figure 46C:
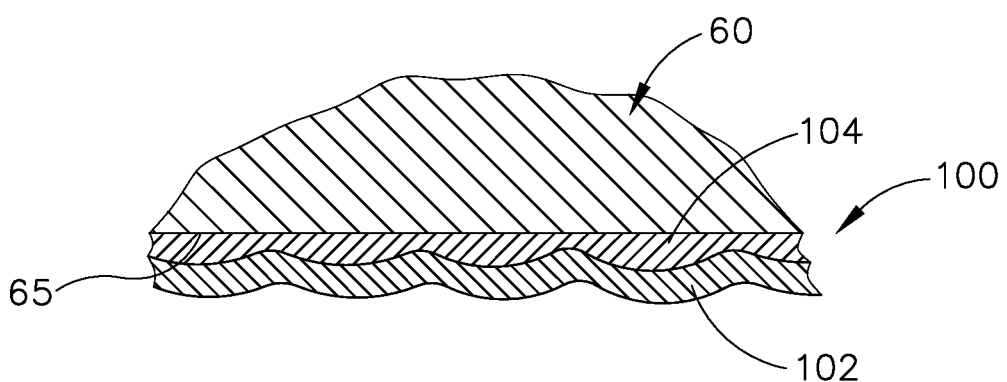
FIG. 46C depicts a partial, cross-sectional end view of the buttress assembly and anvil of FIG. 46B, with the buttress assembly adhered to the anvil.

FIGS. 46A-46C show another exemplary alternative platform (670) that may be readily incorporated into cartridge (600) in place of platform (620). Platform (670) of this example is substantially identical to platform (620) described above, except that platform (670) of this example has a surface geometry in the form of a triangular wave. In some versions, the triangular wave configuration extends along only one cross-sectional dimension, such that the peaks (672) of the triangular wave span across the entire width of platform (670) like ridges. In some other versions, the triangular wave configuration extends along two cross-sectional dimensions, such that the peaks (672) of the triangular wave form discrete points.

As shown in FIG. 46A, peaks (672) directly engage body (102) of buttress assembly (100), and thereby support buttress assembly (100) at a plurality of discrete locations along body (102). FIG. 46B shows anvil (60) clamping down on buttress assembly (100) and platform (670). As shown, peaks (672) provide localized pressure on adhesive layer (104) against the underside (65) of anvil (60). This localization provides greater pressure at the regions associated with peaks (672) than would otherwise be applied on adhesive layer (104) against the underside (65) of anvil (60) if platform (670) lacked peaks (672). When anvil (60) is pulled away from platform (670) (e.g., when end effector (40) is returned to the open position), buttress assembly (100) is adhered to underside (65), with adhesion maximized at the locations associated with peaks (672) as shown in FIG. 46C.

It should be understood that the cylindraceous peg configuration of protrusions (622) and the triangular wave peak configuration of peaks (672) are merely illustrative examples. Other features and surface geometries that may be incorporated into a platform to provide localized pressure will be apparent to those of ordinary skill in the art in view of the teachings herein.

Figure 47:
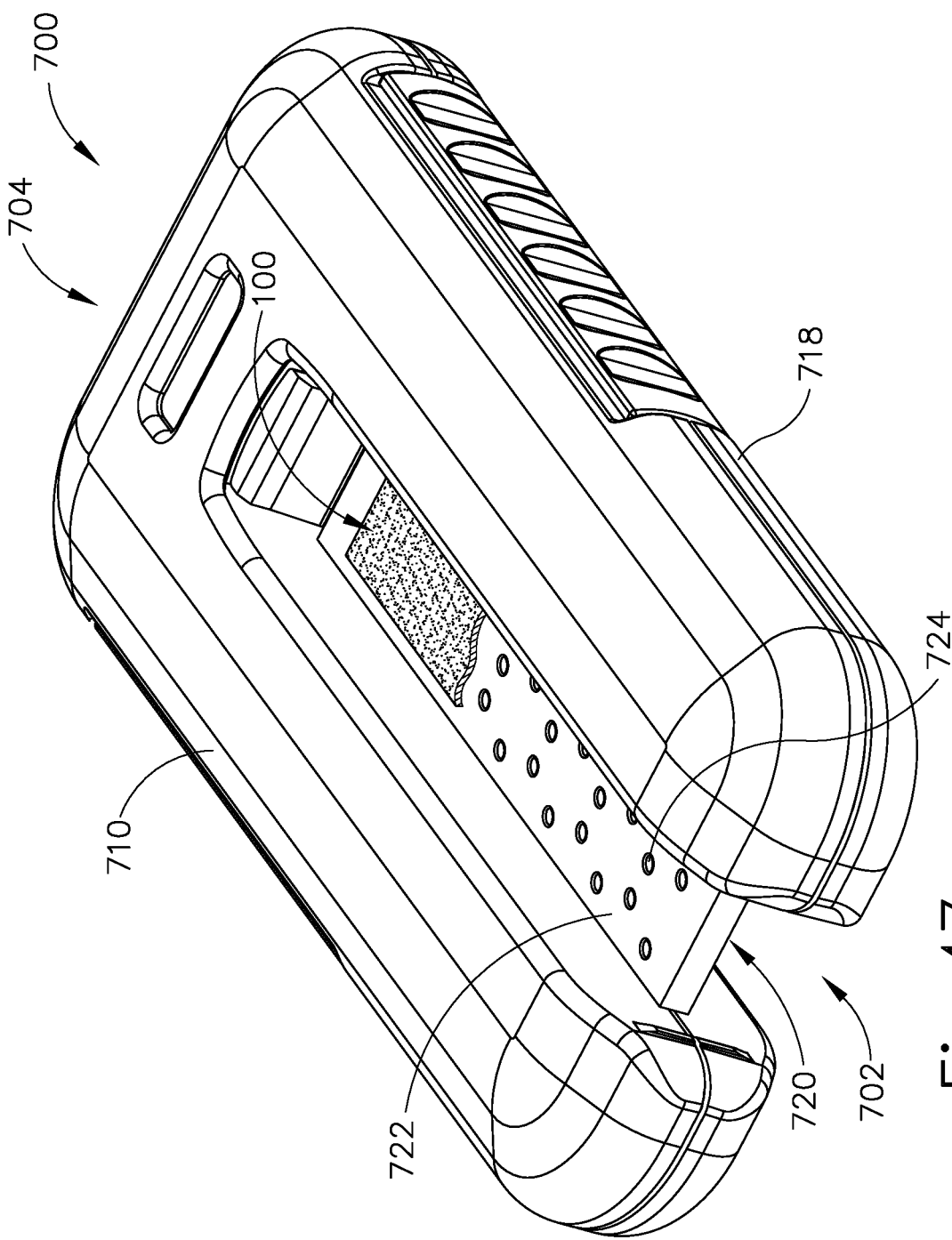
FIG. 47 depicts a perspective view of another exemplary buttress applier cartridge that may be used to carry and apply the buttress assembly of FIG. 5A.

B. Exemplary Buttress Applier Cartridge with Platform Having Regions of Varying Compression Characteristics FIG. 47 shows another exemplary alternative buttress applier cartridge (700) that may be used to support and protect buttress assemblies (100, 110). Cartridge (700) may also be used to easily load buttress assemblies (100, 110) on end effector (40). Cartridge (700) of this example comprises an open end (702) and a closed end (704). Open end (702) is configured to receive end effector (40) as described above. Cartridge (700) further includes a first housing (710) and a second housing (718), which each generally define a "U" shape to present open end (402). A platform (720) is interposed between housings (710, 718).

In some versions, buttress assemblies (100, 110) are adhered to platform (720). By way of example only, buttress assemblies (100, 110) may be adhered to platform (720) using the same adhesive material that is used to adhere buttress assemblies (100, 110) to underside (65) of anvil (60) and deck (73) of staple cartridge (70). In some such versions, the sides of buttress assemblies (100, 110) that are adhered to platform (720) include less adhesive material than the amount of adhesive material that is used to adhere buttress assemblies (100, 110) to underside (65) of anvil (60) and deck (73) of staple cartridge (70), to thereby promote release of buttress assemblies (100, 110) from platform (720) when buttress assemblies (100, 110) are adhered to underside (65) of anvil (60) and deck (73) of staple cartridge (70). For instance, the adhesive may be provided in only discrete portions (e.g., in a pattern) along the sides of buttress assemblies (100, 110) that are adhered to platform (720).

Platform (720) of the present example comprises a body (722) and an array of resilient assemblies (724). Body (722) of the present example is compressible; and resilient assemblies (724) are also compressible. However, body (722) is configured to maintain a generally compressed configuration after being compressed then released; while resilient assemblies (724) are configured to generally return to a non-compressed configuration after being compressed then released. In addition, during compression of platform (720), the resilience of resilient assemblies (724) will provide a greater outward resistance on whatever is compressing platform (720) than the outward resistance provided by body (722) of platform (720). By way of example only, each resilient assembly (724) may comprise a coil spring in a sheath; and resilient assemblies (724) may be snugly fit in respective undersized openings of body (722). Other suitable forms that resilient assemblies (724) may take will be apparent to those of ordinary skill in the art in view of the teachings herein. It should also be understood that a variety of materials and configurations may be used to form body (722), including but not limited to a viscous foam material.

FIGS. 48A-48C show a sequence where buttress assemblies (100, 110) and platform (720) are compressed and released by end effector (40). In this example, buttress assembly (100) is modified to include several integral, discrete protrusions (106) projecting downwardly from body (102). Similarly, buttress assembly (110) is modified to include several integral, discrete protrusions (116) projecting upwardly from body (102). Protrusions (106, 116) may be rigid or semi-rigid. By way of example only, protrusions (106, 116) may be shaped like short, cylindraceous pegs. Alternatively, protrusions (106, 116) may have any other suitable configuration.

At the stage shown in FIG. 48A, before end effector (40) is clamped down on buttress assemblies (100, 110) and platform (720), the upper and lower surfaces of body (722) are flush with the upper and lower ends of resilient assemblies (724), such that the upper and lower surfaces of platform (720) are substantially flat. Buttress assemblies (100, 110) are supported on platform (720) via protrusions (106, 116). In the present example, protrusions (106, 116) and resilient assemblies (724) are positioned and arranged such that protrusions (106, 116) do not engage the ends of any of resilient assemblies (724). In other words, protrusions (106, 116) only engage body (722) of platform (720).

FIG. 48B shows end effector (40) clamping down on where buttress assemblies (100, 110) and platform (720). As shown, protrusions (106, 116) engage body (722) to maximize compression of body (722) relative to resilient assemblies (724). Resilient assemblies (724) bear directly on bodies (102, 112) of buttress assemblies (100, 110), providing localized pressure similar to that provided protrusions (622) as described above. Thus, resilient assemblies (724) simultaneously enhance adhesion of adhesive layer (104) to underside (65) and adhesion of adhesive layer (114) to deck (73).

FIG. 48C shows end effector (40) returning to an open position, carrying buttress assemblies (100, 110) away from platform (720). Platform (720) is thus no longer being compressed by end effector (40). Nevertheless, body (722) maintains a substantially compressed configuration; while resilient assemblies (724) return to a generally uncompressed configuration. Buttress assemblies (100, 110) remain adhered to end effector (40), with enhanced adhesion provided by resilient assemblies (724), such that end effector (40) with buttress assemblies (100, 110) may be used to perform a surgical procedure as described above. It should be understood that body (722) does not necessarily need to maintain a substantially compressed configuration at the stage shown in FIG. 48C. In other words, body (722) may provide some degree of resilience. However, in versions where body (722) is resilient, the resilience of resilient assemblies (724) may be stronger than the resilience of body (722), such that resilient assemblies (724) may effectively provide localized concentrations of pressure against buttress assemblies (100, 110) when end effector (40) is closed upon buttress assemblies (100, 110) and platform (720).

FIGS. 49A-49C show another exemplary alternative platform (770) that may be readily incorporated into cartridge (700) or any other buttress applier cartridge described herein. As with platform (720) described above, buttress assemblies (100, 110) may be adhered to platform (770) in some versions. Platform (770) of this example comprises a body (772) with a plurality of resilient members (774) disposed in body (772). Body (772) of the present example is compressible; and resilient members (774) are also compressible. However, body (772) is configured to maintain a generally compressed configuration after being compressed then released (or at least take longer to return to the non-compressed configuration); while resilient members (774) are configured to generally return to a non-compressed configuration after being compressed then released (or return to the non-compressed configuration faster than body (772)). In other words, body (772) has a greater viscosity than resilient members (774). In addition, during compression of platform (770), the resilience of resilient members (774) will provide a greater outward resistance on whatever is compressing platform (770) than the outward resistance provided by body (772) of platform (770). By way of example only, each resilient member (774) may comprise a cylinder of material that has a greater density than the material forming body (772). In some versions, resilient members (774) and body (772) are formed of the same foam material; yet the foam material forming resilient members (774) has a greater density than the foam material forming body (772). Other suitable forms that resilient members (724) may take will be apparent to those of ordinary skill in the art in view of the teachings herein.

At the stage shown in FIG. 49A, before end effector (40) is clamped down on buttress assemblies (100, 110) and platform (770), the upper and lower surfaces of body (772) are flush with the upper and lower ends of resilient assemblies (774), such that the upper and lower surfaces of platform (770) are substantially flat. Buttress assemblies (100, 110) are supported flatly on platform (770). In some variations, buttress assemblies (100, 11) include protrusions (106, 116) when used with platform (770).

FIG. 49B shows end effector (40) clamping down on where buttress assemblies (100, 110) and platform (770). As shown, resilient members (774) bear directly on bodies (102, 112) of buttress assemblies (100, 110), providing localized pressure similar to that provided protrusions (622) as described above. Thus, resilient members (774) simultaneously enhance adhesion of adhesive layer (104) to underside (65) and adhesion of adhesive layer (114) to deck (73).

FIG. 49C shows end effector (40) returning to an open position, carrying buttress assemblies (100, 110) away from platform (770). Platform (770) is thus no longer being compressed by end effector (40). Nevertheless, body (772) maintains a substantially compressed configuration; while resilient members (774) return to a generally uncompressed configuration. Buttress assemblies (100, 110) remain adhered to end effector (40), with enhanced adhesion provided by resilient members (774), such that end effector (40) with buttress assemblies (100, 110) may be used to perform a surgical procedure as described above. It should be understood that body (772) does not necessarily need to maintain a substantially compressed configuration at the stage shown in FIG. 49C. However, in versions where body (772) is resilient, the resilience of resilient members (774) may be stronger than the resilience of body (772), such that resilient members (774) may effectively provide localized concentrations of pressure against buttress assemblies (100, 110) when end effector (40) is closed upon buttress assemblies (100, 110) and platform (770).

Figure 50:
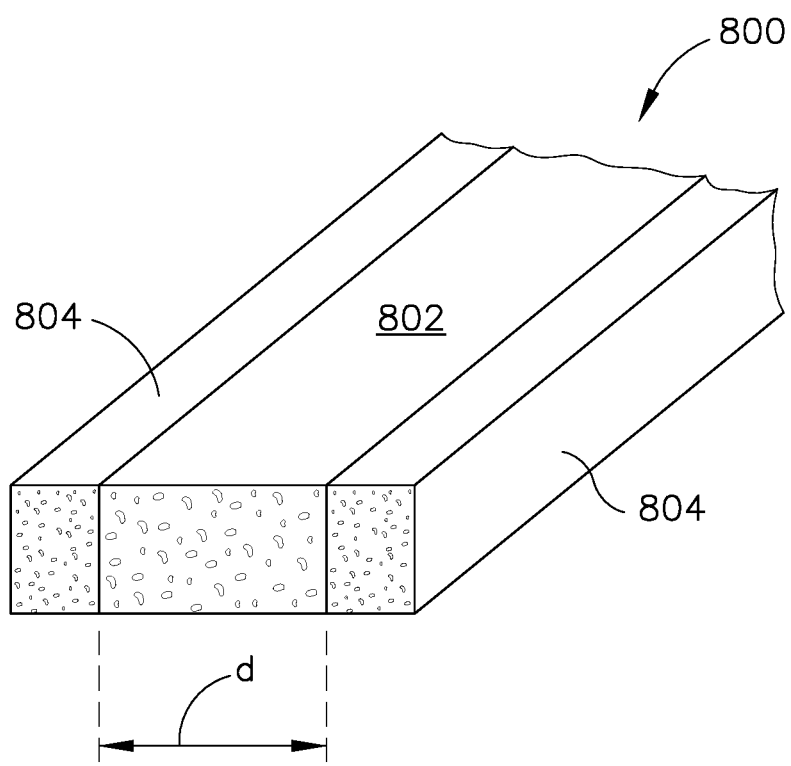
FIG. 50 depicts a partial perspective view of an exemplary alternative platform that may be incorporated into a buttress applier cartridge.

FIG. 50 shows yet another exemplary alternative platform (800) that may be readily incorporated into cartridge (700) or any other buttress applier cartridge described herein. Platform (800) of this example comprises a first longitudinally extending body zone (802) and a pair of second longitudinally extending body zones (804). Body zones (804) extend longitudinally along both lateral sides of body zone (802) and are laterally separated by a distance (d). Body zones (804) are sized and positioned to correspond with the lateral outermost regions of underside (65) of anvil

(60) and deck (73) of staple cartridge (70). In some versions, all body zones (802, 804) are compressible but body zone (802) has a durometer that is different from the durometer of body zones (804). For instance, in some versions body zone (802) is configured to maintain a generally compressed configuration after being compressed then released while body zones (804) are configured to generally return to a non-compressed configuration after being compressed then released. In addition, during compression of platform (800), the resilience of body zones (804) will provide a greater outward resistance on whatever is compressing platform (800) than the outward resistance provided by body zone (802) of platform (800). By way of example only, each body zone (804) may comprise a material that has a greater density than the material forming zone (802). In some versions, body zones (804) and body zone (802) are formed of the same foam material; yet the foam material forming body zones (804) has a greater density than the foam material forming body zone (802). Other suitable forms that body zones (804) may take will be apparent to those of ordinary skill in the art in view of the teachings herein.

Before end effector (40) is clamped down on buttress assemblies (100, 110) and platform (800), the upper and lower surfaces of body zone (802) are flush with the upper and lower ends of body zones (804), such that the upper and lower surfaces of platform (800) are substantially flat. Buttress assemblies (100, 110) are supported flatly on platform (800). When end effector (40) clamps down on where buttress assemblies (100, 110) and platform (800) as described above, body zones (804) bear directly on bodies (102, 112) of buttress assemblies (100, 110), providing localized pressure along the lateral outermost regions of underside (65) of anvil (60) and deck (73) of staple cartridge (70). Thus, body zones (804) simultaneously enhance adhesion of adhesive layer (104) to underside (65) and adhesion of adhesive layer (114) to deck (73).

After end effector (40) returns to an open position, carrying buttress assemblies (100, 110) away from platform (800), body zone (802) may maintain a substantially compressed configuration; while body zones (804) return to a generally uncompressed configuration. Buttress assemblies (100, 110) remain adhered to end effector (40), with enhanced adhesion provided by body zones (804), such that end effector (40) with buttress assemblies (100, 110) may be used to perform a surgical procedure as described above. It should be understood that body zone (802) does not necessarily need to maintain a substantially compressed configuration after end effector (40) returns to an open position. However, in versions where body zone (802) is resilient, the resilience of body zones (804) may be stronger than the resilience of body zone (802), such that body zones (804) may effectively provide localized concentrations of pressure against buttress assemblies (100, 110) when end effector (40) is closed upon buttress assemblies (100, 110) and platform (800).

C. Exemplary Buttress Applier Cartridge with Platform Having Varying Thickness

Figure 51:
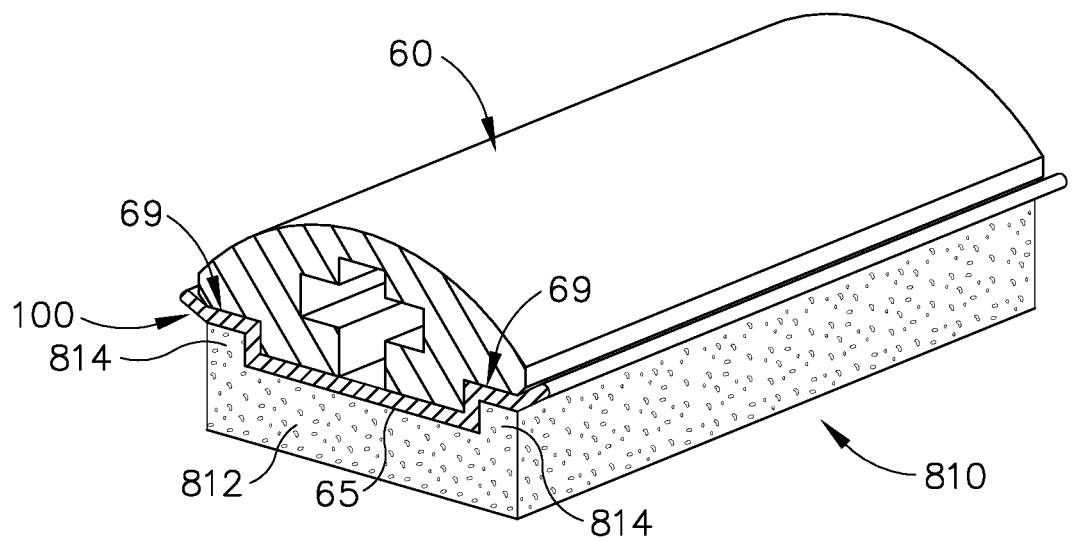
FIG. 51 depicts a partial perspective view of the anvil of the end effector of FIG. 2 compressing a buttress against another exemplary alternative platform that may be incorporated into a buttress applier cartridge.

In addition to or as an alternative to modifying a platform to include surface features or resilient features that provide enhanced pressure in localized regions, it may be desirable to provide a buttress applier cartridge with a platform that has varying thickness to enhance or otherwise promote adhesion between buttress assemblies (100, 110) and end effector (40). For instance, FIG. 51 shows an exemplary platform (810) that may be readily incorporated into cartridge (700) or any other buttress applier cartridge described herein. Platform (810) of this example comprises a longitudinally extending thin region (812) that is flanked by longitudinally extending thick regions (814). In the present example, platform (810) is a single, homogenous continuum of material that is formed to include regions (812, 814). In some other versions, regions (814) are initially formed separately from region (812) and are then joined to regions (812) to form an integral unit.

As shown in FIG. 51, thick regions (814) are configured to complement recessed regions (69) on underside (65) of anvil (60). Regions (812, 814) thus cooperate to ensure that buttress assembly (100) is applied with uniform pressure along the full width of underside (65), including recessed regions (69). It should be understood that, if platform (810) instead had a uniform thickness across the width of platform (810) (e.g., lacking thick regions (814)), buttress assembly (100) may not be adhered as well to recessed regions (69) on underside (65) of anvil (60).

Figure 52:
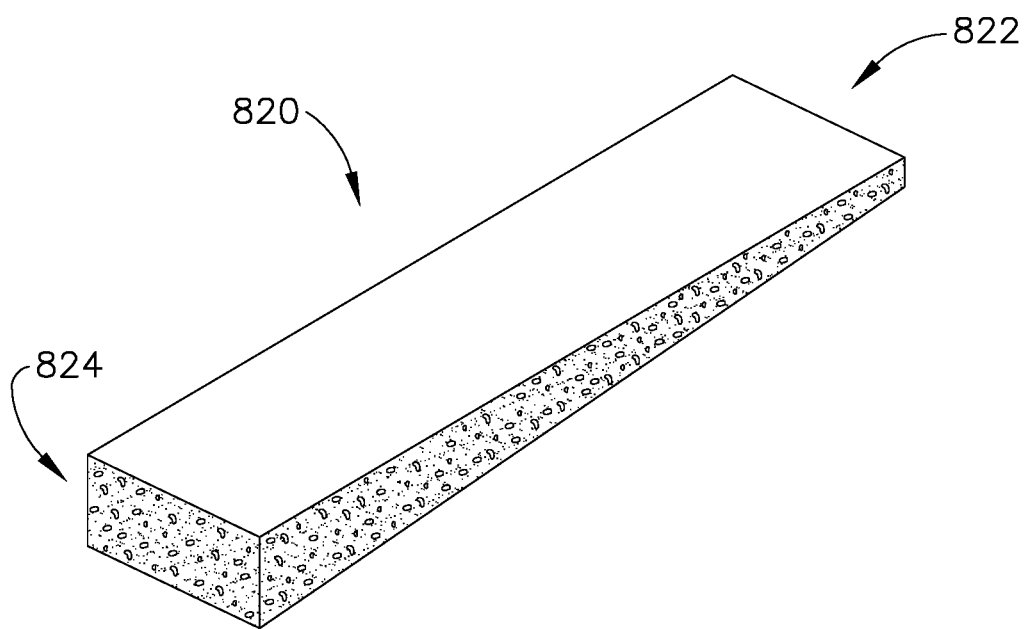
FIG. 52 depicts a perspective view of another exemplary alternative platform that may be incorporated into a buttress applier cartridge.

While the thickness of platform (810) varies along the width of platform (810), it may also be desirable to vary the thickness of a platform along the length of the platform. FIG. 52 shows yet another exemplary platform (820) that may be readily incorporated into cartridge (700) or any other buttress applier cartridge described herein. Platform (820) of this example is tapered along the length of platform (820). In particular, the proximal end (822) of platform (820) is thinner than the distal end (824) of platform (820). When a buttress applier cartridge incorporating platform (820) is positioned in an open end effector (40), proximal end (822) would be positioned closer to the pivot region between anvil (60) and lower jaw (50), and distal end (824) would be positioned closer to the distal ends of anvil (60) and staple cartridge (70).

The tapered profile of platform (820) may complement the closure profile of anvil (60) as anvil (60) is clamped down onto a buttress assembly (100) on platform (820). In particular, as anvil (60) is closed toward lower jaw (50) and staple cartridge (70), anvil (60) may define an acute angle with lower jaw (50) and staple cartridge (70) up until anvil (60) reaches a fully closed position. Once anvil (60) reaches a fully closed position, anvil (60) may be parallel with lower jaw (50) and staple cartridge (70). If an operator fails to fully close anvil (60) when the operator is attempting to adhere a buttress assembly (100) to underside (65), the increased thickness at the distal end (824) of platform (820) may increase the likelihood of successful adhesion in the distal regions of underside (65) and buttress assembly (100) even though anvil (60) never achieves a fully parallel orientation with respect to lower jaw (50) and staple cartridge (70).

Figure 53:
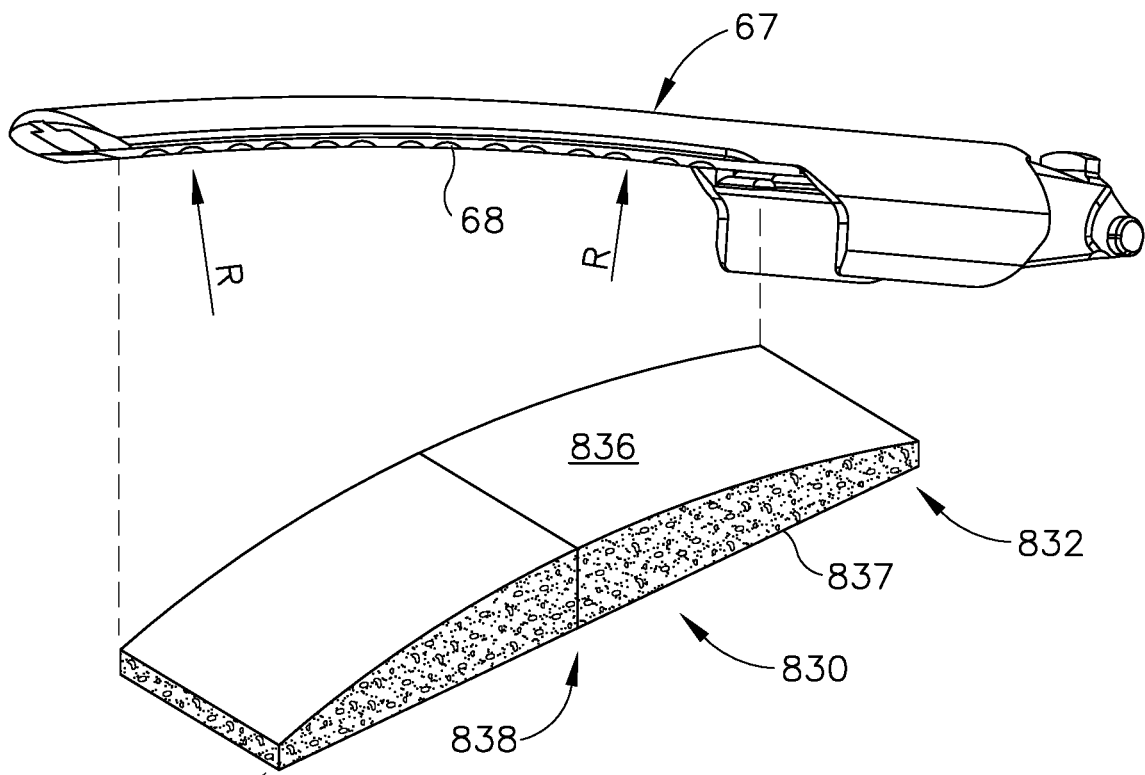
FIG. 53 depicts a perspective view of another exemplary alternative platform that may be incorporated into a buttress applier cartridge, with an exemplary alternative curved anvil positioned over the platform.

FIG. 53 shows yet another exemplary platform (830) that may be readily incorporated into cartridge (700) or any other buttress applier cartridge described herein. Platform (830) of this example has a relatively thin proximal end (832) and distal end (834), with a relatively thick central region (838). Platform (830) has a flat lower surface (837) and a convex upper surface (836). Flat lower surface (837) is configured to complement the generally flat surface of deck (73) of staple cartridge (70). Convex upper surface (836) is configured to complement a curved anvil (67). Anvil (67) of this example is substantially identical to anvil (60) described above and may be readily incorporated into end effector (40). However, anvil (67) of this example has a slightly curved underside (68). In some versions, the radius of curvature of convex upper surface (836) complements the radius of curvature of underside (68), thereby ensuring that a buttress assembly (100) that is disposed on convex upper surface (836) will be adhered to underside (68) with uniform pressure along the full length of underside (68). It should be understood, however, that convex upper surface (836) may have a radius of curvature that is less than the radius of curvature of underside (68). Similarly, platform (830) may be used with an anvil (60) that has a substantially flat underside (68). In such versions, the curvature of convex upper surface (836) may force contact between buttress assembly (100) at the longitudinal center of underside (65) of anvil (60) first; and apply the most pressure to the longitudinal center of underside (65) of anvil (60) to ensure maximum fixation of buttress assembly (100) at the longitudinal center of underside (65) of anvil (60). This may minimize the risk of buttress assembly (100) slipping along underside (65) of anvil (60) during manipulation of tissue or placement of anvil (60) on tissue.

Other suitable ways in which the thickness of a platform may be varied along the width and/or length of the platform will be apparent to those of ordinary skill in the art in view of the teachings herein.

D. Exemplary Alternative Buttress Retention Features for Buttress Applier Cartridges As described above, a cartridge (200) may secure buttress assemblies (100, 110) to platform (220) using arms (252). However, it will be understood that arms (252) are merely illustrative examples of structures that may be used to secure buttress assemblies (100, 110) to platform (220). Several additional structures that may be used to secure buttress assemblies (100, 110) to platform (220) will be described in greater detail below, while still further examples will be apparent to those of ordinary skill in the art in view of the teachings herein. It should be understood that the following teachings may be readily incorporated into any of the various buttress applier cartridges described herein.

1. Exemplary Buttress Retention Features Integrated Into Platform of Buttress Applier Cartridge In cartridge (200) described above, buttress assemblies (100, 110) are secured to platform (220) using features positioned along the outward lateral edges of buttress assemblies (100, 110). In particular, arms (252) secure buttress assemblies (100, 110) in cartridge (200). In addition to or as an alternative to using these kinds of features to secure buttress assemblies (100, 110) to a platform, it may be desirable to incorporate features directly into a platform that secure buttress assemblies (100, 110) to the platform. The following provides merely illustrative examples of how a platform may include integral features that releasably secure buttress assemblies (100, 110) to the platform. Other suitable variations will be apparent to those of ordinary skill in the art in view of the teachings herein.

a. Exemplary Platform with Integral, Collapsible Retainer Posts

Figure 54:
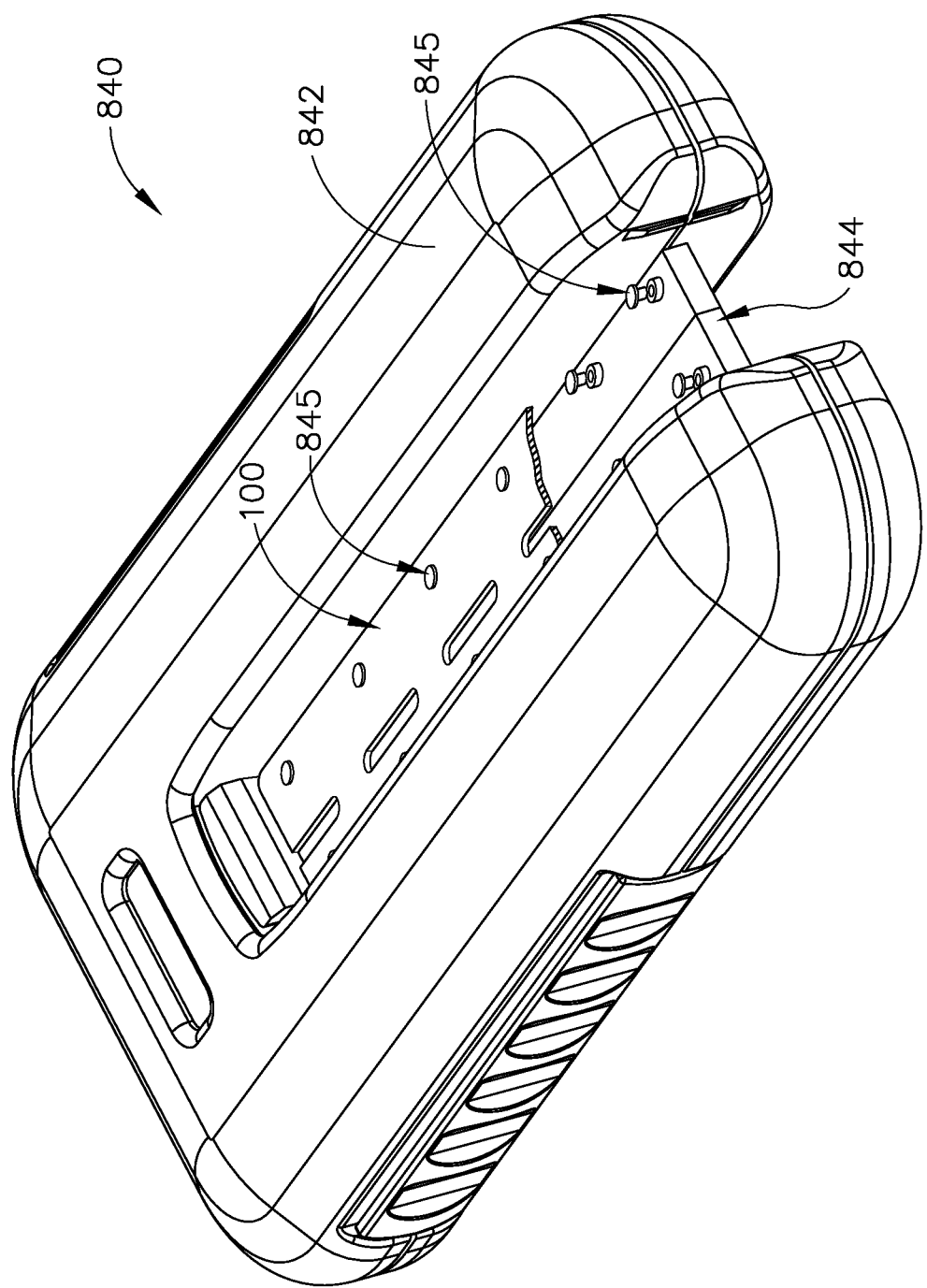
FIG. 54 depicts a partial perspective view of an open end of another exemplary buttress applier cartridge that may be used to carry and apply the buttress assembly of FIG. 5A.

FIG. 54 shows an exemplary alternative buttress applier cartridge (840) that may be used to support and protect buttress assemblies (100, 110). Cartridge (840) may also be used to easily load buttress assemblies (100, 110) on end effector (40). Cartridge (840) of this example includes a housing (842) and a platform (844). Platform (844) of this example is substantially identical to platforms (220) described above, except that platform (844) of this example includes fastener assemblies (845). Fastener assemblies (845) extend through the thickness of platform (844) and buttress assemblies (100, 110); and are arranged in an array such that fastener assemblies (845) are generally equidistantly spaced from each other along the surfaces of buttress assemblies (100, 110). As described in further detail below, fastener assemblies (845) releasably secure buttress assemblies (100, 110) to platform (845). In the present example, cartridge (840) lacks arms (252). In some other versions, fastener assemblies (845) are provided as a supplement to arms (252). It should therefore be understood that fastener assemblies (845) may be used in combination with other features such as arms (252).

Figure 55C:
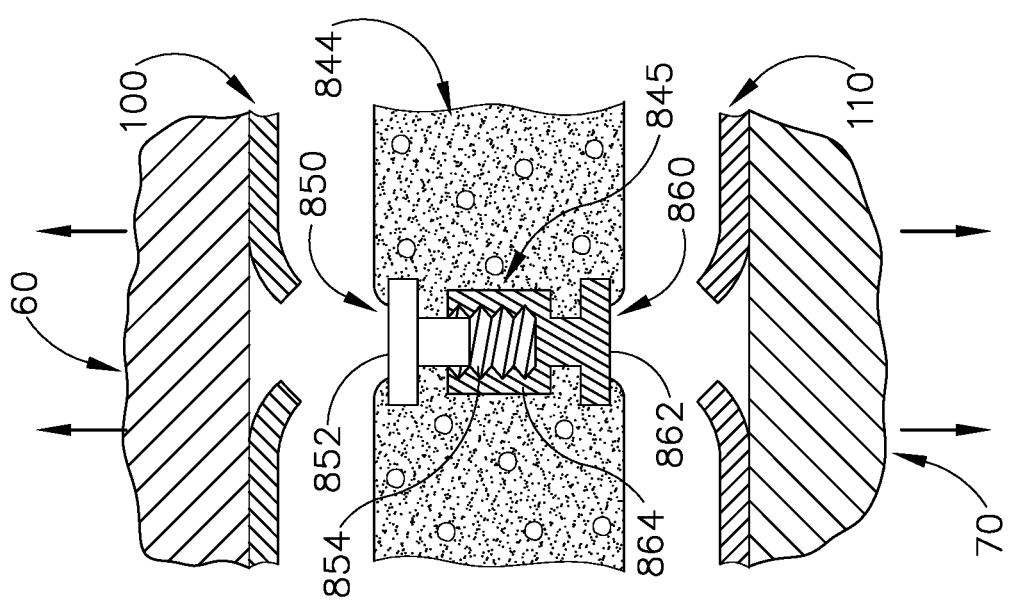
FIG. 55C depicts a partial, cross-sectional end view of the platform and buttress assembly of FIG. 55A, with the end effector in an open configuration, with the buttress assembly adhered to the end effector, and with the retention post assembly remaining in a collapsed state in the platform.
Figure 55B:
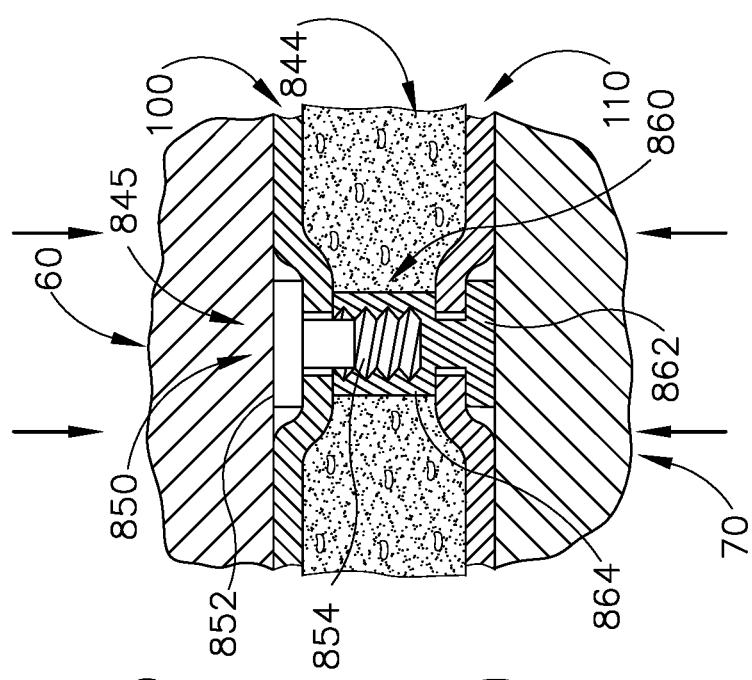
FIG. 55B depicts a partial, cross-sectional end view of the platform and buttress assembly of FIG. 55A, with the end effector of FIG. 2 compressing the platform and buttress assembly, thereby transitioning the retention post assembly to a collapsed state.
Figure 55A:
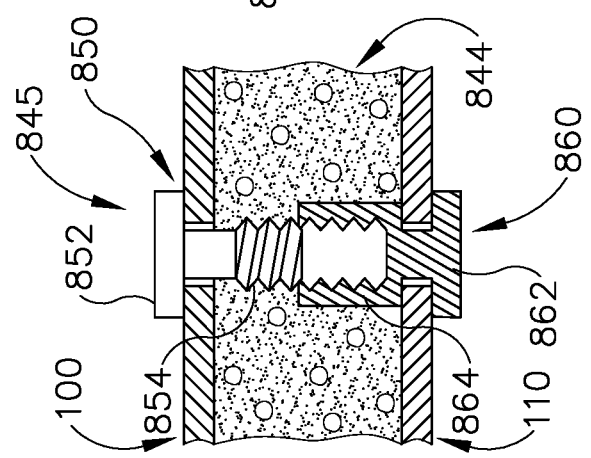
FIG. 55A depicts a partial, cross-sectional end view of a platform and buttress assembly of the buttress applier cartridge of FIG. 54, with a retention post assembly in a non-collapsed state.

As best seen in FIGS. 55A-55C, each fastener assembly (845) comprises a male member (850) and a female member (860). Male member (850) comprises a head (852) and a shank (854) extending downwardly from head (852). Head (852) is positioned on top of buttress assembly (100). Head (852) is sized and configured to releasably hold buttress assembly (100) on platform (844). Shank (854) extends through buttress assembly (100) and platform (844). Shank (854) includes a longitudinally spaced array of annular ridges or barbs. Female member (860) comprises a head (862) and a shank (864) extending upwardly from head (862). Head (862) is positioned below buttress assembly (110). Head (862) is sized and configured to releasably hold buttress assembly (110) on platform (844). Shank (864) extends through buttress assembly (110) and platform (844). Shank (864) includes a recess that includes a longitudinally spaced array of interior annular ridges or barbs. These interior features of shank (864) are configured to complement the exterior features of shank (854).

FIG. 55A shows platform (844), fastener assemblies (845), and buttress assemblies (100, 110) prior to engagement with end effector (40). As shown, shanks (854, 864) are separated from each other. Shanks (854, 864) nevertheless provide enough friction with the material of platform (844) to cooperate with heads (852, 862) in such a way that fastener assemblies (845) secure buttress assemblies (100, 110) to platform (844).

FIG. 55B shows platform (844), fastener assemblies (845), and buttress assemblies (100, 110) being clamped by a closed end effector (40). As shown, closure of end effector (40) compresses platform (844), thereby driving members (850, 860) into engagement with each other. In particular, shank (854) enters shank (864), reducing the effective height of fastener assembly (845). The exterior ridges or barbs of shank (854) ratchetingly engage the complementary interior features of shank (864), thereby fixedly securing members (850, 860) together. At this stage, adhesive layers (102, 112) (not shown in FIG. 55B) secure buttress assemblies (100, 110) to anvil (60) and staple cartridge (70), respectively.

FIG. 55C shows platform (844), fastener assemblies (845), and buttress assemblies (100, 110) after being released by the clamped end effector (40). As shown, members (850, 860) remain engaged with each other due to the engagement between the exterior ridges or barbs of shank (854) and the complementary interior features of shank (864). Platform (844) has self-expanded back to a non-compressed state. Buttress assemblies (100, 110) remain secured to anvil (60) and staple cartridge (70), respectively. During the transition from the stage shown in FIG. 55B to the stage shown in FIG. 55C, heads (852, 862) have torn through buttress assemblies (100, 110). Buttress assemblies (100, 110) are thus released from platform (844) while fastening assemblies (845) remain engaged with platform (844). End effector (40) is then ready for use in a surgical procedure as described above.

b. Exemplary Platform with Integral, Frangible Retainer Stems

FIGS. 56A-56C show another exemplary platform (870) and fastening assembly (880) that may be used in lieu of platform (844) and fastening assembly (845) described above. It should be understood that platform (870) may include an array of fastening assemblies (880), just like platform (844) including an array of fastening assemblies (845) as described above. It should also be understood that platform (870) and fastening assembly (880) may be used in any of the cartridges described herein, with or without additional fastening features such as arms (252), etc.

Fastening assembly (880) of the present example comprises a first head (882), a second head (884), and a frangible stem (886) extending between heads (882, 884). Head (882) is positioned above buttress assembly (100) and is configured to hold buttress assembly (100) on platform (870). Head (884) is positioned below buttress assembly (110) and is configured to hold buttress assembly (110) on platform (870). Stem (886) passes through buttress assemblies (100, 110) and platform (870) to secure heads (882, 884) together. It should therefore be understood that heads (882, 884) and stem (886) cooperate to secure buttress assemblies (100, 110) to platform (870).

FIG. 56A shows platform (870), fastener assembly (880), and buttress assemblies (100, 110) prior to engagement with end effector (40). FIG. 56B shows platform (870), fastener assembly (880), and buttress assemblies (100, 110) being clamped by a closed end effector (40). As shown, closure of end effector (40) compresses platform (870), thereby heads (882, 884) toward each other. This causes stem (864) to fracture. At this stage, adhesive layers (102, 112) (not shown in FIG. 56B) secure buttress assemblies (100, 110) to anvil (60) and staple cartridge (70), respectively.

FIG. 56C shows platform (870), fastener assembly (880), and buttress assemblies (100, 110) after being released by the clamped end effector (40). As shown, platform (870) has self-expanded back to a non-compressed state. Buttress assemblies (100, 110) remain secured to anvil (60) and staple cartridge (70), respectively. Heads (882, 884) remain captured between buttress assemblies (100, 110) remain secured to anvil (60) and staple cartridge (70), respectively. Fractured stem (864) remains disposed in platform (870). During the transition from the stage shown in FIG. 56B to the stage shown in FIG. 56C, friction between the material of stem (864) and platform (870) provides a firm enough grip on stem (864) such that the portions of stem (864) that were initially positioned in platform (870) (i.e., at the stage shown in FIG. 56A) remain in platform (870). In other words, stem (864) will fracture at least once during closure of end effector (40) (FIG. 56A to FIG. 56B); and fracture at least one more time during opening of end effector (40) (FIG. 56B to FIG. 56C). It should be understood that, at the stage shown in FIG. 56C, buttress assemblies (100, 110) are fully secured to end effector (40). End effector (40) is then ready for use in a surgical procedure as described above.

2. Exemplary Buttress Applier Cartridge with Retainers Disposed Over Platform

Figure 57:
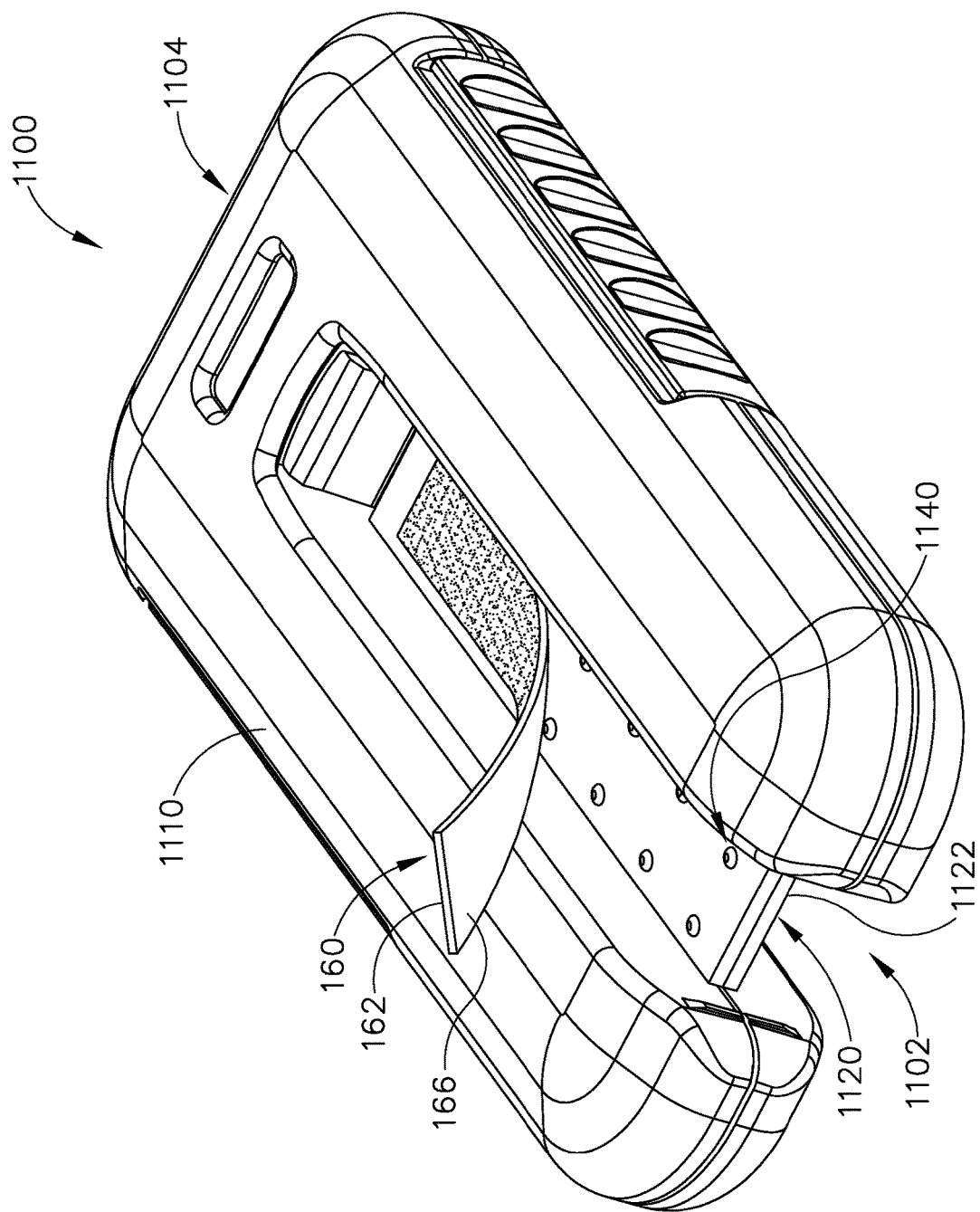
FIG. 57 depicts a perspective view of another exemplary alternative buttress applier cartridge.

FIG. 57 shows yet another exemplary alternative buttress applier cartridge (1100) that may be used to support and protect one or more buttress assemblies (160). Cartridge (1100) may also be used to easily load one or more buttress assemblies (160) on end effector (40). Cartridge (1100) of this example includes an open end (1102) and a closed end (1104) defined by a housing (1110). Cartridge (1100) further includes and a platform (1120) supporting a buttress assembly (160). While only one buttress assembly (160) is shown in FIG. 57, it should be understood that a mirror image buttress assembly (160) may be provided on the underside of platform (1120), such that cartridge (1100) may carry upper and lower buttress assemblies (160) just like other buttress applier cartridges carry buttress assemblies (100, 110) in other examples described herein. Alternatively, cartridge (1100) may be configured to support and release only one buttress assembly (160). In such versions, the single buttress assembly (160) may be configured to be applied to underside (65) of anvil (60) or deck (73) of staple cartridge (70).

Platform (1120) of the present example comprises a body (1122) and a plurality of retainers (1140) positioned on body (1122). Retainers (1140) are arranged in an array such that retainers (1140) are generally equidistantly spaced from each other along the surfaces of buttress assembly (160). As described in further detail below, retainers (1140) releasably secure buttress assembly (160) to platform (1120). In the present example, cartridge (1100) lacks arms (252). In some other versions, retainers (1140) are provided as a supplement to arms (252). It should therefore be understood that retainers (1140) may be used in combination with other features such as arms (252).

As best seen in FIGS. 58A-58C, buttress assembly (160) comprises a body (162) and an adhesive layer (164). Body (162) includes a plurality of integral filaments (166) extending downwardly therefrom. Each filament (166) is associated with a corresponding retainer (1140) as will be described in greater detail below. Aside from the inclusion of filaments (166), buttress assembly (160) may be configured and operable just like buttress assemblies (100, 110) described above.

As also best seen in FIGS. 58A-58C, platform (1120) of the present example comprises a rigid base (1122) that defines a plurality of openings (1124). Each opening (1124) is associated with a corresponding retainer (1140) as will be described in greater detail below.

Each retainer (1140) comprises an annular base (1141) and a set of arms (1142) that are pivotably coupled with annular base (1141) via respective living hinges. Each annular base (1141) is secured to rigid base (1112) of platform in coaxial alignment with corresponding openings (1124). Each arm (1142) includes a filament engaging feature (1144) and a latching feature (1146). While two arms (1142) may be seen in FIGS. 58A-58C, it should be understood that each retainer (1140) may include any suitable number of arms (1142). It should also be understood that arms (1142) may be equidistantly spaced from each other in an angular array about the vertical axis passing through the center of opening (1124) and the center of annular base (1141).

FIG. 58A shows retainer (1140) engaging buttress assembly (160) before cartridge (1100) is engaged by end effector (40). At this stage, filament (166) is captured by filament engaging features (1144) of arms (1142). Arms (1142) are resiliently biased to maintain this engagement, such that filament engaging features (1144) together clamp against filament (166). Retainers (1140) thus secure buttress assembly (160) to platform (1120).

FIG. 58B shows anvil (60) clamping buttress assembly (160) against platform (1120). The force applied by anvil (60) causes arms (1142) to deflect downwardly. During this movement, filament engaging features (1144) disengage filament (166), thereby releasing filament (166). Also during this movement, latching features (1146) engage base (1122). It should be understood that arms (1142) may deform during the transition from the state shown in FIG. 58A to the state shown in FIG. 58B in order to enable latching features (1146) to pass through opening (1124) to engage base (1122). At this stage, adhesive layer (164) has adhered buttress assembly (160) to anvil (60) and latching features (1146) have secured retainer (1140) in a collapsed configuration. With buttress assembly (160) adhered to anvil (60) and released from retainer (1140), buttress assembly (160) may be freely pulled away from platform (1120) as end effector (40) is opened as shown in FIG. 58C. Retainer (1140) remains in the collapsed configuration as buttress assembly (160) is pulled away from platform (1120).

When anvil (60) is driven downwardly against buttress assembly (160) and platform (1120) as shown in FIG. 58B, staple cartridge (70) may be simultaneously driven upwardly against platform (1120) or some other portion of cartridge (1110). Regardless of whether cartridge (1110) includes features enabling a similar buttress assembly (160) to be applied to deck (73) of staple cartridge (70), cartridge (1100) may include features that enable retainers (1140) to reach the collapsed configuration shown in FIG. 58B without interference from deck (73) of staple cartridge (70). Various suitable ways in which cartridge (1100) may prevent upward clamping forces exerted by staple cartridge (70) from interfering with the collapse of retainers (1140) during closure of end effector (40) will be apparent to those of ordinary skill in the art in view of the teachings herein.

XIII. Exemplary Features to Control and Indicate Humidity Conditions in Buttress Applier Cartridge Some versions of buttress assemblies (100, 110) may include features that are sensitive to humidity conditions. For instance, the material forming body (102, 112) may be sensitive to humidity conditions in a way such that the effectiveness of body (102, 112) is adversely affected when body (102, 112) is exposed to humidity for a prolonged period. Similarly, the material forming adhesive layer (104, 114) may be sensitive to humidity conditions in a way such that the effectiveness of adhesive layer (104, 114) is adversely affected when adhesive layer (104, 114) is exposed to humidity for a prolonged period. It may therefore be desirable to incorporate one or more features into a buttress applier cartridge that is/are configured to prevent buttress assemblies (100, 110) from being exposed to humidity for prolonged periods. In addition, it may be desirable to incorporate one or more features into a buttress applier cartridge that is/are configured to indicate if buttress assemblies (100, 110) have been exposed to humidity for prolonged periods. If such an indicator shows that buttress assemblies (100, 110) have been exposed to humidity for prolonged periods, the operator may avoid using those particular buttress assemblies (100, 110).

FIG. 59 shows an exemplary buttress applier cartridge (1700) that includes housings (1710, 1718), a platform (1720) supporting a buttress assembly (100), and a plurality of retention features (1752). Retention features (1752) are configured to releasably secure buttress assembly (100) to platform (1720); and may be configured like any of the various retention features described herein. Platform (1720) includes a plurality of fins (1722). Fins (1722) are configured to fit within the sidewalls defining channel (62) to ensure that anvil (60) is properly aligned with buttress assembly (100) as anvil (60) is closed down toward buttress assembly (100) and platform (1720). It should also be understood that the underside of platform (1720) (i.e., the side carrying buttress assembly (110), associated with staple cartridge (70)), may also include fins (1722). Fins (1722) on the underside of platform (1720) may be sized and arranged to fit in channel (72) of staple cartridge (70). Moreover, as will be described in greater detail below, fins (1722) on the underside of platform (1720) may be configured to prevent cartridge (1700) from being used with a staple cartridge (70) that has already been fired.

Cartridge (1700) of the present example further includes a plurality of indicator beads (1742) that are viewable through a window (1712) formed in housing (1710). Indicator beads (1742) are formed of a color-changing desiccant material. In particular, beads (1742) are configured to reflect a first color when beads (1742) are in a substantially dry state; and a second color when beads (1742) are in a wet state. Beads (1742) may transition to a wet state in response to exposure to humidity that is above a threshold that is suitable for buttress assemblies (100, 110). In some versions, beads (1742) will maintain the second color even if the humidity level later drops back below the threshold level. Beads (1742) will thus provide visual indication to the user to indicate that buttress assemblies (100, 110) have been subject to an unacceptable level of humidity. Of course, beads (1742) may also transition from the first color to the second color if beads (1742) are otherwise exposed to fluid, such as spilled medical fluids, bodily fluids from a patient, etc. Various materials that may be used to form beads (1742) will be apparent to those of ordinary skill in the art in view of the teachings herein.

Cartridge (1700) of the present example further includes a cover (1730) that may be removably secured to housings (1710, 1718). Cover (1730) includes an upper panel (1732) and a lower panel (1734) that are coupled together to define a "U" shape. Cover (1730) is sized and configured to cover the recesses in which platform (1720) and buttress assemblies (100, 110) are disposed when cover (1730) is secured to housings (1710, 1718). Cover (1730) may thus protect buttress assemblies (100, 110) up until an operator is ready to use cartridge (1700). To remove cover (1730), the operator may simply pull cover (1730) away from cartridge (1700). By way of example only, panels (1732, 1734) may be resiliently biased toward each other such that panels (1732, 1734) are oriented to be non-parallel with each other. Thus, panels (1732, 1734) may be deflected away from each other to reach a parallel state when cover (1730) is engaged with housings (1710, 1718), such that panels (1732, 1734) resiliently bear against housings (1710, 1718) to provide a secure fit through friction. Various other suitable configurations that may be used to form cover (1730), and to secure cover (1730) to housings (1710, 1718), will be apparent to those of ordinary skill in the art in view of the teachings herein. It should also be understood that cover (1730) may be used with any of the buttress applier cartridges described herein, such that cover (1730) is not at all limited to cartridge (1700).

In some versions, cover (1730) comprises a desiccant material that is configured to absorb moisture (e.g., from humidity) and thereby prevent that moisture from reaching buttress assemblies (100, 110). In addition or in the alternative, desiccant material may be incorporated into the material forming platform (1720), the material forming housing (1710), packets or compartments located within a cavity defined by housing (1710, 1718), and/or in various other suitable locations/configurations. By way of example only, silica gel may be included in packets that are located within a cavity defined by housing (1710, 1718). Other suitable desiccant materials that may be incorporated into cartridge (1700) will be apparent to those of ordinary skill in the art in view of the teachings herein. Similarly, various other ways in which one or more desiccant materials may be incorporated into cartridge (1700) will be apparent to those of ordinary skill in the art in view of the teachings herein.

XIV. Exemplary Features to Prevent Use of Buttress Applier Cartridge with Spent Staple Cartridge In the present example, after a staple cartridge (70) has been actuated once, that staple cartridge (70) cannot be used again in the same surgical procedure. This is because all of the staples (90) in staple cartridge (70) will have been deployed, such that a spent staple cartridge (70) will be unable to apply more staples (90). Instrument (10) may include various features that are sensitive to the spent state of a staple cartridge (70), such that instrument may prevent firing beam (82) from being actuated as second time through a spent staple cartridge (70). In view of this, it may be desirable to prevent an operator from improperly or inadvertently using a buttress applier cartridge to apply buttress assemblies (100, 110) to an end effector (40) that has a spent staple cartridge (70) loaded in lower jaw (50).

Figure 60:
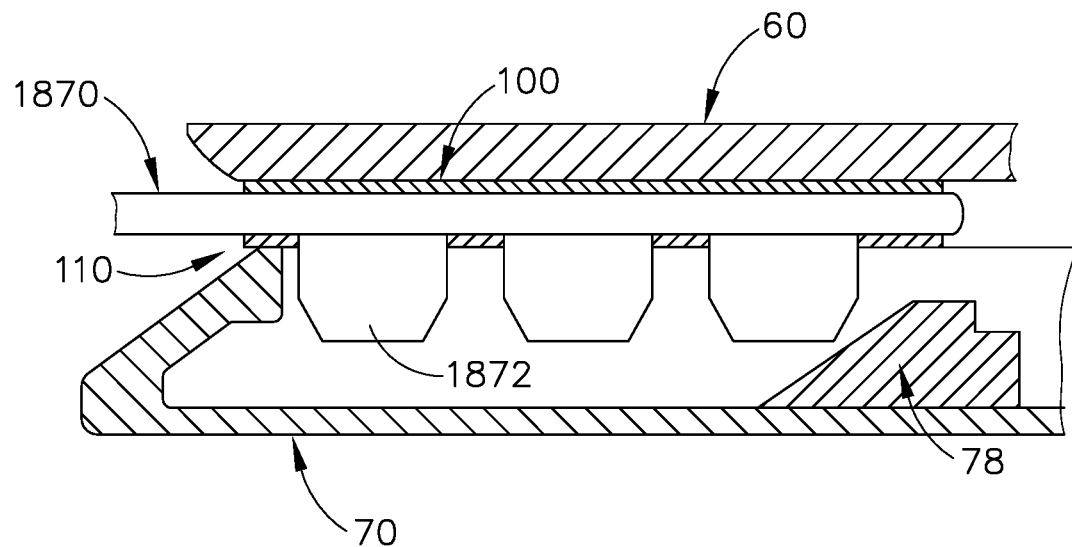
FIG. 60 depicts a cross-sectional side view of another exemplary alternative buttress applier cartridge, similar to the buttress applier cartridge of FIG. 59, with the end effector of FIG. 2 positioned about a platform of the buttress applier cartridge, with the end effector in a closed configuration, and with a staple cartridge of the end effector in a non-spent state.
Figure 61:
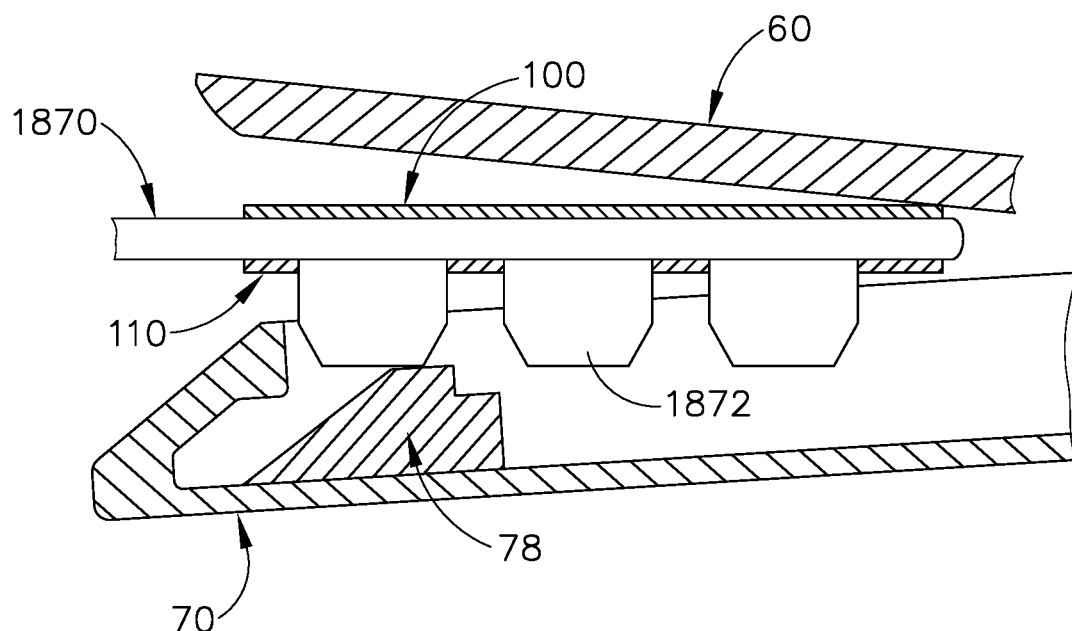
FIG. 61 depicts a cross-sectional side view of the buttress applier cartridge of FIG. 60, with the end effector of FIG. 2 positioned about a platform of the buttress applier cartridge, with the end effector in a partially closed configuration, and with a staple cartridge of the end effector in a spent state.

To that end, FIGS. 60-61 show exemplary features that may be readily incorporated into any of the buttress applier cartridges described herein to prevent the buttress applier cartridge from being used to apply buttress assemblies (100, 110) to an end effector (40) that has a spent staple cartridge (70) loaded in lower jaw (50). In particular, FIGS. 60-61 show a platform (1870) that has a plurality of integral, downwardly extending rigid fins (1872). Fins (1872) of this example are substantially identical to fins (1722) described above, such that fins (1872) are sized and configured to fit in channel (72) of staple cartridge (70). It should therefore be understood that fins (1872) may assist in ensuring proper alignment between buttress assembly (110) and staple cartridge (70).

Fins (1872) will also provide a lockout to prevent full closure of an end effector (40) that includes a spent staple cartridge (70). As shown in FIG. 60, in a non-spent staple cartridge (70), wedge sled (78) is located at a proximal position. Fins (1872) are configured and positioned such that no fin (1872) will engage the proximally positioned wedge sled (78) when end effector (40) is closed on buttress assemblies (100, 110) and platform (1870). In other words, fins (1872) will not prevent full closure of end effector (40) about buttress assemblies (100, 110) and platform (1870) when staple cartridge (70) is in a non-spent state. However, FIG. 61 shows how wedge sled (78) is positioned distally in a spent staple cartridge (70); and how one of the fins (1872) will engage the distally positioned wedge sled (78) to prevent full closure of end effector (40) about buttress assemblies (100, 110) and platform (1870) when staple cartridge (70) is in a spent state. It should therefore be understood that fins (1872) will prevent the operator from being able to apply buttress assembly (110) to deck (73) of a spent staple cartridge (70). Moreover, by physically obstructing full closure of end effector (40) about buttress assemblies (100, 110), fins (1872) will provide the operator with visual and tactile feedback indicating that the operator is improperly attempting to use an end effector (40) with a spent staple cartridge (70).

While platform (1870) only includes downwardly extending fins (1872) in this example, it should be understood that platform (1872) may also include upwardly extending fins like fins (1722) described above. To the extent that such upwardly extending fins may not prevent full closure of end effector (40) about buttress assemblies (100, 110) and platform (1870) when staple cartridge (70) is in a spent state, the upwardly extending fins may nevertheless promote proper alignment between end effector (40) and buttress assemblies (100, 110) as described above.

XV. Exemplary End Effector Alignment Features for Buttress Applier Cartridge

In some instances, it may be desirable to configure buttress assembly (100) such that the lateral width of buttress assembly (100) closely matches the lateral width of underside (65) of anvil (60). Likewise, it may be desirable to configure buttress assembly (110) such that the lateral width of buttress assembly (110) closely matches the lateral width of deck (73) of anvil (70). Matching these widths may present little to no margin of error with respect to alignment of end effector (40) with buttress assemblies (100, 110). It may therefore be desirable to provide features that ensure or otherwise promote proper alignment of end effector (40) with buttress assemblies (100, 110). Such alignment may include proper lateral positioning of end effector along a lateral plane (i.e., a plane that is parallel to the planes defined by buttress assemblies (100, 110)). Such alignment may also include proper "yaw" positioning about an axis that is perpendicular to the same lateral plane (i.e., a plane that is parallel to the planes defined by buttress assemblies (100, 110)). Several examples of features that may be used to ensure or otherwise promote proper alignment of end effector (40) with buttress assemblies (100, 110) are described in greater detail below, while other examples will be apparent to those of ordinary skill in the art in view of the teachings herein.

Figure 62:
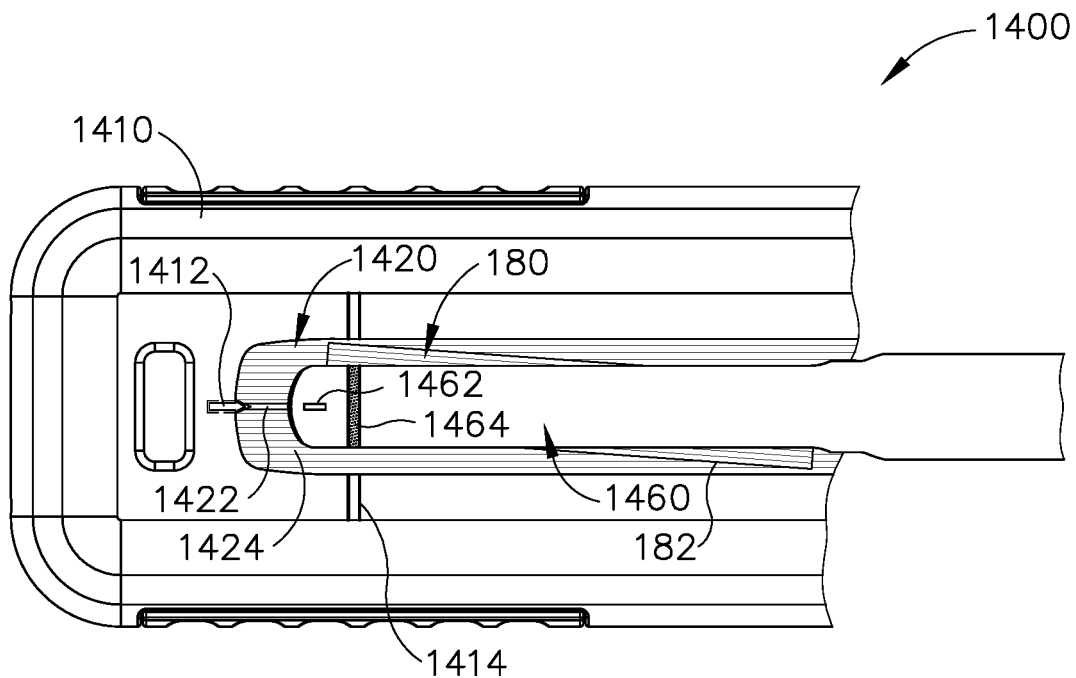
FIG. 62 depicts a top plan view of another exemplary alternative buttress applier cartridge, with a platform of the buttress applier cartridge positioned in the end effector of FIG. 2.

FIG. 62 shows an exemplary buttress applier cartridge (1400) that may be used to support and protect upper and lower buttress assemblies (1420). Cartridge (1400) may also be used to easily load upper and lower buttress assemblies (180) on end effector (40). Cartridge (1400) includes a housing (1410) and a platform (1420) supporting at least one buttress assembly (180). Buttress assembly (180) may be configured and operable just like any other buttress assembly described herein, except for the differences specifically noted below. It should also be understood that buttress assembly (180) may be releasably secured to platform (1420) in accordance with any of the teachings herein relating to securing of buttress assemblies to platforms.

Buttress applier cartridge (1400) is configured to be used with an end effector (40) that incorporates anvil (1460) in place of anvil (60). Anvil (1460) is identical to anvil (60) except that anvil (1460) includes a first marking (1462) and a second marking (1464). First marking (1462) is positioned at the distal end of anvil (1460), extends longitudinally, and is laterally centered along the width of anvil (1460). First marking (1462) is configured to correspond with a first marking (1412) on housing (1410). First marking (1462) is laterally positioned to be centered along the width of the recess in which buttress assembly (180) is disposed. Thus, in order to ensure that anvil (1460) (and, hence, end effector (40)) has proper lateral alignment with cartridge (1400), the operator may view the positions of markings (1412, 1462) in relation to each other to confirm that markings (1412, 1462) are properly aligned with each other.

Second marking (1464) extends cross the width of anvil (1460) and is oriented perpendicularly relative to the longitudinal axis of anvil (1460). Second marking (1464) is configured to correspond with second markings (1414) on housing (1410). Second markings (1414) are located at a predetermined position along the length of the recess in which buttress assembly (180) is disposed. This position is located such that when marking (1464) is aligned with markings (1414), a proper length of buttress assembly (180) and platform (1420) have been received between anvil (1460) and staple cartridge (70). Thus, in order to further ensure that end effector (40) has been advanced to a proper longitudinal position in relation to cartridge (1400), the operator may view the positions of markings (1414, 1464) in relation to each other to confirm that markings (1414, 1464) are properly aligned with each other.

Platform (1420) of the present example further includes markings (1422, 1424) that assist in proper positioning and alignment of end effector (40) relative to cartridge (1400). In particular, platform (1420) includes a marking (1422) in the form of a line that extends longitudinally along the lateral center of platform (1420). Marking (1422) thus aligns with marking (1412) of housing (1410). It should therefore be appreciated that marking (1422) may assist the operator in aligning marking (1462) with marking (1412), such that the operator may observe marking (1422) as representing the same lateral position as marking (1412). It should also be understood that, in versions where marking (1422) is included, marking (1412) may simply be omitted. In addition to including marking (1422), platform (1424) includes markings, which include an array of longitudinally extending lines that are parallel to marking (1422) and that are equidistantly laterally offset from marking (1422). Markings (1422) may assist the operator in achieving a proper yaw orientation of end effector (40) relative to cartridge (1400). In particular, the operator may observe the positioning of the lateral edges of anvil (1460) in relation to markings (1422) to ensure that the lateral edges of anvil (1460) remain parallel with markings (1422).

Figure 63:
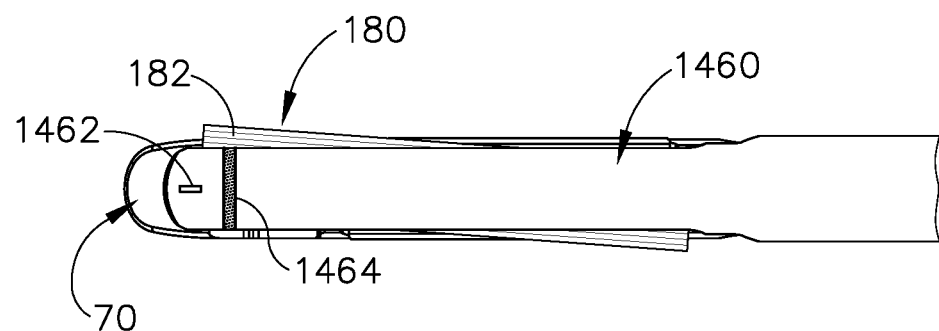
FIG. 63 depicts a top plan view of the end effector of FIG. 2 with a buttress from the buttress applier cartridge of FIG. 62, with the buttress in a skewed position.

In addition to helping ensure proper yaw orientation of end effector (40) relative to cartridge (1400), markings (1422) may also help to ensure proper yaw orientation of buttress assembly (180) on platform (1420). In particular, buttress assembly (180) of this example includes a plurality of markings (182) in the form of longitudinally extending lines that are equidistantly spaced apart across the width of buttress assembly (180). In the present example, the spacing of markings (182) is closer than the spacing of markings (1422) to promote easier visualization of buttress assembly (180) on platform (1420), though it should be understood that the spacings may have any other suitable relationship. Markings (182) of buttress assembly (180) may be viewed in relation to markings (1422) of platform (1420) to ensure that markings (182) are parallel with markings (1422). If markings (182) are not parallel with markings (1422) (e.g., as shown in FIG. 62), this may indicate that buttress assembly (180) does not have a proper yaw orientation on platform (1420), such that cartridge (1400) should be discarded. Markings (182) of buttress assembly (180) may also be viewed in relation to the lateral edges of anvil (1460) to ensure that buttress assembly (180) has a proper yaw orientation on anvil (1460). As shown in FIG. 63, markings (182) may provide visual emphasis to indicate when buttress assembly (180) does not have proper yaw orientation on anvil (1460). If the operator observes this mis-orientation, the operator by peel buttress assembly (180) away from anvil (1460) and apply another buttress assembly (180) to anvil (1460).

XVI. Exemplary Features to Indicate Used State of Buttress Applier Cartridge

Some surgical procedures may call for the use of several buttress applier cartridges since end effector (40) may need to be actuated repeatedly in order to complete a surgical task. This may create a scenario in an operating room where spent buttress applier cartridges and unspent buttress applier cartridges are present in the vicinity of each other, causing a potential for inadvertent commingling and confusion. In some cases, an operator may attempt to use an already spent buttress applier cartridge to apply buttress assemblies (100, 110) to an end effector (40); and may fail to realize that the buttress applier cartridge did not in fact have any buttress assemblies (100, 110) loaded on it before the operator then actuates end effector (40) in the patient. It may therefore be desirable to incorporate one or more features into a buttress applier cartridge in order to enable an operator to more readily ascertain whether the buttress applier cartridge has already been used to apply buttress assemblies (100, 110) to an end effector (40). The following discussion provides several merely illustrative examples of features that may be used to readily indicate the spent state of a buttress applier cartridge. Further examples will be apparent to those of ordinary skill in the art in view of the teachings herein.

A. Exemplary Electrically Activated Indicators

Figures 64A, 64B:
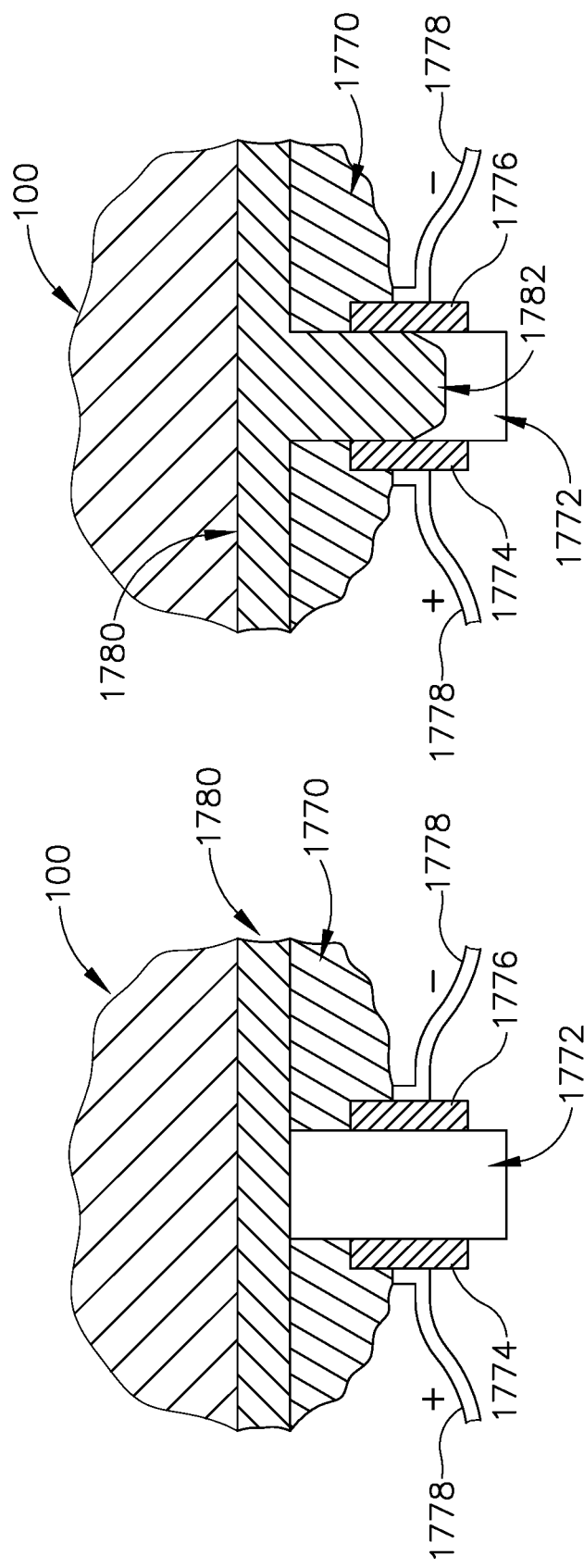
FIG. 64A depicts a cross-sectional detail view of an electrically activated indicator of a buttress applier cartridge, with the indicator in an inactivated state.
FIG. 64B depicts a cross-sectional detail view of the indicator of FIG. 64A, in an activated state.

FIGS. 64A-64B show components that may be readily incorporated into any of the buttress applier cartridges described herein to provide an electrical signal in response to use of the buttress applier cartridge to apply buttress assemblies (100, 110) to an end effector (40). In particular, FIGS. 64A-64B show a base (1770), a layer of medium (1780), and a buttress assembly (100) laid over medium (1780). In some variations, another layer is interposed between buttress assembly (100) and medium (1780). Such an intermediate layer may be substantially non-compressible such that the intermediate layer will efficiently transfer compression forces from buttress assembly (100) to medium (1780) (e.g., when an anvil (60) clamps down on buttress assembly (100)).

Base (1770) may be incorporated into any of the various platforms discussed herein. Medium (1780) of this example comprises a flowable, electrically conductive material. The material forming medium (1780) is configured to maintain a flat structural configuration as shown in FIG. 64A when medium (1780) is not being pressed against base (1770). However, when medium (1780) is pressed against base (1770), such as when an anvil (60) clamps buttress assembly (100) against base (1770) and an underlying platform, medium (1780) will flow into a recess (1772) formed in base (1770) as shown in FIG. 64B. Medium (1780) will then stay in recess (1772).

Various suitable materials that may be used to form medium (1780) will be apparent to those of ordinary skill in the art in view of the teachings herein. By way of example only, medium (1780) may comprise an adhesive material that removably adheres buttress assembly (100) to base (1770). For instance, medium (1780) may comprise PEG blends, PVP/PEG blends, PLC/PGA copolymers, TMC/PGA copolymers, etc., with one or more additives that make the adhesive material electrically conductive. In some versions, medium (1780) comprises the same adhesive material (albeit with electrically conductive material added) that is used to apply buttress assemblies (100, 110) to underside (65) of anvil (60) and deck (73) of staple cartridge (70). By using a similar adhesive material for medium (1780), the flow of medium (1780) into recesses (1772) may occur substantially contemporaneously with the flow of adhesive material forming adhesive layers (102, 112) into the various recesses and other surface features found in underside (65) of anvil (60) and deck (73) of staple cartridge (70). In other words, the flow of medium (1780) into recesses (1772) may be indicative of the flow of adhesive material forming adhesive layers (102, 112) into the various recesses and other surface features found in underside (65) of anvil (60) and deck (73) of staple cartridge (70). Other suitable materials that may be used to form medium (1780) will be apparent to those of ordinary skill in the art in view of the teachings herein.

In the present example, a pair of electrodes (1774, 1776) are fixedly positioned on opposite sides of recess (1772). Electrodes (1774, 1776) include conductive contacts that are exposed to the space within recess (1772). Electrodes (1774, 1776) are coupled with a voltage source (not shown) (e.g., a battery) via wires (1778), such that electrode (1774) provides a positive charge and electrode (1776) provides a negative charge. It should be understood from the foregoing that, it the state shown in FIG. 64A, there is nothing to provide electrical continuity between electrodes (1774, 1776), such that electrical current will not flow through wires (1778). However, once medium (1780) enters recess (1772) as shown in FIG. 64B and thereby provides a path for electrical communication between electrodes (1774, 1776), electrical current will flow through wires (1778).

Various suitable indicator features may be in electrical communication with wires (1778) such that an indicator is electrically activated in response to entry of medium (1780) in recess (1772). By way of example only, such an indicator feature may comprise a light source such as an LED, etc. that is viewable from the exterior of the buttress applier cartridge. In such versions, since the light source is not illuminated until medium (1780) is compressed by closure of anvil (60), the illumination of the light source may provide a clear visual indication that the buttress applier cartridge has already been used to apply buttress assembly (100) to anvil (60). Since medium (1780) will remain in recess (1772), the light source may remain illuminated until the voltage source runs out of power or the circuit is otherwise interrupted. By way of example only, wires (1778) may be in communication with any of the various indicator features described in U.S. patent application Ser. No. 14/926,131, filed Oct. 29, 2015, now U.S. Patent Pub. No. 2017/0119391, published May 4, 2017, issued as U.S. Pat. No. 10,251,649 on Apr. 9, 2019, entitled "Surgical Stapler Buttress Applicator with Data Communication," filed on even date herewith, the disclosure of which is incorporated by reference herein. Other suitable indicators that may be in communication with wires (1778) to indicate a spent state of a buttress applier cartridge will be apparent to those of ordinary skill in the art in view of the teachings herein.

B. Exemplary Fluid Transfer Indicators

Figure 66A:
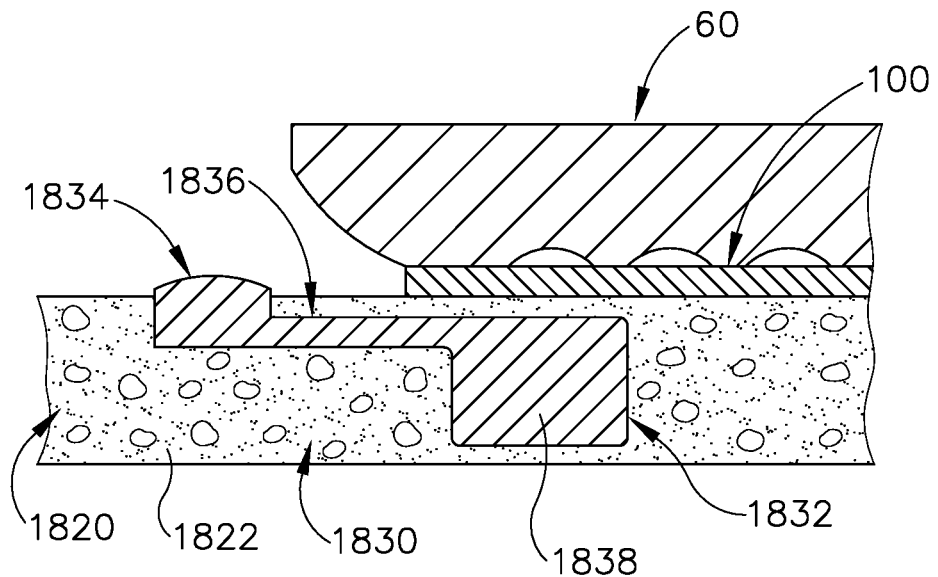
FIG. 66A depicts a cross-sectional detail view of a fluid transfer indicator of the buttress applier cartridge of FIG. 65, with the indicator in a non-actuated state.
Figure 66B:
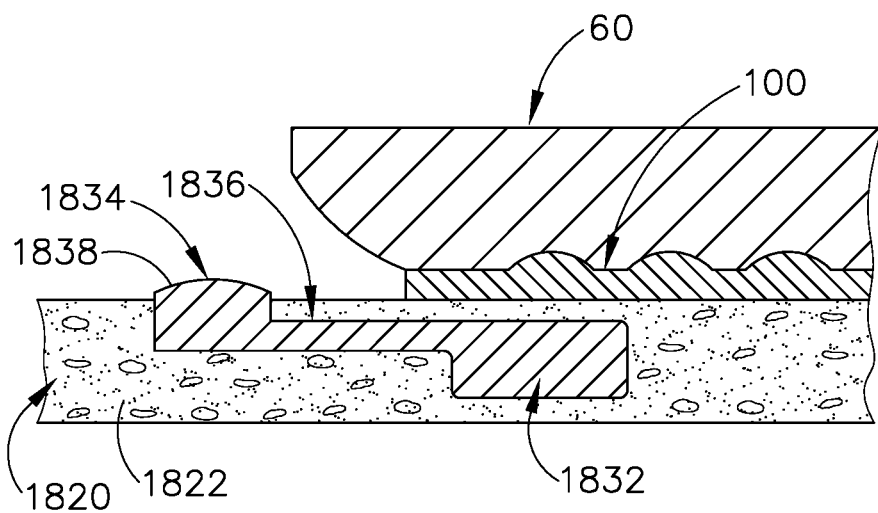
FIG. 66B depicts a cross-sectional detail view of the indicator of FIG. 66A, with the indicator in an actuated state.

FIG. 65 shows another exemplary alternative buttress applier cartridge (1800) that may be used to apply buttress assemblies (100, 110) to an end effector (40). Cartridge (1800) of this example includes a housing (1810) and a platform (1820). Platform (1820) includes a series of indicator assemblies (1830) embedded within the body (1822) of platform (1820). As best seen in FIGS. 66A-66B, each indicator assembly (1830) includes a first reservoir (1832), a second reservoir (1834), and a conduit (1836) extending between reservoirs (1832, 1834). Each set of reservoirs (1832, 1834) and conduit (1836) defines a closed fluid circuit that contains a fixed volume of liquid (1838).

In the present example, body (1822) is formed of a material that is compressible from an expanded thickness (FIG. 66A) to a compressed thickness (FIG. 66B); and is configured to maintain the compressed thickness after body (1822) has been compressed (e.g., even after end effector (40) opens to release platform (1820)). Reservoir (1832) is configured to compress with platform (1820), such that the volume of reservoir (1832) will decrease as platform (1820) is compressed. Reservoir (1834) includes an upper portion that is exposed relative to body (1822), such that an operator may visually observe reservoir (1834). When platform (1820) is in the uncompressed state as shown in FIG. 66A, none of liquid (1838) is positioned in reservoir (1834). As shown in the transition from FIG. 66A to FIG. 66B, some of liquid (1838) will be pressed out of reservoir (1832) when anvil (60) compresses body (1822) of platform (1820). Liquid (1838) will then flow into reservoir (1834). It should be understood that reservoir (1834) may include one or more vent openings (not shown) that will enable air to escape from reservoir (1834) when liquid (1838) is driven into reservoir (1834).

With reservoir (1834) filled with liquid (1838) as shown in FIG. 66B, the operator may readily view the presence of liquid (1838) in reservoir (1834) as a visual indication that the cartridge (1800) has been spent (i.e., that cartridge (1800) no longer has buttress assemblies (100, 110)). Since body (1822) is configured to maintain a compressed state even after platform (1820) is released from end effector (40), liquid (1838) will remain visible in reservoir (1834) to continue indicating that cartridge (1800) has been spent. It should be understood that the materials forming liquid (1838) and body (1822) may be selected to provide a strong contrast, thereby enhancing visibility of liquid (1838) in reservoir (1834).

In addition to providing a visual indication of whether cartridge (1800) has been spent, indicator assemblies (1830) may provide visual feedback to indicate whether the operator has applied sufficient clamping force with end effector (40) in order to successfully transfer buttress assemblies (100, 110) from platform (1820) to end effector (40). In particular, platform (1820) and indicator assemblies (1830) may be configured such that an operator must provide a clamping force with end effector (40) above a certain threshold before liquid (1838) will reach reservoir (1834). Thus, if an operator attempts to clamp end effector (40) on buttress assemblies (100, 110) and platform (1820) yet fails to apply a sufficient clamping force with end effector (40), liquid (1838) will not be driven from reservoir (1832) to reservoir (1834). The operator may thereby determine that the clamping force was insufficient in view of the fact that liquid (1838) is not seen in reservoir (1834). The operator may try again with greater clamping force and then observe reservoir (1834) again for the presence of liquid (1838) to determine whether the additional clamping force was sufficient.

XVII. Exemplary Buttress Applier Cartridge with Fluid Capture Reservoir

Figure 67:
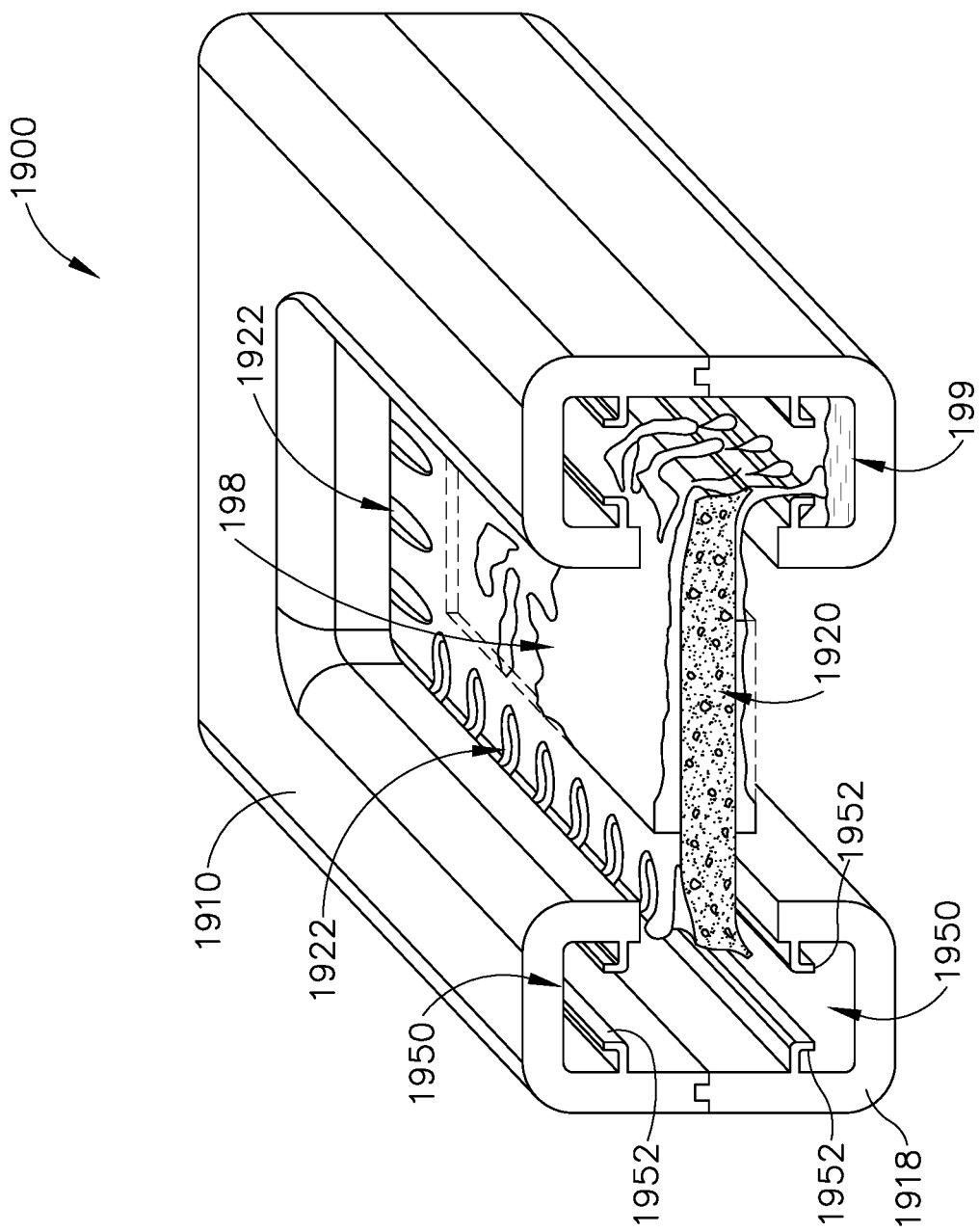
FIG. 67 depicts a perspective cross-sectional view of another exemplary alternative buttress applier cartridge.

Some versions of buttress assemblies (100, 110) may comprise a flowable adhesive material and/or some other flowable material. In some such versions, the flowable material may flow considerably in response to clamping of end effector (40) on buttress assemblies (100, 110), such that the clamping action of end effector (40) drives a flow of adhesive material out from buttress assemblies (100, 110) when end effector (40) clamps down on buttress assemblies (100, 110). It may therefore be desirable to provide features in a buttress applying cartridge to handle excess flowable adhesive material. To that end, FIG. 67 shows an exemplary buttress applier cartridge (1900) that comprises housings (1910, 1918), and a platform (1920). FIG. 67 shows cartridge (1900) in a state where an end effector (40) has already retrieved buttress assemblies (100, 110) from platform (1920), with an excess of flowable material (198) being left on platform (1920). Platform (1920) of this example further comprises a plurality of drainage openings (1922) near the interface regions of housings (1910, 1918). Drainage openings (1922) are in fluid communication with a cavity (1950) that is defined by housings (1910, 1918). Thus, drainage openings (1922) allow the flowable material (198) to drain through drainage openings (1922) and into cavity (1950). The interiors of housings (1910, 1918) further include baffles (1952) in cavity (1950). Baffles (1952) are configured to assist in retaining the excess flowable material (198) in cavity (199). Other suitable features that may be incorporated into a buttress applier cartridge to handle excess flowable materials will be apparent to those of ordinary skill in the art in view of the teachings herein.

As described in greater detail below, some versions of buttress assemblies (100, 110) may be sensitive to certain environmental conditions (e.g., high humidity levels, high temperatures, etc.) such that the effectiveness of buttress assembly (100, 110) may be compromised after buttress assembly (100, 110) has been sufficiently exposed to one or more adverse environmental conditions. In some such versions, flowable material (198) will liquefy in response to sufficient exposure to one or more adverse environmental conditions. If this occurs before buttress assembly (100, 110) is picked up by an end effector (40), flowable material (198) may simply flow off of buttress body (102, 112) and into cavity (199) as described above. In some such instances, buttress assembly (100, 110) may then be rendered inoperable by the absence of flowable material (198). For instance, buttress assembly (100, 110) may be unable to adhere to end effector (40) in the absence of flowable material (198).

XVIII. Exemplary Packaging for Buttress Applier Cartridge

Figure 68:
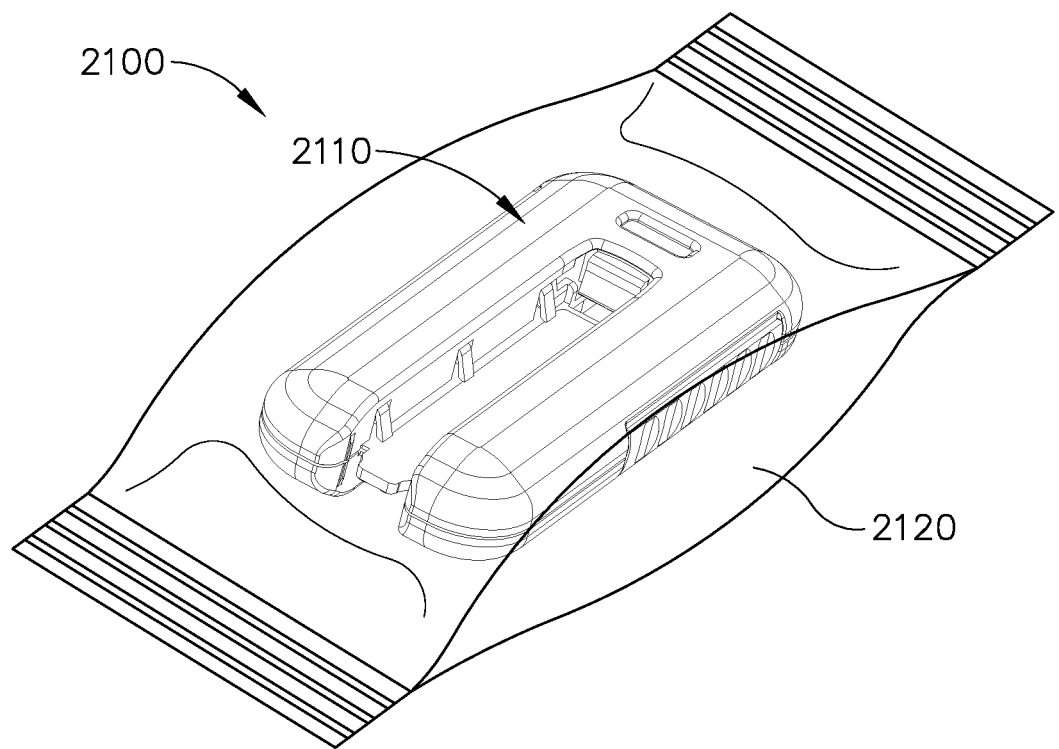
FIG. 68 depicts a perspective view of another exemplary alternative buttress applier cartridge, disposed in a package, with the package in a first state.
Figure 69:
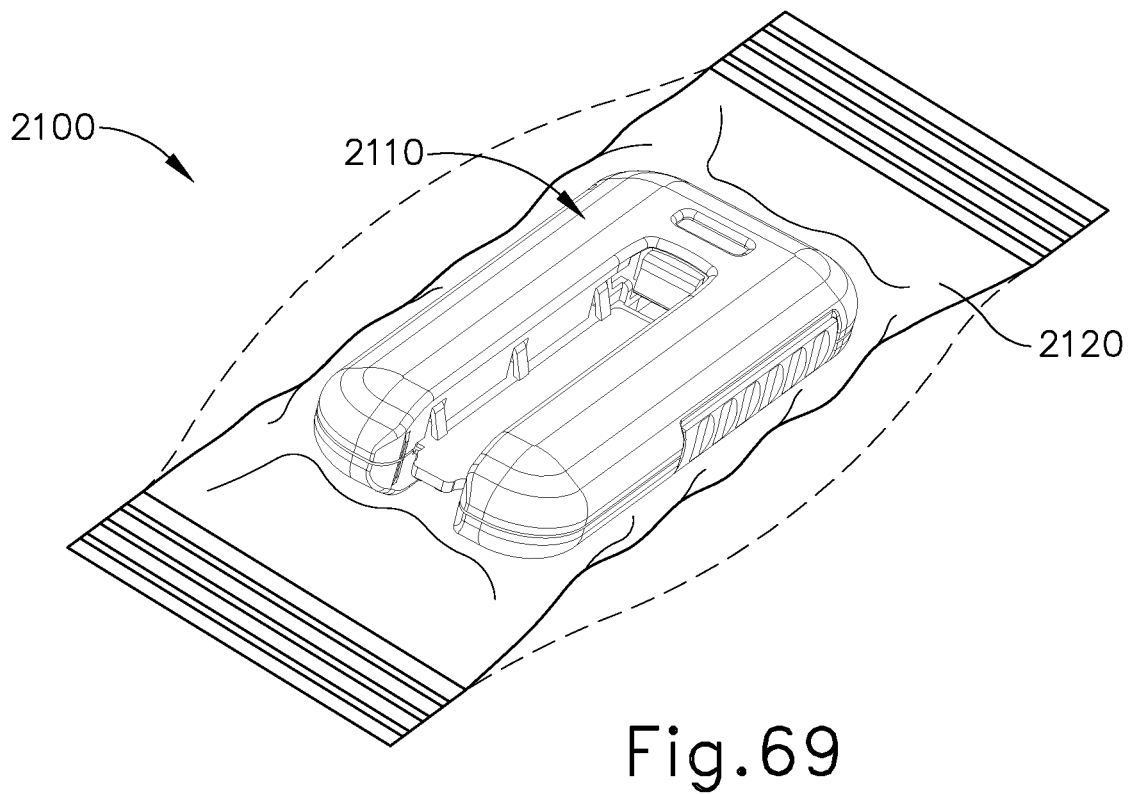
FIG. 69 depicts a perspective view of the buttress applier cartridge and package of FIG. 68, with the package in a second state.

It may be desirable to provide a buttress applier cartridge in a sealed package that maintains the sterility of the buttress applier cartridge. It may also be desirable to configure such packaging in a way that provides an operator with ready indication of whether the seal is being maintain or if the seal has been compromised. To that end, FIGS. 68-69 show a package (2100) comprising a sealed bag (2120) that contains a buttress applier cartridge (2110). Cartridge (2110) may comprise any of the various buttress applier cartridges described herein. As shown in FIG. 68, bag (2120) is filled with air and then sealed, keeping bag (2120) in an inflated state. In the event that the seal is broken, air will escape bag (2120), such that bag (2120) will transition to a deflated state as shown in FIG. 69. An operator may thus readily determine whether the seal of bag (2120) is intact or broken by observing whether bag (2120) is in an inflated state (FIG. 68) or a deflated state (FIG. 69). In some versions, bag (2120) is resiliently biased to conform to the shape of cartridge (2110) or to otherwise shrink in the deflated state, which may make the state of deflation even more readily apparent. It should also be understood that the air that is used to fill bag (2120) may contain a characteristic odor to provide olfactory feedback, such that when the operator opens bag (2120), the operator may observe whether the characteristic odor is present in order to determine whether bag (2120) had maintained a seal before the operator opened bag (2120). Bag (2120) may also provide a popping sound when the operator opens bag (2120), to provide audible feedback to indicate that the seal had been successfully maintained before the operator opened bag (2120). Other suitable ways in which package (2110) may be modified will be apparent to those of ordinary skill in the art in view of the teachings herein.

XIX. Exemplary Features in Buttress Applier Cartridge to React to Environmental Conditions In some instances, it may be desirable to discourage or prevent an operator from loading a buttress assembly (100, 110) onto end effector (40) when that buttress assembly (100, 110) has been exposed to certain environmental conditions that may compromise the effectiveness of buttress assembly (100, 110). For instance, it may be desirable to discourage or prevent an operator from loading a buttress assembly (100, 110) onto end effector (40) when that buttress assembly (100, 110) has been exposed to a humidity level above a certain threshold, other exposure to moisture, a temperature above a certain threshold, and/or some other environmental condition(s) that may compromise the effectiveness of buttress assembly (100, 110). By way of example only, the material forming body (102, 112) may be sensitive to certain environmental conditions in a way such that the effectiveness of body (102, 112) is adversely affected when body (102, 112) is exposed to certain environmental conditions for a prolonged period. Similarly, the material forming adhesive layer (104, 114) may be sensitive to certain environmental conditions in a way such that the effectiveness of adhesive layer (104, 114) is adversely affected when adhesive layer (104, 114) is exposed to certain environmental conditions for a prolonged period. The following examples provide various features that may be incorporated into a buttress applier cartridge in order to discourage or prevent an operator from loading a buttress assembly (100, 110) onto end effector (40) when that buttress assembly (100, 110) has been exposed to certain environmental conditions. It should be understood that the features described below may be readily incorporated into any of the various buttress applier cartridges described herein.

A. Exemplary Features to Control and Visually Indicate Environmental Condition Exposure in Buttress Applier Cartridge One way in which a buttress applier cartridge may discourage an operator from loading a buttress assembly (100, 110) onto end effector (40) when that buttress assembly (100, 110) has been exposed to certain environmental conditions is to provide a visual indication to the operator, indicating to the operator that buttress assembly (100, 110) has been exposed to certain environmental conditions. If such an indicator shows that buttress assemblies (100, 110) have been exposed to certain environmental conditions for prolonged periods, the operator may avoid using those particular buttress assemblies (100, 110). It may also be desirable to incorporate one or more features into a buttress applier cartridge that is/are configured to prevent buttress assemblies (100, 110) from being exposed to certain environmental conditions for prolonged periods. The following examples are provided in the context of excess humidity as an adverse environmental condition, though it should be understood that many of the same teachings may be readily applied to excess temperature as an adverse environmental condition and/or other kinds of adverse environmental conditions.

As noted above, FIG. 59 shows an exemplary buttress applier cartridge (1700) that includes housings (1710, 1718), a platform (1720) supporting a buttress assembly (100), and a plurality of retention features (1752). Retention features (1752) are configured to releasably secure buttress assembly (100) to platform (1720); and may be configured like any of the various retention features described herein. Platform (1720) includes a plurality of fins (1722). Fins (1722) are configured to fit within the sidewalls defining channel (62) to ensure that anvil (60) is properly aligned with buttress assembly (100) as anvil (60) is closed down toward buttress assembly (100) and platform (1720). It should also be understood that the underside of platform (1720) (i.e., the side carrying buttress assembly (110), associated with staple cartridge (70)), may also include fins (1722). Fins (1722) on the underside of platform (1720) may be sized and arranged to fit in channel (72) of staple cartridge (70). It should be understood that fins (1722) are merely optional.

Cartridge (1700) of the present example further includes a plurality of indicator beads (1742) that are viewable through a window (1712) formed in housing (1710). Indicator beads (1742) are formed of a color-changing desiccant material. In particular, beads (1742) are configured to reflect a first color when beads (1742) are in a substantially dry state; and a second color when beads (1742) are in a wet state. Beads (1742) may transition to a wet state in response to exposure to humidity that is above a threshold that is suitable for buttress assemblies (100, 110). In some versions, beads (1742) will maintain the second color even if the humidity level later drops back below the threshold level. Beads (1742) will thus provide visual indication to the user to indicate that buttress assemblies (100, 110) have been subject to an unacceptable level of humidity. Of course, beads (1742) may also transition from the first color to the second color if beads (1742) are otherwise exposed to fluid, such as spilled medical fluids, bodily fluids from a patient, etc. Various materials that may be used to form beads (1742) will be apparent to those of ordinary skill in the art in view of the teachings herein. It should also be understood that buttress assemblies (100, 110) may include materials that change color or otherwise change appearance in response to exposure to adverse environmental conditions.

Cartridge (1700) of the present example further includes a cover (1730) that may be removably secured to housings (1710, 1718). Cover (1730) includes an upper panel (1732) and a lower panel (1734) that are coupled together to define a "U" shape. Cover (1730) is sized and configured to cover the recesses in which platform (1720) and buttress assemblies (100, 110) are disposed when cover (1730) is secured to housings (1710, 1718). Cover (1730) may thus protect buttress assemblies (100, 110) up until an operator is ready to use cartridge (1700). To remove cover (1730), the operator may simply pull cover (1730) away from cartridge (1700). By way of example only, panels (1732, 1734) may be resiliently biased toward each other such that panels (1732, 1734) are oriented to be non-parallel with each other. Thus, panels (1732, 1734) may be deflected away from each other to reach a parallel state when cover (1730) is engaged with housings (1710, 1718), such that panels (1732, 1734) resiliently bear against housings (1710, 1718) to provide a secure fit through friction. Various other suitable configurations that may be used to form cover (1730), and to secure cover (1730) to housings (1710, 1718), will be apparent to those of ordinary skill in the art in view of the teachings herein. It should also be understood that cover (1730) may be used with any of the buttress applier cartridges described herein, such that cover (1730) is not at all limited to cartridge (1700).

In some versions, cover (1730) comprises a desiccant material that is configured to absorb moisture (e.g., from humidity) and thereby prevent that moisture from reaching buttress assemblies (100, 110). In addition or in the alternative, desiccant material may be incorporated into the material forming platform (1720), the material forming housing (1710), packets or compartments located within a cavity defined by housing (1710, 1718), and/or in various other suitable locations/configurations. By way of example only, silica gel may be included in packets that are located within a cavity defined by housing (1710, 1718). Other suitable desiccant materials that may be incorporated into cartridge (1700) will be apparent to those of ordinary skill in the art in view of the teachings herein. Similarly, various other ways in which one or more desiccant materials may be incorporated into cartridge (1700) will be apparent to those of ordinary skill in the art in view of the teachings herein.

B. Exemplary Lockout for Buttress Applier Cartridge

Figure 70:
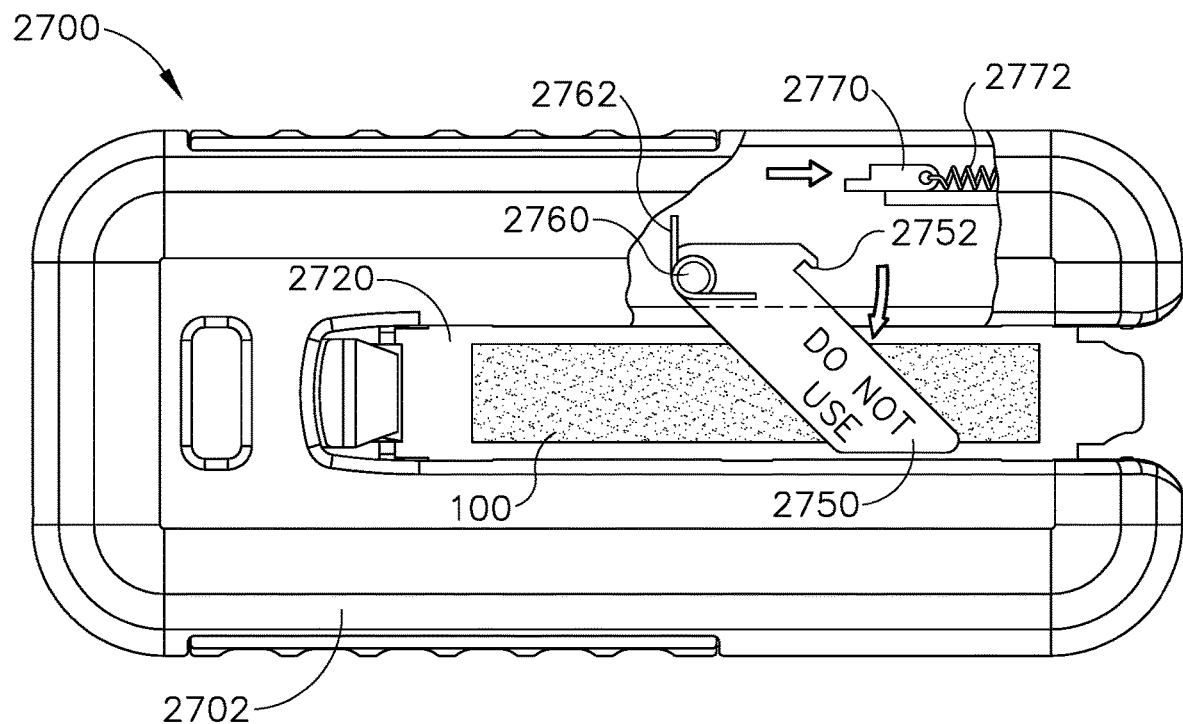
FIG. 70 depicts a top plan view of another exemplary alternative buttress applier cartridge, with a spent cartridge indicator in a deployed position.

In some instances, it may be desirable to physically prevent an operator from loading a buttress assembly (100, 110) onto end effector (40) when that buttress assembly (100, 110) has been exposed to certain environmental conditions that may compromise the effectiveness of buttress assembly (100, 110). For instance, it may be desirable to prevent an operator from loading a buttress assembly (100, 110) onto end effector (40) when that buttress assembly (100, 110) has been exposed to a humidity level above a certain threshold, other exposure to moisture, a temperature above a certain threshold, and/or some other adverse environmental condition(s). To that end, FIG. 70 shows an exemplary alternative buttress applier cartridge (2700) that includes a housing (2702) and a platform (2720) with a buttress assembly (100) disposed on platform (2720). Housing (2702), platform (2720), and buttress assembly (100) may be configured and operable in accordance with any of the various teachings herein. Similarly, buttress assembly (100) may be selectively retained on platform (2720) in accordance with any of the various teachings herein.

Figure 71A:
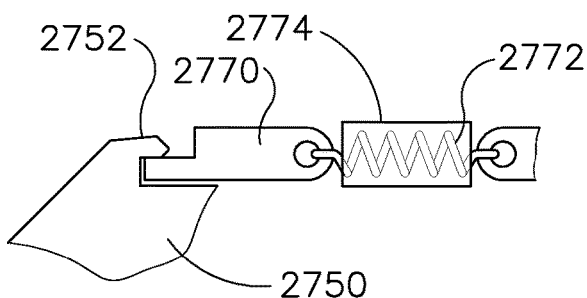
FIG. 71A depicts a partial plan view of the spent cartridge indicator of FIG. 70 in a retracted position and engaged with a retention feature.

Cartridge (2700) of the present example further comprises a lockout panel (2750). Lockout panel (2750) is pivotably coupled with housing (2702) via a pin (2760). A torsion spring (2762) is positioned about pin (2760) and is configured to resiliently bias lockout panel (2750) to the position shown in FIG. 70. In this position, lockout panel (2750) spans the gap defined between the prongs of housing (2702) and thereby covers buttress assembly (100). Lockout panel (2750) thus prevents an end effector (40) from engaging buttress assembly (100) when lockout panel (2750) is in the position shown in FIG. 70. However, lockout panel (2750) may be pivoted away from the position shown in FIG. 70 such that lockout panel (2750) does not cover buttress assembly (100) or otherwise obstruct access to buttress assembly (100) by end effector (40). To selectively hold lockout panel (2750) in a non-blocking position, cartridge (2700) includes a latch (2770). Latch (2770) is coupled with housing (2702) by a coil spring (2772) and is configured to engage a latching feature (2752) of lockout panel (2750) as shown in FIG. 71A. When latch (2770) is engaged with latching feature (2752), latch (2770) is configured to hold lockout panel (2750) in the non-blocking position despite the resilient bias provided by torsion spring (2762).

Figure 71B:
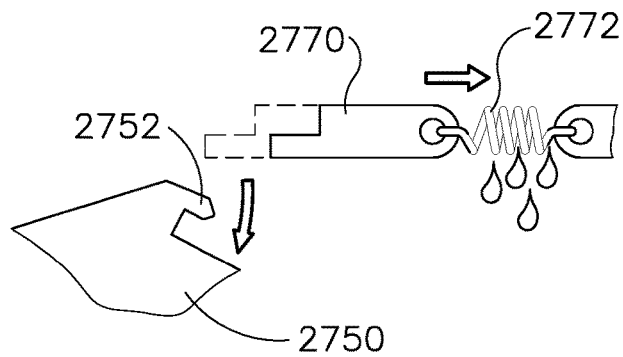
FIG. 71B depicts a partial plan view of the spent cartridge indicator of FIG. 70 in the deployed position and disengaged from the retention feature.

Coil spring (2772) is resiliently biased to assume a compressed configuration. When latch (2770) is engaged with latching feature (2752), coil spring (2772) is in a stretched configuration, such that coil spring (2772) is under stress. To hold coil spring (2772) in the stressed, stretched configuration, a spacing material (2774) is disposed about coil spring. Spacing material (2774) is positioned between coils of coil spring (2772). Under acceptable environmental conditions, spacing material (2774) has sufficient structural integrity to maintain the spacing between the coils of coil spring (2772), thereby maintaining coil spring (2772) in the stressed, stretched configuration, thereby holding lockout panel (2750) in the non-blocking position. However, spacing material (2774) is configured to liquefy and/or otherwise degrade in response to one or more environmental conditions that are adverse to buttress assemblies (100, 110). As shown in FIG. 71B, the liquification or other degradation of spacing material (2774) allows coil spring (2772) to return to a compressed configuration, which will pull latch (2770) out of engagement with latch feature (2752). When latch (2770) is disengaged from latch feature (2752), torsion spring (2762) pivots lockout panel (2750) about pin (2760) to the blocking position as shown in FIG. 70. Thus, cartridge (2700) will prevent the operator from engaging buttress (100) when cartridge (2700) has been exposed to one or more environmental conditions that are adverse to buttress (100). In addition to blocking access to buttress (100), lockout panel (2750) may also include a visual indication (e.g., text reading "do not use," the color red, a stop sign, etc.) to further indicate to the operator that cartridge (2700) has essentially been rendered inoperable.

Those of ordinary skill in the art will recognize that various kinds of materials may be used to form spacing material (2774). By way of example only, spacing material (2774) may comprise wax, PVP (e.g., for humidity sensitivity), PEG (e.g., for temperature sensitivity), and/or any other suitable material(s). It should also be understood that cartridge (2700) may be readily modified to deploy lockout panel (2750) to the blocking position in response to an end effector (40) picking up buttress assembly (100, 110) from platform (2720). Lockout panel (2750) may thus visually indicate to the operator that cartridge (2700) is spent, and may further prevent the operator from clamping end effector on an empty platform (2720). Such functionality may be provided in addition to or in lieu of deployment of lockout panel (2750) in response to adverse environmental conditions.

XX. Exemplary End Effector Alignment Features for Buttress Applier Cartridge

In some instances, it may be desirable to configure buttress assembly (100) such that the lateral width of buttress assembly (100) closely matches the lateral width of underside (65) of anvil (60). Likewise, it may be desirable to configure buttress assembly (110) such that the lateral width of buttress assembly (110) closely matches the lateral width of deck (73) of anvil (70). Matching these widths may present little to no margin of error with respect to alignment of end effector (40) with buttress assemblies (100, 110). It may therefore be desirable to provide features that ensure or otherwise promote proper alignment of end effector (40) with buttress assemblies (100, 110). Such alignment may include proper lateral positioning of end effector along a lateral plane (i.e., a plane that is parallel to the planes defined by buttress assemblies (100, 110)). Such alignment may also include proper "yaw" positioning about an axis that is perpendicular to the same lateral plane (i.e., a plane that is parallel to the planes defined by buttress assemblies (100, 110)). Several examples of features that may be used to ensure or otherwise promote proper alignment of end effector (40) with buttress assemblies (100, 110) are described in greater detail below, while other examples will be apparent to those of ordinary skill in the art in view of the teachings herein.

Figure 72:
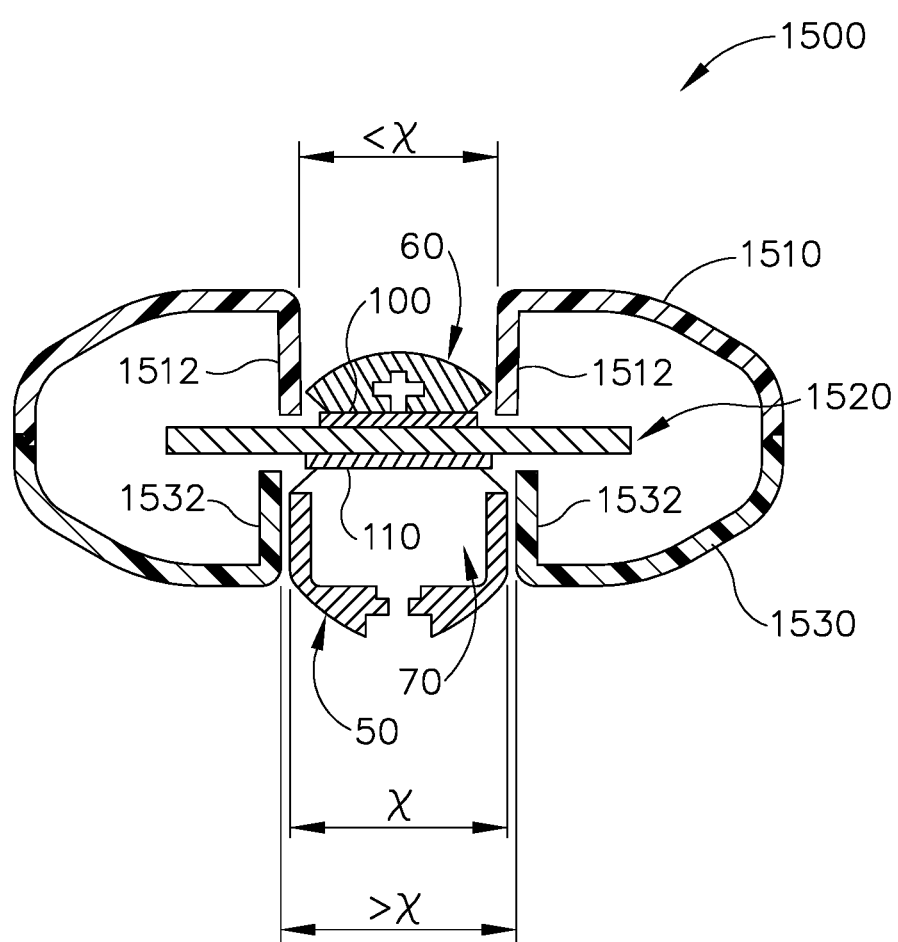
FIG. 72 depicts a cross-sectional end view of another exemplary alternative buttress applier cartridge, with a platform of the buttress applier cartridge positioned in the end effector of FIG. 2.

FIG. 72 shows a buttress applier cartridge (1500) that includes an upper housing (1510) and a lower housing (1530), with a platform (1520) supporting buttress assemblies (100, 110). Platform (1520) is captured between housings (1510, 1530). Buttress assemblies (100, 110) may be removably secured to platform (1520) using any of the various retention structures or techniques described herein. In the present example, buttress assembly (110) has a wider lateral width than buttress assembly (100). This is due to the fact that buttress assembly (110) is configured to be applied to deck (73) of staple cartridge (70), which has a wider lateral width than underside (65) of anvil (60).

Housing (1510) of the present example includes a pair of inner walls (1512) that together define a laterally extending gap. Housing (1532) also includes a pair of walls (1532) that together define a laterally extending gap. These gaps are sized differently in order to accommodate end effector (40) in only one "roll" orientation (i.e., about the longitudinal axis of cartridge (1500), to ensure that an operator will not inadvertently apply buttress assembly (100) to deck (73) and buttress assembly (110) to underside (65). FIG. 72 shows how lower jaw (50) defines a lateral width "x." The gap between inner walls (1512) is smaller than that width "x" while the gap between inner walls (1532) is larger than the width "x." Thus, if an operator positions cartridge (1500) in relation to end effector (40) at a roll orientation that is off by 180 degrees, such that buttress assembly (100) is facing deck (73) and buttress assembly (110) is facing underside (65), the operator will be unable to fully clamp end effector (40) onto buttress assemblies (100, 110) since staple cartridge (70) and lower jaw (50) will not fit in the gap between inner walls (1512).

XXI. Exemplary Features to Control and Indicate Humidity Conditions in Buttress Applier Cartridge Some versions of buttress assemblies (100, 110) may include features that are sensitive to humidity conditions. For instance, the material forming body (102, 112) may be sensitive to humidity conditions in a way such that the effectiveness of body (102, 112) is adversely affected when body (102, 112) is exposed to humidity for a prolonged period. Similarly, the material forming adhesive layer (104, 114) may be sensitive to humidity conditions in a way such that the effectiveness of adhesive layer (104, 114) is adversely affected when adhesive layer (104, 114) is exposed to humidity for a prolonged period. It may therefore be desirable to incorporate one or more features into a buttress applier cartridge that is/are configured to prevent buttress assemblies (100, 110) from being exposed to humidity for prolonged periods. In addition, it may be desirable to incorporate one or more features into a buttress applier cartridge that is/are configured to indicate if buttress assemblies (100, 110) have been exposed to humidity for prolonged periods. If such an indicator shows that buttress assemblies (100, 110) have been exposed to humidity for prolonged periods, the operator may avoid using those particular buttress assemblies (100, 110).

As noted above, FIG. 59 shows an exemplary buttress applier cartridge (1700) that includes housings (1710, 1718), a platform (1720) supporting a buttress assembly (100), and a plurality of retention features (1752). Retention features (1752) are configured to releasably secure buttress assembly (100) to platform (1720); and may be configured like any of the various retention features described herein. Platform (1720) includes a plurality of fins (1722). Fins (1722) are configured and operable just like fins (624) described above, such that fins (1722) may fit within the sidewalls defining channel (62) to ensure that anvil (60) is properly aligned with buttress assembly (100) as anvil (60) is closed down toward buttress assembly (100) and platform (1720). It should also be understood that the underside of platform (1720) (i.e., the side carrying buttress assembly (110), associated with staple cartridge (70)), may also include fins (1722). Fins (1722) on the underside of platform (1720) may be sized and arranged to fit in channel (72) of staple cartridge (70). Moreover, as will be described in greater detail below, fins (1722) on the underside of platform (1720) may be configured to prevent cartridge (1700) from being used with a staple cartridge (70) that has already been fired.

Cartridge (1700) of the present example further includes a plurality of indicator beads (1742) that are viewable through a window (1712) formed in housing (1710). Indicator beads (1742) are formed of a color-changing desiccant material. In particular, beads (1742) are configured to reflect a first color when beads (1742) are in a substantially dry state; and a second color when beads (1742) are in a wet state. Beads (1742) may transition to a wet state in response to exposure to humidity that is above a threshold that is suitable for buttress assemblies (100, 110). In some versions, beads (1742) will maintain the second color even if the humidity level later drops back below the threshold level. Beads (1742) will thus provide visual indication to the user to indicate that buttress assemblies (100, 110) have been subject to an unacceptable level of humidity. Of course, beads (1742) may also transition from the first color to the second color if beads (1742) are otherwise exposed to fluid, such as spilled medical fluids, bodily fluids from a patient, etc. Various materials that may be used to form beads (1742) will be apparent to those of ordinary skill in the art in view of the teachings herein.

Cartridge (1700) of the present example further includes a cover (1730) that may be removably secured to housings (1710, 1718). Cover (1730) includes an upper panel (1732) and a lower panel (1734) that are coupled together to define a "U" shape. Cover (1730) is sized and configured to cover the recesses in which platform (1720) and buttress assemblies (100, 110) are disposed when cover (1730) is secured to housings (1710, 1718). Cover (1730) may thus protect buttress assemblies (100, 110) up until an operator is ready to use cartridge (1700). To remove cover (1730), the operator may simply pull cover (1730) away from cartridge (1700). By way of example only, panels (1732, 1734) may be resiliently biased toward each other such that panels (1732, 1734) are oriented to be non-parallel with each other. Thus, panels (1732, 1734) may be deflected away from each other to reach a parallel state when cover (1730) is engaged with housings (1710, 1718), such that panels (1732, 1734) resiliently bear against housings (1710, 1718) to provide a secure fit through friction. Various other suitable configurations that may be used to form cover (1730), and to secure cover (1730) to housings (1710, 1718), will be apparent to those of ordinary skill in the art in view of the teachings herein. It should also be understood that cover (1730) may be used with any of the buttress applier cartridges described herein, such that cover (1730) is not at all limited to cartridge (1700).

In some versions, cover (1730) comprises a desiccant material that is configured to absorb moisture (e.g., from humidity) and thereby prevent that moisture from reaching buttress assemblies (100, 110). In addition or in the alternative, desiccant material may be incorporated into the material forming platform (1720), the material forming housing (1710), packets or compartments located within a cavity defined by housing (1710, 1718), and/or in various other suitable locations/configurations. By way of example only, silica gel may be included in packets that are located within a cavity defined by housing (1710, 1718). Other suitable desiccant materials that may be incorporated into cartridge (1700) will be apparent to those of ordinary skill in the art in view of the teachings herein. Similarly, various other ways in which one or more desiccant materials may be incorporated into cartridge (1700) will be apparent to those of ordinary skill in the art in view of the teachings herein.

XXII. Exemplary Buttress Applier Cartridge with Data Communication

As noted above, buttress assembly (100) may be applied to the underside (65) of anvil (60), and buttress (110) may be applied to deck (73) of staple cartridge (70), before tissue ($T_1$, $T_2$) is positioned in end effector (40), and before end effector (40) is actuated. Because end effector (40) may be actuated many times during use of instrument (10) in a single surgical procedure, it may be desirable to enable an operator to repeatedly and easily load buttress assemblies (100) on underside (65) of anvil (60) during that single surgical procedure. In other words, because end effector (40) may be actuated many times during use of instrument (10) in a single surgical procedure, it may be insufficient to simply provide anvil (60) pre-loaded with a buttress assembly (100) without facilitating the re-loading of anvil (60) with additional buttress assemblies (100) after end effector (40) has been actuated.

Similarly, those of ordinary skill in the art will recognize that staple cartridge (70) will need to be replaced each time end effector (40) is actuated. When end effector (40) is actuated several times during use of instrument (10) in a single surgical procedure, several staple cartridges (70) may thus be used during that surgical procedure. It may seem that each of these staple cartridges (70) may be provided with buttress assembly (110) pre-loaded on deck (73). However, there are some reasons why it may be undesirable to provide a staple cartridge (70) with buttress assembly (110) pre-loaded on deck (73). In other words, it may be desirable to provide loading of buttress assembly (110) on deck (73) immediately prior to usage of staple cartridge in the surgical procedure, rather than loading buttress assembly (110) on deck (73) a substantial time prior to the surgical procedure. For instance, buttress assembly (110) may not be compatible with the same sterilization techniques as staple cartridge (70), such that it may present processing difficulties to package staple cartridge (70) with buttress assembly (110) pre-loaded on deck (73). In addition, the material forming buttress assembly (110) may have certain environmental sensitivities that staple cartridge (70) does not have, such that it may be beneficial to enable buttress assembly (110) and staple cartridge (70) to be stored separately before use. Moreover, buttress assembly (110) may not be warranted or otherwise desired in some surgical procedures, such that it may be desirable to enable a physician to easily choose whether staple cartridge (70) should be loaded with buttress assembly (110) before that staple cartridge (70) is used in the surgical procedure.

In view of the foregoing, it may be desirable to enable an operator to repeatedly and easily load buttress assemblies (100, 110) on end effector (40) on an ad hoc basis during a given surgical procedure. It may also be desirable to provide a device that provides support and protection to buttress assemblies (100, 110) before buttress assemblies (100, 110) are loaded on end effector (40), in addition to that same device also enabling buttress assemblies (100, 110) to be easily loaded on end effector. The examples described below relate to cartridge assemblies that provide such support, protection, and loading of buttress assemblies (100, 110). It should be understood that the following examples are merely illustrative. Numerous variations will be apparent to those of ordinary skill in the art in view of the teachings herein.

Figure 73:
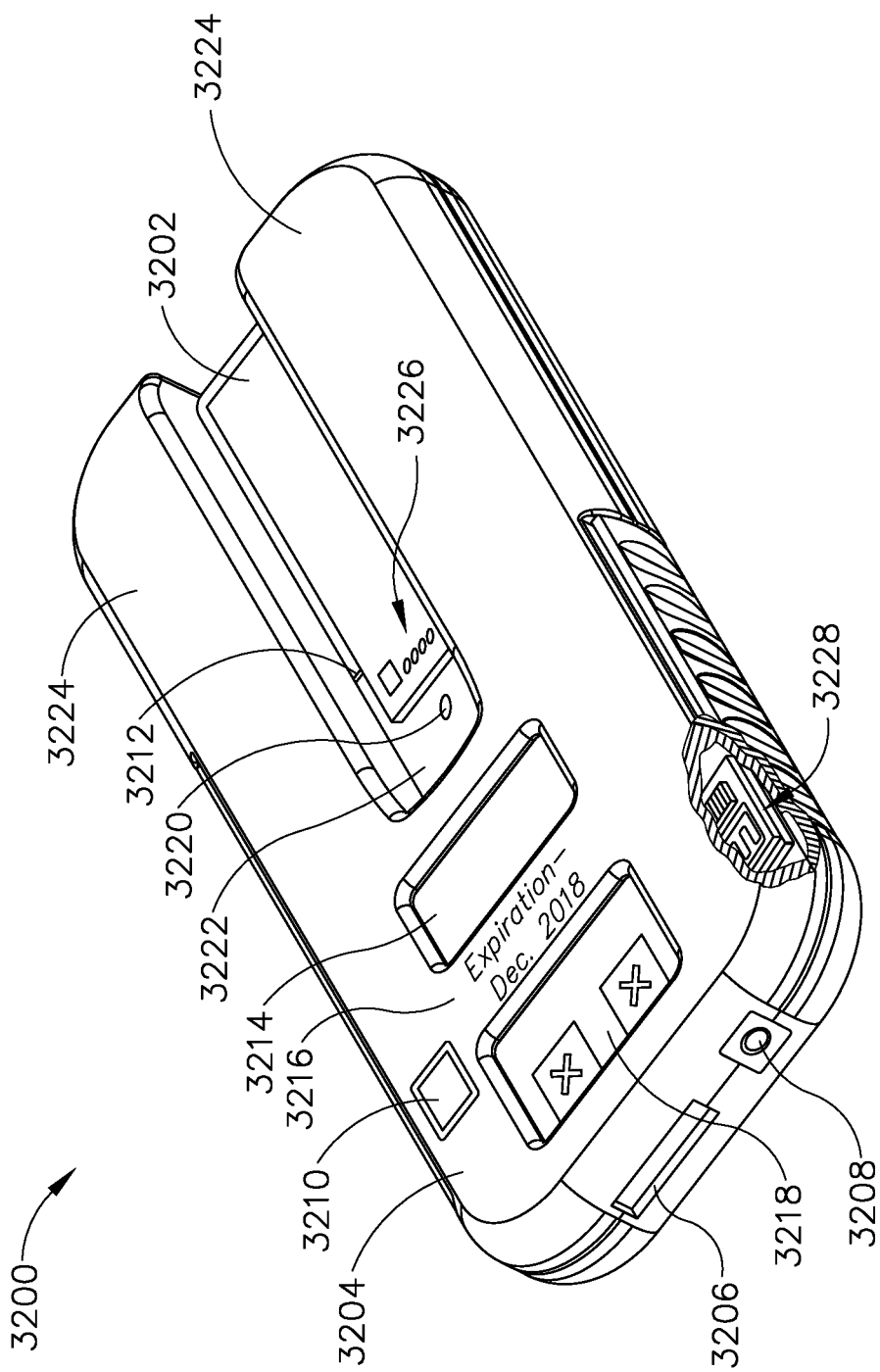
FIG. 73 depicts a perspective view of an exemplary buttress applier cartridge that may be used to carry and apply the buttress assembly of FIG. 5A.
Figure 74:
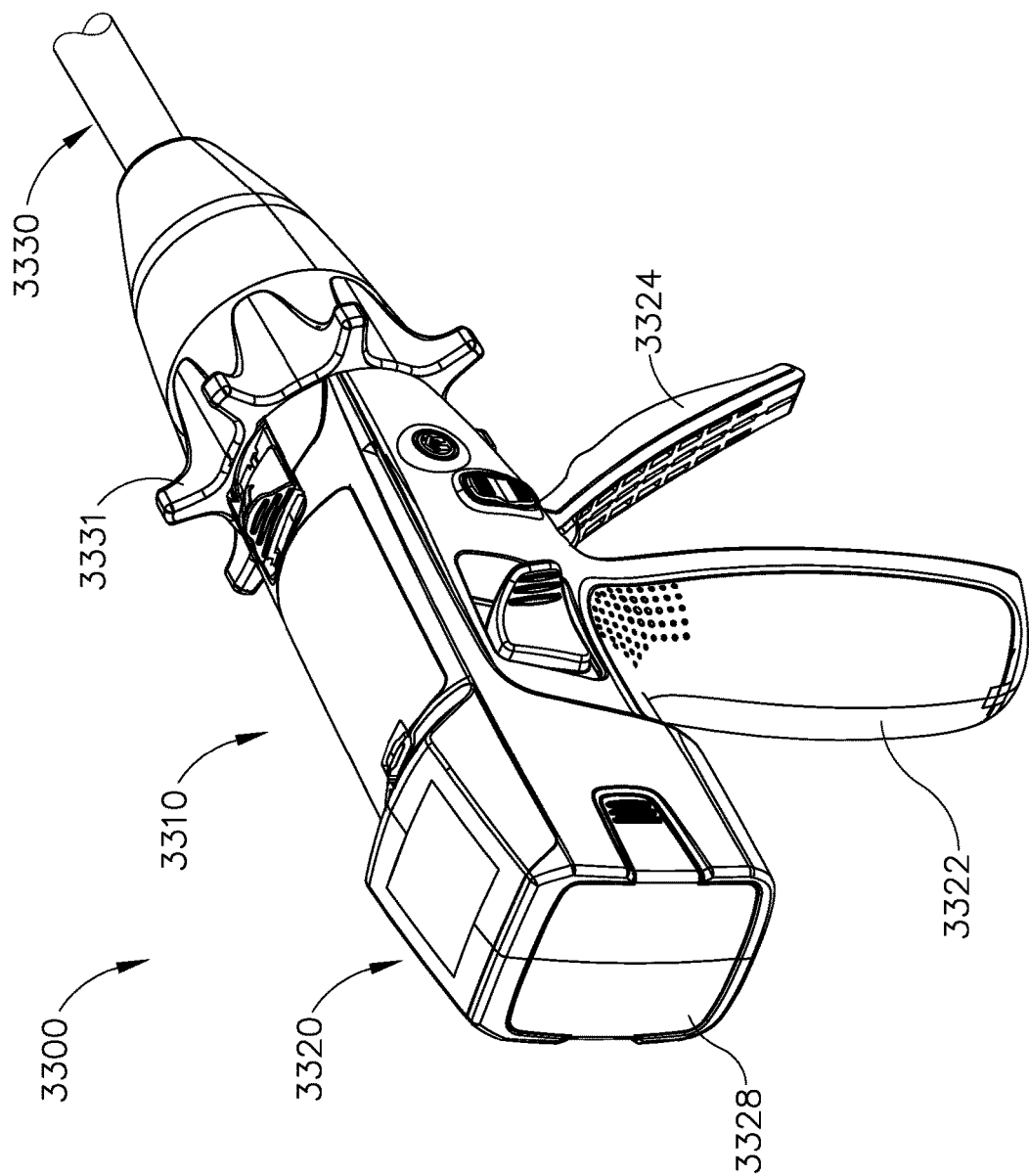
FIG. 74 depicts a perspective view of a handle assembly of an exemplary alternative surgical stapling instrument.

FIG. 73 shows an exemplary buttress applier cartridge (3200) that may be used in conjunction with an exemplary alternative surgical stapling and severing instrument (3300) as shown in FIG. 74. Cartridge (3200) of this example comprises a "U" shaped housing (3204) that defines two prongs (3224) having a space therebetween. As described in greater detail below, this space is sized to accommodate the length and width of an end effector (3340) of instrument (3300). A platform (3222) is located in the space between prongs (3224). A buttress (3202) is supported on platform (3222).

Figure 79A:
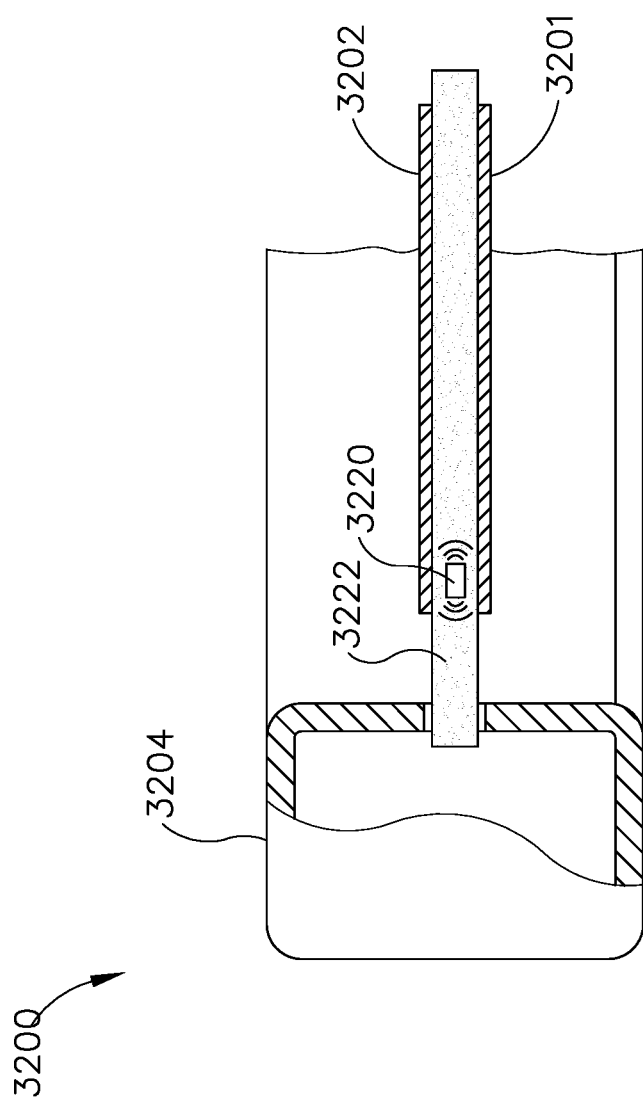
FIG. 79A depicts a cross-sectional side view of the buttress applier cartridge of FIG. 73, loaded with upper and lower buttress assemblies.
Figure 79B:
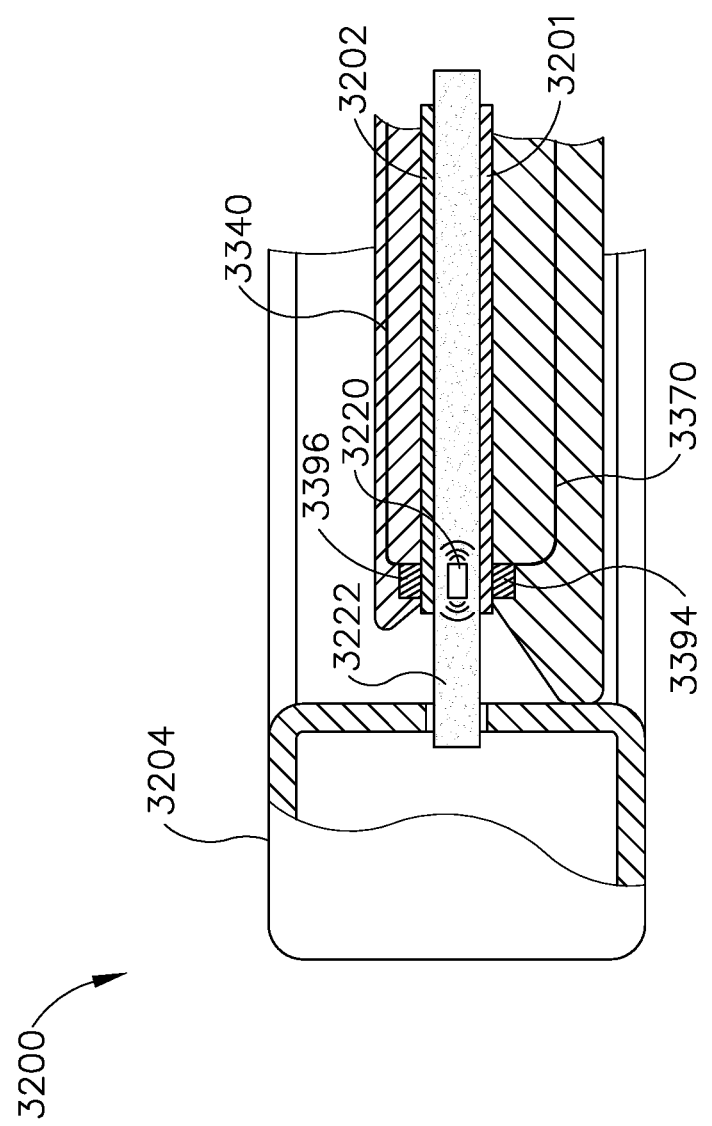
FIG. 79B depicts a cross-sectional side view of the buttress applier cartridge of FIG. 73, with the end effector of FIG. 75 clamped down on the buttress assemblies.

By way of example only, platform (3222) may comprise a sheet of foam material. While only one buttress (3202) is shown on the top side of platform (3222) in FIG. 73, it should be understood that another buttress (3201) may be positioned on the underside of platform (3222), as shown in FIGS. 79A-79B. Buttresses (3201, 3202) may be removably secured to platform (3222) in any suitable fashion, including but not limited to being secured via an adhesive, resiliently biased retainers, etc. As another merely illustrative example, buttresses (3201, 3202) may be removably secured to platform (3222) in accordance with at least some of the teachings of U.S. Patent App. No. 62/209,041, entitled "Method and Apparatus for Applying a Buttress to End Effector of a Surgical Stapler," filed Aug. 24, 2015, the disclosure of which is incorporated by reference herein. Other suitable ways in which buttresses (3201, 3202) may be removably secured to platform (3222) will be apparent to those of ordinary skill in the art in view of the teachings herein.

While cartridge (3200) may be used with instrument (10) described above, cartridge (3200) is particularly configured to be used with instrument (3300). Instrument (3300) of this example is configured and operable just like instrument (10) except for the differences described below. It should also be understood that instrument (3300) may be configured and operable in accordance with at least some of the teachings of U.S. patent application Ser. No. 14/226,142, entitled "Surgical Instrument Comprising a Sensor System," filed Mar. 26, 32014, now U.S. Pat. No. 9,913,642, issued Mar. 13, 2018, the disclosure of which is incorporated by reference herein. As shown in FIG. 74, instrument (3300) of this example comprises a handle assembly (3310) with a display screen (3320), a pistol grip (3322), a pivoting trigger (3324), and a removable battery pack (3328). A shaft assembly (3330) extends distally from handle assembly (3310). A rotary knob (3331) is located at the proximal end of shaft assembly (3330) and is operable to rotate shaft assembly (3330) relative to handle assembly (3310), about the longitudinal axis of shaft assembly (3330). Shaft assembly (3330) of this example is substantially identical to shaft assembly (330) described above, except that shaft assembly (3330) of this example includes one or more wires and/or other features that enable communication of data from end effector (40) to handle assembly (3310). In some versions, shaft assembly (3330) is selectively removable from handle assembly (3310) (e.g., in accordance with the teachings of U.S. patent application Ser. No. 14/226,142 now U.S. Pat. No. 9,913,642, issued Mar. 13, 2018, or in any other suitable fashion).

Figure 75:
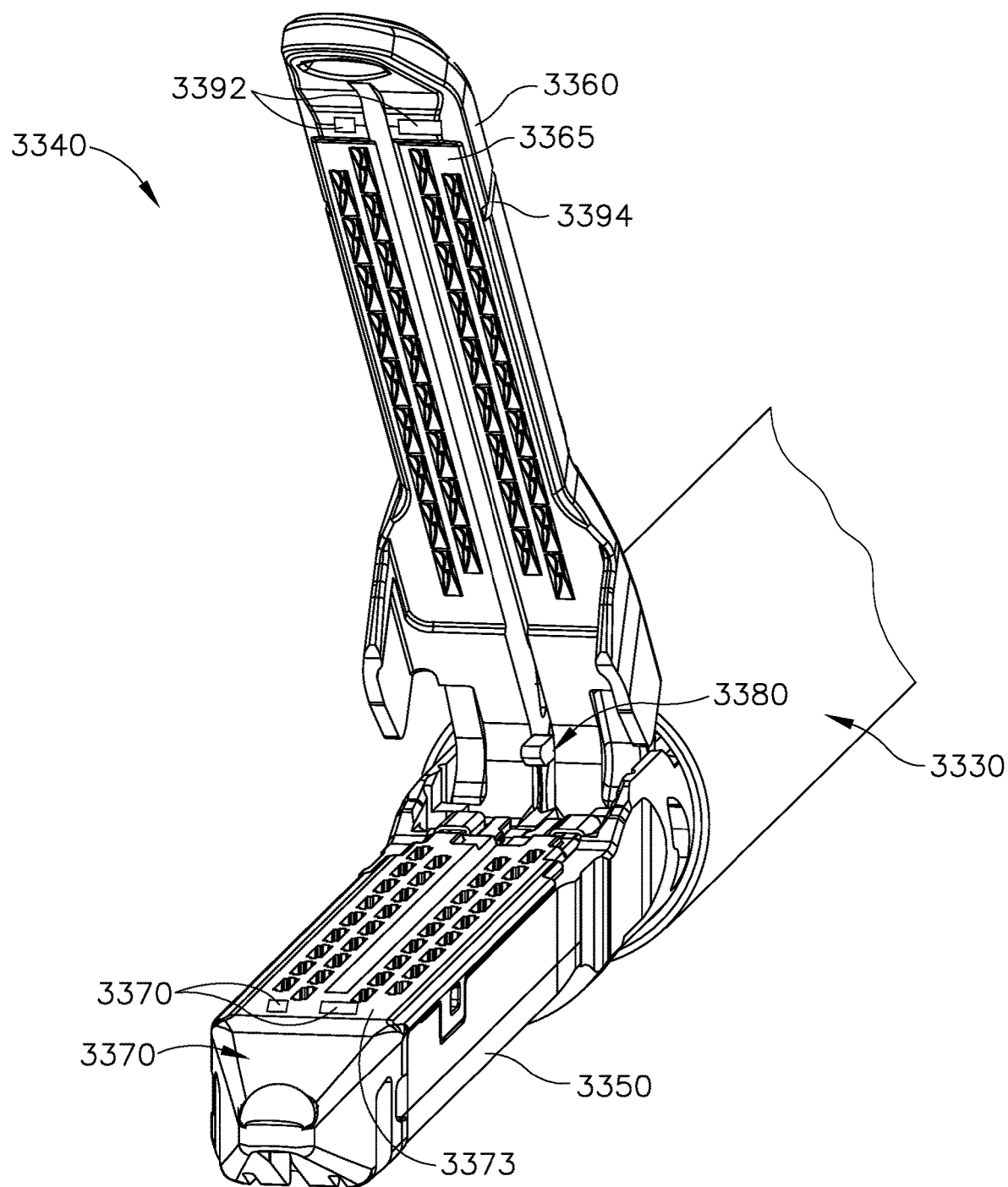
FIG. 75 depicts a perspective view of an end effector of the instrument of FIG. 74, with the end effector in an open configuration.
Figure 76:
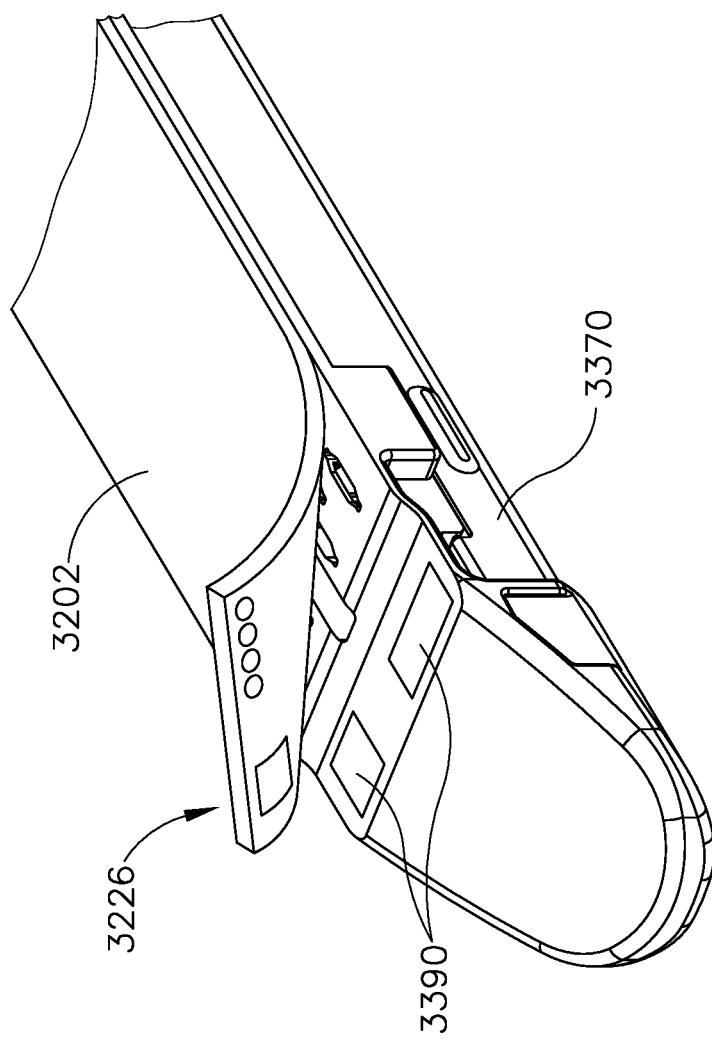
FIG. 76 depicts a partial perspective view of the distal end of a staple cartridge of the end effector of FIG. 75, with a buttress assembly of the buttress applier cartridge of FIG. 73 engaging a deck of the staple cartridge.

As shown in FIG. 75, an end effector (3340) is positioned at the distal end of shaft assembly (3330). End effector (3330) includes a lower jaw (3350), an anvil (3360), and a staple cartridge (3370) that is removably received in lower jaw (3350). A knife member (3380) is configured to translate through end effector (3340) to sever tissue that is captured between underside (3365) of anvil (3360) and deck (3373) of staple cartridge (3370). Knife member (3380) also cooperates with a wedge sled (not shown) in staple cartridge (3370) to drive staples from staple cartridge (3370), through the captured tissue, and into formation against anvil (3360). In the present example, pivotal movement of trigger (3324) toward and away from pistol grip (3322) will pivot anvil (3360) toward and away from staple cartridge (3373). In addition, pivoting of a firing trigger (not shown) on handle assembly (3310) will drive knife member (3380) distally through end effector (3340). It should therefore be understood that end effector (3340) and handle assembly (3310) are configured and operable substantially similar to end effector (40) and handle assembly (320) described above. However, unlike end effector (40), end effector (3340) of this example comprises a set of sensors (3390, 3392, 3394, 3396) and a marking (3394). These features will be described in greater detail below.

While end effector (3340) is described in the present example as being coupled with handle assembly (3310) of FIG. 74, it should be understood that the present teachings may also be readily applied in versions where end effector (3340) is incorporated into a robotic surgical system. For instance, end effector (3340) may be readily incorporated into any of the various robotic surgical systems that are described in the references cited below; and cartridge (3200) may also be readily used in such a combination. Other suitable ways in which end effector (3340) may be incorporated into various kinds of robotic surgical systems, as well as various ways in which cartridge (3200) may be used in such systems, will be apparent to those of ordinary skill in the art in view of the teachings herein.

Referring back to FIG. 73, cartridge (3200) of the present example further includes an internal battery (not shown), a data port (3206), a battery recharge port (3208), a data transmitter (3210), a status indicator window (3214), an expiration date listing (3216), an environmental condition indicator (3218), and an integral circuit board (3228). Circuit board (3228) includes (or is at least in communication with) all of the electronic circuit components that provide the operability described herein. Various suitable components and arrangements that may be incorporated into circuit board (3228) will be apparent to those of ordinary skill in the art in view of the teachings herein. Circuit board (3228) is powered by the internal battery. By way of example only, the internal battery may comprise a button cell battery and/or any other suitable kind of battery. In the present example, the battery is rechargeable, though it should be understood that other versions may include non-rechargeable batteries.

Data port (3206) is configured to enable wired communication between one or more components that are on or otherwise coupled with circuit board (3228) and an external computing device (e.g., desktop computer, laptop computer, tablet computer, smartphone, robotic surgical system, etc.). Data port (3206) may thus be used to communicate data from cartridge (3200) to the external device. For instance, data port (3206) may be used to communicate any of the various kinds of information identified as being communicated below with respect to communication between cartridge (3200) and instrument (3300). In addition or in the alternative, data port (3206) may be used to communicate data from the external device to cartridge (3200). For instance, data port (3206) may be used to provide firmware updates, new information about buttresses (3201, 3202), and/or other information to cartridge (3200).

Battery recharge port (3208) is operable to couple with a wire to provide electrical power that recharges the internal battery in cartridge (3200). In some variations, battery recharge port (3208) comprises an inductive coil that is configured to provide wireless electrical recharging of the internal battery in cartridge (3200). Various suitable ways in which the internal battery in cartridge (3200) may be recharged will be apparent to those of ordinary skill in the art in view of the teachings herein. It should also be understood that some versions may lack recharging capability, such that the internal battery in cartridge (3200) is non-rechargeable. Still other versions of cartridge (3200) may lack an internal battery altogether. For instance, cartridge (3200) may include one or more photovoltaic cells that are configured to provide electrical power. As yet another merely illustrative variation, cartridge (3200) may lack electrically powered components altogether.

Data transmitter (3210) is configured to provide wireless communication between cartridge (3200) and instrument (3300) and/or other external devices (e.g., desktop computer, laptop computer, tablet computer, smartphone, robotic surgical system, etc.). While not shown, it should be understood that instrument (3300) may include a data transmitter that is configured to communicate wirelessly with data transmitter (3210) of cartridge (3200). By way of example only, data transmitter (3210) may be configured to communicate wirelessly using the Bluetooth protocol, the Zigbee protocol, and/or any other suitable wireless communication protocol as will be apparent to those of ordinary skill in the art in view of the teachings herein. In some instances, data transmitter (3210) only transmits data one way, to instrument (3300) and/or other external devices. In some other instances, data transmitter (3210) only receives data one way, from instrument (3300) and/or other external devices. Alternatively, data transmitter (3210) may provide bi-directional communication with instrument (3300) and/or other external devices. Various suitable forms that transmitter (3210) may take will be apparent to those of ordinary skill in the art in view of the teachings herein.

By way of example only, the data communicated by transmitter (3210) may include information relating to the kinds of buttresses (3201, 3202) on platform (3222), information relating to the lot number and/or expiration date associated with buttresses (3201, 3202) on platform, information relating to environmental conditions (e.g., temperature, humidity, etc.) that have been encountered by cartridge (3200), and/or any other suitable kind of information as will be apparent to those of ordinary skill in the art in view of the teachings herein. In some versions, cartridge (3200) is continuously powered by its internal battery and continuously tracks data associated with environmental conditions (e.g., temperature, humidity, etc.) that have been encountered by cartridge (3200), then automatically transmits the information to instrument (3300) via transmitter (3210) in response to end effector (3340) coming into sufficient proximity to cartridge (3200). It should therefore be understood that cartridge (3200) and end effector (3340) may include complementary features that enable cartridge (3200) to determine when end effector (3340) has come within sufficient proximity to cartridge (3200). Various suitable forms that such features may take will be apparent to those of ordinary skill in the art in view of the teachings herein. In some versions, transmitter (3210) sends the information to instrument (3300) In response to end effector (3340) being clamped on buttresses (3201, 3202) and platform (3222); and/or when end effector (3340) pulls buttresses (3201, 3202) away from platform (3222).

Status indicator window (3214) of the present example is configured to indicate status information relating to cartridge (3200) and/or buttresses (3201, 3202). In some versions, status indicator window (3214) provides a fixed display, such as information printed on a sticker or card, etc. In some other versions, status indicator window (3214) provides a dynamic display, such as information rendered through an LCD screen, LED screen, and/or other form of display. By way of example only, status indicator window (3214) may indicate the kind of buttresses (3201, 3202) that are positioned on platform (3222), such as by reference to a type number or some other representation. The operator may view this type number and thereby understand what kind of buttresses (3201, 3202) are positioned on platform (3222) (e.g., whether they have a certain kind of medicament, what material(s) they are formed of, what kinds of surgical procedures they are intended for, etc.). While similar information may be rendered through display screen (3320) based on a reading of indicia (3226) by sensors (3390, 3392), having such information through status indicator window (3214) may enable the operator to select an appropriate cartridge (3200) when presented with various cartridges (3200) to choose from. Moreover, the operator may confirm that the information presented through display screen (3320) is consistent with the information presented through status indicator window (3214). Other suitable information about buttresses (3201, 3202) that may be presented through status indicator window (3214) will be apparent to those of ordinary skill in the art in view of the teachings herein.

In addition to or as an alternative to presenting information about buttresses (3201, 3202), status indicator window (3214) may present information about the state of cartridge (3200). For instance, status indicator window (3214) may indicate whether cartridge (3200) is ready for use. It should also be understood that environmental condition indicator (3218) may be readily integrated into status indicator window (3214). Environmental condition indicator (3218) will be described in greater detail below. Other suitable kinds of information that may be provided through status indicator window (3214) will be apparent to those of ordinary skill in the art in view of the teachings herein.

It should be understood that some versions of buttresses (3201, 3202) may include one or more materials whose effectiveness, integrity, and/or other characteristics may degrade over a period of time. It may therefore be desirable to indicate to the operator when that time has been reached (or when a time has been reached that is some predetermined duration before the degradation of buttress (3201, 3202) would be expected). To that end, expiration date listing (3216) simply lists an expiration date for buttresses (3201, 3202), directly on housing (3204) of cartridge (3200) to enable ready visibility. It should be understood that the operator may alternatively be informed of an expiration date in any other suitable fashion, such that cartridge (3200) may lack expiration date listing (3216) in some versions.

Some versions of buttresses (3201, 3202) may include materials that are sensitive to environmental conditions, including but not limited to temperature and/or humidity. For instance, buttresses (3201, 3202) may transition to an undesirable state if buttresses (3201, 3202) encounter a temperature that is either above or below thresholds that provide upper and lower bounds, respectively, of a predetermined range. Likewise, buttresses (3201, 3202) may transition to an undesirable state if buttresses (3201, 3202) encounter a humidity level that is either above or below thresholds that provide upper and lower bounds, respectively, of a predetermined range. To that end, environmental condition indicator (3218) is configured to indicate environmental conditions encountered by cartridge (3200). In some versions, environmental condition indicator (3218) is printed with environmentally sensitive ink whose properties change in response to environmental conditions. For instance, environmental condition indicator (3218) may be configured to present a checkmark when the humidity level is within an appropriate range; and present an "X" when the humidity level is outside the appropriate range. Similarly, environmental condition indicator (3218) may be configured to present a checkmark when the temperature level is within an appropriate range; and present an "X" when the temperature level is outside the appropriate range. It should also be understood that environmental condition indicator (3218) may include two or more regions. For instance, environmental condition indicator (3218) may have one region that is responsive to humidity, one region that is responsive to temperature, etc. Other suitable conditions that environmental condition indicator (3218) may respond to will be apparent to those of ordinary skill in the art in view of the teachings herein.

Moreover, various suitable inks, features, and/or other components that may be used to form environmental condition indicator (3218) will be apparent to those of ordinary skill in the art in view of the teachings herein. While environmental condition indicator (3218) of the above-described example is passive, some versions of environmental condition indicator (3218) may be active (i.e., electrically powered). It should also be understood that environmental condition indicator (3218) may simply indicate present environmental conditions in real time. In some versions, however, environmental condition indicator (3218) is configured to maintain an indication that one or more environmental conditions has fallen outside of an acceptable range, even if such environmental conditions return to the acceptable range. For instance, if cartridge (3200) is exposed to an unacceptably high temperature or humidity level, the state of environmental condition indicator (3218) may change to indicate that such level has exceeded an appropriate threshold; and environmental condition indicator (3218) may maintain that changed state even after the temperature or humidity level falls back below the threshold. Various suitable ways in which environmental condition indicator (3218) may maintain a changed state despite a return in environmental conditions will be apparent to those of ordinary skill in the art in view of the teachings herein.

Buttresses (3201, 3202) of the present example are substantially identical to buttress assemblies (100, 110) described above, except that buttresses (3201, 3202) of the present example comprises indicia (3226) that are configured to be read by sensors (3390, 3392) (FIG. 75) on end effector (3360). In the present example, indicia (3226) are printed on buttresses (3201, 3202), though it should be understood that indicia (3226) may alternatively be otherwise applied to or otherwise integrated into buttresses (3201, 3202). Indicia (3226) are configured to indicate the type of buttresses (3201, 3202), such as whether buttresses (3201, 3202) carry certain kinds of medicaments, such as whether buttresses (3201, 3202) have certain structural properties, the length of buttresses (3201, 3202), etc. Indicia (3226) may also convey information such as the lot number, expiration date, and/or other data associated with buttresses (3201, 3202). Other suitable ways in which buttresses (3201, 3202) may vary, and how such variations may be conveyed through indicia (3226), will be apparent to those of ordinary skill in the art in view of the teachings herein.

In the present example, sensors (3390, 3392) comprise optical sensors and indicia (3226) comprise QR codes or some other form of optical coding, such that sensors (3390, 3392) are operable to read indicia (3226) by viewing indicia (3226). In some other versions, sensors (3390, 3392) comprise RFID readers and indicia (3226) comprise RFID chips, such that sensors (3390, 3392) read indicia (3226) through RFID sensing. Other suitable forms that sensors (3390, 3392) and indicia (3226) can take will be apparent to those of ordinary skill in the art in view of the teachings herein. Regardless of the form of indicia (3226) and sensors (3390, 3392), instrument (3300) may process the data from indicia (3226) in various ways. For instance, if instrument (3300) determines that the operator is attempting to load end effector (3340) with buttresses (3201, 3202) that are not configured for use with that particular end effector (3340), a control logic in instrument (3300) may notify the operator (e.g., via display screen (3320)) and, in some versions, prevent usage of instrument (3300). In addition or in the alternative, instrument (3300) may vary the force and/or speed with which knife member (3380) is driven based on the detected kind of buttresses (3201, 3202) loaded on end effector (3340). In addition or in the alternative, instrument (3300) may vary the closure force or closure gap provided through end effector (3340) based on the detected kind of buttresses (3201, 3202) loaded on end effector (3340). Other various ways in which instrument (3300) may respond based on the detected kind of buttresses (3201, 3202) loaded on end effector (3340) will be apparent to those of ordinary skill in the art in view of the teachings herein.

Figure 77:
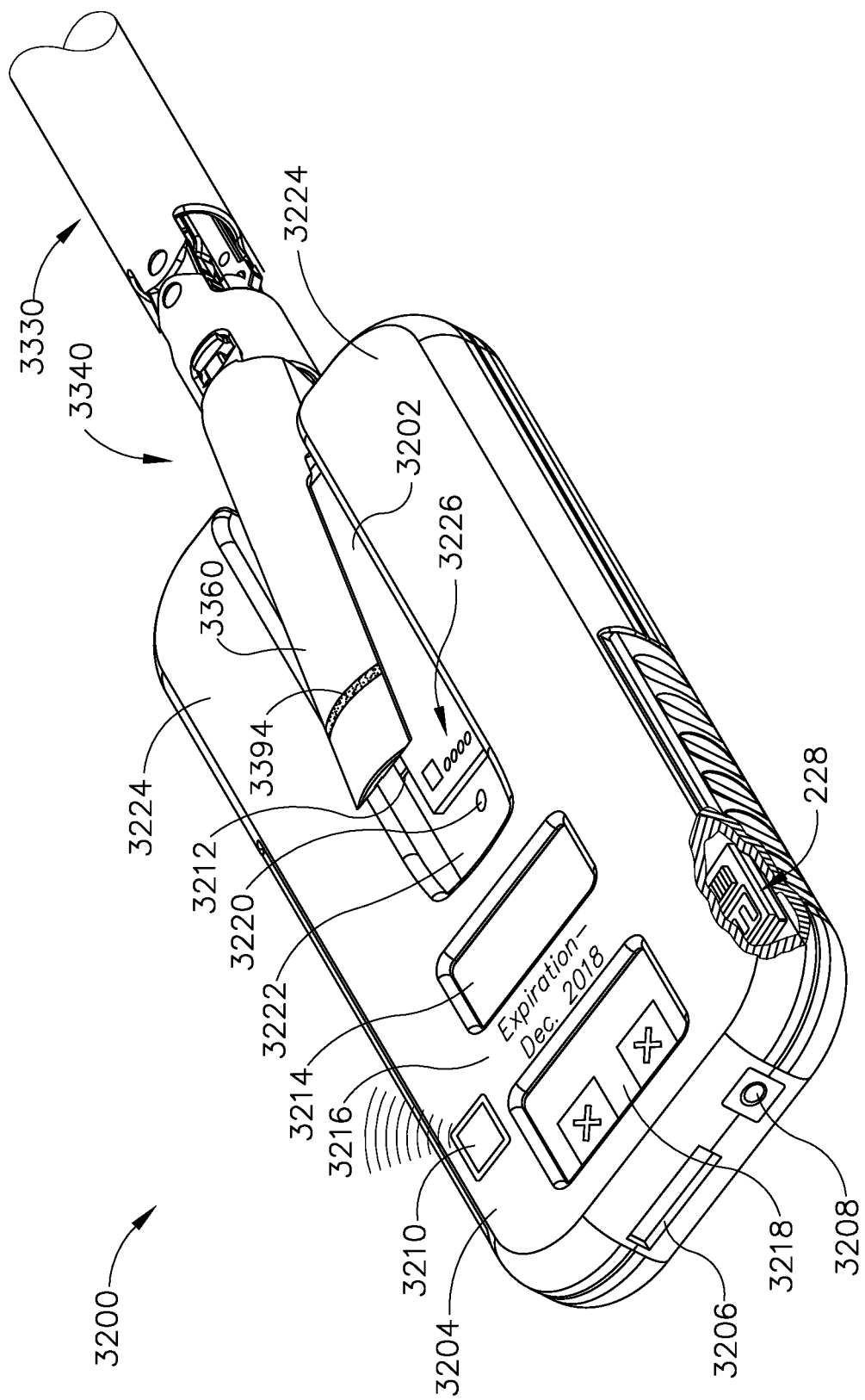
FIG. 77 depicts a perspective view of the end effector of FIG. 75 positioned to engage buttress assemblies of the buttress applier cartridge of FIG. 73.

In the present example, buttress (3202) has a length that corresponds to the length of underside (3365) of anvil (3360); and buttress (3201) has a length that corresponds to the length of deck (3373) of staple cartridge (3370). It may therefore be desirable to ensure that the operator has located end effector (3340) at the appropriate longitudinal position in relation to platform (3222) when end effector (3340) is closed upon buttresses (3201, 3202), to thereby ensure that buttresses (3201, 3202) appropriately span the full lengths of deck (3373) and underside (3365). To that end, platform (3222) of the present example further comprises an alignment marking (3212). Marking (3212) extends perpendicularly relative to the longitudinal axis of platform (3222). Marking (3212) is configured to correspond with marking (3294) of anvil (3360), as shown in FIG. 77. Marking (3294) of anvil (3360) extends perpendicularly relative to the longitudinal axis of anvil (3360). Markings (3212, 3294) are positioned such that markings (3212, 3294) will align with each other when the operator has located end effector (3340) at the appropriate longitudinal position in relation to platform (3222). In the event that markings (3212, 3294) are initially mis-aligned, the operator may simply move end effector (3340) and/or cartridge (3200) until markings (3212, 3294) are aligned. The operator may then fully close end effector (3340) to pick up buttresses (3201, 3202) from platform (3222).

As best seen in FIGS. 79A-79C, platform (3222) of the present example also includes an internal magnet (3220). While magnet (3220) is in platform (3222) in the present example, it should be understood that magnet (3220) may alternatively be located in other locations (e.g., in one or both of prongs (3224)). Magnet (3220) is configured to interact with hall effect sensors (3394, 3396), which are integrated into staple cartridge (3370) and anvil (3340). In particular, as shown in FIG. 79B, hall effect sensors (3394, 3396) sense the magnetic field of magnet (3220) when end effector (3340) is closed upon buttresses (3201, 3202) and platform (3222). A control circuit that is in communication with sensors (3394, 3396) may be tuned to determine when the signal from sensors (3394, 3396) indicates that end effector (3340) has closed upon buttresses (3201, 3202) and platform (3222) with a sufficient force. Of course, there are other ways in which such a determination may be made. For instance, a position sensor in end effector (3340) may sense the closure angle of anvil (3360) relative to staple cartridge (3370) and/or a force sensor in end effector (3340) may sense the closure pressure being applied by anvil (3360) and/or cartridge (3370). As another merely illustrative example, platform (3222) may include a strain gauge or force sensor, etc. Other suitable components and techniques that may be used to sense whether end effector (3340) has closed upon buttresses (3201, 3202) and platform (3222) with a sufficient force will be apparent to those of ordinary skill in the art in view of the teachings herein.

Regardless of the features that are used to determine whether end effector (3340) has closed upon buttresses (3201, 3202) and platform (3222) with a sufficient force, the associated data may be used in numerous ways. For instance, in versions where status indicator window (3214) is dynamic, status indicator window (3214) may be used to provide a visual indication to the operator to indicate that end effector (3340) has closed upon buttresses (3201, 3202) and platform (3222) with a sufficient force. As another merely illustrative example, cartridge (3200) may include a feature that is operable to emit an audible tone to indicate to the operator to indicate that end effector (3340) has closed upon buttresses (3201, 3202) and platform (3222) with a sufficient force. Similar audio and/or visual feedback may be provided through handle assembly (3310), in addition to or in lieu of being provided through cartridge (3200). For instance, display screen (3320) may be used to provide a visual indication to the operator to indicate that end effector (3340) has closed upon buttresses (3201, 3202) and platform (3222) with a sufficient force.

Figure 78:
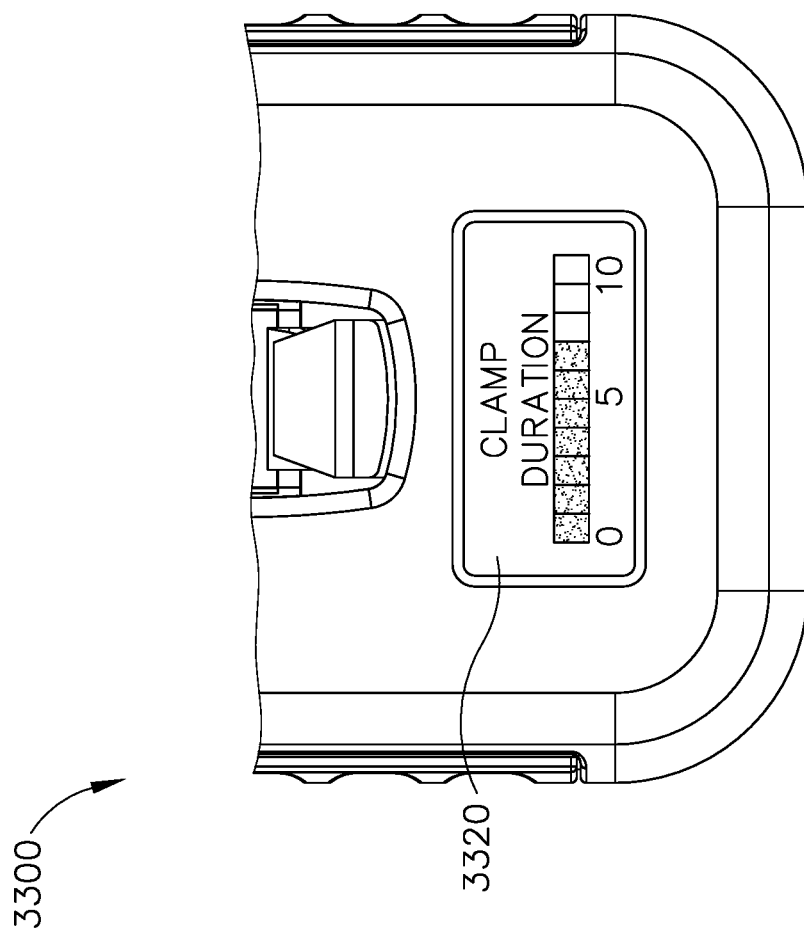
FIG. 78 depicts a top plan view of a display of the handle assembly of FIG. 74.

In some versions, it may be desirable to provide clamping of end effector (3340) on buttresses (3201, 3202) for at least a certain duration in order to ensure proper adhesion of buttresses (3201, 3202) to end effector (3340). To that end, once one or more features detect that end effector (3340) has closed upon buttresses (3201, 3202) and platform (3222) with a sufficient force, a control logic may begin a timer to clock the duration of that force. The control logic may then trigger an audible feedback feature and/or visual feedback feature once the sufficient force has been applied for the predetermined duration. In some such versions, a visual feedback feature may provide the operator with a real time count-up or count-down, enabling the operator to view how much more time the operator will need to hold end effector (3340) in a closed state. FIG. 78 shows one merely illustrative example of how this may be done through display screen (3320). In this example, the control logic begins illuminating discrete visual elements in a linear array when the sufficient force is detected; and further illuminates the visual elements in a progression along the array during the span of the predetermined duration. When all of the visual elements in the array are illuminated, this provides visual feedback to the operator indicating that the predetermined duration has passed. The operator may then open end effector (3340) and pull end effector (3340) away from cartridge (3200). Again, the full illumination of the last visual element in the array may also be accompanied by an audible tone and/or some other form of feedback. Other suitable ways in which an operator may receive feedback indicating whether end effector (3340) has sufficiently clamped on buttresses (3201, 3202) will be apparent to those of ordinary skill in the art in view of the teachings herein.

It should also be understood that different kinds of buttresses (3201, 3202) may warrant different closure forces from end effector (3340) and/or different closure durations in order to be adequately secured to end effector (3340). In such instances, a control logic (e.g., in handle assembly (3310)) may determine which closure force and/or duration to sense based on the kind of buttress (3201, 3202) identified by sensors (3390, 3392) from indicia (3226).

Display screen (3320) may provide various kinds of information in addition to or in lieu of the information noted above. For instance, display screen (3320) may indicate whether buttresses (3201, 3202) are properly aligned in relation to end effector (3340), the initiation of a start-up routine in handle assembly (3310), the identity/type of buttresses (3201, 3202), the kind(s) of medical procedure that the particular buttresses (3201, 3202) are best suited for, the successful loading of buttresses (3201, 3202) on end effector (3340), warnings and precautions associated with the particular kind of buttresses (3201, 3202), the thickness of buttresses (3201, 3202), the thickness of tissue captured between anvil (3360) and staple cartridge (3370), the presence/type of medicament on buttresses (3201, 3202), the compression time required for buttresses (3201, 3202) to be properly adhered to end effector (3340), and/or the duration for which the operator may expect buttresses (3201, 3202) to remain properly adhered to end effector (3340). Other kinds of information that may be indicated through display screen (3320) will be apparent to those of ordinary skill in the art in view of the teachings herein. It also should be understood that such information may come from various sources, including but not limited to cartridge (3200) (e.g., as communicated via transmitter (3210)) buttress (3201, 3202) (e.g., via indicia (3226) and sensors (3390, 3392)); anvil (3360); and/or cartridge (3370). Other suitable sources of information that may be indicated through display screen (3320) will be apparent to those of ordinary skill in the art in view of the teachings herein.

In an exemplary use, the operator views indicator window (3214), expiration date listing (3216), and environmental condition indicator (3218) to confirm that cartridge (3200) is appropriate for the present surgical procedure and is ready for use. The operator then positions end effector positions end effector (3340) between prongs (3224) of housing (3204) as shown in FIG. 77. The operator then closes end effector (3340) on buttresses (3201, 3202) and platform (3222) as shown in FIG. 79B. This causes sensors (3390, 3392) to read indicia (3226), resulting in visual feedback through display screen (3320) indicating information associated with buttresses (3201, 3202) as noted above. As the operator clamps down on buttresses (3201, 3202) and platform (3222) with end effector (3340), hall effect sensors (3394, 3396) sense the magnetic field of magnet (3220) in platform (3222). This results in signals that drive visual feedback through display screen (3320) as shown in FIG. 78. Once the operator confirms that end effector (3340) has been clamped with sufficient force for a sufficient duration, the operator opens end effector (3340). Buttresses (3201, 3202) will be adhered to underside (3365) of anvil (3360) and deck (3373) of cartridge (3370) via adhesive layers of buttresses (3201, 3202), such that the opened end effector (3340) will remove buttresses (3201, 3202) from platform (3222) as shown in FIG. 79C. The operator may then use end effector (3340) on tissue in accordance with the teachings above in relation to FIGS. 5A-6. Other suitable ways in which cartridge (3200) and instrument (3300) may be used will be apparent to those of ordinary skill in the art in view of the teachings herein.

XXIII. Exemplary Protection and Containment Features for Flowable Adhesive

In some instances, it may be desirable to use an adhesive layer (104, 114) that comprises a flowable adhesive material (e.g., an adhesive gel, etc.). Such a flowable adhesive material may comprises PVP blends, ploxymer blends, PCL/PGA blends, and/or various other kinds of materials. By way of example only, providing a flowable adhesive layer (104, 114) may further promote adhesion of buttress assemblies (100, 110) due to the adhesive material flowing into staple forming pockets (64) and/or other nooks and crannies in end effector (440). However, providing flowability in adhesive layers (104, 114) may also present difficulties with respect to containing adhesive layers (104, 114) on buttress bodies (102, 112), as the flowable adhesive layers (104, 114) may have a tendency to migrate off of buttress bodies (102, 112). This may be particularly so when the flowable adhesive layers (104, 114) are exposed to a temperature that exceeds the melting temperature of the flowable adhesive layers (104, 114). It may therefore be desirable to provide a feature that contains a flowable adhesive layer (104, 114) in place on a buttress body (102, 112), up until the point of a procedure where the operator wishes to secure buttress assemblies (100, 110) to end effector (440).

Several merely illustrative examples of features that may be used to contain a flowable adhesive layer (104, 114) in place on a buttress body (102, 112) will be described in greater detail below. Those of ordinary skill in the art will recognize that a feature that contains a flowable adhesive layer (104, 114) in place on a buttress body (102, 112) may also provide protection to adhesive layer (104, 114), such as protection against moisture, debris, etc. It should therefore be understood that the features described below may be used to protect adhesive layer (104, 114) against moisture, debris, etc. Thus, while the following examples are provided in the context of an adhesive layer (104, 114) that is flowable, the features described below may also be used in the context of an adhesive layer that is non-flowable. It should also be understood that the features described below may be used to contain and/or protect substances other than adhesive layers (104, 114), including but not limited to medicaments, in addition to or in lieu of containing and/or protecting adhesive layers (104, 114).

While the following examples are provided in the context of adhesive materials that are flowable, it should be understood that this does not necessarily mean that the adhesive materials would necessarily be flowable under all conditions or even at room temperature. For instance, some adhesive materials may have a melting point that is just slightly higher than room temperature; but that is still low enough to be exceeded during many standard product shipping conditions. Thus, the adhesive containment features described below may prevent the adhesive material from migrating along the underlying buttress body (102, 112) when the melting temperature is exceeded (e.g., during shipment); yet the adhesive material may be re-solidified by the time the adhesive containment feature is removed to reveal the adhesive material.

Figure 80:
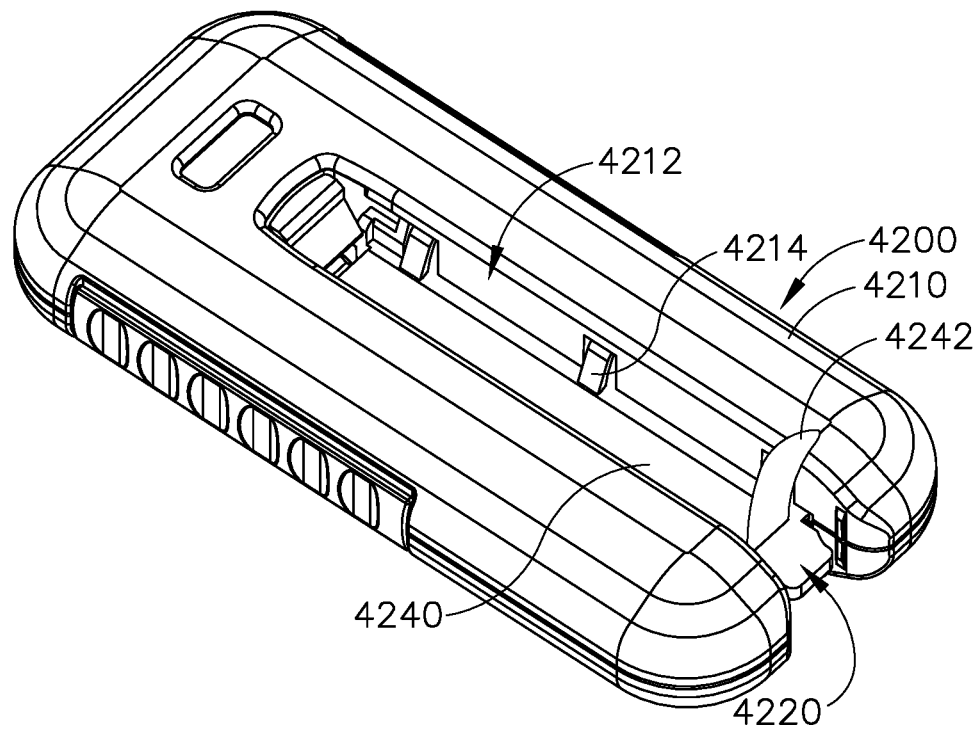
FIG. 80 depicts a perspective view of an exemplary buttress assembly applier cartridge.
Figure 81:
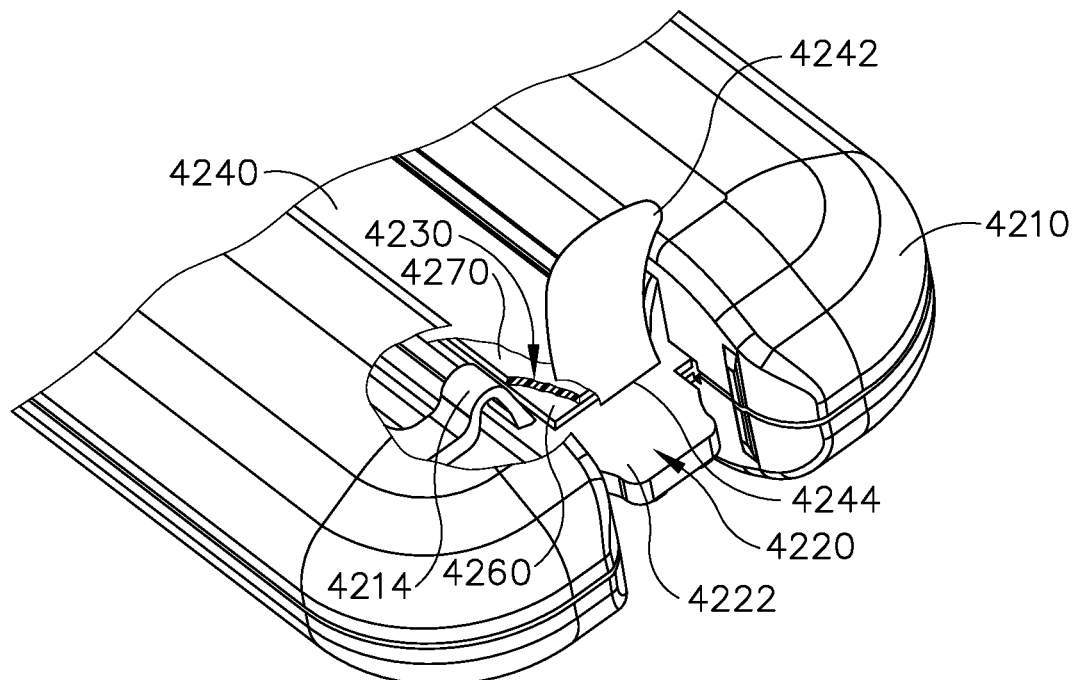
FIG. 81 depicts a partial perspective view of the cartridge of FIG. 80, with portions of the cartridge and buttress assembly cut away to reveal internal components.

A. Exemplary Buttress Assembly Loading Cartridge with Adhesive Containment Sheet FIGS. 80-81 show an exemplary cartridge (4200) that may be used to load a pair of buttress assemblies (4230) on an end effector (440). Cartridge (4200) of this example comprises a housing (4210) that defines a "U" shape including a central recess (4212). Central recess (4212) has a length and width that are sized to accommodate an anvil (60) and a lower jaw (50) loaded with a staple cartridge (70). A platform (4220) is positioned within recess (4212) and supports buttress assembly (4230). In the present example, only one buttress assembly (4230) is shown on an upper surface (4222) of platform (4220). However, it should be understood that another identical buttress assembly (4230) may be positioned on the lower surface of platform (4220) in a similar fashion. A set of resilient retainers (4214) assist in removably securing buttress assembly (4230) to platform (4220) in this example. By way of example only, retainers (4214) and/or other aspects of cartridge (4200) may be constructed and operable in accordance with at least some of the teachings of U.S. Provisional Patent App. No. 62/209,041, entitled "Method and Apparatus for Applying a Buttress to End Effector of a Surgical Stapler," filed Aug. 24, 42015, the disclosure of which is incorporated by reference herein. Alternatively, retainers (4214) may be omitted.

Figure 82:
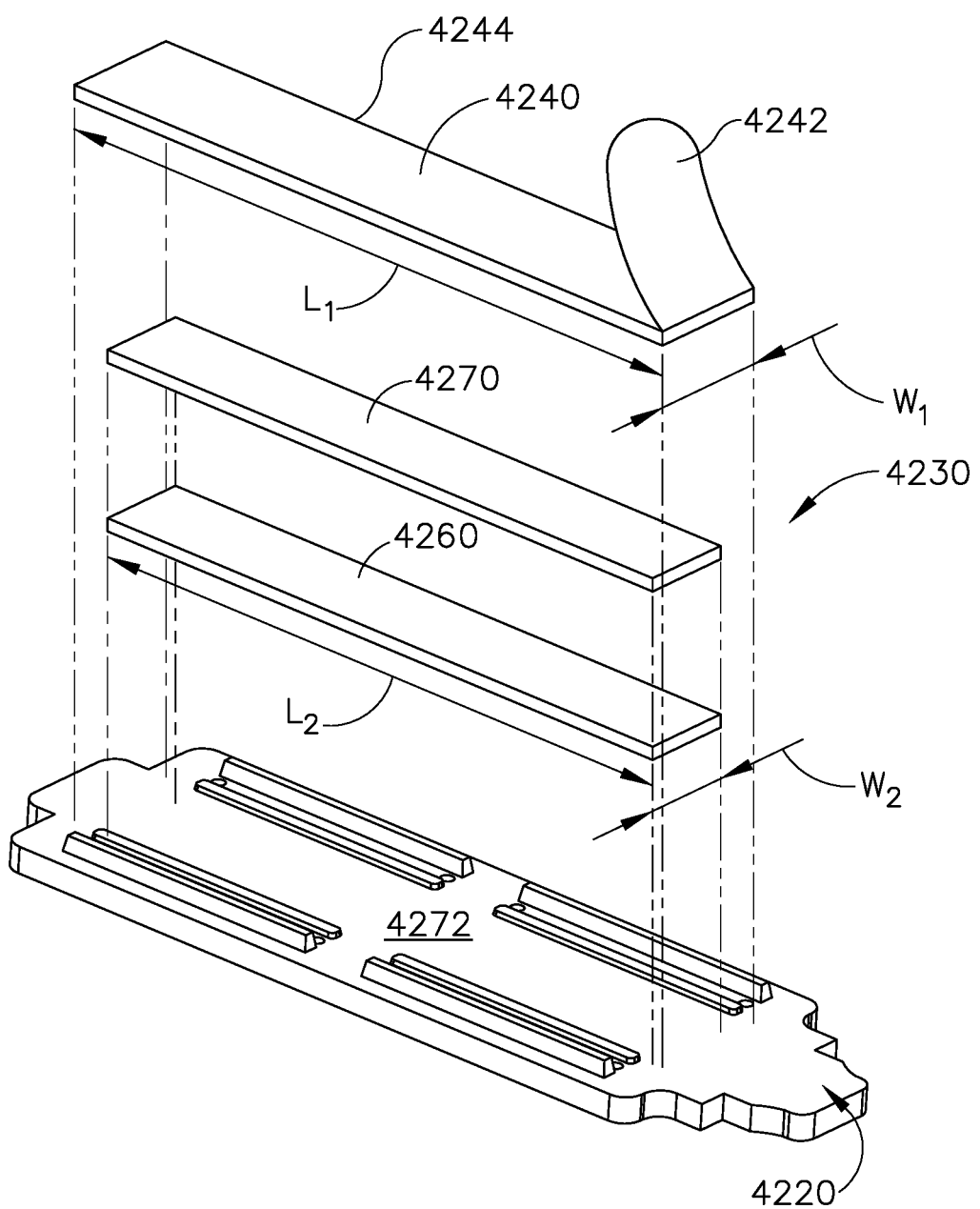
FIG. 82 depicts an exploded perspective view of the buttress assembly and associated mounting portions of the cartridge of FIG. 80.

As best seen in FIGS. 81-82, an adhesive containment sheet (4240) is laid over a buttress assembly (4230), which comprises buttress body (4260) and an adhesive layer (4270). Adhesive containment sheet (4240) may comprise a thin film, foil, or other construction formed of any suitable material or combination of materials as will be apparent to those of ordinary skill in the art in view of the teachings herein. Adhesive containment sheet (4240) is configured such that the material forming adhesive layer (4270) will not pass through containment sheet (4240) or adhere to containment sheet (4240). Various suitable materials that may be used to form containment sheet (4240) will be apparent to those of ordinary skill in the art in view of the teachings herein.

Buttress body (4260) may be constructed and operable just like buttress body (102, 112). By way of example only, buttress body (4260) may be constructed and operable in accordance with at least some of the teachings of U.S. patent application Ser. No. 14/667,842, entitled "Method of Applying a Buttress to a Surgical Stapler," filed Mar. 25, 2015, now U.S. Patent Pub. No. 2016/0278774, published Sep. 26, 2016, issued as U.S. Pat. No. 10,349,939 on Jul. 16, 2019, the disclosure of which is incorporated by reference herein. Adhesive layer (4270) of the present example comprises a flowable adhesive material. By way of example only, adhesive layer (4270) may be constructed and operable in accordance with at least some of the teachings of U.S. patent application Ser. No. 14/667,842, entitled "Method of Applying a Buttress to a Surgical Stapler," filed Mar. 25, 2015, now U.S. Patent Pub. No. 2016/0278774, published Sep. 26, 2016, issued as U.S. Pat. No. 10,349,939 on Jul. 16, 2019, the disclosure of which is incorporated by reference herein.

Buttress body (4260) is laid directly on upper surface (4220) of platform (4220), adhesive layer (4270) is laid directly on buttress body (4260), and adhesive containment sheet (4240) is laid directly on adhesive layer (4270). Adhesive containment sheet (4240) has a length ($L_1$) and a width ($W_1$). In the present example, buttress body (4260) and adhesive layer (4270) are coextensive in length and width, such that buttress body (4260) and adhesive layer (4270) both have a length ($L_2$) and a width ($W_2$). The length ($L_1$) of adhesive containment sheet (4240) is greater than the length ($L_2$) of buttress body (4260) and adhesive layer (4270). Similarly, the width ($W_1$) of adhesive containment sheet (4240) is greater than the width ($W_2$) of buttress body (4260) and adhesive layer (4270). Adhesive containment sheet (4240) is thus sized to completely cover both buttress body (4260) and adhesive layer (4270). In particular, the outer edges (4244) of adhesive containment sheet (4240) are configured to be adhered directly to upper surface (4222) of platform (4220), such that adhesive containment sheet (4240) and platform (4220) cooperate to fully encompass buttress body (4260) and adhesive layer (4270). In some versions, outer edges (4244) of adhesive containment sheet (4240) include an adhesive material that enables outer edges (4244) to be removably adhered to upper surface (4222). In addition or in the alternative, retainers (4214) may assist in removably retaining adhesive containment sheet (4240) against upper surface (4222). Other suitable ways in which adhesive containment sheet (4240) may be removably secured to upper surface (4222) will be apparent to those of ordinary skill in the art in view of the teachings herein. It should be understood that, while adhesive containment sheet (4240) is secured to upper surface (4222), adhesive containment sheet (4240) will contain adhesive layer (4270) by maintaining the position of adhesive layer (4270) on buttress body (4260).

In an exemplary use of cartridge (4200), an operator may first peel adhesive containment sheet (4240) away from platform (4220), adhesive layer (4270), and buttress body (4260). To assist in such peeling away of adhesive containment sheet (4240), adhesive containment sheet (4240) includes an integral pull-tab (4242). The operator may thus grasp pull tub (4242) and thereby peel adhesive containment sheet (4240) away from platform (4220), adhesive layer (4270), and buttress body (4260). This will result in adhesive layer (4270) being exposed. The operator may then position end effector (440) in recess (4212), then actuate anvil (60) to close anvil (60) against platform (4220) as end effector (440) reaches a closed configuration. Lower jaw (50) and staple cartridge (70) will be positioned on the underside of platform (4220), providing an opposing force such that anvil (60) may be clamped against adhesive layer (4270). As anvil (60) clamps against adhesive layer (4270), the adhesive material forming adhesive layer (4270) may flow into staple forming pockets (64) and/or other nooks and crannies in underside (65) of anvil (60). The material forming adhesive layer (4270) may thus adhere buttress body (4260) to underside (65). When the operator pivots anvil (60) away from platform (4220) to return end effector (440) to an open configuration, anvil (60) will pull buttress body (4260) away from platform (4220), and buttress body (4260) will remain adhered to underside (65) by adhesive layer (4270). End effector (440) may then be used as described above with reference to FIGS. 5A-5C.

As noted above, another combination of buttress assembly (4230) and adhesive containment sheet (4240) may be provided on the underside of platform (4220), in addition to or as an alternative to the combination of buttress assembly (4230) and adhesive containment sheet (4240) being provided on upper surface (4222) of platform. An operator may thus employ the same process as described above to adhere a buttress assembly (4230) to deck (73) of staple cartridge (70), in addition to or as an alternative to adhering a buttress assembly (4230) to underside (65) of anvil (60).

B. Exemplary Cartridge Packaging with Integral Adhesive Containment Sheet

Figure 83A:
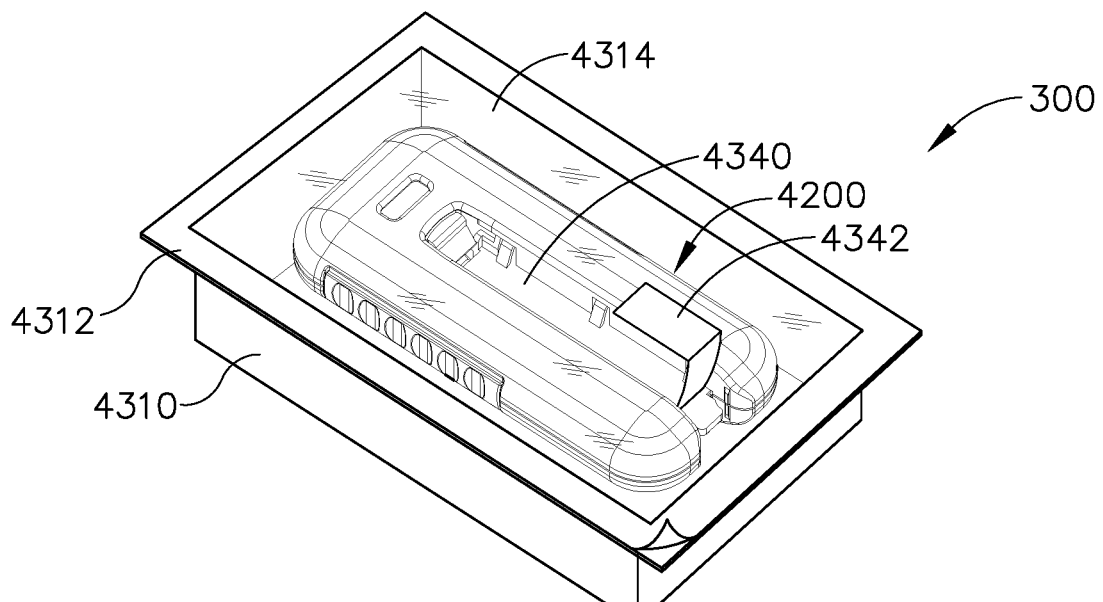
FIG. 83A depicts a perspective view of an exemplary alternative buttress assembly applier cartridge loaded in a container, with a protective film secured to the container.
Figure 83B:
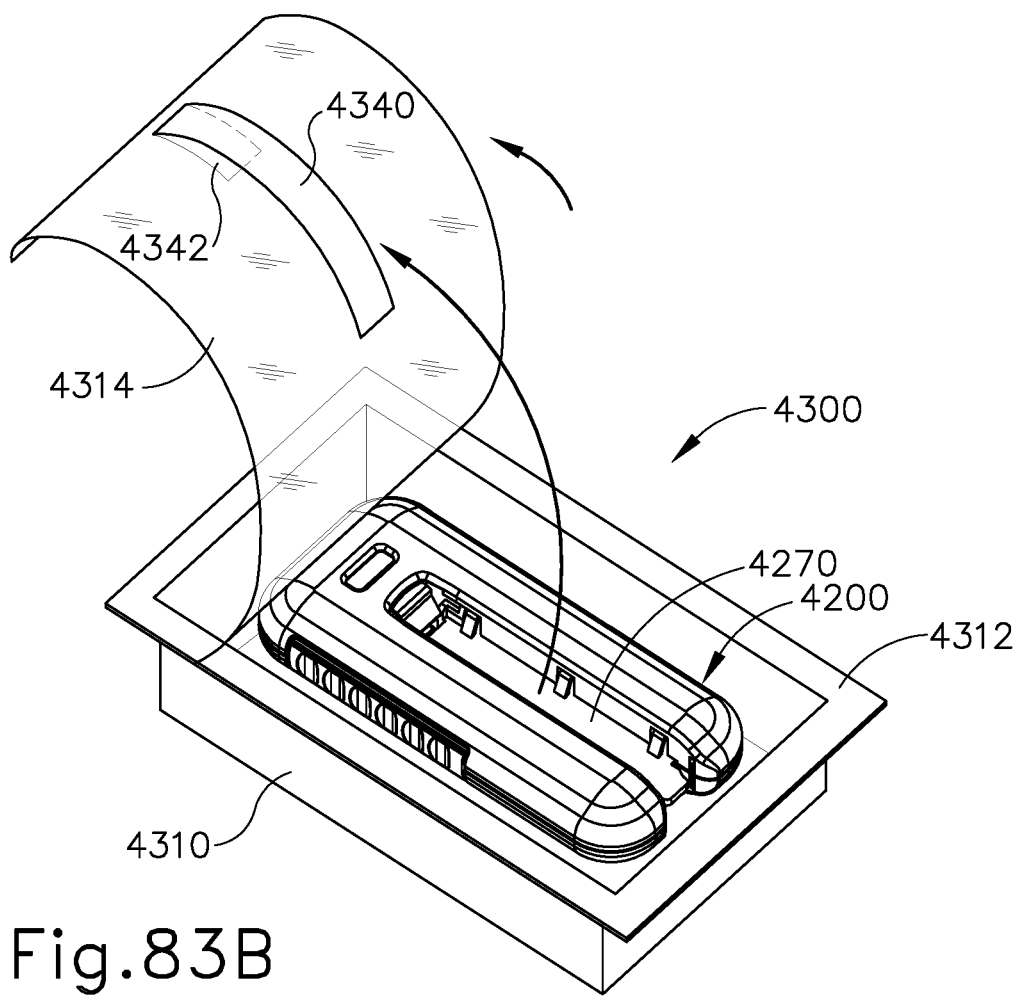
FIG. 83B depicts a perspective view of the cartridge and container of FIG. 83A, with the protective film peeled away from the container.

In some instances, it may be desirable to provide cartridge (4200) in a sterile package for transport and storage, such that the sterile package may protect cartridge (4200) from contamination up until an operator is ready to use cartridge (4200) to apply a buttress assembly to an end effector (440). In versions where cartridge supports a buttress assembly having a flowable adhesive, it may also be desirable to incorporate an adhesive containment feature in such a sterile package. To that end, FIGS. 83A-83B show an exemplary sterile package (4300) that includes an integral adhesive containment strip (4340). Sterile package (4300) of this example includes a container (4310) that is sized to contain the entirety of cartridge (4200). Container (4310) includes an upper lip (4312). A protective film (4314) is adhered to upper lip (4312) thereby hermetically sealing cartridge (4200) in container (4310).

Adhesive containment strip (4340) includes a tab (4342) that is fixedly secured to the underside of protective film (4314). When protective film (4314) is secured to lip (4312) as shown in FIG. 83A, adhesive containment strip (4340) is positioned over adhesive layer (4270) and thus contains adhesive layer (4270) on buttress body (4260). Adhesive containment strip (4340) thus operates just like adhesive containment sheet (4240) when package (4300) is in the sealed state shown in FIG. 83A. However, when protective film (4314) is peeled away from lip (4312) as shown in FIG. 83B, protective film (4314) peels adhesive containment strip (4340) away from adhesive layer (4270) and buttress body (4260). Cartridge (4200) may then be removed from container (4310) and an end effector (440) may be clamped onto platform (4220) as described above to adhere buttress assembly (4230) to underside (65) of anvil (60) via adhesive layer (4270).

Figure 84:
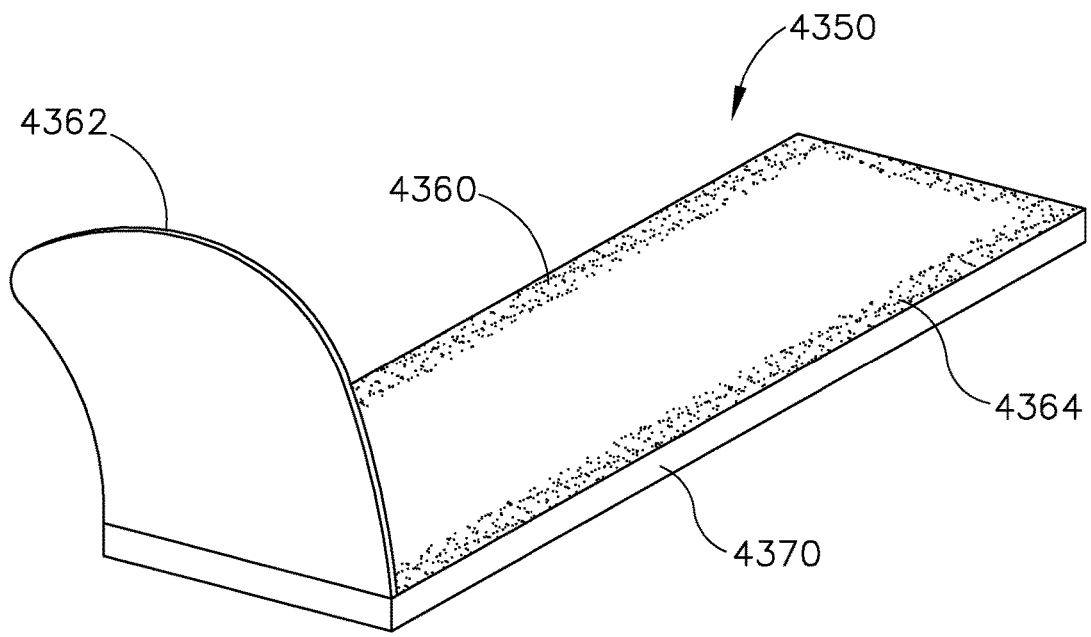
Figure 85:
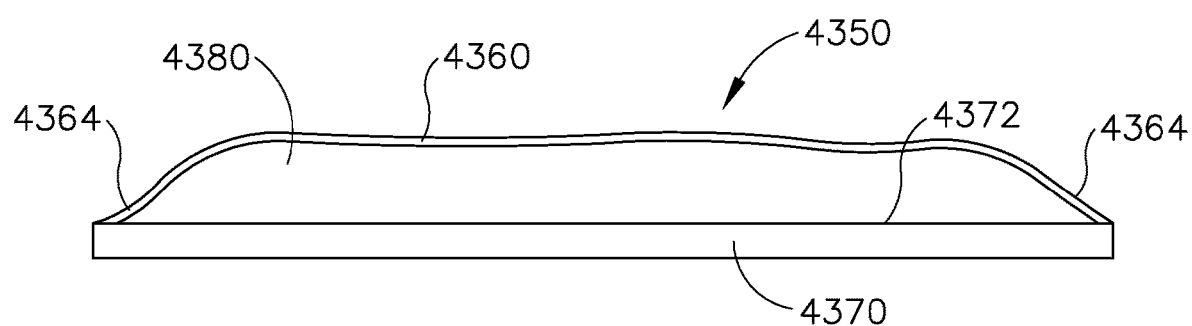
Figure 88:
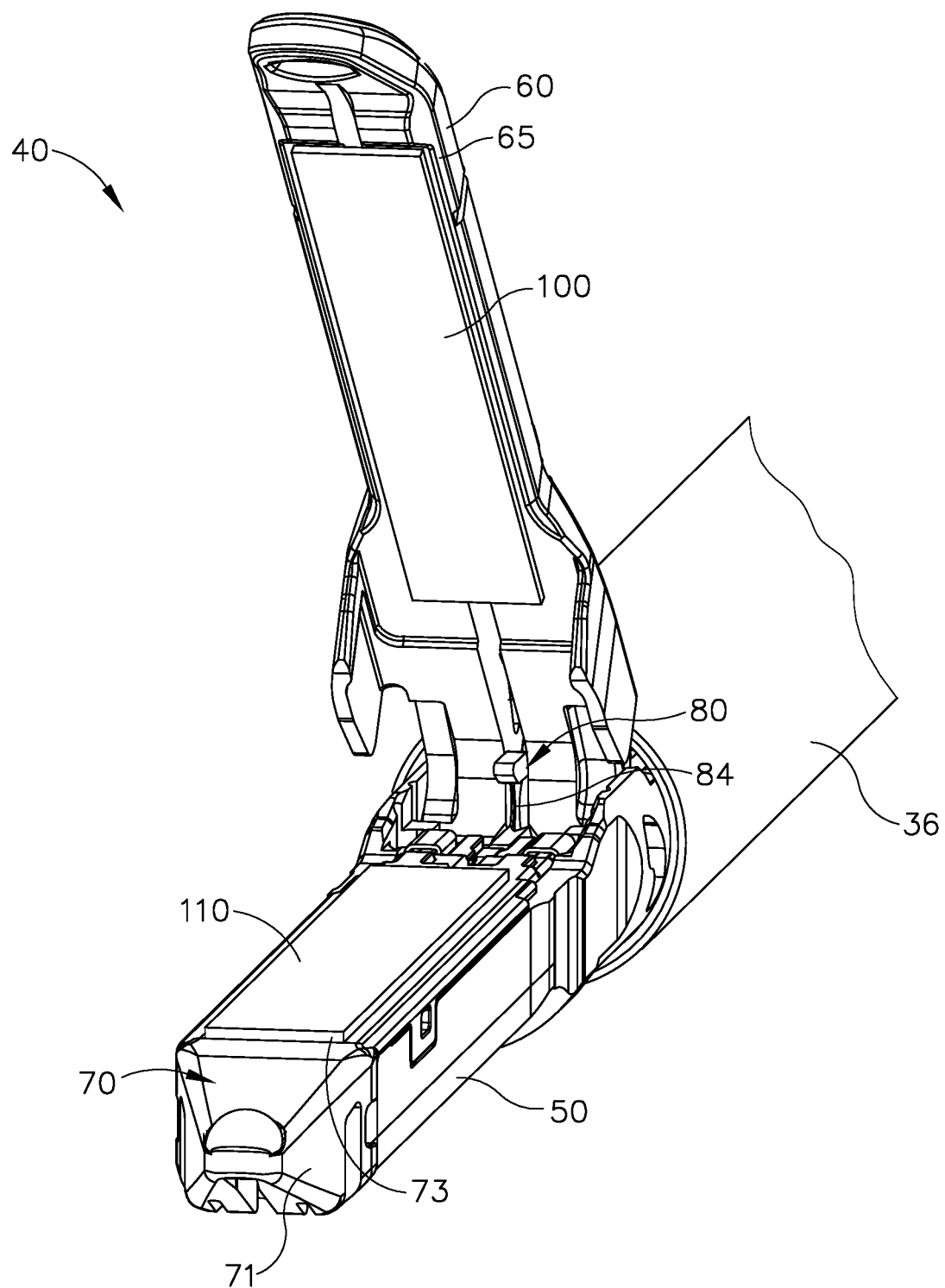
Figure 89:
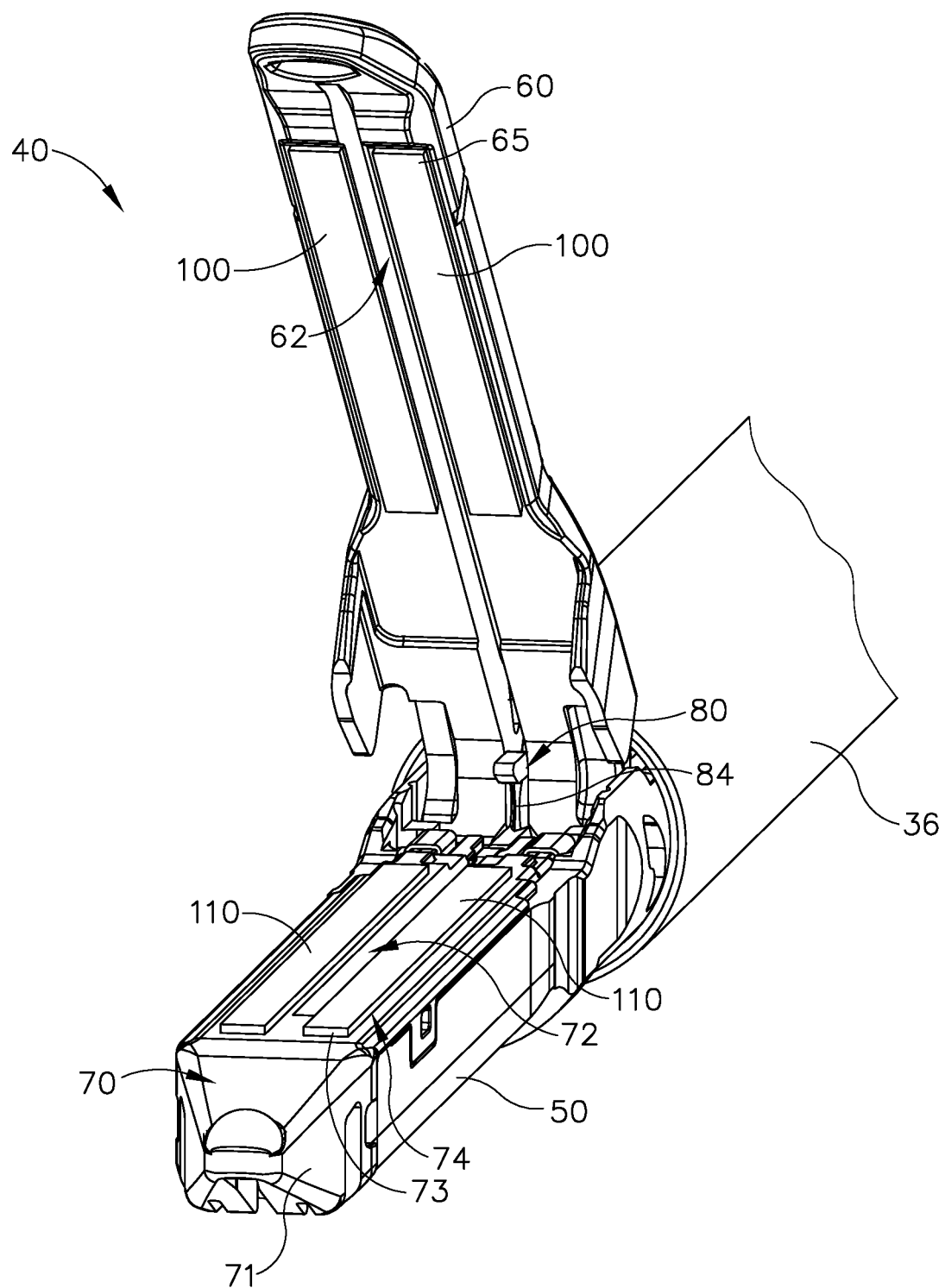

C. Exemplary Buttress Assembly with Adhesive Containment Sheet Secured to Buttress Body FIGS. 84-85 show another exemplary buttress assembly (4350). Buttress assembly (4350) of this example comprises an adhesive containment strip (4360) that is adhered to an upper surface (4372) of a buttress body (4370). Buttress body (4370) may be configured and operable just like any other buttress body described herein or described in any of the various references cited herein. The outer edges (4364) of adhesive containment strip (4360) are adhered to the outer edges of upper surface (4372). A flowable adhesive material (4380) is positioned on upper surface (4372), such that adhesive material (4380) is captured between adhesive containment strip (4360) and buttress body (4370). Adhesive containment strip (4360) thus contains adhesive material (4380) on buttress body (4370). Adhesive containment strip (4360) includes a tab (4362) that an operator may grasp to peel adhesive containment strip (4360) away from buttress body (4370) to thereby reveal adhesive material (4380). The operator may then secure buttress body (4370) to an end effector (440) via adhesive material (4380) by clamping anvil (60) or staple cartridge (70) against the revealed adhesive material (4380). In some versions, buttress assembly (4350) is incorporated into cartridge (4200) as described above. Other suitable ways in which buttress assembly (4350) may be configured and used will be apparent to those of ordinary skill in the art in view of the teachings herein.

D. Exemplary Buttress Adhesive Loading Cartridge with Adhesive Containment Sheet In some instances, it may be desirable to apply adhesive layer (104, 114) to end effector (440) first, then apply buttress body (102, 112) to end effector (440) via adhesive layer (104, 114). This may be desirable in instances where it is beneficial to store and contain buttress body (102, 112) separately from adhesive layer (104, 114). FIGS. 86A-87 show an exemplary adhesive cartridge (4400) that may be used to store and contain an adhesive material (4440) by itself (i.e., without adhesive material (4440) being predisposed on a buttress body). Cartridge (4400) of this example comprises a housing (4410) that defines a "U" shape including a central recess (4412). Central recess (4412) has a length and width that are sized to accommodate an anvil (60) and a lower jaw (50) loaded with a staple cartridge (70). A platform (4420) is positioned within recess (4412) and supports two layers of adhesive material (4440), with one layer of adhesive material (4440) on an upper side of platform (4420) and another layer of adhesive material (4440) on a lower side of platform (4420). Adhesive material (4440) may be constructed and operable in accordance with the teachings herein and/or in accordance with the teachings of any of the references cited herein.

As best seen in FIG. 87, housing (4410) includes ledges (4414) in central recess (4412), adjacent to platform (4420). Ledges (4414) thus provide a stepped transition between platform (4420) and the remainder of platform (4420). As also seen in FIG. 87, adhesive material (4440) is positioned between adjacent regions of ledges (4414), such that ledges (4414) contain adhesive material (4440) to at least some degree. A pair of adhesive containment sheets (4430) are positioned to contain adhesive material (4440) between adjacent regions of ledges (4414). In particular, each adhesive containment sheet covers a corresponding layer of adhesive material (4440). In some versions, outer edges of adhesive containment sheet (4430) include an adhesive material that enables outer edges of adhesive containment sheet (4430) to be removably adhered to platform (4420). Adhesive containment sheet (4430) of the present example comprises a pull-away tab (4432) that is operable to peel adhesive containment sheet (4430) off of ledges (4414), to thereby reveal adhesive material (4440).

In an exemplary use, an operator may grasp tab (4432) and thereby peel adhesive containment sheet (4430) off of ledges (4414), thereby revealing adhesive material (4440). In some instances, the operator may peel just one adhesive containment sheet (4430) off of ledges (4414) (i.e., just the upper adhesive containment sheet (4430) or just the lower adhesive containment sheet (4430)). This may be done if the operator only wishes to apply adhesive material (4440) to anvil (60) or cartridge (70) but not both. Alternatively, the operator may peel both adhesive containment sheets (4430) off of ledges (4414). This may enable the operator to apply adhesive material (4440) to anvil (60) and cartridge (70). In either case, the operator may apply adhesive material (4440) to anvil (60) and/or cartridge (70) by positioning end effector (440) in central recess (4412), then clamping down on the exposed adhesive material (4440) by actuating end effector (440) to the closed configuration. In the event that one of the containment sheets (4430) is left on ledges (4414) when the operator clamps end effector (440) on cartridge (4400), that containment sheet (4430) and the underlying adhesive material (4440) may be left intact. When the operator returns end effector (440) to the open configuration, the adhesive material (4440) may be positioned on underside (65) of anvil (60) and/or deck (73) of cartridge (70).

With adhesive material (4440) applied to underside (65) of anvil (60) and/or deck (73) of cartridge (70), the operator may then apply a buttress body (e.g., similar to any of the buttress bodies referred to herein) to the applied adhesive material (4440). By way of example only, a variation of cartridge (4200) may be configured to carry one or more buttress bodies without also including an adhesive layer or protective sheet. The operator may thus clamp end effector (440) down on the buttress body, and the adhesive material (4440) applied to underside (65) of anvil (60) or deck (73) of cartridge (70) will adhere to the buttress body. Thus, when the operator returns end effector (440) to the open configuration, the applied adhesive material (4440) will have picked up the buttress body and will have thereby adhered the buttress body to underside (65) of anvil (60) or deck (73) of cartridge (70). Other suitable ways in which a buttress body may be applied to an end effector (440) that is preloaded with an adhesive material (4440) will be apparent to those of ordinary skill in the art in view of the teachings herein.

XXIV. Exemplary Multilayer Buttress Body

In some instances, it may be desirable to have a multilayer buttress body instead of one uniform buttress body (102, 112) attached to adhesive layer (104, 114). A buttress body with multiple layers may provide added benefits stemming from the diverse material properties of each layer, either while attached to end effector (70) via adhesive layer (104, 1140) or while attached to tissue ($T_1$, $T_2$) via staples (90). For example, one layer may be utilized to provide the benefit of tissue reinforcement while another layer may be utilized to further promote hemostasis or a combination thereof. Additionally or alternatively, placement of multiple layers relative to each other may provide additional benefits. For instance, a first layer may be placed between adhesive layer (104, 114) and a second layer in order to allow adhesive layer (104, 114) to better adhere to underside (65) of anvil (60) and/or deck (73) of staple cartridge (70). Various examples of multilayer buttress bodies will be described in greater detail below. It should be understood that the following examples may be used in place of buttress assemblies (100, 110) described above.

A. Multilayer Buttress Body with Continuous Film Layer

FIG. 91 shows a multilayer buttress assembly (5200) including a multilayer buttress body (5202) and an adhesive layer (5204). Multilayer buttress assembly (5200) may be used with end effector (40) in place of either or both buttress assemblies (100, 110) as mentioned above. Therefore, adhesive layer (5204) may be substantially similar to adhesive layers (104, 114) mentioned above. As such, multilayer buttress assembly (5200) may be adhered to underside (65) of anvil (60) and/or deck (73) of staple cartridge (70). The material forming adhesive layer (5204) may provide proper positioning of multilayer buttress body (5202) before and during actuation of end effector (40); then allow multilayer buttress body (5202) to separate from end effector (40) after end effector (40) has been actuated, without causing damage to multilayer buttress body (5202) that is substantial enough to compromise the proper subsequent functioning of multilayer buttress body (5202). By way of example only, adhesive layer (5204) may be constructed and operable in accordance with at least some of the teachings of U.S. patent application Ser. No. 14/667,842, entitled "Method of Applying a Buttress to a Surgical Stapler," filed Mar. 25, 2015, now U.S. Patent Pub. No. 2016/0278774, published Sep. 26, 2016, issued as U.S. Pat. No. 10,349,939 on Jul. 16, 2019, the disclosure of which is incorporated by reference herein.

FIGS. 90-91 show multilayer buttress body (5202) including a mesh layer (5206) and a film layer (5208). Film layer (5208) may comprise any suitable bioabsorbable materials, including but not limited to PDS (polydioxanone), polyglactin 910, or polyglecaprone 25. Various other suitable materials that may be used will be apparent to those of ordinary skill in the art in view of the teachings herein. Film layer (5208) is integrally connected to mesh layer (5206) and lies on top of mesh layer (5206). Film layer (5208) may be integrally connected to mesh layer (5206) through a heated press, combining pressure and heat. It should be understood film layer (5208) is a continuous film with minimal porosity in the present example. In other words, film layer (5208) prevents fluid from traveling across its boundaries.

As shown in FIG. 90, mesh layer (5206) is a two dimensional planar construct allowing minimal stretching. Mesh layer (5206) may be made of planar fabrics (5207) that are combined in a matrix. The matrix formed of planar fabrics (5207) may be knitted or woven together in a pattern, or in a random association. FIG. 90 shows matrix formed of planar fabrics (5207) knitted or woven in a square texture pattern. However, any number of suitable texture patterns may be used as would be apparent to a person having ordinary skill in the art in view of the teachings herein.

While FIG. 90 shows mesh layer (5206) in a two dimensional planar construct, it is envisioned mesh layer (5206) may form a three dimensional mesh layer construct in some other versions. For instance, a three dimensional version of mesh layer (5206) may be made out of knitted spacer fabrics, Rachel knitted spacer fabrics, uncut velvet, terry cloth, or any other suitable material as will be apparent to a person having ordinary skill in the art in view of the teachings herein. A three dimensional version of mesh layer (5206) may allow for minimal extensibility in one direction and spring-like extensibility in a perpendicular direction. The direction with minimal extensibility could be utilized for reinforcement of recently severed tissue ($T_1$, $T_2$); while the spring-like extensibility could be utilized in order to compensate for tissue deformation after end effector (40) severs and staples tissue as described above.

As shown in FIG. 91, film layer (5208) is adhered under adhesive layer (5204). Due to film layer (5208) being interposed between mesh layer (5206) and adhesive layer (5204) in combination with the continuous nature and minimal porosity of film layer (5208), film layer (5208) may act as a sealed barrier between mesh layer (5206) and adhesive layer (5204). In other words, fluids are prevented from passing through film layer (5208) in this example. Therefore, if adhesive layer (5204) became viscous, film layer (5208) may prevent adhesive layer (5204) from penetrating into mesh layer (5206). This may prevent the viscous nature or adhesive layer (5204) from spreading too thin, which may compromise the adhesion between multilayer buttress assembly (5200) and end effector (40). In addition, moisture (e.g., bodily fluid, saline, etc.) obtained through mesh layer (5206) may not penetrate onto adhesive layer (5204). This may allow adhesive layer (5204) to properly adhere to underside (65) of anvil (60) or deck (73) of staple cartridge (70) for longer periods of time in a moist environment, such as a surgical site.

It should be understood that because film layer (5208) acts as a barrier between mesh layer (5206) and adhesive layer (5204), mesh layer (5206) will be the portion of multilayer buttress body (5202) in contact with tissue ($T_1$, $T_2$) when end effector (40) clamps, severs, and staples tissue ($T_1$, $T_2$) as described above when utilizing multilayer buttress assembly (5200). Therefore, film layer (5208) will be closer to underside (65) of anvil (60) and/or deck (73) of staple cartridge (70). If multilayer buttress assembly (5200) is used on both underside (65) of anvil (60) and deck (73) of staple cartridge (70), a pair of film layers (5208) would be surrounding both tissue ($T_1$, $T_2$) and mesh layers (5206). This geometry surrounding tissue ($T_1$, $T_2$) may help prevent tissue ($T_1$, $T_2$) from forming an adhesion at the site of stapling and severing.

Film layer (5208) may be made out of a material that is conformable. In other words, once film layer (5208) is punctured by staples (90), film layer (5208) conforms around staple (90) and forms a seal around the portion of staple legs (94) penetrating film layer (5208). This may allow for film layer (5208) to still act as a barrier after multilayer buttress (5200) is detached from end effector (40) and attached to tissue ($T_1$, $T_2$) via staples (90) as shown in FIG. 6. This sealing effect may enhance hemostasis. Also, due to the continuous nature and minimal porosity of film layer (5208), film layer (5208) may also spread pressure from driven staples (90) on a more uniform area of compression on tissue ($T_1$, $T_2$), also potentially enhancing hemostasis.

If multilayer buttress assembly (5200) is located on deck (73) of staple cartridge (70), film layer (5208) may also act as a barrier between tissue ($T_1$, $T_2$) and deck (73) of staple cartridge (70). As described above, deck (73) houses staples (90), which are driven by staple driver (75). Tissue ($T_1$, $T_2$) may exert fluids or flowing tissue into deck (73) when compressed by anvil (60) pivoting towards lower jaw (50). These fluids or flowing tissue may impart of force on individual staples (90) located within deck (73), creating a misalignment between staple crown (92) and staple driver (75). This misalignment may lead to a higher probability of staple legs (94) hitting staple forming pockets (64) in an unintended orientation, possibly leading to an inadequate staple formation. However, the sealed barrier created by film layer (5208) may prevent tissue ($T_1$, $T_2$) exerting fluid or flowing tissue into deck (73), thereby increasing the probability of a proper staple (90) forming against staple forming pocket (64).

Additionally, when end effector (40) clamps, severs, and staples tissue ($T_1$, $T_2$), staples (90) will travel through planar fabrics (5207) of mesh layer (5206), potentially confining staple legs (94) within the matrix defined by mesh layer (5206). This confinement may allow mesh layer (5206) to help interlock individual staples (90) in such a way that staples (90) act as a group. The confinement of staples (90) may also allow mesh layer (5206) to absorb and distribute loads provided by driving staples (90) that would otherwise be directly transferred to tissue ($T_1$, $T_2$), which may help prevent tissue failure due to overstress.

In some exemplary variations of buttress assembly (5200), another film layer may be positioned under mesh layer (5206). By way of example only, this additional film layer may be configured and operable just like film layer (5208) described above. Mesh layer (5206) may thus be interposed between two film layers (5208). By way of further example only, the additional film layer may be added for increased reinforcement strength, increased stiffness, reduced overall porosity, reduced friction or increased adhesion to adhesive layer.

B. Multilayer Buttress Body with Punctured Film Layer

FIG. 92 shows a multilayer buttress assembly (5300) including a multilayer buttress body (5302) and an adhesive layer (5304). Multilayer buttress assembly (5300) may be used with end effector (40) in place of either or all buttress assemblies (100, 110, 5200) mentioned above. Therefore, adhesive layer (5304) may be substantially similar to adhesive layers (104, 114, 5204) mentioned above. As such, multilayer buttress assembly (5300) may be adhered to underside (65) of anvil (60) and/or deck (73) of staple cartridge (70). The material forming adhesive layer (5304) may provide proper positioning of multilayer buttress body (5302) before and during actuation of end effector (40); then allow multilayer buttress body (5302) to separate from end effector (40) after end effector (40) has been actuated, without causing damage to multilayer buttress body (5302) that is substantial enough to compromise the proper subsequent functioning of multilayer buttress body (5302). By way of example only, adhesive layer (5304) may be constructed and operable in accordance with at least some of the teachings of U.S. patent application Ser. No. 14/667,842, entitled "Method of Applying a Buttress to a Surgical Stapler," filed Mar. 25, 2015, now U.S. Patent Pub. No. 2016/0278774, published Sep. 26, 2016, issued as U.S. Pat. No. 10,349,939 on Jul. 16, 2019, the disclosure of which is incorporated by reference herein.

FIGS. 92-93 show multilayer buttress body (5302) including a mesh layer (5306) and a film layer (5308) interposed between mesh layer (5306) and adhesive layer (5304). Mesh layer (5306) further includes a bottom mesh portion (5324), a top mesh portion (5322), and a plurality of open loops (5326) extending from top mesh portion (5322). As will be described in further detail below, loops (5326) may extend within and/or through film layer (5308) in order to promote attachment between adhesive layer (5304) and mesh layer (5306). Therefore, unlike multilayer buttress assembly (5200) described above, mesh layer (5306) could be designed to have some fluid communication with adhesive layer (5304). Loops (5326) may be formed on top mesh portion (5322) through various methods, such as needle tufting, sewing through top mesh portion (5322) with a thread, or any other suitable methods as will be apparent to a person having ordinary skill in the art in view of the teachings herein. It should be understood that loops (5326) are merely optional in order to promote attachment between adhesive layer (5304) and mesh layer (5306). For instance, instead of loops (5326), top mesh portion (5322) may have strings extending from top mesh portion (5322) to promote attachment between adhesive layer (5304) and mesh layer (5306).

Mesh layer (5306) forms a three dimensional mesh layer construct. Three dimensional mesh layer (5306) may be made out of knitted spacer fabrics, Rachel knitted spacer fabrics, uncut velvet, terry cloth, or any other suitable material as will be apparent to a person having ordinary skill in the art in view of the teachings herein. Fibers forming mesh layer (5306) may have surface properties of a multifilament, a monofilament, or any extrudable shapes, any of which could be surface activated for adhesion.

Figure 94A:
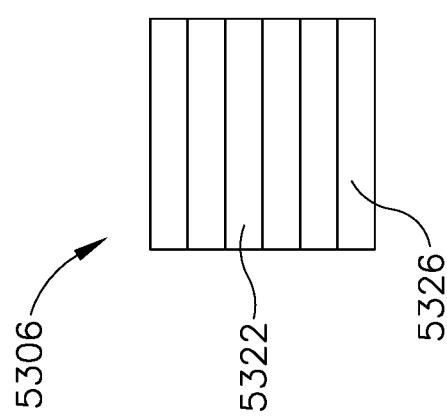

As can be seen in FIGS. 94A-94B, three dimensional mesh layer (5306) of the present example has partial elasticity that provides minimal extensibility in one direction (along the plane defined by mesh layer (5306)) and spring-like extensibility in a perpendicular direction (also along the plane defined by mesh layer (5306)). The direction with minimal extensibility could be utilized for reinforcement of recently severed tissue ($T_1$, $T_2$) while the spring-like extensibility could be utilized in order to compensate for tissue deformation after end effector (40) severs and staples tissue as described above. In the present example, mesh layer (5306) is provided in a rectangular shape, with the longer length extending in a longitudinal direction along a corresponding length of end effector (40); and with the shorter width extending in a lateral direction along a corresponding with of end effector (40). Also in the present example, mesh layer (5306) has the resilient extensibility in the longitudinal direction and the minimal extensibility in the lateral direction. It should therefore be understood that, after buttress assembly (5300) is secured to tissue by staples (90), buttress assembly (5300) will be extensible along a path that is parallel to the longitudinal orientation of crowns (92); while being substantially non-extensible along a path that is perpendicular to the longitudinal orientation of crowns (92).

As previously noted, mesh layer (5306) includes bottom mesh portion (5324) and top mesh portion (5322). Bottom mesh portion (5324) and top mesh portion (5322) may be made out of the same or different material as would be apparent to a person having ordinary skill in the art in view of the teachings herein. However, in the present example, top mesh portion (5322) has a greater density as compared to bottom mesh portion (5324). The high density of top mesh portion (5322) provides reduced porosity of mesh layer (5306). Different densities result in different rates of moisture absorption of bottom mesh portion (5324) and top mesh portion (5322). In particular, the greater density of top mesh portion (5322) restricts the amount of moisture absorbed as compared to bottom mesh portion (5324). The difference in densities between top mesh portion (5322) and bottom mesh portion (5324) could be provided through a meltblown process, electrospinning, or any other methods as will be apparent to a person having ordinary skill in the art in view of the teachings herein.

Since top mesh portion (5322) is closer to adhesive layer (5304), this may result in top mesh portion (5322) acting as a semi-permeable barrier. In other words, fluids are somewhat restricted from passing through top mesh portion (5322). Therefore, if adhesive layer (5304) became viscous, top mesh portion (5322) may absorb some of viscous adhesive layer (5304) but help prevent adhesive layer (5304) from penetrating into bottom mesh portion (5324). In addition, top mesh portion (5322) may absorb some of the moisture obtained through bottom mesh portion (5324) and prevent that moisture from reaching film layer (5308). In some versions, top mesh portion (5322) may provide some degree of porosity so as to allow water moisture to pass but not allow a viscous adhesive to pass.

It should be understood that because film layer (5308) is in contact with adhesive layer (5304) and top mesh portion (5322) is in contact with film layer (5308), bottom mesh portion (5324) will be the portion of multilayer buttress body (5202) in contact with tissue ($T_1$, $T_2$) when end effector (40) clamps, severs, and staples tissue ($T_1$, $T_2$) as described above when utilizing multilayer buttress assembly (5300). Therefore, film layer (5208) will be closer to underside (65) of anvil (60) and/or deck (73) of staple cartridge (70). If multilayer buttress assembly (5300) is used on both underside (65) of anvil (60) and deck (73) of staple cartridge (70), a pair of film layers (5308) would be surrounding both tissue ($T_1$, $T_2$) and mesh layers (5206). This geometry surrounding tissue ($T_1$, $T_2$) may help prevent tissue ($T_1$, $T_2$) from forming an adhesion at the site of stapling and severing.

In some examples, film layer (5308) may be omitted. In such versions, top mesh portion (5322) would be directly interposed between adhesive layer (5304) and bottom mesh portion (5324). Top mesh portion (5322) could be so dense as to absorb some moisture from either bottom mesh portion (5324) or adhesive layer (5304), but not allow the moisture to saturate top mesh portion (5322). This may allow adhesive layer (5304) to properly adhere to underside (65) of anvil (60) or deck (73) of staple cartridge (70) for longer periods of time in a moist environment, such as a surgical site.

In some examples, top mesh portion (5322) may be so dense that bottom mesh portion (5324) would not be needed. In some such versions, top mesh portion (5322) would be such a tightly woven mesh that moisture from a viscous adhesive would be able to penetrate mesh layer (5306), but not saturate mesh layer (5206).

Additionally, when end effector (40) clamps, severs, and staples tissue ($T_1$, $T_2$), staples (90) will travel through mesh layer (5306), potentially confining staple legs (94) within the matrix defined by mesh layer (5306). This confinement may allow mesh layer (5208) to help interlock individual staples (90) in such a way that staples (90) act as a group. The confinement of staples (90) may also allow mesh layer (5306) to absorb and distribute loads provided by driving staples (90) that would otherwise be directly transferred to tissue ($T_1$, $T_2$), which may help prevent tissue failure due to overstress.

Film layer (5308) is substantially the same as film layer (5208), except with possible differences described below. Film layer (5308) may comprise any suitable bioabsorbable materials, including but not limited to PDS (polydioxanone), polyglactin 910, or polyglecaprone 25. Various other suitable materials that may be used will be apparent to those of ordinary skill in the art in view of the teachings herein. Film layer (5308) is integrally connected to mesh layer (5306) and lies on top of mesh layer (5306). Film layer (5308) may be integrally connected to mesh layer (5306) through a heated press, combining pressure and heat. As mentioned above, film layer (5308) may allow loops (5326) of mesh portion (5306) to extend through film layer (5308) in order for mesh portion (5306) to connect with adhesive layer (5304). It should be understood that film layer (5308) or any of its alternatives may be utilized in any of the examples described herein. It should also be understood that the porosity of film layer (5308) and/or top mesh portion (5322) could be sized so water moisture may pass but a viscous adhesive could not.

As shown in FIGS. 95A-95B, unlike film layer (5208), a plurality of slits (5312) are formed in film layer (5308) in the present example. Slits (5312) accommodate longitudinal stretching of film layer (5308) with mesh layer (5306) from a rested position, as shown in FIG. 95A, to a stretched position, as shown in FIG. 95B. Therefore, film layer (5308) may stretch longitudinally with mesh portion (5306), as shown in FIGS. 94A-94B. Slits (5312) allow mesh portion (5306) to extend through film layer (5308). Additionally, slits (5312) permit fluid communication between adhesive portion (5304) and mesh portion (5306).

As can be seen in FIGS. 96-98, slits (5312) are just one of option to provide for selective communication between adhesive portion (5304) and mesh portion (5306). In particular, FIGS. 96-98 show alternative films (5314, 5316, 5318) that are substantially similar to film layer (5308) described above. Alternative films (5314, 5316, 5318) have diamond holes (5315), circular holes (5317), and a "Z" cut holes (5319) respectively, enabling communication between adhesive portion (5304) and mesh portion (5306). However, the present examples should not be seen as limiting. Slits (5312) or holes (5315, 5317, 5319) may have any other suitable shape as will be apparent to a person having ordinary skill in the art in view of the teachings herein.

It should be understood that various techniques may be used to form slits (5312) or holes (5315, 5317, 5319) in film layer (5308). For instance, as shown in FIG. 99, a laser (1) may be used to form slits (5312) or holes (5315, 5317, 5319) in film layer (5308). As another merely illustrative example, a studded roller (52) may be used to form slits (5312) or holes (5315, 5317, 5319) in film layer (5308), as shown in FIG. 100. Here, roller (52) would roll over film layer (5308) to penetrate film layer (5308) to form slits (5312) or holes (5315, 5317, 5319). Roller (52) would have a diameter and specified frequency of studs about the circumference to determine where slits (5312) or holes (5315, 5317, 5319) would be located on film layer (5308). As yet another merely illustrative example, a studded press (53) may be used to form slits (5312) or holes (5315, 5317, 5319) in film layer (5308), as shown in FIG. 101. Here, press (53) would make a plurality of slits (5312) or holes (5315, 5317, 5319) with one penetrating move. Of course, any other suitable devices or techniques may be used to create slits (5312) or holes (5315, 5317, 5319) as will be apparent to a person having ordinary skill in the art in view of the teachings herein.

XXV. Exemplary Alternative Buttress Assemblies with Features for Mechanically Coupling to Staple Cartridge In some instances, it may be desirable to deploy multiple, successive lines of staples (690) with buttress assemblies (100, 110) onto tissue during a surgical operation. Such a task may require the operator to remove end effector (640) from the patient (e.g., through a trocar), remove the spent staple cartridge (670), replace the staple cartridge (670), and re-insert end effector (640) into the patient via the trocar. Before end effector (640) is re-inserted into the patient, the operator may load a new buttress assembly (100) on anvil (60). In addition, the replacement staple cartridge (670) may include a new buttress assembly (110). In some such instances, knife member (680) may need to sever one or two new buttress assemblies (100, 110) each time end effector (640) is actuated. Deploying multiple successive lines of staples and buttress assemblies may thus cause stress and wear on knife member (680) and lead to operator fatigue. It may therefore desirable to reduce the amount of force required to actuate end effector (640), and reducing stress and wear on knife member (680), by reducing or eliminating structures that must be severed by knife member (680) during actuation of end effector (640). Several exemplary features that will prevent knife member (680) from having to sever buttress assembly (110) during actuation of end effector (640) are described below.

Some versions of buttress assemblies (100, 110) are removably secured to end effector (640) via an adhesive. Various examples of how adhesives may be used to secure buttress assemblies (100, 110) to end effector (640) are described in U.S. patent application Ser. No. 14/667,842, entitled "Method of Applying a Buttress to a Surgical Stapler," filed Mar. 25, 2015, now U.S. Patent Pub. No. 2016/0278774, published Sep. 26, 2016, issued as U.S. Pat. No. 10,349,939 on Jul. 16, 2019, the disclosure of which is incorporated by reference herein. It may be desirable to secure buttress assemblies (100, 110) to end effector (640) using something other than adhesives. Various mechanical features that may be used to removably secure buttress assembly (110) to staple cartridge (670) will be described in greater detail below. It should be understood that similar features may be used to secure buttress assembly (100) to anvil (60). It should also be understood that buttress assemblies (100, 110) may otherwise be configured and operable in accordance with at least some of the teachings of U.S. patent application Ser. No. 14/667,842, entitled "Method of Applying a Buttress to a Surgical Stapler," filed Mar. 25, 2015, now U.S. Patent Pub. No. 2016/0278774, published Sep. 26, 2016, issued as U.S. Pat. No. 10,349,939 on Jul. 16, 2019, the disclosure of which is incorporated by reference herein.

A. Buttress Assembly Including Retention Tabs

FIG. 102 shows an exemplary alternative buttress assembly (6210) removably coupled to an exemplary alternative staple cartridge (6270). In the example shown, buttress assembly (6210) is releasably and mechanically coupled to cartridge (6270) rather than being adhesively bonded to cartridge (6270). Buttress assembly (6210) includes a pair of opposing buttress bodies (6212). Buttresses bodies (6212) may be configured to be substantially similar to buttress bodies (100, 112) described above. It should be understood that upon actuation of end effector (640), a series of staples (690) will similarly capture and retain buttress assembly (6210) against layers of tissue ($T_1$, $T_2$), thereby securing buttress assembly (6210) to tissue ($T_1$, $T_2$) in a similar manner as shown in FIG. 6. In some examples, buttress assembly (6210) may be utilized in conjunction with buttress assembly (100) on anvil (60) such that a series of staples (690) will similarly capture and retain buttress assemblies (100, 6210) against layers of tissue ($T_1$, $T_2$), thereby securing buttress assemblies (100, 6210) to tissue ($T_1$, $T_2$) in a similar manner as shown in FIG. 6.

In the present example, one buttress body (6212) is disposed on deck (6273) on one side of channel (6272) and the other buttress body (6212) is disposed on deck (6273) on the other side of channel (6272), such that buttress assembly (6210) does not span across channel (6272), and such that knife member (680) does not cut through buttress assembly (6210) during actuation of end effector (640), thus potentially reducing the force required by an operator to actuate end effector (640).

Staple cartridge (6270) is removably coupled to lower jaw (650) of end effector (640). Staple cartridge (6270) is substantially similar to staple cartridge (670) except for that staple cartridge (6270) includes a plurality of recesses (6280, 6282, 6284) for removably receiving corresponding retention features (6286, 6288, 6290) on buttresses (6212a, 6212b). As shown best in FIGS. 104A-104B, retention feature (6286) comprises a U-shaped tab extending from a rear portion of each buttress body (6212) in a direction parallel to channel (6272). Tab (6286) is configured to fit at least partially within recess (6280). As best seen in FIG. 103, tab (6286) is configured to press fit within recess (6280) when tab (6286) is directed into recess (6280). It should be understood that tab (6286) may comprise a resilient material that provides a bias for the press fit.

Retention feature (6288) comprises a tab extending away from channel (6272), at an oblique angle relative to a plane defined by the faces of buttresses (6212a, 6212b) and downwardly relative to (i.e., toward) cartridge (6270). Tab (6288) is configured to press fit within recess (6282) when tab (6286) is directed into recess (6282). In some versions, tab (6288) comprises a resilient material that provides a bias for the press fit.

Retention feature (6290) comprises a tab extending from a distal end of buttress (6290) in a direction that is generally parallel to slot (6272). Tabs (6286, 6288, 6290) of the present example are configured to press fit into slots (6280, 6282, 6284), respectively, but in other examples tabs (6286, 6288, 6290) may be retained relative to slots (6280, 6282, 6284) in other suitable manners, such as resilient snap fitting, for example. In some examples, recesses may (6280, 6282) include a portion that extends inwardly from an outer portion of recess toward slot (6272) in order to create further interference with tabs (6286, 6288), respectively. Similarly, in some examples, recesses (6284) may include one or more portions that extend inwardly toward a middle of recesses (6284) that create further interference with tabs (6290). Other suitable configurations of recesses (6280, 6282, 6284) and tabs (6286, 6288, 6290) will be apparent to persons skilled in the art in view of the teachings herein.

In the present example, any or all of tabs (6286, 6288, 6290) comprise the same material or materials as buttress bodies (6212). In other examples, any or all of tabs (6286, 6288, 6290) may comprise a plurality of laminate, bioabsorbable layers, which may or may not include a layer that comprises part of buttress bodies (6212). Other suitable configurations and materials that tabs (6286, 6288, 6290) may comprise will be apparent to persons skilled in the art in view of the teachings herein.

The retention force provided between retention features (6286, 6288, 6290) and recesses (6280, 6282, 6284) is sufficient to maintain the removable coupling between buttress assembly (6210) and cartridge (6270) absent a sufficient decoupling force. However, buttress assembly (6210) is configured to decouple from cartridge (6270) in response to a sufficient decoupling force input, as discussed in more detail below. As discussed above with respect to the similarly operable staple cartridge (670), a wedge sled (678) translates longitudinally through cartridge (6270) in order to drive staples (690) upwardly toward anvil (60). In the present example, recesses (6280, 282) are positioned such that camming surface (679) of wedge sled (678) will to contact tabs (6286, 6288) as wedge sled (678) translates through cartridge (6270), and thereby urge contact tabs (6286. 6288) upwardly out of engagement with recesses (6280, 6282), to assist in decoupling buttress assembly (6210) from cartridge (6270).

More particularly, as shown in the transition from FIG. 104A to FIG. 104B, as wedge sled (678) translates longitudinally through cartridge (670) as discussed above, cam surface (679) of sled (678) is urged against tab (6286), thus urging tab (6286) out of recess (6280) and away from cartridge (6270). As sled (678) advances further longitudinally, cam surface (679) of wedge sled (678) is urged against tab (6288), thus urging tab (6288) and a more distal portion of buttress assembly (6210) out of recess (6282) and away from cartridge (6270). Thus, the upward camming force provided by cam surface (679) of sled (678) assists in releasing buttress assembly (6210) from cartridge (6270) such that the release of buttress assembly (6210) from cartridge (6270) does not rely mostly or entirely on being captured by staples (690). In some examples, however, the upward force associated with being captured by staples (690) may be sufficient to release buttress assembly (6210) from cartridge (6270). Tabs (6290) are released from recesses (6284) as the more distal portions of buttress bodies (6212) are captured by staples (690).

B. Buttress Assemblies Including Slots for Engaging with Connector Members on Cartridge Deck FIGS. 105-109 show an exemplary alternative buttress assembly (6310) comprising a buttress body (6312) that is removably coupled to an exemplary alternative staple cartridge (6370). In the example shown, buttress assembly (6310) is releasably and mechanically coupled to cartridge (6370) rather than being adhesively bonded to cartridge (6370). Buttress body (6312) may be configured to be substantially similar to buttress (112) described above. It should be understood that upon actuation of end effector (640), a series of staples (690) will similarly capture and retain buttress assembly (6310) against layers of tissue ($T_1$, $T_2$), thereby securing buttress assembly (6310) to tissue ($T_1$, $T_2$) in a similar manner as shown in FIG. 6. In some examples, buttress assembly (6310) may be utilized in conjunction with buttress assembly (100) on anvil (60) such that a series of staples (690) will similarly capture and retain buttress assemblies (100, 6310) against layers of tissue ($T_1$, $T_2$), thereby securing buttress assemblies (100, 6310) to tissue ($T_1$, $T_2$) in a similar manner as shown in FIG. 6.

Cartridge (6370) is removably coupled to lower jaw (650) of end effector (640). Cartridge (6370) is configured to be substantially similar to cartridge (670) discussed above, except for that cartridge (6370) includes connector members (6380) at opposing portions of cartridge deck (6373) that, as discussed in further detail below, releasably and mechanically couple buttress assembly (6310) to cartridge deck (6373).

As best seen in FIGS. 106-107, buttress (6312) comprises a proximal end (6314), a distal end (6316), with a tapered portion (6318) toward proximal end (6314). Buttress (6312) also includes an elongate slot (6313) extending between the proximal and distal ends, a rectangular proximal recess (6324), and a rectangular distal recess (6326). Slot (6313) and recesses (6324, 6326) are positioned and configured to correspond to channel (6372), such that the majority of buttress (6312) does not span across channel (6372), and such that knife member (680) does not cut through buttress (6312) during actuation of end effector (640). Buttress (6312) further includes a proximal slot (6320) and a distal slot (6322) which, as discussed below, are configured assist in coupling buttress (6312) to cartridge (6370). In the present example, slots (6320, 6322) extend perpendicularly relative to a longitudinal axis (6327) of buttress body (6312).

As best seen in FIG. 105, connector member (6380) includes a first end (6382) with a head (6384) including an aperture (6386), a notch (6387), a middle portion (6388), and a second end (6390) including opposing legs (6392). In the present example, head (6384) has a diamond shape, though it should be understood that head (6384) may have any other suitable shape, including but not limited to the shapes of the various exemplary alternative heads (6884a-688841) shown in FIGS. 114-125. In the present example, connector members (6380) are bonded to cartridge deck (6373) by various suitable methods including, but not limited to, adhesives. In addition or in the alternative, legs (6392) may be fitted into corresponding slots (not shown) in cartridge (6370) and may be secured in those slots using any suitable features and techniques as will be apparent to those of ordinary skill in the art in view of the teachings herein. As shown, connector member (6380) at the proximal end of cartridge (6370) is oriented such that head (6384) points in a distal direction, and connector member (6380) at the distal end of cartridge (6370) is oriented such that head (6384) points in a proximal direction.

FIG. 108 shows one manner of removably coupling buttress body (6212) to connector portions (6380). As shown, an operator may direct the proximal end (6314) of buttress body (6312) toward connector portion (6380) such that head (6384) enters slot (6320) (in a direction parallel to axis (6327)) on second side (6330) of buttress body (6312), until a trailing edge (6394) of connector portion (6380) extends out of slot (6320). Similarly, an operator may direct the distal end (6316) of buttress (6312) toward the other connector portion (6380) such that head (6384) enters slot (6322) (in a direction parallel to axis (6327)) on first side of buttress body (6312), until a trailing edge (6394) of connector portion (6380) extends out of slot (6322), and slot (6322) engages with notch (6387). Due to the configuration of slots (6320, 6322) and head (6384), proximal end (6314) of buttress body (6312) is substantially prevented from moving in the proximal direction, and distal end (6316) of buttress body (6312) is substantially prevented from moving in the distal direction. Thus, the releasable mechanical coupling between buttress body (6312) and connector portions (6380) substantially prevents proximal and distal movement of buttress body (6312).

The retention force provided by the engagement between connector portions (6380) and slots (6320, 6322) is sufficient to maintain the removable coupling between buttress assembly (6310) absent a sufficient decoupling force. However, buttress assembly (6210) is configured to decouple from cartridge (6370) in response to a sufficient decoupling force input. In the present example, the upward force associated with being captured by staples (690) provides sufficient decoupling force to release buttress assembly (6310) from connector portions (6380) of cartridge (6370), as discussed in further detail below.

As noted above, due to the presence of elongate slot (6313), one portion of buttress body (6312) is disposed on deck (6373) on one side of channel (6372) and another portion of buttress body (6312) is disposed on deck (6373) on the other side of channel (6372), such that only a portion of buttress body (6312) spans across channel (6372). Therefore, the effort required to actuate end effector (640) and sever and staple tissue is reduced. As end effector (640) is actuated and staples (690) capture buttress body (6312), the portion of buttress body (6312) near slot (6320) is driven upwardly and slips out of engagement with connector portion (6380). Substantially contemporaneously, knife member (680) may sever the portion of buttress body (6312) near slot (6320) as well as connector portion (6380). By way of example only, connector portion (6380) may be constructed of any suitable material that may be severed by knife member (680), including but not limited to a thin plastic film, a non-woven mesh, a paper-like material, and/or any other suitable kind(s) of material(s) having any suitable form as will be apparent to those of ordinary skill in the art in view of the teachings herein. As knife member (680) and sled (678) travel further longitudinally, proximal portion of buttress body (6312) is captured by staples (690) and subjected to a sufficient decoupling force, and is thus urged away from and out of engagement with other connector portion (6380).

FIGS. 110-113 show exemplary alternative buttress assemblies (6410, 510, 610, 6710), connector portions (6480, 580, 680, 6780), and staple cartridges (6470, 570, 670, 6770), respectively, that are configured to operate substantially similarly to buttress assembly (6310), connector portion (6380), and staple cartridge (670, 6370), except for the differences below. In each of the examples shown in FIGS. 110-113, cartridges (6470, 570, 670, 6770) are removably coupled to lower jaw (650) of end effector (640). It should be understood that upon actuation of end effector (640), a series of staples (690) will similarly capture and retain buttress assembly (6410, 510, 610, 6710) against layers of tissue ($T_1$, $T_2$), thereby securing buttress assembly (6410, 510, 610, 6710) to tissue ($T_1$, $T_2$) in a similar manner as shown in FIG. 6. In some examples, buttress assembly (6410, 510, 610, 6710) may be utilized in conjunction with buttress assembly (100) on anvil (60) such that a series of staples (690) will similarly capture and retain buttress assembly (100) and a buttress assembly (6410, 510, 610, 6710) against layers of tissue ($T_1$, $T_2$), thereby securing buttress assemblies (100) and buttress assembly (6410, 510, 610, 6710) to tissue ($T_1$, $T_2$) in a similar manner as shown in FIG. 6.

As shown in FIG. 110, two connector portions (6480a, 6480b) are adhesively bonded to cartridge deck (6473), though other manners of coupling connector portions (6480a, 6480b) to deck (6473) will be apparent to persons skilled in the art in view of the teachings herein. In the example shown, proximal connector portion (6480a) includes a first end (6482a) with a head (6484a) that is triangularly shaped. Alternative examples of head (6484a) may include any other suitable shape, including the shapes of any one of alternative heads (6884a-6884l) shown in FIGS. 114-125. Second end (6486a) includes a tapered portion to accommodate the shape of lower jaw (650), as well for the travel of knife member (680) through channel (6472). Similarly, distal connector portion (6480b) includes a first end (6482b) with a head (6484b) that is triangularly shaped. Alternative examples of head (6484b) may include any other suitable shape, including the shapes of any one of alternative heads (6884a-6884l) shown in FIGS. 114-125. Second end (6486b) includes a shape that is substantially similar to an end portion of cartridge (6470) and covers a distal portion of channel (6472).

Buttress body (6412) includes an elongate slot (6413) extending between a proximal end (6414) and a distal end (6416). Although not shown, buttress body (6412) includes proximal and distal slots (similar to proximal and distal slots (6320, 6322)) that extend perpendicularly relative to axis (6427) of buttress body (6412). Buttress body (6412) of the present example includes a distal recess (6426) that is longer than distal recess (6326). Buttress body (6412) may be removably coupled to cartridge (6470) via connector portions (6480a, 6480b) in a similar manner as buttress body (6312) and connector portions (6380). That is, buttress body (6412) may be directed into engagement with a first one of the connector portions (6480a, 6480b) such that that one of the heads (6484a, 6484b) enters a respective one of the slots (in a direction parallel to axis (6427)) on first side of buttress body (6312) and the slot engages with notch (not shown). Then, another side of buttress body (6412) may be directed into engagement with a second one of the connector portions (6480a, 6480b) such that that one of the heads (6484a, 6484b) enters a respective one of the slots (in a direction parallel to axis (6427)), and the other slot engages with notch (not shown). Due to the configuration of slots and heads (6484a, 6484b), proximal end (6414) of buttress body (6412) is substantially prevented from moving in the proximal direction, and distal end (6416) of buttress body (6412) is substantially prevented from moving in the distal direction. Thus, the releasable mechanical coupling between buttress body (6412) and connector portions (6480a, 6480b) substantially prevents proximal and distal movement of buttress body (6412).

The retention force provided by the engagement between connector portions (6480a, 6480b) and slots (6420, 6422) is sufficient to maintain the removable coupling between buttress assembly (6410) and cartridge (6470) absent a sufficient decoupling force. However, buttress assembly (6410) is configured to decouple from cartridge (6470) in response to a sufficient decoupling force input. In the present example, the upward force associated with being captured by staples (690) provides sufficient decoupling force to release buttress assembly (6410) from connector portions (6480a, 6480b) of cartridge (6470), as discussed in further detail below.

As shown, one portion of buttress body (6412) is disposed on deck (6473) on one side of channel (6472) and another portion of buttress body (6412) is disposed on deck (6473) on the other side of channel (6472), such that only a portion of buttress body (6312) spans across channel (6472). Therefore, the effort required to actuate end effector (640) and sever and staple tissue is reduced. As end effector (640) is actuated and staples (690) capture buttress body (6412), the portion of buttress body (6412) near the proximal slot and connector portion (6480a) is driven upwardly and slips out of engagement with connector portion (6480a). Substantially contemporaneously, knife member (680) may sever the portion of buttress body (6412) near connector portion (6480a), as well as connector portion. As knife member (680) and sled (678) travel further longitudinally, proximal portion of buttress body (6312) is captured by staples (690) and is thus urged away from and out of engagement with other connector portion (6480b). However, due to the more proximal position of connector portion (6480b) (relative to the example shown in FIG. 109), connector portion (6480b) may also be severed as knife member (680) and sled (678) advance longitudinally further.

Referring to FIG. 111, buttress assembly (6510) includes a pair of buttress bodies (6512). As shown, one buttress body (6512) is disposed on deck (6573) on one side of channel (6572) and the other buttress body (6512) is disposed on deck (6573) on the other side of channel (6572), such that buttress assembly (6510) does not span across channel (6572), and such that knife member (680) does not sever buttress assembly (6210) during actuation of end effector (640), thus potentially reducing the force required by an operator to actuate end effector (640). In the example shown, buttress bodies (6512) each include a proximal slot (6520) and a distal slot (6522) extending perpendicularly relative to axis (6527) of buttress assembly (6510).

Staple cartridge (6570) includes exemplary alternative connector members (6580) on each side of channel (6572) and at each end of cartridge (6570). As shown, each connector member (6580) includes a first end (6582) with a head (6584) including an aperture (6586), a notch (6587), and a second end portion (6590). Alternative examples of head (6584) may include any other suitable shape, including the shapes of any one of alternative heads (6884a-68841) shown in FIGS. 114-125.

To couple a buttress body (6512) to a set of connector portions (6580), proximal end (6514) of buttress body (6512) may be directed toward connector portion (6580) such that head (6584) enters slot (6520) (in a direction parallel to axis (6527)) on second side of buttress body (6512), until a trailing edge of connector portion (6580) extends out of slot (6520) and slot (6520) engages with notch (6587). Similarly, an operator may direct the distal end (6516) of buttress (6512) toward the other connector portion (6580) such that head (6584) enters slot (6522) (in a direction parallel to axis (6527)) on first side of buttress body (6512), until a trailing edge of connector portion (6580) extends out of slot (6522), and slot (6522) engages with notch (6587). As shown, connector member (6380) at the proximal end of cartridge (6570) is oriented such that head (6584) points in a distal direction, and connector member (6580) at the distal end of cartridge (6570) is oriented such that head (6584) points in a proximal direction. Due to the configuration of slots (6520, 6522) and head (6584), proximal end (6514) of buttress body (6512) is substantially prevented from moving in the proximal direction, and distal end (6516) of buttress body (6512) is substantially prevented from moving in the distal direction. Thus, the releasable mechanical coupling between buttress bodies (6512) and connector portions (6580) substantially prevents proximal and distal movement of buttress body (6512).

The retention force provided by the engagement between connector portions (6580) and slots (6520, 522) is sufficient to maintain the removable coupling between buttress assembly (6510) and cartridge (6570) absent a sufficient decoupling force. However, buttress assembly (6510) is configured to decouple from cartridge (6570) in response to a sufficient decoupling force input. In the present example, the upward force associated with being captured by staples (690) provides sufficient decoupling force to release buttress assembly (6510) from connector portions (6580) of cartridge (6570), as discussed in further detail below.

As shown, one buttress body (6512) is disposed on deck (6573) on one side of channel (6572) and another portion of buttress body (6512) is disposed on deck (6573) on the other side of channel (6572), such that no portion of buttress bodies (6512) spans across channel (6572). Therefore, the effort required to actuate end effector (640) and sever and staple tissue is reduced. As end effector (640) is actuated and staples (690) capture buttress body (6512), the portion of buttress body (6512) near the proximal slot (6520) and connector portions (6580) is driven upwardly and slips out of engagement with connector portion (6580). As knife member (680) and sled (678) travel further longitudinally, proximal portion (6514) of buttress body (6512) is captured by staples (690) and the portion of buttress body (6512) near the distal slot (6522) is driven upwardly and slips out of engagement with connector portion (6580). Due to the positions of the buttress bodies (6512) and connector portions (6580) away from channel (6572), knife member (6580) does not sever any of buttress bodies (6512) or connector portions.

FIG. 112 shows another exemplary alternative buttress assembly (6610) in combination with an exemplary alternative staple cartridge (6670) including exemplary alternative connector portions (6680). Buttress assembly (6610) is substantially identical to buttress assembly (6510) discussed above, except for that buttress bodies (6612) include slots (6620, 6622) that extend at an oblique angle (0) relative to the longitudinal axis (6627) of buttress assembly (6610).

Staple cartridge (6670) includes exemplary alternative connector members (6680), each of which extends partially along channel (6672) in a manner so as not to impede traversal of knife member (680) therethrough. As shown, each connector member (6580) includes a first end (6682) with a head (6684) including an aperture (6686), a notch (6687), and a second end portion (not shown) extending downwardly relative to staple deck (6673) Alternative examples of head (6684) may include any other suitable shape, including the shapes of any one of alternative heads (6884a-68841) shown in FIGS. 114-125.

To couple a buttress body (6612) to a set of connector portions (6680), proximal end (6614) of buttress body (6612) is directed toward connector portion (6680) such that head (6384) enters slot (6620) (in a direction transverse to axis (6627)) on second side of buttress body (6612), until a trailing edge of connector portion (6680) extends out of slot (6620) and slot (6620) engages with notch (6687). Similarly, an operator may direct the distal end (6616) of buttress (6612) toward the other connector portion (6680) such that head (6684) enters slot (6622) (in a direction transverse to axis (6627)) on first side of buttress body (6612), until a trailing edge of connector portion (6680) extends out of slot (6622), and slot (6622) engages with notch (6687). As shown, connector member (6680) at the proximal end of cartridge (6670) is oriented such that head (6684) points in a distal direction at angle (0) relative to axis (6627), and connector member (6680) at the distal end of cartridge (6670) is oriented such that head (6684) points in a proximal direction at an angle (0) relative to axis (6627). Due to the configuration of slots (6620, 6622) and head (6684), proximal end (6614) of buttress body (6612) is substantially prevented from moving in the proximal and distal directions (parallel to axis (6627)), and distal end (6616) of buttress body (6612) is substantially prevented from moving in the proximal and distal directions (parallel to axis (6627)). Thus, the releasable mechanical coupling between buttress bodies (6612) and connector portions (6680) substantially resists proximal and distal movement of buttress body (6612).

The retention force provided by the engagement between connector portions (6680) and slots (6620, 6622) is sufficient to maintain the removable coupling between buttress assembly (6610) and cartridge (6670) absent a sufficient decoupling force. However, buttress assembly (6610) is configured to decouple from cartridge (6670) in response to a sufficient decoupling force input. In the present example, the upward force associated with being captured by staples (690) provides sufficient decoupling force to release buttress assembly (6610) from connector portions (6680) of cartridge (6670), as discussed in further detail below.

As shown, one buttress body (6612) is disposed on deck (6673) on one side of channel (6672) and another portion of buttress body (6612) is disposed on deck (6673) on the other side of channel (6672), such that no portion of buttress body (6612) spans across channel (6672). Therefore, the effort required to actuate end effector (640) and sever and staple tissue is reduced. As end effector (640) is actuated and staples (690) capture buttress body (6612), the portion of buttress body (6612) near the proximal slot (6620) and connector portions (6680) is driven upwardly and slips out of engagement with connector portion (6680). As knife member (680) and sled (678) travel further longitudinally, proximal portion of buttress body (6612) is captured by staples (690) and the portion of buttress body (6612) near the distal slot (6622) is driven upwardly and slips out of engagement with connector portion (6680). Due to the positions of the buttress bodies (6612) and connector portions (6680) away from channel (6672) knife member (6680) does not sever any of buttress bodies (6612) or connector portions (6680).

FIG. 113 shows another exemplary alternative buttress assembly (6710) in combination with an exemplary alternative staple cartridge (6770) including exemplary alternative connector portions. Buttress assembly (6710) is substantially identical to buttress assembly (6510, 610) discussed above, except for that buttress bodies (6712) include slots (6720, 6722) that extend parallel to the longitudinal axis (6727) of buttress assembly (6710).

Staple cartridge (6770) includes exemplary alternative connector members (6780), each of which extends partially along channel (6772) in a manner so as not to impede traversal of knife member (680) therethrough. As shown, each connector member (6580) includes a first end (6782) with a head (6784) including an aperture (6786), a notch (6787), and a second end portion (6790) extending transversely relative to axis (6727). As shown in the present example, each second end portion (6790) extends across channel (6772). Thus, each connector member (6780) spans channel (6772) in an opposite direction relative to an adjacent connector member (6780). Thus, heads (6784) of adjacent connector portions (6780) extend in offset, opposite, and parallel directions. Alternative examples of head (6784) may include any other suitable shape, including the shapes of any one of alternative heads (6884a-68841) shown in FIGS. 114-125. Other suitable configurations of connector members (6780) will be apparent to persons skilled in the art in view of the teachings herein.

To couple a buttress body (6712) to a set of connector portions (6780), proximal end (6714) of buttress body (6712) is directed toward connector portion (6780) such that head (6784) enters slot (6720) (in a direction perpendicular to axis (6727)) on second side of buttress body (6712), until a trailing edge of connector portion (6780) extends out of slot (6720) and slot (6720) engages with notch (6787). Similarly, an operator may direct the distal end (6716) of buttress (6712) toward the other connector portion (6780) such that head (6784) enters slot (6722) (in a direction perpendicular to axis (6727)) on first side of buttress body (6712), until a trailing edge of connector portion (6780) extends out of slot (6722), and slot (6722) engages with notch (6787). Due to the configuration of slots (6720, 6722) and head (6784), proximal end (6714) of buttress body (6712) is substantially prevented from moving in the proximal and distal directions (parallel to axis (6727)), and distal end (6716) of buttress body (6712) is substantially prevented from moving in the proximal and distal directions (parallel to axis (6727)). Thus, the releasable mechanical coupling between buttress bodies (6712) and connector portions (6580) substantially prevents proximal and distal movement of buttress body (6712).

The retention force provided by the engagement between connector portions (6780) and slots (6720, 6722) is sufficient to maintain the removable coupling between buttress assembly (6710) and cartridge (6770) absent a sufficient decoupling force. However, buttress assembly (6710) is configured to decouple from cartridge (6770) in response to a sufficient decoupling force input. In the present example, the upward force associated with being captured by staples (690) provides sufficient decoupling force to release buttress assembly (6710) from connector portions (6780) of cartridge (6770), as discussed in further detail below.

As shown, one buttress body (6712) is disposed on deck (6773) on one side of channel (6772) and another portion of buttress body (6712) is disposed on deck (6773) on the other side of channel (6772), such that no portion of buttress body (6712) spans across channel (6772). However, second end portions (6790) span channel (6772). Nonetheless, the effort required to actuate end effector (640) and sever and staple tissue is reduced. As end effector (640) is actuated and staples (690) capture buttress body (6712), the portion of buttress body (6712) near the proximal slot (6720) and connector portions (6780) is driven upward and slips out of engagement with connector portion (6780). As knife member (680) and sled (678) travel further longitudinally, proximal portion of buttress body (6712) is captured by staples (690) and the portion of buttress body (6712) near the distal slot (6722) is driven upward and slips out of engagement with connector portion (6780). Due to the positions buttress bodies (6712) being away from channel (6772), knife member (680) does not sever any of buttress bodies (6712).

C. Buttress Assemblies with Attachment Members for Engaging with Staple Cartridge Deck FIGS. 126 and 129-131 show an exemplary alternative staple cartridge (6970) incorporated into lower jaw (650) of end effector (640). Staple cartridge (6970) is configured to operate substantially similar to staple cartridge (670), except for the differences below. Particularly, staple cartridge (6970) includes a pair of apertures (6990) positioned proximal to staple openings (6945). Apertures (6990) are configured to receive attachment features (6980) of a buttress assembly (6910) in order to removably and mechanically couple buttress assembly (6910), as discussed in further detail below.

As shown best in FIGS. 127-128, buttress assembly (6910) includes a buttress body (6912) including a proximal end (6914), a distal end (6916), and a plurality of apertures (6918) extending along an axis (6927) thereof. Apertures (6916) may reduce the amount of force required for knife member (680) to cut through and traverse past severed tissue and buttress body (6912). While four apertures (6918) are shown in the present example, in alternative examples there may be less than (e.g., three, two, one, or zero) or more than four apertures (6918). Other suitable configurations of apertures (6918) will be apparent to persons skilled in the art in view of the teachings herein.

As shown, at the proximal end (6914), attachment members (6980) extend proximally from buttress body (6912). Particularly, attachment members (6980) include a first portion (6982) extending in a perpendicular direction away from buttress body (6912), and a second portion (6984) extending proximally away from first portion (6982) and parallel to buttress body (6912). In the present example, any or all of attachment members (6980) comprise the same material or materials as buttress body (6912). In other examples, any or all of attachment members (6980) may comprise a plurality of laminate, bioabsorbable layers, which may or may not include a layer that comprises part of buttress body (6912). Other suitable configurations and materials that attachment members (6980) may comprise will be apparent to persons skilled in the art in view of the teachings herein.

In order to removably couple buttress assembly (6910) to cartridge (6970), an operator may direct the second portions (6984) of attachment members (6980) into apertures (6990) proximally and downwardly through apertures (6990) until the first portion (6982) enters apertures (6990) and the bottom face (6913) of buttress body (6912) is flush with cartridge deck (6973). In the present example, apertures (6990) are positioned on cartridge (6970), and attachment members are sized and configured such that when attachment members (6980) are directed into apertures (6990), attachment members (6980) are releasably held between an underneath portion (6973a) of deck (6973) and rails (678a, 678b) of sled (678). In an alternative example, rather than being held between the top of rails (678a, 678b) and underneath portion (6973a) of deck (6973), attachment members may be releasably held (e.g., via an interference fit), between the rails (678a, 678b) of sled.

The retention force provided by the engagement between attachment members (6980), cartridge deck (6973), and sled rails (678a, 678b) is sufficient to maintain the removable coupling between buttress assembly (6910) and cartridge (6770) absent a sufficient decoupling force. However, buttress assembly (6910) is configured to decouple from cartridge (6970) in response to a sufficient decoupling force input. In the present example, longitudinal movement of sled (678) disengages sled rails (678a, 678b) from second portion, reducing the retention force between sled rails (678a, 678b), cartridge deck (6973), and attachment members. Moreover, the upward force associated with being captured by staples (690) provides sufficient decoupling force to release buttress assembly (6910) from connector portions (6980) of cartridge (6970), as discussed in further detail below.

It should be understood that upon actuation of end effector (640), a series of staples (690) will similarly capture and retain buttress assembly (6910) against layers of tissue ($T_1$, $T_2$), thereby securing buttress assembly (6910) to tissue ($T_1$, $T_2$) in a similar manner as shown in FIG. 6. In some examples, buttress assembly (6910) may be utilized in conjunction with buttress assembly (100) on anvil (60) such that a series of staples (690) will similarly capture and retain buttress assemblies (100, 6910) against layers of tissue ($T_1$, $T_2$), thereby securing buttress assemblies (100, 6910) to tissue ($T_1$, $T_2$) in a similar manner as shown in FIG. 6.

FIGS. 132 and 135-136 show an exemplary alternative staple cartridge (61070) incorporated into lower jaw (650) of end effector (640). Staple cartridge (61070) is configured to operate substantially similar to staple cartridge (670), except for the differences below. Particularly, staple cartridge (61070) includes a pair of apertures (61090) positioned proximal to staple openings (6545). Apertures (61090) are configured to receive attachment features (61080) of a buttress assembly (61010) in order to removably and mechanically couple buttress assembly (61010), as discussed in further detail below.

As shown best in FIGS. 133-134, buttress assembly (61010) includes a buttress body (61012) having a proximal end (61014), a distal end (61016), and a plurality of apertures (61018) extending along an axis (1027) thereof. Apertures (61016) may reduce the amount of force required for knife member (680) to cut through and traverse past severed tissue and buttress body (61012). While four apertures (61018) are shown in the present example, in alternative examples there may be less than (e.g., three, two, one, or zero) or more than four apertures (61018). Other suitable configurations of apertures (61018) will be apparent to persons skilled in the art in view of the teachings herein.

As shown, attachment members (61080) include a first portion (61082) extending in a perpendicular direction away from proximal end (61014) of buttress body (61012), and a second portion (61084) extending perpendicularly away from first portion (61082) toward distal end (61016) and parallel to buttress body (61012). In the present example, any or all of attachment members (61080) comprise the same material or materials as buttress body (61012). In other examples, any or all of attachment members (61080) may comprise a plurality of laminate, bioabsorbable layers, which may or may not include a layer that comprises part of buttress body (61012). Other suitable configurations and materials that attachment members (61080) may comprise will be apparent to persons skilled in the art in view of the teachings herein.

In order to removably couple buttress assembly (61010) to cartridge (61070), an operator may direct the second portions (61084) of attachment members (61080) into apertures (61090) distally and downwardly through apertures (61090) until the first portion (61082) may enter apertures (61090) and the bottom face (61013) of buttress body (61012) is flush with cartridge deck (61073). In the present example, apertures (61090) are positioned on cartridge (61070), and attachment members are sized and configured such that when attachment members (61080) are directed into apertures (61090), attachment members (61080) are releasably held between an underneath portion (61073a) of deck (61073) and rails (678a, 678b) of sled (678).

The retention force provided by the engagement between attachment members (61080), cartridge deck (61073), and sled rails (678a, 678b) is sufficient to maintain the removable coupling between buttress assembly (61010) and cartridge (61070) absent a sufficient decoupling force. However, buttress assembly (61010) is configured to decouple from cartridge (61070) in response to a sufficient decoupling force input. In the present example, longitudinal movement of sled (678) disengages sled rails (678a, 678b) from second portion, reducing the retention force between sled rails (678a, 678b), cartridge deck (61073), and attachment members. Moreover, the upward force associated with being captured by staples (690) provides additional and sufficient decoupling force to release buttress assembly (61010) from connector portions (61080) of cartridge (61070), as discussed in further detail below.

It should be understood that upon actuation of end effector (640), a series of staples (690) will similarly capture and retain buttress assembly (61010) against layers of tissue ($T_1$, $T_2$), thereby securing buttress assembly (61010) to tissue ($T_1$, $T_2$) in a similar manner as shown in FIG. 6. In some examples, buttress assembly (61010) may be utilized in conjunction with buttress assembly (100) on anvil (60) such that a series of staples (690) will similarly capture and retain buttress assemblies (100, 61010) against layers of tissue ($T_1$, $T_2$), thereby securing buttress assemblies (100, 61010) to tissue ($T_1$, $T_2$) in a similar manner as shown in FIG. 6.

FIGS. 137 and 140-141 show an exemplary alternative staple cartridge (61170) incorporated into lower jaw (650) of end effector (640). Staple cartridge (61170) is configured to operate substantially similar to staple cartridge (670), except for the differences below. Particularly, staple cartridge (61170) includes a pair of apertures (61190) positioned proximal to staple openings (61145). Apertures are configured to receive attachment features (61180) of a buttress assembly (61110) in order to removably and mechanically couple buttress assembly (61110), as discussed in further detail below.

As shown best in FIGS. 138-139, buttress assembly (61110) includes a buttress body (61112) having a proximal end (61114), a distal end (61116), and a plurality of apertures (61118) extending along an axis (1127) thereof. Apertures (61116) may reduce the amount of force required for knife member (680) to cut through and traverse past severed tissue and buttress body (61112). While four apertures (61116) are shown in the present example, in alternative examples there may be less than (e.g., three, two, one, or zero) or more than four apertures (61116). Other suitable configurations of apertures (61116) will be apparent to persons skilled in the art in view of the teachings herein.

As shown, attachment members (61180) include a first portion (61182) extending in a perpendicular direction away from proximal end (61014) of buttress body (61112). In the present example, any or all of attachment members (61180) comprise the same material or materials as buttress body (61112). In other examples, any or all of attachment members (61180) may comprise a plurality of laminate, bioabsorbable layers, which may or may not include a layer that comprises part of buttress body (61112). Other suitable configurations and materials that attachment members (61180) may comprise will be apparent to persons skilled in the art in view of the teachings herein.

In order to removably couple buttress assembly (61110) to cartridge (61170), an operator may direct the first portions (61182) of attachment members (61180) into apertures (61190) downwardly through apertures (61190) (in a direction perpendicular to deck (61173)) until the bottom face (1113) of buttress body (61112) is flush with cartridge deck (61173). In the present example, apertures (61190) are positioned on cartridge (61170), and attachment members (61180) are sized and configured such that when attachment members (61180) are directed into apertures (61190), each attachment member (61180) is releasably held between each rail (678a, 678b) of sled (678). In the example shown, each attachment member (61180) is interference fit in between each set of sled rails (678a, 678b), but may alternatively be releasably held in other suitable manners.

The retention force provided by the engagement between attachment members (61180) and sled rails (678a, 678b) is sufficient to maintain the removable coupling between buttress assembly (61110) and cartridge (61170) absent a sufficient decoupling force. However, buttress assembly (61110) is configured to decouple from cartridge (61170) in response to a sufficient decoupling force input. In the present example, longitudinal movement of sled (678) disengages sled rails (678a, 678b) from attachment members (61180), reducing or eliminating the retention force between sled rails (678a, 678b) and attachment members (61180). Moreover, the upward force associated with being captured by staples (690) provides additional and sufficient decoupling force to release buttress assembly (61110) from attachment members (61180) of cartridge (61170), as discussed in further detail below.

It should be understood that upon actuation of end effector (640), a series of staples (690) will similarly capture and retain buttress assembly (61110) against layers of tissue ($T_1$, $T_2$), thereby securing buttress assembly (61110) to tissue ($T_1$, $T_2$) in a similar manner as shown in FIG. 6. In some examples, buttress assembly (61110) may be utilized in conjunction with buttress assembly (100) on anvil (60) such that a series of staples (690) will similarly capture and retain buttress assemblies (100, 61110) against layers of tissue ($T_1$, $T_2$), thereby securing buttress assemblies (100, 61110) to tissue ($T_1$, $T_2$) in a similar manner as shown in FIG. 6.

FIG. 142 shows another exemplary alternative buttress assembly (61210) releasably coupled to staple cartridge (670) via an attachment member (61280). Unlike the previous examples, staple cartridge (670) does not need to be modified in order to accommodate an attachment member (61280) of buttress assembly (61210). In the example shown, buttress assembly (61210) comprises a buttress body (61212) extending including a proximal end (61214) and a distal end (61216). Buttress body (61212) extends along a longitudinal axis (61227).

In the example shown in FIG. 143, attachment member (61280a) is in the form of a tab extending perpendicularly relative to the proximal end of buttress body (61212). In the present example, attachment member (61280a) comprises the same material or materials as buttress body (61212). Other suitable configurations and materials that attachment member may comprise will be apparent to persons skilled in the art in view of the teachings herein. For example, as shown in FIG. 144, attachment member (61280b) is substantially identical to attachment member (61280a), except for that attachment member (61280b) comprises a laminate material. Particularly, the laminate material comprises a plurality of laminate, bioabsorbable layers, which may or may not include a layer that comprises part of buttress body (61212). Other suitable configurations and materials that attachment member (61280b) may comprise will be apparent to persons skilled in the art in view of the teachings herein.

In order to removably couple buttress assembly (61210) to cartridge (670), an operator may direct the attachment member (61280a, 61280b) over the proximal end (670a) of cartridge (670) such that attachment member (61280a, 61280b) is positioned between proximal end of cartridge (670) and a distally facing portion of lower jaw, and until the bottom face (61213) of buttress body (61212) is flush with cartridge deck (673). Attachment member (61280a, 61280b) is sized and configured such that when attachment member (61180) is positioned between proximal end of cartridge (670) and lower jaw (650), attachment member (61180a, 61180b) is releasably held therebetween. In the example shown, attachment member (61180a, 61180b) is interference fit in between proximal end (670a) of cartridge (670) and lower jaw (650). It should be understood that buttress assembly (61210) may first be positioned on cartridge (670), and then the combination of buttress assembly (61210) and cartridge (670) may be loaded into lower jaw (650). Alternatively, cartridge (670) may be loaded into lower jaw (650) first; and then buttress assembly (61210) may be loaded onto cartridge (670).

The retention force provided by the engagement between attachment members (61280a, 61280b), proximal end (670a) of cartridge (670), and lower jaw (650) is sufficient to maintain the removable coupling between buttress assembly (61210) and cartridge (670) absent a sufficient decoupling force. However, buttress assembly (61210) is configured to decouple from cartridge (670) in response to a sufficient decoupling force input. In the present example, the upward force associated with being captured by staples (690) provides additional and sufficient decoupling force to release buttress assembly (61210) and connector portions (61280) from engagement with cartridge (670).

FIGS. 145-146 show an exemplary variation of buttress assembly (61210) that includes alternative attachment members (61280c). As shown, each attachment member (61280c) includes a pair of apertures (61290) that are configured to receive similarly shaped extensions on sled (678). Particularly, as shown in FIGS. 145-146, each sled rail (678a, 678b) includes proximally projecting extensions (61295) that are sized and configured to be received in apertures (61290). Thus, in order to removably couple buttress assembly (61210) including attachment members (61280c) to cartridge (670), an operator may direct attachment member (61280c) over the proximal end (670a) of cartridge (670) such that attachment member (61280c) is positioned between proximal end of cartridge (670) and a portion of lower jaw (650), and apertures (61290) engage the corresponding extensions (61295). Moreover, apertures (61290) and extensions (61295) are configured such that when they are engaged, the bottom face (61213) of buttress body (61212) is flush with cartridge deck (673).

The retention force provided by the engagement between apertures (61290) of attachment members (61280c), extensions (61295) of sled (678), and lower jaw (650) is sufficient to maintain the removable coupling between buttress assembly (61210) and cartridge (670) absent a sufficient decoupling force. However, buttress assembly (61210) is configured to decouple from cartridge (670) in response to a sufficient decoupling force input. In the present example, longitudinal movement of sled (678) disengages extensions (61295) from apertures (61290), reducing the retention force between sled rails (678a, 678b) and attachment members (61280c). In the present example, the upward force associated with being captured by staples (690) provides additional and sufficient decoupling force to release buttress assembly (61210) and connector portions (61280) from engagement with cartridge (670).

It should be understood that upon actuation of end effector (640), a series of staples (690) will similarly capture and retain buttress assembly (61210) against layers of tissue ($T_1$, $T_2$), thereby securing buttress assembly (61210) to tissue ($T_1$, $T_2$) in a similar manner as shown in FIG. 6. In some examples, buttress assembly (61210) may be utilized in conjunction with buttress assembly (100) on anvil (60) such that a series of staples (690) will similarly capture and retain buttress assemblies (100, 61210) against layers of tissue ($T_1$, $T_2$), thereby securing buttress assemblies (100, 61210) to tissue ($T_1$, $T_2$) in a similar manner as shown in FIG. 6.

FIGS. 147 and 149A-B show another exemplary alternative staple cartridge (61370) incorporated into lower jaw (650) of end effector (640). Staple cartridge (61370) is configured to operate substantially similar to staple cartridge (670), except for the differences below. Particularly, staple cartridge (61370) includes an aperture (61390) positioned proximal to staple openings (61345). Aperture (61390) is formed as lateral extensions of slot (61372). Aperture (61390) and the portion of slot (61372) that is coincident with aperture (61390) are configured to receive attachment features (61080) of a buttress assembly (61010) in order to removably and mechanically couple buttress assembly (61010), as discussed in further detail below.

As shown best in FIGS. 147-148, buttress assembly (61310) includes a pair of buttress bodies (61312) coupled to a base portion (61315). In the present example, each buttress body (61312) comprises a strong yet flexible material configured to structurally support a line of staples (690). By way of example only, buttress body (61312) may comprise a woven mesh of VICRYL® (polyglactin 910) material by Ethicon US, LLC, and base portion (61315) may comprise the same or different material (e.g., a thin film, etc.). Alternatively, any other suitable materials or combinations of materials may be used in addition to or as an alternative to VICRYL® material to form buttress body (61312) and/or base portion (61315). Of course, buttress body (61312) and base portion (61315) may take any other suitable form and may be constructed of any other suitable material(s).

In the present example, buttress assembly (61310) includes a proximal end (61314) and a distal end (61316) and extends along an axis (61327) thereof. As shown, buttress assembly (61310) includes attachment members (61380) extending from proximal end (61314) of base portion (61315) in a perpendicular direction away from buttress body (61012) and base portion (61315). Attachment members (61380) comprise resilient tabs that comprise the same material or materials as base member (61312). In other examples, any or all of tabs (61380) may comprise a plurality of laminate, bioabsorbable layers, which may or may not include a layer that comprises part of base member (61312). In some examples, any or all of resilient tabs (61380) may comprise a woven, non-woven, or foam material. Other suitable configurations and materials that tabs (61380) may comprise will be apparent to persons skilled in the art in view of the teachings herein.

In order to removably couple buttress assembly (61310) to cartridge (61370), an operator may direct resilient tabs (61380) into aperture (61390) downwardly through aperture (61390) until tabs (61380) engage sled (678), and face (61313) of buttress body (61312) is substantially flush with cartridge deck (61373). As shown best in FIGS. 149A-149B, tabs (61380) resiliently engage sled, thereby releasably coupling buttress assembly (61310) to sled (678), and thereby releasably coupling buttress assembly (61310) to cartridge (61370).

The retention force provided by the engagement between tabs (61380) and sled (678) is sufficient to maintain the removable coupling between buttress assembly (61310) and cartridge (61370) absent a sufficient decoupling force. However, buttress assembly (61310) is configured to decouple from cartridge (61370) in response to a sufficient decoupling force input. In the present example, longitudinal movement of sled (678) disengages sled (678) from tabs (61380), releasing the retention force between sled (678) and tabs (61380). Moreover, the upward force associated with being captured by staples (690) provides additional and sufficient decoupling force to release buttress assembly (61310) from connector portions (61380) of cartridge (61370).

FIG. 150 shows another alternative exemplary buttress assembly (61410). Buttress assembly (61410) is substantially similar to buttress assembly (61310) except for that resilient tabs (61480) are longitudinally staggered. Moreover, buttress assembly (61410) includes a medial cut edge portion (61417) that facilitates severing of buttress body (61412) by knife member (680) and thus traversal of knife member (680) through buttress body (61412). It should be understood that upon actuation of end effector (640), a series of staples (690) will similarly capture and retain buttress assembly (61310, 61410) against layers of tissue ($T_1$, $T_2$), thereby securing buttress assembly (61310, 61410) to tissue ($T_1$, $T_2$) in a similar manner as shown in FIG. 6. In some examples, buttress assembly (61310, 61410) may be utilized in conjunction with buttress assembly (100) on anvil (60) such that a series of staples (690) will similarly capture and retain buttress assemblies (100, 61310, 61410) against layers of tissue ($T_1$, $T_2$), thereby securing buttress assemblies (100, 61310, 61410) to tissue ($T_1$, $T_2$) in a similar manner as shown in FIG. 6.

D. Buttress Assemblies with Features to Facilitate Knife Member Traversal

FIG. 151 shows an exemplary alternative buttress assembly (61510) including a pair of buttress bodies (61512) that are connected by a diagonal woven mesh (61515). While only a portion of buttress assembly (61510) is shown, it will be understood that buttress assembly (61510) may be incorporated into a suitable staple cartridge (e.g., staple cartridge (670)) of a surgical instrument (e.g., instrument (10)) and may be utilized in steps of a surgical stapling procedure, such as those shown in FIGS. 5A-6. Moreover, the construction of buttress assembly (61510) may be readily incorporated into any of the various buttress assemblies described herein.

In the example shown, buttress bodies (61512) are coupled to one another via a woven mesh (61515) of material filaments. A first portion (61516) of filaments which the mesh (61515) comprises extend at an oblique angle (e.g., forty five degrees as shown) relative to the longitudinal axis (61527), and a second portion of filaments (61518) extend orthogonally relative to the first portion (61516) and at an oblique angle relative to the longitudinal axis (61527) (e.g., forty five degrees as shown).

In the present example, filaments comprising mesh (61515) are made of VICRYL® (polyglactin 910) material by Ethicon US, LLC. Buttress body (61512) is comprised of a film or woven mesh of VICRYL® (polyglactin 910) material by Ethicon US, LLC. Alternatively, any other suitable materials or combinations of materials may be used in addition to or as an alternative to VICRYL® material to form buttress body (61512) or filaments of mesh (61515). Of course, buttress body (61512) and mesh (61515) may take any other suitable form and may be constructed of any other suitable material(s).

In the present example, portions of mesh (61515) that are coincident with buttress bodies (61512) are bonded or otherwise coupled to a top portion of buttress bodies (61512). In addition or in the alternative, mesh (61515) may be bonded or otherwise coupled along a bottom portion of buttress bodies (61512). As another merely illustrative alternative, mesh (61515) may be at least partially impregnated within one or both of buttress bodies (61512). In the example shown, mesh (61515) is a woven mesh, but in other examples, mesh (61515) may be knitted or formed in any other suitable manner. In some examples, mesh (61515) may be severed and formed using heat or other forms of energy so as to fuse the filaments together as they are cut to, for example, prevent rough edges. Other suitable manners of coupling buttress bodies (61512) and mesh (61515) to one another, and of forming mesh (61515), will be apparent to persons skilled in the art in view of the teachings herein. In an alternative example, as shown in FIG. 160, buttress body (61512) may include a mesh (61515) according to the teachings just discussed, in combination with an integral film (61526).

Buttress assembly (61510) further includes two lines of perforations (61520) oriented at an oblique angle (forty-five degrees as shown) and parallel to the longitudinal axis (61527). In the present example, perforations (61520) may be formed using heat or other forms of energy so as to fuse the filaments together as they are cut to, for example, prevent rough edges. For example, filaments may be treated with an ultrasonic treatment, a heated knife member, laser, and other modes of treating with energy as will be understood by persons skilled in the art in view of the teachings herein. Perforations (61520) may also be formed in various other suitable manners as will be apparent to persons skilled in the art in view of the teachings herein.

Perforations (61520) facilitate separation of buttress bodies (61512) as knife member (680) traverses therebetween. More particularly, due to the perforations (61520), none of the filaments comprising mesh extend completely from one end of one buttress body to an end of the other buttress body (61512). Rather, the filaments extend from an edge (61522) of buttress body to one of the edges of perforations (61520), as represented by some of filaments extending further away from other edge (61524) of buttress body (61512) Therefore, rather than requiring knife member (680) to sever portions of mesh (61515) extending over channel (672), for example, as knife member (680) traverses channel (672), filaments may simply be pulled out of the way as buttress bodies (61512) are captured by staples (690). Thus, stress on the severed and stapled tissue, and damage and wear on knife member (680), may be decreased.

An alternative example of a buttress assembly (61610) is shown in FIG. 153. Buttress assembly (61610) is similar to buttress assembly (61510) in that in includes a woven mesh (61615). However, woven mesh (61615) includes a first portion (61616) of filaments that extend parallel to the longitudinal axis (61627) of buttress assembly (61610), and a second portion (61618) of filaments that extend parallel to the longitudinal axis (61627). Mesh (61615) connects opposing buttress bodies (61612). A first portion (61616) of filaments that extend parallel to axis (61627) do not extend along a portion between buttress bodies (61612). Thus, first portion of filaments are not present along channel (672) of cartridge (670) when buttress assembly (61610) is utilized with staple cartridge (670). Therefore, rather than requiring the knife member (680) to sever mesh (61515) with both portions of filament, extending over channel (672), for example, as knife member (680) traverses channel (672), knife member (680) only severs first portion (61616) (perpendicular to axis (61627)) of filaments as buttress bodies (61612) are captured by staples (690). Thus, stress on the severed and stapled tissue, and damage and wear on knife member (680), may be decreased.

In the present example, portions of mesh (61615) that are coincident with buttress bodies (61612) are bonded or otherwise coupled to a top portion of buttress bodies (61612). In addition or in the alternative, mesh (61615) may be bonded or otherwise coupled along a bottom portion. As another merely illustrative alternative, mesh (61615) may be at least partially impregnated within one or both of buttress bodies (61612). In the example shown, mesh (61615) is a woven mesh, but in other examples, mesh (61615) may be knitted or formed in any other suitable manner. In some examples, mesh (61615) may be severed and formed using heat or other forms of energy so as to fuse the filaments together as they are cut to, for example, prevent rough edges. For example, filaments may be treated with an ultrasonic treatment, a heated knife member, laser, and other modes of treating with energy as will be understood by persons skilled in the art in view of the teachings herein. Other suitable manners of coupling buttress bodies (61612) and mesh (61615) to one another, and of forming mesh (61615), will be apparent to persons skilled in the art in view of the teachings herein.

FIGS. 154-150 show additional examples of buttress assemblies (61710, 61810) that may be incorporated into a suitable staple cartridge (e.g., staple cartridge (670)) of a surgical instrument (e.g., instrument (10)) and may be utilized in steps of a surgical stapling procedure, such as those shown in FIGS. 5A-6. Buttress assemblies (61710, 61810) include features that may reduce the amount of effort to advance knife member (680) through channel (672) as end effector (640) is actuated. Stress on the severed and stapled tissue, and damage and wear on knife member (680), may therefore be decreased.

As shown in FIG. 154, buttress assembly (61710) includes a buttress body (61712) including a proximal end (61714) having a proximal recess (61715), a distal end (61716) having a distal recess (61717), and a plurality of apertures (61718) extending along an axis (61727) thereof. While five apertures (61718) are shown in the present example, in alternative examples there may be less than (e.g., four, three, two, one, or zero) or more than five apertures (61718). In the present example, apertures (61718) are obround-shaped apertures, and recesses (61715, 61717) are half-obround recesses. Of course, any other suitable shapes may be used. Other suitable configurations of apertures (61718) and recesses (61715, 61717) will be apparent to persons skilled in the art in view of the teachings herein. Referring to FIG. 155, buttress assembly (61810) is substantially identical to buttress assembly (61710), except for that buttress assembly (61810) includes rectangular apertures (61818) and half-rectangular recesses (61815, 61817).

In the present examples, apertures (61718, 61818) and recesses (61715, 61815) may reduce the amount of force required for knife member (680) to cut through and traverse past severed tissue and buttress body (61712). Thus, stress on the severed and stapled tissue, and damage and wear on knife member (680), may be decreased.

Each buttress assembly (61710, 61810) of these examples comprises a buttress body (61712, 61812) and, in some instances, an adhesive layer (not shown). In the present example, each buttress body (61712, 61812) comprises a strong yet flexible material that is configured to structurally support a line of staples (690). By way of example only, each buttress body (61712, 61812) may comprise a woven mesh of VICRYL® (polyglactin 910) material by Ethicon US, LLC. Alternatively, any other suitable materials or combinations of materials may be used in addition to or as an alternative to VICRYL® material to form each buttress body (61712, 61812), such as any of the materials or configurations discussed above with respect to other disclosed buttress bodies. Of course, each buttress body (61712, 61812) may take any other suitable form and may be constructed of any other suitable material(s).

FIG. 156 shows another exemplary alternative buttress assembly (61910) that may be incorporated into a suitable staple cartridge (e.g., staple cartridge (670)) of a surgical instrument (e.g., instrument (10)) and may be utilized in steps of a surgical stapling procedure, such as those shown in FIGS. 5A-6. Buttress assembly (61910) includes features that may reduce the amount of effort to advance knife member (680) through channel (672) as end effector (640) is actuated. In the example shown, buttress assembly (61910) includes a pair of buttress bodies (61912) configured such that when buttress assembly (61910) is incorporated onto staple cartridge (670), buttress bodies (61912) do not span across channel (672), such that knife member (680) does not sever buttress bodies (61912) during actuation of end effector (640). Thus, stress on the severed and stapled tissue, and damage and wear on knife member (680), may be decreased.

As shown in FIG. 156, buttress bodies (61912) are coupled to one another via a connector member (61915), such that knife member (670) would cut through at least a portion of connector member (61915). As shown, connector member (61915) comprises a sheet or thin film of material, such as wax, gelatin, or a woven or non-woven material similar to other buttress bodies described herein. Connector member (61915) may be thinner and/or weaker than buttress bodies (61912), such that knife member (680) will encounter less resistance and/or suffer from less wear when traversing connector member (61915) than knife member (680) would otherwise encounter if knife member (680) were to traverse buttress bodies (61912).

In some versions, connector member (61915) provides additional thickness to buttress bodies (61912) such that, buttress assembly (61910) provided herein may provide a tissue compression effect between anvil (60) and deck (673) of staple cartridge (670), such as that described in U.S. patent application Ser. No. 14/810,786, entitled "Surgical Staple Cartridge with Compression Feature at Knife Slot," filed Jul. 28, 2015, issued as U.S. Pat. No. 10,314,580 on Jun. 11, 2019, now U.S. Patent Pub. No. 2017/0027567, published Feb. 2, 2107, the disclosure of which is incorporated by reference herein; U.S. patent application Ser. No. 14/811,087, entitled "Surgical Staple Cartridge with Compression Feature at Staple Driver Edges," filed Jul. 28, 2015, now U.S. Patent Pub. No. 2017/0027568, published Feb. 2, 2017, issued as U.S. Pat. No. 10,201,348 on Feb. 12, 2019, the disclosure of which is incorporated by reference herein; and U.S. patent application Ser. No. 14/811,154, entitled "Surgical Staple Cartridge with Outer Edge Compression Features," filed Jul. 28, 2015, now U.S. Patent Pub. No. 2017/0027569, published Feb. 2, 2017, issued as U.S. Pat. No. 10,194,912 on Feb. 2, 2017, the disclosure of which is incorporated by reference herein.

FIG. 157 shows another exemplary alternative buttress assembly (62010) that may be incorporated into a suitable staple cartridge (e.g., staple cartridge (670)) of a surgical instrument (e.g., instrument (10)) and may be utilized in steps of a surgical stapling procedure, such as those shown in FIGS. 5A-6. Buttress assembly (62010) includes features that may reduce the amount of effort to advance knife member (680) through channel (672) as end effector (640) is actuated. In the example shown, buttress assembly (62010) includes a pair of buttress bodies (62012) configured such that when buttress assembly (62010) is incorporated onto staple cartridge (670), buttress bodies (62012) do not span across channel (672), such that knife member (680) does not sever buttress bodies (62012) during actuation of end effector (640). As shown, however, buttress bodies (62012) are coupled to one another via discrete connector members (62015) that would span channel (672) when incorporated into staple cartridge (670).

In the example shown, connector members (62015) comprise five lines of adhesive spanning between buttress bodies (62012). However, in other examples, there may be fewer or more than five lines of adhesive spanning buttress bodies (62012). Moreover, in some examples, any or all of connector members (62015) might be alternatively configured. For example, any or all of connector members (62015) may comprise filament impregnated adhesive, filaments, or other elements capable of maintaining buttress bodies (62102) in a releasably couplable relationship but that would not inhibit or impede the traversal of knife member (680). As shown, buttress bodies (62012) each include discrete portions of adhesive (62021) that may be utilized to help releasably couple buttress bodies to cartridge deck (673). As shown, discrete portions of adhesive (62021) are formed as dots and may ease the release of buttress bodies (62012) from deck (673) as buttress bodies (62012) are captured by staples (690) (e.g., as opposed to an entire sheet of adhesive coupling buttress bodies (62012) to deck (673)).

FIG. 158 shows another exemplary alternative connector member (62115) that is configured to be utilized together with a buttress body, such as buttress body (61912) just discussed, and incorporated into a suitable staple cartridge (e.g., staple cartridge (670)) of a surgical instrument (e.g., instrument (10)) and utilized in steps of a surgical stapling procedure, such as those shown in FIGS. 5A-6. As shown, connector member (62115) comprises a matrix-like configuration of intersecting lines forming a generally rectangular shape. Particularly, connector member (62115) includes outer portions (62116) that are configured to lie coincidently with buttress bodies (62112) and an inner portion (62118) that is configured to span channel (672), such that buttress bodies (61912) do not span channel (672). In some versions, connector member (62115) provides an added thickness to a buttress assembly such that the buttress assembly provides a tissue compression effect between anvil (60) and lower jaw (650), such as that described in U.S. patent application Ser. No. 14/810,786, now U.S. Patent Pub. No. 2017/0027567, published Feb. 2, 2017 issued as U.S. Pat. No. 10,314,580 on Jun. 11, 2019; U.S. patent application Ser. No. 14/811,087, now U.S. Patent Pub. No. 2017/0027568, published Feb. 2, 2017, issued as U.S. Pat. No. 10,201,348 on Feb. 12, 2019, the disclosure of which is incorporated by reference herein; and U.S. patent application Ser. No. 14/811,154, now U.S. Patent Pub. No. 2017/0027569, published Feb. 2, 2017, issued as U.S. Pat. No. 10,194,912 on Feb. 5, 2019, the disclosure of which is incorporated by reference herein.

In the present example, connector member (62115) comprises a wax material but in other examples, all or a portion of connector member (62115) may comprise gelatin, a woven or non-woven material similar to buttress bodies (6210), and/or any other suitable material(s). In the present example, buttress bodies (61912, 62012) may comprises a strong yet flexible material configured to structurally support a line of staples (690). By way of example only, buttress body (61912) may comprise a woven mesh of VICRYL® (polyglactin 910) material by Ethicon US, LLC, and base portion may comprise the same or different material. Alternatively, any other suitable materials or combinations of materials may be used in addition to or as an alternative to VICRYL® material to form buttress body (61912) and/or connector member portion (61915, 62015). Of course, buttress body (61912) and base portion (61915) may take any other suitable form and may be constructed of any other suitable material(s).

FIGS. 159A-159B show another exemplary alternative buttress assembly (62210) comprising opposing buttress bodies (62212), incorporated into staple cartridge (670) of a surgical instrument (e.g., instrument (10)), which may be utilized in steps of a surgical stapling procedure, such as those shown in FIGS. 5A-6. By way of example only, buttress bodies (62212) may comprise a woven mesh of VICRYL® (polyglactin 910) material by Ethicon US, LLC. Alternatively, any other suitable materials or combinations of materials may be used in addition to or as an alternative to VICRYL® material to form buttress body (62212), such as the other configurations of buttress bodies disclosed herein.

As shown, buttress bodies (62212) are discrete members that each partially span channel (672). As shown in FIG. 159A, one buttress body (62212) partially overlaps the other buttress body (62212), though it will be understood that other overlapping configurations may be utilized. Rather than having to cut through buttress assembly (62210), as knife member (680) traverses channel (672), knife member (680) displaces buttress bodies (62212) away from channel (672) as shown in FIG. 159B. In some instances, buttress bodies (6212) or knife member (680) may include a lubricious coating to reduce the friction between such components. Stress on the severed and stapled tissue and damage, and wear on knife member (680), may therefore be decreased.

E. Buttress Assemblies Covering Only a Portion of Staple Cavities

FIGS. 161-162B show an exemplary alternative buttress assembly (62310). As shown best in FIG. 161, buttress assembly (62310) is disposed on a staple cartridge (62370) that is configured to operate substantially similarly to staple cartridge (670) discussed above. Cartridge (62370) is removably coupled to lower jaw (650) of end effector (640). In the present example, staple cartridge (62370) includes three rows of staples (690) in three sets of cavities (62345) on each side of channel (62372) instead of two rows of staples cavities (62345). Moreover, cartridge (62370) includes an elongate trough (62379) extending along staple deck (62373). Trough (62379) extends longitudinally along the length of cartridge (62370) and is laterally positioned between the outermost row of cavities (62345) and the middle row of cavities (62345). Trough (62379) has a partially circular cross-sectional profile. In other examples, however, trough (62379) may have any other suitable shapes which as will be apparent to persons skilled in the art in view of the teachings herein.

Buttress assembly (62310) of the present example may be configured in accordance with other buttress assemblies disclosed herein. As shown, buttress body (62312) of buttress assembly (62310) extends along deck (62373) and an end portion (62313) of buttress body (62373) is disposed in a rolled configuration within trough (62379). In the present example, end portion (62313) is biased toward an unrolled configuration, but is retained in the rolled configuration when positioned within trough (62379). Other suitable configurations of buttress assembly (62310) will be apparent to persons skilled in the art in view of the teachings herein.

Upon actuation of end effector (640), staples (690) capture and retain buttress assembly (62310) against layers of tissue ($T_1$, $T_2$), thereby securing buttress assembly (62310) to tissue ($T_1$, $T_2$) in a similar manner as shown in FIG. 6. In the example shown in FIGS. 162A-162B, buttress assembly (62310) has been utilized in conjunction with buttress assembly (100) on anvil (60) such that a series of staples (690) has captured and retained buttress assemblies (100, 62310) against layers of tissue ($T_1$, $T_2$), thereby securing buttress assemblies (100, 62310) to tissue ($T_1$, $T_2$) in a similar manner as shown in FIG. 6. Similar to end portion (62313) of buttress assembly (62310), an end portion of buttress assembly (100) is shown to initially be in a rolled configuration upon being captured onto tissue ($T_1$, $T_2$), with the remaining portions of buttress assemblies covering the two rows of staples (690) closest to channel (62373). Thus, due to the presence of staples (690) and buttress assemblies (100, 62310) captured at the first and second rows of staples (690), there is a relatively higher level of compression at the first and second rows of staples (690), and better profusion at the third row of staples (690). As shown best in FIG. 162B, upon being captured onto tissue ($T_1$, $T_2$), ends (113, 62313) resiliently unfurl to transition to an unrolled position to cover the third row of staples (690). Buttress assemblies (100, 62310) thereby facilitate tissue ingrowth and seal any puncture leaks, if present.

FIGS. 163-164 show an exemplary alternative buttress assembly (62410). As shown best in FIG. 163, buttress assembly (62410) is disposed on a staple cartridge (62470) that is configured to operate substantially similarly to staple cartridge (670) discussed above. Cartridge (62470) is removably coupled to lower jaw (650) of end effector (640). Staple cartridge (62470) of this example includes three rows of staples (62490) in three sets of cavities (62445) on each side of channel (62472) instead of two rows of staples (62445).

Buttress assembly (62410) of the present example may be configured in accordance with other buttress assemblies disclosed herein. Buttress body (62412) of buttress assembly (62410) extends longitudinally along deck (62473) and laterally terminates at a position such that a lateral edge (62413) is between the outermost row of staple cavities (62445) and the middle row of staple cavities (62445). Other suitable configurations of buttress assembly (62410) will be apparent to persons skilled in the art in view of the teachings herein.

Upon actuation of end effector (640), staples (690) capture and retain buttress assembly (62410) against layers of tissue ($T_1$, $T_2$), thereby securing buttress assembly (62410) to tissue ($T_1$, $T_2$) in a similar manner as shown in FIG. 6. As shown, some examples, buttress assembly (62410) has been utilized in conjunction with buttress assembly (100) on anvil (60) such that a series of staples (690) has captured and retained buttress assemblies (100, 62410) against layers of tissue ($T_1$, $T_2$), thereby securing buttress assemblies (100, 62410) to tissue ($T_1$, $T_2$). As shown, lateral edge (62413) of buttress assembly (62410) is positioned between the outermost row of staples (690) and the intermediate row of staples (690). The rest of buttress assembly (62410) has been captured by the first and second rows of staples (690). Thus, due to the presence of staples (690) and buttress assemblies (100, 62410) captured at the first and second rows of staples (690), there is a relatively higher level of compression at the first and second rows of staples, and better profusion at the third row of staples (690).

FIGS. 165-166 show an exemplary alternative buttress assembly (62510). As shown best in FIG. 165, buttress assembly (62510) is disposed on a staple cartridge (62570) that is configured to operate substantially similarly to staple cartridge (670) discussed above. Cartridge (62570) is removably coupled to lower jaw (650) of end effector (640). Cartridge (62570) of this example includes three rows of staples (62590) in three sets of cavities (62545) on each side of channel (62572) instead of two rows of staples (62545).

Buttress assembly (62510) of the present example may be configured in accordance with other buttress assemblies disclosed herein. As shown, buttress body (62512) of buttress assembly (62510) extends along deck (62573) and a distal end portion (62513) of buttress body (62573) terminates such that buttress assembly (62510) does not cover a distal portion (62545*d*) of staple cavities (62545); or a distal portion of channel (62572) or deck (62573). In other words, buttress assembly (62510) does not extend along the full length of deck (62573). Other suitable configurations of buttress assembly (62510**) will be apparent to persons skilled in the art in view of the teachings herein.

Upon actuation of end effector (640), staples (690) capture and retain buttress assembly (62510) against layers of tissue ($T_1$, $T_2$), thereby securing buttress assembly (62510) to tissue ($T_1$, $T_2$) in a similar manner as shown in FIG. 6. FIG. 166 shows a plurality of buttress assemblies (62510) that have been deployed with staples (690) onto tissue, after actuating end effector (640) multiple times. Due to the configuration of buttress assembly (62510) terminating proximal to distal portion (62545*d*), when buttress assembly (62510) and staples (690) are deployed onto tissue, a portion of stapled tissue includes staples (690) but does not include buttress assembly (62510), such as at region (S2). However, at region (S1), which has been severed and stapled with successive lines of staples (690), a region (S2) of overlap occurs. Notably, due to the lack of buttress (62510) at distal portion (62545*d*), successive staple lines overlap (as shown by more than three rows of staples (690) at region (S1)), but overlapping portions of buttress assemblies (62510) are not created.

In some examples, buttress assembly (62510) may be utilized in conjunction with buttress assembly (100) on anvil (60) such that a series of staples (690) will similarly capture and retain buttress assemblies (100, 62510) against layers of tissue ($T_1$, $T_2$), thereby securing buttress assemblies (100, 62510) to tissue ($T_1$, $T_2$) in a similar manner as shown in FIG. 6. Of course, buttress assembly (100) in such instances may be modified to be configured substantially identical to buttress assembly (62510).

XXVI. Exemplary Stretchable Buttress Assembly for Surgical Stapler

In some instances, it may be desirable to equip end effector (40) with a buttress assembly (100, 110) comprising a buttress body (102, 112) that includes an elastic material that is substantially stretchable in at least one direction and that will substantially recover its original shape. The resulting buttress assemblies (100, 110) may advantageously reinforce the mechanical fastening of tissue provided by staples (90), while moving with, rather than restraining, the underlying tissue. Such buttress assemblies (100, 110) may be particularly useful in applications in which the tissue that is fastened may subsequently expand and/or contract. For example, stretchable buttress assemblies (100, 110) may be of use to reinforce the mechanical fastening of a collapsed lung that is then re-inflated, and expands and contracts with the lung during the breathing process.

In some instances where staples (90) are to applied to an anatomical structure that expands and contracts during normal biological functioning (e.g., a lung, etc.), end effector (40) may be modified to apply lines of staples (90) to tissue ($T_1, T_2$) that are also configured to allow stretching of tissue ($T_1, T_2$). For instance, such a modified end effector (40) may be constructed and operable in accordance with at least some of the teachings of U.S. patent application Ser. No. 14/498,145, entitled "Method for Creating a Flexible Staple Line," filed Sep. 26, 2014, now U.S. Patent Pub. No. 2016/0089142, published Mar. 31, 2016, issued as U.S. Pat. No. 10,327,764 on Jun. 25, 2019, the disclosure of which is incorporated by reference herein; and/or U.S. patent application Ser. No. 14/498,070, entitled "Radically Expandable Staple Line," filed Sep. 26, 2014, now U.S. Patent Pub. No. 2016/0089146, published Mar. 31, 2016, issued as U.S. Pat. No. 10,426,476 on Oct. 1, 2019, the disclosure of which is incorporated by reference herein. It should be understood that the following variations of buttress body (102, 112) may be used with end effector (40) described above, with the variation of end effector (40) described in U.S. patent application Ser. No. 14/498,145, now U.S. Patent Pub. No. 2016/0089142, published Mar. 31, 2016, issued as U.S. Pat. No. 10,327,764 on Jun. 25, 2019, and/or U.S. patent application Ser. No. 14/498,070, now U.S. Patent Pub. No. 2016/0089146, published Mar. 31, 2016, issued as U.S. Pat. No. 10,426,476 on Oct. 1, 2019, and/or with any other suitable form of end effector (40).

In illustrative examples of stretchable buttresses assemblies (100, 110), the buttress bodies (102, 112) may comprise fibrous, planar fabric. "Fiber" as used herein means continuous fibers, which are sometimes referred to in the art as "substantially continuous filaments," "filaments," or "yarn," or staple fibers having an average length that is sufficient so that the staple fibers may be knitted and/or woven together. Fibers that are useful may be selected from the group consisting of: monocomponent fibers; multicomponent fibers; bicomponent fibers; biconstituent fibers; and combinations thereof.

"Monocomponent fiber" as used herein, refers to a fiber formed from using one or more extruders from only one polymer; this is not meant to exclude fibers formed from one polymer to which small amounts of additives have been added. Additives may be added to the polymer for the purposes of providing the resulting fiber with coloration, antistatic properties, lubrication, hydrophilicity, and/or other properties.

"Multicomponent fiber" as used herein, refers to a fiber formed from two or more different polymers that are extruded from separate extruders and spun together to form one fiber, "Bicomponent fibers" are one type of multicomponent fiber, and are formed from two different polymers. Bicomponent fibers may sometimes be referred to in the art as "conjugate fibers." Bi component fibers may be comprised of polymers that are substantially continuously positioned in distinct zones, both across the cross-section of the bicomponent fibers and along their length. Non-limiting examples of such bicomponent fibers include, but are not limited to: sheath/core arrangements; wherein one polymer is surrounded by another; side-by-side arrangements; segmented pie arrangements; or even "islands-in-the-sea" arrangements. Each of the aforementioned polymer arrangements is known in the art of multicomponent (including bicomponent) fibers.

Bicomponent fibers can be splittable fibers. Such fibers are capable of being split lengthwise before or during processing into multiple fibers with each of the multiple fibers having a smaller cross-sectional dimension than that of the original bi component fiber. Splittable fibers may provide softer fabrics due to their reduced cross-sectional dimensions.

"Biconstituent fibers" as used herein, refers to fibers which have been formed from at least two starting polymers extruded as a blend from the same extruder. Biconstituent fibers may have the various polymer components arranged in relatively constantly positioned distinct zones across the cross-sectional area of the fiber, and the various polymers are usually not continuous along the entire length of the fiber. In the alternative, bi constituent fibers may comprise a blend, that may be homogeneous or otherwise, of the at least two starting polymers. For example, a bicomponent fiber may be formed from starting polymers which differ only in molecular weight, Biconstituent fibers may form fibrils, which may begin and end at random along the length of the fiber. Biconstituent fibers may sometimes be referred to as multiconstituent fibers.

In illustrative examples of stretchable buttresses assemblies (100, 110), planar fabrics that are useful to make stretchable buttress assemblies (100, 110) comprise fibers that are substantially aligned in one or more preferred directions, such as in the fabric's machine direction, cross-machine direction, or combinations thereof. Useful fabrics may be distinguished from fabric that comprises fibers in random orientations, including but not limited to, melt blown, hydroentangled, and electrospun fabrics. The following provides several merely illustrative examples of fiber arrangements that may be readily incorporated into buttress assemblies (100, 110). It should therefore be understood that the following teachings may be readily combined with the teachings above. It should also be understood that some versions of the following examples include a combination of elastic fibers and non-elastic fibers.

In some surgical applications, it may be desirable to utilize buttress assemblies (100, 110) comprising buttress bodies (102, 112) that do not substantially stretch along the longitudinal axis (LA) of end effector (40) (along which the length of each buttress body (102, 112) runs); but that do stretch laterally along the plane defined by each buttress body (102, 112). In other words, it may be desirable to provide buttress bodies (102, 112) that stretch along the dimension of the width of buttress bodies (102, 112). For example, a surgeon may wish to staple an anatomical structure that is not intended to stretch once fastened with an extensible staple line. However, the surgeon may not wish to stop mid-surgery and exchange instrument (10) and/or shaft assembly (730). By applying to the anatomical structure a buttress assembly (100, 110) that does not substantially stretch along the longitudinal axis (LA) of end effector (40), the stretch of the staple line may be minimized or even eliminated. In an illustrative example, during a lobectomy, a surgeon may wish to apply an extensible staple line to the lung parenchyma but apply a non-extensible staple line to the bronchus. In such settings, the surgeon may apply an extensible staple line without buttress assembly (100, 110) to the parenchyma; then apply an extensible staple line with buttress assembly (100, 110) to the bronchus. The presence of the applied, non-longitudinally-exensible buttress assembly (100, 110) will essentially convert an otherwise extensible staple line into a non-extensible staple line as applied to the bronchus.

In some other surgical applications, it may be desirable to utilize buttress assemblies (100, 110) comprising buttress bodies (102, 112) that do stretch along the longitudinal axis (LA) of end effector (40); but that do not substantially stretch laterally along the plane defined by each buttress body (102, 112). In other words, it may be desirable to provide buttress bodies (102, 112) that stretch along the dimension of the length of buttress bodies (102, 112). Referring back to the example of a lung lobectomy, the lung may be in a collapsed state when the surgeon actuates end effector (40) on the parenchyma of the lung. When the lung is later reinflated, the resulting expansion of the lunch will apply tension in the parenchyma, thereby providing extension along the staple line. An extensible staple line (e.g., as taught in U.S. patent application Ser. No. 14/498,145 now U.S. Patent Pub. No. 2016/0089142, published Mar. 31, 2016, issued as U.S. Pat. No. 10,327,764 on Jun. 25, 2019, and/or U.S. patent application Ser. No. 14/498,070, now U.S. Patent Pub. No. 2016/0089146, published Mar. 31, 2016, issued as U.S. Pat. No. 10,426,476 on Oct. 1, 2019) may thus accommodate such extension. In settings where the surgeon wishes for that staple line to be reinforced by a buttress assembly (100, 110), that buttress assembly (100, 110) may need to be extensible along the longitudinal axis in order to accommodate the expansion of the lung during reinflation. Otherwise, a non-extensible buttress assembly (100, 110) may create stress at the staple line during reinflation, possibly tearing tissue, compromising the integrity of the staple line, resulting in leaks, and/or providing other adverse results. Thus, buttress bodies (102, 112) that substantially stretch along the longitudinal axis (LA) of end effector (40) may be needed.

The following examples relate to various woven or knit configurations that may be provided in fabrics that are used to form buttress bodies (102, 112). In the following examples, such buttress bodies (102, 112) may be formed and oriented such that they provide a stretch axis that is parallel to the longitudinal axis (LA) of end effector (40) (i.e., such that buttress bodies (102, 112) provide a stretch axis that extends along the length of buttress bodies (102, 112)). Alternatively, such buttress bodies (102, 112) may be formed and oriented such that they provide a stretch axis that is perpendicular to the longitudinal axis (LA) of end effector (40) (i.e., such that buttress bodies (102, 112) provide a stretch axis that extends across the width of buttress bodies (102, 112)). As yet another alternative, buttress bodies (102, 112) may be formed and oriented such that they provide a stretch axis that is otherwise oriented in relation to the longitudinal axis (LA) of end effector (40).

In the present example, variations of buttress bodies (102, 112) are formed by a combination of elastic fibers and non-elastic fibers, all of which are arranged in a repeatable pattern. The elastic fibers are oriented along the stretch axis and the non-elastic fibers are oriented transversely relative to the stretch axis. It should be understood that the stretchability of elastic versions of buttress bodies (100, 110) may be manipulated based upon the choice of fiber material, the orientation of the fibers, tension on the fibers during fabric production, and various other factors.

By way of example only, the planar fabric may comprise elastic, i.e., extensible, fibers made from polymers selected from the group consisting of: poly(caprolactone)-co-poly (glycolide) (PCL/PGA); poly(caprolactone)-co-poly(lactide) (PCL/PLA); poly(lactide)-co-trimethylene carbonate (PCL/TMC); poly(p-dioxanone) (PDO); polyglactin 910 polymer mesh; and combinations thereof. Other suitable materials that may be used to form elastic fibers will be apparent to those of ordinary skill in the art in view of the teachings herein. Similarly, various suitable materials that may be used to form the non-elastic fibers will be apparent to those of ordinary skill in the art in view of the teachings herein. Non-elastic, i.e. non-extensible, fibers may be made from polymers selected from the group consisting of: poly (caprolactone)-co-poly(glycolide) (PCL/PGA); poly(caprolactone)-co-poly(lactide) (PCL/PLA); poly(lactide)-co-trimethylene carbonate (PCL/TMC); poly(p-dioxanone) (PDO); polyglactin 910 polymer mesh; polyglycolide (PGA) felt (for example, Neoveil™ felt from Gunze Limited (Kyoto, Japan)); a microporous structure of polyglycolic acid:trimethylcarbonate (PGA:TMC) (for example, Gore® Seamguard® from W.L. Gore & Associates, Inc. (Newark, Del.)); and combinations thereof. It should also be understood that the elastic fibers and the non-elastic fibers may each comprise multifilament fiber, monofilament fiber, or combinations thereof. The relative geometries and constructions of different fibers may be used to change the relative extensibility of the fibers.

In some versions, an elastic planar fabric that is used to form buttress bodies (102, 112) comprises woven fiber structures. Woven fiber structures comprise crossed warp and weft fibers. The warp and weft fibers may be perpendicular to each other, such that they intersect at about a 90° angle. The stretchability of woven fabrics may be more material dependent than pattern dependent. However, woven fabrics may comprise less extensible structures compared to knits. Using an elastomeric yarn in the filling may improve the stretch and recovery of the woven fabrics, in which case, extensibility would likely occur mainly in the cross direction.

In some examples, woven fiber fabrics may preferably comprise monocomponent fibers that are either multifilament or monofilament and of relatively fine denier with a low denier per filament (DPF). In some examples, both multifilament and monofilament fibers may be used in the same buttress construct. In some examples, two or more monocomponent fibers of different polymer composition may be used to achieve desired buttress body properties.

Useful planar fabrics may be woven in any pattern that provides for substantial stretchability in at least one direction (i.e., along a stretch axis) and substantial recovery of the fabric's original shape after being stretched. By way of example only, the planar fabric may be woven in a pattern selected from the group consisting of: twill weave; plain weave; satin weave; and combinations thereof. More particularly, the planar fabric may comprise more than one woven pattern; indeed, while the twill pattern, plain weave pattern, etc. comprise basic arrangements of warp and fill yarns (i.e. weft yarns), any number of desirable designs can be produced by altering the location and frequency of interlacing.

FIG. 167 is a diagram depicting a weave pattern of an exemplary planar fabric (7200) that comprises fibers (7210, 7220) that have been woven such that the warp fibers (7210)

and weft fibers (7220) intersect at angles of about 90°. In this example, warp fibers (7210) are formed of a non-elastic material while weft fibers (7220) are formed of an elastic material. Warp fibers (7210) are arranged in parallel along the machine direction (MD) and perpendicular to the cross-machine direction (CD) of planar fabric (7200). Warp fibers (7210) are also perpendicular to the stretch axis (SA). Weft fibers (7220) are inserted in the transverse direction, parallel to cross-machine direction (CD) of the planar fabric (7200) and perpendicular to the warp fibers (7210). Weft fibers (7220) are thus parallel to the stretch axis (SA). Thus, with respect to the planar fabric (7200) machine direction (MD), warp fibers (7210) are longitudinally oriented, whereas weft fibers (7220) are transversely oriented. The weave pattern of elastic weft fibers (7220) is configured to enable stretching of planar fabric (7200) along the stretch axis (SA). Planar fabric (7200) is thus extensible despite the fact that planar fabric (7200) includes non-elastic warp fibers (7210).

FIG. 168 shows an illustrative example of a buttress body (7250) that comprises the woven planar fabric (7200) of FIG. 167, wherein the planar fabric (7200) is oriented in such a way that the warp fibers (7210) and weft fibers (7220) intersect the stretch axis (SA) of the buttress body (7250) at an angle of about 45°. Buttress body (7250) is shown in a both a relaxed state (7250*a*) and a stretched state (7250*b*). In particular, buttress body (7250) is shown as being stretchable along stretch axis (SA). In some versions, the stretch axis (SA) is parallel to the longitudinal axis (LA) of end effector (40). In some other versions, the stretch axis (SA) is perpendicular to the longitudinal axis (LA) of end effector (40). In still other versions, the stretch axis (SA) has some other angular relationship with the longitudinal axis (LA) of end effector (40). It should be understood that buttress body (7250) may be secured to end effector (40) and originally applied to tissue ($T_1$, $T_2$) while buttress body (7250) is in a relaxed, non-stretched state as is the case with buttress body (7250*a*). In other words, in the present example, buttress body (7250) only reaches the stretched state (7250*b*) after buttress body (7250) has been secured to tissue ($T_1$, $T_2$) by staples (90). Buttress body (7250) would reach the stretched state (7250*b*) to accommodate stretching of tissue ($T_1$, $T_2$). However, the stretching of buttress body (7250) would not adversely impact the securing and sealing of tissue ($T_1$, $T_2$) provided by staples (90) and buttress body (7250).

It should be understood that planar fabric (7200) may be modified in various ways. The performance of buttress body (7250) may nevertheless be substantially the same despite variations in the configuration of planar fabric (7200). For instance, some other versions of planar fabric (7200) comprise a warp knit, weft-inserted fabric. For example, fibers may be knitted in a Raschel weft-insertion pattern using any number of suitable needle beds and guide bars. In some illustrative embodiments, one or two needle beds and four to eight guide bars may be utilized.

FIG. 169 is a diagram depicting an exemplary planar fabric (7300) having a Raschel weft-insertion pattern of fibers. Planar fabric (7300) comprises warp fibers (7310) that have been formed into columns of pillars produced by interlooping the warp fibers (7310) to form a chain stitch, and by laying in weft fibers (7320) to connect the columns of pillars together and form the fabric design. The resulting planar fabric (7300) may be substantially stable in both the machine direction (MD) and cross-machine direction (CD), unless the weft fibers (7320) are elastomeric, in which case, the resulting planar fabric (7300) will substantially stretch in the cross machine direction (CD). In other words, if the weft fibers (7320) are elastomeric, the stretch axis (SA) of the planar fabric (7300) may be perpendicular to its machine direction (MD). In some versions, the planar fabric (7300) may substantially recover its original shape after it has been stretched.

In still other variations of the planar fabric (7300) depicted in FIG. 169, a non-elastic fiber is wrapped around an elastic fiber to form a coil-like spring around a stretchable center. The resulting combination of fibers may then be used as the weft fibers (7320) that are laid in to form the design and connect the columns of pillars of warp fibers (7310) together as shown in FIG. 169.

The foregoing examples include configurations where elastic fibers are combined with non-elastic fibers to form planar fabric (7200) that is used to form buttress bodies (102, 112). As yet another merely illustrative variation, planar fabric (7200) may be formed entirely of non-elastic fibers yet may still provide extensibility along a stretch axis. For instance, planar fabric (7200) may comprise non-elastic fibers that are pre-kinked (e.g., into the shape of a coil spring, zigzag pattern, or some other configuration) to reduce the effective length of the non-elastic fibers. When such non-elastic fibers are pulled longitudinally, the kinks or bends in the non-elastic fibers may accommodate elongation of the effective length of the non-elastic fibers. Moreover, the kinked or otherwise bent non-elastic fibers may provide a resilient bias such that the non-elastic fibers are biased to provide the shorter effective length.

In some versions of planar fabric (7200) that are formed entirely of non-elastic fibers, the non-elastic fibers may be provided as yarns that are woven or knitted into a pre-existing fibrous structure. For instance, the kinked or otherwise bent non-elastic fibers may be woven or knitted into a pre-existing, stretchable sheet of fabric. The kinked or otherwise bent non-elastic fibers may impart a resilient bias to the pre-existing, stretchable sheet of fabric along the stretch axis (SA); yet may still enable the resulting assembly to be extensible along the stretch axis (SA).

Those of ordinary skill in the art will recognize that there are various ways in which non-elastic fibers may be pre-kinked, pre-bent, or otherwise manipulated to provide the properties described above. For instance, such non-elastic fibers may be texturized through airjet entanglement. Alternatively, non-elastic fibers may be mechanically texturized (e.g., using geared rollers, etc.). As yet another merely illustrative example, the non-elastic fibers may be knitted into a knitted arrangement, then de-knitted from that arrangement. In some such versions, the non-elastic fibers are knitted into a fabric and heat set. The heat set may impart the kinked or bent configuration to the non-elastic fibers. After the heat set is performed, the fabric is unraveled, with the non-elastic fibers retaining a kinked or bent configuration due to the heat set. Still other suitable techniques that may be used to pre-kink, pre-bend, or otherwise manipulate non-elastic fibers to provide the properties described above will be apparent to those of ordinary skill in the art in view of the teachings herein XXVII. Exemplary Stretchable Buttress Assembly for Surgical Stapler In some instances, it may be desirable to equip end effector (40) with a buttress assembly (100, 110) comprising an adhesive layer (104, 114) in combination with a buttress body (102, 112) that is constructed from an elastic material that is substantially stretchable in at least one direction and that will substantially recover its original shape. The resulting buttress assemblies (100, 110) may advantageously reinforce the mechanical fastening of tissue provided by staples (890), while moving with, rather than restraining, the underlying tissue. Such buttress assemblies (100, 110) may be particularly useful in applications in which the tissue that is fastened may subsequently expand and/or contract. For example, stretchable buttress assemblies (100, 110) may be of use to reinforce the mechanical fastening of a collapsed lung that is then re-inflated, and expands and contracts with the lung during the breathing process.

In illustrative examples of stretchable buttresses assemblies (100, 110), the buttress bodies (102, 112) may comprise fibrous, planar fabric. "Fiber" as used herein means continuous fibers, which are sometimes referred to in the art as "substantially continuous filaments," "filaments," or "yarn," or staple fibers having an average length that is sufficient so that the staple fibers may be knitted and/or woven together. Fibers that are useful may be selected from the group consisting of: monocomponent fibers; multicomponent fibers; bicomponent fibers; biconstituent fibers; and combinations thereof.

"Monocomponent fiber" as used herein, refers to a fiber formed from using one or more extruders from only one polymer; this is not meant to exclude fibers formed from one polymer to which small amounts of additives have been added. Additives may be added to the polymer for the purposes of providing the resulting fiber with coloration, antistatic properties, lubrication, hydrophilicity, and/or other properties. Monocomponent fibers may be multifilament or monofilament fibers.

"Multicomponent fiber" as used herein, refers to a fiber formed from two or more different polymers that are extruded from separate extruders and spun together to form one fiber.

"Bicomponent fibers" are one type of multicomponent fiber, and are formed from two different polymers. Bicomponent fibers may sometimes be referred to in the art as "conjugate fibers." Bicomponent fibers may be comprised of polymers that are substantially continuously positioned in distinct zones, both across the cross-section of the bicomponent fibers and along their length. Non-limiting examples of such bicomponent fibers include, but are not limited to: sheath/core arrangements, wherein one polymer is surrounded by another; side-by-side arrangements; segmented pie arrangements; or even "islands-in-the-sea" arrangements. Each of the aforementioned polymer arrangements is known in the art of multicomponent (including bicomponent) fibers.

Bicomponent fibers can be splittable fibers. Such fibers are capable of being split lengthwise before or during processing into multiple fibers with each of the multiple fibers having a smaller cross-sectional dimension than that of the original bicomponent fiber. Splittable fibers may provide softer fabrics due to their reduced cross-sectional dimensions.

"Biconstituent fibers" as used herein, refers to fibers which have been formed from at least two starting polymers extruded as a blend from the same extruder. Biconstituent fibers may have the various polymer components arranged in relatively constantly positioned distinct zones across the cross-sectional area of the fiber, and the various polymers are usually not continuous along the entire length of the fiber. In the alternative, biconstituent fibers may comprise a blend, that may be homogeneous or otherwise, of the at least two starting polymers. For example, a bicomponent fiber may be formed from starting polymers which differ only in molecular weight.

Biconstituent fibers may form fibrils, which may begin and end at random along the length of the fiber. Biconstituent fibers may sometimes be referred to as multiconstituent fibers.

In illustrative examples of stretchable buttresses assemblies (100, 110), planar fabrics that are useful to make stretchable buttress assemblies (100, 110) comprise fibers that are substantially aligned in one or more preferred directions, such as in the fabric's machine direction, cross-machine direction, or combinations thereof. Useful fabrics may be distinguished from fabric that comprises fibers in random orientations, including but not limited to, melt blown, hydroentangled, and electrospun fabrics. The following provides several merely illustrative examples of fiber arrangements that may be readily incorporated into buttress assemblies (100, 110). It should therefore be understood that the following teachings may be readily combined with the teachings above.

A. Exemplary Stretchable Buttress Assemblies that Do Not Substantially Stretch Along the Longitudinal Axis of an End Effector In some surgical applications, it may be desirable to utilize buttress assemblies (100, 110) comprising buttress bodies (102, 112) that do not substantially stretch along the longitudinal axis (LA) of end effector (40) (along which the length of each buttress body (102, 112) runs); but that do stretch laterally along the plane defined by each buttress body (102, 112). In other words, it may be desirable to provide buttress bodies (102, 112) that stretch along the dimension of the width of buttress bodies (102, 112). For example, a surgeon may wish to staple an anatomical structure that is not intended to stretch once fastened with an extensible staple line. However, the surgeon may not wish to stop mid-surgery and exchange instrument (10) and/or shaft assembly (30). By applying to the anatomical structure a buttress assembly (100, 110) that does not substantially stretch along the longitudinal axis (LA) of end effector (40), the stretch of the staple line may be minimized or even eliminated. In an illustrative example, during a lobectomy, a surgeon may wish to apply an extensible staple line (e.g., as taught in U.S. patent application Ser. No. 14/498,145, entitled "Method for Creating a Flexible Staple Line," filed Sep. 26, 2014, now U.S. Patent Pub. No. 2016/0089142, published Mar. 31, 2016, issued as U.S. Pat. No. 10,327,764 on Jun. 25, 2019, the disclosure of which is incorporated by reference herein; and/or U.S. patent application Ser. No. 14/498,070, entitled "Radically Expandable Staple Line," filed Sep. 26, 2014 now U.S. Patent Pub. No. 2016/0089146, issued Mar. 31, 2016, issued as U.S. Pat. No. 10,426,476 on Oct. 1, 2019, the disclosure of which is incorporated by reference herein) to the lung parenchyma but apply a non-extensible staple line to the bronchus. In such settings, the surgeon may apply an extensible staple line without buttress assembly (100, 110) to the parenchyma; then apply an extensible staple line with buttress assembly (100, 110) to the bronchus. The presence of the applied, non-longitudinally-extensible buttress assembly (100, 110) will essentially convert an otherwise extensible staple line into a non-extensible staple line as applied to the bronchus.

The following examples relate to various knit or woven configurations that may be provided in fabrics that are used to form buttress bodies (102, 112). In the following examples, such buttress assemblies (100, 110) comprise buttress bodies (102, 112) formed by planar fabric that is constructed from fibers that are substantially unaligned with longitudinal axis (LA) of end effector (40).

1. Exemplary Buttress Assemblies Comprising Warp Knitted Planar Fabric

Planar fabric may comprise looped fiber structures that are obtained through warp knitting. In addition to being substantially stretchable in one direction, warp knitted fabrics may tend not to unravel or curl, particularly as compared to weft knitted fabrics (discussed below). In some versions, planar fabric that is warp knitted comprises fibers that are delivered to the fabric knitting zone in parallel to each other and the edge of the fabric. The edge of the fabric is created as a result of the fibers being delivered in the fabric machine direction (i.e., the "shog") to form loops, the edge being formed by the fibers as they move laterally. In addition to moving laterally across the machine direction, the fibers may move in front of and behind the fabric plane (i.e., the "swing") or between multiple fabric planes (as in a spacer fabric construction) to connect stitches and form fabric loops.

In some examples, warp knitted planar fabric may preferably comprise monocomponent fibers that are either multifilament or mono-filament and of relatively fine denier with a low denier per filament (DPF). In some examples, both multifilament and monofilament fibers may be used in the same warp knit buttress body (102, 112). In some examples, two or more monocomponent fibers of different polymer compositions may be used to achieve desired buttress body (102, 112) properties.

In some illustrative examples, the warp knitted fabric is warp knitted using tricot and/or Raschel knitting machines using needle bed and guide bar configurations known to those skilled in the art, to provide a warp knitted fabric comprising one or more knitted patterns. When utilizing one or more of the aforementioned machines, the resulting warp knit fabric may be formed by a series of overlaps and underlaps which may be arranged in various combinations. In addition, or in the alternative, open and closed stitches may be formed as a result of the direction of the overlaps and underlaps. Useful lapping patterns include but are not limited to: pillar lap, 1&1 lap (tricot lap), 2&1 lap, 3&1 lap, 4&1 lap, atlas lap and combinations thereof. Since some Raschel knitting machines comprise a greater number of guide bars than tricot knitting machines, they may provide for a greater number of possible knitting patterns. In some examples in which spacer fabrics are desired, a double needle bar Raschel machine may be used such that a unique secondary knitted fabric layer is being simultaneously produced and connected to a first fabric layer.

FIG. 170 is a diagram depicting a knit pattern of an exemplary planar fabric (8750) that comprises fibers (8751) knitted in a tricot pattern using two guide bars, although up to four guide bars could be utilized to increase the complexity of the tricot pattern. As can be seen in FIG. 170, fibers (8751) zigzag along the cross-machine direction of the fabric to connect stitches and form fiber loops (8752). The resulting planar fabric may be substantially stretchable in the cross-machine direction of the fabric, but may not be substantially stretchable in the machine direction of the fabric. In some instances, after the resulting planar fabric is stretched, it may substantially recover its original shape.

Warp knitted planar fabric (8750, 8850) may be formed into buttress bodies (102, 112) such that the buttress bodies (102, 112) will not substantially stretch along longitudinal axis (LA) of end effector (40). However, such buttress bodies (102, 112) may nevertheless stretch in directions that are transverse to longitudinal axis (LA) of end effector (40) along the planes defined by buttress bodies (102, 112). Such buttress bodies (102, 112) may be useful when a surgeon wishes to staple an anatomical structure that will naturally stretch in directions that are transverse to longitudinal axis of the staple line. It may also be beneficial to permit stretching in directions that are transverse to longitudinal axis of the staple line in cases where there is a series of staple lines arranged generally end-to-end, where the longitudinal axes of the staple lines are not perfectly aligned with each other.

2. Exemplary Buttress Assemblies Comprising Weft Knitted Planar Fabric

Planar fabric may comprise looped fiber structures that are obtained through weft knitting. As compared to warp knitted fabrics, weft knitted fabrics may by characterized by greater stretch and recoverability, and may also be made utilizing fewer fiber spools, even a single fiber spool. In some versions, planar fabric that is weft knitted comprises fibers that are delivered to the fabric knitting zone in a horizontal, cross-machine and circular direction. In some versions, the weft knitted fabric is knitted in a ribbed pattern.

In some examples, weft knitted planar fabric may preferably comprise monocomponent fibers that are either multifilament or monofilament and of relatively fine average denier with a low average denier per filament (DPF). In some examples, both multifilament and monofilament fibers may be used in the same warp knit buttress body (102, 112) construct. In some examples, two or more monocomponent fibers of different polymer composition may be used to achieve desired buttress body (102, 112) properties.

FIG. 171 is a diagram depicting an exemplary weft knit planar fabric (8850) that comprises fibers (8851) knitted in a weft-insertion pattern using a Raschel knitting machine. As can be seen in FIG. 171, the fibers (8851) zigzag along the cross-machine direction of the fabric to connect stitches and form fiber loops (8852). The resulting planar fabric (8850) may be substantially stretchable in the cross-machine direction of the fabric, but may not be substantially stretchable in the machine direction of the fabric. In some instances, after the resulting planar fabric is stretched, it may substantially recover its original shape.

FIG. 172 is a diagram depicting a knit pattern of another exemplary planar fabric (8950) that comprises fibers (8951) knitted in a weft pattern. As can be seen in FIG. 172, each fiber loop (8952) is formed from the previous fiber loop (8952). The resulting planar fabric (8950) may be characterized by stretchability in the cross-machine direction of the fabric and good recoverability of its original shape.

Weft knitted planar fabrics (8950) may be formed into buttress bodies (102, 112) such that the buttress bodies (102, 112) will not substantially stretch along longitudinal axis (LA) of end effector (40). However, such buttress bodies (102, 112) may nevertheless stretch in directions that are transverse to longitudinal axis (LA) of end effector (40) along the planes defined by buttress bodies (102, 112). Such buttress bodies (102, 112) may be useful when a surgeon wishes to staple an anatomical structure that will naturally stretch in directions that are transverse to longitudinal axis of the staple line. It may also be beneficial to permit stretching in directions that are transverse to longitudinal axis of the staple line in cases where there is a series of staple lines arranged generally end-to-end, where the longitudinal axes of the staple lines are not perfectly aligned with each other.

3. Exemplary Buttress Assemblies Comprising Woven Planar Fabric

Planar fabric may comprise woven fiber structures. Woven fiber structures comprise crossed warp and weft fibers. The warp and weft fibers are perpendicular to each other, such that they intersect at about a 90° angle.

In some examples, woven fiber structures may preferably comprise monocomponent fibers that are either multifilament or monofilament and of relatively fine denier with a low denier per filament (DPF). In some examples, both multifilament and monofilament fibers may be used in the same warp knit buttress body (102, 112) construct. In some examples, two or more monocomponent fibers of different polymer composition may be used to achieve desired buttress body (102, 112) properties.

Useful planar fabrics may be woven in any pattern that provides for substantial stretchability in at least one direction and substantial recovery of the fabric's original shape after being stretched. By way of example only, the planar fabric may be woven in a pattern selected from the group consisting of: twill weave; plain weave; and combinations thereof. In further examples, planar fabric may comprise more than one woven pattern, indeed while the twill pattern, plain weave pattern, etc. comprise basic arrangements of warp and fill yarns, any number of desirable designs can be produced by altering the location and frequency of interlacing.

FIG. 173 is a diagram depicting an exemplary planar fabric (81050) having a Raschel weft-insertion pattern of fibers. Planar fabric (81050) comprises warp fibers (81051a) that have been formed into columns of pillars produced by interlooping the warp fibers (81051a) to form a chain stitch, and by laying in weft fibers (81051b) to connect the columns of pillars together and form the fabric design. The resulting planar fabric (81050) may be substantially stable in both the machine direction (MD) and cross-machine direction (CD), unless the weft fibers (81051b) are elastomeric, in which case, the resulting planar fabric (81050) will substantially stretch in the cross machine direction (CD). In other words, if the weft fibers (81051b) are elastomeric, the stretch axis (SA) of the planar fabric (81050) may be perpendicular to its machine direction (MD). In some versions, the planar fabric (81050) may substantially recover its original shape after it has been stretched. In still other variations of the planar fabric (81050) depicted in FIG. 173, a non-elastic fiber is wrapped around an elastic fiber to form a coil-like spring around a stretchable center. The resulting combination of fibers may then be used as the weft fibers (81051b) that are laid in to form the design and connect the columns of pillars of warp fibers (81051a) together as shown in FIG. 173.

An illustrative example of the stretchability of woven planar fabric is depicted in FIG. 174. In particular, a woven planar fabric (81150) comprises warp fibers (81151a) and weft fibers (81151b) that intersect at angles of about 90°. The woven planar fabric (81150) is oriented in such a way that the longitudinal axis of the fabric (81150) is at about an angle of 45° relative to the warp fibers (81151a) and weft fibers (81151b). When the planar fabric is in its unstretched or relaxed state (81150a), the warp fibers and weft fibers intersect at a first angle, $A_1$, and the fabric is characterized by a first width, $W_1$, and first length, $L_1$. When the planar fabric is in its stretched state (81150b), the warp fibers and weft fibers intersect at a second angle, $A_2$, which is greater than $A_1$, but which is still not equal to 90°. In addition, when the planar fabric is in its stretched state (81150b), it is further characterized by a width, $W_2$, that is greater than $W_1$, and a length, $L_2$ that is greater than $L_1$. When forces that cause the planar fabric to be in its stretched state (81150b) are removed, the planar fabric may substantially return to its relaxed state (81150a), or to a state that is somewhere in between the stretched state (81150a) and the relaxed state (81150b).

Woven planar fabric (81050, 81150) may be formed into a buttress body (102, 112) such that the planar fabric that does not substantially stretch along longitudinal axis (LA) of end effector (40). However, such buttress bodies (102, 112) may nevertheless stretch in directions that are transverse to longitudinal axis (LA) of end effector (40) along the planes defined by buttress bodies (102, 112). Such buttress bodies (102, 112) may be useful when a surgeon wishes to staple an anatomical structure that will naturally stretch in directions that are transverse to longitudinal axis of the staple line. It may also be beneficial to permit stretching in directions that are transverse to longitudinal axis of the staple line in cases where there is a series of staple lines arranged generally end-to-end, where the longitudinal axes of the staple lines are not perfectly aligned with each other.

An illustrative example of a buttress body (81202) that comprises the woven planar fabric (81150) of FIG. 174 is shown in FIG. 175. The buttress body (81202) is shown in a both a relaxed state (81202a) and a stretched state (81202b).

B. Exemplary Stretchable Buttress Assemblies that Substantially Stretch Along the Longitudinal Axis of an End Effector In some other surgical applications, it may be desirable to utilize buttress assemblies (100, 110) comprising buttress bodies (102, 112) that do stretch along the longitudinal axis (LA) of end effector (40); but that do not substantially stretch laterally along the plane defined by each buttress body (102, 112). In other words, it may be desirable to provide buttress bodies (102, 112) that stretch along the dimension of the length of buttress bodies (102, 112). Referring back to the example of a lung lobectomy, the lung may be in a collapsed state when the surgeon actuates end effector (40) on the parenchyma of the lung. When the lung is later reinflated, the resulting expansion of the lunch will apply tension in the parenchyma, thereby providing extension along the staple line. An extensible staple line (e.g., as taught in U.S. patent application Ser. No. 14/498,145, entitled "Method for Creating a Flexible Staple Line," filed Sep. 26, 2014 now U.S. Patent Pub. No. 2016/0089142, published Mar. 31, 2016, issued as U.S. Pat. No. 10,327,764 on Jun. 25, 2019, the disclosure of which is incorporated by reference herein; and/or U.S. patent application Ser. No. 14/498,070, entitled "Radically Expandable Staple Line," filed Sep. 26, 2014, now U.S. Patent Pub. No. 2016/0089146, published Mar. 31, 2016, issued as U.S. Pat. No. 10,426,476 on Oct. 1, 2019, the disclosure of which is incorporated by reference herein) may thus accommodate such extension. In settings where the surgeon wishes for that staple line to be reinforced by a buttress assembly (100, 110), that buttress assembly (100, 110) may need to be extensible along the longitudinal axis in order to accommodate the expansion of the lung during reinflation. Otherwise, a non-extensible buttress assembly (100, 110) may create stress at the staple line during reinflation, possibly tearing tissue, compromising the integrity of the staple line, resulting in leaks, and/or providing other adverse results. Thus, buttress bodies (102, 112) that substantially stretch along the longitudinal axis (LA) of end effector (40) may be needed.

In some versions, the stretchability of the buttress bodies (100, 110) may be manipulated based upon the choice of fiber material, the orientation of the fibers, tension on the fibers during fabric production, and combinations thereof. Orientation of the fibers may refer to the way that warp fibers are threaded through the needles (called the threading pattern—each guide bar can be fully threaded or partially threaded), which can affect the density of the fabric and therefore its extensibility. In warp and weft knit constructs, elasticity or "stretchability" of the fabric may be impacted by the tension on both the fiber systems and the fabric (being taken up onto a roll after knitting) during the fabric forming process. Tension may impact the size of the loops that are formed. Slight adjustments in tension and the resulting impact on fiber loop size may allow for more extensibility and recovery.

Elastic fibers may be utilized in the construction of the planar fabric. By way of example only, the planar fabric may comprise elastic fibers made from copolymers selected from the group consisting of: poly(caprolactone)-co-poly(glycolide) (PCL/PGA); poly(caprolactone)-co-poly(lactide) (PCL/PLA); poly(lactide)-co-trimethylene carbonate (PCL/TMC); and combinations thereof.

In some examples, the elastic fibers comprising either multifilament or monofilament fibers (depending on the degree of fabric stiffness, strength and elongation that is desired) may be utilized. In some examples, the elastic fibers are bicomponent fibers comprising non-elastic fibers that are wrapped around elastic fibers to form a coil-like spring around a stretchable center. Planar fabric comprising elastic fibers may be formed into a buttress body (102, 112) such that the planar fabric that substantially stretches along the longitudinal axis (LA) of end effector (40).

XXVIII. Exemplary Multi-Layer Adhesive Arrangement for Buttress Assembly

In some instances, it may be desirable to provide a version of a buttress assembly (100, 110) where adhesive layer (104, 114) comprises two or more layers of different kinds of adhesive material having different properties. For instance, FIGS. 176-177 show an exemplary buttress assembly (9200) that comprises a buttress body (9202), a first adhesive layer (9204) laid over buttress body (9202), and a second adhesive layer (9206) laid over first adhesive layer (9204). It should be understood that, with buttress body (9202) at the bottom of buttress assembly (9200), buttress assembly (9200) is analogous to buttress assembly (100) described above and may be similarly secured to underside (65) of anvil (60). Alternatively, buttress assembly (9200) may be flipped upside-down for an arrangement where buttress assembly (9200) would be secured to deck (73) of staple cartridge (70). In such versions, second adhesive layer (9206) would be at the bottom, first adhesive layer (9204) would be laid over second adhesive layer (9206), and buttress body (9202) would be laid over first adhesive layer (9204).

Buttress body (9202) may be constructed and operable just like buttress bodies (102, 112) described above. Moreover, buttress body (9202) may be constructed and operable in accordance with at least some of the teachings of U.S. patent application Ser. No. 14/667,842, entitled "Method of Applying a Buttress to a Surgical Stapler," filed Mar. 25, 92015, now U.S. Patent Pub. No. 2016/0278774, published Sep. 26, 2016, issued as U.S. Pat. No. 10,346,939 on Jul. 16, 2019, the disclosure of which is incorporated by reference herein. Other suitable forms that buttress body (9202) may take will be apparent to those of ordinary skill in the art in view of the teachings herein.

First adhesive layer (9204) is formed of an adhesive material that is different from the adhesive material forming second adhesive layer (9206). In some versions, first adhesive layer (9204) is formed of a material that has greater pliability and tackiness than the material forming second adhesive layer (9206). In some such versions, second adhesive layer (9206) serves as a protectant for first adhesive layer (9204). For instance, second adhesive layer (9206) may protect first adhesive layer (9204) from humidity, temperature fluctuations, and/or other environmental conditions that may be encountered during shipment and/or storage of buttress assembly (9200). In other words, second adhesive layer (9206) may be more resistant to moisture and/or temperature than first adhesive layer (9206). In some other variations, second adhesive layer (9206) is replaced with a non-adhesive protective layer. By way of example only, second adhesive layer (9206) may be replaced by a film or other structure that is biocompatible and bioabsorbable, dissolvable, or otherwise capable of temporarily confining the material forming first adhesive layer (9204) (e.g., to prevent first adhesive layer from seeping, migrating, or otherwise flowing out of buttress assembly (9200) during storage, shipping, handling before surgery, etc.). When anvil (60) is pressed against buttress assembly (9200) both adhesive layers (9204, 9206) may nevertheless cooperate to adhere buttress assembly (9200) to underside (65) of anvil (60).

In some versions, second adhesive layer (9206) is sprayed onto first adhesive layer (9204) while first adhesive layer is maintained at a temperature and humidity level that keeps first adhesive layer (9204) solid. It should be understood that the combination of different adhesive layers (9204, 9206) may be more soluble against anvil (60) and/or less sticky against anvil (60) than just a single adhesive layer (9204) might be. This may prevent an undesirable buildup of adhesive material on underside (65) of anvil (60) as a series of buttress assemblies (9200) are applied to underside (65) for a series of end effector (40) actuations during a surgical procedure. It should also be understood that adhesive layers (9204, 9206) may provide different ratios of two molecular weight blends in different layers (9204, 9206). In addition, adhesive layers (9204, 9206) may have cross-linking differences and/or come from different families of adhesive. By way of further example only, adhesive layers (9204, 9206) formed by higher molecular weight poloxamers may be stiffer and less prone to flow with temperature. Thus, using a poloxamer blend with higher molecular weight to form adhesive layer (9206) may contain a lower molecular weight material forming adhesive layer (9204), even if adhesive layer (9204) becomes fluid with temperature. Materials with higher degrees of cross-linking may have higher transition temperatures and therefore flow less at temperature extremes. An example of different families could be a poloxamer blend in adhesive layer (9204) with a thin layer of PCL/PGA co-ploymer sprayed onto adhesive layer (9204) to form adhesive layer (9206).

Various suitable materials that may be used to form second adhesive layer (9206) and non-adhesive substitutes for second adhesive layer will be apparent to those of ordinary skill in the art in view of the teachings herein. By way of example only, first adhesive layer (9204) may be configured and operable in accordance with at least some of the teachings of U.S. patent application Ser. No. 14/926,045, filed Oct. 28, 2015, entitled "Surgical Stapler Buttress Assembly with Humidity Tolerant Adhesive," filed on even date herewith, now U.S. Patent Pub. No. 2017/0119379, published May 4, 2017, issued as U.S. Pat. No. 10,238,388 on Mar. 26, 2019, the disclosure of which is incorporated by reference herein; U.S. patent application Ser. No. 14/926,057, filed Oct. 29, 2015, entitled "Surgical Stapler Buttress Assembly with Adhesion to Wet End Effector," filed on even date herewith, now U.S. Patent Pub. No. 2017/0119385, issued as U.S. Pat. No. 10,517,592 on Dec. 31, 2019, the disclosure of which is incorporated by reference herein; and/or any other references cited herein.

In buttress assembly (9200), the outer edges of first adhesive layer (9204) are left exposed by second adhesive layer (9206). FIGS. 178-179 show an exemplary alternative buttress assembly (9300) where the outer edges of a first adhesive layer (9304) are covered by downwardly projecting regions (9308) of a second adhesive layer (9306). Downwardly projecting regions (9308) extend along the full width and the full length of first adhesive layer (9304) in this example. Downwardly projecting regions (9308) also extend downwardly into contact with the upper surface of buttress body (9302). Buttress body (9302) and second adhesive layer (9306) thus cooperate to completely encapsulate first adhesive layer (9304). Buttress body (9302), first adhesive layer (9304), and second adhesive layer (9306) may be otherwise identical to buttress body (9202), first adhesive layer (9204), and second adhesive layer (9206) as described above. Other suitable ways in which adhesive layers (9304, 9306) may be configured and arranged in relation to a buttress body (9302) will be apparent to those of ordinary skill in the art in view of the teachings herein.

XXIX. Exemplary Humidity Tolerant Adhesive Materials and Techniques for Providing Adhesion of Buttress to Moist Surgical Stapler and/or Moist Tissue In some surgical applications, it may be desirable to provide a buttress body (102, 112) with one or more adhesive materials (104, 114) that will maintain adhesive properties in a humid (i.e., moist or wet) environment, when buttress body (102, 112) is used intraoperatively, for a sufficient amount of time to complete the surgical procedure. Such humidity tolerant adhesive materials may provide for temporary attachment of a buttress body (102, 112) to a wet jaw (50) or wet anvil (60) of the end effector (40) of a surgical stapling instrument (10), serve as an adjunct to reinforce the mechanical fastening of moist tissue ($T_1$, $T_2$) that is provided by staples (90), and combinations thereof. Such humidity tolerant adhesives may ultimately degrade and be absorbed by the body.

In some instances, the one or more adhesive materials (104, 114) have a humidity tolerance that is defined as the ability to maintain the temporary attachment of a buttress body (102, 112) to a jaw (50) or anvil (60) of an end effector (40) for at least ten minutes in an environment having 100% humidity (e.g., inside a patient) after buttress assembly (100, 110) has previously been exposed to a relative humidity of from 20% to 60% for a period up to sixty minutes at a temperature of from about 15° C. to about 25° C.

By way of example, FIG. 180 shows an exemplary buttress assembly (10200) that may be used in place of buttress assembly (100) described above. Buttress assembly (10200) of this example comprises an upper buttress body (10202) with a lower adhesive layer (10214). Buttress assembly (10200) of this example further comprises a lower buttress body (10212) with an upper adhesive layer (10204). In use, the lower and upper adhesive layers (10214, 10204) temporarily adhere to wet tissue ($T_1$, $T_2$) to serve as an adjunct to reinforce the mechanical fastening of the tissue provided by staples (90) as shown in FIG. 181. Of course, the applied staples (90) will also secure buttress assembly (10200) to tissue ($T_1$, $T_2$). Before buttress assembly (10200) is applied to tissue ($T_1$, $T_2$), buttress assembly (10200) may be removably secured to end effector (40) in any suitable fashion as will be apparent to those of ordinary skill in the art in view of the teachings herein.

FIG. 182 shows another exemplary buttress assembly (10300) that may be used in place of buttress assembly (100) described above. Buttress assembly (10300) of this example comprises an upper buttress body (10302) that has an upper adhesive layer (10304a) and a lower adhesive layer (10314a). Buttress assembly (10300) further comprises a lower buttress body (10312) having an upper adhesive layer (10304b) and a lower adhesive layer (10314b). In use, upper and lower adhesive layers (10304a, 10314b) respectively provide for temporary attachment of the buttress bodies (10302, 10312) to underside (65) of anvil (60) and deck (73) of staple cartridge (70). Lower and upper adhesive layers (10314a, 10304b) temporarily adhere to tissue ($T_1$, $T_2$) to serve as an adjunct to reinforce the mechanical fastening of wet tissue provided by staples (90). Of course, the applied staples (90) will also secure buttress assembly (10300) to tissue ($T_1$, $T_2$).

In some instances, the humidity tolerant adhesive materials (e.g., one or more of layers (104, 10204, 10304, 114, 10214, 10314)) for a buttress body (102, 10202, 10302, 112, 10212, 10312) comprise bioabsorbable polymers. Various physiomechanical properties of polymers may be modified in order to provide different adhesive properties. Such variable characteristics include but are not limited to copolymer composition, polymer architecture (e.g., random vs. block copolymers and/or branching), glass transition temperature (Tg), molecular weight (number average or weight average), inherent viscosity (IV), crystallinity, sequence distribution, copolymer chain composition, melting temperature (Tm), surface tension and rheological properties. Several exemplary combinations of these variables will be provided below, though it should be understood that these examples are merely illustrative. It should also be understood that these examples of adhesive materials may be provided in upper adhesive layer (104, 10204, 10304). In addition or in the alternative, these examples of adhesive materials may be provided in lower adhesive layer (114, 10214, 10314). In addition or in the alternative, these examples of adhesive materials may be otherwise integrated into buttress body (102, 10202, 10302, 112, 10212, 10312). It should therefore be understood that the adhesive material need not necessarily constitute a separate layer that is discretely identifiable as being different from a layer defined by buttress body (102, 10202, 10302, 112, 10212, 10312).

One of the aforementioned physiomechanical properties of polymers is glass transition temperature (Tg). Glass transition temperature (Tg) is the temperature at which the mechanical properties of a copolymer change dramatically from a flowable adhesive to a brittle plastic. It may thus be of importance that the glass transition temperature (Tg) is sufficiently below the operating temperature of the adhesive in order to allow for polymer chain mobility. The glass transition temperature (Tg) is lower than the melting point of the crystalline form of the same copolymer. The glass transition temperature (Tg) may be indicative of how the polymer behaves under ambient conditions. The glass transition temperature (Tg) can be effected by composition, polymer chain configuration and stiffness, molecular weight, viscosity, shear modulus, heat capacity, thermal expansion, cross-linking and other factors. It is therefore possible to have a relatively low glass transition temperature (Tg) material composition that does not always correspond to low molecular weight or low inherent viscosity (IV).

The melting temperature of a polymer may be referred to as the "first-order transition," which is where the polymer changes from a solid to liquid. Crystalline polymers have a true melting point, which is the temperature at which the crystallites melt and the total mass of plastic becomes amorphous. Amorphous polymers do not have a true melting point, but they do have a first-order transition wherein their mechanical behavior transitions from a rubbery nature to viscous rubbery flow. Suitable polymers for use in forming adhesive layers (104, 10204, 10304, 114, 10214, 10314) may have a percentage of crystallinity making them semi-crystalline, thus having both amorphous and crystalline domains. The melting point of the polymer may be sufficiently high above the operating temperature of the adhesive to maintain cohesive strength and provide dimensional stability of the applied adhesive.

Inherent viscosity (IV) reflects a measurement of molecular size. It is based on the flow time of a polymer solution through small capillary channels over time. The inherent viscosity (IV) and molecular weight of a polymer are related, but that relational agreement is different for each copolymer composition. For instance, the correlation of inherent viscosity (IV) to molecular weight may be logarithmic with only a small midsection of the curve being linear. This logarithmic correlation may differ as the copolymer composition differs. It is not necessarily required to have a low molecular weight copolymer in order to manifest adhesive and malleable properties. Low molecular weight copolymers may also have shortened degradation cycles and reduced structural strength. The ideal adhesion film or adhesive substrate to use in adhesive layers (104, 10204, 10304, 114, 10214, 10314) may have higher molecular weight and low inherent viscosity (IV) to be both strong and adhesive. This may be achieved, for example, by the introduction of polymer branching. The molecular weight of the adhesive may need to be high enough to provide mechanical strength to the adhesive to avoid cohesive failure, but also sufficiently low enough that it can be cleared from the body through degradation in an acceptable amount of time.

Further important properties of the polymers include their surface tension and rheological properties. If there is a sufficiently large mismatch between the surface tension of the adhesive and the surfaces to be adhered to, adhesion may be energetically unfavorable. Similarly, the rheological properties of the polymer such as bulk moduli may need to be such that the polymer can flow to conform to the surface topography of deck (73) or underside (65), while simultaneously providing enough integrity to maintain cohesive strength and to resist shearing off and/or peeling off of end effector (40).

In some instances, the humidity tolerant adhesive materials may be malleable. Malleable humidity tolerant adhesives may be highly viscous yet flowable at room temperature. A malleable humidity tolerant adhesive may, in response to pressure being applied to it, take the form of a surface with which it is engaged. In other words, if a malleable humidity tolerant adhesive is pressed against deck (73) of staple cartridge (70), the adhesive may take the form of the one or more features of the deck (73) that it the adhesive is pressed against. Similarly, if a malleable humidity tolerant polymer adhesive is pressed against underside (65) of anvil (60), the adhesive may take the form of the one or more features of underside (65) that the adhesive is pressed against. By deforming to the geometry that it is pressed against, the malleable humidity tolerant adhesive may adhere to the geometry, and may further provide re-applicable attachment. If the desired positioning of buttress assembly (100, 110) on deck (73) or underside (65) is not achieved, the malleable humidity tolerant adhesive may permit buttress assembly (100, 110) to be removed, repositioned, and re-adhered to deck (73) or underside (65). It should be understood that the humidity tolerant adhesives may be malleable at room temperature, such that additional heating or other treatment is not necessary in order to provide malleability.

Providing the humidity tolerant adhesive material in the form of a malleable polymer may minimize the impact of fluids and debris on the adhesion of buttress assembly (100, 110) to deck (73) of staple cartridge (70) or underside (65) of anvil (60). The malleable humidity tolerant adhesive material may also be hydrophilic (e.g., at least in certain regions of buttress assembly (100, 110)), encouraging adhesion in a wet environment. In addition or in the alternative, adhesive layer (104, 114) of buttress assembly (100) may include a combination of adhesive material and hydrophobic material in respective localized regions. The hydrophobic material may drive fluids out of the adhesion areas, thereby improving adhesion at the localized regions of adhesive material. In some examples, the humidity tolerant adhesive material may be combined with a buttress body (102,112) as disclosed in U.S. patent application Ser. No. 14/667,842, entitled "Method of Applying a Buttress to a Surgical Stapler," filed Mar. 25, 2015, now U.S. Patent Pub. No. 2016/0278774, published Sep. 26, 2016, issued as U.S. Pat. No. 10,349,939 on Jul. 16, 2019, the disclosure of which is incorporated by reference herein.

In some instances, the humidity tolerant adhesive materials may be extrudable. The extrudable adhesive may be extruded through a die that may be positioned directly next to or adjacent to the extruder. A melt pump may be used between the die and extruder. The die may be used to form an extrudate that is generally planar and continuous or to form discrete deposits (e.g., rod-shaped deposits) on the surface of a buttress assembly (100, 110) before it is pressed against a deck (73) of staple cartridge (70) or pressed against the underside of an anvil (60).

A. Exemplary Humidity Tolerant Adhesives with A-B-A Block Polymer Configurations In some instances, the humidity tolerant adhesive materials (e.g., one or more of layers (104, 10204, 10304, 114, 10214, 10314)) for a buttress body (102, 10202, 10302, 112, 10212, 10312) comprise polymers having a general A-B-A block configuration. In illustrative examples, the A-B-A block polymers comprise by the percentage of their molecular weight: from about 1% to about 50%, or more particularly from about 5% to about 30% of A polymer blocks; and from about 50% to about 99%, or more particularly from about 70% to about 95%, of B polymer blocks.

The A polymer blocks are biodegradable, bioabsorbable, highly crystalline segments, which are homopolymers that may be characterized by a relatively high glass transition temperature (Tg) and/or a relatively high crystallinity. In illustrative examples, the A homopolymers may be characterized by a glass transition temperature (Tg) of at least about 0° C., preferably at least about 21° C. (i.e., room temperature). In addition, or in the alternative, the A homopolymers may be characterized by a crystallinity as measured by X-ray diffraction of at least about 30%, preferably at least about 40%, or more preferably at least about 45%. In addition, or in the alternative, the A homopolymers may have a molecular weight of at least about 5 kDa. Such exemplary A homopolymers may further be characterized by a melting temperature (Tm) of at least about 50° C., preferably at least about 60° C., and more preferably at least about 70° C.

Exemplary A homopolymers may be selected from the group of: poly(L-lactide) (PLLA); poly(caprolactone) (PCL); polyglycolide (PGA); poly(103-hydroxybutyrate) ($PH_3B$); poly(103-hydroxyvalerate) (PHV); and poly(p-dioxanone) (PPDO). It may be difficult to synthesize 100% A homopolymers. In some instances, the A homopolymers may contain a small percentage of residual B monomers. For example, exemplary A homopolymers may contain a small percentage (e.g., up to about 10% by weight) of B monomers.

The B polymer blocks are biodegradable, bioabsorbable homopolymers or co-polymers, which are predominantly amorphous and may be characterized by a relatively low to moderate glass transition temperature (Tg). In illustrative examples, the B polymers as homopolymers or co-polymers may be characterized by glass transition temperature (Tg) of at least about −40° C., more particularly at least about −30° C., and more particularly at least about −20° C. In addition, or in the alternative, the B homopolymers or co-polymers may be characterized by a crystallinity as measured by X-ray diffraction of at most about 25%, more particularly at most about 10%, or more particularly at most about 5%. In addition, or in the alternative, the B polymers as homopolymers or co-polymers may have a molecular weight of from about 20 to about 80 kDa, more particularly from about 30 to about 70 kDa, and more particularly, from about 40 to about 65 kDa.

Exemplary B homopolymers or co-polymers comprise monomers selected from the group consisting of: caprolactone (CL), L-Lactide (LLA), D,L-Lactide ((D,L)LA), Glycolide (GA), Polydioxanone (PDO), Trimethylene carbonate (TMC), sebacic acid (SA), 1,6-bis(carboxyphenoxy)hexane (CPH), and combinations thereof.

In some instances, the humidity tolerant adhesive materials having a general A-B-A block configuration may be blended with a tackifying agent to provide for an extrudable adhesive. Such extrudable humidity tolerant adhesive materials may be manufactured using hot melt extrusion. In illustrative examples, the A-B-A block polymer may be fed into a hot melt compounding twin-screw extruder. Once the A-B-A block polymer is sufficiently masticated and melted, the tackifying agent is added into the extruder. In some versions, additional compounds may be added in one or more additional steps to the extruder. Such additional compounds may selected from the group consisting of: plasticizing molecules; preservatives (e.g. antioxidants); fillers; and combinations thereof. Once mixing in the extruder is completed, the resulting adhesive may be fed through an extruder die and produced as a stand-alone flexible film that is then applied to a buttress body (102, 112). In addition, or in the alternative, the resulting adhesive may be fed through an extruder die and deposited directly onto a buttress body (102, 112). In any case, the adhesive may then be annealed to obtain any necessary phase separation at, near or above the A-block melting temperature, $T_m$. In addition, or in the alternative, the resulting adhesive may be sterilized, such as by treating it with ethylene oxide at a high temperature.

In illustrative examples, the tackifying agent may comprise a substantially amorphous biodegradable, bioabsorbable polymer with a molecular weight below the entanglement molecular weight. In addition, or alternative, the tackifying agent may have a glass transition above about 0° C., more particularly above about 20° C. In some examples, the tackifying agent may comprise a random copolymer of poly(L-lactide)-co-polyglycolide (PLGA) having a molecular weight of from about 1 to about 8 kDA, more particularly from about 1.5 to about 5 kDa.

In illustrative examples, an extrudable hot melt adhesive comprises ratios of polymer A-B-A and tackifying agent such that the glass transition of the blend ranges from about −5° C. to about 15° C., more particularly from 0° C. to about 10° C. In addition, or in the alternative, the rheological properties of the polymer such as bulk moduli need to be such that the polymer can flow to conform to the surface topography of deck (73) or underside (65), while at the same time, providing enough integrity to maintain cohesive strength and resisting shearing off and/or peeling off of end effector (40).

B. Exemplary Humidity Tolerant Adhesives with A-B-C Block Terpolymer Configurations In some instances, the humidity tolerant adhesive materials (e.g., one or more of layers (104, 10204, 10304, 114, 10214, 10314)) for a buttress body (102, 10202, 10302, 112, 10212, 10312) comprise polymers having a general A-B-C block terpolymer configuration, in which the C polymer block comprises a hydrophilic polymer. Generally it is theorized, but in no way limits the scope of this invention, that humidity tolerant adhesives comprising hydrophilic polymers may have better wet surface retention characteristics than adhesives comprising only hydrophobic polymers.

In some versions, the A-B-C block terpolymers may be combined with a water sorbent. Useful water sorbents may be selected from the group consisting of: carboxymethyl cellulose (CMC); polyvinylpyrrolidine (PVP); gelatin; hyaluronan; and combinations thereof. In some such examples, the A-B-C block terpolymers may be combined with water sorbent such that the resulting mixture comprises by its weight percentage from about 1% to about 60%, preferably from about 20% to about 40%, of the water sorbent.

The A polymer blocks are biodegradable, bioabsorbable, non-elastic, highly crystalline segments, which are homopolymers that may be characterized by a relatively high glass transition temperature (Tg) and/or a relatively high crystallinity. In illustrative examples, the A homopolymers may be characterized by a glass transition temperature (Tg) of at least about 0° C., more particularly at least about 21° C. (i.e., room temperature). In addition, or in the alternative, the A homopolymers may be characterized by a crystallinity as measured by X-ray diffraction of at least about 30%, more particularly at least about 40%, or more particularly at least about 45%. In addition, or in the alternative, the A homopolymers may have a molecular weight of at least about 5 kDa. Such exemplary A homopolymers may further be characterized by a melting temperature (Tm) of at least about 50° C., more particularly at least about 60° C., and more particularly at least about 70° C.

Exemplary A homopolymers may be selected from the group of: poly(L-lactide) (PLLA); poly(caprolactone) (PCL); polyglycolide (PGA); poly(103-hydroxybutyrate) ($PH_3B$); poly(103-hydroxyvalerate) (PHV); and poly(p-dioxanone) (PPDO). It may be difficult to synthesize 100% A homopolymers. The A homopolymers may thus contain a small percentage of residual B monomers. For example, exemplary A homopolymers may contain a small percentage (e.g., up to about 10% by weight) of B monomers.

The B polymer blocks are biodegradable, bioabsorbable, elastomeric homopolymers or co-polymers, which are predominantly amorphous and may be characterized by a relatively low to moderate glass transition temperature (Tg). In illustrative examples, the B polymers as homopolymers or co-polymers may be characterized by glass transition temperature (Tg) of at least about −40° C., more particularly at least about −30° C., and more particularly at least about −20° C. In addition, or in the alternative, the B homopolymers or co-polymers may be characterized by a crystallinity as measured by X-ray diffraction of at most about 25%, more particularly at most about 10%, or more particularly at most about 5%. In addition, or in the alternative, the B polymers as homopolymers or co-polymers may have a molecular weight of from about 20 to about 80 kDa, more particularly from about 30 to about 70 kDa, and more particularly, from about 40 to about 65 kDa. In addition, or in the alternative, the B polymers as homopolymers may have a an entanglement molecular weight of from about 3 to 4 kDa.

Exemplary B homopolymers or co-polymers comprise monomers selected from the group consisting of: caprolactone (CL), L-Lactide (LLA), D,L-Lactide ((D,L)LA), Glycolide (GA), Polydioxanone (PDO), Trimethylene carbonate (TMC), sebacic acid (SA), 1,6-bis(carboxyphenoxy)hexane (CPH), and combinations thereof. As another merely illustrative example, B polymers or co-polymers may be selected from the group of: caprolactone-co-glycolide (CAP-co-GLY); poly(L-lactide)-co-glycolide (PLGA); poly(D,L-lactide) (P(D,L)LA); poly(caprolactone)-co-glycolide (PCL-co-GA); poly[(1,6-bis(p-carboxyphenoxy)hexane)-co-sebacic acid (PCPH-co-SA); poly(trimethylene carbonate) (PTMC); poly(trimethylene carbonate)-co-glycolide (PTMC-co-GA; and poly(trimethylene carbonate)-co-caprolactone (PTMC-co-CL).

The C polymer blocks are biodegradable, bioabsorbable, hydrophilic homopolymers or co-polymers and may be characterized by miscibility with water at 37° C. Exemplary C homopolymers and co-polymers may be selected from the group of: polyethylene oxide (PEO); polyethylene oxide-co-polypropylene oxide (PEO-co-PPO); polyethylene oxide-co-polysulfone (PEO-co-PSO); polyvinylpyrrolidine (PVP); polyacrylic acid (PAA); and polyvinyl alcohol (PVOH).

In an illustrative example of a useful A-B-C block terpolymer, A is glycolide (GLY), B is a co-polymer of caprolactone-glycolide (CAP-co-GLY) and C is polyethylene oxide (PEO).

XXX. Techniques for Providing and/or Improving Adhesion of Buttress to Wet End Effector One of ordinary skill in the art will recognize that, during some uses of instrument (10), the operator may need to actuate end effector (40) several times within a patient. Each actuation may require the operator to remove end effector (40) from the patient, reload a new staple cartridge (70) into lower jaw (50), apply new buttress assemblies (100, 110) to anvil (60) and staple cartridge (70), and then insert the reloaded end effector (40) into the patient. Each time end effector (40) is removed from the patient, anvil (60) may be substantially wet with bodily fluids from the patient and/or other fluids in the surgical field. Even when a new cartridge (70) is installed in lower jaw (50), the new cartridge (70) may also receive fluids from other portions of end effector (40) that were already wet. The presence of fluids on underside (65) of anvil (60) and/or on deck (73) of staple cartridge (70) may make it difficult to adhere buttress assemblies (100, 110) to anvil (60) and staple cartridge (70). The following examples relate to various compositions and configurations that may be used to promote proper adhesion of buttress assemblies (100, 110) to anvil (60) and staple cartridge (70) when buttress assemblies (100, 110) to anvil (60) and staple cartridge (70) are wet with one or more fluids.

A. Adhesion of Buttress to Wet End Effector Using Humidity Tolerant Adhesive Materials In some surgical applications, it may be desirable to provide a buttress body (102, 112) with one or more humidity tolerant adhesive materials that will at least temporarily adhere to a wet end effector (40), particularly when it is being used intraoperatively. In some instances, humidity tolerant adhesive materials may provide for temporary attachment of a buttress body (102, 112) to the wet deck (73) of staple cartridge (70) or the wet underside (65) of anvil (60). A humidity tolerant adhesive material is defined herein as an adhesive material that holds a buttress body (102, 112) in place on an anvil (60) or staple cartridge (70) for at least five minutes in an environment of 100% relative humidity (e.g., in a patient's body, at a normal body temperature of approximately 37° C.), preferably after the buttress body (102, 112) has been exposed to a relative humidity of from about 20% to about 60% for up to one hour at room temperature (e.g., between approximately 20° C. and approximately 22° C.). In some instances, a humidity tolerant adhesive material may hold a buttress body (102, 112) in place on an anvil (60) or staple cartridge (70) for at least ten minutes in an environment of 100% relative humidity (e.g., in a patient's body, at a normal body temperature of approximately 37° C.), preferably after the buttress body (102, 112) has been exposed to a relative humidity of from about 20% to about 60% for up to one hour at room temperature (e.g., between approximately 20° C. and approximately 22° C.). A pressure sensitive humidity tolerant adhesive material is defined herein as a humidity tolerant adhesive material that can be transferred from a delivery device onto an anvil (60) or staple cartridge (70) by the pressure respectively exerted by the anvil (60) or staple cartridge (70).

As noted above, FIG. 4 shows buttress assemblies (100, 110) that each comprises a buttress body (102, 112) and an adhesive layer (104, 114). adhesive layers (104, 114) respectively provide for temporary attachment of the buttress bodies (102, 112) to underside (65) of anvil (60) and deck (73) of staple cartridge (70). It should be understood that the humidity tolerant adhesive material need not necessarily constitute a separate adhesive layer (104, 114) that is discretely identifiable as being different from a layer defined by buttress body (102, 112). Examples of humidity tolerant adhesive materials that may be otherwise integrated onto or into a buttress body (102, 112) are described in further detail below.

In some instances, the humidity tolerant adhesive materials (e.g., one or more of layers (104, 114)) for a buttress body (102, 112), comprise polymers that are either bioabsorbable or of a molecular weight that is sufficiently low so as to be cleared from the patient's body (e.g., less than approximately 30,000 KDa). Various physiomechanical properties of polymers may be modified in order to provide different adhesive properties. Such variable characteristics include but are not limited to the following: copolymer composition; copolymer architecture (e.g., random vs. block configurations, polymer branching, etc.); glass transition temperature (Tg); molecular weight; crystallinity; sequence distribution; copolymer chain composition; melting temperature (Tm); solubility or dissolution rate; rheological properties; surface tension; and combinations thereof. Several exemplary combinations of these variables will be provided below, though it should be understood that these examples are merely illustrative.

In addition or in the alternative to the aforementioned modifications to the physiomechanical properties of polymers, some exemplary humidity tolerant adhesive materials may comprise polymers that are combined with sorbents. Useful sorbents may be selected from the group consisting of: polysaccharides such as cellulose; cellulose derivatives, e.g., sodium carboxymethylcellulose (Na-CMC); starch;

starch derivates; natural gums, e.g., agar and alginates; chitosan; pectin; gelatin; and combinations thereof. In some examples, a hydrocolloid of one or more sorbents may be mixed with the polymers. In some examples, the humidity tolerant adhesive material comprises a blend of sorbent and polymer in a ratio in a range of 70:30 sorbent to polymer, more particularly in a range of 50:50 sorbent to polymer, more preferably in a range of 10:90 sorbent to polymer. Generally it is theorized, but in no way limits the scope of this invention, that sorbents may act to absorb moisture away from the surface interface between the humidity tolerant adhesive material and the surface to which it is adhered (e.g., a wet end effector (40)), and to maintain the adherence of the buttress body (102, 112) to said surface until such time as the buttress body (102, 112) is deployed or released from end effector (40) (see, for example, FIG. 5C).

One of the aforementioned physiomechanical properties of polymers is glass transition temperature (Tg). Glass transition temperature is the temperature at which the mechanical properties of a copolymer change dramatically from a flowable adhesive to a brittle plastic. It may thus be of importance that the glass transition temperature (Tg) is sufficiently below the operating temperature of the humidity tolerant adhesive material in order to allow for sufficient polymer chain mobility. The melting temperature (Tm) of a polymer may be referred to as the "first-order transition," which is where the polymer changes state from solid to liquid. Crystalline polymers have a true melting point, which is the temperature at which the crystallites melt and the total mass of plastic becomes liquid. Amorphous polymers do not have a true melting point, but they do have a first-order transition wherein their mechanical behavior transitions from a rubbery nature to viscous rubbery flow. Suitable polymers for use in humidity tolerant adhesive materials may be semi-crystalline, i.e., they may have both amorphous and crystalline segments. Suitable polymers may have a melting point that is sufficiently above the operating temperature of the humidity tolerant adhesive material to maintain cohesive strength and to provide dimensional stability of the applied humidity tolerant adhesive material.

The molecular weight of non-bioabsorbable polymers should be high enough to provide mechanical strength to the resulting adhesive material in order to avoid cohesive failure, yet low enough that they can be cleared by the patient's body. In the case of biodegradable polymers, an upper limit on molecular weight may not be required to provide polymer breakdown products are small enough to be cleared by the patient's body.

The solubility or dissolution rate of polymers in the aqueous environments that may be encountered during surgery depend upon a number of polymer characteristics including, but not limited to: polymer composition; polymer architecture; degree of cross-linking; block length; crystallinity; molecular weight; branching; and combinations thereof. In illustrative examples described below, certain polymers and co-polymers are chosen and combined with these characteristics in mind in order to decrease the dissolution rate of the resulting humidity tolerant adhesive materials that are of use for adhering a buttress body (102, 112) to a wet end effector (40) during surgery, and maintaining the adherence of the buttress body to the wet end effector (40) until such time as the buttress body (102, 112) is deployed or released from end effector (40) (see, for example, FIG. 5C).

The surface tension and rheology of polymers present in a humidity tolerant adhesive material may also impact its adhesive properties. For example, if there is a sufficiently large mismatch between the surface tension of the polymers and the surfaces to which it will adhere, adhesion between the two may be energetically unfavorable. Similarly, the rheological properties of the polymer such as bulk modulus may be such that the humidity tolerant adhesive material can flow to conform to the surface topography of the end effector (40), while at the same time providing sufficient integrity to maintain cohesive strength and resist shearing and peeling of the buttress body (102, 112) from the end effector (40).

1. Exemplary Humidity Tolerant Adhesive Materials Comprising Poloxamer Blends

In some examples, the humidity tolerant adhesive materials (e.g., one or more of layers (104, 114)) for a buttress body (102, 112) may comprise a blend of "plastic fats", more particularly, poloxamers. In illustrative examples, the blend of poloxamers may comprise a blend of poloxamers selected from the group consisting of: poloxamer 188, for example Kolliphor® P188 from BASF (Florham Park, N.J.); Synperonic® PE/P84 from Croda Inc. (Edison, N.J.); poloxamer 124, for example Pluronic® L44 from BASF (Florham Park, N.J.); poloxamer 407, for example Pluronic® F-127 from BASF (Florham Park, N.J.); and combinations thereof. Preferably, the poloxamers are of National Formulary grade. The resulting poloxamer-based humidity tolerant adhesive materials may be putty-like materials with a relatively low crystallinity and low glass transition temperature (Tg). Generally it is theorized, but in no way limits the scope of this invention, that the presence of polypropylene oxide repeat units in the backbone of the poloxamers provides for a poloxamer blend having a slower dissolution rate, which may desirably provide for humidity tolerant adhesive materials having a greater humidity (i.e., wetness) tolerance. In turn, a buttress body (102, 112), to which poloxamer-based adhesive materials have been applied, may desirably remain adhered to a wet end effector (40) of a surgical stapling instrument (10) during a surgical procedure until such time as buttress body (102, 112) is deployed (see, for example, FIG. 5C).

In some examples, the humidity tolerant adhesive materials comprise a poloxamer blend of poloxamer 188 and Synperonic® PE/P84 in a molar ratio in the range of from 1:3 to 1:4 of poloxamer 188 to Synperonic® PE/P84. In some other examples, humidity tolerant adhesive materials comprise a poloxamer blend of poloxamer 188 and poloxamer 124 in a molar ratio in the range of from about 1:1 to about 1:4, more particularly from about 1:1.5 to about 1:3, of poloxamer 188 to poloxamer 124. In yet some other examples, the poloxamer blend may comprise a blend of poloxamer 407 and poloxamer 124 in a molar ratio in the range of from about 1:1, to about 1:5, more particularly from about 1:1.5 to about 1:3 of poloxamer 407 to poloxamer 124.

In yet some other examples, the poloxamers may be combined with non-ionic surfactants to modify the hydrophobicity of the resulting humidity tolerant adhesive material. In some such examples, the poloxamers may be combined with non-ionic surfactants selected from the group consisting of: polysorbates; polyethylene glycol hexadecyl ether, for example Brij 52 from Croda Inc. (Edison, N.J.); sorbitane monooleate, for example, Span® 80 from Sigma Aldrich (Saint Louis, Mo.); and combinations thereof.

In each of the foregoing exemplary poloxamer blends, it may be important to control the crystallite size of the poloxamers in order to achieve the desirable adhesive characteristics in the resulting humidity tolerant adhesive material.

2. Exemplary Humidity Tolerant Adhesive Materials Comprising Polyethylene Glycol or Polyethylene-Polyethylene Glycol Co-polymer In some examples, the humidity tolerant adhesive materials (e.g., one or more of layers (104, 114)) for a buttress body (102, 112) comprise polyethylene glycol (PEG) or polyethylene-polyethylene glycol co-polymers (PE-co-PEG). The resulting humidity tolerant adhesive materials may be putty-like, malleable and extrudable.

In yet further examples, the pressure sensitive humidity tolerant adhesive materials comprise, or consist essentially of, polyethylene-polyethylene glycol co-polymers (PE-co-PEG) with a molecular weight that is sufficiently low so as to be cleared from the patient's body (e.g., less than approximately 30,000 KDa).

In yet further examples, the humidity tolerant adhesive materials comprise a blend of polyethylene-polyethylene glycol copolymers (PE-co-PEG) and poly(caprolactone)-glycolide copolymers (PCL/PGA) in the ratio of about 40:60 PCL:PGA, preferably in a ratio of about 50:50 PCL:PGA, more preferably in a ratio of about 60:40 PCL:PGA. Such a blend may have low crystallinity and may even be near amorphous.

In yet further examples, the humidity tolerant adhesive materials comprise a blend of polyethylene glycol having different molecular weights that is in turn blended with a polymer or co-polymer selected from the group consisting of: poloxamers; poly(caprolactone)-glycolide copolymers (PCL/PGA); lactide (PLA); and combinations thereof. By way of example only, the blend may include polyethylene glycol 3350 (PEG 3350), polyethylene glycol 400 (PEG 400), and/or other polyethylene glycols.

In yet further examples, the humidity tolerant adhesive materials comprise a block copolymer of polyethylene glycol 20,000 (PEG 20,000) and poly(caprolactone)-glycolide copolymers (PCL/PGA) that are characterized by a molar-ratio of 65:35 poly(caprolactone) (PCL) to glycolide (PGA). The resulting blends may have a relatively high molecular weight and lower solubility.

As yet another merely illustrative example, the humidity tolerant adhesive materials comprise a blend of other water soluble copolymers with poloxamers or PEG, with a molecular weight low enough to be cleared from the patient's body. Such a blend may be substituted for a component of any of the blends described above; or for the entirety of any of the blends described above. By way of further example only, the polymer(s) in such a blend may be biodegradable such as PCL/PGA, etc.

3. Exemplary Humidity Tolerant Adhesive Materials Comprising Solid Triglycerides in Oil In some examples, the humidity tolerant adhesive materials (e.g., one or more of layers (104, 114)) for a buttress body (102, 112) comprise "plastic fats" comprising solid triglycerides in oil. In some illustrative examples, such humidity tolerant adhesive materials further comprise sorbents. Useful sorbents may be selected from the group consisting of: polysaccharides such as cellulose; cellulose derivatives, e.g., sodium carboxymethylcellulose (Na-CMC); starch; starch derivates; natural gums, e.g., agar and alginates; chitosan; pectin; gelatin; and combinations thereof. Useful triglycerides may be selected from the group consisting of: decanoyl glycerides; octanoyl glycerides; and combinations thereof—for example, Miglyol® 810, 812, 818 and 829 from Caesar & Loretz GMBH (Hilden, Del.). Useful oils may be selected from the group consisting of: bis-diglyceryl polyacyladipate-1; glycerol trioheptanoate; and combinations thereof—for example, Softisan® 645 and Spezialöl from Cremer Care (Hamburg, GE). The resulting humidity tolerant adhesive materials may desirably provide for good adhesion to end effector (40) and good spreading properties.

4. Exemplary humidity Tolerant Adhesive Materials Comprising Hydrocolloid Gels In some examples, the humidity tolerant adhesive materials (e.g., one or more of layers (104, 114)) for a buttress body (102, 112) comprise hydrocolloid gels. In some illustrative examples, useful hydrocolloid gels may be selected from the group consisting of gels comprising: chitosan; carboxymethyl cellulose (CMC); ethyl cellulose; hydroxypropylmethyl cellulose; gelatin; and combinations thereof. The resulting humidity tolerant adhesive materials may have a relatively high water binding capacity.

B. Exemplary Patterning of Humidity Tolerant Adhesive Materials on Buttress Body Patterning of humidity tolerant adhesive material on a buttress body (102, 112) may be utilized to impact the strength of the adhesive bond of the buttress body (102, 112) to an end effector (40), particularly a wet end effector (40). In exemplary embodiments in which it is desired to reduce the overall adhesion of a buttress body (102, 112) to an end effector (40) so that it may be more easily deployed or released from end effector (40) (as in FIG. 5C for example), the humidity tolerant adhesive material may be applied to a buttress body (102, 112) in a pattern selected from the group consisting of: stripes; discrete dots; lattices; and combinations thereof. Conversely, in exemplary embodiments in which it is desired to increase the overall adhesion of a buttress body (102, 112) to an end effector (40) so that it less readily deployed or released from end effector (40) (as in FIG. 5C for example), the humidity tolerant adhesive materials may be applied in an adhesive layer (104, 114), that extends continuously along the entire surface of buttress body (102, 112).

FIG. 183 shows an exemplary buttress body (11702) in which humidity tolerant adhesive material is applied to the buttress body (11702) in a pattern of obliquely oriented stripes (11704). Generally it is theorized, but in no way limits the scope of this invention, that oblique stripes (11704) present a continuous line to resist side loads that may be encountered during surgery by a buttress body (11704) that has been adhered to an end effector (40). In addition, it is believed that oblique stripes (11704) minimize the percentage of area that is coated by the adhesive material along the axis of the buttress body (11702) in the direction of the forces that will release the buttress body (11702), so as allow the buttress body (11702) to be readily deployed from the end effector (40) during a surgical procedure (as in FIG. 5C for example). In the present example, oblique stripes (11704) are oblique in the sense that stripes (11704) extend along paths that are obliquely oriented relative to axes that are parallel to the longitudinal axis of buttress body (11702). In some exemplary variations, stripes (11704) extend along axial paths that are parallel to the longitudinal axis of buttress body (11702).

FIG. 184 depicts a perspective view of an exemplary buttress body (11802) in which humidity tolerant adhesive material has been applied in a pattern of discrete, semi-rigid dots (11804). The discrete, rigid semi-dots (11804) may be sized and positioned to correspond with the positioning of staple forming pockets (64) of anvil (60). Thus, the discrete, semi-rigid dots of adhesive material (11804) may be arranged in four longitudinally extending linear arrays, with each longitudinally extending linear array corresponding the longitudinally arrayed arrangement of staple forming pockets (64) of anvil (60). Alternatively, any other suitable arrangement may be used. Generally it is theorized, but in no way limits the scope of this invention, that adding the rigid dots (11804) boosts the modulus of the humidity tolerant adhesive material, while having little impact on its cohesive strength.

FIG. 185 shows how buttress body (11902) provides a lattice defining a plurality of cells (11908). Due to the presence of cells (11908) and the porous nature of buttress body (11902), when the humidity tolerant adhesive material (11904) is applied to the buttress body (11902), it forms a lattice pattern by entering into some of those cells (11908), thereby partially infusing buttress body (11902) with the adhesive material. In other words, buttress body (11902) acts like a sponge absorbing the adhesive material, allowing the adhesive material to deform, surround, and essentially grab hold of the lattice connections within buttress body (11902).

In some instances, the humidity tolerant adhesive material is initially applied to buttress body (11902) when the adhesive material is in a relatively highly viscous form. Buttress body (11902) is then heated to decrease the viscosity of the adhesive material, causing the adhesive material to enter some of the cells (11908) of buttress body (11902). Buttress body (11902) is then cooled or allowed to cool, causing the viscosity of the adhesive material to increase back to its previous state. Buttress body (11902) may then be heated again as buttress body (11902) is being applied to end effector (40) as described above. In some other versions, the adhesive material already has a low enough viscosity to enter cells (11908) when the adhesive material is applied, without requiring the adhesive material to be heated. In other words, the adhesive material may wick into cells (11908) of buttress body (11902). In some such versions, a protective film (e.g., polytetrafluoroethylene (PTFE)) may be applied over the adhesive material to protect and/or contain the adhesive material before buttress body (11902) is applied to end effector (40). Other suitable ways in which buttress assembly (11902) may be formed and provided are disclosed in U.S. patent application Ser. No. 14/667,842, entitled "Method of Applying a Buttress to a Surgical Stapler," filed Mar. 25, 2015, now U.S. Patent Pub. No. 2016/0278774, published Sep. 26, 2016, issued as U.S. Pat. No. 10,349,939 on Jul. 16, 2019, the disclosure of which is incorporated by reference herein.

C. Reduction of Spontaneous Separation of Buttress from Humidity Tolerant Adhesive Material In some surgical applications, it may be desirable to reduce the spontaneous separation of a buttress body (102, 112) from the humidity tolerant adhesive material that has been applied thereto. Such spontaneous separation or "de-wetting" may occur as a result of moisture being present on the end effector (40) to which the buttress body (102, 112) has been adhered. In some instances, de-wetting may be minimized by one or more steps selected from the group consisting of: drying; priming; absorbing water; and combinations thereof. Each of these steps is explained in further detail below.

In some instances, de-wetting may be minimized by drying the end effector (40) prior to adhering a buttress body (102, 112) thereto. In exemplary embodiments, drying the end effector (40) may be accomplished by applying an absorbent to the end effector (40). For instance, end effector (40) may be temporary clamped onto an absorbent platform (e.g., comprising a polyacrylate pad) in order to substantially dry underside (65) of anvil (60) and deck (73) of staple cartridge (70) as described in U.S. Patent App. No. 62/209,041, entitled "Method and Apparatus for Applying a Buttress to an End Effector of a Surgical Stapler," filed Aug. 24, 2015, the disclosure of which is incorporated by reference herein. Other suitable ways in which end effector (40) may be dried prior to adhering a buttress body (102, 112) thereto will be apparent to those of ordinary skill in the art in view of the teachings herein.

In some instances, de-wetting may be additionally or alternatively minimized by priming the end effector (40) with a hydrophobic layer prior to adhering a buttress body (102, 112) thereto. In exemplary embodiments, a sponge with an adhesive-miscible hydrophobe may be clamped onto the end effector (40) to make it temporarily hydrophobic prior to adhering a buttress body (102, 112) thereto. In exemplary embodiments, adhesive-miscible hydrophobes may be selected from the group consisting of: ethyl citrate; triacetin; triolein; and combinations thereof.

In some versions, the adhesive-miscible hydrophobes may be applied as follows. One or more adhesive-miscible hydrophobes may be pre-loaded into an open cell foam layer. The open cell foam layer may be loaded and squeezed between the buttress bodies (102, 112) after the buttress bodies (102, 112) have been adhered onto the anvil (60) and lower jaw (50) of the end effector (40). During squeezing of the open cell foam layer, at least a portion of the adhesive-miscible hydrophobe(s) may migrate from the open cell foam layer, through the buttress bodies (102, 112) to the interface between the humidity tolerant adhesive material and the anvil (60) or staple cartridge (70) of the end effector (40), creating a temporarily hydrophobic environment that may be favorable to maintaining good adhesive properties.

In some instances, de-wetting may be additionally or alternatively minimized by coating all or a portion of the end effector (40), e.g. the anvil (60) and/or staple cartridge (70), with a hydrophobic lubricious coating comprising calcium stearate or magnesium stearate.

In some instances, de-wetting may be additionally or alternatively minimized by absorbing moisture away from the surface of the end effector (40). In some such versions, this may be accomplished by mixing a hydrocolloid into the humidity tolerant adhesive material at the time that the adhesive is made. Generally it is theorized, but in no way limits the scope of this invention, that hydrocolloids provide the resulting humidity tolerant adhesive material with wet tack characteristics that enable the adhesive material to stick to both wet and dry surfaces. Suitable compositions that may form the hydrocolloid may be selected from the group consisting of: carboxy methylcellulose (CMC); gelatin; hyaluronate; and combinations thereof.

In some instances, moisture may additionally or alternatively be absorbed away from the surface of the end effector (40) by adding a hydrophilic block to one of the polymers or co-polymers that form the humidity tolerant adhesive material. Suitable hydrophilic blocks may be selected from the group consisting of: polyethylene glycol (PEG); polyvinyl pyrrolidine (PVP); and combinations thereof.

D. Reduction of Forces on Buttress Bodies Against Tissue

As noted above in reference to FIG. 6, a series of staples (1190) may capture and retain buttress assemblies (100, 110) against layers of tissue ($T_1$, $T_2$), thereby securing buttress assemblies (100, 110) to tissue ($T_1$, $T_2$). In some surgical procedures, it may be desirable to reduce forces that are exerted against the buttress assemblies (100, 110) when they are being placed, or are in place, against the layers of tissue ($T_1$, $T_2$). Such a reduction in force may allow for better adhesion of the buttress bodies (102, 112) to the end effector (40). In addition, or in the alternative, it may be desirable to reduce forces that may damage the layers of tissue ($T_1$, $T_2$)

that are to be, or have been, secured. In illustrative examples, this may be accomplished by treating the tissue-contacting surfaces of one or more buttress assemblies (100, 110) so that they become lubricious. Generally it is theorized, but in no way limits the scope of this invention, that a lubricious buttress body (102, 112) surface may reduce the shear force, i.e., drag force, that is applied between the layers of tissue ($T_1$, $T_2$) and buttress assemblies (100, 110). Exemplary substances that may be applied to the tissue-contacting surfaces of one or more buttress assemblies (100, 110) to make them lubricious may be selected from the group consisting of: polyethylene glycol 200 (PEG 200); silicone; oil; and combinations thereof.

In further illustrative examples, forces may additionally or alternatively be reduced by modifying the edges of the buttress body assembly (100, 110). Generally it is theorized, but in no way limits the scope of this invention, that such modifications of the edges of the buttress body assembly (100, 110) may minimize snagging and/or gripping on the layers of tissue ($T_1$, $T_2$) by the buttress assemblies (100, 110) when they are being placed, or are in place, against the layers of tissue ($T_1$, $T_2$), and vice versa. Useful means of modifying the edges of the buttress body assembly (100, 110) may be selected from the group consisting of: radiusing; chamfering; and combinations thereof.

XXXI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of securing a buttress to an end effector, wherein the end effector comprises an upper jaw member and a lower jaw member, the method comprising: (a) positioning a platform of a buttress applier cartridge between the upper and lower jaw members while the upper and lower jaw members are in an open configuration, wherein the platform has a buttress disposed thereon during the act of positioning the platform between the upper and lower jaw members, wherein the buttress applier cartridge has at least one retainer member retaining the buttress on the platform during the act of positioning the platform between the upper and lower jaw members; (b) driving one or both of the upper or lower jaw members toward the platform to thereby engage the buttress with the end effector, wherein the buttress applier cartridge further comprises a resilient member that drives the at least one retainer away from the buttress to thereby release the buttress in response to the act of driving one or both of the upper or lower jaw members toward the platform; and (c) driving one or both of the upper or lower jaw members way from the platform to thereby pull the buttress off of the platform.

Example 2

The method of Example 1, wherein the platform applies at least two different amounts of pressure against the first buttress assembly in response to the act of driving one or both of the upper or lower jaw members toward the platform to thereby engage the buttress with the end effector.

Example 3

The method of any one or more of Examples 1 through 2, further comprising: (a) actuating the end effector on tissue, thereby providing a spent staple cartridge; and (b) attempting to close the actuated end effector about a second platform of a second buttress applier cartridge, wherein the second platform has features that engage the spent staple cartridge and thereby prevent full closure of the actuated end effector about the second platform.

Example 4

The method of one or more of Examples 1 through 3, further comprising viewing an indicator on the buttress applier cartridge to confirm that the buttress applier cartridge is loaded before performing the act of driving one or both of the upper or lower jaw members toward the platform.

Example 5

The method of one or more of Examples 1 through 4, further comprising changing a state of an indicator on the buttress applier cartridge in response to the act of driving one or both of the upper or lower jaw members toward the platform.

Example 6

The method of one or more of Examples 1 through 5, further comprising driving a fluid from the buttress in response to the act of driving one or both of the upper or lower jaw members toward the platform.

Example 7

The method of Example 6, wherein the buttress applier cartridge has a reservoir that receives some of the fluid driven from the buttress in response to the act of driving a fluid from the buttress.

Example 8

The method of one or more of Examples 1 through 7, further comprising receiving feedback from the buttress applier cartridge confirming successful closure of the end effector about the platform.

Example 9

The method of one or more of Examples 1 through 8, wherein the buttress applier cartridge further comprises a latch, wherein the latch secures the position of the retainer member during the act of positioning the platform between the first and second jaw members, wherein the act of driving one or both of the upper or lower jaw members toward the platform comprises: (i) engaging a first portion of the latch with the upper jaw member, and (ii) engaging a second portion of the latch with the lower jaw member while simultaneously engaging the first portion of the latch with the upper jaw member, wherein the simultaneous engagement of the first and second portions of the latch causes the latch to release the at least one retainer, wherein the release of the at least one retainer by the latch causes the at least one retainer to release the buttress from the platform.

Example 10

The method of one or more of Examples 1 through 9, wherein the act of driving one or both of the upper or lower jaw members toward the platform further comprises activating a data communication feature.

Example 11

The method of Example 10, wherein the act of activating a data communication feature comprises receiving electronic data wirelessly from the buttress applier cartridge.

Example 12

The method of one or more of Examples 1 through 11, further comprising viewing an indicator on the buttress applier cartridge to confirm that the buttress applier cartridge has not been exposed to an adverse environmental condition before performing the act of driving one or both of the upper or lower jaw members toward the platform.

Example 13

The method of one or more of Examples 1 through 12, further comprising viewing a display screen on the buttress applier cartridge to observe a characteristic of the buttress applier cartridge before performing the act of driving one or both of the upper or lower jaw members toward the platform.

Example 14

The method of one or more of Examples 1 through 13, further comprising: (a) opening a container cover of a container; (b) retrieving the buttress applier cartridge from the container; and (c) removing a buttress cover from the buttress to expose an adhesive on the buttress.

Example 15

The method of Example 14, wherein the buttress cover is secured to the container cover such that the act of opening the container cover and the act of removing the buttress cover are performed simultaneously.

Example 16

The method of one or more of Examples 1 through 15, further comprising actuating the end effector, wherein the act of actuating the end effector comprises driving a first plurality of staples from the end effector through at the buttress.

Example 17

The method of Example 16, wherein the act of actuating the end effector further comprises driving a second plurality of staples from the end effector separately from the buttress.

Example 18

The method of one or more of Examples 1 through 17, further comprising sliding the platform longitudinally relative to a housing of the buttress applier cartridge.

Example 19

A method of securing series of buttresses to an end effector, wherein the end effector comprises an upper jaw member and a lower jaw member, the method comprising: (a) positioning a platform of a buttress applier cartridge between the upper and lower jaw members while the upper and lower jaw members are in an open configuration, wherein the platform has a plurality of buttresses disposed thereon; (b) closing the jaw members about the platform to adhere a first buttress of the plurality of buttresses to the end effector; (c) opening the jaw members to pull the first buttress from the platform; (d) actuating the end effector in a patient, thereby securing the first buttress in the patient; (e) closing the jaw members about the platform to adhere a second buttress of the plurality of buttresses to the end effector; (f) opening the jaw members to pull the second buttress from the platform; and (g) actuating the end effector in a patient, thereby securing the second buttress in the patient.

Example 20

A method of securing a buttress to an end effector, wherein the end effector comprises an upper jaw member and a lower jaw member, the method comprising: (a) positioning a platform of a buttress applier cartridge between the upper and lower jaw members while the upper and lower jaw members are in an open configuration, wherein the platform has a buttress disposed thereon; (b) observing a first alignment marking on the end effector in relation to a second alignment marker on the buttress applier cartridge to confirm proper alignment of the end effector relative to the buttress applier cartridge; (c) closing the jaw members about the platform to adhere the buttress to the end effector; (d) opening the jaw members to pull the buttress from the platform; and (e) observing alignment markings on the buttress in relation to the end effector to confirm proper alignment of the buttress relative to the end effector.

Any of the Examples set forth in U.S. patent application Ser. No. 14/926,267, filed Oct. 29, 2015, entitled "Surgical Stapler Buttress Applicator with End Effector Actuated Release Mechanism," filed on even date herewith, now U.S. Patent Pub. No. 2017/0056016, published Mar. 2, 2017, issued as U.S. Pat. No. 10,342,542 on Jul. 9, 2019, the disclosure of which is incorporated by reference herein.

Any of the Examples set forth in U.S. patent application Ser. No. 14/926,296, filed Oct. 29, 2015, entitled "Surgical Stapler Buttress Applicator with Multi-Zone Platform for Pressure Focused Release," filed on even date herewith, now U.S. Patent Pub. No. 2017/0056017, published Mar. 2, 2017, issued as U.S. Pat. No. 10,639,039 on May 5, 2020, the disclosure of which is incorporated by reference herein.

Any of the Examples set forth in U.S. patent application Ser. No. 14/926,322, filed Oct. 29, 2015, entitled "Surgical Stapler Buttress Applicator with Spent Staple Cartridge Lockout," filed on even date herewith, now U.S. Patent Pub. No. 2017/0055980, published Mar. 2, 2017, issued as U.S. Pat. No. 11,039,832 on Jun. 22, 2021, the disclosure of which is incorporated by reference herein.

Any of the Examples set forth in U.S. patent application Ser. No. 14/926,358, filed Oct. 29, 2015, entitled "Surgical Stapler Buttress Applicator with State Indicator," filed on even date herewith, now U.S. Patent Pub. No. 2017/0056018, published Mar. 2, 2017, issued as U.S. Pat. No. 10,349,940 on Jul. 16, 2019, the disclosure of which is incorporated by reference herein.

Any of the Examples set forth in U.S. patent application Ser. No. 14/926,609, filed Oct. 29, 2015, entitled "Surgical Stapler Buttress Applicator with Multi-Point Actuated Release Mechanism," filed on even date herewith, now U.S. Patent Pub. No. 2017/0055982, published Mar. 2, 2017, issued as U.S. Pat. No. 10,342,532 on Jul. 9, 2019, the disclosure of which is incorporated by reference herein.

Any of the Examples set forth in U.S. patent application Ser. No. 14/926,131, filed Oct. 29, 2015, entitled "Surgical Stapler Buttress Applicator with Data Communication," filed on even date herewith, now U.S. Patent Pub. No. 2017/0119391, published May 4, 2017, issued as U.S. Pat. No. 10,251,649 on Apr. 9, 2019, the disclosure of which is incorporated by reference herein.

Any of the Examples set forth in U.S. patent application Ser. No. 14/926,027, filed Oct. 29, 2015, entitled "Surgical Stapler Buttress Assembly with Gel Adhesive Retainer," filed on even date herewith, now U.S. Patent Pub. No. 2017/0119386, published May 4, 2017, issued as U.S. Pat. No. 10,433,839 on Oct. 8, 2019, the disclosure of which is incorporated by reference herein.

Any of the Examples set forth in U.S. patent application Ser. No. 14/926,029, filed Oct. 29, 2015, entitled "Fluid Penetrable Buttress Assembly for Surgical Stapler," filed on even date herewith, now U.S. Patent Pub. No. 2017/0119389, published May 4, 2017, issued as U.S. Pat. No. 10,314,588 on Jun. 11, 2019, the disclosure of which is incorporated by reference herein.

Any of the Examples set forth in U.S. patent application Ser. No. 14/926,072, filed Oct. 29, 2015, entitled "Surgical Stapler Buttress Assembly with Features to Interact with Movable End Effector Components," filed on even date herewith, now U.S. Patent Pub. No. 2017/0119390, published May 4, 2017, issued as U.S. Pat. No. 10,499,918 on Dec. 10, 2019, the disclosure of which is incorporated by reference herein.

Any of the Examples set forth in U.S. patent application Ser. No. 14/926,090, filed Oct. 29, 2015, entitled "Extensible Buttress Assembly for Surgical Stapler," filed on even date herewith, now U.S. Patent Pub. No. 2017/0119387, published May 4, 2017, issued as U.S. Pat. No. 10,357,248 on Jul. 23, 2019, the disclosure of which is incorporated by reference herein.

Any of the Examples set forth in U.S. patent application Ser. No. 14/926,194, filed Oct. 29, 2015, entitled "Extensible Buttress Assembly for Surgical Stapler," filed on even date herewith, now U.S. Pat. No. 10,085,745, issued Oct. 2, 2018, the disclosure of which is incorporated by reference herein.

Any of the Examples set forth in U.S. patent application Ser. No. 14/926,160, filed Oct. 29, 2015, entitled "Multi-Layer Surgical Stapler Buttress Assembly," filed on even date herewith, now U.S. Patent Pub. No. 2017/0119392, published May 4, 2017, issued as U.S. Pat. No. 10,441,286 on Oct. 15, 2019, the disclosure of which is incorporated by reference herein.

Any of the Examples set forth in U.S. patent application Ser. No. 14/926,045, filed Oct. 29, 2015, entitled "Surgical Stapler Buttress Assembly with Humidity Tolerant Adhesive," filed on even date herewith, now U.S. Patent Pub. No. 2017/0119379, published May 4, 2017, issued as U.S. Pat. No. 10,238,388 on Mar. 26, 2019, the disclosure of which is incorporated by reference herein.

Any of the Examples set forth in U.S. patent application Ser. No. 14/926,057, filed Oct. 27, 2018, entitled "Surgical Stapler Buttress Assembly with Adhesion to Wet End Effector," filed on even date herewith, now U.S. Patent Pub. No. 2017/0119385, published May 4, 2017, issued as U.S. Pat. No. 10,517,592 on Dec. 31, 2019, the disclosure of which is incorporated by reference herein.

XXXII. Miscellaneous

While the terms "buttress" and "buttress assembly" are used throughout this disclosure, it should be understood that the term is not intended to limit the scope of the present invention in any way. For instance, use of the terms "buttress" and "buttress assembly" is not intended to demonstrate contemplation that a "buttress" or "buttress assembly" can only be used to provide structural support to a staple line or serve any other particular purpose. It is contemplated that "buttress" or "buttress assembly" may serve a variety of purposes in addition to or as an alternative to providing structural support to a staple line. The terms "buttress" and "buttress assembly" should therefore be read broadly to include any kind of adjunct to a staple line that serves any suitable purpose.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, now U.S. Patent Pub. No. 2016/0278774, published Sep. 26, 2016, issued as U.S. Pat. No. 10,349,939 on Jul. 16, 2019, the disclosure of which is incorporated by reference herein; U.S. patent application Ser. No. 14/827,856, entitled "Implantable Layers for a Surgical Instrument," filed Aug. 17, 2015, now U.S. Patent Pub. No. 2017/0049444, published Feb. 23, 2017, issued as U.S. Pat. No. 10,835,249 on Nov. 17, 2020, the disclosure of which is incorporated by reference herein; U.S. patent application Ser. No. 14/871,071, entitled "Compressible Adjunct with Crossing Spacer Fibers," filed Sep. 30, 2015 now U.S. Patent Pub. No. 2017/0086837, published Mar. 30, 2017, issued as U.S. Pat. No. 10,433,846 on Oct. 8, 2019, the disclosure of which is incorporated by reference herein; and U.S. patent application Ser. No. 14/871,131, entitled "Method for Applying an Implantable Layer to a Fastener Cartridge," filed Sep. 30, 2015, now U.S. Patent Pub. No. 2017/0086842, published Mar. 30, 2017, the disclosure of which is incorporated by reference herein. Furthermore, in addition to the methods described herein, any of the various buttress assemblies described herein may be applied to end effector (40) in accordance with at least some of the teachings of U.S. Provisional Patent App. No. 62/209,041, entitled "Method and Apparatus for Applying a Buttress to End Effector of a Surgical Stapler," filed Aug. 24, 2015, the disclosure of which is incorporated by reference herein; and/or U.S. patent application Ser. No. 14/871,131, entitled "Method for Applying an Implantable Layer to a Fastener Cartridge," filed Sep. 30, 2015, now U.S. Patent Pub. No. 2017/0086842, published Mar. 30, 2017, the disclosure of which is incorporated by reference herein. Various suitable ways in which the teachings herein may be combined with various teachings of the above-cited references will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, now U.S. Pat. No. 8,844,789, issued Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, Now. U.S. Pat. No. 8,820,605, issued Sep. 2, 2014, the disclosure of which is incorporated by reference herein; U.S. Pub. No. 2012/0132450, entitled "Shiftable Drive Interface for Robotically-Controlled Surgical Tool," published May 31, 2012, now U.S. Pat. No. 8,616,431, issued Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, now U.S. Pat. No. 8,573,461, issued Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, now U.S. Pat. No. 8,602,288, issued Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued Apr. 5, 2016, the disclosure of which is incorporated by reference herein; U.S. Pub. No. 2012/0203247, entitled "Robotically-Controlled Surgical End Effector System," published Aug. 9, 2012 now U.S. Pat. No. 8,783,541, issued Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012 now U.S. Pat. No. 8,479,969, issued Jul. 9, 2013; U.S. Pub. No. 2012/0138660, entitled "Robotically-Controlled Cable-Based Surgical End Effectors," published Jun. 7, 2012, now U.S. Pat. No. 8,800,838, issued Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, now U.S. Pat. No. 8,573,465, issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A buttress assembly configured for use with an end effector of a surgical stapler, comprising:
   (a) a buttress body having a mesh layer; and
   (b) an adhesive layer disposed over and integrally coupled with the buttress body, wherein the adhesive layer includes a pressure sensitive adhesive arranged non-uniformly along a length of the buttress body, wherein the adhesive layer is configured to releasably adhere to one of an anvil or a staple cartridge of the end effector in response to closure of the end effector on the buttress assembly,
   wherein the buttress body is configured to contact tissue clamped by the end effector during closure thereof,
   wherein the buttress body is further configured to be pierced and captured by staples ejected from the staple cartridge into the clamped tissue and thereby reinforce the engagement between the ejected staples with the clamped tissue.

2. The buttress assembly of claim 1, wherein the mesh layer includes a plurality of fibers arranged in a matrix.

3. The buttress assembly of claim 2, wherein the fibers are interwoven with one another.

4. The buttress assembly of claim 1, wherein the mesh layer includes a plurality of interstices configured to receive legs of the ejected staples therethrough to thereby constrain the ejected staples relative to one another.

5. The buttress assembly of claim 1, wherein the pressure sensitive adhesive is arranged in a plurality of discrete segments along the buttress body.

6. The buttress assembly of claim 1, wherein the pressure sensitive adhesive comprises a humidity tolerant adhesive.

7. The buttress assembly of claim 1, wherein the pressure sensitive adhesive comprises a flowable adhesive.

8. The buttress assembly of claim 1, wherein at least the buttress body of the buttress assembly is configured to separate from the one of the anvil or the staple cartridge in response to opening of the end effector after the staples have been ejected into the clamped tissue.

9. The buttress assembly of claim 1, further comprising a film layer disposed between the buttress body and the adhesive layer.

10. The buttress assembly of claim 9, wherein the film layer is configured to provide a liquid impermeable barrier.

11. The buttress assembly of claim 9, wherein the film layer is configured to form a seal around legs of staples that pierce therethrough.

12. A buttress assembly configured for use with an end effector of a surgical stapler, comprising:
    (a) a buttress body; and
    (b) an adhesive layer disposed over and integrally coupled with the buttress body, wherein the adhesive layer includes a pressure sensitive adhesive arranged in a plurality of discrete segments along the buttress body, wherein the adhesive layer is configured to releasably adhere to a stapling surface of the end effector in response to closure of the end effector on the buttress assembly,
    wherein the buttress body is configured to contact tissue clamped by the end effector during closure thereof,
    wherein the buttress body is further configured to be pierced and captured by staples ejected from the end effector into the clamped tissue and thereby reinforce the engagement between the ejected staples with the clamped tissue.

13. The buttress assembly of claim 12, wherein each discrete segment of the plurality of discrete segments includes a dot.

14. The buttress assembly of claim 12, wherein each discrete segment of the plurality of discrete segments includes a stripe.

15. The buttress assembly of claim 14, wherein each stripe is obliquely oriented relative to a longitudinal axis of the buttress body.

16. A buttress assembly configured for use with an end effector of a surgical stapler, comprising:
    (a) a buttress body; and
    (b) an adhesive layer disposed over and integrally coupled with the buttress body, wherein the adhesive layer includes a pressure sensitive adhesive arranged in a plurality of discrete segments along the buttress body, wherein each discrete segment of the plurality of discrete segments includes at least one of a dot or a stripe, wherein the adhesive layer is configured to releasably adhere to one of an anvil or a staple cartridge of the end effector in response to closure of the end effector on the buttress assembly,
    wherein the buttress body is configured to contact tissue clamped by the end effector during closure thereof,
    wherein the buttress body is further configured to be pierced and captured by staples ejected from the staple cartridge into the clamped tissue and thereby reinforce the engagement between the ejected staples with the clamped tissue.

* * * * *